US012584118B2

(12) United States Patent
Liu et al.

(10) Patent No.: US 12,584,118 B2
(45) Date of Patent: *Mar. 24, 2026

(54) Cas9 VARIANTS AND USES THEREOF

(71) Applicant: President and Fellows of Harvard College, Cambridge, MA (US)

(72) Inventors: David R. Liu, Cambridge, MA (US); John Paul Guilinger, Cambridge, MA (US); David B. Thompson, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 379 days.

This patent is subject to a terminal disclaimer.

(21) Appl. No.: 17/937,203

(22) Filed: Sep. 30, 2022

(65) Prior Publication Data

US 2023/0056852 A1 Feb. 23, 2023

Related U.S. Application Data

(63) Continuation of application No. 17/103,233, filed on Nov. 24, 2020, which is a continuation of application No. 14/916,681, filed as application No. PCT/US2014/054291 on Sep. 5, 2014, now Pat. No. 10,858,639, which is a continuation of application No. 14/320,498, filed on Jun. 30, 2014, now Pat. No. 9,322,037, said application No. PCT/US2014/054291 is a continuation of application No. 14/320,467, filed on Jun. 30, 2014, now Pat. No. 9,388,430.

(60) Provisional application No. 61/980,315, filed on Apr. 16, 2014, provisional application No. 61/915,414, filed on Dec. 12, 2013, provisional application No. 61/874,609, filed on Sep. 6, 2013.

(51) Int. Cl.
| | |
|---|---|
| *C12N 9/22* | (2006.01) |
| *A61K 38/00* | (2006.01) |
| *A61K 38/46* | (2006.01) |
| *A61K 47/00* | (2006.01) |
| *C07K 14/315* | (2006.01) |
| *C12N 9/12* | (2006.01) |
| *C12N 15/01* | (2006.01) |
| *C12N 15/90* | (2006.01) |

(52) U.S. Cl.
CPC .............. *C12N 9/22* (2013.01); *A61K 38/465* (2013.01); *C07K 14/315* (2013.01); *C12N 9/1241* (2013.01); *C12N 15/01* (2013.01); *C12N 15/907* (2013.01); *A61K 38/00* (2013.01); *A61K 47/00* (2013.01); *C07K 2319/80* (2013.01)

(58) Field of Classification Search
CPC ...... C12N 9/22; C12N 9/1241; C12N 15/907; C12N 15/01; A61K 38/465; A61K 38/00; A61K 47/00; C07K 14/315; C07K 2319/80
See application file for complete search history.

(56) References Cited

U.S. PATENT DOCUMENTS

| | | | |
|---|---|---|---|
| 4,182,449 | A | 1/1980 | Kozlow |
| 4,186,183 | A | 1/1980 | Steck et al. |
| 4,217,344 | A | 8/1980 | Vanlerberghe et al. |
| 4,235,871 | A | 11/1980 | Papahadjopoulos et al. |
| 4,261,975 | A | 4/1981 | Fullerton et al. |
| 4,485,054 | A | 11/1984 | Mezei et al. |
| 4,501,728 | A | 2/1985 | Geho et al. |
| 4,663,290 | A | 5/1987 | Weis et al. |
| 4,737,323 | A | 4/1988 | Martin et al. |
| 4,774,085 | A | 9/1988 | Fidler |
| 4,797,368 | A | 1/1989 | Carter et al. |
| 4,837,028 | A | 6/1989 | Allen |
| 4,873,316 | A | 10/1989 | Meade et al. |
| 4,880,635 | A | 11/1989 | Janoff et al. |
| 4,889,818 | A | 12/1989 | Gelfand et al. |
| 4,897,355 | A | 1/1990 | Eppstein et al. |
| 4,906,477 | A | 3/1990 | Kurono et al. |
| 4,911,928 | A | 3/1990 | Wallach |
| 4,917,951 | A | 4/1990 | Wallach |
| 4,920,016 | A | 4/1990 | Allen et al. |
| 4,921,757 | A | 5/1990 | Wheatley et al. |
| 4,946,787 | A | 8/1990 | Eppstein et al. |
| 4,965,185 | A | 10/1990 | Grischenko et al. |

(Continued)

FOREIGN PATENT DOCUMENTS

| | | |
|---|---|---|
| AU | 2012244264 A1 | 11/2012 |
| AU | 2012354062 A1 | 7/2014 |

(Continued)

OTHER PUBLICATIONS

U.S. Appl. No. 61/716,256, filed Oct. 19, 2012, Jinek et al..

(Continued)

*Primary Examiner* — Li N Komatsu

(74) *Attorney, Agent, or Firm* — Wolf, Greenfield & Sacks, P.C.

(57) ABSTRACT

Some aspects of this disclosure provide compositions, methods, and kits for improving the specificity of RNA-programmable endonucleases, such as Cas9. Also provided are variants of Cas9, e.g., Cas9 dimers and fusion proteins, engineered to have improved specificity for cleaving nucleic acid targets. Also provided are compositions, methods, and kits for site-specific nucleic acid modification using Cas9 fusion proteins (e.g., nuclease-inactivated Cas9 fused to a nuclease catalytic domain or a recombinase catalytic domain). Such Cas9 variants are useful in clinical and research settings involving site-specific modification of DNA, for example, genomic modifications.

20 Claims, 35 Drawing Sheets

Specification includes a Sequence Listing.

(56)                 References Cited

U.S. PATENT DOCUMENTS

| | | | |
|---|---|---|---|
| 5,017,492 A | 5/1991 | Kotewicz et al. |
| 5,047,342 A | 9/1991 | Chatterjee |
| 5,049,386 A | 9/1991 | Eppstein et al. |
| 5,079,352 A | 1/1992 | Gelfand et al. |
| 5,139,941 A | 8/1992 | Muzyczka et al. |
| 5,173,414 A | 12/1992 | Lebkowski et al. |
| 5,223,409 A | 6/1993 | Ladner et al. |
| 5,244,797 A | 9/1993 | Kotewicz et al. |
| 5,270,179 A | 12/1993 | Chatterjee |
| 5,374,553 A | 12/1994 | Gelfand et al. |
| 5,405,776 A | 4/1995 | Kotewicz et al. |
| 5,436,149 A | 7/1995 | Barnes |
| 5,449,639 A | 9/1995 | Wei et al. |
| 5,478,745 A | 12/1995 | Samulski et al. |
| 5,496,714 A | 3/1996 | Comb et al. |
| 5,512,462 A | 4/1996 | Cheng |
| 5,580,737 A | 12/1996 | Polisky et al. |
| 5,614,365 A | 3/1997 | Tabor et al. |
| 5,652,094 A | 7/1997 | Usman et al. |
| 5,658,727 A | 8/1997 | Barbas et al. |
| 5,668,005 A | 9/1997 | Kotewicz et al. |
| 5,677,152 A | 10/1997 | Birch et al. |
| 5,767,099 A | 6/1998 | Harris et al. |
| 5,780,053 A | 7/1998 | Ashley et al. |
| 5,830,430 A | 11/1998 | Unger et al. |
| 5,834,247 A | 11/1998 | Comb et al. |
| 5,835,699 A | 11/1998 | Kimura |
| 5,844,075 A | 12/1998 | Kawakami et al. |
| 5,849,548 A | 12/1998 | Haseloff et al. |
| 5,851,548 A | 12/1998 | Dattagupta et al. |
| 5,855,910 A | 1/1999 | Ashley et al. |
| 5,856,463 A | 1/1999 | Blankenborg et al. |
| 5,962,313 A | 10/1999 | Podsakoff et al. |
| 5,981,182 A | 11/1999 | Jacobs, Jr. et al. |
| 6,015,794 A | 1/2000 | Haseloff et al. |
| 6,057,153 A | 5/2000 | George et al. |
| 6,063,608 A | 5/2000 | Kotewicz et al. |
| 6,077,705 A | 6/2000 | Duan et al. |
| 6,099,857 A | 8/2000 | Gross |
| 6,156,509 A | 12/2000 | Schellenberger |
| 6,183,998 B1 | 2/2001 | Ivanov et al. |
| 6,355,415 B1 | 3/2002 | Wagner et al. |
| 6,416,997 B1 | 7/2002 | Mir-Shekari et al. |
| 6,429,298 B1 | 8/2002 | Ellington et al. |
| 6,453,242 B1 | 9/2002 | Eisenberg et al. |
| 6,479,264 B1 | 11/2002 | Louwrier |
| 6,503,717 B2 | 1/2003 | Case et al. |
| 6,534,261 B1 | 3/2003 | Cox, III et al. |
| 6,558,671 B1 | 5/2003 | Slingluff et al. |
| 6,589,768 B1 | 7/2003 | Kotewicz et al. |
| 6,599,692 B1 | 7/2003 | Case et al. |
| 6,607,882 B1 | 8/2003 | Cox, III et al. |
| 6,610,522 B1 | 8/2003 | Kotewicz et al. |
| 6,689,558 B2 | 2/2004 | Case |
| 6,716,973 B2 | 4/2004 | Baskerville et al. |
| 6,815,194 B2 | 11/2004 | Honjo et al. |
| 6,824,978 B1 | 11/2004 | Cox, III et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,045,337 B2 | 5/2006 | Schultz et al. |
| 7,067,650 B1 | 6/2006 | Tanaka |
| 7,070,928 B2 | 7/2006 | Liu et al. |
| 7,078,208 B2 | 7/2006 | Smith et al. |
| 7,083,970 B2 | 8/2006 | Schultz et al. |
| 7,163,824 B2 | 1/2007 | Cox, III et al. |
| 7,192,739 B2 | 3/2007 | Liu et al. |
| 7,223,545 B2 | 5/2007 | Liu et al. |
| 7,329,807 B2 | 2/2008 | Vadrucci et al. |
| 7,354,761 B2 | 4/2008 | Schultz et al. |
| 7,368,275 B2 | 5/2008 | Schultz et al. |
| 7,419,669 B2 | 9/2008 | Kosmatopoulos et al. |
| 7,442,160 B2 | 10/2008 | Liu et al. |
| 7,476,500 B1 | 1/2009 | Liu et al. |
| 7,476,734 B2 | 1/2009 | Liu |
| 7,479,573 B2 | 1/2009 | Chu et al. |
| 7,488,718 B2 | 2/2009 | Scheinberg et al. |
| 7,491,494 B2 | 2/2009 | Liu et al. |
| 7,510,706 B2 | 3/2009 | Yonemitsu et al. |
| 7,541,450 B2 | 6/2009 | Liu et al. |
| 7,556,940 B2 | 7/2009 | Galarza et al. |
| 7,557,068 B2 | 7/2009 | Liu et al. |
| 7,595,179 B2 | 9/2009 | Chen et al. |
| 7,638,300 B2 | 12/2009 | Schultz et al. |
| 7,670,807 B2 | 3/2010 | Lampson et al. |
| 7,678,554 B2 | 3/2010 | Liu et al. |
| 7,713,721 B2 | 5/2010 | Schultz et al. |
| 7,771,935 B2 | 8/2010 | Liu et al. |
| 7,794,931 B2 | 9/2010 | Breaker et al. |
| 7,807,408 B2 | 10/2010 | Liu et al. |
| 7,851,658 B2 | 12/2010 | Liu et al. |
| 7,915,025 B2 | 3/2011 | Schultz et al. |
| 7,919,277 B2 | 4/2011 | Russell et al. |
| 7,993,672 B2 | 8/2011 | Huang et al. |
| 7,998,904 B2 | 8/2011 | Liu et al. |
| 7,999,071 B2 | 8/2011 | Schlom et al. |
| 8,012,739 B2 | 9/2011 | Schultz et al. |
| 8,017,323 B2 | 9/2011 | Liu et al. |
| 8,017,755 B2 | 9/2011 | Liu et al. |
| 8,030,074 B2 | 10/2011 | Schultz et al. |
| 8,067,556 B2 | 11/2011 | Hogrefe et al. |
| 8,114,648 B2 | 2/2012 | Schultz et al. |
| 8,173,364 B2 | 5/2012 | Schultz et al. |
| 8,173,392 B2 | 5/2012 | Schultz et al. |
| 8,183,012 B2 | 5/2012 | Schultz et al. |
| 8,183,178 B2 | 5/2012 | Liu et al. |
| 8,206,914 B2 | 6/2012 | Liu et al. |
| 8,354,380 B2 | 1/2013 | Liu et al. |
| 8,361,725 B2 | 1/2013 | Russell et al. |
| 8,394,604 B2 | 3/2013 | Liu et al. |
| 8,420,104 B2 | 4/2013 | Charneau et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,492,082 B2 | 7/2013 | De Franciscis et al. |
| 8,546,553 B2 | 10/2013 | Terns et al. |
| 8,569,256 B2 | 10/2013 | Heyes et al. |
| 8,586,363 B2 | 11/2013 | Voytas et al. |
| 8,673,612 B2 | 3/2014 | Klatzmann et al. |
| 8,680,069 B2 | 3/2014 | De Fougerolles et al. |
| 8,691,729 B2 | 4/2014 | Liu et al. |
| 8,691,750 B2 | 4/2014 | Constien et al. |
| 8,697,359 B1 | 4/2014 | Zhang |
| 8,697,439 B2 | 4/2014 | Mangeot et al. |
| 8,697,853 B2 | 4/2014 | Voytas et al. |
| 8,709,466 B2 | 4/2014 | Coady et al. |
| 8,728,526 B2 | 5/2014 | Heller |
| 8,729,038 B2 | 5/2014 | Gruber et al. |
| 8,741,279 B2 | 6/2014 | Kasahara et al. |
| 8,748,667 B2 | 6/2014 | Budzik et al. |
| 8,758,810 B2 | 6/2014 | Okada et al. |
| 8,759,103 B2 | 6/2014 | Kim et al. |
| 8,759,104 B2 | 6/2014 | Unciti-Broceta et al. |
| 8,771,728 B2 | 7/2014 | Huang et al. |
| 8,790,664 B2 | 7/2014 | Pitard et al. |
| 8,795,965 B2 | 8/2014 | Zhang |
| 8,822,663 B2 | 9/2014 | Schrum et al. |
| 8,846,578 B2 | 9/2014 | McCray et al. |
| 8,889,418 B2 | 11/2014 | Zhang et al. |
| 8,900,814 B2 | 12/2014 | Yasukawa et al. |
| 8,945,839 B2 | 2/2015 | Zhang |
| 8,975,232 B2 | 3/2015 | Liu et al. |
| 8,993,233 B2 | 3/2015 | Zhang et al. |
| 8,999,641 B2 | 4/2015 | Zhang et al. |
| 9,023,594 B2 | 5/2015 | Liu et al. |
| 9,023,649 B2 | 5/2015 | Mali et al. |
| 9,068,179 B1 | 6/2015 | Liu et al. |
| 9,150,626 B2 | 10/2015 | Liu et al. |
| 9,163,271 B2 | 10/2015 | Schultz et al. |
| 9,163,284 B2 | 10/2015 | Liu et al. |
| 9,181,535 B2 | 11/2015 | Liu et al. |
| 9,200,045 B2 | 12/2015 | Liu et al. |
| 9,221,886 B2 | 12/2015 | Liu et al. |
| 9,228,207 B2 | 1/2016 | Liu et al. |

(56)          References Cited

U.S. PATENT DOCUMENTS

| | | |
|---|---|---|
| 9,234,213 B2 | 1/2016 | Wu |
| 9,243,038 B2 | 1/2016 | Liu et al. |
| 9,267,127 B2 | 2/2016 | Liu et al. |
| 9,290,773 B2 | 3/2016 | Edgerton |
| 9,296,790 B2 | 3/2016 | Chatterjee et al. |
| 9,322,006 B2 | 4/2016 | Liu et al. |
| 9,322,037 B2 | 4/2016 | Liu et al. |
| 9,340,799 B2 | 5/2016 | Liu et al. |
| 9,340,800 B2 | 5/2016 | Liu et al. |
| 9,359,599 B2 | 6/2016 | Liu et al. |
| 9,388,430 B2 | 7/2016 | Liu et al. |
| 9,394,537 B2 | 7/2016 | Liu et al. |
| 9,434,774 B2 | 9/2016 | Liu et al. |
| 9,458,484 B2 | 10/2016 | Ma et al. |
| 9,512,446 B1 | 12/2016 | Joung et al. |
| 9,526,784 B2 | 12/2016 | Liu et al. |
| 9,534,210 B2 | 1/2017 | Park et al. |
| 9,580,698 B1 | 2/2017 | Xu et al. |
| 9,637,739 B2 | 5/2017 | Siksnys et al. |
| 9,737,604 B2 | 8/2017 | Liu et al. |
| 9,738,693 B2 | 8/2017 | Telford et al. |
| 9,771,574 B2 | 9/2017 | Liu et al. |
| 9,783,791 B2 | 10/2017 | Hogrefe et al. |
| 9,840,538 B2 | 12/2017 | Telford et al. |
| 9,840,690 B2 | 12/2017 | Karli et al. |
| 9,840,699 B2 | 12/2017 | Liu et al. |
| 9,840,702 B2 | 12/2017 | Collingwood et al. |
| 9,850,521 B2 | 12/2017 | Braman et al. |
| 9,932,567 B1 | 4/2018 | Xu et al. |
| 9,944,933 B2 | 4/2018 | Storici et al. |
| 9,999,671 B2 | 6/2018 | Liu et al. |
| 10,059,940 B2 | 8/2018 | Zhong |
| 10,077,453 B2 | 9/2018 | Liu et al. |
| 10,113,163 B2 | 10/2018 | Liu et al. |
| 10,150,955 B2 | 12/2018 | Lambowitz et al. |
| 10,167,457 B2 | 1/2019 | Liu et al. |
| 10,179,911 B2 | 1/2019 | Liu et al. |
| 10,189,831 B2 | 1/2019 | Arrington et al. |
| 10,202,658 B2 | 2/2019 | Parkin et al. |
| 10,227,581 B2 | 3/2019 | Liu et al. |
| 10,323,236 B2 | 6/2019 | Liu et al. |
| 10,336,997 B2 | 7/2019 | Liu et al. |
| 10,358,670 B2 | 7/2019 | Janulaitis et al. |
| 10,392,674 B2 | 8/2019 | Liu et al. |
| 10,407,697 B2 | 9/2019 | Doudna et al. |
| 10,465,176 B2 | 11/2019 | Liu et al. |
| 10,508,298 B2 | 12/2019 | Liu et al. |
| 10,597,679 B2 | 3/2020 | Liu et al. |
| 10,612,011 B2 | 4/2020 | Liu et al. |
| 10,682,410 B2 | 6/2020 | Liu et al. |
| 10,704,062 B2 | 7/2020 | Liu et al. |
| 10,745,677 B2 | 8/2020 | Maianti et al. |
| 10,858,639 B2 | 12/2020 | Liu et al. |
| 10,912,833 B2 | 2/2021 | Liu et al. |
| 10,930,367 B2 | 2/2021 | Zhang et al. |
| 10,947,530 B2 | 3/2021 | Liu et al. |
| 10,954,548 B2 | 3/2021 | Liu et al. |
| 11,046,948 B2 | 6/2021 | Liu et al. |
| 11,053,481 B2 | 7/2021 | Liu et al. |
| 11,078,429 B2 | 8/2021 | Liu et al. |
| 11,124,782 B2 | 9/2021 | Liu et al. |
| 11,268,082 B2 | 3/2022 | Liu et al. |
| 11,299,755 B2 | 4/2022 | Liu et al. |
| 11,306,324 B2 | 4/2022 | Liu et al. |
| 11,447,770 B1 | 9/2022 | Liu et al. |
| 11,732,274 B2 | 8/2023 | Liu et al. |
| 11,795,443 B2 | 10/2023 | Liu et al. |
| 11,795,452 B2 | 10/2023 | Liu et al. |
| 11,820,969 B2 | 11/2023 | Maianti et al. |
| 11,898,179 B2 | 2/2024 | Maianti et al. |
| 11,912,985 B2 | 2/2024 | Liu et al. |
| 11,920,181 B2 | 3/2024 | Liu et al. |
| 11,932,884 B2 | 3/2024 | Liu et al. |
| 11,999,947 B2 | 6/2024 | Liu et al. |
| 12,006,520 B2 | 6/2024 | Liu et al. |
| 12,031,126 B2 | 7/2024 | Liu et al. |
| 12,043,852 B2 | 7/2024 | Liu et al. |
| 12,084,663 B2 | 9/2024 | Maianti et al. |
| 12,157,760 B2 | 12/2024 | Liu et al. |
| 12,215,365 B2 | 2/2025 | Liu et al. |
| 12,281,303 B2 | 4/2025 | Liu et al. |
| 12,281,338 B2 | 4/2025 | Liu et al. |
| 12,344,869 B2 | 7/2025 | Liu et al. |
| 12,351,837 B2 | 7/2025 | Kim et al. |
| 12,359,218 B2 | 7/2025 | Liu et al. |
| 12,390,514 B2 | 8/2025 | Maianti et al. |
| 12,398,406 B2 | 8/2025 | Liu et al. |
| 12,406,749 B2 | 9/2025 | Shen et al. |
| 2003/0082575 A1 | 5/2003 | Schultz et al. |
| 2003/0087817 A1 | 5/2003 | Cox et al. |
| 2003/0096337 A1 | 5/2003 | Hillman et al. |
| 2003/0103939 A1 | 6/2003 | Engelhardt et al. |
| 2003/0108885 A1 | 6/2003 | Schultz et al. |
| 2003/0119764 A1 | 6/2003 | Loeb et al. |
| 2003/0167533 A1 | 9/2003 | Yadav et al. |
| 2003/0203480 A1 | 10/2003 | Kovesdi et al. |
| 2004/0003420 A1 | 1/2004 | Kuhn et al. |
| 2004/0028687 A1 | 2/2004 | Waelti |
| 2004/0115184 A1 | 6/2004 | Smith et al. |
| 2004/0156861 A1 | 8/2004 | Figdor et al. |
| 2004/0203109 A1 | 10/2004 | Lal et al. |
| 2005/0100890 A1 | 5/2005 | Davidson et al. |
| 2005/0136429 A1 | 6/2005 | Guarente et al. |
| 2005/0222030 A1 | 10/2005 | Allison |
| 2005/0260626 A1 | 11/2005 | Lorens et al. |
| 2006/0088864 A1 | 4/2006 | Smolke et al. |
| 2006/0104984 A1 | 5/2006 | Littlefield et al. |
| 2006/0216702 A1 | 9/2006 | Compans et al. |
| 2006/0246568 A1 | 11/2006 | Honjo et al. |
| 2007/0015238 A1 | 1/2007 | Snyder et al. |
| 2007/0049533 A1 | 3/2007 | Liu et al. |
| 2007/0264692 A1 | 11/2007 | Liu et al. |
| 2007/0269817 A1 | 11/2007 | Shapero |
| 2007/0298118 A1 | 12/2007 | Lotvall et al. |
| 2008/0051317 A1 | 2/2008 | Church et al. |
| 2008/0124725 A1 | 5/2008 | Barrangou et al. |
| 2008/0182254 A1 | 7/2008 | Hall et al. |
| 2008/0220502 A1 | 9/2008 | Schellenberger et al. |
| 2009/0111119 A1 | 4/2009 | Doyon et al. |
| 2009/0130718 A1 | 5/2009 | Short |
| 2009/0202622 A1 | 8/2009 | Fleury et al. |
| 2009/0215878 A1 | 8/2009 | Tan et al. |
| 2009/0234109 A1 | 9/2009 | Han et al. |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2010/0105134 A1 | 4/2010 | Quay et al. |
| 2010/0273857 A1 | 10/2010 | Thakker et al. |
| 2010/0305197 A1 | 12/2010 | Che |
| 2010/0316643 A1 | 12/2010 | Eckert et al. |
| 2011/0016540 A1 | 1/2011 | Weinstein et al. |
| 2011/0059160 A1 | 3/2011 | Essner et al. |
| 2011/0059502 A1 | 3/2011 | Chalasani |
| 2011/0077199 A1* | 3/2011 | Schellenberger ......... A61P 5/06 |
| | | 435/243 |
| 2011/0104787 A1 | 5/2011 | Church et al. |
| 2011/0123509 A1 | 5/2011 | Jantz et al. |
| 2011/0177495 A1 | 7/2011 | Liu et al. |
| 2011/0189775 A1 | 8/2011 | Ainley et al. |
| 2011/0189776 A1 | 8/2011 | Terns et al. |
| 2011/0206672 A1 | 8/2011 | Little |
| 2011/0217739 A1 | 9/2011 | Terns et al. |
| 2011/0301073 A1 | 12/2011 | Gregory et al. |
| 2012/0129759 A1 | 5/2012 | Liu et al. |
| 2012/0141523 A1 | 6/2012 | Castado et al. |
| 2012/0159653 A1 | 6/2012 | Weinstein et al. |
| 2012/0244601 A1 | 9/2012 | Bertozzi et al. |
| 2012/0270273 A1 | 10/2012 | Zhang et al. |
| 2012/0322861 A1 | 12/2012 | Byrne et al. |
| 2013/0053426 A1 | 2/2013 | Seow et al. |
| 2013/0059931 A1 | 3/2013 | Petersen-Mahrt et al. |
| 2013/0108657 A1 | 5/2013 | Yee et al. |
| 2013/0117869 A1 | 5/2013 | Duchateau et al. |
| 2013/0130248 A1 | 5/2013 | Haurwitz et al. |

(56) References Cited

U.S. PATENT DOCUMENTS

| | | |
|---|---|---|
| 2013/0158245 A1 | 6/2013 | Russell et al. |
| 2013/0165389 A1 | 6/2013 | Schellenberger et al. |
| 2013/0309720 A1 | 11/2013 | Schultz et al. |
| 2013/0344117 A1 | 12/2013 | Mirosevich et al. |
| 2013/0345064 A1 | 12/2013 | Liu et al. |
| 2014/0004280 A1 | 1/2014 | Loomis |
| 2014/0005269 A1 | 1/2014 | Ngwuluka et al. |
| 2014/0017214 A1 | 1/2014 | Cost |
| 2014/0018404 A1 | 1/2014 | Chen et al. |
| 2014/0044793 A1 | 2/2014 | Goll et al. |
| 2014/0065711 A1 | 3/2014 | Liu et al. |
| 2014/0068797 A1 | 3/2014 | Doudna et al. |
| 2014/0127752 A1 | 5/2014 | Zhou et al. |
| 2014/0141094 A1 | 5/2014 | Smyth et al. |
| 2014/0141487 A1 | 5/2014 | Feldman et al. |
| 2014/0179770 A1 | 6/2014 | Zhang et al. |
| 2014/0186843 A1 | 7/2014 | Zhang et al. |
| 2014/0186958 A1 | 7/2014 | Zhang et al. |
| 2014/0201858 A1 | 7/2014 | Ostertag et al. |
| 2014/0234289 A1 | 8/2014 | Liu et al. |
| 2014/0248702 A1 | 9/2014 | Zhang et al. |
| 2014/0256046 A1* | 9/2014 | Zhang ................... C12N 15/63 |
| | | 435/455 |
| 2014/0273037 A1 | 9/2014 | Wu |
| 2014/0273226 A1 | 9/2014 | Wu |
| 2014/0273230 A1 | 9/2014 | Chen et al. |
| 2014/0273234 A1 | 9/2014 | Zhang et al. |
| 2014/0283156 A1 | 9/2014 | Zador et al. |
| 2014/0295556 A1 | 10/2014 | Joung et al. |
| 2014/0295557 A1 | 10/2014 | Joung et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0377868 A1 | 12/2014 | Joung et al. |
| 2015/0010526 A1 | 1/2015 | Liu et al. |
| 2015/0031089 A1 | 1/2015 | Lindstrom |
| 2015/0031132 A1 | 1/2015 | Church et al. |
| 2015/0031133 A1 | 1/2015 | Church et al. |
| 2015/0044191 A1 | 2/2015 | Liu et al. |
| 2015/0044192 A1 | 2/2015 | Liu et al. |
| 2015/0044772 A1 | 2/2015 | Zhao |
| 2015/0050699 A1 | 2/2015 | Siksnys et al. |
| 2015/0056177 A1 | 2/2015 | Liu et al. |
| 2015/0056629 A1 | 2/2015 | Guthrie-Honea |
| 2015/0064138 A1 | 3/2015 | Lu et al. |
| 2015/0064789 A1 | 3/2015 | Paschon et al. |
| 2015/0071898 A1 | 3/2015 | Liu et al. |
| 2015/0071899 A1 | 3/2015 | Liu et al. |
| 2015/0071900 A1 | 3/2015 | Liu et al. |
| 2015/0071901 A1 | 3/2015 | Liu et al. |
| 2015/0071902 A1 | 3/2015 | Liu et al. |
| 2015/0071903 A1 | 3/2015 | Liu et al. |
| 2015/0071906 A1 | 3/2015 | Liu et al. |
| 2015/0079680 A1 | 3/2015 | Bradley et al. |
| 2015/0079681 A1 | 3/2015 | Zhang |
| 2015/0098954 A1 | 4/2015 | Hyde et al. |
| 2015/0118216 A1 | 4/2015 | Liu et al. |
| 2015/0132269 A1 | 5/2015 | Orkin et al. |
| 2015/0140664 A1 | 5/2015 | Byrne et al. |
| 2015/0159172 A1 | 6/2015 | Miller et al. |
| 2015/0165054 A1 | 6/2015 | Liu et al. |
| 2015/0166980 A1 | 6/2015 | Liu et al. |
| 2015/0166981 A1 | 6/2015 | Liu et al. |
| 2015/0166982 A1 | 6/2015 | Liu et al. |
| 2015/0166983 A1 | 6/2015 | Liu et al. |
| 2015/0166984 A1 | 6/2015 | Liu et al. |
| 2015/0166985 A1 | 6/2015 | Liu et al. |
| 2015/0191744 A1 | 7/2015 | Wolfe et al. |
| 2015/0197759 A1 | 7/2015 | Xu et al. |
| 2015/0211058 A1 | 7/2015 | Carstens |
| 2015/0218573 A1 | 8/2015 | Loque et al. |
| 2015/0225773 A1 | 8/2015 | Farmer et al. |
| 2015/0241440 A1 | 8/2015 | Fasan et al. |
| 2015/0252358 A1 | 9/2015 | Maeder et al. |
| 2015/0275202 A1 | 10/2015 | Liu et al. |
| 2015/0291965 A1 | 10/2015 | Zhang et al. |
| 2015/0307889 A1 | 10/2015 | Petolino et al. |
| 2015/0315252 A1 | 11/2015 | Haugwitz et al. |
| 2015/0344549 A1 | 12/2015 | Muir et al. |
| 2016/0017393 A1 | 1/2016 | Jacobson et al. |
| 2016/0017396 A1 | 1/2016 | Cann et al. |
| 2016/0032292 A1 | 2/2016 | Storici et al. |
| 2016/0032353 A1 | 2/2016 | Braman et al. |
| 2016/0040155 A1 | 2/2016 | Maizels et al. |
| 2016/0046952 A1 | 2/2016 | Hittinger et al. |
| 2016/0046961 A1 | 2/2016 | Jinek et al. |
| 2016/0046962 A1 | 2/2016 | May et al. |
| 2016/0053272 A1 | 2/2016 | Wurtzel et al. |
| 2016/0053304 A1 | 2/2016 | Wurtzel et al. |
| 2016/0074535 A1 | 3/2016 | Ranganathan et al. |
| 2016/0076093 A1 | 3/2016 | Shendure et al. |
| 2016/0090603 A1 | 3/2016 | Carnes et al. |
| 2016/0090622 A1 | 3/2016 | Liu et al. |
| 2016/0115488 A1 | 4/2016 | Zhang et al. |
| 2016/0137716 A1 | 5/2016 | El Andaloussi et al. |
| 2016/0138046 A1 | 5/2016 | Wu |
| 2016/0153003 A1 | 6/2016 | Joung et al. |
| 2016/0186214 A1 | 6/2016 | Brouns et al. |
| 2016/0200779 A1 | 7/2016 | Liu et al. |
| 2016/0201040 A1 | 7/2016 | Liu et al. |
| 2016/0201089 A1 | 7/2016 | Gersbach et al. |
| 2016/0206566 A1 | 7/2016 | Lu et al. |
| 2016/0208243 A1 | 7/2016 | Zhang et al. |
| 2016/0208288 A1 | 7/2016 | Liu et al. |
| 2016/0215275 A1 | 7/2016 | Zhong |
| 2016/0215276 A1 | 7/2016 | Liu et al. |
| 2016/0215300 A1 | 7/2016 | May et al. |
| 2016/0244784 A1 | 8/2016 | Jacobson et al. |
| 2016/0244829 A1 | 8/2016 | Bang et al. |
| 2016/0264934 A1 | 9/2016 | Giallourakis et al. |
| 2016/0272593 A1 | 9/2016 | Ritter et al. |
| 2016/0272965 A1 | 9/2016 | Zhang et al. |
| 2016/0281072 A1 | 9/2016 | Zhang |
| 2016/0298136 A1 | 10/2016 | Chen et al. |
| 2016/0304846 A1 | 10/2016 | Liu et al. |
| 2016/0304855 A1 | 10/2016 | Stark et al. |
| 2016/0312304 A1 | 10/2016 | Sorrentino et al. |
| 2016/0319262 A1 | 11/2016 | Doudna et al. |
| 2016/0333389 A1 | 11/2016 | Liu et al. |
| 2016/0340622 A1 | 11/2016 | Abdou |
| 2016/0340662 A1 | 11/2016 | Zhang et al. |
| 2016/0345578 A1 | 12/2016 | Barrangou et al. |
| 2016/0346360 A1 | 12/2016 | Quake et al. |
| 2016/0346361 A1 | 12/2016 | Quake et al. |
| 2016/0346362 A1 | 12/2016 | Quake et al. |
| 2016/0348074 A1 | 12/2016 | Quake et al. |
| 2016/0348096 A1 | 12/2016 | Liu et al. |
| 2016/0350476 A1 | 12/2016 | Quake et al. |
| 2016/0355796 A1 | 12/2016 | Davidson et al. |
| 2016/0369262 A1 | 12/2016 | Reik et al. |
| 2017/0009224 A1 | 1/2017 | Liu et al. |
| 2017/0009242 A1 | 1/2017 | Mckinley et al. |
| 2017/0014449 A1 | 1/2017 | Bangera et al. |
| 2017/0020922 A1 | 1/2017 | Wagner et al. |
| 2017/0037432 A1 | 2/2017 | Donohoue et al. |
| 2017/0044520 A1 | 2/2017 | Liu et al. |
| 2017/0044592 A1 | 2/2017 | Peter et al. |
| 2017/0053729 A1 | 2/2017 | Kotani et al. |
| 2017/0058271 A1 | 3/2017 | Joung et al. |
| 2017/0058272 A1 | 3/2017 | Carter et al. |
| 2017/0058298 A1 | 3/2017 | Kennedy et al. |
| 2017/0073663 A1 | 3/2017 | Wang et al. |
| 2017/0073670 A1 | 3/2017 | Nishida et al. |
| 2017/0087224 A1 | 3/2017 | Quake |
| 2017/0087225 A1 | 3/2017 | Quake |
| 2017/0088587 A1 | 3/2017 | Quake |
| 2017/0088828 A1 | 3/2017 | Quake |
| 2017/0107536 A1 | 4/2017 | Zhang et al. |

(56) References Cited

U.S. PATENT DOCUMENTS

| | | |
|---|---|---|
| 2017/0107560 A1 | 4/2017 | Peter et al. |
| 2017/0114367 A1 | 4/2017 | Hu et al. |
| 2017/0121693 A1 | 5/2017 | Liu et al. |
| 2017/0145394 A1 | 5/2017 | Yeo et al. |
| 2017/0145405 A1 | 5/2017 | Tang et al. |
| 2017/0145438 A1 | 5/2017 | Kantor |
| 2017/0152528 A1 | 6/2017 | Zhang |
| 2017/0152787 A1 | 6/2017 | Kubo et al. |
| 2017/0159033 A1 | 6/2017 | Kamtekar et al. |
| 2017/0166928 A1 | 6/2017 | Vyas et al. |
| 2017/0175104 A1 | 6/2017 | Doudna et al. |
| 2017/0175142 A1 | 6/2017 | Zhang et al. |
| 2017/0191047 A1 | 7/2017 | Terns et al. |
| 2017/0191078 A1 | 7/2017 | Zhang et al. |
| 2017/0198269 A1 | 7/2017 | Zhang et al. |
| 2017/0198277 A1 | 7/2017 | Kmiec et al. |
| 2017/0198302 A1 | 7/2017 | Feng et al. |
| 2017/0226522 A1 | 8/2017 | Hu et al. |
| 2017/0233703 A1 | 8/2017 | Xie et al. |
| 2017/0233756 A1 | 8/2017 | Begemann et al. |
| 2017/0247671 A1 | 8/2017 | Yung et al. |
| 2017/0247703 A1 | 8/2017 | Sloan et al. |
| 2017/0268022 A1 | 9/2017 | Liu et al. |
| 2017/0275665 A1 | 9/2017 | Silas et al. |
| 2017/0283797 A1 | 10/2017 | Robb et al. |
| 2017/0283831 A1 | 10/2017 | Zhang et al. |
| 2017/0314016 A1 | 11/2017 | Kim et al. |
| 2017/0362635 A1 | 12/2017 | Chamberlain et al. |
| 2018/0064077 A1 | 3/2018 | Dunham et al. |
| 2018/0066258 A1 | 3/2018 | Powell |
| 2018/0068062 A1 | 3/2018 | Zhang et al. |
| 2018/0073012 A1 | 3/2018 | Liu et al. |
| 2018/0080051 A1 | 3/2018 | Sheikh et al. |
| 2018/0087046 A1 | 3/2018 | Badran et al. |
| 2018/0100147 A1 | 4/2018 | Yates et al. |
| 2018/0105867 A1 | 4/2018 | Xiao et al. |
| 2018/0119118 A1 | 5/2018 | Lu et al. |
| 2018/0127759 A1 | 5/2018 | Lu et al. |
| 2018/0127780 A1 | 5/2018 | Liu et al. |
| 2018/0155708 A1 | 6/2018 | Church et al. |
| 2018/0155720 A1 | 6/2018 | Donohoue et al. |
| 2018/0163213 A1 | 6/2018 | Aneja et al. |
| 2018/0170984 A1 | 6/2018 | Harris et al. |
| 2018/0179503 A1 | 6/2018 | Maianti et al. |
| 2018/0179547 A1 | 6/2018 | Zhang et al. |
| 2018/0201921 A1 | 7/2018 | Malcolm |
| 2018/0230464 A1 | 8/2018 | Zhong |
| 2018/0230471 A1 | 8/2018 | Storici et al. |
| 2018/0236081 A1 | 8/2018 | Liu et al. |
| 2018/0237758 A1 | 8/2018 | Liu et al. |
| 2018/0237787 A1 | 8/2018 | Maianti et al. |
| 2018/0245066 A1 | 8/2018 | Yao et al. |
| 2018/0258418 A1 | 9/2018 | Kim |
| 2018/0265864 A1 | 9/2018 | Li et al. |
| 2018/0273939 A1 | 9/2018 | Yu et al. |
| 2018/0282722 A1 | 10/2018 | Jakimo et al. |
| 2018/0298391 A1 | 10/2018 | Jakimo et al. |
| 2018/0305688 A1 | 10/2018 | Zhong |
| 2018/0305704 A1 | 10/2018 | Zhang |
| 2018/0312822 A1 | 11/2018 | Lee et al. |
| 2018/0312825 A1 | 11/2018 | Liu et al. |
| 2018/0312828 A1 | 11/2018 | Liu et al. |
| 2018/0312835 A1 | 11/2018 | Yao et al. |
| 2018/0327756 A1 | 11/2018 | Zhang et al. |
| 2019/0010481 A1 | 1/2019 | Joung et al. |
| 2019/0055543 A1 | 2/2019 | Tran et al. |
| 2019/0093099 A1 | 3/2019 | Liu et al. |
| 2019/0119701 A1 | 4/2019 | Liang et al. |
| 2019/0185883 A1 | 6/2019 | Liu et al. |
| 2019/0225955 A1 | 7/2019 | Liu et al. |
| 2019/0233814 A1 | 8/2019 | Zhang et al. |
| 2019/0233847 A1 | 8/2019 | Savage et al. |
| 2019/0241633 A1 | 8/2019 | Fotin-Mleczek et al. |
| 2019/0256842 A1 | 8/2019 | Liu et al. |
| 2019/0264202 A1 | 8/2019 | Church et al. |
| 2019/0276816 A1 | 9/2019 | Liu et al. |
| 2019/0322992 A1 | 10/2019 | Liu et al. |
| 2019/0352632 A1 | 11/2019 | Liu et al. |
| 2019/0367891 A1 | 12/2019 | Liu et al. |
| 2020/0010818 A1 | 1/2020 | Liu et al. |
| 2020/0010835 A1 | 1/2020 | Maianti et al. |
| 2020/0063127 A1 | 2/2020 | Lu et al. |
| 2020/0071722 A1 | 3/2020 | Liu et al. |
| 2020/0109398 A1 | 4/2020 | Rubens et al. |
| 2020/0172931 A1 | 6/2020 | Liu et al. |
| 2020/0181619 A1 | 6/2020 | Tang et al. |
| 2020/0190493 A1 | 6/2020 | Liu et al. |
| 2020/0216833 A1 | 7/2020 | Liu et al. |
| 2020/0255868 A1 | 8/2020 | Liu et al. |
| 2020/0277587 A1 | 9/2020 | Liu et al. |
| 2020/0323984 A1 | 10/2020 | Liu et al. |
| 2020/0399619 A1 | 12/2020 | Maianti et al. |
| 2020/0399626 A1 | 12/2020 | Liu et al. |
| 2021/0054416 A1 | 2/2021 | Liu et al. |
| 2021/0115428 A1 | 4/2021 | Maianti et al. |
| 2021/0196809 A1 | 7/2021 | Maianti et al. |
| 2021/0198330 A1 | 7/2021 | Liu et al. |
| 2021/0214698 A1 | 7/2021 | Liu et al. |
| 2021/0230577 A1 | 7/2021 | Liu et al. |
| 2021/0254127 A1 | 8/2021 | Liu et al. |
| 2021/0315994 A1 | 10/2021 | Liu et al. |
| 2021/0317440 A1 | 10/2021 | Liu et al. |
| 2022/0033785 A1 | 2/2022 | Liu et al. |
| 2022/0119785 A1 | 4/2022 | Liu et al. |
| 2022/0170013 A1 | 6/2022 | Liu et al. |
| 2022/0177877 A1 | 6/2022 | Church et al. |
| 2022/0204975 A1 | 6/2022 | Liu et al. |
| 2022/0213507 A1 | 7/2022 | Liu et al. |
| 2022/0220462 A1 | 7/2022 | Liu et al. |
| 2022/0238182 A1 | 7/2022 | Shen et al. |
| 2022/0249697 A1 | 8/2022 | Liu et al. |
| 2022/0282275 A1 | 9/2022 | Liu et al. |
| 2022/0290115 A1 | 9/2022 | Liu et al. |
| 2022/0307001 A1 | 9/2022 | Liu et al. |
| 2022/0307003 A1 | 9/2022 | Liu et al. |
| 2022/0315906 A1 | 10/2022 | Liu et al. |
| 2022/0356469 A1 | 11/2022 | Liu et al. |
| 2022/0380740 A1 | 12/2022 | Liu et al. |
| 2022/0389395 A1 | 12/2022 | Liu et al. |
| 2023/0002745 A1 | 1/2023 | Liu et al. |
| 2023/0021641 A1 | 1/2023 | Liu et al. |
| 2023/0058176 A1 | 2/2023 | Liu et al. |
| 2023/0078265 A1 | 3/2023 | Liu et al. |
| 2023/0086199 A1 | 3/2023 | Liu et al. |
| 2023/0090221 A1 | 3/2023 | Liu et al. |
| 2023/0108687 A1 | 4/2023 | Liu et al. |
| 2023/0123669 A1 | 4/2023 | Liu et al. |
| 2023/0127008 A1 | 4/2023 | Liu et al. |
| 2023/0159913 A1 | 5/2023 | Liu et al. |
| 2023/0193295 A1 | 6/2023 | Maianti et al. |
| 2023/0220374 A1 | 7/2023 | Liu et al. |
| 2023/0272425 A1 | 8/2023 | Liu et al. |
| 2023/0279443 A1 | 9/2023 | Liu et al. |
| 2023/0332144 A1 | 10/2023 | Liu et al. |
| 2023/0340465 A1 | 10/2023 | Liu et al. |
| 2023/0340466 A1 | 10/2023 | Liu et al. |
| 2023/0340467 A1 | 10/2023 | Liu et al. |
| 2023/0348883 A1 | 11/2023 | Liu et al. |
| 2023/0357766 A1 | 11/2023 | Liu et al. |
| 2023/0383289 A1 | 11/2023 | Liu et al. |
| 2024/0035017 A1 | 2/2024 | Liu et al. |
| 2024/0076652 A1 | 3/2024 | Liu et al. |
| 2024/0110166 A1 | 4/2024 | Maianti et al. |
| 2024/0124866 A1 | 4/2024 | Liu et al. |
| 2024/0173430 A1 | 5/2024 | Liu et al. |
| 2024/0209329 A1 | 6/2024 | Liu et al. |
| 2024/0229077 A1 | 7/2024 | Liu et al. |
| 2024/0271116 A1 | 8/2024 | Maianti et al. |
| 2024/0287487 A1 | 8/2024 | Liu et al. |
| 2024/0327872 A1 | 10/2024 | Liu et al. |
| 2024/0401018 A1 | 12/2024 | Liu et al. |
| 2024/0417715 A1 | 12/2024 | Liu et al. |
| 2024/0417719 A1 | 12/2024 | Liu et al. |
| 2024/0417753 A1 | 12/2024 | Liu et al. |

(56) References Cited

U.S. PATENT DOCUMENTS

| | | |
|---|---|---|
| 2025/0011748 A1 | 1/2025 | Liu et al. |
| 2025/0027114 A1 | 1/2025 | Liu et al. |
| 2025/0034549 A1 | 1/2025 | Liu et al. |
| 2025/0059244 A1 | 2/2025 | Liu et al. |
| 2025/0064979 A1 | 2/2025 | Liu et al. |
| 2025/0064981 A1 | 2/2025 | Liu et al. |
| 2025/0084399 A1 | 3/2025 | Liu et al. |
| 2025/0084400 A1 | 3/2025 | Liu et al. |
| 2025/0090687 A1 | 3/2025 | Liu et al. |
| 2025/0092374 A1 | 3/2025 | Liu et al. |
| 2025/0092382 A1 | 3/2025 | Liu et al. |
| 2025/0101395 A1 | 3/2025 | Liu et al. |
| 2025/0215418 A1 | 7/2025 | Liu et al. |
| 2025/0228981 A1 | 7/2025 | Liu et al. |
| 2025/0236855 A1 | 7/2025 | Liu et al. |
| 2025/0263680 A1 | 8/2025 | Liu et al. |
| 2025/0270527 A1 | 8/2025 | Liu et al. |
| 2025/0270593 A1 | 8/2025 | Liu et al. |

FOREIGN PATENT DOCUMENTS

| | | | |
|---|---|---|---|
| AU | 2015252023 A1 | 11/2015 | |
| AU | 2015101792 A4 | 1/2016 | |
| AU | 2012354062 B2 | 9/2017 | |
| BR | 112015013786 A2 | 7/2017 | |
| CA | 2480696 A1 | 10/2003 | |
| CA | 2894668 A1 | 6/2014 | |
| CA | 2894681 A1 | 6/2014 | |
| CA | 2894684 A1 | 6/2014 | |
| CA | 2852593 A1 | 11/2015 | |
| CN | 1069962 A | 3/1993 | |
| CN | 101460619 A | 6/2009 | |
| CN | 101873862 A | 10/2010 | |
| CN | 102057039 A | 5/2011 | |
| CN | 102892777 A | 1/2013 | |
| CN | 103224947 A | 7/2013 | |
| CN | 103233028 A | 8/2013 | |
| CN | 103388006 A | 11/2013 | |
| CN | 103614415 A | 3/2014 | |
| CN | 103642836 A | 3/2014 | |
| CN | 103668472 A | 3/2014 | |
| CN | 103820441 A | 5/2014 | |
| CN | 103820454 A | 5/2014 | |
| CN | 103911376 A | 7/2014 | |
| CN | 103923911 A | 7/2014 | |
| CN | 103088008 A | 8/2014 | |
| CN | 103981211 A | 8/2014 | |
| CN | 103981212 A | 8/2014 | |
| CN | 104004778 A | 8/2014 | |
| CN | 104004782 A | 8/2014 | |
| CN | 104017821 A | 9/2014 | |
| CN | 104109687 A | 10/2014 | |
| CN | 104178461 A | 12/2014 | |
| CN | 104342457 A | 2/2015 | |
| CN | 104404036 A | 3/2015 | |
| CN | 104450774 A | 3/2015 | |
| CN | 104480144 A | 4/2015 | |
| CN | 104498493 A | 4/2015 | |
| CN | 104504304 A | 4/2015 | |
| CN | 104531704 A | 4/2015 | |
| CN | 104531705 A | 4/2015 | |
| CN | 104560864 A | 4/2015 | |
| CN | 104561095 A | 4/2015 | |
| CN | 104593418 A | 5/2015 | |
| CN | 104593422 A | 5/2015 | |
| CN | 104611370 A | 5/2015 | |
| CN | 104651392 A | 5/2015 | |
| CN | 104651398 A | 5/2015 | |
| CN | 104651399 A | 5/2015 | |
| CN | 104651401 A | 5/2015 | |
| CN | 104673816 A | 6/2015 | |
| CN | 104725626 A | 6/2015 | |
| CN | 104726449 A | 6/2015 | |
| CN | 104726494 A | 6/2015 | |
| CN | 104745626 A | 7/2015 | |
| CN | 104762321 A | 7/2015 | |
| CN | 104805078 A | 7/2015 | |
| CN | 104805099 A | 7/2015 | |
| CN | 104805118 A | 7/2015 | |
| CN | 104846010 A | 8/2015 | |
| CN | 104894068 A | 9/2015 | |
| CN | 104894075 A | 9/2015 | |
| CN | 104928321 A | 9/2015 | |
| CN | 105039339 A | 11/2015 | |
| CN | 105039399 A | 11/2015 | |
| CN | 105063061 A | 11/2015 | |
| CN | 105087620 A | 11/2015 | |
| CN | 105112422 A | 12/2015 | |
| CN | 105112445 A | 12/2015 | |
| CN | 105112519 A | 12/2015 | |
| CN | 105121648 A | 12/2015 | |
| CN | 105132427 A | 12/2015 | |
| CN | 105132451 A | 12/2015 | |
| CN | 105177038 A | 12/2015 | |
| CN | 105177126 A | 12/2015 | |
| CN | 105210981 A | 1/2016 | |
| CN | 105219799 A | 1/2016 | |
| CN | 105238806 A | 1/2016 | |
| CN | 105255937 A | 1/2016 | |
| CN | 105274144 A | 1/2016 | |
| CN | 105296518 A | 2/2016 | |
| CN | 105296537 A | 2/2016 | |
| CN | 105316324 A | 2/2016 | |
| CN | 105316327 A | 2/2016 | |
| CN | 105316337 A | 2/2016 | |
| CN | 105331607 A | 2/2016 | |
| CN | 105331608 A | 2/2016 | |
| CN | 105331609 A | 2/2016 | |
| CN | 105331627 A | 2/2016 | |
| CN | 105400773 A | 3/2016 | |
| CN | 105400779 A | 3/2016 | |
| CN | 105400810 A | 3/2016 | |
| CN | 105441451 A | 3/2016 | |
| CN | 105462968 A | 4/2016 | |
| CN | 105463003 A | 4/2016 | |
| CN | 105463027 A | 4/2016 | |
| CN | 105492608 A | 4/2016 | |
| CN | 105492609 A | 4/2016 | |
| CN | 105505976 A | 4/2016 | |
| CN | 105505979 A | 4/2016 | |
| CN | 105518134 A | 4/2016 | |
| CN | 105518135 A | 4/2016 | |
| CN | 105518137 A | 4/2016 | |
| CN | 105518138 A | 4/2016 | |
| CN | 105518139 A | 4/2016 | |
| CN | 105518140 A | 4/2016 | |
| CN | 105543228 A | 5/2016 | |
| CN | 105543266 A | 5/2016 | |
| CN | 105543270 A | 5/2016 | |
| CN | 105567688 A | 5/2016 | |
| CN | 105567689 A | 5/2016 | |
| CN | 105567734 A | 5/2016 | |
| CN | 105567735 A | 5/2016 | |
| CN | 105567738 A | 5/2016 | |
| CN | 105593367 A | 5/2016 | |
| CN | 105594664 A | 5/2016 | |
| CN | 105602987 A | 5/2016 | |
| CN | 105624146 A | 6/2016 | |
| CN | 105624187 A | 6/2016 | |
| CN | 105646719 A | 6/2016 | |
| CN | 105647922 A | 6/2016 | |
| CN | 105647962 A | 6/2016 | |
| CN | 105647968 A | 6/2016 | |
| CN | 105647969 A | 6/2016 | |
| CN | 105671070 A | 6/2016 | |
| CN | 105671083 A | 6/2016 | |
| CN | 105695485 A | 6/2016 | |
| CN | 105779448 A | 7/2016 | |
| CN | 105779449 A | 7/2016 | |
| CN | 105802980 A | 7/2016 | |
| CN | 105821039 A | 8/2016 | |
| CN | 105821040 A | 8/2016 | |
| CN | 105821049 A | 8/2016 | |
| CN | 105821072 A | 8/2016 | |

(56)　　　　　References Cited

FOREIGN PATENT DOCUMENTS

| CN | 105821075 A | 8/2016 |
| CN | 105821116 A | 8/2016 |
| CN | 105838733 A | 8/2016 |
| CN | 105861547 A | 8/2016 |
| CN | 105861552 A | 8/2016 |
| CN | 105861554 A | 8/2016 |
| CN | 105886498 A | 8/2016 |
| CN | 105886534 A | 8/2016 |
| CN | 105886616 A | 8/2016 |
| CN | 105907758 A | 8/2016 |
| CN | 105907785 A | 8/2016 |
| CN | 105925608 A | 9/2016 |
| CN | 105934516 A | 9/2016 |
| CN | 105950560 A | 9/2016 |
| CN | 105950626 A | 9/2016 |
| CN | 105950633 A | 9/2016 |
| CN | 105950639 A | 9/2016 |
| CN | 105985985 A | 10/2016 |
| CN | 106011104 A | 10/2016 |
| CN | 106011150 A | 10/2016 |
| CN | 106011167 A | 10/2016 |
| CN | 106011171 A | 10/2016 |
| CN | 106032540 A | 10/2016 |
| CN | 106047803 A | 10/2016 |
| CN | 106047877 A | 10/2016 |
| CN | 106047930 A | 10/2016 |
| CN | 106086008 A | 11/2016 |
| CN | 106086028 A | 11/2016 |
| CN | 106086061 A | 11/2016 |
| CN | 106086062 A | 11/2016 |
| CN | 106109417 A | 11/2016 |
| CN | 106119275 A | 11/2016 |
| CN | 106119283 A | 11/2016 |
| CN | 106148286 A | 11/2016 |
| CN | 106148370 A | 11/2016 |
| CN | 106148416 A | 11/2016 |
| CN | 106167525 A | 11/2016 |
| CN | 106167808 A | 11/2016 |
| CN | 106167810 A | 11/2016 |
| CN | 106167821 A | 11/2016 |
| CN | 106172238 A | 12/2016 |
| CN | 106190903 A | 12/2016 |
| CN | 106191057 A | 12/2016 |
| CN | 106191061 A | 12/2016 |
| CN | 106191062 A | 12/2016 |
| CN | 106191064 A | 12/2016 |
| CN | 106191071 A | 12/2016 |
| CN | 106191099 A | 12/2016 |
| CN | 106191107 A | 12/2016 |
| CN | 106191113 A | 12/2016 |
| CN | 106191114 A | 12/2016 |
| CN | 106191116 A | 12/2016 |
| CN | 106191124 A | 12/2016 |
| CN | 106222177 A | 12/2016 |
| CN | 106222193 A | 12/2016 |
| CN | 106222203 A | 12/2016 |
| CN | 106244555 A | 12/2016 |
| CN | 106244557 A | 12/2016 |
| CN | 106244591 A | 12/2016 |
| CN | 106244609 A | 12/2016 |
| CN | 106282241 A | 1/2017 |
| CN | 106318934 A | 1/2017 |
| CN | 106318973 A | 1/2017 |
| CN | 106350540 A | 1/2017 |
| CN | 106367435 A | 2/2017 |
| CN | 106399306 A | 2/2017 |
| CN | 106399311 A | 2/2017 |
| CN | 106399360 A | 2/2017 |
| CN | 106399367 A | 2/2017 |
| CN | 106399375 A | 2/2017 |
| CN | 106399377 A | 2/2017 |
| CN | 106434651 A | 2/2017 |
| CN | 106434663 A | 2/2017 |
| CN | 106434688 A | 2/2017 |
| CN | 106434737 A | 2/2017 |
| CN | 106434748 A | 2/2017 |
| CN | 106434752 A | 2/2017 |
| CN | 106434782 A | 2/2017 |
| CN | 106446600 A | 2/2017 |
| CN | 106479985 A | 3/2017 |
| CN | 106480027 A | 3/2017 |
| CN | 106480036 A | 3/2017 |
| CN | 106480067 A | 3/2017 |
| CN | 106480080 A | 3/2017 |
| CN | 106480083 A | 3/2017 |
| CN | 106480097 A | 3/2017 |
| CN | 106544351 A | 3/2017 |
| CN | 106544353 A | 3/2017 |
| CN | 106544357 A | 3/2017 |
| CN | 106554969 A | 4/2017 |
| CN | 106566838 A | 4/2017 |
| CN | 106701763 A | 5/2017 |
| CN | 106701808 A | 5/2017 |
| CN | 106701818 A | 5/2017 |
| CN | 106701823 A | 5/2017 |
| CN | 106701830 A | 5/2017 |
| CN | 106754912 A | 5/2017 |
| CN | 106755026 A | 5/2017 |
| CN | 106755077 A | 5/2017 |
| CN | 106755088 A | 5/2017 |
| CN | 106755091 A | 5/2017 |
| CN | 106755097 A | 5/2017 |
| CN | 106755424 A | 5/2017 |
| CN | 106801056 A | 6/2017 |
| CN | 106834323 A | 6/2017 |
| CN | 106834341 A | 6/2017 |
| CN | 106834347 A | 6/2017 |
| CN | 106845151 A | 6/2017 |
| CN | 106868008 A | 6/2017 |
| CN | 106868031 A | 6/2017 |
| CN | 106906240 A | 6/2017 |
| CN | 106906242 A | 6/2017 |
| CN | 106916820 A | 7/2017 |
| CN | 106916852 A | 7/2017 |
| CN | 106939303 A | 7/2017 |
| CN | 106947750 A | 7/2017 |
| CN | 106947780 A | 7/2017 |
| CN | 106957830 A | 7/2017 |
| CN | 106957831 A | 7/2017 |
| CN | 106957844 A | 7/2017 |
| CN | 106957855 A | 7/2017 |
| CN | 106957858 A | 7/2017 |
| CN | 106967697 A | 7/2017 |
| CN | 106967726 A | 7/2017 |
| CN | 106978428 A | 7/2017 |
| CN | 106987570 A | 7/2017 |
| CN | 106987757 A | 7/2017 |
| CN | 107012164 A | 8/2017 |
| CN | 107012174 A | 8/2017 |
| CN | 107012213 A | 8/2017 |
| CN | 107012250 A | 8/2017 |
| CN | 107022562 A | 8/2017 |
| CN | 107034188 A | 8/2017 |
| CN | 107034218 A | 8/2017 |
| CN | 107034229 A | 8/2017 |
| CN | 107043775 A | 8/2017 |
| CN | 107043779 A | 8/2017 |
| CN | 107043787 A | 8/2017 |
| CN | 107058320 A | 8/2017 |
| CN | 107058328 A | 8/2017 |
| CN | 107058358 A | 8/2017 |
| CN | 107058372 A | 8/2017 |
| CN | 107083392 A | 8/2017 |
| CN | 107099533 A | 8/2017 |
| CN | 107099850 A | 8/2017 |
| CN | 107119053 A | 9/2017 |
| CN | 107119071 A | 9/2017 |
| CN | 107129999 A | 9/2017 |
| CN | 107130000 A | 9/2017 |
| CN | 107142272 A | 9/2017 |
| CN | 107142282 A | 9/2017 |
| CN | 107177591 A | 9/2017 |
| CN | 107177595 A | 9/2017 |
| CN | 107177625 A | 9/2017 |

(56)           References Cited

FOREIGN PATENT DOCUMENTS

| | | | |
|---|---|---|---|
| CN | 107177631 | A | 9/2017 |
| CN | 107190006 | A | 9/2017 |
| CN | 107190008 | A | 9/2017 |
| CN | 107217042 | A | 9/2017 |
| CN | 107217075 | A | 9/2017 |
| CN | 107227307 | A | 10/2017 |
| CN | 107227352 | A | 10/2017 |
| CN | 107236737 | A | 10/2017 |
| CN | 107236739 | A | 10/2017 |
| CN | 107236741 | A | 10/2017 |
| CN | 107245502 | A | 10/2017 |
| CN | 107254485 | A | 10/2017 |
| CN | 107266541 | A | 10/2017 |
| CN | 107267515 | A | 10/2017 |
| CN | 107287245 | A | 10/2017 |
| CN | 107298701 | A | 10/2017 |
| CN | 107299114 | A | 10/2017 |
| CN | 107304435 | A | 10/2017 |
| CN | 107312785 | A | 11/2017 |
| CN | 107312793 | A | 11/2017 |
| CN | 107312795 | A | 11/2017 |
| CN | 107312798 | A | 11/2017 |
| CN | 107326042 | A | 11/2017 |
| CN | 107326046 | A | 11/2017 |
| CN | 107354156 | A | 11/2017 |
| CN | 107354173 | A | 11/2017 |
| CN | 107356793 | A | 11/2017 |
| CN | 107362372 | A | 11/2017 |
| CN | 107365786 | A | 11/2017 |
| CN | 107365804 | A | 11/2017 |
| CN | 107384894 | A | 11/2017 |
| CN | 107384922 | A | 11/2017 |
| CN | 107384926 | A | 11/2017 |
| CN | 107400677 | A | 11/2017 |
| CN | 107418974 | A | 12/2017 |
| CN | 107435051 | A | 12/2017 |
| CN | 107435069 | A | 12/2017 |
| CN | 107446922 | A | 12/2017 |
| CN | 107446923 | A | 12/2017 |
| CN | 107446924 | A | 12/2017 |
| CN | 107446932 | A | 12/2017 |
| CN | 107446951 | A | 12/2017 |
| CN | 107446954 | A | 12/2017 |
| CN | 107460196 | A | 12/2017 |
| CN | 107474129 | A | 12/2017 |
| CN | 107475300 | A | 12/2017 |
| CN | 107488649 | A | 12/2017 |
| CN | 107502608 | A | 12/2017 |
| CN | 107502618 | A | 12/2017 |
| CN | 107513531 | A | 12/2017 |
| CN | 107519492 | A | 12/2017 |
| CN | 107523567 | A | 12/2017 |
| CN | 107523583 | A | 12/2017 |
| CN | 107541525 | A | 1/2018 |
| CN | 107557373 | A | 1/2018 |
| CN | 107557378 | A | 1/2018 |
| CN | 107557381 | A | 1/2018 |
| CN | 107557390 | A | 1/2018 |
| CN | 107557393 | A | 1/2018 |
| CN | 107557394 | A | 1/2018 |
| CN | 107557455 | A | 1/2018 |
| CN | 107574179 | A | 1/2018 |
| CN | 107586777 | A | 1/2018 |
| CN | 107586779 | A | 1/2018 |
| CN | 107604003 | A | 1/2018 |
| CN | 107619829 | A | 1/2018 |
| CN | 107619837 | A | 1/2018 |
| CN | 107630006 | A | 1/2018 |
| CN | 107630041 | A | 1/2018 |
| CN | 107630042 | A | 1/2018 |
| CN | 107630043 | A | 1/2018 |
| CN | 107641631 | A | 1/2018 |
| CN | 107653256 | A | 2/2018 |
| CN | 107686848 | A | 2/2018 |
| CN | 206970581 | U | 2/2018 |
| CN | 107760652 | A | 3/2018 |
| CN | 107760663 | A | 3/2018 |
| CN | 107760684 | A | 3/2018 |
| CN | 107760715 | A | 3/2018 |
| CN | 107784200 | A | 3/2018 |
| CN | 107794272 | A | 3/2018 |
| CN | 107794276 | A | 3/2018 |
| CN | 107815463 | A | 3/2018 |
| CN | 107828738 | A | 3/2018 |
| CN | 107828794 | A | 3/2018 |
| CN | 107828826 | A | 3/2018 |
| CN | 107828874 | A | 3/2018 |
| CN | 107858346 | A | 3/2018 |
| CN | 107858373 | A | 3/2018 |
| CN | 107880132 | A | 4/2018 |
| CN | 107881184 | A | 4/2018 |
| CN | 107893074 | A | 4/2018 |
| CN | 107893075 | A | 4/2018 |
| CN | 107893076 | A | 4/2018 |
| CN | 107893080 | A | 4/2018 |
| CN | 107893086 | A | 4/2018 |
| CN | 107904261 | A | 4/2018 |
| CN | 107937427 | A | 4/2018 |
| CN | 107937432 | A | 4/2018 |
| CN | 107937501 | A | 4/2018 |
| CN | 107974466 | A | 5/2018 |
| CN | 107988229 | A | 5/2018 |
| CN | 107988246 | A | 5/2018 |
| CN | 107988256 | A | 5/2018 |
| CN | 107988268 | A | 5/2018 |
| CN | 108018316 | A | 5/2018 |
| CN | 108034656 | A | 5/2018 |
| CN | 108048466 | A | 5/2018 |
| CN | 108102940 | A | 6/2018 |
| CN | 108103092 | A | 6/2018 |
| CN | 108103098 | A | 6/2018 |
| CN | 108103586 | A | 6/2018 |
| CN | 108148835 | A | 6/2018 |
| CN | 108148837 | A | 6/2018 |
| CN | 108148873 | A | 6/2018 |
| CN | 108192956 | A | 6/2018 |
| CN | 108251423 | A | 7/2018 |
| CN | 108251451 | A | 7/2018 |
| CN | 108251452 | A | 7/2018 |
| CN | 108342480 | A | 7/2018 |
| CN | 108359691 | A | 8/2018 |
| CN | 108359712 | A | 8/2018 |
| CN | 108384784 | A | 8/2018 |
| CN | 108396027 | A | 8/2018 |
| CN | 108410877 | A | 8/2018 |
| CN | 108410906 | A | 8/2018 |
| CN | 108410907 | A | 8/2018 |
| CN | 108410911 | A | 8/2018 |
| CN | 108424931 | A | 8/2018 |
| CN | 108441519 | A | 8/2018 |
| CN | 108441520 | A | 8/2018 |
| CN | 108486108 | A | 9/2018 |
| CN | 108486111 | A | 9/2018 |
| CN | 108486145 | A | 9/2018 |
| CN | 108486146 | A | 9/2018 |
| CN | 108486154 | A | 9/2018 |
| CN | 108486159 | A | 9/2018 |
| CN | 108486234 | A | 9/2018 |
| CN | 108504657 | A | 9/2018 |
| CN | 108504685 | A | 9/2018 |
| CN | 108504693 | A | 9/2018 |
| CN | 108513575 | A | 9/2018 |
| CN | 108546712 | A | 9/2018 |
| CN | 108546717 | A | 9/2018 |
| CN | 108546718 | A | 9/2018 |
| CN | 108559730 | A | 9/2018 |
| CN | 108559732 | A | 9/2018 |
| CN | 108559745 | A | 9/2018 |
| CN | 108559760 | A | 9/2018 |
| CN | 108570479 | A | 9/2018 |
| CN | 108588071 | A | 9/2018 |
| CN | 108588123 | A | 9/2018 |
| CN | 108588128 | A | 9/2018 |
| CN | 108588182 | A | 9/2018 |

(56)                  References Cited

FOREIGN PATENT DOCUMENTS

| | | | |
|---|---|---|---|
| CN | 108610399 | A | 10/2018 |
| CN | 108611364 | A | 10/2018 |
| CN | 108624622 | A | 10/2018 |
| CN | 108642053 | A | 10/2018 |
| CN | 108642055 | A | 10/2018 |
| CN | 108642077 | A | 10/2018 |
| CN | 108642078 | A | 10/2018 |
| CN | 108642090 | A | 10/2018 |
| CN | 108690844 | A | 10/2018 |
| CN | 108707604 | A | 10/2018 |
| CN | 108707620 | A | 10/2018 |
| CN | 108707621 | A | 10/2018 |
| CN | 108707628 | A | 10/2018 |
| CN | 108707629 | A | 10/2018 |
| CN | 108715850 | A | 10/2018 |
| CN | 108728476 | A | 11/2018 |
| CN | 108728486 | A | 11/2018 |
| CN | 108753772 | A | 11/2018 |
| CN | 108753783 | A | 11/2018 |
| CN | 108753813 | A | 11/2018 |
| CN | 108753817 | A | 11/2018 |
| CN | 108753832 | A | 11/2018 |
| CN | 108753835 | A | 11/2018 |
| CN | 108753836 | A | 11/2018 |
| CN | 108795902 | A | 11/2018 |
| CN | 108822217 | A | 11/2018 |
| CN | 108823248 | A | 11/2018 |
| CN | 108823249 | A | 11/2018 |
| CN | 108823291 | A | 11/2018 |
| CN | 108841845 | A | 11/2018 |
| CN | 108853133 | A | 11/2018 |
| CN | 108866093 | A | 11/2018 |
| CN | 108893529 | A | 11/2018 |
| CN | 108913664 | A | 11/2018 |
| CN | 108913691 | A | 11/2018 |
| CN | 108913714 | A | 11/2018 |
| CN | 108913717 | A | 11/2018 |
| CN | 208034188 | U | 11/2018 |
| CN | 109517841 | A | 3/2019 |
| EP | 0264166 | A1 | 4/1988 |
| EP | 0321201 | B2 | 6/1989 |
| EP | 0519463 | A1 | 12/1992 |
| EP | 1085892 | A2 | 3/2001 |
| EP | 1092770 | A2 | 4/2001 |
| EP | 2350295 | B1 | 5/2013 |
| EP | 2604255 | A1 | 6/2013 |
| EP | 2840140 | A1 | 2/2015 |
| EP | 2877490 | A2 | 6/2015 |
| EP | 2966170 | A1 | 1/2016 |
| EP | 3009511 | A2 | 4/2016 |
| EP | 3031921 | A1 | 6/2016 |
| EP | 3045537 | A1 | 7/2016 |
| EP | 3115457 | A | 1/2017 |
| EP | 3144390 | A1 | 3/2017 |
| EP | 3199632 | A1 | 8/2017 |
| EP | 3216867 | A1 | 9/2017 |
| EP | 3252160 | A1 | 12/2017 |
| EP | 3450553 | B1 | 12/2019 |
| ES | 2740248 | T3 | 2/2020 |
| GB | 2528177 | A | 1/2016 |
| GB | 2531454 | A1 | 4/2016 |
| GB | 2542653 | A | 3/2017 |
| HK | 1208045 | A1 | 2/2016 |
| JP | 2007-501626 | A | 2/2007 |
| JP | 2008-515405 | A | 5/2008 |
| JP | 2010-033344 | A | 2/2010 |
| JP | 2010-535744 | A | 11/2010 |
| JP | 2010-539929 | A | 12/2010 |
| JP | 2011-081011 | A | 4/2011 |
| JP | 2011-523353 | A | 8/2011 |
| JP | 2012-525146 | A | 10/2012 |
| JP | 2012-210172 | A | 11/2012 |
| JP | 2012-531909 | A | 12/2012 |
| JP | 2013-534417 | A | 9/2013 |
| JP | 2015-523856 | A | 8/2015 |
| JP | 2015-532654 | A | 11/2015 |
| JP | 2016-525888 | A | 9/2016 |
| JP | 2016-534132 | A | 11/2016 |
| JP | 2017-500035 | A | 1/2017 |
| JP | 6629734 | B2 | 1/2020 |
| JP | 6633524 | B2 | 1/2020 |
| JP | 6830517 | B2 | 2/2021 |
| JP | 7324523 | B2 | 8/2023 |
| KR | 101584933 | B1 | 1/2016 |
| KR | 2016-0050069 | A | 5/2016 |
| KR | 20160133380 | A | 11/2016 |
| KR | 20170037025 | A | 4/2017 |
| KR | 20170037028 | A | 4/2017 |
| KR | 101748575 | B1 | 6/2017 |
| KR | 20170128137 | A | 11/2017 |
| KR | 2018-0022465 | A | 3/2018 |
| RU | 2016104674 | A | 8/2017 |
| RU | 2634395 | C1 | 10/2017 |
| RU | 2652899 | C1 | 5/2018 |
| RU | 2015128057 | A | 3/2019 |
| RU | 2015128098 | A | 3/2019 |
| RU | 2687451 | C1 | 5/2019 |
| RU | 2019112514 | A | 6/2019 |
| RU | 2019127300 | A | 9/2019 |
| RU | 2701850 | C2 | 10/2019 |
| SG | 10201707569 | Y | 10/2017 |
| SG | 10201710486 | A | 1/2018 |
| SG | 10201710487 | A | 1/2018 |
| SG | 10201710488 | T | 1/2018 |
| TW | I608100 | B | 12/2017 |
| TW | 2018-29773 | A | 8/2018 |
| WO | WO 1990/002809 | | 3/1990 |
| WO | WO 1990/002809 | A1 | 3/1990 |
| WO | WO 1991/003162 | A1 | 3/1991 |
| WO | WO 1991/016024 | A1 | 10/1991 |
| WO | WO 1991/017271 | A1 | 11/1991 |
| WO | WO 1991/017424 | A1 | 11/1991 |
| WO | WO 1992/006188 | A2 | 4/1992 |
| WO | WO 1992/006200 | A1 | 4/1992 |
| WO | WO 1992/007065 | A1 | 4/1992 |
| WO | WO 1993/015187 | A1 | 8/1993 |
| WO | WO 1993/024641 | A2 | 12/1993 |
| WO | WO 1994/018316 | A2 | 8/1994 |
| WO | WO 1994/026877 | A1 | 11/1994 |
| WO | WO 1996/004403 | A1 | 2/1996 |
| WO | WO 1996/010640 | A1 | 4/1996 |
| WO | WO 1997/025416 | A2 | 7/1997 |
| WO | WO 1998/032845 | A1 | 7/1998 |
| WO | WO 1998/050538 | A1 | 11/1998 |
| WO | WO 2001/036452 | A2 | 5/2001 |
| WO | WO 2001/038547 | A2 | 5/2001 |
| WO | WO 2001/083692 | A2 | 11/2001 |
| WO | WO 2002/059296 | A2 | 8/2002 |
| WO | WO 2002/068676 | A2 | 9/2002 |
| WO | WO 2002/103028 | A2 | 12/2002 |
| WO | WO 2003/004608 | A2 | 1/2003 |
| WO | WO 2004/007684 | A2 | 1/2004 |
| WO | WO 2005/014791 | A2 | 2/2005 |
| WO | WO 2005/019415 | A2 | 3/2005 |
| WO | WO 2006/002547 | A1 | 1/2006 |
| WO | WO 2006/042112 | A2 | 4/2006 |
| WO | WO 2007/025097 | A2 | 3/2007 |
| WO | WO 2007/037444 | A1 | 4/2007 |
| WO | WO 2007/066923 | A1 | 6/2007 |
| WO | WO 2007/136815 | A2 | 11/2007 |
| WO | WO 2007/143574 | A1 | 12/2007 |
| WO | WO 2008/005529 | A2 | 1/2008 |
| WO | WO 2008/108989 | A2 | 9/2008 |
| WO | WO 2009/002418 | A2 | 12/2008 |
| WO | WO 2009/019317 | A1 | 2/2009 |
| WO | WO 2009/098290 | A1 | 8/2009 |
| WO | WO 2009/134808 | A2 | 11/2009 |
| WO | WO 2010/011961 | A2 | 1/2010 |
| WO | WO 2010/012902 | A1 | 2/2010 |
| WO | WO 2010/028347 | A2 | 3/2010 |
| WO | WO 2010/054108 | A2 | 5/2010 |
| WO | WO 2010/054154 | A2 | 5/2010 |
| WO | WO 2010/068289 | A2 | 6/2010 |
| WO | WO 2010/075424 | A2 | 7/2010 |

(56)  References Cited

FOREIGN PATENT DOCUMENTS

| | | | |
|---|---|---|---|
| WO | WO 2010/091122 | A1 | 8/2010 |
| WO | WO 2010/102257 | A2 | 9/2010 |
| WO | WO 2010/104749 | A2 | 9/2010 |
| WO | WO 2010/129019 | A2 | 11/2010 |
| WO | WO 2010/129023 | A2 | 11/2010 |
| WO | WO 2010/132092 | A2 | 11/2010 |
| WO | WO 2010/144150 | A2 | 12/2010 |
| WO | WO 2011/002503 | A1 | 1/2011 |
| WO | WO 2011/017293 | A2 | 2/2011 |
| WO | WO 2011/053868 | A1 | 5/2011 |
| WO | WO 2011/053982 | A2 | 5/2011 |
| WO | WO 2011/068810 | A1 | 6/2011 |
| WO | WO 2011/075627 | A1 | 6/2011 |
| WO | WO 2011/091311 | A2 | 7/2011 |
| WO | WO 2011/091396 | A1 | 7/2011 |
| WO | WO 2011/109031 | A1 | 9/2011 |
| WO | WO 2011/143124 | A2 | 11/2011 |
| WO | WO 2011/147590 | A2 | 12/2011 |
| WO | WO 2011/159369 | A1 | 12/2011 |
| WO | WO 2012/054726 | A1 | 4/2012 |
| WO | WO 2012/061815 | A2 | 5/2012 |
| WO | WO 2012/065043 | A2 | 5/2012 |
| WO | WO 2012/088381 | A2 | 6/2012 |
| WO | WO 2012/125445 | A2 | 9/2012 |
| WO | WO 2012/138927 | A2 | 10/2012 |
| WO | WO 2012/149470 | A1 | 11/2012 |
| WO | WO 2012/158985 | A2 | 11/2012 |
| WO | WO 2012/158986 | A2 | 11/2012 |
| WO | WO 2012/164565 | A1 | 12/2012 |
| WO | WO 2012/170930 | A1 | 12/2012 |
| WO | WO 2013/012674 | A1 | 1/2013 |
| WO | WO 2013/013105 | A1 | 1/2013 |
| WO | WO 2013/039857 | A1 | 3/2013 |
| WO | WO 2013/039861 | A2 | 3/2013 |
| WO | WO 2013/040093 | A2 | 3/2013 |
| WO | WO 2013/045632 | A1 | 4/2013 |
| WO | WO 2013/047844 | A1 | 4/2013 |
| WO | WO 2013/066438 | A2 | 5/2013 |
| WO | WO 2013/086441 | A2 | 6/2013 |
| WO | WO 2013/086444 | A2 | 6/2013 |
| WO | WO 2013/098244 | A1 | 7/2013 |
| WO | WO 2013/119602 | A1 | 8/2013 |
| WO | WO 2013/120022 | A2 | 8/2013 |
| WO | WO 2013/122617 | A1 | 8/2013 |
| WO | WO 2013/126794 | A1 | 8/2013 |
| WO | WO 2013/130683 | A2 | 9/2013 |
| WO | WO 2013/130824 | A1 | 9/2013 |
| WO | WO 2013/141680 | A1 | 9/2013 |
| WO | WO 2013/142578 | A1 | 9/2013 |
| WO | WO 2013/142578 | A2 | 9/2013 |
| WO | WO 2013/152359 | A1 | 10/2013 |
| WO | WO 2013/160230 | A1 | 10/2013 |
| WO | WO 2013/166315 | A1 | 11/2013 |
| WO | WO 2013/169398 | A2 | 11/2013 |
| WO | WO 2013/169802 | A1 | 11/2013 |
| WO | WO 2013/176772 | A1 | 11/2013 |
| WO | WO 2013/176772 | A2 | 11/2013 |
| WO | WO 2013/176915 | A1 | 11/2013 |
| WO | WO 2013/176916 | A1 | 11/2013 |
| WO | WO 2013/181440 | A1 | 12/2013 |
| WO | WO 2013/186754 | A2 | 12/2013 |
| WO | WO 2013/188037 | A2 | 12/2013 |
| WO | WO 2013/188522 | A2 | 12/2013 |
| WO | WO 2013/188638 | A1 | 12/2013 |
| WO | WO 2013/192278 | A1 | 12/2013 |
| WO | WO 2013/142378 | A9 | 1/2014 |
| WO | WO 2014/004336 | A2 | 1/2014 |
| WO | WO 2014/005042 | A2 | 1/2014 |
| WO | WO 2014/011237 | A1 | 1/2014 |
| WO | WO 2014/011901 | A2 | 1/2014 |
| WO | WO 2014/018423 | A2 | 1/2014 |
| WO | WO 2014/020608 | A1 | 2/2014 |
| WO | WO 2014/022120 | A1 | 2/2014 |
| WO | WO 2014/022702 | A2 | 2/2014 |
| WO | WO 2014/036219 | A2 | 3/2014 |
| WO | WO 2014/039513 | A2 | 3/2014 |
| WO | WO 2014/039523 | A1 | 3/2014 |
| WO | WO 2014/039585 | A2 | 3/2014 |
| WO | WO 2014/039684 | A1 | 3/2014 |
| WO | WO 2014/039692 | A2 | 3/2014 |
| WO | WO 2014/039702 | A2 | 3/2014 |
| WO | WO 2014/039872 | A1 | 3/2014 |
| WO | WO 2014/039970 | A1 | 3/2014 |
| WO | WO 2014/041327 | A1 | 3/2014 |
| WO | WO 2014/043143 | A1 | 3/2014 |
| WO | WO 2014/047103 | A2 | 3/2014 |
| WO | WO 2014/055782 | A1 | 4/2014 |
| WO | WO 2014/059173 | A2 | 4/2014 |
| WO | WO 2014/059255 | A1 | 4/2014 |
| WO | WO 2014/065596 | A1 | 5/2014 |
| WO | WO 2014/066505 | A1 | 5/2014 |
| WO | WO 2014/068346 | A2 | 5/2014 |
| WO | WO 2014/070887 | A1 | 5/2014 |
| WO | WO 2014/071006 | A1 | 5/2014 |
| WO | WO 2014/071219 | A1 | 5/2014 |
| WO | WO 2014/071235 | A1 | 5/2014 |
| WO | WO 2014/072941 | A1 | 5/2014 |
| WO | WO 2014/081729 | A1 | 5/2014 |
| WO | WO 2014/081730 | A1 | 5/2014 |
| WO | WO 2014/081855 | A1 | 5/2014 |
| WO | WO 2014/082644 | A1 | 6/2014 |
| WO | WO 2014/085261 | A1 | 6/2014 |
| WO | WO 2014/085593 | A1 | 6/2014 |
| WO | WO 2014/085830 | A2 | 6/2014 |
| WO | WO 2014/089212 | A1 | 6/2014 |
| WO | WO 2014/089290 | A1 | 6/2014 |
| WO | WO 2014/089348 | A1 | 6/2014 |
| WO | WO 2014/089513 | A1 | 6/2014 |
| WO | WO 2014/089533 | A2 | 6/2014 |
| WO | WO 2014/089541 | A2 | 6/2014 |
| WO | WO 2014/093479 | A1 | 6/2014 |
| WO | WO 2014/093595 | A1 | 6/2014 |
| WO | WO 2014/093622 | A2 | 6/2014 |
| WO | WO 2014/093635 | A1 | 6/2014 |
| WO | WO 2014/093655 | A2 | 6/2014 |
| WO | WO 2014/093661 | A2 | 6/2014 |
| WO | WO 2014/093694 | A1 | 6/2014 |
| WO | WO 2014/093701 | A1 | 6/2014 |
| WO | WO 2014/093709 | A1 | 6/2014 |
| WO | WO 2014/093712 | A1 | 6/2014 |
| WO | WO 2014/093718 | A1 | 6/2014 |
| WO | WO 2014/093736 | A1 | 6/2014 |
| WO | WO 2014/093768 | A1 | 6/2014 |
| WO | WO 2014/093852 | A1 | 6/2014 |
| WO | WO 2014/096972 | A2 | 6/2014 |
| WO | WO 2014/099744 | A1 | 6/2014 |
| WO | WO 2014/099750 | A2 | 6/2014 |
| WO | WO 2014/104878 | A1 | 7/2014 |
| WO | WO 2014/110006 | A1 | 7/2014 |
| WO | WO 2014/110552 | A1 | 7/2014 |
| WO | WO 2014/113493 | A1 | 7/2014 |
| WO | WO 2014/123967 | A2 | 8/2014 |
| WO | WO 2014/124226 | A1 | 8/2014 |
| WO | WO 2014/125668 | A1 | 8/2014 |
| WO | WO 2014/127287 | A1 | 8/2014 |
| WO | WO 2014/128324 | A1 | 8/2014 |
| WO | WO 2014/128659 | A1 | 8/2014 |
| WO | WO 2014/130706 | A1 | 8/2014 |
| WO | WO 2014/130955 | A1 | 8/2014 |
| WO | WO 2014/131833 | A1 | 9/2014 |
| WO | WO 2014/138379 | A1 | 9/2014 |
| WO | WO 2014/143381 | A1 | 9/2014 |
| WO | WO 2014/144094 | A1 | 9/2014 |
| WO | WO 2014/144155 | A1 | 9/2014 |
| WO | WO 2014/144288 | A1 | 9/2014 |
| WO | WO 2014/144592 | A2 | 9/2014 |
| WO | WO 2014/144761 | A2 | 9/2014 |
| WO | WO 2014/144951 | A1 | 9/2014 |
| WO | WO 2014/145599 | A2 | 9/2014 |
| WO | WO 2014/145736 | A2 | 9/2014 |
| WO | WO 2014/150624 | A1 | 9/2014 |
| WO | WO 2014/152432 | A2 | 9/2014 |
| WO | WO 2014/152940 | A1 | 9/2014 |
| WO | WO 2014/153118 | A1 | 9/2014 |

(56)                 References Cited

FOREIGN PATENT DOCUMENTS

| | | |
|---|---|---|
| WO | WO 2014/153470 A2 | 9/2014 |
| WO | WO 2014/158593 A1 | 10/2014 |
| WO | WO 2014/161821 A1 | 10/2014 |
| WO | WO 2014/164466 A1 | 10/2014 |
| WO | WO 2014/165177 A1 | 10/2014 |
| WO | WO 2014/165349 A1 | 10/2014 |
| WO | WO 2014/165612 A2 | 10/2014 |
| WO | WO 2014/165707 A2 | 10/2014 |
| WO | WO 2014/165825 A2 | 10/2014 |
| WO | WO 2014/172458 A1 | 10/2014 |
| WO | WO 2014/172470 A2 | 10/2014 |
| WO | WO 2014/172489 A2 | 10/2014 |
| WO | WO 2014/173955 A1 | 10/2014 |
| WO | WO 2014/182700 A1 | 11/2014 |
| WO | WO 2014/183071 A2 | 11/2014 |
| WO | WO 2014/184143 A1 | 11/2014 |
| WO | WO 2014/184741 A1 | 11/2014 |
| WO | WO 2014/184744 A1 | 11/2014 |
| WO | WO 2014/186585 A2 | 11/2014 |
| WO | WO 2014/186686 A2 | 11/2014 |
| WO | WO 2014/190181 A1 | 11/2014 |
| WO | WO 2014/191128 A1 | 12/2014 |
| WO | WO 2014/191518 A1 | 12/2014 |
| WO | WO 2014/191521 A2 | 12/2014 |
| WO | WO 2014/191525 A1 | 12/2014 |
| WO | WO 2014/191527 A1 | 12/2014 |
| WO | WO 2014/193583 A2 | 12/2014 |
| WO | WO 2014/194190 A1 | 12/2014 |
| WO | WO 2014/197568 A2 | 12/2014 |
| WO | WO 2014/197748 A2 | 12/2014 |
| WO | WO 2014/199358 A1 | 12/2014 |
| WO | WO 2014/200659 A1 | 12/2014 |
| WO | WO 2014/201015 A2 | 12/2014 |
| WO | WO 2014/204578 A1 | 12/2014 |
| WO | WO 2014/204723 A1 | 12/2014 |
| WO | WO 2014/204724 A1 | 12/2014 |
| WO | WO 2014/204725 A1 | 12/2014 |
| WO | WO 2014/204726 A1 | 12/2014 |
| WO | WO 2014/204727 A1 | 12/2014 |
| WO | WO 2014/204728 A1 | 12/2014 |
| WO | WO 2014/204729 A1 | 12/2014 |
| WO | WO 2014/205192 A2 | 12/2014 |
| WO | WO 2014/207043 A1 | 12/2014 |
| WO | WO 2015/002780 A1 | 1/2015 |
| WO | WO 2015/004241 A2 | 1/2015 |
| WO | WO 2015/006290 A1 | 1/2015 |
| WO | WO 2015/006294 A2 | 1/2015 |
| WO | WO 2015/006437 A1 | 1/2015 |
| WO | WO 2015/006498 A2 | 1/2015 |
| WO | WO 2015/006747 A2 | 1/2015 |
| WO | WO 2015/007194 A1 | 1/2015 |
| WO | WO 2015/010114 A1 | 1/2015 |
| WO | WO 2015/011483 A1 | 1/2015 |
| WO | WO 2015/013583 A2 | 1/2015 |
| WO | WO 2015/017866 A1 | 2/2015 |
| WO | WO 2015/018503 A1 | 2/2015 |
| WO | WO 2015/021353 A1 | 2/2015 |
| WO | WO 2015/021426 A1 | 2/2015 |
| WO | WO 2015/021990 A1 | 2/2015 |
| WO | WO 2015/024017 A2 | 2/2015 |
| WO | WO 2015/024986 A1 | 2/2015 |
| WO | WO 2015/026883 A1 | 2/2015 |
| WO | WO 2015/026885 A1 | 2/2015 |
| WO | WO 2015/026886 A1 | 2/2015 |
| WO | WO 2015/026887 A1 | 2/2015 |
| WO | WO 2015/027134 A1 | 2/2015 |
| WO | WO 2015/028969 A2 | 3/2015 |
| WO | WO 2015/030881 A1 | 3/2015 |
| WO | WO 2015/031619 A1 | 3/2015 |
| WO | WO 2015/031775 A1 | 3/2015 |
| WO | WO 2015/032494 A2 | 3/2015 |
| WO | WO 2015/033293 A1 | 3/2015 |
| WO | WO 2015/034872 A2 | 3/2015 |
| WO | WO 2015/034885 A1 | 3/2015 |
| WO | WO 2015/035136 A2 | 3/2015 |
| WO | WO 2015/035139 A2 | 3/2015 |
| WO | WO 2015/035162 A2 | 3/2015 |
| WO | WO 2015/040075 A1 | 3/2015 |
| WO | WO 2015/040402 A1 | 3/2015 |
| WO | WO 2015/042393 A2 | 3/2015 |
| WO | WO 2015/042585 A1 | 3/2015 |
| WO | WO 2015/048577 A2 | 4/2015 |
| WO | WO 2015/048690 A1 | 4/2015 |
| WO | WO 2015/048707 A2 | 4/2015 |
| WO | WO 2015/048801 A2 | 4/2015 |
| WO | WO 2015/049897 A1 | 4/2015 |
| WO | WO 2015/051191 A1 | 4/2015 |
| WO | WO 2015/052133 A1 | 4/2015 |
| WO | WO 2015/052231 A2 | 4/2015 |
| WO | WO 2015/052335 A1 | 4/2015 |
| WO | WO 2015/053995 A1 | 4/2015 |
| WO | WO 2015/054253 A1 | 4/2015 |
| WO | WO 2015/054315 A1 | 4/2015 |
| WO | WO 2015/057671 A1 | 4/2015 |
| WO | WO 2015/057834 A1 | 4/2015 |
| WO | WO 2015/057852 A1 | 4/2015 |
| WO | WO 2015/057976 A1 | 4/2015 |
| WO | WO 2015/057980 A1 | 4/2015 |
| WO | WO 2015/059265 A1 | 4/2015 |
| WO | WO 2015/065964 A1 | 5/2015 |
| WO | WO 2015/066119 A1 | 5/2015 |
| WO | WO 2015/066634 A2 | 5/2015 |
| WO | WO 2015/066636 A2 | 5/2015 |
| WO | WO 2015/066637 A1 | 5/2015 |
| WO | WO 2015/066638 A2 | 5/2015 |
| WO | WO 2015/066643 A1 | 5/2015 |
| WO | WO 2015/069682 A2 | 5/2015 |
| WO | WO 2015/070083 A1 | 5/2015 |
| WO | WO 2015/070193 A1 | 5/2015 |
| WO | WO 2015/070212 A1 | 5/2015 |
| WO | WO 2015/071474 A2 | 5/2015 |
| WO | WO 2015/073683 A2 | 5/2015 |
| WO | WO 2015/073867 A1 | 5/2015 |
| WO | WO 2015/073990 A1 | 5/2015 |
| WO | WO 2015/075056 A1 | 5/2015 |
| WO | WO 2015/075154 A2 | 5/2015 |
| WO | WO 2015/075175 A1 | 5/2015 |
| WO | WO 2015/075195 A1 | 5/2015 |
| WO | WO 2015/075557 A2 | 5/2015 |
| WO | WO 2015/077058 A2 | 5/2015 |
| WO | WO 2015/077290 A2 | 5/2015 |
| WO | WO 2015/077318 A1 | 5/2015 |
| WO | WO 2015/079056 A1 | 6/2015 |
| WO | WO 2015/079057 A2 | 6/2015 |
| WO | WO 2015/086795 A1 | 6/2015 |
| WO | WO 2015/086798 A2 | 6/2015 |
| WO | WO 2015/088643 A1 | 6/2015 |
| WO | WO 2015/089046 A1 | 6/2015 |
| WO | WO 2015/089077 A2 | 6/2015 |
| WO | WO 2015/089277 A1 | 6/2015 |
| WO | WO 2015/089351 A1 | 6/2015 |
| WO | WO 2015/089354 A1 | 6/2015 |
| WO | WO 2015/089364 A1 | 6/2015 |
| WO | WO 2015/089406 A1 | 6/2015 |
| WO | WO 2015/089419 A2 | 6/2015 |
| WO | WO 2015/089427 A1 | 6/2015 |
| WO | WO 2015/089462 A1 | 6/2015 |
| WO | WO 2015/089465 A1 | 6/2015 |
| WO | WO 2015/089473 A1 | 6/2015 |
| WO | WO 2015/089486 A1 | 6/2015 |
| WO | WO 2015/089486 A2 | 6/2015 |
| WO | WO 2015/095804 A1 | 6/2015 |
| WO | WO 2015/099850 A1 | 7/2015 |
| WO | WO 2015/100929 A1 | 7/2015 |
| WO | WO 2015/103057 A1 | 7/2015 |
| WO | WO 2015/103153 A1 | 7/2015 |
| WO | WO 2015/105928 A1 | 7/2015 |
| WO | WO 2015/108993 A1 | 7/2015 |
| WO | WO 2015/109752 A1 | 7/2015 |
| WO | WO 2015/110474 A1 | 7/2015 |
| WO | WO 2015/112790 A2 | 7/2015 |
| WO | WO 2015/112896 A2 | 7/2015 |
| WO | WO 2015/113063 A1 | 7/2015 |
| WO | WO 2015/114365 A1 | 8/2015 |

(56)         References Cited

FOREIGN PATENT DOCUMENTS

| | | | |
|---|---|---|---|
| WO | WO 2015/115903 | A1 | 8/2015 |
| WO | WO 2015/116686 | A1 | 8/2015 |
| WO | WO 2015/116969 | A2 | 8/2015 |
| WO | WO 2015/117021 | A1 | 8/2015 |
| WO | WO 2015/117041 | A1 | 8/2015 |
| WO | WO 2015/117081 | A2 | 8/2015 |
| WO | WO 2015/118156 | A1 | 8/2015 |
| WO | WO 2015/119941 | A2 | 8/2015 |
| WO | WO 2015/121454 | A1 | 8/2015 |
| WO | WO 2015/122967 | A1 | 8/2015 |
| WO | WO 2015/123339 | A1 | 8/2015 |
| WO | WO 2015/124715 | A1 | 8/2015 |
| WO | WO 2015/124718 | A1 | 8/2015 |
| WO | WO 2015/126927 | A2 | 8/2015 |
| WO | WO 2015/127428 | A1 | 8/2015 |
| WO | WO 2015/127439 | A1 | 8/2015 |
| WO | WO 2015/129686 | A1 | 9/2015 |
| WO | WO 2015/131101 | A1 | 9/2015 |
| WO | WO 2015/133554 | A1 | 9/2015 |
| WO | WO 2015/134121 | A2 | 9/2015 |
| WO | WO 2015/134812 | A1 | 9/2015 |
| WO | WO 2015/136001 | A1 | 9/2015 |
| WO | WO 2015/138510 | A1 | 9/2015 |
| WO | WO 2015/138739 | A2 | 9/2015 |
| WO | WO 2015/138855 | A1 | 9/2015 |
| WO | WO 2015/138870 | A2 | 9/2015 |
| WO | WO 2015/139008 | A1 | 9/2015 |
| WO | WO 2015/139139 | A1 | 9/2015 |
| WO | WO 2015/143046 | A2 | 9/2015 |
| WO | WO 2015/143177 | A1 | 9/2015 |
| WO | WO 2015/145417 | A1 | 10/2015 |
| WO | WO 2015/148431 | A1 | 10/2015 |
| WO | WO 2015/148670 | A1 | 10/2015 |
| WO | WO 2015/148680 | A1 | 10/2015 |
| WO | WO 2015/148761 | A1 | 10/2015 |
| WO | WO 2015/148860 | A1 | 10/2015 |
| WO | WO 2015/148863 | A2 | 10/2015 |
| WO | WO 2015/153760 | A2 | 10/2015 |
| WO | WO 2015/153780 | A1 | 10/2015 |
| WO | WO 2015/153789 | A1 | 10/2015 |
| WO | WO 2015/153791 | A1 | 10/2015 |
| WO | WO 2015/153889 | A2 | 10/2015 |
| WO | WO 2015/153940 | A1 | 10/2015 |
| WO | WO 2015/155341 | A1 | 10/2015 |
| WO | WO 2015/155686 | A2 | 10/2015 |
| WO | WO 2015/157070 | A2 | 10/2015 |
| WO | WO 2015/157534 | A1 | 10/2015 |
| WO | WO 2015/159068 | A1 | 10/2015 |
| WO | WO 2015/159086 | A1 | 10/2015 |
| WO | WO 2015/159087 | A1 | 10/2015 |
| WO | WO 2015/160683 | A1 | 10/2015 |
| WO | WO 2015/161276 | A2 | 10/2015 |
| WO | WO 2015/163733 | A1 | 10/2015 |
| WO | WO 2015/164740 | A1 | 10/2015 |
| WO | WO 2015/164748 | A1 | 10/2015 |
| WO | WO 2015/165274 | A1 | 11/2015 |
| WO | WO 2015/165275 | A1 | 11/2015 |
| WO | WO 2015/165276 | A1 | 11/2015 |
| WO | WO 2015/166272 | A2 | 11/2015 |
| WO | WO 2015/167766 | A1 | 11/2015 |
| WO | WO 2015/167956 | A1 | 11/2015 |
| WO | WO 2015/168125 | A1 | 11/2015 |
| WO | WO 2015/168158 | A1 | 11/2015 |
| WO | WO 2015/168404 | A1 | 11/2015 |
| WO | WO 2015/168547 | A2 | 11/2015 |
| WO | WO 2015/168800 | A1 | 11/2015 |
| WO | WO 2015/171603 | A1 | 11/2015 |
| WO | WO 2015/171894 | A1 | 11/2015 |
| WO | WO 2015/171932 | A1 | 11/2015 |
| WO | WO 2015/172128 | A1 | 11/2015 |
| WO | WO 2015/173436 | A1 | 11/2015 |
| WO | WO 2015/175642 | A2 | 11/2015 |
| WO | WO 2015/179540 | A1 | 11/2015 |
| WO | WO 2015/183025 | A1 | 12/2015 |
| WO | WO 2015/183026 | A1 | 12/2015 |
| WO | WO 2015/183885 | A1 | 12/2015 |
| WO | WO 2015/184259 | A1 | 12/2015 |
| WO | WO 2015/184262 | A1 | 12/2015 |
| WO | WO 2015/184268 | A1 | 12/2015 |
| WO | WO 2015/188056 | A1 | 12/2015 |
| WO | WO 2015/188065 | A1 | 12/2015 |
| WO | WO 2015/188094 | A1 | 12/2015 |
| WO | WO 2015/188109 | A1 | 12/2015 |
| WO | WO 2015/188132 | A1 | 12/2015 |
| WO | WO 2015/188135 | A1 | 12/2015 |
| WO | WO 2015/188191 | A1 | 12/2015 |
| WO | WO 2015/189693 | A1 | 12/2015 |
| WO | WO 2015/191693 | A2 | 12/2015 |
| WO | WO 2015/191899 | A1 | 12/2015 |
| WO | WO 2015/191911 | A2 | 12/2015 |
| WO | WO 2015/193858 | A1 | 12/2015 |
| WO | WO 2015/195547 | A1 | 12/2015 |
| WO | WO 2015/195621 | A1 | 12/2015 |
| WO | WO 2015/195798 | A1 | 12/2015 |
| WO | WO 2015/198020 | A1 | 12/2015 |
| WO | WO 2015/200334 | A1 | 12/2015 |
| WO | WO 2015/200378 | A1 | 12/2015 |
| WO | WO 2015/200555 | A2 | 12/2015 |
| WO | WO 2015/200805 | A2 | 12/2015 |
| WO | WO 2016/001978 | A1 | 1/2016 |
| WO | WO 2016/004010 | A1 | 1/2016 |
| WO | WO 2016/004318 | A1 | 1/2016 |
| WO | WO 2016/007347 | A1 | 1/2016 |
| WO | WO 2016/007604 | A1 | 1/2016 |
| WO | WO 2016/007948 | A1 | 1/2016 |
| WO | WO 2016/011080 | A2 | 1/2016 |
| WO | WO 2016/011210 | A2 | 1/2016 |
| WO | WO 2016/011428 | A1 | 1/2016 |
| WO | WO 2016/012544 | A2 | 1/2016 |
| WO | WO 2016/012552 | A1 | 1/2016 |
| WO | WO 2016/014409 | A1 | 1/2016 |
| WO | WO 2016/014565 | A2 | 1/2016 |
| WO | WO 2016/014794 | A1 | 1/2016 |
| WO | WO 2016/014837 | A1 | 1/2016 |
| WO | WO 2016/016119 | A1 | 2/2016 |
| WO | WO 2016/016358 | A1 | 2/2016 |
| WO | WO 2016/019144 | A2 | 2/2016 |
| WO | WO 2016/020399 | A1 | 2/2016 |
| WO | WO 2016/021972 | A1 | 2/2016 |
| WO | WO 2016/021973 | A1 | 2/2016 |
| WO | WO 2016/022363 | A2 | 2/2016 |
| WO | WO 2016/022866 | A1 | 2/2016 |
| WO | WO 2016/022931 | A1 | 2/2016 |
| WO | WO 2016/025131 | A1 | 2/2016 |
| WO | WO 2016/025469 | A1 | 2/2016 |
| WO | WO 2016/025759 | A1 | 2/2016 |
| WO | WO 2016/026444 | A1 | 2/2016 |
| WO | WO 2016/028682 | A1 | 2/2016 |
| WO | WO 2016/028843 | A1 | 2/2016 |
| WO | WO 2016/028843 | A2 | 2/2016 |
| WO | WO 2016/028887 | A1 | 2/2016 |
| WO | WO 2016/033088 | A1 | 3/2016 |
| WO | WO 2016/033230 | A1 | 3/2016 |
| WO | WO 2016/033246 | A1 | 3/2016 |
| WO | WO 2016/033298 | A1 | 3/2016 |
| WO | WO 2016/035044 | A1 | 3/2016 |
| WO | WO 2016/035918 | A1 | 3/2016 |
| WO | WO 2016/036754 | A1 | 3/2016 |
| WO | WO 2016/037157 | A2 | 3/2016 |
| WO | WO 2016/040030 | A1 | 3/2016 |
| WO | WO 2016/040594 | A1 | 3/2016 |
| WO | WO 2016/044182 | A1 | 3/2016 |
| WO | WO 2016/044416 | A1 | 3/2016 |
| WO | WO 2016/046635 | A1 | 3/2016 |
| WO | WO 2016/049024 | A2 | 3/2016 |
| WO | WO 2016/049163 | A2 | 3/2016 |
| WO | WO 2016/049230 | A1 | 3/2016 |
| WO | WO 2016/049251 | A1 | 3/2016 |
| WO | WO 2016/049258 | A2 | 3/2016 |
| WO | WO 2016/053397 | A2 | 4/2016 |
| WO | WO 2016/054326 | A1 | 4/2016 |
| WO | WO 2016/057061 | A2 | 4/2016 |
| WO | WO 2016/057821 | A2 | 4/2016 |
| WO | WO 2016/057835 | A2 | 4/2016 |

(56) References Cited

FOREIGN PATENT DOCUMENTS

| | | | |
|---|---|---|---|
| WO | WO 2016/057850 A1 | 4/2016 |
| WO | WO 2016/057951 A2 | 4/2016 |
| WO | WO 2016/057961 A1 | 4/2016 |
| WO | WO 2016/061073 A1 | 4/2016 |
| WO | WO 2016/061374 A1 | 4/2016 |
| WO | WO 2016/061481 A1 | 4/2016 |
| WO | WO 2016/061523 A1 | 4/2016 |
| WO | WO 2016/064894 A2 | 4/2016 |
| WO | WO 2016/065364 A1 | 4/2016 |
| WO | WO 2016/069282 A1 | 5/2016 |
| WO | WO 2016/069283 A1 | 5/2016 |
| WO | WO 2016/069591 A2 | 5/2016 |
| WO | WO 2016/069774 A1 | 5/2016 |
| WO | WO 2016/069910 A1 | 5/2016 |
| WO | WO 2016/069912 A1 | 5/2016 |
| WO | WO 2016/070037 A2 | 5/2016 |
| WO | WO 2016/070070 A1 | 5/2016 |
| WO | WO 2016/070129 A1 | 5/2016 |
| WO | WO 2016/072399 A1 | 5/2016 |
| WO | WO 2016/072936 A1 | 5/2016 |
| WO | WO 2016/073433 A1 | 5/2016 |
| WO | WO 2016/073559 A1 | 5/2016 |
| WO | WO 2016/073990 A2 | 5/2016 |
| WO | WO 2016/075662 A2 | 5/2016 |
| WO | WO 2016/076672 A1 | 5/2016 |
| WO | WO 2016/077273 A1 | 5/2016 |
| WO | WO 2016/077350 A1 | 5/2016 |
| WO | WO 2016/080097 A1 | 5/2016 |
| WO | WO 2016/080795 A1 | 5/2016 |
| WO | WO 2016/081923 A2 | 5/2016 |
| WO | WO 2016/081924 A1 | 5/2016 |
| WO | WO 2016/082135 A1 | 6/2016 |
| WO | WO 2016/083811 A1 | 6/2016 |
| WO | WO 2016/084084 A1 | 6/2016 |
| WO | WO 2016/084088 A1 | 6/2016 |
| WO | WO 2016/086177 A2 | 6/2016 |
| WO | WO 2016/089433 A1 | 6/2016 |
| WO | WO 2016/089866 A1 | 6/2016 |
| WO | WO 2016/089883 A1 | 6/2016 |
| WO | WO 2016/090385 A1 | 6/2016 |
| WO | WO 2016/094679 A1 | 6/2016 |
| WO | WO 2016/094845 A2 | 6/2016 |
| WO | WO 2016/094867 A1 | 6/2016 |
| WO | WO 2016/094872 A1 | 6/2016 |
| WO | WO 2016/094874 A1 | 6/2016 |
| WO | WO 2016/094880 A1 | 6/2016 |
| WO | WO 2016/094888 A1 | 6/2016 |
| WO | WO 2016/097212 A1 | 6/2016 |
| WO | WO 2016/097231 A2 | 6/2016 |
| WO | WO 2016/097751 A1 | 6/2016 |
| WO | WO 2016/099887 A1 | 6/2016 |
| WO | WO 2016/100272 A1 | 6/2016 |
| WO | WO 2016/100389 A1 | 6/2016 |
| WO | WO 2016/100568 A1 | 6/2016 |
| WO | WO 2016/100571 A1 | 6/2016 |
| WO | WO 2016/100951 A2 | 6/2016 |
| WO | WO 2016/100955 A2 | 6/2016 |
| WO | WO 2016/100974 A1 | 6/2016 |
| WO | WO 2016/103233 A2 | 6/2016 |
| WO | WO 2016/104716 A1 | 6/2016 |
| WO | WO 2016/106236 A1 | 6/2016 |
| WO | WO 2016/106239 A1 | 6/2016 |
| WO | WO 2016/106244 A1 | 6/2016 |
| WO | WO 2016/106338 A2 | 6/2016 |
| WO | WO 2016/108926 A1 | 7/2016 |
| WO | WO 2016/109255 A1 | 7/2016 |
| WO | WO 2016/109840 A2 | 7/2016 |
| WO | WO 2016/110214 A1 | 7/2016 |
| WO | WO 2016/110453 A1 | 7/2016 |
| WO | WO 2016/110511 A1 | 7/2016 |
| WO | WO 2016/110512 A1 | 7/2016 |
| WO | WO 2016/111546 A2 | 7/2016 |
| WO | WO 2016/112242 A1 | 7/2016 |
| WO | WO 2016/112351 A1 | 7/2016 |
| WO | WO 2016/112963 A1 | 7/2016 |
| WO | WO 2016/113357 A1 | 7/2016 |
| WO | WO 2016/114972 A1 | 7/2016 |
| WO | WO 2016/115179 A1 | 7/2016 |
| WO | WO 2016/115326 A1 | 7/2016 |
| WO | WO 2016/115355 A1 | 7/2016 |
| WO | WO 2016/116032 A1 | 7/2016 |
| WO | WO 2016/120480 A1 | 8/2016 |
| WO | WO 2016/123071 A1 | 8/2016 |
| WO | WO 2016/123230 A1 | 8/2016 |
| WO | WO 2016/123243 A1 | 8/2016 |
| WO | WO 2016/123578 A1 | 8/2016 |
| WO | WO 2016/126747 A1 | 8/2016 |
| WO | WO 2016/130600 A2 | 8/2016 |
| WO | WO 2016/130697 A1 | 8/2016 |
| WO | WO 2016/131009 A1 | 8/2016 |
| WO | WO 2016/132122 A1 | 8/2016 |
| WO | WO 2016/133165 A1 | 8/2016 |
| WO | WO 2016/135507 A1 | 9/2016 |
| WO | WO 2016/135557 A2 | 9/2016 |
| WO | WO 2016/135558 A2 | 9/2016 |
| WO | WO 2016/135559 A2 | 9/2016 |
| WO | WO 2016/137774 A1 | 9/2016 |
| WO | WO 2016/137949 A1 | 9/2016 |
| WO | WO 2016/141224 A1 | 9/2016 |
| WO | WO 2016/141893 A1 | 9/2016 |
| WO | WO 2016/142719 A1 | 9/2016 |
| WO | WO 2016/145150 A2 | 9/2016 |
| WO | WO 2016/148994 A1 | 9/2016 |
| WO | WO 2016/149484 A2 | 9/2016 |
| WO | WO 2016/149547 A1 | 9/2016 |
| WO | WO 2016/150336 A1 | 9/2016 |
| WO | WO 2016/150855 A1 | 9/2016 |
| WO | WO 2016/154016 A2 | 9/2016 |
| WO | WO 2016/154579 A2 | 9/2016 |
| WO | WO 2016/154596 A1 | 9/2016 |
| WO | WO 2016/155482 A1 | 10/2016 |
| WO | WO 2016/161004 A1 | 10/2016 |
| WO | WO 2016/161207 A1 | 10/2016 |
| WO | WO 2016/161260 A1 | 10/2016 |
| WO | WO 2016/161380 A1 | 10/2016 |
| WO | WO 2016/161446 A1 | 10/2016 |
| WO | WO 2016/164356 A1 | 10/2016 |
| WO | WO 2016/164797 A1 | 10/2016 |
| WO | WO 2016/166340 A1 | 10/2016 |
| WO | WO 2016/167300 A1 | 10/2016 |
| WO | WO 2016/168631 A1 | 10/2016 |
| WO | WO 2016/170484 A1 | 10/2016 |
| WO | WO 2016/172359 A2 | 10/2016 |
| WO | WO 2016/172727 A1 | 10/2016 |
| WO | WO 2016/174056 A1 | 11/2016 |
| WO | WO 2016/174151 A1 | 11/2016 |
| WO | WO 2016/174250 A1 | 11/2016 |
| WO | WO 2016/176191 A1 | 11/2016 |
| WO | WO 2016/176404 A1 | 11/2016 |
| WO | WO 2016/176690 A2 | 11/2016 |
| WO | WO 2016/177682 A1 | 11/2016 |
| WO | WO 2016/178207 A1 | 11/2016 |
| WO | WO 2016/179038 A1 | 11/2016 |
| WO | WO 2016/179112 A1 | 11/2016 |
| WO | WO 2016/181357 A1 | 11/2016 |
| WO | WO 2016/182893 A1 | 11/2016 |
| WO | WO 2016/182917 A1 | 11/2016 |
| WO | WO 2016/182959 A1 | 11/2016 |
| WO | WO 2016/183236 A1 | 11/2016 |
| WO | WO 2016/183298 A2 | 11/2016 |
| WO | WO 2016/183345 A1 | 11/2016 |
| WO | WO 2016/183402 A2 | 11/2016 |
| WO | WO 2016/183438 A1 | 11/2016 |
| WO | WO 2016/183448 A1 | 11/2016 |
| WO | WO 2016/184955 A2 | 11/2016 |
| WO | WO 2016/184989 A1 | 11/2016 |
| WO | WO 2016/185411 A1 | 11/2016 |
| WO | WO 2016/186745 A1 | 11/2016 |
| WO | WO 2016/186772 A2 | 11/2016 |
| WO | WO 2016/186946 A1 | 11/2016 |
| WO | WO 2016/186953 A1 | 11/2016 |
| WO | WO 2016/187717 A1 | 12/2016 |
| WO | WO 2016/187904 A1 | 12/2016 |
| WO | WO 2016/191684 A1 | 12/2016 |

(56)         References Cited

FOREIGN PATENT DOCUMENTS

| | | |
|---|---|---|
| WO | WO 2016/191869 A1 | 12/2016 |
| WO | WO 2016/196273 A1 | 12/2016 |
| WO | WO 2016/196282 A1 | 12/2016 |
| WO | WO 2016/196308 A1 | 12/2016 |
| WO | WO 2016/196361 A1 | 12/2016 |
| WO | WO 2016/196499 A1 | 12/2016 |
| WO | WO 2016/196539 A2 | 12/2016 |
| WO | WO 2016/196655 A1 | 12/2016 |
| WO | WO 2016/196805 A1 | 12/2016 |
| WO | WO 2016/196887 A1 | 12/2016 |
| WO | WO 2016/197132 A1 | 12/2016 |
| WO | WO 2016/197133 A1 | 12/2016 |
| WO | WO 2016/197354 A1 | 12/2016 |
| WO | WO 2016/197355 A1 | 12/2016 |
| WO | WO 2016/197356 A1 | 12/2016 |
| WO | WO 2016/197357 A1 | 12/2016 |
| WO | WO 2016/197358 A1 | 12/2016 |
| WO | WO 2016/197359 A1 | 12/2016 |
| WO | WO 2016/197360 A1 | 12/2016 |
| WO | WO 2016/197361 A1 | 12/2016 |
| WO | WO 2016/197362 A1 | 12/2016 |
| WO | WO 2016/198361 A1 | 12/2016 |
| WO | WO 2016/198500 A1 | 12/2016 |
| WO | WO 2016/200263 A1 | 12/2016 |
| WO | WO 2016/201047 A1 | 12/2016 |
| WO | WO 2016/201138 A1 | 12/2016 |
| WO | WO 2016/201152 A1 | 12/2016 |
| WO | WO 2016/201153 A1 | 12/2016 |
| WO | WO 2016/201155 A1 | 12/2016 |
| WO | WO 2016/205276 A1 | 12/2016 |
| WO | WO 2016/205613 A1 | 12/2016 |
| WO | WO 2016/205623 A1 | 12/2016 |
| WO | WO 2016/205680 A1 | 12/2016 |
| WO | WO 2016/205688 A2 | 12/2016 |
| WO | WO 2016/205703 A1 | 12/2016 |
| WO | WO 2016/205711 A1 | 12/2016 |
| WO | WO 2016/205728 A1 | 12/2016 |
| WO | WO 2016/205745 A2 | 12/2016 |
| WO | WO 2016/205749 A1 | 12/2016 |
| WO | WO 2016/205759 A1 | 12/2016 |
| WO | WO 2016/205764 A1 | 12/2016 |
| WO | WO 2017/001572 A1 | 1/2017 |
| WO | WO 2017/001988 A1 | 1/2017 |
| WO | WO 2017/004261 A1 | 1/2017 |
| WO | WO 2017/004279 A2 | 1/2017 |
| WO | WO 2017/004616 A1 | 1/2017 |
| WO | WO 2017/005807 A1 | 1/2017 |
| WO | WO 2017/009399 A1 | 1/2017 |
| WO | WO 2017/010556 A1 | 1/2017 |
| WO | WO 2017/011519 A1 | 1/2017 |
| WO | WO 2017/011721 A1 | 1/2017 |
| WO | WO 2017/011804 A1 | 1/2017 |
| WO | WO 2017/015015 A1 | 1/2017 |
| WO | WO 2017/015101 A1 | 1/2017 |
| WO | WO 2017/015545 A1 | 1/2017 |
| WO | WO 2017/015567 A1 | 1/2017 |
| WO | WO 2017/015637 A1 | 1/2017 |
| WO | WO 2017/017016 A1 | 2/2017 |
| WO | WO 2017/019867 A1 | 2/2017 |
| WO | WO 2017/019895 A1 | 2/2017 |
| WO | WO 2017/023803 A1 | 2/2017 |
| WO | WO 2017/023974 A1 | 2/2017 |
| WO | WO 2017/024047 A1 | 2/2017 |
| WO | WO 2017/024319 A1 | 2/2017 |
| WO | WO 2017/024343 A1 | 2/2017 |
| WO | WO 2017/024602 A1 | 2/2017 |
| WO | WO 2017/025323 A1 | 2/2017 |
| WO | WO 2017/027423 A1 | 2/2017 |
| WO | WO 2017/028768 A1 | 2/2017 |
| WO | WO 2017/029664 A1 | 2/2017 |
| WO | WO 2017/031360 A1 | 2/2017 |
| WO | WO 2017/031483 A1 | 2/2017 |
| WO | WO 2017/035416 A2 | 3/2017 |
| WO | WO 2017/040348 A1 | 3/2017 |
| WO | WO 2017/040511 A1 | 3/2017 |
| WO | WO 2017/040709 A1 | 3/2017 |
| WO | WO 2017/040786 A1 | 3/2017 |
| WO | WO 2017/040793 A1 | 3/2017 |
| WO | WO 2017/040813 A2 | 3/2017 |
| WO | WO 2017/043573 A1 | 3/2017 |
| WO | WO 2017/043656 A1 | 3/2017 |
| WO | WO 2017/044419 A1 | 3/2017 |
| WO | WO 2017/044776 A1 | 3/2017 |
| WO | WO 2017/044857 A2 | 3/2017 |
| WO | WO 2017/048390 A1 | 3/2017 |
| WO | WO 2017/049129 A2 | 3/2017 |
| WO | WO 2017/050963 A1 | 3/2017 |
| WO | WO 2017/053312 A1 | 3/2017 |
| WO | WO 2017/053431 A2 | 3/2017 |
| WO | WO 2017/053713 A1 | 3/2017 |
| WO | WO 2017/053729 A1 | 3/2017 |
| WO | WO 2017/053753 A1 | 3/2017 |
| WO | WO 2017/053762 A1 | 3/2017 |
| WO | WO 2017/053879 A1 | 3/2017 |
| WO | WO 2017/054721 A1 | 4/2017 |
| WO | WO 2017/058658 A2 | 4/2017 |
| WO | WO 2017/059241 A1 | 4/2017 |
| WO | WO 2017/062605 A1 | 4/2017 |
| WO | WO 2017/062723 A1 | 4/2017 |
| WO | WO 2017/062754 A1 | 4/2017 |
| WO | WO 2017/062855 A1 | 4/2017 |
| WO | WO 2017/062886 A1 | 4/2017 |
| WO | WO 2017/062983 A1 | 4/2017 |
| WO | WO 2017/064439 A1 | 4/2017 |
| WO | WO 2017/064546 A1 | 4/2017 |
| WO | WO 2017/064566 A2 | 4/2017 |
| WO | WO 2017/066175 A1 | 4/2017 |
| WO | WO 2017/066497 A2 | 4/2017 |
| WO | WO 2017/066588 A2 | 4/2017 |
| WO | WO 2017/066707 A1 | 4/2017 |
| WO | WO 2017/066781 A1 | 4/2017 |
| WO | WO 2017/068077 A1 | 4/2017 |
| WO | WO 2017/068377 A1 | 4/2017 |
| WO | WO 2017/069829 A2 | 4/2017 |
| WO | WO 2017/070029 A1 | 4/2017 |
| WO | WO 2017/070032 A1 | 4/2017 |
| WO | WO 2017/070169 A1 | 4/2017 |
| WO | WO 2017/070284 A1 | 4/2017 |
| WO | WO 2017/070598 A1 | 4/2017 |
| WO | WO 2017/070605 A1 | 4/2017 |
| WO | WO 2017/070632 A2 | 4/2017 |
| WO | WO 2017/070633 A2 | 4/2017 |
| WO | WO 2017/072590 A1 | 5/2017 |
| WO | WO 2017/074526 A1 | 5/2017 |
| WO | WO 2017/074962 A1 | 5/2017 |
| WO | WO 2017/075261 A1 | 5/2017 |
| WO | WO 2017/075335 A1 | 5/2017 |
| WO | WO 2017/075475 A1 | 5/2017 |
| WO | WO 2017/077135 A1 | 5/2017 |
| WO | WO 2017/077329 A2 | 5/2017 |
| WO | WO 2017/078751 A1 | 5/2017 |
| WO | WO 2017/079400 A1 | 5/2017 |
| WO | WO 2017/079428 A1 | 5/2017 |
| WO | WO 2017/079673 A1 | 5/2017 |
| WO | WO 2017/079724 A1 | 5/2017 |
| WO | WO 2017/081097 A1 | 5/2017 |
| WO | WO 2017/081288 A1 | 5/2017 |
| WO | WO 2017/083368 A1 | 5/2017 |
| WO | WO 2017/083722 A1 | 5/2017 |
| WO | WO 2017/083766 A1 | 5/2017 |
| WO | WO 2017/087395 A1 | 5/2017 |
| WO | WO 2017/090724 A1 | 6/2017 |
| WO | WO 2017/091510 A1 | 6/2017 |
| WO | WO 2017/091630 A1 | 6/2017 |
| WO | WO 2017/092201 A1 | 6/2017 |
| WO | WO 2017/093370 A1 | 6/2017 |
| WO | WO 2017/093969 A1 | 6/2017 |
| WO | WO 2017/095111 A1 | 6/2017 |
| WO | WO 2017/096041 A1 | 6/2017 |
| WO | WO 2017/096237 A1 | 6/2017 |
| WO | WO 2017/100158 A1 | 6/2017 |
| WO | WO 2017/100431 A2 | 6/2017 |
| WO | WO 2017/104404 A1 | 6/2017 |
| WO | WO 2017/105251 A1 | 6/2017 |

(56) References Cited

FOREIGN PATENT DOCUMENTS

| | | | |
|---|---|---|---|
| WO | WO 2017/105350 | A1 | 6/2017 |
| WO | WO 2017/105991 | A1 | 6/2017 |
| WO | WO 2017/106414 | A1 | 6/2017 |
| WO | WO 2017/106528 | A2 | 6/2017 |
| WO | WO 2017/106537 | A2 | 6/2017 |
| WO | WO 2017/106569 | A1 | 6/2017 |
| WO | WO 2017/106616 | A1 | 6/2017 |
| WO | WO 2017/106657 | A1 | 6/2017 |
| WO | WO 2017/106767 | A1 | 6/2017 |
| WO | WO 2017/109134 | A1 | 6/2017 |
| WO | WO 2017/109757 | A1 | 6/2017 |
| WO | WO 2017/112620 | A1 | 6/2017 |
| WO | WO 2017/115268 | A1 | 7/2017 |
| WO | WO 2017/117395 | A1 | 7/2017 |
| WO | WO 2017/118598 | A1 | 7/2017 |
| WO | WO 2017/118720 | A1 | 7/2017 |
| WO | WO 2017/123609 | A1 | 7/2017 |
| WO | WO 2017/123910 | A1 | 7/2017 |
| WO | WO 2017/124086 | A1 | 7/2017 |
| WO | WO 2017/124100 | A1 | 7/2017 |
| WO | WO 2017/124652 | A1 | 7/2017 |
| WO | WO 2017/126987 | A1 | 7/2017 |
| WO | WO 2017/127807 | A1 | 7/2017 |
| WO | WO 2017/131237 | A1 | 8/2017 |
| WO | WO 2017/132112 | A1 | 8/2017 |
| WO | WO 2017/132580 | A2 | 8/2017 |
| WO | WO 2017/136520 | A1 | 8/2017 |
| WO | WO 2017/136629 | A1 | 8/2017 |
| WO | WO 2017/136794 | A1 | 8/2017 |
| WO | WO 2017/139264 | A1 | 8/2017 |
| WO | WO 2017/139505 | A2 | 8/2017 |
| WO | WO 2017/141173 | A2 | 8/2017 |
| WO | WO 2017/142835 | A1 | 8/2017 |
| WO | WO 2017/142999 | A2 | 8/2017 |
| WO | WO 2017/143042 | A2 | 8/2017 |
| WO | WO 2017/147056 | A1 | 8/2017 |
| WO | WO 2017/147278 | A1 | 8/2017 |
| WO | WO 2017/147432 | A1 | 8/2017 |
| WO | WO 2017/147446 | A1 | 8/2017 |
| WO | WO 2017/147555 | A1 | 8/2017 |
| WO | WO 2017/151444 | A1 | 9/2017 |
| WO | WO 2017/151719 | A1 | 9/2017 |
| WO | WO 2017/152015 | A1 | 9/2017 |
| WO | WO 2017/155717 | A1 | 9/2017 |
| WO | WO 2017/157422 | A1 | 9/2017 |
| WO | WO 2017/158153 | A1 | 9/2017 |
| WO | WO 2017/160689 | A1 | 9/2017 |
| WO | WO 2017/160752 | A1 | 9/2017 |
| WO | WO 2017/160890 | A1 | 9/2017 |
| WO | WO 2017/161068 | A1 | 9/2017 |
| WO | WO 2017/165826 | A1 | 9/2017 |
| WO | WO 2017/165862 | A1 | 9/2017 |
| WO | WO 2017/172644 | A2 | 10/2017 |
| WO | WO 2017/172645 | A2 | 10/2017 |
| WO | WO 2017/172860 | A1 | 10/2017 |
| WO | WO 2017/173004 | A1 | 10/2017 |
| WO | WO 2017/173054 | A1 | 10/2017 |
| WO | WO 2017/173092 | A1 | 10/2017 |
| WO | WO 2017/174329 | A1 | 10/2017 |
| WO | WO 2017/176529 | A1 | 10/2017 |
| WO | WO 2017/176806 | A1 | 10/2017 |
| WO | WO 2017/178590 | A1 | 10/2017 |
| WO | WO 2017/180694 | A1 | 10/2017 |
| WO | WO 2017/180711 | A1 | 10/2017 |
| WO | WO 2017/180915 | A2 | 10/2017 |
| WO | WO 2017/180926 | A1 | 10/2017 |
| WO | WO 2017/181107 | A2 | 10/2017 |
| WO | WO 2017/181735 | A2 | 10/2017 |
| WO | WO 2017/182468 | A1 | 10/2017 |
| WO | WO 2017/184334 | A1 | 10/2017 |
| WO | WO 2017/184768 | A1 | 10/2017 |
| WO | WO 2017/184786 | A1 | 10/2017 |
| WO | WO 2017/186550 | A1 | 11/2017 |
| WO | WO 2017/189308 | A1 | 11/2017 |
| WO | WO 2017/189336 | A1 | 11/2017 |
| WO | WO 2017/190041 | A1 | 11/2017 |
| WO | WO 2017/190257 | A1 | 11/2017 |
| WO | WO 2017/190664 | A1 | 11/2017 |
| WO | WO 2017/191210 | A1 | 11/2017 |
| WO | WO 2017/191274 | A2 | 11/2017 |
| WO | WO 2017/192172 | A1 | 11/2017 |
| WO | WO 2017/192512 | A2 | 11/2017 |
| WO | WO 2017/192544 | A1 | 11/2017 |
| WO | WO 2017/192573 | A1 | 11/2017 |
| WO | WO 2017/193029 | A2 | 11/2017 |
| WO | WO 2017/193053 | A1 | 11/2017 |
| WO | WO 2017/196768 | A1 | 11/2017 |
| WO | WO 2017/197038 | A1 | 11/2017 |
| WO | WO 2017/197238 | A1 | 11/2017 |
| WO | WO 2017/197301 | A1 | 11/2017 |
| WO | WO 2017/201476 | A1 | 11/2017 |
| WO | WO 2017/205290 | A1 | 11/2017 |
| WO | WO 2017/205423 | A1 | 11/2017 |
| WO | WO 2017/207589 | A1 | 12/2017 |
| WO | WO 2017/208247 | A1 | 12/2017 |
| WO | WO 2017/209809 | A1 | 12/2017 |
| WO | WO 2017/213896 | A1 | 12/2017 |
| WO | WO 2017/213898 | A2 | 12/2017 |
| WO | WO 2017/214460 | A1 | 12/2017 |
| WO | WO 2017/216392 | A1 | 12/2017 |
| WO | WO 2017/216771 | A2 | 12/2017 |
| WO | WO 2017/218185 | A1 | 12/2017 |
| WO | WO 2017/219027 | A1 | 12/2017 |
| WO | WO 2017/219033 | A1 | 12/2017 |
| WO | WO 2017/220751 | A1 | 12/2017 |
| WO | WO 2017/222370 | A1 | 12/2017 |
| WO | WO 2017/222773 | A1 | 12/2017 |
| WO | WO 2017/222834 | A1 | 12/2017 |
| WO | WO 2017/223107 | A1 | 12/2017 |
| WO | WO 2017/223330 | A1 | 12/2017 |
| WO | WO 2018/000657 | A1 | 1/2018 |
| WO | WO 2018/002719 | A1 | 1/2018 |
| WO | WO 2018/005117 | A1 | 1/2018 |
| WO | WO 2018/005289 | A2 | 1/2018 |
| WO | WO 2018/005691 | A1 | 1/2018 |
| WO | WO 2018/005782 | A1 | 1/2018 |
| WO | WO 2018/005873 | A1 | 1/2018 |
| WO | WO 2018/06693 | A1 | 1/2018 |
| WO | WO 2018/009520 | A1 | 1/2018 |
| WO | WO 2018/009562 | A1 | 1/2018 |
| WO | WO 2018/009822 | A1 | 1/2018 |
| WO | WO 2018/013821 | A1 | 1/2018 |
| WO | WO 2018/013932 | A1 | 1/2018 |
| WO | WO 2018/013990 | A1 | 1/2018 |
| WO | WO 2018/014384 | A1 | 1/2018 |
| WO | WO 2018/015444 | A1 | 1/2018 |
| WO | WO 2018/015936 | A2 | 1/2018 |
| WO | WO 2018/017754 | A1 | 1/2018 |
| WO | WO 2018/018979 | A1 | 2/2018 |
| WO | WO 2018/020248 | A1 | 2/2018 |
| WO | WO 2018/021878 | A1 | 2/2018 |
| WO | WO 2018/022480 | A1 | 2/2018 |
| WO | WO 2018/022634 | A1 | 2/2018 |
| WO | WO 2018/025206 | A1 | 2/2018 |
| WO | WO 2018/026723 | A1 | 2/2018 |
| WO | WO 2018/026976 | A1 | 2/2018 |
| WO | WO 2018/027078 | A1 | 2/2018 |
| WO | WO 2018/030608 | A1 | 2/2018 |
| WO | WO 2018/031683 | A1 | 2/2018 |
| WO | WO 2018/035250 | A1 | 2/2018 |
| WO | WO 2018/035300 | A1 | 2/2018 |
| WO | WO 2018/035423 | A1 | 2/2018 |
| WO | WO 2018/035503 | A1 | 2/2018 |
| WO | WO 2018/039145 | A1 | 3/2018 |
| WO | WO 2018/039438 | A1 | 3/2018 |
| WO | WO 2018/039440 | A1 | 3/2018 |
| WO | WO 2018/039448 | A1 | 3/2018 |
| WO | WO 2018/045630 | A1 | 3/2018 |
| WO | WO 2018/048827 | A1 | 3/2018 |
| WO | WO 2018/049073 | A1 | 3/2018 |
| WO | WO 2018/049168 | A1 | 3/2018 |
| WO | WO 2018/051347 | A1 | 3/2018 |
| WO | WO 2018/058064 | A1 | 3/2018 |
| WO | WO 2018/062866 | A2 | 4/2018 |

(56)         References Cited

FOREIGN PATENT DOCUMENTS

| | | |
|----|----|----|
| WO | WO 2018/064352 A1 | 4/2018 |
| WO | WO 2018/064371 A1 | 4/2018 |
| WO | WO 2018/064516 A1 | 4/2018 |
| WO | WO 2018/067546 A1 | 4/2018 |
| WO | WO 2018/067846 A1 | 4/2018 |
| WO | WO 2018/068053 A2 | 4/2018 |
| WO | WO 2018/069474 A1 | 4/2018 |
| WO | WO 2018/071623 A2 | 4/2018 |
| WO | WO 2018/071663 A1 | 4/2018 |
| WO | WO 2018/071868 A1 | 4/2018 |
| WO | WO 2018/071892 A1 | 4/2018 |
| WO | WO 2018/074979 A1 | 4/2018 |
| WO | WO 2018/079134 A1 | 5/2018 |
| WO | WO 2018/080573 A1 | 5/2018 |
| WO | WO 2018/081504 A1 | 5/2018 |
| WO | WO 2018/081535 A2 | 5/2018 |
| WO | WO 2018/081728 A1 | 5/2018 |
| WO | WO 2018/083128 A2 | 5/2018 |
| WO | WO 2018/083606 A1 | 5/2018 |
| WO | WO 2018/085288 A1 | 5/2018 |
| WO | WO 2018/085414 A1 | 5/2018 |
| WO | WO 2018/086623 A1 | 5/2018 |
| WO | WO 2018/089664 A1 | 5/2018 |
| WO | WO 2018/093990 A1 | 5/2018 |
| WO | WO 2018/098383 A1 | 5/2018 |
| WO | WO 2018/098480 A1 | 5/2018 |
| WO | 2018/119354 A1 | 6/2018 |
| WO | 2018/119359 A1 | 6/2018 |
| WO | WO 2018/098587 A1 | 6/2018 |
| WO | WO 2018/099256 A1 | 6/2018 |
| WO | WO 2018/103686 A1 | 6/2018 |
| WO | WO 2018/106268 A1 | 6/2018 |
| WO | WO 2018/107028 A1 | 6/2018 |
| WO | WO 2018/107103 A1 | 6/2018 |
| WO | WO 2018/107129 A1 | 6/2018 |
| WO | WO 2018/108272 A1 | 6/2018 |
| WO | WO 2018/109101 A1 | 6/2018 |
| WO | WO 2018/111946 A1 | 6/2018 |
| WO | WO 2018/111947 A1 | 6/2018 |
| WO | WO 2018/112336 A1 | 6/2018 |
| WO | WO 2018/112446 A2 | 6/2018 |
| WO | 2018/120283 A1 | 7/2018 |
| WO | WO 2018/130830 A1 | 7/2018 |
| WO | WO 2018/135838 A2 | 7/2018 |
| WO | WO 2018/136396 A2 | 7/2018 |
| WO | WO 2018/138385 A1 | 8/2018 |
| WO | WO 2018/142364 A1 | 8/2018 |
| WO | WO 2018/148246 A1 | 8/2018 |
| WO | WO 2018/148256 A1 | 8/2018 |
| WO | WO 2018/148647 A2 | 8/2018 |
| WO | WO 2018/149418 A1 | 8/2018 |
| WO | WO 2018/149888 A1 | 8/2018 |
| WO | WO 2018/149915 A1 | 8/2018 |
| WO | WO 2018/152197 A1 | 8/2018 |
| WO | WO 2018/152418 A1 | 8/2018 |
| WO | WO 2018/154380 A1 | 8/2018 |
| WO | WO 2018/154387 A1 | 8/2018 |
| WO | WO 2018/154412 A1 | 8/2018 |
| WO | WO 2018/154413 A1 | 8/2018 |
| WO | WO 2018/154418 A1 | 8/2018 |
| WO | WO 2018/154439 A1 | 8/2018 |
| WO | WO 2018/154459 A1 | 8/2018 |
| WO | WO 2018/154462 A2 | 8/2018 |
| WO | WO 2018/156372 A1 | 8/2018 |
| WO | WO 2018/156824 A1 | 8/2018 |
| WO | WO 2018/161009 A1 | 9/2018 |
| WO | WO 2018/165504 A1 | 9/2018 |
| WO | WO 2018/165629 A1 | 9/2018 |
| WO | WO 2018/170015 A1 | 9/2018 |
| WO | WO 2018/170340 A1 | 9/2018 |
| WO | WO 2018/175502 A2 | 9/2018 |
| WO | WO 2018/176009 A1 | 9/2018 |
| WO | WO 2018/177351 A1 | 10/2018 |
| WO | WO 2018/179578 A1 | 10/2018 |
| WO | WO 2018/183403 A1 | 10/2018 |
| WO | WO 2018/189184 A1 | 10/2018 |
| WO | WO 2018/191388 A1 | 10/2018 |
| WO | WO 2018/195402 A1 | 10/2018 |
| WO | WO 2018/195545 A2 | 10/2018 |
| WO | WO 2018/195555 A1 | 10/2018 |
| WO | WO 2018/197020 A1 | 11/2018 |
| WO | WO 2018/197495 A1 | 11/2018 |
| WO | WO 2018/202800 A1 | 11/2018 |
| WO | WO 2018/204493 A1 | 11/2018 |
| WO | WO 2018/208755 A1 | 11/2018 |
| WO | WO 2018/208998 A1 | 11/2018 |
| WO | WO 2018/209158 A2 | 11/2018 |
| WO | WO 2018/209320 A1 | 11/2018 |
| WO | WO 2018/213351 A1 | 11/2018 |
| WO | WO 2018/213708 A1 | 11/2018 |
| WO | WO 2018/213726 A1 | 11/2018 |
| WO | WO 2018/213771 A1 | 11/2018 |
| WO | WO 2018/213791 A1 | 11/2018 |
| WO | WO 2018/217852 A1 | 11/2018 |
| WO | WO 2018/217981 A1 | 11/2018 |
| WO | WO 2018/218166 A1 | 11/2018 |
| WO | WO 2018/218188 A2 | 11/2018 |
| WO | WO 2018/218206 A1 | 11/2018 |
| WO | WO 2019/005884 A1 | 1/2019 |
| WO | WO 2019/005886 A1 | 1/2019 |
| WO | WO 2019/010384 A1 | 1/2019 |
| WO | WO 2019/023680 A1 | 1/2019 |
| WO | WO 2019/051097 A1 | 3/2019 |
| WO | WO 2019/079347 A1 | 4/2019 |
| WO | WO 2019/084062 A1 | 5/2019 |
| WO | WO 2019/118949 A1 | 6/2019 |
| WO | WO 2019/123430 A1 | 6/2019 |
| WO | WO 2019/126709 A1 | 6/2019 |
| WO | WO 2019/139645 A2 | 7/2019 |
| WO | WO 2019/139951 A1 | 7/2019 |
| WO | WO 2019/147014 A1 | 8/2019 |
| WO | WO 2019/161251 A1 | 8/2019 |
| WO | WO 2019/168953 A1 | 9/2019 |
| WO | WO 2019/226953 A1 | 11/2019 |
| WO | WO 2019/236566 A1 | 12/2019 |
| WO | WO 2019/241649 A1 | 12/2019 |
| WO | WO 2020/014261 A1 | 1/2020 |
| WO | WO 2020/028555 A2 | 2/2020 |
| WO | WO 2020/041751 A1 | 2/2020 |
| WO | WO 2020/047124 A1 | 3/2020 |
| WO | WO 2020/051360 A1 | 3/2020 |
| WO | WO 2020/086908 A1 | 4/2020 |
| WO | WO 2020/092453 A1 | 5/2020 |
| WO | WO 2020/102659 A1 | 5/2020 |
| WO | WO 2020/154500 A1 | 7/2020 |
| WO | WO 2020/157008 A1 | 8/2020 |
| WO | WO 2020/180975 A1 | 9/2020 |
| WO | WO 2020/181178 A1 | 9/2020 |
| WO | WO 2020/181180 A1 | 9/2020 |
| WO | WO 2020/181193 A1 | 9/2020 |
| WO | WO 2020/181195 A1 | 9/2020 |
| WO | WO 2020/181202 A1 | 9/2020 |
| WO | WO 2020/191153 A1 | 9/2020 |
| WO | WO 2020/191153 A2 | 9/2020 |
| WO | WO 2020/191171 A1 | 9/2020 |
| WO | WO 2020/191233 A1 | 9/2020 |
| WO | WO 2020/191234 A1 | 9/2020 |
| WO | WO 2020/191239 A1 | 9/2020 |
| WO | WO 2020/191241 A1 | 9/2020 |
| WO | WO 2020/191242 A1 | 9/2020 |
| WO | WO 2020/191243 A1 | 9/2020 |
| WO | WO 2020/191245 A1 | 9/2020 |
| WO | WO 2020/191246 A1 | 9/2020 |
| WO | WO 2020/191248 A1 | 9/2020 |
| WO | WO 2020/191249 A1 | 9/2020 |
| WO | WO 2020/210751 A1 | 10/2020 |
| WO | WO 2020/214842 A1 | 10/2020 |
| WO | WO 2020/236982 A1 | 11/2020 |
| WO | WO 2021/025750 A1 | 2/2021 |
| WO | WO 2021/030666 A1 | 2/2021 |
| WO | WO 2021/072328 A1 | 4/2021 |
| WO | WO 2021/108717 A2 | 6/2021 |
| WO | WO 2021/138469 A1 | 7/2021 |
| WO | WO 2021/155065 A1 | 8/2021 |

(56) References Cited

FOREIGN PATENT DOCUMENTS

| WO | WO 2021/158921 A2 | 8/2021 |
| WO | WO 2021/158995 A1 | 8/2021 |
| WO | WO 2021/158999 A1 | 8/2021 |
| WO | WO 2021/188996 A1 | 9/2021 |
| WO | WO 2021/222318 A1 | 11/2021 |
| WO | WO 2021/226558 A1 | 11/2021 |
| WO | WO 2021/252924 A1 | 12/2021 |
| WO | WO 2022/067130 A2 | 3/2022 |
| WO | WO 2022/150790 A2 | 7/2022 |
| WO | WO 2023/015309 A2 | 2/2023 |
| WO | WO 2023/102537 A2 | 6/2023 |
| WO | WO 2023/102538 A1 | 6/2023 |
| WO | WO 2023/102550 A2 | 6/2023 |
| WO | WO 2023/173140 A2 | 9/2023 |
| WO | WO 2024/155741 A1 | 7/2024 |
| WO | WO 2024/155745 A1 | 7/2024 |
| WO | WO 2024/215652 A2 | 10/2024 |
| WO | WO 2024/254346 A1 | 12/2024 |

OTHER PUBLICATIONS

U.S. Appl. No. 61/717,324, filed Oct. 23, 2012, Cho et al..

U.S. Appl. No. 61/734,256, filed Dec. 6, 2012, Chen et al..

U.S. Appl. No. 61/758,624, filed Jan. 30, 2013, Chen et al..

U.S. Appl. No. 61/761,046, filed Feb. 5, 2013, Knight et al..

U.S. Appl. No. 61/794,422, filed Mar. 15, 2013, Knight et al..

U.S. Appl. No. 61/803,599, filed Mar. 20, 2013, Kim et al..

U.S. Appl. No. 61/836,080, filed Jun. 17, 2013, Zhang et al..

U.S. Appl. No. 61/837,481, filed Jun. 20, 2013, Cho et al..

U.S. Appl. No. 61/838,178, filed Jun. 21, 2013, Joung et al.

U.S. Appl. No. 61/874,682, filed Sep. 6, 2013, Liu et al.

U.S. Appl. No. 61/874,746, filed Sep. 6, 2013, Liu et al.

U.S. Appl. No. 62/288,661, filed Jan. 29, 2016, Muir et al.

U.S. Appl. No. 62/357,332, filed Jun. 30, 2016, Liu et al.

U.S. Appl. No. 62/498,686.

Invitation to Pay Additional Fees for PCT/US2014/054291, mailed Dec. 18, 2014.

International Search Report and Written Opinion for PCT/US2014/054291, mailed Mar. 27, 2015.

International Preliminary Report on Patentability for PCT/US2014/054291, mailed Mar. 17, 2016.

Extended European Search Report for EP18199195.1, mailed Feb. 12, 2019.

Extended European Search Report for EP 19181479.7, mailed Oct. 31, 2019.

International Preliminary Report on Patentability for PCT/US2014/048390, mailed on Mar. 7, 2019.

International Preliminary Report on Patentability for PCT/US2017/068114, mailed on Jul. 4, 2019.

International Preliminary Report on Patentability for PCT/US2017/068105, mailed on Jul. 4, 2019.

International Preliminary Report on Patentability for PCT/US2018/021880, mailed on Sep. 19, 2019.

International Preliminary Report on Patentability for PCT/US2017/046144, mailed Feb. 21, 2019.

International Preliminary Report on Patentability for PCT/US2017/045381, mailed Feb. 14, 2019.

International Preliminary Report on Patentability for PCT/US2018/021664, mailed on Sep. 19, 2019.

International Preliminary Report on Patentability for PCT/US2017/056671, mailed on Apr. 25, 2019.

International Preliminary Report on Patentability for PCT/US2018/021878, mailed on Sep. 19, 2019.

International Preliminary Report on Patentability for PCT/US2018/024208, mailed on Oct. 3, 2019.

[No Author Listed] NCBI Accession No. XP_015843220.1. C →U editing enzyme APOBEC-1 [Peromyscus maniculatus bairdii], XP002793540. Mar. 21, 2016.

[No Author Listed] Score result for SEQ 355 to WO2017032580. Muir et al. 2016.

[No Author Listed], "Lambda DNA" from Catalog & Technical Reference. New England Biolabs Inc. 2002/2003. pp. 133 and 270-273.

[No Author Listed], EMBL Accession No. Q99ZW2. Nov. 2012. 2 pages.

[No Author Listed], Invitrogen Lipofectamine™ 2000 product sheets, 2002. 2 pages.

[No Author Listed], Invitrogen Lipofectamine™ 2000 product sheets, 2005. 3 pages.

[No Author Listed], Invitrogen Lipofectamine™ LTX product sheets, 2011. 4 pages.

[No Author Listed], Mus musculus (Mouse). UniProtKB Accession No. P51908 (ABEC1_MOUSE). Oct. 1, 1996. 10 pages.

[No Author Listed], Thermo Fisher Scientific—How Cationic Lipid Mediated Transfection Works, retrieved from the internet Aug. 27, 2015. 2 pages.

Abremski et al., Bacteriophage P1 site-specific recombination. Purification and properties of the Cre recombinase protein. J Biol Chem. Feb. 10, 1984;259(3):1509-14.

Abudayyeh et al., C2c2 is a single-component programmable RNA-guided RNA-targeting CRISPR effector. Science Aug. 2016;353(6299):aaf5573. DOI: 10.1126/science.aaf5573.

Ada et al., Carbohydrate-protein conjugate vaccines. Clin Microbiol Infect. Feb. 2003;9(2):79-85. doi: 10.1046/j.1469-0691.2003.00530.x.

Adamala et al., Programmable RNA-binding protein composed of repeats of a single modular unit. Proc Natl Acad Sci U S A. May 10, 2016;113(19):E2579-88. doi: 10.1073/pnas.1519368113. Epub Apr. 26, 2016.

Adams et al., New biarsenical ligands and tetracysteine motifs for protein labeling in vitro and in vivo: synthesis and biological applications. J Am Chem Soc. May 29, 2002;124(21):6063-76. doi: 10.1021/ja017687n.

Aguilo et al., Coordination of m(6)A mRNA Methylation and Gene Transcription by ZFP217 Regulates Pluripotency and Reprogramming. Cell Stem Cell. Dec. 3, 2015;17(6):689-704. doi: 10.1016/j.stem.2015.09.005. Epub Oct. 29, 2015.

Ahmad et al., Antibody-mediated specific binding and cytotoxicity of liposome-entrapped doxorubicin to lung cancer cells in vitro. Cancer Res. Sep. 1, 1992;52(17):4817-20.

Aihara et al., A conformational switch controls the DNA cleavage activity of lambda integrase. Mol Cell. Jul. 2003;12(1):187-98.

Aik et al., Structure of human RNA $N^6$-methyladenine demethylase ALKBH5 provides insights into its mechanisms of nucleic acid recognition and demethylation. Nucleic Acids Res. Apr. 2014;42(7):4741-54. doi: 10.1093/nar/gku085. Epub Jan. 30, 2014.

Akins et al., Mitochondrial plasmids of Neurospora: integration into mitochondrial DNA and evidence for reverse transcription in mitochondria. Cell. Nov. 21, 1986;47(4):505-16. doi: 10.1016/0092-8674(86)90615-x.

Akinsheye et al., Fetal hemoglobin in sickle cell anemia. Blood. Jul. 7, 2011;118(1):19-27. doi: 10.1182/blood-2011-03-325258. Epub Apr. 13, 2011.

Akopian et al., Chimeric recombinases with designed DNA sequence recognition. Proc Natl Acad Sci U S A. Jul. 22, 2003;100(15):8688-91. Epub Jul. 1, 2003.

Alarcón et al., HNRNPA2B1 Is a Mediator of m(6)A-Dependent Nuclear RNA Processing Events. Cell. Sep. 10, 2015;162(6):1299-308. doi: 10.1016/j.cell.2015.08.011. Epub Aug. 27, 2015.

Alarcón et al., N6-methyladenosine marks primary microRNAs for processing. Nature. Mar. 26, 2015;519(7544):482-5. doi: 10.1038/nature14281. Epub Mar. 18, 2015.

Alexander, HFE-associated hereditary hemochromatosis. Genet Med. May 2009;11(5):307-13. doi: 10.1097/GIM.0b013e31819d30f2.

Alexandrov et al., Signatures of mutational processes in human cancer. Nature. Aug. 22, 2013;500(7463):415-21. doi: 10.1038/nature12477. Epub Aug. 14, 2013.

Ali et al., Novel genetic abnormalities in Bernard-Soulier syndrome in India. Ann Hematol. Mar. 2014;93(3):381-4. doi: 10.1007/s00277-013-1895-x. Epub Sep. 1, 2013.

Altschul et al., Basic local alignment search tool. J Mol Biol. Oct. 5, 1990;215(3):403-10. doi: 10.1016/S0022-2836(05)80360-2.

(56) References Cited

OTHER PUBLICATIONS

Amato et al., Interpreting elevated fetal hemoglobin in pathology and health at the basic laboratory level: new and known γ-gene mutations associated with hereditary persistence of fetal hemoglobin. Int J Lab Hematol. Feb. 2014;36(1):13-9. doi: 10.1111/ijlh. 12094. Epub Apr. 29, 2013.

Ames et al., A eubacterial riboswitch class that senses the coenzyme tetrahydrofolate. Chem Biol. Jul. 30, 2010;17(7):681-5. doi: 10.1016/j.chembiol.2010.05.020.

Amrann et al., Tightly regulated tac promoter vectors useful for the expression of unfused and fused proteins in Escherichia coli. Gene. Sep. 30, 1988;69(2):301-15.

Anders et al., Chapter One: In Vitro Enzymology of Cas9. in Methods in Enzymology, eds Doudna et al. 2014: 546:1-20.

Anders et al., Structural basis of PAM-dependent target DNA recognition by the Cas9 endonuclease. Nature. Sep. 25, 2014;513(7519):569-73. doi: 10.1038/nature13579. Epub Jul. 27, 2014.

Anderson, Human gene therapy. Science. May 8, 1992;256(5058):808-13. doi: 10.1126/science.1589762.

André et al., Axotomy-induced expression of calcium-activated chloride current in subpopulations of mouse dorsal root ganglion neurons. J Neurophysiol. Dec. 2003;90(6):3764-73. doi: 10.1152/jn.00449.2003. Epub Aug. 27, 2003.

Anzalone et al., Reprogramming eukaryotic translation with ligand-responsive synthetic RNA switches. Nat Methods. May 2016;13(5):453-8. doi: 10.1038/nmeth.3807. Epub Mar. 21, 2016.

Aplan, Causes of oncogenic chromosomal translocation. Trends Genet. Jan. 2006;22(1):46-55. doi: 10.1016/j.tig.2005.10.002. Epub Oct. 2, 20058.

Arakawa et al., A method to convert mRNA into a gRNA library for CRISPR/Cas9 editing of any organism. Sci Adv. Aug. 24, 2016;2(8):e1600699. doi: 10.1126/sciadv.1600699.

Araki et al., Comparative analysis of right element mutant lox sites on recombination efficiency in embryonic stem cells. BMC Biotechnol. Mar. 31, 2010;10:29. doi: 10.1186/1472-6750-10-29.

Araki et al., Site-specific recombinase, R, encoded by yeast plasmid pSR1. J Mol Biol. May 5, 1992;225(1):25-37. doi: 10.1016/0022-2836(92)91023-i.

Araki et al., Targeted integration of DNA using mutant lox sites in embryonic stem cells. Nucleic Acids Res. Feb. 15, 1997;25(4):868-72. doi: 10.1093/nar/25.4.868.

Arambula et al., Surface display of a massively variable lipoprotein by a Legionella diversity-generating retroelement. Proc Natl Acad Sci U S A. May 14, 2013;110(20):8212-7. doi: 10.1073/pnas.1301366110. Epub Apr. 30, 2013.

Arbab et al., Cloning-free CRISPR. Stem Cell Reports. Nov. 10, 2015;5(5):908-917. doi: 10.1016/j.stemcr.2015.09.022. Epub Oct. 29, 2015.

Arezi et al., Novel mutations in Moloney Murine Leukemia Virus reverse transcriptase increase thermostability through tighter binding to template-primer. Nucleic Acids Res. Feb. 2009;37(2):473-81. doi: 10.1093/nar/gkn952. Epub Dec. 4, 2008.

Arnold et al., Mutants of Tn3 resolvase which do not require accessory binding sites for recombination activity. EMBO J. Mar. 1, 1999;18(5):1407-14.

Asante et al., A naturally occurring variant of the human prion protein completely prevents prion disease. Nature. Jun. 25, 2015;522(7557):478-81. doi: 10.1038/nature14510. Epub Jun. 10, 2015.

Asokan et al., The AAV vector toolkit: poised at the clinical crossroads. Mol Ther. Apr. 2012;20(4):699-708. doi: 10.1038/mt. 2011.287. Epub Jan. 24, 2012.

Atkins et al., Ribosomal frameshifting and transcriptional slippage: From genetic steganography and cryptography to adventitious use. Nucleic Acids Res. Sep. 6, 2016;44(15):7007-78. doi: 10.1093/nar/gkw530. Epub Jul. 19, 2016.

Auer et al., Highly efficient CRISPR/Cas9-mediated knock-in in zebrafish by homology-independent DNA repair. Genome Res. Jan. 2014;24(1):142-53. doi: 10.1101/gr.161638.113. Epub Oct. 31, 2013.

Auricchio et al., Exchange of surface proteins impacts on viral vector cellular specificity and transduction characteristics: the retina as a model. Hum Mol Genet. Dec. 15, 2001;10(26):3075- 81. doi: 10.1093/hmg/10.26.3075.

Autieri et al., IRT-1, a novel interferon-gamma-responsive transcript encoding a growth-suppressing basic leucine zipper protein. J Biol Chem. Jun. 12, 1998;273(24):14731-7. doi: 10.1074/jbc.273.24. 14731.

Avidan et al., The processivity and fidelity of DNA synthesis exhibited by the reverse transcriptase of bovine leukemia virus. Eur J Biochem. Feb. 2002;269(3):859-67. doi: 10.1046/j.0014-2956. 2001.02719.x.

Baba et al., Construction of Escherichia coli K-12 in-frame, single-gene knockout mutants: the Keio collection. Mol Syst Biol. 2006;2:2006. 0008. doi: 10.1038/msb4100050. Epub Feb. 21, 2006.

Bacman et al., Specific elimination of mutant mitochondrial genomes in patient-derived cells by mitoTALENs. Nat Med. Sep. 2013;19(9):1111-3. doi: 10.1038/nm.3261. Epub Aug. 4, 2013.

Badran et al., Continuous evolution of Bacillus thuringiensis toxins overcomes insect resistance. Nature. May 5, 2016;533(7601):58-63. doi: 10.1038/nature17938. Epub Apr. 27, 2016.

Badran et al., Development of potent in vivo mutagenesis plasmids with broad mutational spectra. Nat Commun. Oct. 7, 2015;6:8425. doi: 10.1038/ncomms9425.

Badran et al., In vivo continuous directed evolution. Curr Opin Chem Biol. Feb. 2015;24:1-10. doi: 10.1016/j.cbpa.2014.09.040. Epub Nov. 7, 2014.

Bae et al., Cas-OFFinder: a fast and versatile algorithm that searches for potential off-target sites of Cas9 RNA-guided endonucleases. Bioinformatics. May 15, 2014;30(10):1473-5. doi: 10.1093/bioinformatics/btu048. Epub Jan. 24, 2014.

Bae et al., Microhomology-based choice of Cas9 nuclease target sites. Nat Methods. Jul. 2014;11(7):705-6. doi: 10.1038/nmeth. 3015.

Bagal et al., Recent progress in sodium channel modulators for pain. Bioorg Med Chem Lett. Aug. 15, 2014;24(16):3690-9. doi: 10.1016/j.bmcl.2014.06.038. Epub Jun. 21, 2014.

Balakrishnan et al., Flap endonuclease 1. Annu Rev Biochem. 2013;82:119-38. doi: 10.1146/annurev-biochem-072511-122603. Epub Feb. 28, 2013.

Baldari et al., A novel leader peptide which allows efficient secretion of a fragment of human interleukin 1 beta in Saccharomyces cerevisiae. EMBO J. Jan. 1987;6(1):229-34.

Banerjee et al., Cadmium inhibits mismatch repair by blocking the ATPase activity of the MSH2-MSH6 complex [published correction appears in Nucleic Acids Res. 2005;33(5):1738]. Nucleic Acids Res. 2005;33(4):1410-1419. Published Mar. 3, 2005. doi: 10.1093/nar/gki291.

Banerji et al., A lymphocyte-specific cellular enhancer is located downstream of the joining region in immunoglobulin heavy chain genes. Cell. Jul. 1983;33(3):729-40. doi: 10.1016/0092-8674(83)90015-6.

Bannert et al., Retroelements and the human genome: new perspectives on an old relation. Proc Natl Acad Sci U S A. Oct. 5, 2004;101 Suppl 2(Suppl 2):14572-9. doi: 10.1073/pnas.0404838101. Epub Aug. 13, 2004.

Baranauskas et al., Generation and characterization of new highly thermostable and processive M-MuLV reverse transcriptase variants. Protein Eng Des Sel. Oct. 2012;25(10):657-68. doi: 10.1093/protein/gzs034. Epub Jun. 12, 2012.

Barmania et al., C—C chemokine receptor type five (CCR5): An emerging target for the control of HIV infection. Appl Transl Genom. May 26, 2013;2:3-16. doi: 10.1016/j.atg.2013.05.004.

Barnes et al., Repair and genetic consequences of endogenous DNA base damage in mammalian cells. Annu Rev Genet. 2004;38:445-76.

Barnes et al., The fidelity of Taq polymerase catalyzing PCR is improved by an N-terminal deletion. Gene. Mar. 1, 1992;112(1):29-35. doi: 10.1016/0378-1119(92)90299-5.

Barrangou et al., CRISPR provides acquired resistance against viruses in prokaryotes. Science. Mar. 23, 2007;315(5819):1709-12.

Barrangou, RNA-mediated programmable DNA cleavage. Nat Biotechnol. Sep. 2012;30(9):836-8. doi: 10.1038/nbt.2357.

(56)　　　　　References Cited

OTHER PUBLICATIONS

Bartlett et al., Efficient expression of protein coding genes from the murine U1 small nuclear RNA promoters. Proc Natl Acad Sci U S A. Aug. 20, 1996;93(17):8852-7. doi: 10.1073/pnas.93.17.8852.

Bass, B.L., RNA editing by adenosine deaminases that act on RNA. Annu Rev Biochem. 2002;71:817-46. doi: 10.1146/annurev.biochem. 71.110601.135501. Epub Nov. 9, 2001.

Basturea et al., Substrate specificity and properties of the *Escherichia coli* 16S rRNA methyltransferase, RsmE. RNA. Nov. 2007;13(11):1969-76. doi: 10.1261/rna.700507. Epub Sep. 13, 2007.

Batey et al., Structure of a natural guanine-responsive riboswitch complexed with the metabolite hypoxanthine. Nature. Nov. 18, 2004;432(7015):411-5.

Beale et al., Comparison of the differential context-dependence of DNA deamination by APOBEC enzymes: correlation with mutation spectra in vivo. J Mol Biol. Mar. 26, 2004;337(3):585-96.

Beaudry et al., Directed evolution of an RNA enzyme. Science. Jul. 31, 1992;257(5070):635-41. doi: 10.1126/science.1496376.

Bebenek et al., Error-prone polymerization by HIV-1 reverse transcriptase. Contribution of template-primer misalignment, miscoding, and termination probability to mutational hot spots. J Biol Chem. May 15, 1993;268(14):10324-34.

Bedell et al., In vivo genome editing using a high-efficiency TALEN system. Nature. Nov. 1, 2012;491(7422):114-8. Doi: 10.1038/nature11537. Epub Sep. 23, 2012.

Begley, Scientists unveil the 'most clever CRISPR gadget' so far. STAT, Apr. 20, 2016. https://www.statnews.com/2016/04/20/clever-crispr-advance-unveiled/.

Behr, Gene transfer with synthetic cationic amphiphiles: prospects for gene therapy. Bioconjug Chem. Sep.-Oct. 1994;5(5):382-9. doi: 10.1021/bc00029a002.

Bell et al., Ribozyme-catalyzed excision of targeted sequences from within RNAs. Biochemistry. Dec. 24, 2002;41(51):15327-33. doi: 10.1021/bi0267386.

Belshaw et al., Controlling programmed cell death with a cyclophilin-cyclosporin-based chemical inducer of dimerization. Chem Biol. Sep. 1996;3(9):731-8. doi: 10.1016/s1074-5521(96)90249-5.

Belshaw et al., Controlling protein association and subcellular localization with a synthetic ligand that induces heterodimerization of proteins. Proc Natl Acad Sci U S A. May 14, 1996;93(10):4604-7. doi: 10.1073/pnas.93.10.4604.

Benarroch, HCN channels: function and clinical implications. Neurology. Jan. 15, 2013;80(3):304-10. doi: 10.1212/WNL. 0b013e31827dec42.

Bennett et al., Painful and painless channelopathies. Lancet Neurol. Jun. 2014;13(6):587-99. doi: 10.1016/S1474-4422(14)70024-9. Epub May 6, 2014.

Bentin, T., A ribozyme transcribed by a ribozyme. Artif DNA PNA XNA. Apr. 2011;2(2):40-42. doi: 10.4161/adna.2.2.16852.

Berger et al., Reverse transcriptase and its associated ribonuclease H: interplay of two enzyme activities controls the yield of single-stranded complementary deoxyribonucleic acid. Biochemistry. May 10, 1983;22(10):2365-72. doi: 10.1021/bi00279a010.

Berges et al., Transduction of brain by herpes simplex virus vectors. Mol Ther. Jan. 2007;15(1):20-9. doi: 10.1038/sj.mt.6300018.

Berkhout et al., Identification of an active reverse transcriptase enzyme encoded by a human endogenous HERV-K retrovirus. J Virol. Mar. 1999;73(3):2365-75. doi: 10.1128/JVI.73.3.2365-2375. 1999.

Bernhart et al., Local RNA base pairing probabilities in large sequences. Bioinformatics. Mar. 1, 2006;22(5):614-5. doi: 10.1093/bioinformatics/btk014. Epub Dec. 20, 2005.

Bernstein et al., Role for a bidentate ribonuclease in the initiation step of RNA interference. Nature. Jan. 18, 2001;409(6818):363-6. doi: 10.1038/35053110.

Bershtein et al., Advances in laboratory evolution of enzymes. Curr Opin; Chem Biol. Apr. 2008;12(2):151-8. doi: 10.1016/j.cbpa.2008. 01.027. Epub Mar. 7, 2008. Review.

Bertolotti et al., Toward genosafe endonuclease-boosted gene targeting using breakthrough CRISP/Cas9 for next generation stem cell gene therapy culminating in efficient ex Vivo in Vivo gene repair/genomic editing. Molecular Therapy. May 2015;23(Suppl1):S139. Abstract 350. 18th Ann Meeting of the American Society of Gene and Cell Therapy. ASGCT 2015. New Orleans, LA. May 13, 2015-May 16, 2015.

Bertrand et al., Localization of ASH1 mRNA particles in living yeast. Mol Cell. Oct. 1998;2(4):437-45. doi: 10.1016/s1097-2765(00)80143-4.

Beumer et al., Efficient gene targeting in *Drosophila* with zinc-finger nucleases. Genetics. Apr. 2006;172(4):2391-403. Epub Feb. 1, 2006.

Bhagwat, DNA-cytosine deaminases: from antibody maturation to antiviral defense. DNA Repair (Amst). Jan. 5, 2004;3(1):85-9.

Bi et al., Pseudo attP sites in favor of transgene integration and expression in cultured porcine cells identified by Streptomyces phage phiC31 integrase. BMC Mol Biol. Sep. 8, 2013;14:20. doi: 10.1186/1471-2199-14-20.

Bibb et al., Integration and excision by the large serine recombinase phiRv1 integrase. Mol Microbiol. Mar. 2005;55(6):1896-910. doi: 10.1111/j.1365-2958.2005.04517.x.

Bibikova et al., Stimulation of homologous recombination through targeted cleavage by chimeric nucleases. Mol Cell Biol. Jan. 2001;21(1):289-97.

Birling et al., Site-specific recombinases for manipulation of the mouse genome. Methods Mol Biol. 2009;561:245-63. doi: 10.1007/978-1-60327-019-9_16.

Biswas et al., A structural basis for allosteric control of DNA recombination by lambda integrase. Nature. Jun. 23, 2005;435(7045):1059-66. doi: 10.1038/nature03657.

Bitinaite et al., FokI dimerization is required for DNA cleavage. Proc Natl Acad Sci U S A. Sep. 1, 1998;95(18):10570-5.

Blaese et al., Vectors in cancer therapy: how will they deliver? Cancer Gene Ther. Dec. 1995;2(4):291-7.

Blain et al., Nuclease activities of Moloney murine leukemia virus reverse transcriptase. Mutants with altered substrate specificities. J Biol Chem. Nov. 5, 1993;268(31):23585-92.

Blaisonneau et al., A circular plasmid from the yeast Torulaspora delbrueckii. Plasmid. 1997;38(3):202-9. doi: 10.1006/plas.1997. 1315.

Blau et al., A proliferation switch for genetically modified cells. PNAS Apr. 1, 1997 94 (7) 3076-3081; https://doi.org/10.1073/pnas. 94.7.3076.

Blauw et al., SMN1 gene duplications are associated with sporadic ALS. Neurology. Mar. 1, 20123;78(11):776-80. doi: 10.1212/WNL. 0b013e318249f697. Epub Feb. 8, 2012.

Bloom et al., Evolving strategies for enzyme engineering. Curr Opin Struct Biol. Aug. 2005; 15(4):447-52.

Boch, TALEs of genome targeting. Nat Biotechnol. Feb. 2011;29(2):135-6. Doi: 10.1038/nbt.1767.

Bodi et al., Yeast m6A Methylated mRNAs Are Enriched on Translating Ribosomes during Meiosis, and under Rapamycin Treatment. PLoS One. Jul. 17, 2015;10(7):e0132090. doi: 10.1371/journal. pone.0132090.

Boeckle et al., Melittin analogs with high lytic activity at endosomal pH enhance transfection with purified targeted PEI polyplexes. J Control Release. May 15, 2006;112(2):240-8. Epub Mar. 20, 2006.

Boersma et al., Selection strategies for improved biocatalysts. Febs J. May 2007;274(9):2181-95.

Bogdanove et al., TAL effectors: customizable proteins for DNA targeting. Science. Sep. 3, 20110;333(6051):1843-6. doi: 10.1126/science.1204094.

Bohlke et al., Sense codon emancipation for proteome-wide incorporation of noncanonical amino acids: rare isoleucine codon AUA as a target for genetic code expansion. FEMS Microbiol Lett. Feb. 2014;351(2):133-44. doi: 10.1111/1574-6968.12371. Epub Jan. 27, 2014.

Bolotin et al., Clustered regularly interspaced short palindrome repeats (CRISPRs) have spacers of extrachromosomal origin. Microbiology. Aug. 2005;151(Pt 8):2551-61.

Bolusani et al., Evolution of variants of yeast site-specific recombinase Flp that utilize native genomic sequences as recombination target sites. Nucleic Acids Res. 2006;34(18):5259-69. Epub Sep. 26, 2006.

(56)          References Cited

OTHER PUBLICATIONS

Bondeson et al., Inversion of the IDS gene resulting from recombination with IDS-related sequences is a common cause of the Hunter syndrome. Hum Mol Genet. Apr. 1995;4(4):615-21. doi: 10.1093/hmg/4.4.615.

Borchardt et al., Controlling mRNA stability and translation with the CRISPR endoribonuclease Csy4. RNA. Nov. 2015;21(11):1921-30. doi: 10.1261/rna.051227.115. Epub Sep. 9, 2015.

Borman, Improved route to single-base genome editing. Chemical & Engineering News, Apr. 25, 2016;94(17)p5. http://cen.acs.org/articles/94/i17/Improved-route-single-base-genome.html.

Bourinet et al., Silencing of the Cav3.2 T-type calcium channel gene in sensory neurons demonstrates its major role in nociception. EMBO J. Jan. 26, 2005;24(2):315-24. doi: 10.1038/sj.emboj.7600515. Epub Dec. 16, 2004.

Boutabout et al., DNA synthesis fidelity by the reverse transcriptase of the yeast retrotransposon Ty1. Nucleic Acids Res. Jun. 1, 2001;29(11):2217-22. doi: 10.1093/nar/29.11.2217.

Box et al., A multi-domain protein system based on the HC fragment of tetanus toxin for targeting DNA to neuronal cells. J Drug Target. Jul. 2003;11(6):333-43. doi: 10.1080/10611863100001634667.

Branden and Tooze, Introduction to Protein Structure. 1999; 2nd edition. Garland Science Publisher: 3-12.

Braun et al., Immunogenic duplex nucleic acids are nuclease resistant. J Immunol. Sep. 15, 1988;141(6):2084-9.

Brierley et al., Viral RNA pseudoknots: versatile motifs in gene expression and replication. Nat Rev Microbiol. Aug. 2007;5(8):598-610. doi: 10.1038/nrmicro1704.

Briner et al., Guide RNA functional modules direct Cas9 activity and orthogonality. Mol Cell. Oct. 23, 2014;56(2):333-339. doi: 10.1016/j.molcel.2014.09.019.

Britt et al., Re-engineering plant gene targeting. Trends Plant Sci. Feb. 2003;8(2):90-5.

Brouns et al., Small CRISPR RNAs guide antiviral defense in prokaryotes. Science. Aug. 15, 2008;321(5891):960-4. doi: 10.1126/science.1159689.

Brown et al., A mammalian protein targeted by G1-arresting rapamycin-receptor complex. Nature. Jun. 30, 1994;369(6483):756-8. doi: 10.1038/369756a0.

Brown et al., Characterization of the genetic elements required for site-specific integration of plasmid pSE211 in Saccharopolyspora erythraea. J Bacteriol. Apr. 1990;172(4):1877-88. doi: 10.1128/jb.172.4.1877-1888.1990.

Brown et al., Serine recombinases as tools for genome engineering. Methods. Apr. 2011;53(4):372-9. doi: 10.1016/j.ymeth.2010.12.031. Epub Dec. 30, 2010.

Brown et al., Structural insights into the stabilization of MALAT1 noncoding RNA by a bipartite triple helix. Nat Struct Mol Biol. Jul. 2014;21(7):633-40. doi: 10.1038/nsmb.2844. Epub Jun. 22, 2014.

Brusse et al., Spinocerebellar ataxia associated with a mutation in the fibroblast growth factor 14 gene (SCA27): A new phenotype. Mov Disord. Mar. 2006;21(3):396-401.

Brutlag et al., Improved sensitivity of biological sequence database searches. Comput Appl Biosci. Jul. 1990;6(3):237-45. doi: 10.1093/bioinformatics/6.3.237.

Brzezicha et al., Identification of human tRNA:m5C methyltransferase catalysing intron-dependent m5C formation in the first position of the anticodon of the pre-tRNA Leu (CAA). Nucleic Acids Res. 2006;34(20):6034-43. doi: 10.1093/nar/gk1765. Epub Oct. 27, 2006.

Buchholz et al., Alteration of Cre recombinase site specificity by substrate-linked protein evolution. Nat Biotechnol. Nov. 2001;19(11):1047-52.

Buchschacher et al., Human immunodeficiency virus vectors for inducible expression of foreign genes. J Virol. May 1992;66(5):2731-9. doi: 10.1128/JVI.66.5.2731-2739.1992.

Buchwald et al., Long-term, continuous intravenous heparin administration by an implantable infusion pump in ambulatory patients with recurrent venous thrombosis. Surgery. Oct. 1980;88(4):507-16.

Buckley et al., Targeting the von Hippel-Lindau E3 ubiquitin ligase using small molecules to disrupt the VHL/HIF-1 α interaction. J Am Chem Soc. Mar. 14, 2012;134(10):4465-8. doi: 10.1021/ja209924v. Epub Feb. 27, 2012.

Budisa et al., Residue-specific bioincorporation of non-natural, biologically active amino acids into proteins as possible drug carriers: structure and stability of the per-thiaproline mutant of annexin V. Proc Natl Acad Sci U S A. Jan. 20, 1998;95(2):455-9.

Budker et al., Protein/amphipathic polyamine complexes enable highly efficient transfection with minimal toxicity. Biotechniques. Jul. 1997;23(1):139, 142-7. doi: 10.2144/97231rr02.

Budworth et al., A brief history of triplet repeat diseases. Methods Mol Biol. 2013; 1010:3-17. doi: 10.1007/978-1-62703-411-1_1.

Bulow et al., Multienzyme systems obtained by gene fusion. Trends Biotechnol. Jul. 1991;9(7):226-31.

Burke et al., Activating mutations of Tn3 resolvase marking interfaces important in recombination catalysis and its regulation. Mol Microbiol. Feb. 2004;51(4):937-48.

Burke et al., RNA Aptamers to the Adenosine Moiety of S-adenosyl Methionine: Structural Inferences From Variations on a Theme and the Reproducibility of SELEX. Nucleic Acids Res. May 15, 1997;25(10):2020-4. doi: 10.1093/nar/25.10.2020.

Burton et al., Gene delivery using herpes simplex virus vectors. DNA Cell Biol. Dec. 2002;21(12):915-36. doi: 10.1089/104454902762053864.

Buskirk et al., Directed evolution of ligand dependence: small-molecule-activated protein splicing. Proc Natl Acad Sci U S A. Jul. 20, 2004;101(29):10505-10. Epub Jul. 9, 2004.

Buskirk et al., In vivo evolution of an RNA-based transcriptional activator. Chem Biol. Jun. 2003;10(6):533-40. doi: 10.1016/s1074-5521(03)00109-1.

Byrne et al., Multiplex gene regulation: a two-tiered approach to transgene regulation in transgenic mice. Proc Natl Acad Sci U S A. Jul. 1989;86(14):5473-7. doi: 10.1073/pnas.86.14.5473.

Böck et al., Selenocysteine: the 21st amino acid. Mol Microbiol. Mar. 1991;5(3):515-20.

Cade et al., Highly efficient generation of heritable zebrafish gene mutations using homo-and heterodimeric TALENs. Nucleic Acids Res. Sep. 2012;40(16):8001-10. Doi: 10.1093/nar/gks518. Epub Jun. 7, 2012.

Cadwell et al., Randomization of genes by PCR mutagenesis. PCR Methods Appl. Aug. 1992;2(1):28-33. doi: 10.1101/gr.2.1.28.

Cai et al., Reconstruction of ancestral protein sequences and its applications. BMC Evol Biol. Sep. 17, 2004;4:33. doi: 10.1186/1471-2148-4-33.

Calame et al., Transcriptional controlling elements in the immunoglobulin and T cell receptor loci. Adv Immunol. 1988;43:235-75. doi: 10.1016/s0065-2776(08)60367-3.

Caldecott et al., Single-strand break repair and genetic disease. Nat Rev Genet. Aug. 2008;9(8):619-31. doi: 10.1038/nrg2380.

Camarero et al., Biosynthesis of a Head-to-Tail Cyclized Protein with Improved Biological Activity. J. Am. Chem. Soc. May 29, 1999; 121(23):5597-5598. https://doi.org/10.1021/ja990929n.

Cameron, Recent advances in transgenic technology. Mol Biotechnol. Jun. 1997;7(3):253-65.

Camper et al., Postnatal repression of the alpha-fetoprotein gene is enhancer independent. Genes Dev. Apr. 1989;3(4):537-46. doi: 10.1101/gad.3.4.537.

Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.

Canchaya et al., Genome analysis of an inducible prophage and prophage remnants integrated in the *Streptococcus pyogenes* strain SF370. Virology. Oct. 25, 2002;302(2):245-58. doi: 10.1006/viro.2002.1570.

Canver et al., Customizing the genome as therapy for the ß-hemoglobinopathies. Blood. May 26, 2016;127(21):2536-45. doi: 10.1182/blood-2016-01-678128. Epub Apr. 6, 2016.

Cao et al., Rapamycin reverses cellular phenotypes and enhances mutant protein clearance in Hutchinson-Gilford progeria syndrome cells. Sci Transl Med. Jun. 29, 2011;3(89):89ra58. doi: 10.1126/scitranslmed.3002346.

(56)                References Cited

OTHER PUBLICATIONS

Cargill et al., Characterization of single-nucleotide polymorphisms in coding regions of human genes. Nat Genet. Jul. 1999;22(3):231-8.

Carlier et al., Burkholderia cenocepacia H111 Rhy-family protein. Apr. 16, 2015. Retrieved from the Internet via https://www.ebi.ac.uk/ena/browser/api/embl/CDN65395.1?lineLimit=1000. Last retrieved Apr. 26, 2021.

Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.

Caron et al., Intracellular delivery of a Tat-eGFP fusion protein into muscle cells. Mol Ther. Mar. 2001;3(3):310-8.

Carr et al., Genome engineering. Nat Biotechnol. Dec. 2009;27(12):1151-62. doi: 10.1038/nbt.1590.

Carroll et al., Gene targeting in Drosophila and Caenorhabditis elegans with zinc-finger nucleases. Methods Mol Biol. 2008;435:63-77. doi: 10.1007/978-1-59745-232-8_5.

Carroll et al., Progress and prospects: zinc-finger nucleases as gene therapy agents. Gene Ther. Nov. 2008;15(22):1463-8. doi: 10.1038/gt.2008.145. Epub Sep. 11, 2008.

Carroll, A CRISPR approach to gene targeting. Mol Ther. Sep. 2012;20(9):1658-60. doi: 10.1038/mt.2012.171.

Carroll, Genome engineering with zinc-finger nucleases. Genetics. Aug. 2011;188(4):773-82. doi: 10.1534/genetics.111.131433. Review.

Cartegni et al., Determinants of exon 7 splicing in the spinal muscular atrophy genes, SMN1 and SMN2. Am J Hum Genet. Jan. 2006;78(1):63-77. doi: 10.1086/498853. Epub Nov. 16, 2005.

Carvalho et al., Evolution in health and medicine Sackler colloquium: Genomic disorders: a window into human gene and genome evolution. Proc Natl Acad Sci U S A. Jan. 26, 2010;107 Suppl 1(Suppl 1):1765-71. doi: 10.1073/pnas.0906222107. Epub Jan. 13, 2010.

Caspi et al., Distribution of split DnaE inteins in cyanobacteria. Mol Microbiol. Dec. 2003;50(5):1569-77. doi: 10.1046/j.1365-2958.2003.03825.x.

Cattaneo et al., SEL1L affects human pancreatic cancer cell cycle and invasiveness through modulation of PTEN and genes related to cell-matrix interactions. Neoplasia. 2005;7(11):1030-1038.

Ceccaldi et al., Repair Pathway Choices and Consequences at the Double-Strand Break. Trends Cell Biol. Jan. 2016;26(1):52-64. doi: 10.1016/j.tcb.2015.07.009. Epub Oct. 1, 2015.

Cermak et al., Efficient design and assembly of custom TALEN and other TAL effector-based constructs for DNA targeting. Nucleic Acids Res. Jul. 2011;39(12):e82. Doi: 10.1093/nar/gkr218. Epub Apr. 14, 2011.

Chadalavada et al., Wild-type is the optimal sequence of the HDV ribozyme under cotranscriptional conditions. RNA. Dec. 2007;13(12):2189-201. doi: 10.1261/rna.778107. Epub Oct. 23, 2007.

Chaikind et al., A programmable Cas9-serine recombinase fusion protein that operates on DNA sequences in mammalian cells. Nucleic Acids Res. Nov. 16, 2016;44(20):9758-9770. Epub Aug. 11, 2016.

Chalberg et al., Integration specificity of phage phiC31 integrase in the human genome. J Mol Biol. Mar. 17, 2006;357(1):28-48. doi: 10.1016/j.jmb.2005.11.098. Epub Dec. 22, 2005.

Chalberg et al., phiC31 integrase confers genomic integration and long-term transgene expression in rat retina. Invest Ophthalmol Vis Sci. Jun. 2005;46(6):2140-6. doi: 10.1167/iovs.04-1252.

Chan et al., Novel selection methods for DNA-encoded chemical libraries. Curr Opin Chem Biol. 2015;26:55-61. doi:10.1016/j.cbpa.2015.02.010.

Chan et al., The choice of nucleotide inserted opposite abasic sites formed within chromosomal DNA reveals the polymerase activities participating in translesion DNA synthesis. DNA Repair (Amst). Nov. 2013;12(11):878-89. doi: 10.1016/j.dnarep.2013.07.008. Epub Aug. 26, 2013.

Chang et al., Degradation of survival motor neuron (SMN) protein is mediated via the ubiquitin/proteasome pathway. Neurochem Int. Dec. 2004;45(7):1107-12. doi: 10.1016/j.neuint.2004.04.005.

Chang et al., Modification of DNA ends can decrease end joining relative to homologous recombination in mammalian cells. Proc Natl Acad Sci U S A. Jul. 1987;84(14):4959-63.

Chapman et al., Playing the end game: DNA double-strand break repair pathway choice. Mol Cell. Aug. 24, 2012;47(4):497-510. doi: 10.1016/j.molcel.2012.07.029.

Chari et al., Unraveling CRISPR-Cas9 genome engineering parameters via a library-on-library approach. Nat Methods. Sep. 2015;12(9):823-6. doi: 10.1038/nmeth.3473. Epub Jul. 13, 2015.

Charpentier et al., Biotechnology: Rewriting a genome. Nature. Mar. 7, 2013;495(7439):50-1. doi: 10.1038/495050a.

Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.

Chavez et al., Highly efficient Cas9-mediated transcriptional programming. Nat Methods. Apr. 2015;12(4):326-8. doi: 10.1038/nmeth.3312. Epub Mar. 2, 2015.

Chavez et al., Precise Cas9 targeting enables genomic mutation prevention. bioRxiv. Jun. 14, 2016; http://dx/doi.oreg/10.1101/058974. 6 pages. bioRxiv preprint first posted online Jun. 14, 2016.

Chavez et al., Therapeutic applications of the ΦC31 integrase system. Curr Gene Ther. Oct. 2011;11(5):375-81. Review.

Chawla et al., An atlas of RNA base pairs involving modified nucleobases with optimal geometries and accurate energies. Nucleic Acids Res. Aug. 18, 2015;43(14):6714-29. doi: 10.1093/nar/gkv606. Epub Jun. 27, 2015.

Chelico et al., Biochemical basis of immunological and retroviral responses to DNA-targeted cytosine deamination by activation-induced cytidine deaminase and APOBEC3G. J Biol Chem. Oct. 9, 2009;284(41):27761-5. doi: 10.1074/jbc.R109.052449. Epub Aug. 13, 2009.

Chelico et al., Stochastic properties of processive cytidine DNA deaminases AID and APOBEC3G. Philos Trans R Soc Lond B Biol Sci. Mar. 12, 2009;364(1517):583-93. doi: 10.1098/rstb.2008.0195.

Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.

Chen et al., Alterations in PMS2, MSH2 and MLH1 expression in human prostate cancer. Int J Oncol. May 2003;22(5):1033-43.

Chen et al., Fusion protein linkers: property, design and functionality. Adv Drug Deliv Rev. Oct. 2013;65(10):1357-69. doi: 10.1016/j.addr.2012.09.039. Epub Sep. 29, 2012.

Chen et al., Genome-wide CRISPR screen in a mouse model of tumor growth and metastasis. Cell. Mar. 12, 2015;160(6):1246-60. doi: 10.1016/j.cell.2015.02.038. Epub Mar. 5, 2015.

Chen et al., Highly Efficient Mouse Genome Editing by CRISPR Ribonucleoprotein Electroporation of Zygotes. J Biol Chem. Jul. 8, 2016;291(28):14457-67. doi: 10.1074/jbc.M116.733154. Epub May 5, 2016.

Chen et al., m(6)A RNA methylation is regulated by microRNAs and promotes reprogramming to pluripotency. Cell Stem Cell. Mar. 5, 2015;16(3):289-301. doi: 10.1016/j.stem.2015.01.016. Epub Feb. 12, 2015.

Chen et al., Structure of the DNA deaminase domain of the HIV-1 restriction factor APOBEC3G. Nature. Mar. 6, 2008;452(7183):116-9. doi: 10.1038/nature06638. Epub Feb. 20, 2008.

Cheng et al., Multiplexed activation of endogenous genes by CRISPR-on, an RNA-guided transcriptional activator system. Cell Res. Oct. 2013;23(10):1163-71. doi: 10.1038/cr.2013.122. Epub Aug. 27, 2013.

Chester et al., The apolipoprotein B mRNA editing complex performs a multifunctional cycle and suppresses nonsense-mediated decay. EMBO J. Aug. 1, 2003;22(15):3971-82. doi: 10.1093/emboj/cdg369.

Chew et al., A multifunctional AAV-CRISPR-Cas9 and its host response. Nat Methods. Oct. 2016; 13(10):868-74. doi: 10.1038/nmeth.3993. Epub Sep. 5, 2016.

(56)                    References Cited

OTHER PUBLICATIONS

Chew et al., A multifunctional AAV-CRISPR-Cas9 and its host response. Nat Methods. Oct. 2016;13(10):868-74. doi: 10.1038/nmeth.3993. Epub Sep. 5, 2016. Supplementary Information.

Chichili et al., Linkers in the structural biology of protein-protein interactions. Protein Science. 2013;22:153-67.

Chin, Expanding and reprogramming the genetic code of cells and animals. Annu Rev Biochem. 2014;83:379-408. doi: 10.1146/annurev-biochem-060713-035737. Epub Feb. 10, 2014.

Chipev et al., A leucine—proline mutation in the H1 subdomain of keratin 1 causes epidermolytic hyperkeratosis. Cell. Sep. 4, 1992;70(5):821-8.

Cho et al., A degron created by SMN2 exon 7 skipping is a principal contributor to spinal muscular atrophy severity. Genes Dev. Mar. 1, 2010;24(5):438-42. doi: 10.1101/gad.1884910.

Cho et al., Analysis of off-target effects of CRISPR/Cas-derived RNA-guided endonucleases and nickases. Genome Res. Jan. 2014;24(1):132-41. doi: 10.1101/gr.162339.113. Epub Nov. 19, 2013.

Cho et al., Site-specific recombination of bacteriophage P22 does not require integration host factor. J Bacteriol. Jul. 1999;181(14):4245-9. doi: 10.1128/JB.181.14.4245-4249.1999.

Cho et al., Targeted genome engineering in human cells with the Cas9 RNA-guided endonuclease. Nat Biotechnol. Mar. 2013;31(3):230-2. doi: 10.1038/nbt.2507. Epub Jan. 29, 2013.

Cho et al., The calcium-activated chloride channel anoctamin 1 acts as a heat sensor in nociceptive neurons. Nat Neurosci. May 27, 2012;15(7):1015-21. doi: 10.1038/nn.3111.

Choi et al., N(6)-methyladenosine in mRNA disrupts tRNA selection and translation-elongation dynamics. Nat Struct Mol Biol. Feb. 2016;23(2):110-5. doi: 10.1038/nsmb.3148. Epub Jan. 11, 2016.

Choi et al., Protein trans-splicing and characterization of a split family B-type DNA polymerase from the hyperthermophilic archaeal parasite Nanoarchaeum equitans. J Mol Biol. Mar. 10, 2006;356(5):1093-106. doi: 10.1016/j.jmb.2005.12.036. Epub Dec. 27, 2005.

Choi et al., Translesion synthesis across abasic lesions by human B-family and Y-family DNA polymerases α, δ, η, ι, κ, and REV1. J Mol Biol. Nov. 19, 2010;404(1):34-44. doi: 10.1016/j.jmb.2010.09.015. Epub Oct. 1, 2010.

Choi et at al., Translesion synthesis across abasic lesions by human B-family and Y-family DNA polymerases ?, ?, ?, ?, ?, and REV1. J Mol Biol. Nov. 19, 2010;404(1):34-44. doi: 10.1016/j.jmb.2010.09.015. Epub Oct. 1, 2010.

Chong et al., Utilizing the C-terminal cleavage activity of a protein splicing element to purify recombinant proteins in a single chromatographic step. Nucleic Acids Res. Nov. 15, 1998;26(22):5109-15. doi: 10.1093/nar/26.22.5109.

Chong et al., Modulation of protein splicing of the Saccharomyces cerevisiae vacuolar membrane ATPase intein. J Biol Chem. Apr. 24, 1998;273(17):10567-77. doi: 10.1074/jbc.273.17.10567.

Chong et al., Protein splicing involving the Saccharomyces cerevisiae VMA intein. The steps in the splicing pathway, side reactions leading to protein cleavage, and establishment of an in vitro splicing system. J Biol Chem. Sep. 6, 1996;271(36):22159-68. doi: 10.1074/jbc.271.36.22159.

Chong et al., Protein splicing of the Saccharomyces cerevisiae VMA intein without the endonuclease motifs. J Biol Chem. Jun. 20, 1997;272(25):15587-90. doi: 10.1074/jbc.272.25.15587.

Chong et al., Single-column purification of free recombinant proteins using a self-cleavable affinity tag derived from a protein splicing element. Gene. Jun. 19, 1997;192(2):271-81. doi: 10.1016/s0378-1119(97)00105-4.

Choudhury et al., CRISPR-dCas9 mediated TET1 targeting for selective DNA demethylation at BRCA1 promoter. Oncotarget. Jul. 19, 2016;7(29):46545-46556. doi: 10.18632/oncotarget.10234.

Choudhury et al., Engineering RNA endonucleases with customized sequence specificities. Nat Commun. 2012;3:1147. doi: 10.1038/ncomms2154.

Choulika et al., Induction of homologous recombination in mammalian chromosomes by using the I-SceI system of Saccharomyces cerevisiae. Mol Cell Biol. Apr. 1995; 15(4):1968-73. doi: 10.1128/MCB.15.4.1968.

Christian et al., Targeting G with TAL effectors: a comparison of activities of TALENs constructed with NN and NK repeat variable di-residues. PLoS One. 2012;7(9):e45383. doi: 10.1371/journal.pone.0045383. Epub Sep. 24, 2012.

Christian et al., Targeting DNA double-strand breaks with TAL effector nucleases. Genetics. Oct. 2010;186(2):757-61. Doi: 10.1534/genetics.110.120717. Epub Jul. 26, 2010.

Christiansen et al., Characterization of the lactococcal temperate phage TP901-1 and its site-specific integration. J Bacteriol. Feb. 1994;176(4):1069-76. doi: 10.1128/jb.176.4.1069-1076.1994.

Chu et al., Increasing the efficiency of homology-directed repair for CRISPR-Cas9-induced precise gene editing in mammalian cells. Nat Biotech. Feb. 13, 2015;33:543-8. doi: 10.1038/nbt.3198. Epub Mar. 24, 2015.

Chuai et al., In Silico Meets In Vivo: Towards Computational CRISPR-Based sgRNA Design. Trends Biotechnol. Jan. 2017;35(1):12-21. doi: 10.1016/j.tibtech.2016.06.008. Epub Jul. 11, 2016.

Chuang et al., Novel Heterotypic Rox Sites for Combinatorial Dre Recombination Strategies. G3 (Bethesda). Dec. 29, 2015;6(3):559-71. doi: 10.1534/g3.115.025841.

Chujo et al., Trmt61B is a methyltransferase responsible for 1-methyladenosine at position 58 of human mitochondrial tRNAs. RNA. Dec. 2012;18(12):2269-76. doi: 10.1261/rna.035600.112. Epub Oct. 24, 2012.

Chung-Il et al., Artificial control of gene expression in mammalian cells by modulating RNA interference through aptamer-small molecule interaction. RNA. May 2006;12(5):710-6. Epub Apr. 10, 2006.

Chylinski et al., The tracrRNA and Cas9 families of type II CRISPR-Cas immunity systems. RNA Biol. May 2013;10(5):726-37. doi: 10.4161/rna.24321. Epub Apr. 5, 2013.

Clackson et al., Redesigning an FKBP-ligand interface to generate chemical dimerizers with novel specificity. Proc Natl Acad Sci U S A. Sep. 1, 1998;95(18):10437-42. doi: 10.1073/pnas.95.18.10437.

Cobb et al., Directed evolution as a powerful synthetic biology tool. Methods. Mar. 15, 2013;60(1):81-90. doi: 10.1016/j.ymeth.2012.03.009. Epub Mar. 23, 2012.

Cokol et al., Finding nuclear localization signals. EMBO Rep. Nov. 2000;1(5):411-5. doi: 10.1093/embo-reports/kvd092.

Cole et al., Reconstructing evolutionary adaptive paths for protein engineering. Methods Mol Biol. 2013;978:115-25. doi: 10.1007/978-1-62703-293-3_8.

Cole-Strauss et al., Correction of the mutation responsible for sickle cell anemia by an RNA-DNA oligonucleotide. Science. Sep. 6, 1996;273(5280):1386-9.

Collinge, Prion diseases of humans and animals: their causes and molecular basis. Annu Rev Neurosci. 2001;24:519-50. doi: 10.1146/annurev.neuro.24.1.519.

Cong et al., Multiplex genome engineering using CRISPR/Cas systems. Science. Feb. 15, 2013;339(6121):819-23. doi: 10.1126/science.1231143. Epub Jan. 3, 2013.

Conrad et al., A Kaposi's sarcoma virus RNA element that increases the nuclear abundance of intronless transcripts. EMBO J. May 18, 2005;24(10):1831-41. doi: 10.1038/sj.emboj.7600662. Epub Apr. 28, 2005.

Conticello, The AID/APOBEC family of nucleic acid mutators. Genome Biol. 2008;9(6):229. doi: 10.1186/GB-2008-9-6-229. Epub Jun. 17, 2008.

Corcia et al., The importance of the SMN genes in the genetics of sporadic ALS. Amyotroph Lateral Scler. Oct.-Dec. 2009;10(5-6):436-40. doi: 10.3109/17482960902759162.

Corti et al., Genetic correction of human induced pluripotent stem cells from patients with spinal muscular atrophy. Sci Transl Med. Dec. 19, 2012;4(165):165ra162. doi: 10.1126/scitranslmed.3004108.

Costa et al., Frequent use of the same tertiary motif by self-folding RNAs. EMBO J. Mar. 15, 1995;14(6):1276-85.

(56)　　　　　References Cited

OTHER PUBLICATIONS

Cotton et al., Insertion of a Synthetic Peptide into a Recombinant Protein Framework: A Protein Biosensor. J. Am. Chem. Soc. Jan. 22, 1999; 121(5):1100-1. https://doi.org/10.1021/ja983804b.

Cox et al., An SCN9A channelopathy causes congenital inability to experience pain. Nature. Dec. 14, 2006;444(7121):894-8. doi: 10.1038/nature05413.

Cox et al., Conditional gene expression in the mouse inner ear using Cre-loxP. J Assoc Res Otolaryngol. Jun. 2012;13(3):295-322. doi: 10.1007/s10162-012-0324-5. Epub Apr. 24, 2012.

Cox et al., Congenital insensitivity to pain: novel SCN9A missense and in-frame deletion mutations. Hum Mutat. Sep. 2010;31(9):E1670-86. doi: 10.1002/humu.21325.

Cox et al., Therapeutic genome editing: prospects and challenges. Nat Med. Feb. 2015;21(2):121-31. doi: 10.1038/nm.3793.

Cox, Proteins pinpoint double strand breaks. Elife. Oct. 29, 2013;2:e01561. doi: 10.7554/eLife.01561.

Crabtree et al., Three-part inventions: intracellular signaling and induced proximity. Trends Biochem Sci. Nov. 1996;21(11):418-22. doi: 10.1016/s0968-0004(96)20027-1.

Cradick et al., CRISPR/Cas9 systems targeting β-globin and CCR5 genes have substantial off-target activity. Nucleic Acids Res. Nov. 1, 2013;41(20):9584-92. doi: 10.1093/nar/gkt714. Epub Aug. 11, 2013.

Cradick et al., ZFN-site searches genomes for zinc finger nuclease target sites and off-target sites. BMC Bioinformatics. May 13, 2011;12:152. doi: 10.1186/1471-2105-12-152.

Cradick et al., Zinc-finger nucleases as a novel therapeutic strategy for targeting hepatitis B virus DNAs. Mol Ther. May 2010;18(5):947-54. Doi: 10.1038/mt.2010.20. Epub Feb. 16, 2010.

Crick, On protein synthesis. Symp Soc Exp Biol. 1958;12:138-63.

Cronican et al., A class of human proteins that deliver functional proteins into mammalian cells in vitro and in vivo. Chem Biol. Jul. 29, 2011;18(7):833-8. doi: 10.1016/j.chembiol.2011.07.003.

Cronican et al., Potent delivery of functional proteins into Mammalian cells in vitro and in vivo using a supercharged protein. ACS Chem Biol. Aug. 20, 2010;5(8):747-52. doi:10.1021/cb1001153.

Crystal, Transfer of genes to humans: early lessons and obstacles to success. Science. Oct. 20, 1995;270(5235):404-10. doi: 10.1126/science.270.5235.404.

Cucchiarini et al., Enhanced expression of the central survival of motor neuron (SMN) protein during the pathogenesis of osteoarthritis. J Cell Mol Med. Jan. 2014;18(1):115-24. doi: 10.1111/jcmm.12170. Epub Nov. 17, 2013.

Cui et al., Consequences of Cas9 cleavage in the chromosome of Escherichia coli. Nucleic Acids Res. May 19, 2016;44(9):4243-51. doi: 10.1093/nar/gkw223. Epub Apr. 8, 2016.

Cui et al., Targeted integration in rat and mouse embryos with zinc-finger nucleases. Nat Biotechnol. Jan. 2011;29(1):64-7. Doi: 10.1038/nbt.1731. Epub Dec. 12, 2010.

Cunningham et al., Ensembl 2015. Nucleic Acids Res. Jan. 2015;43(Database issue):D662-9. doi: 10.1093/nar/gku1010. Epub Oct. 28, 2014.

Cupples et al., A set of lacZ mutations in Escherichia coli that allow rapid detection of each of the six base substitutions. Proc Natl Acad Sci U S A. Jul. 1989;86(14):5345-9.

D'Adda di Fagagna et al., The Gam protein of bacteriophage Mu is an orthologue of eukaryotic Ku. EMBO Rep. Jan. 2003;4(1):47-52.

Dahlem et al., Simple methods for generating and detecting locus-specific mutations induced with TALENs in the zebrafish genome. PLoS Genet. 2012;8(8):e1002861. doi: 10.1371/journal.pgen.1002861. Epub Aug. 16, 2012.

Dahlgren et al., A novel mutation in ribosomal protein S4 that affects the function of a mutated RF1. Biochimie. Aug. 2000;82(8):683-91.

Dahlman et al., Orthogonal gene knockout and activation with a catalytically active Cas9 nuclease. Nat Biotechnol. Nov. 2015;33(11):1159-61. doi: 10.1038/nbt.3390.

Dang et al., Optimizing sgRNA structure to improve CRISPR-Cas9 knockout efficiency. Genome Biol. Dec. 15, 2015;16:280. doi: 10.1186/s13059-015-0846-3.

Das et al.,The crystal structure of the monomeric reverse transcriptase from Moloney murine leukemia virus. Structure. May 2004;12(5):819-29. doi: 10.1016/j.str.2004.02.032.

Dassa et al., Fractured genes: a novel genomic arrangement involving new split inteins and a new homing endonuclease family. Nucleic Acids Res. May 2009;37(8):2560-73. doi: 10.1093/nar/gkp095. Epub Mar. 5, 2009.

Dassa et al., Trans protein splicing of cyanobacterial split inteins in endogenous and exogenous combinations. Biochemistry. Jan. 9, 2007;46(1):322-30. doi: 10.1021/bi0611762.

Database EBI Accession No. ADE34233 Jan. 29, 2004.

Database UniProt Accession No. G813E0. Jan. 14, 2012.

Datsenko et al., One-step inactivation of chromosomal genes in Escherichia coli K-12 using PCR products. Proc Natl Acad Sci U S A. Jun. 6, 2000;97(12):6640-5.

Davidson et al., Viral vectors for gene delivery to the nervous system. Nat Rev Neurosci. May 2003;4(5):353-64. doi: 10.1038/nrn1104.

Davis et al., DNA double strand break repair via non-homologous end-joining. Transl Cancer Res. Jun. 2013;2(3):130-143.

Davis et al., Homology-directed repair of DNA nicks via pathways distinct from canonical double-strand break repair. Proc Natl Acad Sci U S A. Mar. 11, 2014;111(10):E924-32. doi: 10.1073/pnas.1400236111. Epub Feb. 20, 2014.

Davis et al., Small molecule-triggered Cas9 protein with improved genome-editing specificity. Nat Chem Biol. May 2015;11(5):316-8. doi: 10.1038/nchembio.1793. Epub Apr. 6, 2015.

De Felipe et al., Co-translational, intraribosomal cleavage of poly-peptides by the foot-and-mouth disease virus 2A peptide. J Biol Chem. Mar. 28, 2003;278(13):11441-8. doi: 10.1074/jbc.M211644200. Epub Jan. 8, 2003.

De Sandre-Giovannoli et al., Lamin a truncation in Hutchinson-Gilford progeria. Science. Jun. 27, 2003;300(5628):2055. doi: 10.1126/science.1084125. Epub Apr. 17, 2003.

De Souza, Primer: genome editing with engineered nucleases. Nat Methods. Jan. 2012;9(1):27.

Dean et al., Genetic restriction of HIV-1 infection and progression to AIDS by a deletion allele of the CKR5 structural gene. Hemophilia Growth and Development Study, Multicenter AIDS Cohort Study, Multicenter Hemophilia Cohort Study, San Francisco City Cohort, ALIVE Study. Science. Sep. 27, 1996;273(5283):1856-62. doi: 10.1126/science.273.5283.1856.

Dekosky et al., Large-scale sequence and structural comparisons of human naive and antigen-experienced antibody repertoires. Proc Natl Acad Sci U S A. May 10, 2016;113(19):E2636-45. doi: 10.1073/pnas.1525510113. Epub Apr. 25, 2016.

Delebecque et al., Organization of intracellular reactions with rationally designed RNA assemblies. Science. Jul. 22, 2011;333(6041):470-4. doi: 10.1126/science.1206938. Epub Jun. 23, 2011.

Deltcheva et al., CRISPR RNA maturation by trans-encoded small RNA and host factor RNase III. Nature. Mar. 31, 2011;471(7340):602-7. doi: 10.1038/nature09886.

Deng et al., Widespread occurrence of N6-methyladenosine in bacterial mRNA. Nucleic Acids Res. Jul. 27, 2015;43(13):6557-67. doi: 10.1093/nar/gkv596. Epub Jun. 11, 2015.

Deriano et al., Modernizing the nonhomologous end-joining repertoire: alternative and classical NHEJ share the stage. Annu Rev Genet. 2013;47:433-55. doi: 10.1146/annurev-genet-110711-155540. Epub Sep. 11, 2013.

Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.

Deverman et al., Cre-dependent selection yields AAV variants for widespread gene transfer to the adult brain. Nat Biotechnol. Feb. 2016;34(2):204-9. doi: 10.1038/nbt.3440. Epub Feb. 1, 2016.

Devigili et al., Paroxysmal itch caused by gain-of-function Nav1.7 mutation. Pain. Sep. 2014;155(9):1702-1707. doi: 10.1016/j.pain.2014.05.006. Epub May 10, 2014.

(56) References Cited

OTHER PUBLICATIONS

Dianov et al., Mammalian base excision repair: the forgotten archangel. Nucleic Acids Res. Apr. 1, 2013;41(6):3483-90. doi: 10.1093/nar/gkt076. Epub Feb. 13, 2013.

Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.

Dicarlo et al., Safeguarding CRISPR-Cas9 gene drives in yeast. Nat Biotechnol. Dec. 2015;33(12):1250-1255. doi: 10.1038/nbt.3412. Epub Nov. 16, 2015.

Dickey et al., Single-stranded DNA-binding proteins: multiple domains for multiple functions. Structure. Jul. 2, 2013;21(7):1074-84. doi: 10.1016/j.str.2013.05.013.

Dickinson et al., Experimental interrogation of the path dependence and stochasticity of protein evolution using phage-assisted continuous evolution. Proc Natl Acad Sci USA. May 2013;110(22):9007-12.

Dillon, Regulating gene expression in gene therapy. Trends Biotechnol. May 1993;11(5):167-73. doi: 10.1016/0167-7799(93)90109-M.

Ding et al., A TALEN genome-editing system for generating human stem cell-based disease models. Cell Stem Cell. Feb. 7, 2013;12(2):238-51. Doi: 10.1016/j.stem.2012.11.011. Epub Dec. 13, 2012.

Ding et al., Permanent alteration of PCSK9 with in vivo CRISPR-Cas9 genome editing. Circ Res. Aug. 15, 2014;115(5):488-92. doi: 10.1161/CIRCRESAHA.115.304351. Epub Jun. 10, 2014.

Dingwall et al., Nuclear targeting sequences—a consensus? Trends Biochem Sci. Dec. 1991;16(12):478-81. doi: 10.1016/0968-0004(91)90184-w.

Diver et al., Single-Step Synthesis of Cell-Permeable Protein Dimerizers That Activate Signal Transduction and Gene Expression. J. Am. Chem. Soc. Jun. 4, 1997;119(22):5106-5109. https://doi.org/10.1021/ja963891c.

Dixon et al., Reengineering orthogonally selective riboswitches. Proc Natl Acad Sci U S A. Feb. 16, 2010;107(7):2830-5. doi: 10.1073/pnas.0911209107. Epub Jan. 26, 2010.

Doench et al., Optimized sgRNA design to maximize activity and minimize off-target effects of CRISPR-Cas9. Nat Biotechnol. Feb. 2016;34(2):184-191. doi: 10.1038/nbt.3437.

Doench et al., Rational design of highly active sgRNAs for CRISPR-Cas9-mediated gene inactivation. Nat Biotechnol. Dec. 2014;32(12):1262-7. doi: 10.1038/nbt.3026. Epub Sep. 3, 2014.

Dolan et al., Trans-splicing with the group I intron ribozyme from Azoarcus. RNA. Feb. 2014;20(2):202-13. doi: 10.1261/rna.041012. 113. Epub Dec. 16, 2013.

Dominissini et al., Topology of the human and mouse m6A RNA methylomes revealed by m6A-seq. Nature. Apr. 29, 2012;485(7397):201-6. doi: 10.1038/nature11112.

Dorgan et al., An enzyme-coupled continuous spectrophotometric assay for S-adenosylmethionine-dependent methyltransferases. Anal Biochem. Mar. 15, 2006;350(2):249-55. doi: 10.1016/j.ab.2006.01.004. Epub Feb. 7, 2006.

Dormiani et al., Long-term and efficient expression of human β-globin gene in a hematopoietic cell line using a new site-specific integrating non-viral system. Gene Ther. Aug. 2015;22(8):663-74. doi: 10.1038/gt.2015.30. Epub Apr. 1, 2015.

Dorr et al., Reprogramming the specificity of sortase enzymes. Proc Natl Acad Sci U S A. Sep. 16, 2014;111(37):13343-8. doi: 10.1073/pnas.1411179111. Epub Sep. 3, 2014.

Doudna et al., Genome editing. The new frontier of genome engineering with CRISPR-Cas9. Science. Nov. 28, 2014;346(6213):1258096. doi: 10.1126/science.1258096.

Dove et al., Conversion of the omega subunit of *Escherichia coli* RNA polymerase into a transcriptional activator or an activation target. Genes Dev. Mar. 1, 1998;12(5):745-54.

Doyon et al., Directed evolution and substrate specificity profile of homing endonuclease I-SceI. J Am Chem Soc. Feb. 22, 2006;128(7):2477-84.

Doyon et al., Heritable targeted gene disruption in zebrafish using designed zinc-finger nucleases. Nat Biotechnol. Jun. 2008;26(6):702-8. Doi: 10.1038/nbt1409. Epub May 25, 2008.

Drake, A constant rate of spontaneous mutation in DNA-based microbes. Proc Natl Acad Sci USA. Aug. 15, 1991;88(16):7160-4.

Drenth et al., Mutations in sodium-channel gene SCN9A cause a spectrum of human genetic pain disorders. J Clin Invest. Dec. 2007;117(12):3603-9. doi: 10.1172/JCI33297.

Drost et al., Inactivation of DNA mismatch repair by variants of uncertain significance in the PMS2 gene. Hum Mutat. Nov. 2013;34(11):1477-80. doi: 10.1002/humu.22426. Epub Sep. 11, 2013.

Duan et al., Enhancement of muscle gene delivery with pseudotyped adeno-associated virus type 5 correlates with myoblast differentiation. J Virol. Aug. 2001;75(16):7662-71. doi: 10.1128/JVI.75.16.7662-7671.2001.

Dumas et al., Designing logical codon reassignment—Expanding the chemistry in biology. Chem Sci. Jan. 1, 2015;6(1):50-69. doi: 10.1039/c4sc01534g. Epub Jul. 14, 2014. Review.

Dunaime, Breakthrough method means CRISPR just got a lot more relevant to human health. The Verge. Apr. 20, 2016. http://www.theverge.com/2016/4/20/11450262/crispr-base-editing-single-nucleotides-dna-gene-liu-harvard.

Dupuy et al., Le syndrome de De La Chapelle [De La Chapelle syndrome]. Presse Med. Mar. 3, 2001;30(8):369-72. French.

Durai et al., A bacterial one-hybrid selection system for interrogating zinc finger-DNA interactions. Comb Chem High Throughput Screen. May 2006;9(4):301-11.

Durai et al., Zinc finger nucleases: custom-designed molecular scissors for genome engineering of plant and mammalian cells. Nucleic Acids Res. Oct. 26, 2005;33(18):5978-90. doi: 10.1093/nar/gki912.

During et al., Controlled release of dopamine from a polymeric brain implant: in vivo characterization. Ann Neurol. Apr. 1989;25(4):351-6.

Edlund et al., Cell-specific expression of the rat insulin gene: evidence for role of two distinct 5' flanking elements. Science. Nov. 22, 1985;230(4728):912-6. doi: 10.1126/science.3904002.

Edwards et al., An *Escherichia coli* tyrosine transfer RNA is a leucine-specific transfer RNA in the yeast *Saccharomyces cerevisiae*. Proc Natl Acad Sci U S A. Feb. 15, 1991;88(4):1153-6.

Edwards et al., Crystal structures of the thi-box riboswitch bound to thiamine pyrophosphate analogs reveal adaptive RNA-small molecule recognition. Structure. Sep. 2006;14(9):1459-68.

Eiler et al., Structural Basis for the Fast Self-Cleavage Reaction Catalyzed by the Twister Ribozyme. Proc Natl Acad Sci U S A. Sep. 9, 2014;111(36):13028-33. doi: 10.1073/pnas.1414571111. Epub Aug. 25, 2014.

Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.

Emery et al., HCN2 ion channels play a central role in inflammatory and neuropathic pain. Science. Sep. 9, 2011;333(6048):1462-6. doi: 10.1126/science.1206243.

Endo et al., Toward establishing an efficient and versatile gene targeting system in higher plants. Biocatalysis and Agricultural Biotechnology 2014;3,(1):2-6.

Engelward et al., Base excision repair deficient mice lacking the Aag alkyladenine DNA glycosylase. Proc Natl Acad Sci U S A. Nov. 25, 1997;94(24):13087-92.

England, Unnatural amino acid mutagenesis: a precise tool for probing protein structure and function. Biochemistry. Sep. 21, 2004;43(37):11623-9.

Enyeart et al., Biotechnological applications of mobile group II introns and their reverse transcriptases: gene targeting, RNA-seq, and non-coding RNA analysis. Mobile DNA 5, 2 (2014). https://doi.org/10.1186/1759-8753-5-2. https://doi.org/10.1186/1759-8753-5-2.

Epstein, HSV-1-based amplicon vectors: design and applications. Gene Ther. Oct. 2005;12 Suppl 1:S154-8. doi: 10.1038/sj.gt.3302617.

Eriksson et al., Recurrent de novo point mutations in lamin A cause Hutchinson-Gilford progeria syndrome. Nature. May 15, 2003;423(6937):293-8. doi: 10.1038/nature01629. Epub Apr. 25, 2003. PMID: 12714972.

(56) References Cited

OTHER PUBLICATIONS

Estacion et al., A sodium channel gene SCN9A polymorphism that increases nociceptor excitability. Ann Neurol. Dec. 2009;66(6):862-6. doi: 10.1002/ana.21895.

Esvelt et al., A system for the continuous directed evolution of biomolecules. Nature. Apr. 28, 2011;472(7344):499-503. doi: 10.1038/nature09929. Epub Apr. 10, 2011.

Esvelt et al., Genome-scale engineering for systems and synthetic biology. Mol Syst Biol. 2013;9:641. doi: 10.1038/msb.2012.66.

Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.

Evans et al., Protein trans-splicing and cyclization by a naturally split intein from the dnaE gene of Synechocystis species PCC6803. J Biol Chem. Mar. 31, 2000;275(13):9091-4. doi: 10.1074/jbc.275.13.9091.

Evans et al., Semisynthesis of cytotoxic proteins using a modified protein splicing element. Protein Sci. Nov. 1998;7(11):2256-64. doi: 10.1002/pro.5560071103.

Evans et al., The cyclization and polymerization of bacterially expressed proteins using modified self-splicing inteins. J Biol Chem. Jun. 25, 1999;274(26):18359-63. doi: 10.1074/jbc.274.26.18359.

Evans et al., The in vitro ligation of bacterially expressed proteins using an intein from Methanobacterium thermoautotrophicum. J Biol Chem. Feb. 12, 1999;274(7):3923-6. doi: 10.1074/jbc.274.7.3923.

Evers et al., CRISPR knockout screening outperforms shRNA and CRISPRi in identifying essential genes. Nat Biotechnol. Jun. 2016;34(6):631-3. doi: 10.1038/nbt.3536. Epub Apr. 25, 2016.

Fagerlund et al., The Cpf1 CRISPR-Cas protein expands genome-editing tools. Genome Biology Nov. 17, 2015;16:251. https://doi.org/10.1186/s13059-015-0824-9.

Falnes et al., DNA repair by bacterial AlkB proteins. Res Microbiol. Oct. 2003;154(8):531-8. doi: 10.1016/S0923-2508(03)00150-5.

Falnes et al., Repair of methyl lesions in DNA and RNA by oxidative demethylation. Neuroscience. Apr. 14, 2007;145(4):1222-32. doi: 10.1016/j.neuroscience.2006.11.018. Epub Dec. 18, 2006.

Fang et al., Synthetic Studies Towards Halichondrins: Synthesis of the Left Halves of Norhalichondrins and Homohalichondrins. Tetrahedron Letters 1992;33(12):1557-1560.

Farboud et al., Dramatic enhancement of genome editing by CRISPR/Cas9 through improved guide RNA design. Genetics. Apr. 2015;199(4):959-71. doi: 10.1534/genetics.115.175166. Epub Feb. 18, 2015.

Farhood et al., Codelivery to mammalian cells of a transcriptional factor with cis-acting element using cationic liposomes. Anal Biochem. Feb. 10, 1995;225(1):89-93.

Fawcett et al., Transposable elements controlling I-R hybrid dysgenesis in D. melanogaster are similar to mammalian LINEs. Cell. Dec. 26, 1986;47(6):1007-15. doi: 10.1016/0092-8674(86)90815-9.

Feldstein et al., Two sequences participating in the autolytic processing of satellite tobacco ringspot virus complementary RNA. Gene. Oct. 15, 1989;82(1):53-61. doi: 10.1016/0378-1119(89)90029-2.

Feng et al., Crystal structures of the human RNA demethylase Alkbh5 reveal basis for substrate recognition. J Biol Chem. Apr. 25, 2014;289(17):11571-11583. doi: 10.1074/jbc.M113.546168. Epub Mar. 10, 2014.

Feng et al., Human L1 retrotransposon encodes a conserved endonuclease required for retrotransposition. Cell. Nov. 29, 1996;87(5):905-16. doi: 10.1016/s0092-8674(00)81997-2.

Ferretti et al., Complete genome sequence of an M1 strain of Streptococcus pyogenes. Proc Natl Acad Sci U S A. Apr. 10, 2001;98(8):4658-63.

Feuk, Inversion variants in the human genome: role in disease and genome architecture. Genome Med. Feb. 12, 2010;2(2):11. doi: 10.1186/gm132.

Filippov et al., A novel type of RNase III family proteins in eukaryotes. Gene. Mar. 7, 2000;245(1):213-21. doi: 10.1016/s0378-1119(99)00571-5.

Fine et al., Trans-spliced Cas9 allows cleavage of HBB and CCR5 genes in human cells using compact expression cassettes. Scientific Reports 2015;5(1):Article No. 10777. doi:10.1038/srep10777. With Supplementary Information.

Fire et al., Potent and specific genetic interference by double-stranded RNA in Caenorhabditis elegans. Nature. Feb. 19, 1998;391(6669):806-11. doi: 10.1038/35888.

Fischbach et al., Directed evolution can rapidly improve the activity of chimeric assembly-line enzymes. Proc Natl Acad Sci U S A. Jul. 17, 2007;104(29):11951-6. doi: 10.1073/pnas.0705348104. Epub Jul. 9, 2007.

Fischer et al., Cryptic epitopes induce high-titer humoral immune response in patients with cancer. J Immunol. Sep. 1, 2010;185(5):3095-102. doi: 10.4049/jimmunol.0902166. Epub Jul. 26, 2010.

Fitzjohn, Diversitree: comparative phylogenetic analyses of diversification in R. Methods in Evology and Evolution. Dec. 2012;3(6):1084-92 .doi: 10.1111/j.2041-210X.2012.00234.x.

Flajolet et al., Woodchuck hepatitis virus enhancer I and enhancer II are both involved in N-myc2 activation in woodchuck liver tumors. J Virol. Jul. 1998;72(7):6175-80. doi: 10.1128/JVI.72.7.6175-6180.1998.

Flaman et al., A rapid PCR fidelity assay. Nucleic Acids Res. Aug. 11, 1994;22(15):3259-60. doi: 10.1093/nar/22.15.3259.

Flynn et al., CRISPR-mediated genotypic and phenotypic correction of a chronic granulomatous disease mutation in human iPS cells. Exp Hematol. Oct. 2015;43(10):838-848.e3. doi: 10.1016/j.exphem.2015.06.002. Epub Jun. 19, 2015. Including supplementary figures and data.

Fogg et al., New applications for phage integrases. J Mol Biol. Jul. 29, 2014;426(15):2703-16. doi: 10.1016/j.jmb.2014.05.014. Epub May 22, 2014.

Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013. Including Supplementary Information.

Forster et al., Self-cleavage of virusoid RNA is performed by the proposed 55-nucleotide active site. Cell. Jul. 3, 1987;50(1):9-16. doi: 10.1016/0092-8674(87)90657-x.

Fortini et al., Different DNA polymerases are involved in the short- and long-patch base excision repair in mammalian cells. Biochemistry. Mar. 17, 1998;37(11):3575-80. doi: 10.1021/bi972999h.

Fouts et al., Sequencing Bacillus anthracis typing phages gamma and cherry reveals a common ancestry. J Bacteriol. May 2006;188(9):3402-8. doi: 10.1128/JB.188.9.3402-3408.2006.

Freitas et al., Mechanisms and signals for the nuclear import of proteins. Curr Genomics. Dec. 2009;10(8):550-7. doi: 10.2174/138920209789503941.

Freshney, Culture of Animal Cells. A Manual of Basic Technique. Alan R. Liss, Inc. New York. 1983;4.

Friedman, J. H., Greedy function approximation: A gradient boosting machine. Ann. Statist. Oct. 2001;29(5):1189-232. doi: 10.1214/aos/1013203451.

Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.

Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.

Fu et al., Promises and Pitfalls of Intracellular Delivery of Proteins. Bioconjugate Chemistry. Aug. 2014;25:1602-8.

Fuchs et al., Polyarginine as a multifunctional fusion tag. Protein Sci. Jun. 2005;14(6):1538-44.

Fujisawa et al., Disease-associated mutations in CIAS1 induce cathepsin B-dependent rapid cell death of human THP-1 monocytic cells. Blood. Apr. 1, 2007;109(7):2903-11.

Fukui et al., DNA Mismatch Repair in Eukaryotes and Bacteria. J Nucleic Acids. Jul. 27, 2010;2010. pii: 260512. doi: 10.4061/2010/260512.

(56) References Cited

OTHER PUBLICATIONS

Fung et al., Repair at single targeted DNA double-strand breaks in pluripotent and differentiated human cells. PLoS One. 2011;6(5):e20514. doi: 10.1371/journal.pone.0020514. Epub May 25, 2011.

Furukawa et al., In vitro selection of allosteric ribozymes that sense the bacterial second messenger c-di-GMP. Methods Mol Biol. 2014;1111:209-20. doi: 10.1007/978-1-62703-755-6_15.

Fusi et al., In Silico Predictive Modeling of CRISPR/Cas9 guide efficiency. Jun. 26, 2015; bioRxiv. http://dx.doi.org/10.1101/021568.

Gaj et al., 3rd. Genome engineering with custom recombinases. Methods Enzymol. 2014;546:79-91. doi: 10.1016/B978-0-12-801185-0.00004-0.

Gaj et al., A comprehensive approach to zinc-finger recombinase customization enables genomic targeting in human cells. Nucleic Acids Res. Feb. 6, 2013;41(6):3937-46.

Gaj et al., Enhancing the specificity of recombinase-mediated genome engineering through dimer interface redesign. J Am Chem Soc. Apr. 2, 2014;136(13):5047-56. doi: 10.1021/ja4130059. Epub Mar. 20, 2014.

Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.

Gaj et al., Structure-guided reprogramming of serine recombinase DNA sequence specificity. Proc Natl Acad Sci U S A. Jan. 11, 2011;108(2):498-503. doi: 10.1073/pnas.1014214108. Epub Dec. 27, 2010.

Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.

Gallo et al., A novel pathogenic PSEN1 mutation in a family with Alzheimer's disease: phenotypical and neuropathological features. J Alzheimers Dis. 2011;25(3):425-31. doi: 10.3233/JAD-2011-110185.

Gao et al., Cationic liposome-mediated gene transfer. Gene Ther. Dec. 1995;2(10):710-22.

Gao et al., DNA-guided genome editing using the Natronobacterium gregoryi Argonaute. Nat Biotechnol. Jul. 2016;34(7):768-73. doi: 10.1038/nbt.3547. Epub May 2, 2016.

Gao et al., Self-processing of ribozyme-flanked RNAs into guide RNAs in vitro and in vivo for CRISPR-mediated genome editing. J Integr Plant Biol. Apr. 2014;56(4):343-9. doi: 10.1111/jipb.12152. Epub Mar. 6, 2014.

Garcia et al., Transglycosylation: a mechanism for RNA modification (and editing?). Bioorg Chem. Jun. 2005;33(3):229-51. doi: 10.1016/j.bioorg.2005.01.001. Epub Feb. 23, 2005.

Gardlik et al., Vectors and delivery systems in gene therapy. Med Sci Monit. Apr. 2005;11(4):RA110-21. Epub Mar. 24, 2005.

Garibyan et al., Use of the rpoB gene to determine the specificity of base substitution mutations on the *Escherichia coli* chromosome. DNA Repair (Amst). May 13, 2003;2(5):593-608.

Garneau et al., The CRISPR/Cas bacterial immune system cleaves bacteriophage and plasmid DNA. Nature. Nov. 4, 2010;468(7320):67-71. doi: 10.1038/nature09523.

Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.

Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.

GenBank Accession No. J01600.1. Brooks et al., *E. coli* dam gene coding for DNA adenine methylase. Apr. 26, 1993.

GenBank Accession No. U07651.1. Lu, *Escherichia coli* K12 negative regulator of replication initiation (seqA) gene, complete cds. Jul. 19, 1994.

GenBank Submission; NIH/NCBI Accession No. 4UN5_B. Anders et al., Jul. 23, 2014. 5 pages.

GenBank Submission; NIH/NCBI, Accession No. AAA66622.1. Martinelli et al., May 18, 1995. 2 pages.

GenBank Submission; NIH/NCBI, Accession No. AGT42196. Farzadfar et al., Nov. 2, 2013. 2 pages.

GenBank Submission; NIH/NCBI, Accession No. AIT42264.1. Hyun et al., Oct. 15, 2014. 2 pages.

GenBank Submission; NIH/NCBI, Accession No. AKA60242.1. Tong et al., Apr. 5, 2015. 1 page.

GenBank Submission; NIH/NCBI, Accession No. AKQ21048.1. Gilles et al., Jul. 19, 2015. 1 page.

GenBank Submission; NIH/NCBI, Accession No. AKS40380.1. Nodvig et al., Aug. 2, 2015. 1 page.

GenBank Submission; NIH/NCBI, Accession No. BDB43378. Zhang et al., Aug. 11, 2016. 2 pages.

GenBank Submission; NIH/NCBI, Accession No. J04623. Kita et al., Apr. 26, 1993. 2 pages.

GenBank Submission; NIH/NCBI, Accession No. KR710351.1. Sahni et al., Jun. 1, 2015. 2 pages.

GenBank Submission; NIH/NCBI, Accession No. NC_002737.1. Ferretti et al., Jun. 27, 2013. 1 page.

GenBank Submission; NIH/NCBI, Accession No. NC_015683.1. Trost et al., Jul. 6, 2013. 1 page.

GenBank Submission; NIH/NCBI, Accession No. NC_016782.1. Trost et al., Jun. 11, 2013. 1 page.

GenBank Submission; NIH/NCBI, Accession No. NC_016786.1. Trost et al., Aug. 28, 2013. 1 page.

GenBank Submission; NIH/NCBI, Accession No. NC_017053.1. Fittipaldi et al., Jul. 6, 2013. 1 page.

GenBank Submission; NIH/NCBI, Accession No. NC_017317.1. Trost et al., Jun. 11, 2013. 1 page.

GenBank Submission; NIH/NCBI, Accession No. NC_017861.1. Heidelberg et al., Jun. 11, 2013. 1 page.

GenBank Submission; NIH/NCBI, Accession No. NC_018010.1. Lucas et al., Jun. 11, 2013. 2 pages.

GenBank Submission; NIH/NCBI, Accession No. NC_018721.1. Feng et al., Jun. 11, 2013. 1 pages.

GenBank Submission; NIH/NCBI, Accession No. NC_021284.1. Ku et al., Jul. 12, 2013. 1 page.

GenBank Submission; NIH/NCBI, Accession No. NC_021314.1. Zhang et al., Jul. 15, 2013. 1 page.

GenBank Submission; NIH/NCBI, Accession No. NC_021846.1. Lo et al., Jul. 22, 2013. 1 page.

GenBank Submission; NIH/NCBI, Accession No. NM_174936. Guo et al., Oct. 28, 2015. 6 pages.

GenBank Submission; NIH/NCBI, Accession No. NM_174936.3. Bernardini et al., Oct. 28, 2015. 2 pages.

GenBank Submission; NIH/NCBI, Accession No. NP_472073.1. Glaser et al., Jun. 27, 2013. 2 pages.

GenBank Submission; NIH/NCBI, Accession No. NP_628093.1. Hsiao et al., Aug. 3, 2016. 2 pages.

GenBank Submission; NIH/NCBI, Accession No. P42212. Prasher et al., Mar. 19, 2014. 7 pages.

GenBank Submission; NIH/NCBI, Accession No. WP_002989955.1. No Author Listed, May 6, 2013. 1 page.

GenBank Submission; NIH/NCBI, Accession No. WP_010922251.1. No Author Listed, May 15, 2013. 1 page.

GenBank Submission; NIH/NCBI, Accession No. WP_011054416.1. No Author Listed, May 15, 2013. 1 page.

GenBank Submission; NIH/NCBI, Accession No. WP_011284745.1. No Author Listed, May 16, 2013. 1 page.

GenBank Submission; NIH/NCBI, Accession No. WP_011285506.1. No Author Listed, May 16, 2013. 1 page.

GenBank Submission; NIH/NCBI, Accession No. WP_011527619.1. No Author Listed, May 16, 2013. 1 page.

GenBank Submission; NIH/NCBI, Accession No. WP_012560673.1. No Author Listed, May 17, 2013. 1 page.

GenBank Submission; NIH/NCBI, Accession No. WP_014407541.1. No Author Listed, May 18, 2013. 1 page.

GenBank Submission; NIH/NCBI, Accession No. WP_020905136.1. No Author Listed, Jul. 25, 2013. 1 page.

GenBank Submission; NIH/NCBI, Accession No. WP_023080005.1. No Author Listed, Oct. 27, 2013. 1 page.

(56) References Cited

OTHER PUBLICATIONS

GenBank Submission; NIH/NCBI, Accession No. WP_023610282. 1. No Author Listed, Nov. 27, 2013. 1 page.

GenBank Submission; NIH/NCBI, Accession No. WP_030125963. 1. No Author Listed, Jul. 9, 2014. 1 page.

GenBank Submission; NIH/NCBI, Accession No. WP_030126706. 1. No Author Listed, Jul. 9, 2014. 1 page.

GenBank Submission; NIH/NCBI, Accession No. WP_031488318. 1. No Author Listed., Aug. 5, 2014. 1 page.

GenBank Submission; NIH/NCBI, Accession No. WP_032460140. 1. No Author Listed, Oct. 4, 2014. 1 page.

GenBank Submission; NIH/NCBI, Accession No. WP_032461047. 1. No Author Listed, Oct. 4, 2014. 1 page.

GenBank Submission; NIH/NCBI, Accession No. WP_032462016. 1. Haft et al., Oct. 4, 2014. 1 page.

GenBank Submission; NIH/NCBI, Accession No. WP_032462936. 1. No Author Listed, Oct. 4, 2014. 1 page.

GenBank Submission; NIH/NCBI, Accession No. WP_032464890. 1. No Author Listed, Oct. 4, 2014. 1 page.

GenBank Submission; NIH/NCBI, Accession No. WP_038431314. 1. No Author Listed, Dec. 26, 2014. 1 page.

GenBank Submission; NIH/NCBI, Accession No. WP_038432938. 1. No Author Listed, Dec. 26, 2014. 1 page.

GenBank Submission; NIH/NCBI, Accession No. WP_038434062. 1. No Author Listed, Dec. 26, 2014. 1 page.

GenBank Submission; NIH/NCBI, Accession No. WP_048327215. 1. No Author Listed, Jun. 26, 2015. 1 page.

GenBank Submission; NIH/NCBI, Accession No. WP_049519324. 1. No Author Listed, Jul. 20, 2015. 1 page.

GenBank Submission; NIH/NCBI, Accession No. YP_002342100. 1. Bernardini et al., Jun. 10, 2013. 2 pages.

GenBank Submission; NIH/NCBI, Accession No. YP_002344900. 1. Gundogdu et al., Mar. 19, 2014. 2 pages.

GenBank Submission; NIH/NCBI, Accession No. YP_820832.1. Makarova et al., Aug. 27, 2013. 2 pages.

George et al., Adenosine deaminases acting on RNA, RNA editing, and interferon action. J Interferon Cytokine Res. Jan. 2011;31(1):99-117. doi: 10.1089/jir.2010.0097. Epub Dec. 23, 2010. PMID: 21182352; PMCID: PMC3034097.

Gerard et al., Influence on stability in *Escherichia coli* of the carboxy-terminal structure of cloned Moloney murine leukemia virus reverse transcriptase. DNA. Aug. 1986;5(4):271-9. doi: 10.1089/dna.1986.5.271.

Gerard et al., Purification and characterization of the DNA polymerase and RNase H activities in Moloney murine sarcoma-leukemia virus. J Virol. Apr. 1975;15(4):785-97. doi: 10.1128/JVI.15.4.785-797.1975.

Gerard et al., The role of template-primer in protection of reverse transcriptase from thermal inactivation. Nucleic Acids Res. Jul. 15, 2002;30(14):3118-29. doi: 10.1093/nar/gkf417.

Gerber et al., An adenosine deaminase that generates inosine at the wobble position of tRNAs. Science. Nov. 5, 1999;286(5442):1146-9. doi: 10.1126/science.286.5442.1146.

Gerber et al., RNA editing by base deamination: more enzymes, more targets, new mysteries. Trends Biochem Sci. Jun. 2001;26(6):376-84.

Gersbach et al., Directed evolution of recombinase specificity by split gene reassembly. Nucleic Acids Res. Jul. 2010;38(12):4198-206. doi: 10.1093/nar/gkq125. Epub Mar. 1, 2010.

Gersbach et al., Targeted plasmid integration into the human genome by an engineered zinc-finger recombinase. Nucleic Acids Res. Sep. 1, 2011;39(17):7868-78. doi: 10.1093/nar/gkr421. Epub Jun. 7, 2011.

Gibson et al., Enzymatic assembly of DNA molecules up to several hundred kilobases. Nat Methods. May 2009;6(5):343-5. doi: 10.1038/nmeth.1318. Epub Apr. 12, 2009.

Gil, Position-dependent sequence elements downstream of AAUAAA are required for efficient rabbit beta-globin mRNA 3' end formation. Cell. May 8, 1987;49(3):399-406. doi: 10.1016/0092-8674(87)90292-3.

Gilbert et al., CRISPR-mediated modular RNA-guided regulation of transcription in eukaryotes. Cell. 2013 154(2):442-51.

Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.

Glasgow et al.,DNA-binding properties of the Hin recombinase. J Biol Chem. Jun. 15, 1989;264(17):10072-82.

Glassner et al., Generation of a strong mutator phenotype in yeast by imbalanced base excision repair. Proc Natl Acad Sci U S A. Aug. 18, 1998;95(17):9997-10002.

Goldberg et al., Epigenetics: a landscape takes shape. Cell. Feb. 23, 2007;128(4):635-8. doi: 10.1016/j.cell.2007.02.006.

Goldberg et al., Loss-of-function mutations in the Nav1.7 gene underlie congenital indifference to pain in multiple human populations. Clin Genet. Apr. 2007;71(4):311-9. doi: 10.1111/j.1399-0004.2007.00790.x.

Gong et al., Active DNA demethylation by oxidation and repair. Cell Res. Dec. 2011;21(12):1649-51. doi: 10.1038/cr.2011.140. Epub Aug. 23, 2011.

Gonzalez et al., An iCRISPR platform for rapid, multiplexable, and inducible genome editing in human pluripotent stem cells. Cell Stem Cell. Aug. 7, 2014;15(2):215-26. doi: 10.1016/j.stem.2014.05.018. Epub Jun. 12, 2014.

Goodnough et al., Development of a delivery vehicle for intracellular transport of botulinum neurotoxin antagonists. FEBS Lett. Feb. 27, 2002;513(2-3):163-8.

Gordley et al., Evolution of programmable zinc finger-recombinases with activity in human cells. J Mol Biol. Mar. 30, 2007;367(3):802-13. Epub Jan. 12, 2007.

Gordley et al., Synthesis of programmable integrases. Proc Natl Acad Sci U S A. Mar. 31, 2009;106(13):5053-8. doi: 10.1073/pnas.0812502106. Epub Mar. 12, 2009.

Grainge et al., The integrase family of recombinase: organization and function of the active site. Mol Microbiol. Aug. 1999;33(3):449-56.

Gregory et al., Integration site for Streptomyces phage phiBT1 and development of site-specific integrating vectors. J Bacteriol. Sep. 2003;185(17):5320-3. doi: 10.1128/jb.185.17.5320-5323.2003.

Griffiths, Endogenous retroviruses in the human genome sequence. Genome Biol. 2001;2(6):Reviews1017. doi: 10.1186/gb-2001-2-6-reviews1017. Epub Jun. 5, 2001.

Grindley et al., Mechanisms of site-specific recombination. Annu Rev Biochem. 2006;75:567-605. doi: 10.1146/annurev.biochem.73.011303.073908.

Grishok et al., Genes and Mechanisms Related to RNA Interference Regulate Expression of the Small Temporal RNAs that Control C. elegans Developmental Timing. Jul. 13, 2001:106(1):P23-4.

Groher et al., Synthetic riboswitches—A tool comes of age. Biochim Biophys Acta. Oct. 2014;1839(10):964-973. doi: 10.1016/j.bbagrm.2014.05.005. Epub May 17, 2014.

Groth et al., Construction of transgenic *Drosophila* by using the site-specific integrase from phage phiC31. Genetics. Apr. 2004;166(4):1775-82. doi: 10.1534/genetics.166.4.1775.

Groth et al., Phage integrases: biology and applications. J Mol Biol. Jan. 16, 2004;335(3):667-78.

Gruber et al., Strategies for measuring evolutionary conservation of RNA secondary structures. BMC Bioinformatics. Feb. 26, 2008;9:122. doi: 10.1186/1471-2105-9-122.

Gruber et al., The Vienna RNA websuite. Nucleic Acids Res. Jul. 1, 2008;36(Web Server issue):W70-4. doi: 10.1093/nar/gkn188. Epub Apr. 19, 2008.

Grunebaum et al., Recent advances in understanding and managing adenosine deaminase and purine nucleoside phosphorylase deficiencies. Curr Opin Allergy Clin Immunol. Dec. 2013;13(6):630-8. doi: 10.1097/ACI.0000000000000006.

Guedon et al., Current gene therapy using viral vectors for chronic pain. Mol Pain. May 13, 2015;11:27. doi: 10.1186/s12990-015-0018-1.

Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.

(56)        References Cited

OTHER PUBLICATIONS

Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.

Guo et al., Evolution of Tetrahymena ribozyme mutants with increased structural stability. Nat Struct Biol. Nov. 2002;9(11):855-61. doi: 10.1038/nsb850.

Guo et al., Facile functionalization of FK506 for biological studies by the thiol-ene 'click' reaction. RSC Advances. 2014;22:11400-3.

Guo et al., Protein tolerance to random amino acid change. Proc Natl Acad Sci U S A. Jun. 22, 2004;101(25):9205-10. Epub Jun. 14, 2004.

Guo et al., Structure of Cre recombinase complexed with DNA in a site-specific recombination synapse. Nature. Sep. 4, 1997;389(6646):40-6.

Gupta et al., Cross-talk between cognate and noncognate RpoE sigma factors and Zn(2+)-binding anti-sigma factors regulates photooxidative stress response in Azospirillum brasilense. Antioxid Redox Signal. Jan. 1, 2014;20(1):42-59. doi: 10.1089/ars.2013.5314. Epub Jul. 19, 2013.

Gupta et al., Sequences in attB that affect the ability of phiC31 integrase to synapse and to activate DNA cleavage. Nucleic Acids Res. 2007;35(10):3407-19. doi: 10.1093/nar/gkm206. Epub May 3, 2007.

Gutschner et al., Post-translational Regulation of Cas9 during G1 Enhances Homology-Directed Repair. Cell Rep. Feb. 16, 2016;14(6):1555-1566. doi: 10.1016/j.celrep.2016.01.019. Epub Feb. 4, 2016.

Guzman et al., Tight regulation, modulation, and high-level expression by vectors containing the arabinose PBAD promoter. J Bacteriol. 1995;177(14):4121-4130.

Haddada et al., Gene therapy using adenovirus vectors. Curr Top Microbiol Immunol. 1995;199 ( Pt 3):297-306. doi: 10.1007/978-3-642-79586-2_14.

Haeussler et al., Evaluation of off-target and on-target scoring algorithms and integration into the guide RNA selection tool CRISPOR. Genome Biol. Jul. 5, 2016;17(1):148. doi: 10.1186/s13059-016-1012-2.

Halbert et al., Repeat transduction in the mouse lung by using adeno-associated virus vectors with different serotypes. J Virol. Feb. 2000;74(3):1524-32. doi: 10.1128/jvi.74.3.1524-1532.2000.

Hale et al., RNA-guided RNA cleavage by a CRISPR RNA-Cas protein complex. Cell. Nov. 25, 2009;139(5):945-56. doi: 10.1016/j.cell.2009.07.040.

Halvas et al., Role of murine leukemia virus reverse transcriptase deoxyribonucleoside triphosphate-binding site in retroviral replication and in vivo fidelity. J Virol. Nov. 2000;74(22):10349-58. doi: 10.1128/jvi.74.22.10349-10358.2000.

Hamano-Takaku et al., A mutant *Escherichia coli* tyrosyl-tRNA synthetase utilizes the unnatural amino acid azatyrosine more efficiently than tyrosine. J Biol Chem. Dec. 22, 2000;275(51):40324-8.

Han, New CRISPR/Cas9-based Tech Edits Single Nucleotides Without Breaking DNA. Genome Web, Apr. 20, 2016. https://www.genomeweb.com/gene-silencinggene-editing/new-crisprcas9-based-tech-edits-single-nucleotides-without-breaking-dna.

Hardt et al.,Missense variants in hMLH1 identified in patients from the German HNPCC consortium and functional studies. Fam Cancer. Jun. 2011;10(2):273-84. doi: 10.1007/s10689-011-9431-4.

Harms et al., Evolutionary biochemistry: revealing the historical and physical causes of protein properties. Nat Rev Genet. Aug. 2013;14(8):559-71. doi: 10.1038/nrg3540.

Harris et al., RNA Editing Enzyme APOBEC1 and Some of Its Homologs Can Act as DNA Mutators. Mol Cell. Nov. 2002;10(5):1247-53.

Hart et al., High-Resolution CRISPR Screens Reveal Fitness Genes and Genotype-Specific Cancer Liabilities. Cell. Dec. 3, 2015;163(6):1515-26. doi: 10.1016/j.cell.2015.11.015. Epub Nov. 25, 2015.

Hartung et al., Correction of metabolic, craniofacial, and neurologic abnormalities in Mps I mice treated at birth with adeno-associated virus vector transducing the human alpha-L-iduronidase gene. Mol Ther. Jun. 2004;9(6):866-75.

Hartung et al., Cre mutants with altered DNA binding properties. J Biol Chem. Sep. 4, 1998;273(36):22884-91.

Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.

Hasegawa et al., Spontaneous mutagenesis associated with nucleotide excision repair in *Escherichia coli*. Genes Cells. May 2008;13(5):459-69. doi: 10.1111/j.1365-2443.2008.01185.x.

Hayes et al., Stop codons preceded by rare arginine codons are efficient determinants of SsrA tagging in *Escherichia coli*. Proc Natl Acad Sci U S A. Mar. 19, 2002;99(6):3440-5. Epub Mar. 12, 2002.

Heidenreich et al., Non-homologous end joining as an important mutagenic process in cell cycle-arrested cells. EMBO J. May 1, 2003;22(9):2274-83. doi: 10.1093/emboj/cdg203.

Held et al., In vivo correction of murine hereditary tyrosinemia type I by phiC31 integrase-mediated gene delivery. Mol Ther. Mar. 2005;11(3):399-408. doi: 10.1016/j.ymthe.2004.11.001.

Heller et al., Replisome assembly and the direct restart of stalled replication forks. Nat Rev Mol Cell Biol. Dec. 2006;7(12):932-43. Epub Nov. 8, 2006.

Hendel et al., Chemically modified guide RNAs enhance CRISPR-Cas genome editing in human primary cells. Nat Biotechnol. Sep. 2015;33(9):985-989. doi: 10.1038/nbt.3290. Epub Jun. 29, 2015. Author Manuscript. 14 pages.

Hendricks et al., The S. cerevisiae Mag1 3-methyladenine DNA glycosylase modulates susceptibility to homologous recombination. DNA Repair (Amst). 2002;1(8):645-659.

Hermonat et al., Use of adeno-associated virus as a mammalian DNA cloning vector: transduction of neomycin resistance into mammalian tissue culture cells. Proc Natl Acad Sci U S A. Oct. 1984;81(20):6466-70. doi: 10.1073/pnas.81.20.6466.

Herschhorn et al., Retroviral reverse transcriptases. Cell Mol Life Sci. Aug. 2010;67(16):2717-47. doi: 10.1007/s00018-010-0346-2. Epub Apr. 1, 2010.

Herzig et al., A Novel Leu92 Mutant of HIV-1 Reverse Transcriptase with a Selective Deficiency in Strand Transfer Causes a Loss of Viral Replication. J Virol. Aug. 2015;89(16):8119-29. doi: 10.1128/JVI.00809-15. Epub May 20, 2015.

Hickford et al., Antitumour polyether macrolides: four new halichondrins from the New Zealand deep-water marine sponge *Lissodendoryx* sp. Bioorg Med Chem. Mar. 15, 2009;17(6):2199-203. doi: 10.1016/j.bmc.2008.10.093. Epub Nov. 19, 2008.

Hida et al., Directed evolution for drug and nucleic acid; delivery. Adv Drug Deliv Rev. Dec. 22, 2007;59(15):1562-78. Epub Aug. 28, 2007.; Review.

Higgs et al., Genetic complexity in sickle cell disease. Proc Natl Acad Sci U S A. Aug. 19, 2008;105(33):11595-6. doi: 10.1073/pnas.0806633105. Epub Aug. 11, 2008.

Hilbers et al., New developments in structure determination of pseudoknots. Biopolymers. 1998;48(2-3):137-53. doi: 10.1002/(SICI)1097-0282(1998)48:2<137::AID-BIP4>3.0.CO;2-H.

Hill et al., Functional analysis of conserved histidines in ADP-glucose pyrophosphorylase from *Escherichia coli*.Biochem Biophys Res Commun. Mar. 17, 1998;244(2):573-7.

Hilton et al., Enabling functional genomics with genome engineering. Genome Res. Oct. 2015;25(10):1442-55. doi: 10.1101/gr.190124.115.

Hirano et al., Site-specific recombinases as tools for heterologous gene integration. Appl Microbiol Biotechnol. Oct. 2011;92(2):227-39. doi: 10.1007/s00253-011-3519-5. Epub Aug. 7, 2011. Review.

Hirano et al., Structural Basis for the Altered PAM Specificities of Engineered CRISPR-Cas9. Mol Cell. Mar. 17, 2016;61(6):886-94. doi: 10.1016/j.molcel.2016.02.018.

Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.

Hockemeyer et al., Genetic engineering of human pluripotent cells using TALE nucleases. Nat Biotechnol. Jul. 7, 2011;29(8):731-4. doi: 10.1038/nbt.1927.

(56) References Cited

OTHER PUBLICATIONS

Hoernes et al., Translating the epitranscriptome. Wiley Interdiscip Rev RNA. Jan. 2017;8(1):e1375. doi: 10.1002/wrna.1375. Epub Jun. 27, 2016.

Hoess et al., DNA specificity of the Cre recombinase resides in the 25 kDa carboxyl domain of the protein. J Mol Biol. Dec. 20, 1990;216(4):873-82. doi: 10.1016/S0022-2836(99)80007-2.

Holden et al., Crystal structure of the anti-viral APOBEC3G catalytic domain and functional implications. Nature. Nov. 6, 2008;456(7218):121-4. doi: 10.1038/nature07357. Epub Oct. 12, 2008.

Hollis et al., Phage integrases for the construction and manipulation of transgenic mammals. Reprod Biol Endocrinol. Nov. 7, 2003;1:79. doi: 10.1186/1477-7827-1-79.

Holsinger et al., Signal transduction in T lymphocytes using a conditional allele of Sos. Proc Natl Acad Sci U S A. Oct. 10, 1995;92(21):9810-4. doi: 10.1073/pnas.92.21.9810.

Holt et al., Human hematopoietic stem/progenitor cells modified by zinc-finger nucleases targeted to CCR5 control HIV-1 in vivo. Nat Biotechnol. Aug. 2010;28(8):839-47. doi: 10.1038/nbt.1663. Epub Jul. 2, 2010.

Hondares et al., Peroxisome Proliferator-activated Receptor α (PPARα) Induces PPARγ Coactivator 1α (PGC-1α) Gene Expression and Contributes to Thermogenic Activation of Brown Fat. J Biol. Chem Oct. 2011;286(50):43112-22. doi: 10.1074/jbc.M111.252775.

Hoogenboom et al., Natural and designer binding sites made by phage display technology. Immunol Today. Aug. 2000;21(8):371-8.

Horvath et al., CRISPR/Cas, the immune system of bacteria and archaea. Science. Jan. 8, 2010;327(5962):167-70. doi: 10.1126/science.1179555.

Horvath et al., Diversity, Activity, and Evolution of CRISPR Loci in *Streptococcus Thermophilus*. J Bacteriol. Feb. 2008;190(4):1401-12. doi: 10.1128/JB.01415-07. Epub Dec. 7, 2007.

Hotta et al., [Neurotropic viruses—classification, structure and characteristics]. Nihon Rinsho. Apr. 1997;55(4):777-82. Japanese.

Hou et al., Efficient genome engineering in human pluripotent stem cells using Cas9 from Neisseria meningitidis. Proc Natl Acad Sci U S A. Sep. 24, 2013;110(39):15644-9. doi: 10.1073/pnas.1313587110. Epub Aug. 12, 2013.

Houdebine, The methods to generate transgenic animals and to control transgene expression. J Biotechnol. Sep. 25, 2002;98(2-3):145-60.

Housden et al., Identification of potential drug targets for tuberous sclerosis complex by synthetic screens combining CRISPR-based knockouts with RNAi. Sci Signal. Sep. 8, 2015;8(393):rs9. doi: 10.1126/scisignal.aab3729.

Howard et al., Intracerebral drug delivery in rats with lesion-induced memory deficits. J Neurosurg. Jul. 1989;71(1):105-12.

Hower et al., Shape-based peak identification for ChIP-Seq. BMC Bioinformatics. Jan. 12, 2011;12:15. doi: 10.1186/1471-2105-12-15.

Hsu et al., DNA targeting specificity of RNA-guided Cas9 nucleases. Nat Biotechnol. Sep. 2013;31(9):827-32. doi: 10.1038/nbt.2647. Epub Jul. 21, 2013.

Hsu et al., DNA targeting specificity of RNA-guided Cas9 nucleases. Nat Biotechnol. Sep. 2013;31(9):827-32. doi: 10.1038/nbt.2647. Epub Jul. 21, 2013. Supplementary Information. 27 pages.

Hu et al., Chemical Biology Approaches to Genome Editing: Understanding, Controlling, and Delivering Programmable Nucleases. Cell Chem Biol. Jan. 21, 2016;23(1):57-73. doi: 10.1016/j.chembiol.2015.12.009.

Huang et al., Gain-of-function mutations in sodium channel Na(v)1.9 in painful neuropathy. Brain. Jun. 2014;137(Pt 6):1627-42. doi: 10.1093/brain/awu079. Epub Apr. 27, 2014.

Huang et al., Heritable gene targeting in zebrafish using customized TALENs. Nat Biotechnol. Aug. 5, 2011;29(8):699-700. doi: 10.1038/nbt.1939.

Huggins et al., Flap endonuclease 1 efficiently cleaves base excision repair and DNA replication intermediates assembled into nucleosomes. Mol Cell. Nov. 2002;10(5):1201-11. doi: 10.1016/s1097-2765(02)00736-0.

Humbert et al., Targeted gene therapies: tools, applications, optimization. Crit Rev Biochem Mol Biol. May-Jun. 2012;47(3):264-81. doi: 10.3109/10409238.2012.658112.

Hung et al., Protein localization in disease and therapy. J Cell Sci. Oct. 15, 2011;124(Pt 20):3381-92. doi: 10.1242/jcs.089110.

Hurt et al., Highly specific zinc finger proteins obtained by directed domain shuffling and cell-based selection. Proc Natl Acad Sci U S A. Oct. 14, 2003;100(21):12271-6. Epub Oct. 3, 2003.

Husimi, Selection and evolution of bacteriophages in cellstat. Adv Biophys. ; 1989;25:1-43. Review.

Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.

Hwang et al., Efficient In Vivo Genome Editing Using RNA-Guided Nucleases. Nat Biotechnol. Mar. 2013;31(3):227-229. doi: 10.1038/nbt.2501. Epub Jan. 29, 2013.

Ibba et al., Relaxing the substrate specificity of an aminoacyl-tRNA synthetase allows in vitro and in vivo synthesis of proteins containing unnatural amino acids. FEBS Lett. May 15, 1995;364(3):272-5.

Ibba et al., Substrate specificity is determined by amino acid binding pocket size in *Escherichia coli* phenylalanyl-tRNA synthetase. Biochemistry. Jun. 14, 1994;33(23):7107-12.

Iida et al., A site-specific, conservative recombination system carried by bacteriophage P1. Mapping the recombinase gene cin and the cross-over sites cix for the inversion of the C segment. EMBO J. 1982;1(11):1445-53.

Iida et al., The Min DNA inversion enzyme of plasmid p15B of *Escherichia coli* 15T-: a new member of the Din family of site-specific recombinases. Mol Microbiol. Jun. 1990;4(6):991-7. doi: 10.1111/j.1365-2958.1990.tb00671.x.

Ikediobi et al., Mutation analysis of 24 known cancer genes in the NCI-60 cell line set. Mol Cancer Ther. Nov. 2006;5(11):2606-12. Epub Nov. 6, 2006.

Imburgio et al., Studies of promoter recognition and start site selection by T7 RNA polymerase using a comprehensive collection of promoter variants. Biochemistry. Aug. 29, 2000;39(34):10419-30.

Ingram, A specific chemical difference between the globins of normal human and sickle-cell anaemia haemoglobin. Nature. Oct. 13, 1956;178(4537):792-4. doi: 10.1038/178792a0.

Irion et al., Identification and targeting of the ROSA26 locus in human embryonic stem cells. Nat Biotechnol. Dec. 2007;25(12):1477-82. doi: 10.1038/nbt1362. Epub Nov. 25, 2007.

Irrthum et al., Congenital hereditary lymphedema caused by a mutation that inactivates VEGFR3 tyrosine kinase. Am J Hum Genet. Aug. 2000;67(2):295-301. Epub Jun. 9, 2000.

Isaacs et al., Engineered riboregulators enable post-transcriptional control of gene expression. Nat Biotechnol. Jul. 2004;22(7):841-7. doi: 10.1038/nbt986. Epub Jun. 20, 2004.

Ishino et al., Nucleotide sequence of the iap gene, responsible for alkaline phosphatase isozyme conversion in *Escherichia coli*, and identification of the gene product. J Bacteriol. Dec. 1987;169(12):5429-33.

Iwai et al., Circular beta-lactamase: stability enhancement by cyclizing the backbone. FEBS Lett. Oct. 8, 1999;459(2):166-72. doi: 10.1016/s0014-5793(99)01220-x.

Iwai et al., Highly efficient protein trans-splicing by a naturally split DnaE intein from Nostoc punctiforme. FEBS Lett. Mar. 20, 2006;580(7):1853-8. doi: 10.1016/j.febslet.2006.02.045. Epub Feb. 24, 2006.

Iyama et al., DNA repair mechanisms in dividing and non-dividing cells. DNA Repair (Amst). Aug. 2013;12(8):620-36. doi: 10.1016/j.dnarep.2013.04.015. Epub May 16, 2013.

Jamieson et al., Drug discovery with engineered zinc-finger proteins. Nat Rev Drug Discov. May 2003;2(5):361-8.

Jansen et al., Backbone and nucleobase contacts to glucosamine-6-phosphate in the glmS ribozyme. Nat Struct Mol Biol. Jun. 2006;13(6):517-23. Epub May 14, 2006.

(56) References Cited

OTHER PUBLICATIONS

Jansen et al., Identification of genes that are associated with DNA repeats in prokaryotes. Mol Microbiol. Mar. 2002;43(6):1565-75.

Jardine et al., HIV-1 Vaccines. Priming a broadly neutralizing antibody response to HIV-1 using a germline-targeting immunogen. Science. Jul. 10, 2015;349(6244):156-61. doi: 10.1126/science. aac5894. Epub Jun. 18, 2015.

Jasin et al., Repair of strand breaks by homologous recombination. Cold Spring Harb Perspect Biol. Nov. 1, 2013;5(11):a012740. doi: 10.1101/cshperspect.a012740.

Jeggo, DNA breakage and repair. Adv Genet. 1998;38:185-218. doi: 10.1016/s0065-2660(08)60144-3.

Jemielity et al., Novel "anti-reverse" cap analogs with superior translational properties. RNA. Sep. 2003;9(9):1108-22. doi: 10.1261/rna.5430403.

Jenkins et al., Comparison of a preQ1 riboswitch aptamer in metabolite-bound and free states with implications for gene regulation. J Biol Chem. Jul. 15, 2011;286(28):24626-37. doi: 10.1074/jbc.M111.230375. Epub May 18, 2011.

Jeong et al., Measurement of deoxyinosine adduct: Can it be a reliable tool to assess oxidative or nitrosative DNA damage? Toxicol Lett. Oct. 17, 2012;214(2):226-33. doi: 10.1016/j.toxlet. 2012.08.013. Epub Aug. 23, 2012.

Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.

Jiang et al., Structural Biology. A Cas9-guide RNA Complex Preorganized for Target DNA Recognition. Science. Jun. 26, 2015;348(6242):1477-81. doi: 10.1126/science.aab1452.

Jiang et al., Structures of a CRISPR-Cas9 R-loop complex primed for DNA cleavage. Science. Feb. 19, 2016;351(6275):867-71. doi: 10.1126/science.aad8282. Epub Jan. 14, 2016.

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Jinek et al., RNA-programmed genome editing in human cells. Elife. Jan. 29, 2013;2:e00471. doi: 10.7554/eLife.00471.

Jinek et al., Structures of Cas9 endonucleases reveal RNA-mediated conformational activation. Science. Mar. 14, 2014;343(6176):1247997. doi: 10.1126/science.1247997. Epub Feb. 6, 2014.

Jiricny, The multifaceted mismatch-repair system. Nat Rev Mol Cell Biol. May 2006;7(5):335-46. doi: 10.1038/nrm1907.

Johann et al., GLVR1, a receptor for gibbon ape leukemia virus, is homologous to a phosphate permease of Neurospora crassa and is expressed at high levels in the brain and thymus. J Virol. Mar. 1992;66(3):1635-40. doi: 10.1128/JVI.66.3.1635-1640.1992.

Johansson et al., RNA Recognition by the MS2 Phage Coat Protein. Seminars in Virology. 1997;8(3):176-85. https://doi.org/10.1006/smvy.1997.0120.

Johansson et al., Selenocysteine in proteins-properties and biotechnological use. Biochim Biophys Acta. Oct. 30, 2005;1726(1):1-13. Epub Jun. 1, 2005.

Johns et al., The promise and peril of continuous in vitro evolution. J Mol Evol. Aug. 2005;61(2):253-63. Epub Jun. 27, 2005.

Johnson et al., Trans insertion-splicing: ribozyme-catalyzed insertion of targeted sequences into RNAs. Biochemistry. Aug. 9, 2005;44(31):10702-10. doi: 10.1021/bi0504815.

Joho et al., Identification of a region of the bacteriophage T3 and T7 RNA polymerases that determines promoter specificity. J Mol Biol. Sep. 5, 1990;215(1):31-9.

Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.

Joung et al., TALENs: a widely applicable technology for targeted genome editing. Nat Rev Mol Cell Biol. Jan. 2013;14(1):49-55. doi: 10.1038/nrm3486. Epub Nov. 21, 2012.

Joyce et al., Amplification, mutation and selection of catalytic RNA. Gene. Oct. 15, 1989;82(1):83-7. doi: 10.1016/0378-1119(89)90033-4.

Jyothy et al., Translocation Down syndrome. Indian J Med Sci. Mar. 2002;56(3):122-6.

Kacian et al., Purification of the DNA polymerase of avian myeloblastosis virus. Biochim Biophys Acta. Sep. 24, 1971;246(3):365-83. doi: 10.1016/0005-2787(71)90773-8.

Kaczmarczyk et al., Manipulating the Prion Protein Gene Sequence and Expression Levels with CRISPR/Cas9. PLoS One. Apr. 29, 2016;11(4):e0154604. doi: 10.1371/journal.pone.0154604.

Kadoch et al., Reversible disruption of mSWI/SNF (BAF) complexes by the SS18-SSX oncogenic fusion in synovial sarcoma. Cell. Mar. 28, 2013;153(1):71-85. doi: 10.1016/j.cell.2013.02.036.

Kahmann et al., G inversion in bacteriophage Mu DNA is stimulated by a site within the invertase gene and a host factor. Cell. Jul. 1985;41(3):771-80. doi: 10.1016/s0092-8674(85)80058-1.

Kaiser et al., Gene therapy. Putting the fingers on gene repair. Science. Dec. 23, 2005;310(5756):1894-6.

Kakiyama et al., A peptide release system using a photo-cleavable linker in a cell array format for cell-toxicity analysis. Polymer J. Feb. 27, 2013;45:535-9.

Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.

Kang et al., Structural Insights into riboswitch control of the biosynthesis of queuosine, a modified nucleotide found in the anticodon of tRNA. Mol Cell. Mar. 27, 2009;33(6):784-90. doi: 10.1016/j.molcel.2009.02.019. Epub Mar. 12, 2009.

Kao et al., Cleavage specificity of *Saccharomyces cerevisiae* flap endonuclease 1 suggests a double-flap structure as the cellular substrate. J Biol Chem. Apr. 26, 2002;277(17):14379-89. doi: 10.1074/jbc.M110662200. Epub Feb. 1, 2002.

Kappel et al., Regulating gene expression in transgenic animals. Curr Opin Biotechnol. Oct. 1992;3(5):548-53.

Karimova et al., Discovery of Nigri/nox and Panto/pox site-specific recombinase systems facilitates advanced genome engineering. Sci Rep. Jul. 22, 2016;6:30130. doi: 10.1038/srep30130.

Karimova et al., Vika/vox, a novel efficient and specific Cre/loxP-like site-specific recombination system. Nucleic Acids Res. Jan. 2013;41(2):e37. doi: 10.1093/nar/gks1037. Epub Nov. 9, 2012.

Karpenshif et al., From yeast to mammals: recent advances in genetic control of homologous recombination. DNA Repair (Amst). Oct. 1, 2012;11(10):781-8. doi: 10.1016/j.dnarep.2012.07.001. Epub Aug. 11, 2012. Review.

Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.

Katafuchi et al., DNA polymerases involved in the incorporation of oxidized nucleotides into DNA: their efficiency and template base preference. Mutat Res. Nov. 28, 2010;703(1):24-31. doi: 10.1016/j.mrgentox.2010.06.004. Epub Jun. 11, 2010.

Kato et al., Improved purification and enzymatic properties of three forms of reverse transcriptase from avian myeloblastosis virus. J Virol Methods. Dec. 1984;9(4):325-39. doi: 10.1016/0166-0934(84)90058-2.

Katoh et al., MAFFT multiple sequence alignment software version 7: improvements in performance and usability. Mol Biol Evol. Apr. 2013;30(4):772-80. doi: 10.1093/molbev/mst010. Epub Jan. 16, 2013.

Kaufman et al., Translational efficiency of polycistronic mRNAs and their utilization to express heterologous genes in mammalian cells. EMBO J. Jan. 1987;6(1):187-93.

Kavli et al., Excision of cytosine and thymine from DNA by mutants of human uracil-DNA glycosylase. EMBO J. Jul. 1, 1996;15(13):3442-7.

Kawarasaki et al., Enhanced crossover SCRATCHY: construction and high-throughput screening of a combinatorial library containing multiple non-homologous crossovers. Nucleic Acids Res. Nov. 1, 2003;31(21):e126.

Kay et al., Viral vectors for gene therapy: the art of turning infectious agents into vehicles of therapeutics. Nat Med. Jan. 2001;7(1):33-40.

(56) References Cited

OTHER PUBLICATIONS

Kaya et al., A bacterial Argonaute with noncanonical guide RNA specificity. Proc. Natl. Acad. Sci. USA Apr. 2016;113(15):4057-62.

Keijzers et al., Human exonuclease 1 (EXO1) activity characterization and its function on flap structures. Biosci Rep. Apr. 25, 2015;35(3):e00206. doi: 10.1042/BSR20150058.

Kellendonk et al., Regulation of Cre recombinase activity by the synthetic steroid RU 486. Nucleic Acids Res. Apr. 15, 1996;24(8):1404-11.

Kelman, PCNA: structure, functions and interactions. Oncogene. Feb. 13, 1997;14(6):629-40. doi: 10.1038/sj.onc.1200886.

Keravala et al., A diversity of serine phage integrases mediate site-specific recombination in mammalian cells. Mol Genet Genomics. Aug. 2006;276(2):135-46. doi: 10.1007/s00438-006-0129-5. Epub May 13, 2006.

Kessel et al., Murine developmental control genes. Science. Jul. 27, 1990;249(4967):374-9. doi: 10.1126/science.1974085.

Kessler et al., Gene delivery to skeletal muscle results in sustained expression and systemic delivery of a therapeutic protein. Proc Natl Acad Sci U S A. Nov. 26, 1996;93(24):14082-7. doi: 10.1073/pnas. 93.24.14082.

Ketha et al., Application of bioinformatics-coupled experimental analysis reveals a new transport-competent nuclear localization signal in the nucleoprotein of Influenza A virus strain. BMC Cell Biol. Apr. 28, 2008; 9:22. https://doi.org/10.1186/1471-2121-9-22.

Kiga et al., An engineered *Escherichia coli* tyrosyl-tRNA synthetase for site-specific incorporation of an unnatural amino acid into proteins in eukaryotic translation and its application in a wheat germ cell-free system. Proc Natl Acad Sci U S A. Jul. 23, 2002;99(15):9715-20. Epub Jul. 3, 2002.

Kilbride et al., Determinants of product topology in a hybrid Cre-Tn3 resolvase site-specific recombination system. J Mol Biol. Jan. 13, 2006;355(2):185-95. Epub Nov. 9, 2005.

Kilcher et al., Brochothrix thermosphacta bacteriophages feature heterogeneous and highly mosaic genomes and utilize unique prophage insertion sites. J Bacteriol. Oct. 2010;192(20):5441-53. doi: 10.1128/JB.00709-10. Epub Aug. 13, 2010.

Kim et al., DJ-1, a novel regulator of the tumor suppressor PTEN. Cancer Cell. 2005;7(3):263-273.

Kim et al., A library of TAL effector nucleases spanning the human genome. Nat Biotechnol. Mar. 2013;31(3):251-8. Doi: 10.1038/nbt. 2517. Epub Feb. 17, 2013.

Kim et al., Genome-wide target specificities of CRISPR RNA-guided programmable deaminases. Nat Biotechnol. May 2017;35(5):475-480. doi: 10.1038/nbt.3852. Epub Apr. 10, 2017.

Kim et al., High cleavage efficiency of a 2A peptide derived from porcine teschovirus-1 in human cell lines, zebrafish and mice. PLoS One. 2011;6(4):e18556. doi: 10.1371/journal.pone.0018556. Epub Apr. 29, 2011.

Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.

Kim et al., Hybrid restriction enzymes: zinc finger fusions to Fok I cleavage domain. Proc Natl Acad Sci U S A. Feb. 6, 1996;93(3):1156-60.

Kim et al., Mycobacteriophage Bxb1 integrates into the *Mycobacterium smegmatis* groEL1 gene. Mol Microbiol. Oct. 2003;50(2):463-73. doi: 10.1046/j.1365-2958.2003.03723.x.

Kim et al., RAD51 mutants cause replication defects and chromosomal instability. Mol Cell Biol. Sep. 2012;32(18):3663-80. doi: 10.1128/MCB.00406-12. Epub Jul. 9, 2012.

Kim et al., Structural and kinetic characterization of *Escherichia coli* TadA, the wobble-specific tRNA deaminase. Biochemistry. May 23, 2006;45(20):6407-16. doi: 10.1021/bi0522394. PMID: 16700551.

Kim et al., TALENs and ZFNs are associated with different mutationsignatures. Nat Methods. Mar. 2013;10(3):185. doi: 10.1038/nmeth.2364. Epub Feb. 10, 2013.

Kim et al., Targeted genome editing in human cells with zinc finger nucleases constructed via modular assembly. Genome Res. Jul. 2009; 19(7):1279-88. doi: 10.1101/gr.089417.108. Epub May 21, 2009.

Kim et al., The role of apolipoprotein E in Alzheimer's disease. Neuron. Aug. 13, 2009;63(3):287-303. doi: 10.1016/j.neuron.2009. 06.026.

Kim et al., Transcriptional repression by zinc finger peptides. Exploring the potential for applications in gene therapy. J Biol Chem. Nov. 21, 1997;272(47):29795-800.

King et al., No gain, no pain: NaV1.7 as an analgesic target. ACS Chem Neurosci. Sep. 17, 2014;5(9):749-51. doi: 10.1021/cn500171p. Epub Aug. 11, 2014.

Kitamura et al., Uracil DNA glycosylase counteracts APOBEC3G-induced hypermutation of hepatitis B viral genomes: excision repair of covalently closed circular DNA. PLoS Pathog. 2013;9(5):e1003361. doi: 10.1371/journal.ppat.1003361. Epub May 16, 2013.

Klapacz et al., Frameshift mutagenesis and microsatellite instability induced by human alkyladenine DNA glycosylase. Mol Cell. Mar. 26, 2010;37(6):843-53. doi: 10.1016/j.molcel.2010.01.038.

Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.

Klein et al., Cocrystal structure of a class I preQ1 riboswitch reveals a pseudoknot recognizing an essential hypermodified nucleobase. Nat Struct Mol Biol. Mar. 2009; 16(3):343-4. doi: 10.1038/nsmb. 1563.Epub Feb. 22, 2009.

Kleiner et al., In vitro selection of a DNA-templated small-molecule library reveals a class of macrocyclic kinase inhibitors. J Am Chem Soc. Aug. 25, 2010;132(33):11779-91. doi: 10.1021/ja104903x.

Kleinstiver et al., Broadening the targeting range of *Staphylococcus aureus* CRISPR-Cas9 by modifying PAM recognition. Nat Biotechnol. Dec. 2015;33(12):1293-1298. doi: 10.1038/nbt.3404. Epub Nov. 2, 2015.

Kleinstiver et al., Engineered CRISPR-Cas9 nucleases with altered PAM specificities. Nature. Jul. 23, 2015;523(7561):481-5 and Supplementary Materials. doi: 10.1038/nature14592. Epub Jun. 22, 2015. 27 pages.

Kleinstiver et al., Engineered CRISPR-Cas9 nucleases with altered PAM specificities. Nature. Jul. 23, 2015;523(7561):481-5. doi: 10.1038/nature14592. Epub Jun. 22, 2015.

Kleinstiver et al., High-fidelity CRISPR-Cas9 nucleases with no detectable genome-wide off-target effects. Nature. Jan. 28, 2016;529(7587):490-5. doi: 10.1038/nature16526. Epub Jan. 6, 2016.

Kleinstiver et al., Monomeric site-specific nucleases for genome editing. Proc Natl Acad Sci U S A. May 22, 2012;109(21):8061-6. doi: 10.1073/pnas.1117984109. Epub May 7, 2012.

Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.

Klippel et al., Isolation and characterization of unusual gin mutants. EMBO J. Dec. 1, 1988;7(12):3983-9.

Klippel et al., The DNA invertase Gin of phage Mu: formation of a covalent complex with DNA via a phosphoserine at amino acid position 9. EMBO J. Apr. 1988;7(4):1229-37.

Kohli et al., A portable hot spot recognition loop transfers sequence preferences from APOBEC family members to activation-induced cytidine deaminase. J Biol Chem. Aug. 21, 2009;284(34):22898-904. doi: 10.1074/jbc.M109.025536. Epub Jun. 26, 2009.

Kohli et al., Local sequence targeting in the AID/APOBEC family differentially impacts retroviral restriction and antibody diversification. J Biol Chem. Dec. 24, 2010;285(52):40956-64. doi: 10.1074/jbc. M110.177402. Epub Oct. 6, 2010.

Koike-Yusa et al., Genome-wide recessive genetic screening in mammalian cells with a lentiviral CRISPR-guide RNA library. Nat Biotechnol. Mar. 2014;32(3):267-73. doi: 10.1038/nbt.2800. Epub Dec. 23, 2013.

Kolot et al., Site promiscuity of coliphage HK022 integrase as a tool for gene therapy. Gene Ther. Jul. 2015;22(7):521-7. doi: 10.1038/gt.2015.9. Epub Mar. 12, 2015.

(56)　　　　References Cited

OTHER PUBLICATIONS

Kolot et al., Site-specific recombination in mammalian cells expressing the Int recombinase of bacteriophage HK022. Mol Biol Rep. Aug. 1999;26(3):207-13. doi: 10.1023/a:1007096701720.

Komor et al., Programmable editing of a target base in genomic DNA without double-stranded DNA cleavage. Nature. Apr. 20, 2016;533(7603):420-4. doi: 10.1038/nature17946.

Konermann et al., Genome-scale transcriptional activation by an engineered CRISPR-Cas9 complex. Nature. Jan. 29, 2015;517(7536):583-8. doi: 10.1038/nature14136. Epub Dec. 10, 2014.

Kotewicz et al., Cloning and overexpression of Moloney murine leukemia virus reverse transcriptase in *Escherichia coli*. Gene. 1985;35(3):249-58. doi: 10.1016/0378-1119(85)90003-4.

Kotewicz et al., Isolation of cloned Moloney murine leukemia virus reverse transcriptase lacking ribonuclease H activity. Nucleic Acids Res. Jan. 11, 1988;16(1):265-77. doi: 10.1093/nar/16.1.265.

Kotin, Prospects for the use of adeno-associated virus as a vector for human gene therapy. Hum Gene Ther. Jul. 1994;5(7):793-801. doi: 10.1089/hum.1994.5.7-793.

Kouzminova et al., Patterns of chromosomal fragmentation due to uracil-DNA incorporation reveal a novel mechanism of replication-dependent double-stranded breaks. Mol Microbiol. Apr. 2008;68(1):202-15. doi: 10.1111/j.1365-2958.2008.06149.x.

Kowal et al., Exploiting unassigned codons in Micrococcus luteus for tRNA-based amino acid mutagenesis. Nucleic Acids Res. Nov. 15, 1997;25(22):4685-9.

Kozak, An analysis of 5'-noncoding sequences from 699 vertebrate messenger RNAs. Nucleic Acids Res. Oct. 26, 1987;15(20):8125-48. doi: 10.1093/nar/15.20.8125.

Kraft et al., Deletions, Inversions, Duplications: Engineering of Structural Variants using CRISPR/Cas in Mice. Cell Rep. Feb. 10, 2015;10(5):833-839. doi: 10.1016/j.celrep.2015.01.016. Epub Feb. 7, 2015.

Kremer et al., Adenovirus and adeno-associated virus mediated gene transfer. Br Med Bull. Jan. 1995;51(1):31-44. doi: 10.1093/oxfordjournals.bmb.a072951.

Krokan et al., Uracil in DNA—occurrence, consequences and repair. Oncogene. Dec. 16, 2002;21(58):8935-48. doi: 10.1038/sj.onc.1205996.

Krokan et al., Base excision repair. Cold Spring Harb Perspect Biol. Apr. 1, 2013;5(4):a012583. doi: 10.1101/cshperspect.a012583.

Kumar et al., Gene therapy for chronic neuropathic pain: how does it work and where do we stand today? Pain Med. May 2011;12(5):808-22. doi: 10.1111/j.1526-4637.2011.01120.x.

Kumar et al., Structural and functional consequences of the mutation of a conserved arginine residue in alphaA and alphaB crystallins. J Biol Chem. Aug. 20, 1999;274(34):24137-41.

Kundu et al., Leucine to proline substitution by SNP at position 197 in Caspase-9 gene expression leads to neuroblastoma: a bioinformatics analysis. 3 Biotech. 2013; 3:225-34.

Kunkel et al., Eukaryotic Mismatch Repair in Relation to DNA Replication. Annu Rev Genet. 2015;49:291-313. doi: 10.1146/annurev-genet-112414-054722.

Kunz et al., DNA Repair in mammalian cells: Mismatched repair: variations on a theme. Cell Mol Life Sci. Mar. 2009;66(6):1021-38. doi: 10.1007/s00018-009-8739-9.

Kurjan et al., Structure of a yeast pheromone gene (MF alpha): a putative alpha-factor precursor contains four tandem copies of mature alpha-factor. Cell. Oct. 1982;30(3):933-43. doi: 10.1016/0092-8674(82)90298-7.

Kuscu et al., Genome-wide analysis reveals characteristics of off-target sites bound by the Cas9 endonuclease. Nat Biotechnol. Jul. 2014;32(7):677-83. doi: 10.1038/nbt.2916. Epub May 18, 2014.

Kwon et al., Chemical basis of glycine riboswitch cooperativity. RNA. Jan. 2008;14(1):25-34. Epub Nov. 27, 2007.

Köhrer et al., A possible approach to site-specific insertion of two different unnatural amino acids into proteins in mammalian cells via nonsense suppression. Chem Biol. Nov. 2003;10(11):1095-102.

Köhrer et al., Complete set of orthogonal 21st aminoacyl-tRNA synthetase-amber, ochre and opal suppressor tRNA pairs: concomitant suppression of three different termination codons in an mRNA in mammalian cells. Nucleic Acids Res. Dec. 1, 2004;32(21):6200-11. Print 2004.

Kügler et al., Human synapsin 1 gene promoter confers highly neuron-specific long-term transgene expression from an adenoviral vector in the adult rat brain depending on the transduced area. Gene Ther. Feb. 2003;10(4):337-47. doi: 10.1038/sj.gt.3301905.

Lada et al., Mutator effects and mutation signatures of editing deaminases produced in bacteria and yeast. Biochemistry (Mosc). Jan. 2011;76(1):131-46.

Lakich et al., Inversions disrupting the factor VIII gene are a common cause of severe haemophilia A. Nat Genet. Nov. 1993;5(3):236-41. doi: 10.1038/ng1193-236.

Lancaster et al., Limited trafficking of a neurotropic virus through inefficient retrograde axonal transport and the type I interferon response. PLoS Pathog. Mar. 5, 2010;6(3):e1000791. doi: 10.1371/journal.ppat.1000791.

Landrum et al., ClinVar: public archive of interpretations of clinically relevant variants. Nucleic Acids Res. Jan. 4, 2016;44(D1):D862-8. doi: 10.1093/nar/gkv1222. Epub Nov. 17, 2015.

Landrum et al., ClinVar: public archive of relationships among sequence variation and human phenotype. Nucleic Acids Res. Jan. 2014;42(Database issue): D980-5. doi: 10.1093/nar/gkt1113. Epub Nov. 14, 2013.

Langer et al., Chemical and Physical Structure of Polymers as Carriers for Controlled Release of Bioactive Agents: A Review. Journal of Macromolecular Science, 2006;23(1):61-126. DOI: 10.1080/07366578308079439.

Langer et al., New methods of drug delivery. Science. Sep. 28, 1990;249(4976):1527-33.

Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.

Lau et al., Molecular basis for discriminating between normal and damaged bases by the human alkyladenine glycosylase, AAG. Proc Natl Acad Sci U S A. Dec. 5, 2000;97(25):13573-8.

Lauer et al., Construction, characterization, and use of two Listeria monocytogenes site-specific phage integration vectors. J Bacteriol. Aug. 2002;184(15):4177-86. doi: 10.1128/jb.184.15.4177-4186. 2002.

Lavergne et al., Defects in type IIA von Willebrand disease: a cysteine 509 to arginine substitution in the mature von Willebrand factor disrupts a disulphide loop involved in the interaction with platelet glycoprotein Ib-IX. Br J Haematol. Sep. 1992;82(1):66-72.

Lawyer et al., High-level expression, purification, and enzymatic characterization of full-length Thermus aquaticus DNA polymerase and a truncated form deficient in 5' to 3' exonuclease activity. PCR Methods Appl. May 1993;2(4):275-87. doi: 10.1101/gr.2.4.275.

Lazar et al., Transforming growth factor alpha: mutation of aspartic acid 47 and leucine 48 results in different biological activities. Mol Cell Biol. Mar. 1988;8(3):1247-52.

Lazarevic et al., Nucleotide sequence of the Bacillus subtilis temperate bacteriophage SPbetac2. Microbiology (Reading). May 1999;145 ( Pt 5):1055-1067. doi: 10.1099/13500872-145-5-1055.

Le et al., SMNDelta7, the major product of the centromeric survival motor neuron (SMN2) gene, extends survival in mice with spinal muscular atrophy and associates with full-length SMN. Hum Mol Genet. Mar. 15, 2005;14(6):845-57. doi: 10.1093/hmg/ddi078. Epub Feb. 9, 2005.

Le Grice et al., Purification and characterization of recombinant equine infectious anemia virus reverse transcriptase. J Virol. Dec. 1991;65(12):7004-7. doi: 10.1128/JVI.65.12.7004-7007.1991.

Leaver-Fay et al., ROSETTA3: an object-oriented software suite for the simulation and design of macromolecules. Methods Enzymol. 2011;487:545-74. doi: 10.1016/B978-0-12-381270-4.00019-6.

Leconte et al., A population-based experimental model for protein evolution: effects of mutation rate and selection stringency on evolutionary outcomes. Biochemistry. Feb. 26, 2013;52(8):1490-9. doi: 10.1021/bi3016185. Epub Feb. 14, 2013.

(56) References Cited

OTHER PUBLICATIONS

Ledford, Gene-editing hack yields pinpoint precision. Nature, Apr. 20, 2016. http://www.nature.com/news/gene-editing-hack-yields-pinpoint-precision-1.19773.

Lee et al., A chimeric thyroid hormone receptor constitutively bound to DNA requires retinoid X receptor for hormone-dependent transcriptional activation in yeast. Mol Endocrinol. Sep. 1994;8(9):1245-52.

Lee et al., A monoclonal antibody that targets a NaV1.7 channel voltage sensor for pain and itch relief. Cell. Jun. 5, 2014;157(6):1393-1404. doi: 10.1016/j.cell.2014.03.064. Epub May 22, 2014. Retraction in: Cell. Jun. 25, 2020;181(7):1695.

Lee et al., An allosteric self-splicing ribozyme triggered by a bacterial second messenger. Science. Aug. 13, 2010;329(5993):845-8. doi: 10.1126/science.1190713.

Lee et al., PIK3CA gene is frequently mutated in breast carcinomas and hepatocellular carcinomas. Oncogene. Feb. 17, 2005;24(8):1477-80.

Lee et al., Recognition of liposomes by cells: in vitro binding and endocytosis mediated by specific lipid headgroups and surface charge density. Biochim Biophys Acta. Jan. 31, 1992;1103(2):185-97.

Lee et al., Site-specific integration of mycobacteriophage L5: integration-proficient vectors for *Mycobacterium smegmatis, Mycobacterium tuberculosis*, and bacille Calmette-Guérin. Proc Natl Acad Sci U S A. Apr. 15, 1991;88(8):3111-5. doi: 10.1073/pnas.88.8.3111.

Lee et al., Targeted chromosomal deletions in human cells using zinc finger nucleases. Genome Res. Jan. 2010 20: 81-89; Published in Advance Dec. 1, 2009, doi:10.1101/gr.099747.109.

Lee et al., Transcriptional regulation and its misregulation in disease. Cell. Mar. 14, 2013;152(6):1237-51. doi: 10.1016/j.cell.2013.02.014.

Lefebvre et al., Identification and characterization of a spinal muscular atrophy-determining gene. Cell. Jan. 13, 1995;80(1):155-65. doi: 10.1016/0092-8674(95)90460-3.

Lei et al., Efficient targeted gene disruption in Xenopus embryos using engineered transcription activator-like effector nucleases (TALENs). Proc Natl Acad Sci U S A. Oct. 23, 2012;109(43):17484-9. Doi: 10.1073/pnas.1215421109. Epub Oct. 8, 2012.

Leipold et al., A de novo gain-of-function mutation in SCN11A causes loss of pain perception. Nat Genet. Nov. 2013;45(11):1399-404. doi: 10.1038/ng.2767. Epub Sep. 15, 2013.

Lenk et al., Pathogenic mechanism of the FIG4 mutation responsible for Charcot-Marie-Tooth disease CMT4J. PLoS Genet. Jun. 2011;7(6):e1002104. doi: 10.1371/journal.pgen.1002104. Epub Jun. 2, 2011.

Lesinski et al., The potential for targeting the STAT3 pathway as a novel therapy for melanoma. Future Oncol. Jul. 2013;9(7):925-7. doi: 10.2217/fon.13.83. Author Manuscript. 4 pages.

Levy et al., Inhibition of calcification of bioprosthetic heart valves by local controlled-release diphosphonate. Science. Apr. 12, 1985;228(4696):190-2.

Lew et al., Protein splicing in vitro with a semisynthetic two-component minimal intein. J Biol Chem. Jun. 26, 1998;273(26):15887-90. doi: 10.1074/jbc.273.26.15887.

Lewis et al., A serum-resistant cytofectin for cellular delivery of antisense oligodeoxynucleotides and plasmid DNA. Proc Natl Acad Sci U S A. Apr. 16, 1996;93(8):3176-81.

Lewis et al., Codon 129 polymorphism of the human prion protein influences the kinetics of amyloid formation. J Gen Virol. Aug. 2006;87(Pt 8):2443-9.

Lewis et al., Cytosine deamination and the precipitous decline of spontaneous mutation during Earth's history. Proc Natl Acad Sci U S A. Jul. 19, 2016;113(29):8194-9. doi: 10.1073/pnas.1607580113. Epub Jul. 5, 2016.

Li et al., A Radioactivity-Based Assay for Screening Human m6A-RNA Methyltransferase, METTL3-METTL14 Complex, and Demethylase ALKBH5. J Biomol Screen. Mar. 2016;21(3):290-7. doi: 10.1177/1087057115623264. Epub Dec. 23, 2015.

Li et al., Current approaches for engineering proteins with diverse biological properties. Adv Exp Med Biol. 2007;620:18-33.

Li et al., Fast and accurate short read alignment with Burrows-Wheeler transform. Bioinformatics. Jul. 15, 2009;25(14):1754-60. doi: 10.1093/bioinformatics/btp324. Epub May 18, 2009.

Li et al., Lagging strand DNA synthesis at the eukaryotic replication fork involves binding and stimulation of FEN-1 by proliferating cell nuclear antigen. J Biol Chem. Sep. 22, 1995;270(38):22109-12. doi: 10.1074/jbc.270.38.22109.

Li et al., Loss of post-translational modification sites in disease. Pac Symp Biocomput. 2010:337-47. doi: 10.1142/9789814295291_0036.

Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.

Li et al., Multiplex and homologous recombination-mediated genome editing in *Arabidopsis* and Nicotiana benthamiana using guide RNA and Cas9. Nat Biotechnol. Aug. 2013;31(8):688-91. doi: 10.1038/nbt.2654.

Li et al., Protein trans-splicing as a means for viral vector-mediated in vivo gene therapy. Hum Gene Ther. Sep. 2008;19(9):958-64. doi: 10.1089/hum.2008.009.

Li et al., RSEM: accurate transcript quantification from RNA-Seq data with or without a reference genome. BMC Bioinformatics. Aug. 4, 2011;12:323. doi: 10.1186/1471-2105-12-323.

Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.

Li, Mechanisms and functions of DNA mismatch repair. Cell Res. Jan. 2008;18(1):85-98. doi: 10.1038/cr.2007.115.

Liang et al., Homology-directed repair is a major double-strand break repair pathway in mammalian cells. Proc Natl Acad Sci U S A. Apr. 28, 1998;95(9):5172-7. doi: 10.1073/pnas.95.9.5172.

Liang et al., Rapid and highly efficient mammalian cell engineering via Cas9 protein transfection. Send to; J Biotechnol. Aug. 20, 2015;208:44-53. doi: 10.1016/j.jbiotec.2015.04.024.

Lieber et al., Mechanism and regulation of human non-homologous DNA end-joining. Nat Rev Mol Cell Biol. Sep. 2003;4(9):712-20.

Liefke et al., The oxidative demethylase ALKBH3 marks hyperactive gene promoters in human cancer cells. Genome Med. Jun. 30, 2015;7(1):66. doi: 10.1186/s13073-015-0180-0.

Lienert et al., Two- and three-input TALE-based and logic computation in embryonic stem cells. Nucleic Acids Res. Nov. 2013;41(21):9967-75. doi: 10.1093/nar/gkt758. Epub Aug. 27, 2013.

Lilley, D.M. The Varkud Satellite Ribozyme. RNA. Feb. 2004;10(2):151-8.doi: 10.1261/rna.5217104.

Lim et al., Crystal structure of the moloney murine leukemia virus RNase H domain. J Virol. Sep. 2006;80(17):8379-89. doi: 10.1128/JVI.00750-06.

Lim et al., Viral vectors for neurotrophic factor delivery: a gene therapy approach for neurodegenerative diseases of the CNS. Pharmacol Res. Jan. 2010;61(1):14-26. doi: 10.1016/j.phrs.2009.10.002. Epub Oct. 17, 2009.

Lin et al., [Construction and evaluation of DnaB split intein high expression vector and a six amino acids cyclic peptide library]. Sheng Wu Gong Cheng Xue Bao. Nov. 2008;24(11):1924-30. Chinese.

Lin et al., Enhanced homology-directed human genome engineering by controlled timing of CRISPR/Cas9 delivery. Elife. Dec. 15, 2014;3:e04766. doi: 10.7554/eLife.04766.

Lin et al., The human REV1 gene codes for a DNA template-dependent dCMP transferase. Nucleic Acids Res. Nov. 15, 1999;27(22):4468-75. doi: 10.1093/nar/27.22.4468.

Lindahl, T., Instability and decay of the primary structure of DNA. Nature. Apr. 22, 1993;362(6422):709-15. doi: 10.1038/362709a0.

Link et al., Engineering ligand-responsive gene-control elements: lessons learned from natural riboswitches. Gene Ther. Oct. 2009;16(10):1189-201. doi: 10.1038/gt.2009.81. Epub Jul. 9, 2009. Review.

Liu et al., Split dnaE genes encoding multiple novel inteins in Trichodesmium erythraeum. J Biol Chem. Jul. 18, 2003;278(29):26315-8. doi: 10.1074/jbc.C300202200. Epub May 24, 2003.

(56)         References Cited

OTHER PUBLICATIONS

Liu et al., A METTL3-METTL14 complex mediates mammalian nuclear RNA N6-adenosine methylation. Nat Chem Biol. Feb. 2014;10(2):93-5. doi: 10.1038/nchembio.1432. Epub Dec. 6, 2013.

Liu et al., Adding new chemistries to the genetic code. Annu Rev Biochem. 2010;79:413-44. doi: 10.1146/annurev.biochem.052308.105824.

Liu et al., Apolipoprotein E and Alzheimer disease: risk, mechanisms and therapy. Nat Rev Neurol. Feb. 2013;9(2):106-18. doi: 10.1038/nrneurol.2012.263. Epub Jan. 8, 2013.

Liu et al., Balancing AID and DNA repair during somatic hypermutation. Trends Immunol. Apr. 2009;30(4):173-81. doi: 10.1016/j.it.2009.01.007.

Liu et al., Calcineurin is a common target of cyclophilin-cyclosporin A and FKBP-FK506 complexes. Cell. Aug. 23, 1991;66(4):807-15. doi: 10.1016/0092-8674(91)90124-h.

Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.

Liu et al., Design of polydactyl zinc-finger proteins for unique addressing within complex genomes. Proc Natl Acad Sci U S A. May 27, 1997;94(11):5525-30.

Liu et al., Distance determination by GIY-YIG intron endonucleases: discrimination between repression and cleavage functions. Nucleic Acids Res. Mar. 31, 2006;34(6):1755-64. Print 2006.

Liu et al., Engineering a tRNA and aminoacyl-tRNA synthetase for the site-specific incorporation of unnatural amino acids into proteins in vivo. Proc Natl Acad Sci U S A. Sep. 16, 1997;94(19):10092-7.

Liu et al., Fast Colorimetric Sensing of Adenosine and Cocaine Based on a General Sensor Design Involving Aptamers and Nanoparticles. Angew Chem. Dec. 16, 2006;45(1):90-4. DOI: 10.1002/anie.200502589.

Liu et al., Fast Colorimetric Sensing of Adenosine and Cocaine Based on a General Sensor Design Involving Aptamers and Nanoparticles. Angew Chem. 2006;118(1):96-100.

Liu et al., Flap endonuclease 1: a central component of DNA metabolism. Annu Rev Biochem. 2004;73:589-615. doi:10.1146/annurev.biochem.73.012803.092453.

Liu et al., Functional Nucleic Acid Sensors. Chem Rev. May 2009;109(5):1948-98. doi: 10.1021/cr030183i.

Liu et al., Genetic incorporation of unnatural amino acids into proteins in mammalian cells. Nat Methods. Mar. 2007;4(3):239-44. Epub Feb. 25, 2007.

Liu et al., Human BRCA2 protein promotes RAD51 filament formation on RPA-covered single-stranded DNA. Nat Struct Mol Biol. Oct. 2010;17(10):1260-2. doi: 10.1038/nsmb.1904. Epub Aug. 22, 2010.

Liu et al., N(6)-methyladenosine-dependent RNA structural switches regulate RNA-protein interactions. Nature. Feb. 26, 2015;518(7540):560-4. doi: 10.1038/nature14234.

Liu et al., Probing N6-methyladenosine RNA modification status at single nucleotide resolution in mRNA and long noncoding RNA. RNA. Dec. 2013;19(12):1848-56. doi: 10.1261/rna.041178.113. Epub Oct. 18, 2013.

Liu et al., Reverse transcriptase of foamy virus. Purification of the enzymes and immunological identification. Arch Virol. 1977;55(3):187-200. doi: 10.1007/BF01319905.

Liu et al., Reverse transcriptase-mediated tropism switching in Bordetella bacteriophage. Science. Mar. 15, 2002;295(5562):2091-4. doi: 10.1126/science.1067467.

Liu et al., Saccharomyces cerevisiae flap endonuclease 1 uses flap equilibration to maintain triplet repeat stability. Mol Cell Biol. May 2004;24(9):4049-64. doi: 10.1128/MCB.24.9.4049-4064.2004.

Loessner et al., Complete nucleotide sequence, molecular analysis and genome structure of bacteriophage A118 of Listeria monocytogenes: implications for phage evolution. Mol Microbiol. Jan. 2000;35(2):324-40. doi: 10.1046/j.1365-2958.2000.01720.x.

Lombardo et al., Gene editing in human stem cells using zinc finger nucleases and integrase-defective lentiviral vector delivery. Nat Biotechnol. Nov. 2007;25(11):1298-306. Epub Oct. 28, 2007.

Long et al., Postnatal genome editing partially restores dystrophin expression in a mouse model of muscular dystrophy. Science. Jan. 22, 2016;351(6271):400-3. doi: 10.1126/science.aad5725. Epub Dec. 31, 2015.

Lopez-Girona et al., Cereblon is a direct protein target for immunomodulatory and antiproliferative activities of lenalidomide and pomalidomide. Leukemia. Nov. 2012;26(11):2326-35. doi: 10.1038/leu.2012.119. Epub May 3, 2012.

Lorenz et al., ViennaRNA Package 2.0. Algorithms Mol Biol. Nov. 24, 2011;6:26. doi: 10.1186/1748-7188-6-26.

Lorson et al., A single nucleotide in the SMN gene regulates splicing and is responsible for spinal muscular atrophy. Proc Natl Acad Sci U S A. May 25, 1999;96(11):6307-11. doi: 10.1073/pnas.96.11.6307.

Losey et al., Crystal structure of Staphylococcus sureus tRNA adenosine deaminase tadA in complex with RNA. Nature Struct. Mol. Biol. Feb. 2006;13(2):153-9.

Luan et al., Reverse transcription of R2Bm RNA is primed by a nick at the chromosomal target site: a mechanism for non-LTR retrotransposition. Cell. Feb. 26, 1993;72(4):595-605. doi: 10.1016/0092-8674(93)90078-5.

Luckow et al., High level expression of nonfused foreign genes with Autographa californica nuclear polyhedrosis virus expression vectors. Virology. May 1989;170(1):31-9. doi: 10.1016/0042-6822(89)90348-6.

Lukacsovich et al., Repair of a specific double-strand break generated within a mammalian chromosome by yeast endonuclease I-SceI. Nucleic Acids Res. Dec. 25, 1994;22(25):5649-57. doi: 10.1093/nar/22.25.5649.

Lundberg et al., Delivery of short interfering RNA using endosomolytic cell-penetrating peptides. FASEB J. Sep. 2007;21(11):2664-71. Epub Apr. 26, 2007.

Lundquist et al., Site-directed mutagenesis and characterization of uracil-DNA glycosylase inhibitor protein. Role of specific carboxylic amino acids in complex formation with Escherichia coli uracil-DNA glycosylase. J Biol Chem. Aug. 22, 1997;272(34):21408-19.

Lutz et al., Postsymptomatic restoration of SMN rescues the disease phenotype in a mouse model of severe spinal muscular atrophy. J Clin Invest. Aug. 2011;121(8):3029-41. doi: 10.1172/JCI57291. Epub Jul. 25, 2011.

Lynch, Evolution of the mutation rate. Trends Genet. Aug. 2010;26(8):345-52. doi: 10.1016/j.tig.2010.05.003. Epub Jun. 30, 2010.

Lyons et al., Efficient Recognition of an Unpaired Lesion by a DNA Repair Glycosylase. J. Am. Chem. Soc., 2009;131(49):17742-3. DOI: 10.1021/ja908378y.

Luke et al., Partial purification and characterization of the reverse transcriptase of the simian immunodeficiency virus TYO-7 isolated from an African green monkey. Biochemistry. Feb. 20, 1990;29(7):1764-9. doi: 10.1021/bi00459a015.

Ma et al., Identification of pseudo attP sites for phage phiC31 integrase in bovine genome. Biochem Biophys Res Commun. Jul. 7, 2006;345(3):984-8. doi: 10.1016/j.bbrc.2006.04.145. Epub May 3, 2006.

Ma et al., In vitro protein engineering using synthetic tRNA(Ala) with different anticodons. Biochemistry. Aug. 10, 1993;32(31):7939-45.

Ma et al., PhiC31 integrase induces efficient site-specific recombination in the Capra hircus genome. DNA Cell Biol. Aug. 2014;33(8):484-91. doi: 10.1089/dna.2013.2124. Epub Apr. 22, 2014.

Ma et al., Single-Stranded DNA Cleavage by Divergent CRISPR-Cas9 Enzymes. Mol Cell. Nov. 5, 2015;60(3):398-407. doi: 10.1016/j.molcel.2015.10.030.

Maas et al., Identification and characterization of a human tRNA-specific adenosine deaminase related to the ADAR family of pre-mRNA editing enzymes. Proc Natl Acad Sci U S A. Aug. 3, 1999;96(16):8895-900. doi: 10.1073/pnas.96.16.8895.

(56)        References Cited

OTHER PUBLICATIONS

Macbeth et al., Inositol hexakisphosphate is bound in the ADAR2 core and required for RNA editing. Science. Sep. 2, 2005;309(5740):1534-9. doi: 10.1126/science.1113150.

Macrae et al., Ribonuclease revisited: structural insights into ribonuclease III family enzymes. Curr Opin Struct Biol. Feb. 2007;17(1):138-45. doi: 10.1016/j.sbi.2006.12.002. Epub Dec. 27, 2006.

Madura et al., Structural basis for ineffective T-cell responses to MHC anchor residue-improved "heteroclitic" peptides. Eur J Immunol. Feb. 2015;45(2):584-91. doi: 10.1002/eji.201445114. Epub Dec. 28, 2014.

Maeder et al., CRISPR RNA-guided activation of endogenous human genes. Nat Methods. Oct. 2013;10(10):977-9. doi: 10.1038/nmeth.2598. Epub Jul. 25, 2013.

Maeder et al., Rapid "open-source" engineering of customized zinc-finger nucleases for highly efficient gene modification. Mol Cell. Jul. 25, 2008;31(2):294-301. doi:10.1016/j.molcel.2008.06.016.

Maeder et al., Robust, synergistic regulation of human gene expression using TALE activators. Nat Methods. Mar. 2013;10(3):243-5. doi: 10.1038/nmeth.2366. Epub Feb. 10, 2013.

Magin et al., Corf, the Rev/Rex homologue of HTDV/HERV-K, encodes an arginine-rich nuclear localization signal that exerts a trans-dominant phenotype when mutated. Virology. Aug. 15, 2000;274(1):11-6. doi: 10.1006/viro.2000.0438.

Mahfouz et al., De novo-engineered transcription activator-like effector (TALE) hybrid nuclease with novel DNA binding specificity creates double-strand breaks. Proc Natl Acad Sci U S A. Feb. 8, 2011;108(6):2623-8. doi: 10.1073/pnas.1019533108. Epub Jan. 24, 2011.

Makarova et al., Prokaryotic homologs of Argonaute proteins are predicted to function as key components of a novel system of defense against mobile genetic elements. Biology Direct 2009;4:29.

Makarova et al., An updated evolutionary classification of CRISPR-Cas systems. Nat Rev Microbiol. Nov. 2015;13(11):722-36. doi: 10.1038/nrmicro3569. Epub Sep. 28, 2015.

Makarova et al., Evolution and classification of the CRISPR-Cas systems. Nat Rev Microbiol. Jun. 2011;9(6):467-77. doi: 10.1038/nrmicro2577. Epub May 9, 2011.

Makarova et al., Prokaryotic homologs of Argonaute proteins are predicted to function as key components of a novel system of defense against mobile genetic elements. Biology Direct 2009;4:29. doi: 10.1186/1745-6150-4-29.

Makeyev et al., Evolutionary potential of an RNA virus. J Virol. Feb. 2004;78(4):2114-20.

Malashkevich et al., Crystal structure of tRNA adenosine deaminase TadA from *Escherichia coli*. Deposited: Mar. 10, 2005 Released: Feb. 21, 2006 doi:10.2210/pdb1z3a/pdb (2006).

Mali et al., Cas9 as a versatile tool for engineeringbiology. Nat Methods. Oct. 2013;10(10):957-63. doi: 10.1038/nmeth.2649.

Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.

Mali et al., RNA-guided human genome engineering via Cas9. Science. Feb. 15, 2013;339(6121):823-6. doi: 10.1126/science.1232033. Epub Jan. 3, 2013.

Malito et al., Structural basis for lack of toxicity of the diphtheria toxin mutant CRM197. Proc Natl Acad Sci U S A. Apr. 3, 2012;109(14):5229-34. doi: 10.1073/pnas.1201964109. Epub Mar. 19, 2012.

Mandal et al., Efficient ablation of genes in human hematopoietic stem and effector cells using CRISPR/Cas9. Cell Stem Cell. Nov. 6, 2014;15(5):643-52. doi: 10.1016/j.stem.2014.10.004. Epub Nov. 6, 2014.

Mandal et al., Riboswitches Control Fundamental Biochemical Pathways in Bacillus Subtilis and Other Bacteria. Cell. May 30, 2003;113(5):577-86. doi: 10.1016/s0092-8674(03)00391-x.

Mani et al., Design, engineering, and characterization of zinc finger nucleases. Biochem Biophys Res Commun. Sep. 23, 2005;335(2):447-57.

Marceau, Functions of single-strand DNA-binding proteins in DNA replication, recombination, and repair. Methods Mol Biol. 2012;922:1-21. doi: 10.1007/978-1-62703-032-8_1.

Maresca et al., Obligate ligation-gated recombination (ObLiGaRe): custom-designed nuclease-mediated targeted integration through nonhomologous end joining. Genome Res. Mar. 2013;23(3):539-46. Doi: 10.1101/gr.145441.112. Epub Nov. 14, 2012.

Marioni et al., DNA methylation age of blood predicts all-cause mortality in later life. Genome Biol. Jan. 30, 2015;16:25. doi: 10.1186/s13059-015-0584-6.

Marraffini et al., CRISPR interference limits horizontal gene transfer in staphylococci by targeting DNA. Science. Dec. 19, 2008;322(5909):1843-5. doi: 10.1126/science.1165771.

Marsden et al., The Tumor-Associated Variant RAD51 G151D Induces a Hyper-Recombination Phenotype. PLoS Genet. Aug. 11, 2016;12(8):e1006208. doi: 10.1371/journal.pgen.1006208.

Martinez et al., Hypermutagenesis of RNA using human immunodeficiency virus type 1 reverse transcriptase and biased dNTP concentrations. Proc Natl Acad Sci U S A. Dec. 6, 1994;91(25):11787-91. doi: 10.1073/pnas.91.25.11787.

Martsolf et al., Complete trisomy 17p a relatively new syndrome. Ann Genet. 1988;31(3):172-4.

Martz, L., Nav-i-gating antibodies for pain. Science-Business exchange. Jun. 12, 2014;7(662):1-2. doi: 10.1038/scibx.2014.662.

Maruyama et al., Increasing the efficiency of precise genome editing with CRISPR-Cas9 by inhibition of nonhomologous end joining. Nat Biotechnol. May 2015;33(5):538-42. doi: 10.1038/nbt.3190. Epub Mar. 23, 2015.

Mascola et al., HIV-1 neutralizing antibodies: understanding nature's pathways. Immunol Rev. Jul. 2013;254(1):225-44. doi: 10.1111/imr.12075.

Mathys et al., Characterization of a self-splicing mini-intein and its conversion into autocatalytic N- and C-terminal cleavage elements: facile production of protein building blocks for protein ligation. Gene. Apr. 29, 1999;231(1-2):1-13. doi: 10.1016/s0378-1119(99)00103-1.

Matsuura et al., A gene essential for the site-specific excision of actinophage r4 prophage genome from the chromosome of a lysogen. J Gen Appl Microbiol. 1995;41(1):53-61.

Matthews, Structures of human ADAR2 bound to dsRNA reveal base-flipping mechanism and basis for site selectivity. Nat Struct Mol Biol. May 2016;23(5):426-33. doi: 10.1038/nsmb.3203. Epub Apr. 11, 2016.

McCarroll et al., Copy-number variation and association studies of human disease. Nat Genet. Jul. 2007;39(7 Suppl):S37-42. doi: 10.1038/ng2080.

McDonald et al., Characterization of mutations at the mouse phenylalanine hydroxylase locus. Genomics. Feb. 1, 1997;39(3):402-5. doi: 10.1006/geno.1996.4508.

McInerney et al., Error Rate Comparison during Polymerase Chain Reaction by DNA Polymerase. Mol Biol Int. 2014;2014:287430. doi: 10.1155/2014/287430. Epub Aug. 17, 2014.

McKenna et al., Whole-organism lineage tracing by combinatorial and cumulative genome editing. Science. Jul. 29, 2016;353(6298):aaf7907. doi: 10.1126/science.aaf7907. Epub May 26, 2016.

Mcnaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.

Mcvey et al., MMEJ repair of double-strand breaks (director's cut): deleted sequences and alternative endings. Trends Genet. Nov. 2008;24(11):529-38. doi: 10.1016/j.tig.2008.08.007. Epub Sep. 21, 2008.

Mead et al., A novel protective prion protein variant that colocalizes with kuru exposure. N Engl J Med. Nov. 19, 2009;361(21):2056-65. doi: 10.1056/NEJMoa0809716.

Mei et al., Recent Progress in CRISPR/Cas9 Technology. J Genet Genomics. Feb. 20, 2016;43(2):63-75. doi: 10.1016/j.jgg.2016.01.001. Epub Jan. 18, 2016.

(56) References Cited

OTHER PUBLICATIONS

Meinke et al., Cre Recombinase and Other Tyrosine Recombinases. Chem Rev. Oct. 26, 2016;116(20):12785-12820. doi: 10.1021/acs.chemrev.6b00077. Epub May 10, 2016.

Meng et al., Targeted gene inactivation in zebrafish using engineered zinc-finger nucleases. Nat Biotechnol. Jun. 2008;26(6):695-701. doi: 10.1038/nbt1398. Epub May 25, 2008.

Menéndez-Arias, Mutation rates and intrinsic fidelity of retroviral reverse transcriptases. Viruses. Dec. 2009;1(3):1137-65. doi: 10.3390/v1031137. Epub Dec. 4, 2009.

Mercer et al., Chimeric TALE recombinases with programmable DNA sequence specificity. Nucleic Acids Res. Nov. 2012;40(21):11163-72. doi: 10.1093/nar/gks875. Epub Sep. 26, 2012.

Mertens et al., Site-specific recombination in bacteriophage Mu: characterization of binding sites for the DNA invertase Gin. EMBO J. Apr. 1988;7(4):1219-27.

Meyer et al., Comprehensive analysis of mRNA methylation reveals enrichment in 3' UTRs and near stop codons. Cell. Jun. 22, 2012;149(7):1635-46. doi: 10.1016/j.cell.2012.05.003. Epub May 17, 2012.

Meyer et al., Confirmation of a second natural preQ1 aptamer class in Streptococcaceae bacteria. RNA. Apr. 2008;14(4):685-95. doi: 10.1261/rna.937308. Epub Feb. 27, 2008.

Meyer et al., Library generation by gene shuffling. Curr Protoc Mol Biol. Jan. 6, 2014;105:Unit 15.12.. doi: 10.1002/0471142727.mb1512s105.

Meyer et al., Ribosome biogenesis factor Tsr3 is the aminocarboxypropyl transferase responsible for 18S rRNA hypermodification in yeast and humans. Nucleic Acids Res. May 19, 2016;44(9):4304-16. doi: 10.1093/nar/gkw244. Epub Apr. 15, 2016.

Meyer et al., The dynamic epitranscriptome: N6-methyladenosine and gene expression control. Nat Rev Mol Cell Biol. May 2014;15(5):313-26. doi: 10.1038/nrm3785. Epub Apr. 9, 2014.

Michel et al., Mitochondrial class II introns encode proteins related to the reverse transcriptases of retroviruses. Nature. Aug. 15-21, 1985;316(6029):641-3. doi: 10.1038/316641a0.

Mihai et al., PTEN inhibition improves wound healing in lung epithelia through changes in cellular mechanics that enhance migration. Am J Physiol Lung Cell Mol Physiol. 2012;302(3):L287-L299.

Mijakovic et al., Bacterial single-stranded DNA-binding proteins are phosphorylated on tyrosine. Nucleic Acids Res. Mar. 20, 2006;34(5):1588-96. doi: 10.1093/nar/gkj514.

Miller et al., A TALE nuclease architecture for efficient genome editing. Nat Biotechnol. Feb. 2011;29(2):143-8. doi:10.1038/nbt.1755. Epub Dec. 22, 2010.

Miller et al., An improved zinc-finger nuclease architecture for highly specific genome editing. Nat Biotechnol. Jul. 2007;25(7):778-85. Epub Jul. 1, 2007.

Miller et al., Construction and properties of retrovirus packaging cells based on gibbon ape leukemia virus. J Virol. May 1991;65(5):2220-4. doi: 10.1128/JVI.65.5.2220-2224.1991.

Miller, Human gene therapy comes of age. Nature. Jun. 11, 1992;357(6378):455-60. doi: 10.1038/357455a0.

Mills et al., Protein splicing in trans by purified N- and C-terminal fragments of the Mycobacterium tuberculosis RecA intein. Proc Natl Acad Sci U S A. Mar. 31, 1998;95(7):3543-8. doi: 10.1073/pnas.95.7.3543.

Minoche et al., Evaluation of genomic high-throughput sequencing data generated on Illumina HiSeq and genome analyzer systems. Genome Biol. Nov. 8, 2011;12(11):R112. doi: 10.1186/GB-2011-12-11-r112.

Minoretti et al., A W148R mutation in the human FOXD4 gene segregating with dilated cardiomyopathy, obsessive-compulsive disorder, and suicidality. Int J Mol Med. Mar. 2007;19(3):369-72.

Mir et al., Two Active Site Divalent Ions in the Crystal Structure of the Hammerhead Ribozyme Bound to a Transition State Analogue. Biochemistry. . Feb. 2, 2016;55(4):633-6. doi: 10.1021/acs.biochem.5b01139. Epub Jan. 19, 2016.

Mishina et al., Conditional gene targeting on the pure C57BL/6 genetic background. Neurosci Res. Jun. 2007;58(2):105-12. doi: 10.1016/j.neures.2007.01.004. Epub Jan. 18, 2007.

Mitani et al., Delivering therapeutic genes—matching approach and application. Trends Biotechnol. May 1993;11(5):162-6. doi: 10.1016/0167-7799(93)90108-L.

Mitton-Fry et al., Poly(A) tail recognition by a viral RNA element through assembly of a triple helix. Science. Nov. 26, 2010;330(6008):1244-7. doi: 10.1126/science.1195858.

Miyaoka et al., Systematic quantification of HDR and NHEJ reveals effects of locus, nuclease, and cell type on genome-editing. Sci Rep. Mar. 31, 2016;6:23549. doi: 10.1038/srep23549.

Moede et al., Identification of a nuclear localization signal, RRMKWKK, in the homeodomain transcription factor PDX-1. FEBS Lett. Nov. 19, 1999;461(3):229-34. doi: 10.1016/s0014-5793(99)01446-5.

Mohr et al., Thermostable group II intron reverse transcriptase fusion proteins and their use in cDNA synthesis and next-generation RNA sequencing. RNA. Jul. 2013;19(7):958-70. doi: 10.1261/rna.039743.113. Epub May 22, 2013.

Mojica et al., Intervening sequences of regularly spaced prokaryotic repeats derive from foreign genetic elements. J Mol Evol. Feb. 2005;60(2):174-82.

Mol et al., Crystal structure and mutational analysis of human uracil-DNA glycosylase: structural basis for specificity and catalysis. Cell. Mar. 24, 1995;80(6):869-78. doi: 10.1016/0092-8674(95)90290-2.

Mol et al., Crystal structure of human uracil-DNA glycosylase in complex with a protein inhibitor: protein mimicry of DNA. Cell. Sep. 8, 1995;82(5):701-8.

Monahan et al., Site-specific incorporation of unnatural amino acids into receptors expressed in Mammalian cells. Chem Biol. Jun. 2003;10(6):573-80.

Monani et al., A single nucleotide difference that alters splicing patterns distinguishes the SMA gene SMN1 from the copy gene SMN2. Hum Mol Genet. Jul. 1999;8(7):1177-83. doi: 10.1093/hmg/8.7.1177.

Monot et al., The specificity and flexibility of 11 reverse transcription priming at imperfect T-tracts. PLoS Genet. May 2013;9(5):e1003499. doi: 10.1371/journal.pgen.1003499. Epub May 9, 2013.

Montange et al., Structure of the S-adenosylmethionine riboswitch regulatory mRNA element. Nature. Jun. 29, 2006;441(7097):1172-5.

Moore et al., Improved somatic mutagenesis in zebrafish using transcription activator-like effector nucleases (TALENs). PloS One. 2012;7(5):e37877. Doi: 10.1371/journal.pone.0037877. Epub May 24, 2012.

Mootz et al., Conditional protein splicing: a new tool to control protein structure and function in vitro and in vivo. J Am Chem Soc. Sep. 3, 2003;125(35):10561-9.

Mootz et al., Protein splicing triggered by a small molecule. J Am Chem Soc. Aug. 7, 2002;124(31):9044-5 and Supporting Information. doi: 10.1021/ja0267690. 4 pages.

Mootz et al., Protein splicing triggered by a small molecule. J Am Chem Soc. Aug. 7, 2002;124(31):9044-5.

Morbitzer et al., Assembly of custom TALE-type DNA binding domains by modular cloning. Nucleic Acids Res. Jul. 2011;39(13):5790-9. doi: 10.1093/nar/gkr151. Epub Mar. 18, 2011.

Moreno-Mateos et al., CRISPRscan: designing highly efficient sgRNAs for CRISPR-Cas9 targeting in vivo. Nat Methods. Oct. 2015;12(10):982-8. doi: 10.1038/nmeth.3543. Epub Aug. 31, 2015.

Morita et al., The site-specific recombination system of actinophage TG1. FEMS Microbiol Lett. Aug. 2009;297(2):234-40. doi: 10.1111/j.1574-6968.2009.01683.x.

Morris et al., A peptide carrier for the delivery of biologically active proteins into mammalian cells. Nat Biotechnol. Dec. 2001;19(12):1173-6.

Moscou et al., A simple cipher governs DNA recognition by TAL effectors. Science. Dec. 11, 2009;326(5959):1501. doi: 10.1126/science.1178817.

Muir et al., Expressed protein ligation: a general method for protein engineering. Proc Natl Acad Sci U S A. Jun. 9, 1998;95(12):6705-10. doi: 10.1073/pnas.95.12.6705.

(56) References Cited

OTHER PUBLICATIONS

Muller et al., Nucleotide exchange and excision technology (NExT) DNA shuffling: a robust method for DNA fragmentation and directed evolution. Nucleic Acids Res. Aug. 1, 2005;33(13):e117. doi: 10.1093/nar/gni116. PMID: 16061932; PMCID: PMC1182171.

Mullins et al., Transgenesis in nonmurine species. Hypertension. Oct. 1993;22(4):630-3.

Mumtsidu et al., Structural features of the single-stranded DNA-binding protein of Epstein-Barr virus. J Struct Biol. Feb. 2008;161(2):172-87. doi: 10.1016/j.jsb.2007.10.014. Epub Nov. 1, 2007.

Murphy, Phage recombinases and their applications. Adv Virus Res. 2012;83:367-414. doi: 10.1016/B978-0-12-394438-2.00008-6. Review.

Murray et al., Selective vulnerability of motor neurons and dissociation of pre- and post-synaptic pathology at the neuromuscular junction in mouse models of spinal muscular atrophy. Hum Mol Genet. Apr. 1, 2008;17(7):949-62. doi: 10.1093/hmg/ddm367. Epub Dec. 8, 2007.

Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.

Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.

Muzyczka et al., Adeno-associated virus (AAV) vectors: will they work? J Clin Invest. Oct. 1994;94(4):1351. doi: 10.1172/JCI117468.

Myerowitz et al., The major defect in Ashkenazi Jews with Tay-Sachs disease is an insertion in the gene for the alpha-chain of beta-hexosaminidase. J Biol Chem. Dec. 15, 1988;263(35):18587-9.

Myers et al., Insulin signal transduction and the IRS proteins. Annu Rev Pharmacol Toxicol. 1996;36:615-58. doi: 10.1146/annurev.pa.36.040196.003151.

Nabel et al., Direct gene transfer for immunotherapy and immunization. Trends Biotechnol. May 1993;11(5):211-5. doi: 10.1016/0167-7799(93)90117-R.

Nahvi et al., Coenzyme B12 riboswitches are widespread genetic control elements in prokaryotes. Nucleic Acids Res. Jan. 2, 2004;32(1):143-50.

Nakade et al., Microhomology-mediated end-joining-dependent integration of donor DNA in cells and animals using TALENs and CRISPR/Cas9. Nat Commun. Nov. 20, 2014;5:5560. doi: 10.1038/ncomms6560.

Nakamura et al., Codon usage tabulated from international DNA sequence databases: status for the year 2000. Nucleic Acids Res. Jan. 1, 2000;28(1):292. doi: 10.1093/nar/28.1.292.

Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.

Navaratnam et al., An overview of cytidine deaminases. Int J Hematol. Apr. 2006;83(3):195-200.

NCBI Reference Sequence: NM_002427.3. Wu et al., May 3, 2014. 5 pages.

Neel et al., Riboswitches: Classification, function and in silico approach, International Journal of Pharma Sciences and Research. 2010;1(9):409-420.

Nelson et al., Filamentous phage DNA cloning vectors: a noninfective mutant with a nonpolar deletion in gene III. Virology. 1981; 108(2): 338-50.

Nelson et al., In vivo genome editing improves muscle function in a mouse model of Duchenne muscular dystrophy. Science. Jan. 22, 2016;351(6271):403-7. doi: 10.1126/science.aad5143. Epub Dec. 31, 2015.

Nelson et al., The unstable repeats—three evolving faces of neurological disease. Neuron. Mar. 6, 2013;77(5):825-43. doi: 10.1016/j.neuron.2013.02.022.

Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.

Nguyen et al., IQ-TREE: a fast and effective stochastic algorithm for estimating maximum-likelihood phylogenies. Mol Biol Evol. Jan. 2015;32(1):268-74. doi: 10.1093/molbev/msu300. Epub Nov. 3, 2014.

Ni et al., A PCSK9-binding antibody that structurally mimics the EGF(A) domain of LDL-receptor reduces LDL cholesterol in vivo. J Lipid Res. 2011;52:76-86.

Ni et al., Nucleic acid aptamers: clinical applications and promising new horizons. Curr Med Chem. 2011;18(27):4206-14. Review.

Nishida et al., Targeted nucleotide editing using hybrid prokaryotic and vertebrate adaptive immune systems. Science. Sep. 16, 2016;353(6305):1248. pii: aaf8729. doi: 10.1126/science.aaf8729. Epub Aug. 4, 2016.

Nishikura, Functions and regulation of RNA editing by ADAR deaminases. Annu Rev Biochem. 2010;79:321-349. doi:10.1146/annurev-biochem-060208-105251.

Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.

Nishimasu et al., Crystal Structure of Staphylococcus aureus Cas9. Cell. Aug. 27, 2015;162(5):1113-26. doi: 10.1016/j.cell.2015.08.007.

Nomura et al., Controlling Mammalian Gene Expression by Allosteric Hepatitis Delta Virus Ribozymes. ACS Synth Biol. Dec. 20, 2013;2(12):684-9. doi: 10.1021/sb400037a. Epub May 22, 2013.

Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.

Noris et al., A phenylalanine-55 to serine amino-acid substitution in the human glycoprotein IX leucine-rich repeat is associated with Bernard-Soulier syndrome. Br J Haematol. May 1997;97(2):312-20.

Nottingham et al., RNA-seq of human reference RNA samples using a thermostable group II intron reverse transcriptase. RNA. Apr. 2016;22(4):597-613. doi: 10.1261/rna.055558.115. Epub Jan. 29, 2016.

Nowak et al., Characterization of single-stranded DNA-binding proteins from the psychrophilic bacteria Desulfotalea psychrophila, Flavobacterium psychrophilum, Psychrobacter arcticus, Psychrobacter cryohalolentis, Psychromonas ingrahamii, Psychroflexus torquis, and Photobacterium profundum. BMC Microbiol. Apr. 14, 2014;14:91. doi: 10.1186/1471-2180-14-91.

Nowak et al., Structural analysis of monomeric retroviral reverse transcriptase in complex with an RNA/DNA hybrid. Nucleic Acids Res. Apr. 1, 2013;41(6):3874-87. doi: 10.1093/nar/gkt053. Epub Feb. 4, 2013.

Numrych et al., A comparison of the effects of single-base and triple-base changes in the integrase arm-type binding sites on the site-specific recombination of bacteriophage lambda. Nucleic Acids Res. Jul. 11, 1990;18(13):3953-9. doi: 10.1093/nar/18.13.3953.

Nyerges et al., A highly precise and portable genome engineering method allows comparison of mutational effects across bacterial species. Proc Natl Acad Sci U S A. Mar. 1, 2016;113(9):2502-7. doi: 10.1073/pnas.1520040113. Epub Feb. 16, 2016.

O'Connell et al., Programmable RNA recognition and cleavage by CRISPR/Cas9. Nature. Dec. 11, 2014;516(7530):263-6. doi: 10.1038/nature13769. Epub Sep. 28, 2014.

O'Maille et al., Structure-based combinatorial protein engineering (SCOPE). J Mol Biol. Aug. 23, 2002;321(4):677-91.

Oakes et al., Profiling of engineering hotspots identifies an allosteric CRISPR-Cas9 switch. Nat Biotechnol. Jun. 2016;34(6):646-51. doi: 10.1038/nbt.3528. Epub May 2, 2016.

Oakes et al., Protein engineering of Cas9 for enhanced function. Methods Enzymol. 2014;546:491-511.

Odsbu et al., Specific N-terminal interactions of the Escherichia coli SeqA protein are required to form multimers that restrain negative supercoils and form foci. Genes Cells. Nov. 2005;10(11):1039-49.

(56)                 References Cited

OTHER PUBLICATIONS

Oeemig et al., Solution structure of DnaE intein from Nostoc punctiforme: structural basis for the design of a new split intein suitable for site-specific chemical modification. FEBS Lett. May 6, 2009;583(9):1451-6.

Offord, Advances in Genome Editing. The Scientist, Apr. 20, 2016. http://www.the-scientist.com/?articles.view/articleNo/45903/title/Advances-in-Genome-Editing/.

Oh et al., Positional cloning of a gene for Hermansky-Pudlak syndrome, a disorder of cytoplasmic organelles. Nat Genet. Nov. 1996;14(3):300-6. doi: 10.1038/ng1196-300.

Ohe et al., Purification and properties of xanthine dehydrogenase from Streptomyces cyanogenus. J Biochem. Jul. 1979;86(1):45-53.

Olivares et al., Site-specific genomic integration produces therapeutic Factor IX levels in mice. Nat Biotechnol. Nov. 2002;20(11):1124-8. doi: 10.1038/nbt753. Epub Oct. 15, 2002.

Olorunniji et al., Site-specific recombinases: molecular machines for the Genetic Revolution. Biochem J. Mar. 15, 2016;473(6):673-84. doi: 10.1042/BJ20151112.

Olorunniji et al., Synapsis and catalysis by activated Tn3 resolvase mutants. Nucleic Acids Res. Dec. 2008;36(22):7181-91. doi: 10.1093/nar/gkn885. Epub Nov. 10, 2008.

Orlando et al., Zinc-finger nuclease-driven targeted integration into mammalian genomes using donors with limited chromosomal homology. Nucleic Acids Res. Aug. 2010;38(15):e152. doi: 10.1093/nar/gkq512. Epub Jun. 8, 2010.

Orthwein et al., A mechanism for the suppression of homologous recombination in G1 cells. Nature. Dec. 17, 2015;528(7582):422-6. doi: 10.1038/nature16142. Epub Dec. 9, 2015.

Ortiz-Urda et al., Stable nonviral genetic correction of inherited human skin disease. Nat Med. Oct. 2002;8(10):1166-70. doi: 10.1038/nm766. Epub Sep. 16, 2002. Erratum in: Nat Med. Feb. 2003;9(2):237.

Osborn et al., TALEN-based gene correction for epidermolysis bullosa. Mol Ther. Jun. 2013;21(6):1151-9. doi: 10.1038/mt.2013.56. Epub Apr. 2, 2013.

Ostermeier et al., A combinatorial approach to hybrid enzymes independent of DNA homology. Nat Biotechnol. Dec. 1999;17(12):1205-9.

Ostertag et al., Biology of mammalian L1 retrotransposons. Annu Rev Genet. 2001;35:501-38. doi: 10.1146/annurev.genet.35.102401.091032.

Otomo et al., Improved segmental isotope labeling of proteins and application to a larger protein. J Biomol NMR. Jun. 1999;14(2):105-14. doi: 10.1023/a:1008308128050.

Otomo et al., NMR observation of selected segments in a larger protein: central-segment isotope labeling through intein-mediated ligation. Biochemistry. Dec. 7, 1999;38(49):16040-4. doi: 10.1021/bi991902j.

Otto et al., The probability of fixation in populations of changing size. Genetics. Jun. 1997;146(2):723-33.

Packer et al., Methods for the directed evolution of proteins. Nat Rev Genet. Jul. 2015;16(7):379-94. doi: 10.1038/nrg3927. Epub Jun. 9, 2015.

Paige et al., RNA mimics of green fluorescent protein. Science. Jul. 29, 2011;333(6042):642-6. doi: 10.1126/science.1207339.

Pan et al., Biological and biomedical applications of engineered nucleases. Mol Biotechnol. Sep. 2013;55(1):54-62. doi: 10.1007/s12033-012-9613-9.

Paquet et al., Efficient introduction of specific homozygous and heterozygous mutations using CRISPR/Cas9. Nature. May 5, 2016;533(7601):125-9. doi: 10.1038/nature17664. Epub Apr. 27, 2016.

Park et al., Sendai virus, an RNA virus with no risk of genomic integration, delivers CRISPR/Cas9 for efficient gene editing. Mol Ther Methods Clin Dev. Aug. 24, 2016;3:16057. doi: 10.1038/mtm.2016.57.

Parker et al., Admixture mapping identifies a quantitative trait locus associated with FEV1/FVC in the COPDGene Study. Genet Epidemiol. Nov. 2014;38(7):652-9. doi: 10.1002/gepi.21847. Epub Aug. 11, 2014.

Passini et al., Antisense oligonucleotides delivered to the mouse CNS ameliorate symptoms of severe spinal muscular atrophy. Sci Transl Med. Mar. 2, 2011;3(72):72ra18. doi: 10.1126/scitranslmed.3001777.

Patel et al., Flap endonucleases pass 5'-flaps through a flexible arch using a disorder-thread-order mechanism to confer specificity for free 5'-ends. Nucleic Acids Res. May 2012;40(10):4507-19. doi: 10.1093/nar/gks051. Epub Feb. 8, 2012.

Pattanayak et al., Determining the specificities of TALENs, Cas9, and other genome-editing enzymes. Methods Enzymol. 2014;546:47-78. doi: 10.1016/B978-0-12-801185-0.00003-9.

Pattanayak et al., High-throughput profiling of off-target DNA cleavage reveals RNA-programmed Cas9 nuclease specificity. Nat Biotechnol. Sep. 2013;31(9):839-43. doi: 10.1038/nbt.2673. Epub Aug. 11, 2013.

Pattanayak et al., Revealing off-target cleavage specificities of zinc-finger nucleases by in vitro selection. Nat Methods. Aug. 7, 2011;8(9):765-70. doi: 10.1038/nmeth.1670.

Pavletich et al., Zinc finger-DNA recognition: crystal structure of a Zif268-DNA complex at 2.1 A. Science. May 10, 1991;252(5007):809-17.

Pawson et al., Protein phosphorylation in signaling—50 years and counting. Trends Biochem Sci. Jun. 2005;30(6):286-90. doi: 10.1016/j.tibs.2005.04.013.

Pearl, Structure and function in the uracil-DNA glycosylase superfamily. Mutat Res. Aug. 30, 2000;460(3-4):165-81.

Peck et al., Directed evolution of a small-molecule-triggered intein with improved splicing properties in mammalian cells. Chem Biol. May 27, 2011;18(5):619-30. doi: 10.1016/j.chembiol.2011.02.014.

Pellegrini et al., Insights into DNA recombination from the structure of a RAD51-BRCA2 complex. Nature. Nov. 21, 2002;420(6913):287-93. doi: 10.1038/nature01230. Epub Nov. 10, 2002.

Pennisi et al., The CRISPR craze. Science. Aug. 23, 2013;341(6148):833-6. doi: 10.1126/science.341.6148.833.

Pennisi et al., The tale of the TALEs. Science. Dec. 14, 2012;338(6113):1408-11. doi: 10.1126/science.338.6113.1408.

Perach et al., Catalytic features of the recombinant reverse transcriptase of bovine leukemia virus expressed in bacteria. Virology. Jun. 20, 1999;259(1):176-89. doi: 10.1006/viro.1999.9761.

Perez et al., Establishment of HIV-1 resistance in CD4+ T cells by genome editing using zinc-finger nucleases. Nat Biotechnol. Jul. 2008;26(7):808-16. Doi: 10.1038/nbt1410. Epub Jun. 29, 2008.

Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.

Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.

Perler et al., Protein splicing and autoproteolysis mechanisms. Curr Opin Chem Biol. Oct. 1997;1(3):292-9. doi: 10.1016/s1367-5931(97)80065-8.

Perler et al., Protein splicing elements: inteins and exteins—a definition of terms and recommended nomenclature. Nucleic Acids Res. Apr. 11, 1994;22(7):1125-7. doi: 10.1093/nar/22.7.1125.

Perler, InBase, the New England Biolabs Intein Database. Nucleic Acids Res. Jan. 1, 1999;27(1):346-7. doi: 10.1093/nar/27.1.346.

Perler, Protein splicing of inteins and hedgehog autoproteolysis: structure, function, and evolution. Cell. Jan. 9, 1998;92(1):1-4. doi: 10.1016/s0092-8674(00)80892-2.

Perreault et al., Mixed deoxyribo- and ribo-oligonucleotides with catalytic activity. Nature. Apr. 5, 1990;344(6266):565-7. doi: 10.1038/344565a0.

Petek et al., Frequent endonuclease cleavage at off-target locations in vivo. Mol Ther. May 2010;18(5):983-6. Doi: 10.1038/mt.2010.35. Epub Mar. 9, 2010.

Petersen-Mahrt et al., AID mutates E. coli suggesting a DNA deamination mechanism for antibody diversification. Nature. Jul. 4, 2002;418(6893):99-103.

Petolino et al., Editing Plant Genomes: a new era of crop improvement. Plant Biotechnol J. Feb. 2016;14(2):435-6. doi: 10.1111/pbi.12542.

(56)     References Cited

OTHER PUBLICATIONS

Peyrottes et al., Oligodeoxynucleoside phosphoramidates (P-NH2): synthesis and thermal stability of duplexes with DNA and RNA targets. Nucleic Acids Res. May 15, 1996;24(10):1841-8.

Pfeiffer et al., Mechanisms of DNA double-strand break repair and their potential to induce chromosomal aberrations. Mutagenesis. Jul. 2000;15(4):289-302. doi: 10.1093/mutage/15.4.289.

Pham et al., Reward versus risk: DNA cytidine deaminases triggering immunity and disease. Biochemistry. Mar. 1, 2005;44(8):2703-15.

Phillips, The challenge of gene therapy and DNA delivery. J Pharm Pharmacol. Sep. 2001;53(9):1169-74.

Pickart et al., Ubiquitin: structures, functions, mechanisms. Biochim Biophys Acta. Nov. 29, 2004;1695(1-3):55-72. doi: 10.1016/j.bbamcr. 2004.09.019.

Pieken et al., Kinetic characterization of ribonuclease-resistant 2'-modified hammerhead ribozymes. Science. Jul. 19, 1991;253(5017):314-7. doi: 10.1126/science.1857967.

Pinkert et al., An albumin enhancer located 10 kb upstream functions along with its promoter to direct efficient, liver-specific expression in transgenic mice. Genes Dev. May 1987;1(3):268-76. doi: 10.1101/gad.1.3.268.

Pirakitikulr et al., PCRless library mutagenesis via oligonucleotide recombination in yeast. Protein Sci. Dec. 2010;19(12):2336-46. doi: 10.1002/pro.513.

Plasterk et al., DNA inversions in the chromosome of *Escherichia coli* and in bacteriophage Mu: relationship to other site-specific recombination systems. Proc Natl Acad Sci U S A. Sep. 1983;80(17):5355-8.

Plosky et al., CRISPR-Mediated Base Editing without DNA Double-Strand Breaks. Mol Cell. May 19, 2016;62(4):477-8. doi: 10.1016/j.molcel.2016.05.006.

Pluciennik et al., PCNA function in the activation and strand direction of MutLα endonuclease in mismatch repair. Proc Natl Acad Sci U S A. Sep. 14, 2010;107(37):16066-71. doi: 10.1073/pnas.1010662107. Epub Aug. 16, 2010.

Poller et al., A leucine-to-proline substitution causes a defective alpha 1-antichymotrypsin allele associated with familial obstructive lung disease. Genomics. Sep. 1993;17(3):740-3.

Popp et al., Sortagging: a versatile method for protein labeling. Nat Chem Biol. Nov. 2007;3(11):707-8. doi: 10.1038/nchembio.2007.31. Epub Sep. 23, 2007.

Porensky et al., A single administration of morpholino antisense oligomer rescues spinal muscular atrophy in mouse. Hum Mol Genet. Apr. 1, 2012;21(7):1625-38. doi: 10.1093/hmg/ddr600. Epub Dec. 20, 2011.

Porteus, Design and testing of zinc finger nucleases for use in mammalian cells. Methods Mol Biol. 2008;435:47-61. doi: 10.1007/978-1-59745-232-8_4.

Posnick et al., Imbalanced base excision repair increases spontaneous mutation and alkylation sensitivity in *Escherichia coli*. J Bacteriol. Nov. 1999;181(21):6763-71.

Pospísilová et al., Hydrolytic cleavage of N6-substituted adenine derivatives by eukaryotic adenine and adenosine deaminases. Biosci Rep. 2008;28(6):335-347. doi:10.1042/BSR20080081.

Pourcel et al., CRISPR elements in Yersinia pestis acquire new repeats by preferential uptake of bacteriophage DNA, and provide additional tools for evolutionary studies. Microbiology. Mar. 2005;151(Pt 3):653-63.

Prasad et al., Visualizing the assembly of human Rad51 filaments on double-stranded DNA. J Mol Biol. Oct. 27, 2006;363(3):713-28. doi: 10.1016/j.jmb.2006.08.046. Epub Aug. 22, 2006.

Prashant et al., CAS9 transcriptional activators for target specificity screening and paired nickases for cooperative genome engineering. Nature Biotechnology 2013;31(9):833-8.

Prorocic et al., Zinc-finger recombinase activities in vitro. Nucleic Acids Res. Nov. 2011;39(21):9316-28. doi: 10.1093/nar/gkr652. Epub Aug. 17, 2011.

Proudfoot et al., Zinc finger recombinases with adaptable DNA sequence specificity. PLoS One. Apr. 29, 2011;6(4):e19537. doi: 10.1371/journal.pone.0019537.

Pruschy et al., Mechanistic studies of a signaling pathway activated by the organic dimerizer FK1012. Chem Biol. Nov. 1994;1(3):163-72. doi: 10.1016/1074-5521(94)90006-x.

Prykhozhij et al., CRISPR multitargeter: a web tool to find common and unique CRISPR single guide RNA targets in a set of similar sequences. PLoS One. Mar. 5, 2015;10(3):e0119372. doi: 10.1371/journal.pone.0119372. eCollection 2015.

Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46.

Qi et al., Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.

Qi et al., Repurposing CRISPR as an RNA-guided platform for sequence-specific control of gene expression. Cell. Feb. 28, 2013;152(5):1173-83. doi: 10.1016/j.cell.2013.02.022.

Queen et al., Immunoglobulin gene transcription is activated by downstream sequence elements. Cell. Jul. 1983;33(3):741-8. doi: 10.1016/0092-8674(83)90016-8.

Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.

Raghavan et al., Abstract 27: Therapeutic Targeting of Human Lipid Genes with in vivo CRISPR-Cas9 Genome Editing. Oral Abstract Presentations: Lipoprotein Metabolism and Therapeutic Targets. Arterioscler THromb Vasc Biol. 2015;35(Suppl. 1):Abstract 27. 5 pages.

Raillard et al., Targeting sites within HIV-1 cDNA with a DNA-cleaving ribozyme. Biochemistry. Sep. 10, 1996;35(36):11693-701. doi: 10.1021/bi960845g.

Raina et al., PROTAC-induced BET protein degradation as a therapy for castration-resistant prostate cancer. Proc Natl Acad Sci U S A. Jun. 28, 2016;113(26):7124-9. doi: 10.1073/pnas.1521738113. Epub Jun. 6, 2016.

Rajagopal et al., High-throughput mapping of regulatory DNA. Nat Biotechnol. Feb. 2016;34(2):167-74. doi: 10.1038/nbt.3468. Epub Jan. 25, 2016.

Rakonjac et al., Roles of PIII in filamentous phage assembly. J Mol Biol. 1998; 282(1)25-41.

Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.

Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.

Ramirez et al., Unexpected failure rates for modular assembly of engineered zinc fingers. Nat Methods. May 2008;5(5):374-5. Doi: 10.1038/nmeth0508-374.

Ran et al., Double Nicking by RNA-guided CRISPR Cas9 for Enhanced Genome Editing Specificity. Cell. Sep. 12, 2013;154(6):1380-9. doi: 10.1016/j.cell.2013.08.021. Epub Aug. 29, 2013.

Ran et al., Genome engineering using the CRISPR-Cas9 system. Nat Protoc. Nov. 2013;8(11):2281-308. doi: 10.1038/nprot.2013.143. Epub Oct. 24, 2013.

Ran et al., In vivo genome editing using *Staphylococcus aureus* Cas9. Nature. Apr. 9, 2015;520(7546):186-91. doi: 10.1038/nature14299. Epub Apr. 1, 2015.

Rashel et al., A novel site-specific recombination system derived from bacteriophage phiMR11. Biochem Biophys Res Commun. Apr. 4, 2008;368(2):192-8. doi: 10.1016/j.bbrc.2008.01.045. Epub Jan. 22, 2008.

Rasila et al., Critical evaluation of random mutagenesis by error-prone polymerase chain reaction protocols, *Escherichia coli* mutator strain, and hydroxylamine treatment. Anal Biochem. May 1, 2009;388(1):71-80. doi: 10.1016/j.ab.2009.02.008. Epub Feb. 10, 2009.

(56)        References Cited

OTHER PUBLICATIONS

Raskin et al., Substitution of a single bacteriophage T3 residue in bacteriophage T7 RNA polymerase at position 748 results in a switch in promoter specificity. J Mol Biol. Nov. 20, 1992;228(2):506-15.

Raskin et al., T7 RNA polymerase mutants with altered promoter specificities. Proc Natl Acad Sci U S A. Apr. 15, 1993;90(8):3147-51.

Rath et al., Fidelity of end joining in mammalian episomes and the impact of Metnase on joint processing. BMC Mol Biol. Mar. 22, 2014;15:6. doi: 10.1186/1471-2199-15-6.

Ravishankar et al., X-ray analysis of a complex of Escherichia coli uracil DNA glycosylase (EcUDG) with a proteinaceous inhibitor. The structure elucidation of a prokaryotic UDG. Nuclei Acids Res. 26 (21): 4880-4887 (1998).

Ray et al., A compendium of RNA-binding motifs for decoding gene regulation. Nature. Jul. 11, 2013;499(7457):172-7. doi: 10.1038/nature12311.

Ray et al., Homologous recombination: ends as the means. Trends Plant Sci. Oct. 2002;7(10):435-40.

Rebar et al., Phage display methods for selecting zinc finger proteins with novel DNA-binding specificities. Methods Enzymol. 1996;267:129-49.

Rebuzzini et al., New mammalian cellular systems to study mutations introduced at the break site by non-homologous end-joining. DNA Repair (Amst). May 2, 2005;4(5):546-55.

Relph et al., Recent developments and current status of gene therapy using viral vectors in the United Kingdom. BMJ. 2004;329(7470):839-842. doi:10.1136/bmj.329.7470.839.

Remy et al., Gene transfer with a series of lipophilic DNA-binding molecules. Bioconjug Chem. Nov.-Dec. 1994;5(6):647-54. doi: 10.1021/bc00030a021.

Ren et al., In-line Alignment and Mg$^{2+}$ Coordination at the Cleavage Site of the env22 Twister Ribozyme. Nat Commun. Nov. 20, 2014;5:5534. doi: 10.1038/ncomms6534.

Ren et al., Pistol Ribozyme Adopts a Pseudoknot Fold Facilitating Site-Specific In-Line Cleavage. Nat Chem Biol. Sep. 2016;12(9):702-8. doi: 10.1038/nchembio.2125. Epub Jul. 11, 2016.

Reynaud et al., What role for AID: mutator, or assembler of the immunoglobulin mutasome? Nat Immunol. Jul. 2003;4(7):631-8.

Reyon et al., FLASH assembly of TALENs for high-throughput genome editing. Nat Biotechnol. May 2012;30(5):460-5. doi: 10.1038/nbt.2170.

Richardson et al., Enhancing homology-directed genome editing by catalytically active and inactive CRISPR-Cas9 using asymmetric donor DNA. Nat Biotechnol. Mar. 2016;34(3):339-44. doi: 10.1038/nbt.3481. Epub Jan. 20, 2016.

Richardson et al., Frequent chromosomal translocations induced by DNA double-strand breaks. Nature. Jun. 8, 2000;405(6787):697-700. doi: 10.1038/35015097.

Richter et al., Function and regulation of clustered regularly interspaced short palindromic repeats (CRISPR) / CRISPR associated (Cas) systems. Viruses. Oct. 19, 2012;4(10):2291-311. doi: 10.3390/v4102291.

Riechmann et al., The C-terminal domain of TolA is the coreceptor for filamentous phage infection of *E. coli*. Cell. 1997; 90(2):351-60. PMID:9244308.

Ringrose et al., The Kw recombinase, an integrase from Kluyveromyces waltii. Eur J Biochem. Sep. 15, 1997;248(3):903-12. doi: 10.1111/j.1432-1033.1997.00903.x.

Risso et al., Hyperstability and substrate promiscuity in laboratory resurrections of Precambrian β-lactamases. J Am Chem Soc. Feb. 27, 2013;135(8):2899-902. doi: 10.1021/ja311630a. Epub Feb. 14, 2013.

Ritchie et al., limma powers differential expression analyses for RNA-sequencing and microarray studies. Nucleic Acids Res. Apr. 20, 2015;43(7):e47. doi: 10.1093/nar/gkv007. Epub Jan. 20, 2015.

Robertson et al., DNA repair in mammalian cells: Base excision repair: the long and short of it. Cell Mol Life Sci. Mar. 2009;66(6):981-93. doi: 10.1007/s00018-009-8736-z.

Robertson et al., Selection in vitro of an RNA enzyme that specifically cleaves single-stranded DNA. Nature. Mar. 29, 1990;344(6265):467-8. doi: 10.1038/344467a0.

Robinson et al., The protein tyrosine kinase family of the human genome. Oncogene. Nov. 20, 2000;19(49):5548-57. doi: 10.1038/sj.onc.1203957.

Rogozin et al., Evolution and diversification of lamprey antigen receptors: evidence for involvement of an AID-APOBEC family cytosine deaminase. Nat Immunol. Jun. 2007;8(6):647-56. doi: 10.1038/ni1463. Epub Apr. 29, 2007.

Rong et al., Homologous recombination in human embryonic stem cells using CRISPR/Cas9 nickase and a long DNA donor template. Protein Cell. Apr. 2014;5(4):258-60. doi: 10.1007/s13238-014-0032-5.

Rongrong et al., Effect of deletion mutation on the recombination activity of Cre recombinase. Acta Biochim Pol. 2005;52(2):541-4. Epub May 15, 2005.

Roth et al., A widespread self-cleaving ribozyme class is revealed by bioinformatics. Nat Chem Biol. Jan. 2014;10(1):56-60. doi: 10.1038/nchembio.1386. Epub Nov. 17, 2013.

Roth et al., Purification and characterization of murine retroviral reverse transcriptase expressed in *Escherichia coli*. J Biol Chem. Aug. 5, 1985;260(16):9326-35.

Rouet et al., Expression of a site-specific endonuclease stimulates homologous recombination in mammalian cells. Proc Natl Acad Sci U S A. Jun. 21, 1994;91(13):6064-8. doi: 10.1073/pnas.91.13.6064.

Rouet et al., Introduction of double-strand breaks into the genome of mouse cells by expression of a rare-cutting endonuclease. Mol Cell Biol. Dec. 1994;14(12):8096-106. doi: 10.1128/mcb.14.12.8096.

Rowland et al., Regulatory mutations in Sin recombinase support a structure-based model of the synaptosome. Mol Microbiol. Oct. 2009;74(2):282-98. doi: 10.1111/j.1365-2958.2009.06756.x. Epub Jun. 8, 2009.

Rowland et al., Sin recombinase from *Staphylococcus aureus*: synaptic complex architecture and transposon targeting. Mol Microbiol. May 2002;44(3):607-19. doi: 10.1046/j.1365-2958.2002.02897.x.

Rowley, Chromosome translocations: dangerous liaisons revisited. Nat Rev Cancer. Dec. 2001;1(3):245-50. doi: 10.1038/35106108.

Rubio et al., An adenosine-to-inosine tRNA-editing enzyme that can perform C-to-U deamination of DNA. Proc Natl Acad Sci U S A. May 8, 2007;104(19):7821-6. doi: 10.1073/pnas.0702394104. Epub May 1, 2007. PMID: 17483465; PMCID: PMC1876531.

Rubio et al., Transfer RNA travels from the cytoplasm to organelles. Wiley Interdiscip Rev RNA. Nov.-Dec. 2011;2(6):802-17. doi: 10.1002/wrna.93. Epub Jul. 11, 2011.

Rudolph et al., Synthetic riboswitches for the conditional control of gene expression in Streptomyces coelicolor. Microbiology. Jul. 2013;159(Pt 7):1416-22. doi: 10.1099/mic.0.067322-0. Epub May 15, 2013.

Rutherford et al., Attachment site recognition and regulation of directionality by the serine integrases. Nucleic Acids Res. Sep. 2013;41(17):8341-56. doi: 10.1093/nar/gkt580. Epub Jul. 2, 2013.

Rüfer et al., Non-contact positions impose site selectivity on Cre recombinase. Nucleic Acids Res. Jul. 1, 2002;30(13):2764-71. doi: 10.1093/nar/gkf399.

Sadelain et al., Safe harbours for the integration of new DNA in the human genome. Nat Rev Cancer. Dec. 1, 2011;12(1):51-8. doi: 10.1038/nrc3179.

Sadowski, The Flp recombinase of the 2-microns plasmid of Saccharomyces cerevisiae. Prog Nucleic Acid Res Mol Biol. 1995;51:53-91.

Sage et al., Proliferation of functional hair cells in vivo in the absence of the retinoblastoma protein. Science. Feb. 18, 2005;307(5712):1114-8. Epub Jan. 13, 2005.

Sakuma et al., MMEJ-assisted gene knock-in using TALENs and CRISPR-Cas9 with the PITCh systems. Nat Protoc. Jan. 2016;11(1):118-33. doi: 10.1038/nprot.2015.140. Epub Dec. 17, 2015.

Sale et al., Y-family DNA polymerases and their role in tolerance of cellular DNA damage. Nat Rev Mol Cell Biol. Feb. 23, 2012;13(3):141-52. doi: 10.1038/nrm3289.

(56) References Cited

OTHER PUBLICATIONS

Saleh-Gohari et al., Conservative homologous recombination preferentially repairs DNA double-strand breaks in the S phase of the cell cycle in human cells. Nucleic Acids Res. Jul. 13, 2004;32(12):3683-8. Print 2004.

Samal et al., Cationic polymers and their therapeutic potential. Chem Soc Rev. Nov. 7, 2012;41(21):7147-94. doi: 10.1039/c2cs35094g. Epub Aug. 10, 2012.

Samulski et al., Helper-free stocks of recombinant adeno-associated viruses: normal integration does not require viral gene expression. J Virol. Sep. 1989;63(9):3822-8. doi: 10.1128/JVI.63.9.3822-3828. 1989.

San Filippo et al., Mechanism of eukaryotic homologous recombination. Annu Rev Biochem. 2008;77:229-57. doi: 10.1146/annurev.biochem.77.061306.125255.

Sander et al., CRISPR-Cas systems for editing, regulating and targeting genomes. Nat Biotechnol. Apr. 2014;32(4):347-55. doi: 10.1038/nbt.2842. Epub Mar. 2, 2014.

Sander et al., In silico abstraction of zinc finger nuclease cleavage profiles reveals an expanded landscape of off-target sites. Nucleic Acids Res. Oct. 2013;41(19):e181. doi: 10.1093/nar/gkt716. Epub Aug. 14, 2013.

Sander et al., Targeted gene disruption in somatic zebrafish cells using engineered TALENs. Nat Biotechnol. Aug. 5, 2011;29(8):697-8. doi: 10.1038/nbt.1934.

Sang et al., A unique uracil-DNA binding protein of the uracil DNA glycosylase superfamily. Nucleic Acids Res. Sep. 30, 2015;43(17):8452-63. doi: 10.1093/nar/gkv854. Epub Aug. 24, 2015.

Sang, Prospects for transgenesis in the chick. Mech Dev. Sep. 2004; 121(9):1179-86.

Sanjana et al., A transcription activator-like effector toolbox for genome engineering. Nat Protoc. Jan. 5, 2012;7(1):171-92. doi: 10.1038/nprot.2011.431.

Santiago et al., Targeted gene knockout in mammalian cells by using engineered zinc-finger nucleases. Proc Natl Acad Sci U S A. Apr. 15, 2008;105(15):5809-14. doi: 10.1073/pnas.0800940105. Epub Mar. 21, 2008.

Santoro et al., Directed evolution of the site specificity of Cre recombinase. Proc Natl Acad Sci U S A. Apr. 2, 2002;99(7):4185-90. Epub Mar. 19, 2002.

Saparbaev et al., Excision of hypoxanthine from DNA containing dIMP residues by the *Escherichia coli*, yeast, rat, and human alkylpurine DNA glycosylases. Proc Natl Acad Sci U S A. Jun. 21, 1994;91(13):5873-7. doi: 10.1073/pnas.91.13.5873.

Sapranauskas et al., *The Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.

Sapunar et al., Dorsal root ganglion—a potential new therapeutic target for neuropathic pain. J Pain Res. 2012;5:31-8. doi: 10.2147/JPR.S26603. Epub Feb. 16, 2012.

Saraconi et al., The RNA editing enzyme APOBEC1 induces somatic mutations and a compatible mutational signature is present in esophageal adenocarcinomas. Genome Biol. Jul. 31, 2014;15(7):417. doi: 10.1186/s13059-014-0417-z.

Sarkar et al., HIV-1 proviral DNA excision using an evolved recombinase. Science. Jun. 29, 2007;316(5833):1912-5. doi: 10.1126/science.1141453.

Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.

Sasidharan et al., The selection of acceptable protein mutations. PNAS; Jun. 12, 2007;104(24):10080-5. www.pnas.org/cgi/doi/10.1073.pnas.0703737104.

Saudek et al., A preliminary trial of the programmable implantable medication system for insulin delivery. N Engl J Med. Aug. 31, 1989;321(9):574-9.

Sauer et al., DNA recombination with a heterospecific Cre homolog identified from comparison of the pac-c1 regions of P1-related phages. Nucleic Acids Res. Nov. 18, 2004;32(20):6086-95. doi: 10.1093/nar/gkh941.

Saville et al., A site-specific self-cleavage reaction performed by a novel RNA in Neurospora mitochondria. Cell. May 18, 1990;61(4):685-96. doi: 10.1016/0092-8674(90)90480-3.

Savva et al., The structural basis of specific base-excision repair by uracil-DNA glycosylase. Nature. Feb. 9, 1995;373(6514):487-93. doi: 10.1038/373487a0.

Schaaper et al., Base selection, proofreading, and mismatch repair during DNA replication in *Escherichia coli*. J Biol Chem. Nov. 15, 1993;268(32):23762-5.

Schaaper et al., Spectra of spontaneous mutations in Escherichia coli strains defective in mismatch correction: the nature of in vivo DNA replication errors. Proc Natl Acad Sci U S A. Sep. 1987;84(17):6220-4.

Schechner et al., Multiplexable, locus-specific targeting of long RNAs with CRISPR-Display. Nat Methods. Jul. 2015;12(7):664-70. doi: 10.1038/nmeth.3433. Epub Jun. 1, 2015. Author manuscript entitled CRISPR Display: A modular method for locus-specific targeting of long noncoding RNAs and synthetic RNA devices in vivo.

Schek et al., Definition of the upstream efficiency element of the simian virus 40 late polyadenylation signal by using in vitro analyses. Mol Cell Biol. Dec. 1992;12(12):5386-93. doi: 10.1128/mcb.12.12.5386.

Schenk et al., MPDU1 mutations underlie a novel human congenital disorder of glycosylation, designated type If. J Clin Invest. Dec. 2001;108(11):1687-95. doi: 10.1172/JCI13419.

Schlacher et al., Double-strand break repair-independent role for BRCA2 in blocking stalled replication fork degradation by MRE11. Cell. May 13, 2011;145(4):529-42. doi: 10.1016/j.cell.2011.03.041. Erratum in: Cell. Jun. 10, 2011;145(6):993.

Schmitz et al., Behavioral abnormalities in prion protein knockout mice and the potential relevance of PrP(C) for the cytoskeleton. Prion. 2014;8(6):381-6. doi: 10.4161/19336896.2014.983746.

Schrank et al., Inactivation of the survival motor neuron gene, a candidate gene for human spinal muscular atrophy, leads to massive cell death in early mouse embryos. Proc Natl Acad Sci USA. Sep. 2, 1997;94(18):9920-5. doi: 10.1073/pnas.94.18.9920.

Schriefer et al., Low pressure DNA shearing: a method for random DNA sequence analysis. Nucleic Acids Res. Dec. 25, 1990;18(24):7455-6.

Schultz et al., Expression and secretion in yeast of a 400-kDa envelope glycoprotein derived from Epstein-Barr virus. Gene. 1987;54(1):113-23. doi: 10.1016/0378-1119(87)90353-2.

Schultz et al., Oligo-2'-fluoro-2'-deoxynucleotide N3'→P5' phosphoramidates: synthesis and properties. Nucleic Acids Res. Aug. 1, 1996;24(15):2966-73.

Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.

Schwarze et al., In vivo protein transduction: delivery of a biologically active protein into the mouse. Science. Sep. 3, 1999;285(5433):1569-72.

Sclimenti et al., Directed evolution of a recombinase for improved genomic integration at a native human sequence. Nucleic Acids Res. Dec. 15, 2001;29(24):5044-51.

Score Results for Luetticken et al., Complete genome sequence of a *Streptococcus dysgalactiae* subsp. RT equisimilis strain possessing Lancefield's group A antigen. RL Submitted to the EMBL/GenBank/DDBJ databases. May 2012. 3 pages.

Score Results for Okumura et al., Evolutionary paths of streptococcal and staphylococcal superantigens. RL BMC Genomics. 2012;13:404-404. 3 pages.

Score Results for Shimomura et al., Complete Genome Sequencing and Analysis of a Lancefield Group G RT *Streptococcus dysagalactiae* Subsp. Equisimilis Strain Causing Streptococcal RT Toxic Shock Syndrome (STSS). RL BMC Genomics. 2011;12:17-17. 3 pages.

Scott et al., Production of cyclic peptides and proteins in vivo. Proc Natl Acad Sci U S A. Nov. 23, 1999;96(24):13638-43. doi: 10.1073/pnas.96.24.13638.

(56) References Cited

OTHER PUBLICATIONS

Seed, An LFA-3 cDNA encodes a phospholipid-linked membrane protein homologous to its receptor CD2. Nature. Oct. 29-Nov. 4, 1987;329(6142):840-2. doi: 10.1038/329840a0.

Sefton et al., Implantable pumps. Crit Rev Biomed Eng. 1987;14(3):201-40.

Segal et al., Toward controlling gene expression at will: selection and design of zinc finger domains recognizing each of the 5'-GNN-3' DNA target sequences. Proc Natl Acad Sci U S A. Mar. 16, 1999;96(6):2758-63.

Sells et al., Delivery of protein into cells using polycationic liposomes. Biotechniques. Jul. 1995;19(1):72-6, 78.

Semenova et al., Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.

Serganov et al., Coenzyme recognition and gene regulation by a flavin mononucleotide riboswitch. Nature. Mar. 12, 2009;458(7235):233-7. doi: 10.1038/nature07642. Epub Jan. 25, 2009.

Serganov et al., Structural basis for discriminative regulation of gene expression by adenine-and guanine-sensing mRNAs. Chem Biol. Dec. 2004;11(12):1729-41.

Serganov et al., Structural basis for gene regulation by a thiamine pyrophosphate-sensing riboswitch. Nature. Jun. 29, 2006;441(7097):1167-71. Epub May 21, 2006.

Seripa et al., The missing ApoE allele. Ann Hum Genet. Jul. 2007;71(Pt 4):496-500. Epub Jan. 22, 2007.

Serrano-Heras et al., Protein p56 from the Bacillus subtilis phage phi29 inhibits DNA-binding ability of uracil-DNA glycosylase. Nucleic Acids Res. 2007;35(16):5393-401. Epub Aug. 13, 2007.

Severinov et al., Expressed protein ligation, a novel method for studying protein-protein interactions in transcription. J Biol Chem. Jun. 26, 1998;273(26):16205-9. doi: 10.1074/jbc.273.26.16205.

Shah et al., Inteins: nature's gift to protein chemists. Chem Sci. 2014;5(1):446-461.

Shah et al., Kinetic control of one-pot trans-splicing reactions by using a wild-type and designed split intein. Angew Chem Int Ed Engl. Jul. 11, 2011;50(29):6511-5. doi: 10.1002/anie.201102909. Epub Jun. 8, 2011.

Shah et al., Protospacer recognition motifs: mixed identities and functional diversity. RNA Biol. May 2013;10(5):891-9. doi: 10.4161/rna.23764. Epub Feb. 12, 2013.

Shah et al., Target-specific variants of Flp recombinase mediate genome engineering reactions in mammalian cells. FEBS J. Sep. 2015;282(17):3323-33. doi: 10.1111/febs.13345. Epub Jul. 1, 2015.

Shaikh et al., Chimeras of the Flp and Cre recombinases: tests of the mode of cleavage by Flp and Cre. J Mol Biol. Sep. 8, 2000;302(1):27-48.

Shalem et al., Genome-scale CRISPR-Cas9 knockout screening in human cells. Science. Jan. 3, 2014;343(6166):84-7. doi: 10.1126/science.1247005. Epub Dec. 12, 2013.

Shalem et al., High-throughput functional genomics using CRISPR-Cas9. Nat Rev Genet. May 2015;16(5):299-311. doi: 10.1038/nrg3899. Epub Apr. 9, 2015.

Sharbeen et al., Ectopic restriction of DNA repair reveals that UNG2 excises AID-induced uracils predominantly or exclusively during G1 phase. J Exp Med. May 7, 2012;209(5):965-74. doi: 10.1084/jem.20112379. Epub Apr. 23, 2012.

Sharer et al., The ARF-like 2 (ARL2)-binding protein, BART. Purification, cloning, and initial characterization. J Biol Chem. Sep. 24, 1999;274(39):27553-61. doi: 10.1074/jbc.274.39.27553.

Sharma et al., Efficient introduction of aryl bromide functionality into proteins in vivo. FEBS Lett. Feb. 4, 2000;467(1):37-40.

Sharma et al., Identification of novel methyltransferases, Bmt5 and Bmt6, responsible for the m3U methylations of 25S rRNA in *Saccharomyces cerevisiae*. Nucleic Acids Res. Mar. 2014;42(5):3246-60. doi: 10.1093/nar/gkt1281. Epub Dec. 12, 2013.

Shaw et al., Implications of human genome architecture for rearrangement-based disorders: the genomic basis of disease. Hum Mol Genet. Apr. 1, 2004;13 Spec No. 1:R57-64. doi: 10.1093/hmg/ddh073. Epub Feb. 5, 2004.

Shcherbakova et al., Near-infrared fluorescent proteins for multicolor in vivo imaging. Nat Methods. Aug. 2013;10(8):751-4. doi: 10.1038/nmeth.2521. Epub Jun. 16, 2013.

Shechner et al., Multiplexable, locus-specific targeting of long RNAs with CRISPR-Display. Nat Methods. Jul. 2015;12(7):664-70. doi: 10.1038/nmeth.3433. Epub Jun. 1, 2015.

Shee et al., Engineered proteins detect spontaneous DNA breakage in human and bacterial cells. Elife. Oct. 29, 2013;2:e01222. doi: 10.7554/eLife.01222.

Shen et al., Efficient genome modification by CRISPR-Cas9 nickase with minimal off-target effects. Nat Methods. Apr. 2014;11(4):399-402. doi: 10.1038/nmeth.2857. Epub Mar. 2, 2014.

Shen et al., Herpes simplex virus 1 (HSV-1) for cancer treatment. Cancer Gene Ther. Nov. 2006;13(11):975-92. doi: 10.1038/sj.cgt.7700946. Epub Apr. 7, 2006.

Sheridan, First CRISPR-Cas patent opens race to stake out intellectual property. Nat Biotechnol. 2014;32(7):599-601.

Sheridan, Gene therapy finds its niche. Nat Biotechnol. Feb. 2011;29(2):121-8. doi: 10.1038/nbt.1769.

Sherwood et al., Discovery of directional and nondirectional pioneer transcription factors by modeling DNase profile magnitude and shape. Nat Biotechnol. Feb. 2014;32(2):171-178. doi: 10.1038/nbt.2798. Epub Jan. 19, 2014.

Shimojima et al., Spinocerebellar ataxias type 27 derived from a disruption of the fibroblast growth factor 14 gene with mimicking phenotype of paroxysmal non-kinesigenic dyskinesia. Brain Dev. Mar. 2012;34(3):230-3. doi: 10.1016/j.braindev.2011.04.014. Epub May 19, 2011.

Shindo et al., A Comparison of Two Single-Stranded DNA Binding Models by Mutational Analysis of APOBEC3G. Biology (Basel). Aug. 2, 2012;1(2):260-76. doi: 10.3390/biology1020260.

Shingledecker et al., Molecular dissection of the *Mycobacterium tuberculosis* RecA intein: design of a minimal intein and of a trans-splicing system involving two intein fragments. Gene. Jan. 30, 1998;207(2):187-95. doi: 10.1016/s0378-1119(97)00624-0.

Shmakov et al., Discovery and Functional Characterization of Diverse Class 2 CRISPR Cas Systems. Molecular Cell Nov. 2015;60(3):385-97.

Shultz et al., A genome-wide analysis of FRT-like sequences in the human genome. PLoS One. Mar. 23, 2011;6(3):e18077. doi: 10.1371/journal.pone.0018077.

Siebert et al., An improved PCR method for walking in uncloned genomic DNA. Nucleic Acids Res. Mar. 25, 1995;23(6):1087-8.

Silas et al., Direct CRISPR spacer acquisition from RNA by a natural reverse transcriptase-Cas1 fusion protein. Science. Feb. 26, 2016;351(6276):aad4234. doi: 10.1126/science.aad4234.

Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.

Simonelli et al., Base excision repair intermediates are mutagenic in mammalian cells. Nucleic Acids Res. Aug. 2, 2005;33(14):4404-11. Print 2005.

Singh et al., Cross-talk between diverse serine integrases. J Mol Biol. Jan. 23, 2014;426(2):318-31. doi: 10.1016/j.jmb.2013.10.013. Epub Oct. 22, 2013.

Singh et al., Splicing of a critical exon of human Survival Motor Neuron is regulated by a unique silencer element located in the last intron. Mol Cell Biol. Feb. 2006;26(4):1333-46. doi: 10.1128/MCB.26.4.1333-1346.2006.

Sirk et al., Expanding the zinc-finger recombinase repertoire: directed evolution and mutational analysis of serine recombinase specificity determinants. Nucleic Acids Res. Apr. 2014;42(7):4755-66. doi: 10.1093/nar/gkt1389. Epub Jan. 21, 2014.

Sivalingam et al., Biosafety assessment of site-directed transgene integration in human umbilical cord-lining cells. Mol Ther. Jul. 2010;18(7):1346-56. doi: 10.1038/mt.2010.61. Epub Apr. 27, 2010.

Sjoblom et al., The consensus coding sequences of human breast and colorectal cancers. Science. Oct. 13, 2006;314(5797):268-74. Epub Sep. 7, 2006.

(56)         References Cited

OTHER PUBLICATIONS

Skretas et al., Regulation of protein activity with small-molecule-controlled inteins. Protein Sci. Feb. 2005;14(2):523-32. Epub Jan. 4, 2005.

Slaymaker et al., Rationally engineered Cas9 nucleases with improved specificity. Science. Jan. 1, 2016;351(6268):84-8. doi: 10.1126/science.aad5227. Epub Dec. 1, 2015.

Slupphaug et al., A nucleotide-flipping mechanism from the structure of human uracil-DNA glycosylase bound to DNA. Nature. Nov. 7, 1996;384(6604):87-92. doi: 10.1038/384087a0.

Smith et al., Diversity in the serine recombinases. Mol Microbiol. Apr. 2002;44(2):299-307. Review.

Smith et al., Expression of a dominant negative retinoic acid receptor y in Xenopus embryos leads to partial resistance to retinoic acid. Roux Arch Dev Biol. Mar. 1994;203(5):254-265. doi: 10.1007/BF00360521.

Smith et al., Herpesvirus transport to the nervous system and back again. Annu Rev Microbiol. 2012;66:153-76. doi: 10.1146/annurev-micro-092611-150051. Epub Jun. 15, 2012.

Smith et al., Production of human beta interferon in insect cells infected with a baculovirus expression vector. Mol Cell Biol. Dec. 1983;3(12):2156-65. doi: 10.1128/mcb.3.12.2156.

Smith et al., Single-step purification of polypeptides expressed in *Escherichia coli* as fusions with glutathione S-transferase. Gene. Jul. 15, 1988;67(1):31-40. doi: 10.1016/0378-1119(88)90005-4.

Smith, Filamentous fusion phage: novel expression vectors that display cloned antigens on the virion surface. Science. Jun. 14, 1985;228(4705):1315-7.

Smith, Phage-encoded Serine Integrases and Other Large Serine Recombinases. Microbiol Spectr. Aug. 2015;3(4). doi: 10.1128/microbiolspec.MDNA3-0059-2014.

Somanathan et al., AAV vectors expressing LDLR gain-of-function variants demonstrate increased efficacy in mouse models of familial hypercholesterolemia. Circ Res. Aug. 29, 2014;115(6):591-9. doi: 10.1161/CIRCRESAHA.115.304008. Epub Jul. 14, 2014.

Sommerfelt et al., Receptor interference groups of 20 retroviruses plating on human cells. Virology. May 1990;176(1):58-69. doi: 10.1016/0042-6822(90)90230-0.

Song et al., RS-1 enhances CRISPR/Cas9- and TALEN-mediated knock-in efficiency. Nat Commun. Jan. 28, 2016;7:10548. doi: 10.1038/ncomms10548.

Southworth et al., Control of protein splicing by intein fragment reassembly. EMBO J. Feb. 16, 1998;17(4):918-26. doi: 10.1093/emboj/17.4.918.

Southworth et al., Purification of proteins fused to either the amino or carboxy terminus of the *Mycobacterium xenopi* gyrase A intein. Biotechniques. Jul. 1999;27(1):110-4, 116, 118-20. doi: 10.2144/99271st04.

Spencer et al., A general strategy for producing conditional alleles of Src-like tyrosine kinases. Proc Natl Acad Sci U S A. Oct. 10, 1995;92(21):9805-9. doi: 10.1073/pnas.92.21.9805.

Spencer et al., Controlling signal transduction with synthetic ligands. Science. Nov. 12, 1993;262(5136):1019-24. doi: 10.1126/science.7694365.

Spencer et al., Functional analysis of Fas signaling in vivo using synthetic inducers of dimerization. Curr Biol. Jul. 1, 1996;6(7):839-47. doi: 10.1016/s0960-9822(02)00607-3.

Srivastava et al., An inhibitor of nonhomologous end-joining abrogates double-strand break repair and impedes cancer progression. Cell. Dec. 21, 2012;151(7):1474-87. doi: 10.1016/j.cell.2012.11.054.

Stadtman, Selenocysteine. Annu Rev Biochem. 1996;65:83-100.

Stark et al., ATP hydrolysis by mammalian RAD51 has a key role during homology-directed DNA repair. J Biol Chem. Jun. 7, 2002;277(23):20185-94. doi: 10.1074/jbc.M112132200. Epub Mar. 28, 2002.

Steele et al., The prion protein knockout mouse: a phenotype under challenge. Prion. Apr.-Jun. 2007;1(2):83-93. doi: 10.4161/pri.1.2.4346. Epub Apr. 25, 2007.

Steiner et al., The neurotropic herpes viruses: herpes simplex and varicella-zoster. Lancet Neurol. Nov. 2007;6(11):1015-28. doi: 10.1016/S1474-4422(07)70267-3.

Stenglein et al., APOBEC3 proteins mediate the clearance of foreign DNA from human cells. Nat Struct Mol Biol. Feb. 2010;17(2):222-9. doi: 10.1038/nsmb.1744. Epub Jan. 10, 2010.

Stephens et al., The landscape of cancer genes and mutational processes in breast cancer. Nature Jun. 2012;486:400-404. doi: 10.1038/nature11017.

Sternberg et al., Conformational control of DNA target cleavage by CRISPR-Cas9. Nature. Nov. 5, 2015;527(7576):110-3. doi: 10.1038/nature15544. Epub Oct. 28, 2015.

Sternberg et al., DNA interrogation by the CRISPR RNA-guided endonuclease Cas9. Nature.Mar. 6, 2014;507(7490):62-7. doi: 10.1038/nature13011. Epub Jan. 29, 2014.

Sterne-Weiler et al., Exon identity crisis: disease-causing mutations that disrupt the splicing code. Genome Biol. Jan. 23, 2014;15(1):201. doi: 10.1186/gb4150.

Stevens et al., Design of a Split Intein with Exceptional Protein-Splicing Activity. J Am Chem Soc. Feb. 24, 2016;138(7):2162-5. doi: 10.1021/jacs.5b13528. Epub Feb. 8, 2016.

Stockwell et al., Probing the role of homomeric and heteromeric receptor interactions in TGF-beta signaling using small molecule dimerizers. Curr Biol. Jun. 18, 1998;8(13):761-70. doi: 10.1016/s0960-9822(98)70299-4.

Sudarsan et al., An mRNA structure in bacteria that controls gene expression by binding lysine. Genes Dev. Nov. 1, 2003;17(21):2688-97.

Sudarsan et al., Riboswitches in eubacteria sense the second messenger cyclic di-GMP. Science. Jul. 18, 2008;321(5887):411-3. doi: 10.1126/science.1159519.

Suess et al., A theophylline responsive riboswitch based on helix slipping controls gene expression in vivo. Nucleic Acids Res. Mar. 5, 2004;32(4):1610-4.

Sullenger et al., Ribozyme-mediated repair of defective mRNA by targeted, trans-splicing. Nature. Oct. 13, 1994;371(6498):619-22. doi: 10.1038/371619a0.

Sun et al., Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.

Sun et al., The CRISPR/Cas9 system for gene editing and its potential application in pain research. Transl Periop & Pain Med. Aug. 3, 2016;1(3):22-33.

Suzuki et al., VCre/VloxP and SCre/SloxP: new site-specific recombination systems for genome engineering. Nucleic Acids Res. Apr. 2011;39(8):e49. doi: 10.1093/nar/gkq1280. Epub Feb. 1, 2011.

Swarts et al., Argonaute of the archaeon Pyrococcus furiosus is a DNA-guided nuclease that targets cognate DNA. Nucleic Acids Res. May 26, 2015;43(10):5120-9. doi: 10.1093/nar/gkv415. Epub Apr. 29, 2015.

Swarts et al., DNA-guided DNA interference by a prokaryotic Argonaute. Nature. Mar. 13, 2014;507(7491):258-61. doi: 10.1038/nature12971. Epub Feb. 16, 2014.

Swarts et al., The evolutionary journey of Argonaute proteins. Nat Struct Mol Biol. Sep. 2014;21(9):743-53. doi: 10.1038/nsmb.2879.

Szczepek et al., Structure-based redesign of the dimerization interface reduces the toxicity of zinc-finger nucleases. Nat Biotechnol. Jul. 2007;25(7):786-93. Epub Jul. 1, 2007.

Tabebordbar et al., In vivo gene editing in dystrophic mouse muscle and muscle stem cells. Science. Jan. 22, 2016;351(6271):407-411. doi: 10.1126/science.aad5177. Epub Dec. 31, 2015.

Tagalakis et al., Lack of RNA-DNA oligonucleotide (chimeraplast) mutagenic activity in mouse embryos. Mol Reprod Dev. Jun. 2005;71(2):140-4.

Tajiri et al., Functional cooperation of MutT, MutM and MutY proteins in preventing mutations caused by spontaneous oxidation of guanine nucleotide in *Escherichia coli*. Mutat Res. May 1995;336(3):257-67. doi: 10.1016/0921-8777(94)00062-b.

Takimoto et al., Stereochemical basis for engineered pyrrolysyl-tRNA synthetase and the efficient in vivo incorporation of structurally divergent non-native amino acids. ACS Chem Biol. Jul. 15, 2011;6(7):733-43. doi: 10.1021/cb200057a. Epub May 5, 2011.

(56)         References Cited

OTHER PUBLICATIONS

Talbot et al., Spinal muscular atrophy. Semin Neurol. Jun. 2001;21(2):189-97. doi: 10.1055/s-2001-15264.

Tambunan et al., Vaccine Design for H5N1 Based on B- and T-cell Epitope Predictions. Bioinform Biol Insights. Apr. 28, 2016;10:27-35. doi: 10.4137/BBI.S38378.

Tanenbaum et al., A protein-tagging system for signal amplification in gene expression and fluorescence imaging. Cell. Oct. 23, 2014;159(3):635-46. doi: 10.1016/j.cell.2014.09.039. Epub Oct. 9, 2014.

Tanese et al., Expression of enzymatically active reverse transcriptase in *Escherichia coli*. Proc Natl Acad Sci U S A. Aug. 1985;82(15):4944-8. doi: 10.1073/pnas.82.15.4944.

Tang et al., Evaluation of Bioinformatic Programmes for the Analysis of Variants within Splice Site Consensus Regions. Adv Bioinformatics. 2016;2016:5614058. doi: 10.1155/2016/5614058. Epub May 24, 2016.

Tassabehji, Williams-Beuren syndrome: a challenge for genotype-phenotype correlations. Hum Mol Genet. Oct. 15, 2003;12 Spec No. 2:R229-37. doi: 10.1093/hmg/ddg299. Epub Sep. 2, 2003.

Taube et al., Reverse transcriptase of mouse mammary tumour virus: expression in bacteria, purification and biochemical characterization. Biochem J. Feb. 1, 1998;329 ( Pt 3)(Pt 3):579-87. doi: 10.1042/bj3290579. Erratum in: Biochem J Jun. 15, 1998;332(Pt 3):808.

Tebas et al., Gene editing of CCR5 in autologous CD4 T cells of persons infected with HIV. N Engl J Med. Mar. 6, 2014;370(10):901-10. doi: 10.1056/NEJMoa1300662.

Tee et al., Polishing the craft of genetic diversity creation in directed evolution. Biotechnol Adv. Dec. 2013;31(8):1707-21. doi: 10.1016/j.biotechadv.2013.08.021. Epub Sep. 6, 2013.

Telenti et al., The *Mycobacterium xenopi* GyrA protein splicing element: characterization of a minimal intein. J Bacteriol. Oct. 1997;179(20):6378-82. doi: 10.1128/jb.179.20.6378-6382.1997.

Telesnitsky et al., RNase H domain mutations affect the interaction between Moloney murine leukemia virus reverse transcriptase and its primer-template. Proc Natl Acad Sci U S A. Feb. 15, 1993;90(4):1276-80. doi: 10.1073/pnas.90.4.1276.

Teng et al., Mutational analysis of apolipoprotein B mRNA editing enzyme (APOBEC1). structure-function relationships of RNA editing and dimerization. J Lipid Res. Apr. 1999;40(4):623-35.

Tessarollo et al., Targeted mutation in the neurotrophin-3 gene results in loss of muscle sensory neurons. Proc Natl Acad Sci U S A. Dec. 6, 1994;91(25):11844-8.

Tesson et al., Knockout rats generated by embryo microinjection of TALENs. Nat Biotechnol. Aug. 5, 2011;29(8):695-6. doi: 10.1038/nbt.1940.

Thompson et al., Engineering and identifying supercharged proteins for macromolecule delivery into mammalian cells. Methods Enzymol. 2012;503:293-319. doi: 10.1016/B978-0-12-396962-0.00012-4.

Thomson et al., Mutational analysis of loxP sites for efficient Cre-mediated insertion into genomic DNA. Genesis. Jul. 2003;36(3):162-7. doi: 10.1002/gene.10211.

Thorpe et al., Functional correction of episomal mutations with short DNA fragments and RNA-DNA oligonucleotides. J Gene Med. Mar.-Apr. 2002;4(2):195-204.

Thyagarajan et al., Creation of engineered human embryonic stem cell lines using phiC31 integrase. Stem Cells. Jan. 2008;26(1):119-26. doi: 10.1634/stemcells.2007-0283. Epub Oct. 25, 2007.

Thyagarajan et al., Mammalian genomes contain active recombinase recognition sites. Gene. Feb. 22, 2000;244(1-2):47-54.

Thyagarajan et al., Site-specific genomic integration in mammalian cells mediated by phage phiC31 integrase. Mol Cell Biol. Jun. 2001;21(12):3926-34.

Tinland et al., The T-DNA-linked VirD2 protein contains two distinct functional nuclear localization signals. Proc Natl Acad Sci U S A. Aug. 15, 1992;89(16):7442-6. doi: 10.1073/pnas.89.16.7442.

Tirumalai et al., Recognition of core-type DNA sites by lambda integrase. J Mol Biol. Jun. 12, 1998;279(3):513-27.

Tom et al., Mechanism whereby proliferating cell nuclear antigen stimulates flap endonuclease 1. J Biol Chem. Apr. 7, 2000;275(14):10498-505. doi: 10.1074/jbc.275.14.10498.

Tone et al., Single-stranded DNA binding protein Gp5 of Bacillus subtilis phage Φ is required for viral DNA replication in growth-temperature dependent fashion. Biosci Biotechnol Biochem. 2012;76(12):2351-3. doi: 10.1271/bbb.120587. Epub Dec. 7, 2012.

Toor et al., Crystal structure of a self-spliced group II intron. Science. Apr. 4, 2008;320(5872):77-82. doi: 10.1126/science.1153803.

Torres et al., Non-integrative lentivirus drives high-frequency cre-mediated cassette exchange in human cells. PLoS One. 2011;6(5):e19794. doi: 10.1371/journal.pone.0019794. Epub May 23, 2011.

Tourdot et al., A general strategy to enhance immunogenicity of low-affinity HLA-A2. 1-associated peptides: implication in the identification of cryptic tumor epitopes. Eur J Immunol. Dec. 2000;30(12):3411-21.

Townsend et al., Role of HFE in iron metabolism, hereditary haemochromatosis, anaemia of chronic disease, and secondary iron overload. Lancet. Mar. 2, 2002;359(9308):786-90. doi: 10.1016/S0140-6736(02)07885-6.

Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.

Tratschin et al., A human parvovirus, adeno-associated virus, as a eucaryotic vector: transient expression and encapsidation of the procaryotic gene for chloramphenicol acetyltransferase. Mol Cell Biol. Oct. 1984;4(10):2072-81. doi: 10.1128/mcb.4.10.2072.

Tratschin et al., Adeno-associated virus vector for high-frequency integration, expression, and rescue of genes in mammalian cells. Mol Cell Biol. Nov. 1985;5(11):3251-60. doi: 10.1128/mcb.5.11.3251.

Trausch et al., The structure of a tetrahydrofolate-sensing riboswitch reveals two ligand binding sites in a single aptamer. Structure. Oct. 12, 2011;19(10):1413-23. doi: 10.1016/j.str.2011.06.019. Epub Sep. 8, 2011.

Traxler et al., A genome-editing strategy to treat β-hemoglobinopathies that recapitulates a mutation associated with a benign genetic condition. Nat Med. Sep. 2016;22(9):987-90. doi: 10.1038/nm.4170. Epub Aug. 15, 2016.

Trojan et al., Functional analysis of hMLH1 variants and HNPCC-related mutations using a human expression system. Gastroenterology. Jan. 2002;122(1):211-9. doi: 10.1053/gast.2002.30296.

Trudeau et al., On the Potential Origins of the High Stability of Reconstructed Ancestral Proteins. Mol Biol Evol. Oct. 2016;33(10):2633-41. doi: 10.1093/molbev/msw138. Epub Jul. 12, 2016.

Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015. With Supplementary Data.

Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.

Tsai et al., GUIDE-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.

Tsang et al., Specialization of the DNA-cleaving activity of a group I ribozyme through in vitro evolution. J Mol Biol. Sep. 13, 1996;262(1):31-42. doi: 10.1006/jmbi.1996.0496.

Tsutakawa et al., Human flap endonuclease structures, DNA double-base flipping, and a unified understanding of the FEN1 superfamily. Cell. Apr. 15, 2011;145(2):198-211. doi: 10.1016/j.cell.2011.03.004.

Turan et al., Recombinase-mediated cassette exchange (RMCE)—a rapidly-expanding toolbox for targeted genomic modifications. Gene. Feb. 15, 2013;515(1):1-27. doi: 10.1016/j.gene.2012.11.016. Epub Nov. 29, 2012.

Turan et al., Recombinase-mediated cassette exchange (RMCE): traditional concepts and current challenges. J Mol Biol. Mar. 25, 2011;407(2):193-221. doi: 10.1016/j.jmb.2011.01.004. Epub Jan. 15, 2011.

(56) References Cited

OTHER PUBLICATIONS

Turan et al., Site-specific recombinases: from tag-and-target- to tag-and-exchange-based genomic modifications. FASEB J. Dec. 2011;25(12):4088-107. doi: 10.1096/fj.11-186940. Epub Sep. 2, 2011. Review.

UniProt Submission; UniProt, Accession No. P01011. Last modified Jun. 11, 2014, version 2. 15 pages.

UniProt Submission; UniProt, Accession No. P01011. Last modified Sep. 18, 2013, version 2. 15 pages.

UniProt Submission; UniProt, Accession No. P04264. Last modified Jun. 11, 2014, version 6. 15 pages.

UniProt Submission; UniProt, Accession No. P04275. Last modified Jul. 9, 2014, version 107. 29 pages.

UniProtKB Submission; Accession No. F0NH53. May 3, 2011. 4 pages.

UniProtKB Submission; Accession No. F0NN87. May 3, 2011. 4 pages.

UniProtKB Submission; Accession No. T0D7A2. Oct. 16, 2013. 10 pages.

Urasaki et al., Functional dissection of the Tol2 transposable element identified the minimal cis-sequence and a highly repetitive sequence in the subterminal region essential for transposition. Genetics. Oct. 2006;174(2):639-49. doi: 10.1534/genetics.106.060244. Epub Sep. 7, 2006.

Urnov et al., Genome editing with engineered zinc finger nucleases. Nat Rev Genet. Sep. 2010;11(9):636-46. doi: 10.1038/nrg2842.

Urnov et al., Highly efficient endogenous human gene correction using designed zinc-finger nucleases. Nature. Jun. 2, 2005;435(7042):646-51. Epub Apr. 3, 2005.

Usman et al., Exploiting the chemical synthesis of RNA. Trends Biochem Sci. Sep. 1992;17(9):334-9. doi: 10.1016/0968-0004(92)90306-t.

Vagner et al., Efficiency of homologous DNA recombination varies along the Bacillus subtilis chromosome. J Bacteriol. Sep. 1988;170(9):3978-82.

Van Brunt et al., Genetically Encoded Azide Containing Amino Acid in Mammalian Cells Enables Site-Specific Antibody-Drug Conjugates Using Click Cycloaddition Chemistry. Bioconjug Chem. Nov. 18, 2015;26(11):2249-60. doi: 10.1021/acs.bioconjchem.5b00359. Epub Sep. 11, 2015.

Van Brunt et al., Molecular Farming: Transgenic Animals as Bioreactors. Biotechnology (NY). 1988;6(10):1149-1154. doi: 10.1038/nbt1088-1149.

Van Den Oord et al., Pixel Recurrent Neural Networks. Proceedings of the 33rd International Conference on Machine Learning. Journal of Machine Learning Research. Aug. 19, 2016. vol. 48. 11 pages.

Van Overbeek et al., DNA Repair Profiling Reveals Nonrandom Outcomes at Cas9-Mediated Breaks. Mol Cell. Aug. 18, 2016;63(4):633-646. doi: 10.1016/j.molcel.2016.06.037. Epub Aug. 4, 2016.

Van Swieten et al., A mutation in the fibroblast growth factor 14 gene is associated with autosomal dominant cerebellar ataxia [corrected]. Am J Hum Genet. Jan. 2003;72(1):191-9. Epub Dec. 13, 2002.

Van Wijk et al., Identification of 51 novel exons of the Usher syndrome type 2A (USH2A) gene that encode multiple conserved functional domains and that are mutated in patients with Usher syndrome type II. Am J Hum Genet. Apr. 2004;74(4):738-44. doi: 10.1086/383096. Epub Mar. 10, 2004.

Vanamee et al., FokI requires two specific DNA sites for cleavage. J Mol Biol. May 25, 2001;309(1):69-78.

Varga et al., Progressive vascular smooth muscle cell defects in a mouse model of Hutchinson-Gilford progeria syndrome. Proc Natl Acad Sci U S A. Feb. 28, 2006;103(9):3250-5. doi: 10.1073/pnas.0600012103. Epub Feb. 21, 2006.

Vellore et al., A group II intron-type open reading frame from the thermophile Bacillus (Geobacillus) stearothermophilus encodes a heat-stable reverse transcriptase. Appl Environ Microbiol. Dec. 2004;70(12):7140-7. doi: 10.1128/AEM.70.12.7140-7147.2004.

Venken et al., Genome-wide manipulations of Drosophila melanogaster with transposons, Flp recombinase, and ΦC31 integrase. Methods Mol Biol. 2012;859:203-28. doi: 10.1007/978-1-61779-603-6_12.

Verma, The reverse transcriptase. Biochim Biophys Acta. Mar. 21, 1977;473(1):1-38. doi: 10.1016/0304-419x(77)90005-1.

Vigne et al., Third-generation adenovectors for gene therapy. Restor Neurol Neurosci. Jan. 1, 1995;8(1):35-6. doi: 10.3233/RNN-1995-81208.

Vik et al., Endonuclease V cleaves at inosines in RNA. Nat Commun. 2013;4:2271. doi: 10.1038/ncomms3271.

Vilenchik et al., Endogenous DNA double-strand breaks: production, fidelity of repair, and induction of cancer. Proc Natl Acad Sci U S A. Oct. 28, 2003;100(22):12871-6. doi: 10.1073/pnas.2135498100. Epub Oct. 17, 2003.

Vitreschak et al., Regulation of the vitamin B12 metabolism and transport in bacteria by a conserved RNA structural element. RNA. Sep. 2003;9(9):1084-97.

Voigt et al., Rational evolutionary design: the theory of in vitro protein evolution. Adv Protein Chem. 2000;55:79-160.

Wacey et al., Disentangling the perturbational effects of amino acid substitutions in the DNA-binding domain of p53. Hum Genet. Jan. 1999;104(1):15-22.

Wadia et al., Modulation of cellular function by TAT mediated transduction of full length proteins. Curr Protein Pept Sci. Apr. 2003;4(2):97-104.

Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.

Wah et al., Structure of FokI has implications for DNA cleavage. Proc Natl Acad Sci U S A. Sep. 1, 1998;95(18):10564-9.

Wals et al., Unnatural amino acid incorporation in E. coli: current and future applications in the design of therapeutic proteins. Front Chem. Apr. 1, 2014;2:15. doi: 10.3389/fchem.2014.00015. eCollection 2014.

Wang et al., AID upmutants isolated using a high-throughput screen highlight the immunity/cancer balance limiting DNA deaminase activity. Nat Struct Mol Biol. Jul. 2009;16(7):769-76. doi: 10.1038/nsmb.1623. Epub Jun. 21, 2009.

Wang et al., CRISPR-Cas9 Targeting of PCSK9 in Human Hepatocytes In Vivo-Brief Report. Arterioscler Thromb Vasc Biol. May 2016;36(5):783-6. doi: 10.1161/ATVBAHA.116.307227. Epub Mar. 3, 2016.

Wang et al., Efficient delivery of genome-editing proteins using bioreducible lipid nanoparticles. Proc Natl Acad Sci U S A. Feb. 29, 2016. pii: 201520244. [Epub ahead of print].

Wang et al., Evolution of new nonantibody proteins via iterative somatic hypermutation. Proc Natl Acad Sci U S A. Nov. 30, 2004;101(48):16745-9. Epub Nov. 19, 2004.

Wang et al., Expanding the genetic code. Annu Rev Biophys Biomol Struct. 2006;35:225-49. Review.

Wang et al., Genetic screens in human cells using the CRISPR-Cas9 system. Science. Jan. 3, 2014;343(6166):80-4. doi: 10.1126/science.1246981. Epub Dec. 12, 2013.

Wang et al., Highly efficient CRISPR/HDR-mediated knock-in for mouse embryonic stem cells and zygotes. Biotechniques. 2015:59,201-2;204;206-8.

Wang et al., N(6)-methyladenosine Modulates Messenger RNA Translation Efficiency. Cell. Jun. 4, 2015;161(6):1388-99. doi: 10.1016/j.cell.2015.05.014.

Wang et al., N6-methyladenosine-dependent regulation of messenger RNA stability. Nature. Jan. 2, 2014;505(7481):117-20. doi: 10.1038/nature12730. Epub Nov. 27, 2013.

Wang et al., Nucleation, propagation and cleavage of target RNAs in Ago silencing complexes. Nature. Oct. 8, 2009;461(7265):754-61. doi: 10.1038/nature08434.

Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.

Wang et al., Programming cells by multiplex genome engineering and accelerated evolution. Nature. Aug. 13, 2009;460(7257):894-8. Epub Jul. 26, 2009.

(56) References Cited

OTHER PUBLICATIONS

Wang et al., Reading RNA methylation codes through methyl-specific binding proteins. RNA Biol. 2014;11(6):669-72. doi: 10.4161/rna.28829. Epub Apr. 24, 2014.

Wang et al., Recombinase technology: applications and possibilities. Plant Cell Rep. Mar. 2011;30(3):267-85. doi: 10.1007/s00299-010-0938-1. Epub Oct. 24, 2010.

Wang et al., Riboswitches that sense S-adenosylhomocysteine and activate genes involved in coenzyme recycling. Mol Cell. Mar. 28, 2008;29(6):691-702. doi: 10.1016/j.molcel.2008.01.012.

Wang et al., *Staphylococcus aureus* protein SAUGI acts as a uracil-DNA glycosylase inhibitor. Nucleic Acids Res. Jan. 2014;42(2):1354-64. doi: 10.1093/nar/gkt964. Epub Oct. 22, 2013.

Wang et al., Structural basis of N(6)-adenosine methylation by the METTL3-METTL14 complex. Nature. Jun. 23, 2016;534(7608):575-8. doi: 10.1038/nature18298. Epub May 25, 2016.

Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.

Wang et al., Uracil-DNA glycosylase inhibitor gene of bacteriophage PBS2 encodes a binding protein specific for uracil-DNA glycosylase. J Biol Chem. Jan. 15, 1989;264(2):1163-71.

Warren et al., A chimeric Cre recombinase with regulated directionality. Proc Natl Acad Sci USA. Nov. 25, 2008;105(47):18278-83. doi: 10.1073/pnas.0809949105. Epub Nov. 14, 2008.

Warren et al., Mutations in the amino-terminal domain of lambda-integrase have differential effects on integrative and excisive recombination. Mol Microbiol. Feb. 2005;55(4):1104-12.

Watowich, The erythropoietin receptor: molecular structure and hematopoietic signaling pathways. J Investig Med. Oct. 2011;59(7):1067-72. doi: 10.2310/JIM.0b013e31820fb28c.

Waxman et al., Regulating excitability of peripheral afferents: emerging ion channel targets. Nat Neurosci. Feb. 2014;17(2):153-63. doi: 10.1038/nn.3602. Epub Jan. 28, 2014.

Weber et al., Assembly of designer TAL effectors by Golden Gate cloning. PLoS One. 2011;6(5):e19722. doi: 10.1371/journal.pone.0019722. Epub May 19, 2011.

Weill et al., DNA polymerases in adaptive immunity. Nat Rev Immunol. Apr. 2008;8(4):302-12. doi: 10.1038/nri2281. Epub Mar. 14, 2008.

Weinberg et al., New Classes of Self-Cleaving Ribozymes Revealed by Comparative Genomics Analysis. Nat Chem Biol. Aug. 2015;11(8):606-10. doi: 10.1038/nchembio.1846. Epub Jul. 13, 2015.

Weinberg et al., The aptamer core of SAM-IV riboswitches mimics the ligand-binding site of SAM-I riboswitches. RNA. May 2008;14(5):822-8. doi: 10.1261/rna.988608. Epub Mar. 27, 2008.

Weinberger et al., Disease-causing mutations C277R and C277Y modify gating of human ClC-1 chloride channels in myotonia congenita. J Physiol. Aug. 1, 2012;590(Pt 15):3449-64. doi: 0.1113/jphysiol.2012.232785. Epub May 28, 2012.

Weiss et al., Loss-of-function mutations in sodium channel Nav1.7 cause anosmia. Nature. Apr. 14, 2011;472(7342):186-90. doi: 10.1038/nature09975. Epub Mar. 23, 2011.

Wen et al., Inclusion of a universal tetanus toxoid CD4(+) T cell epitope P2 significantly enhanced the immunogenicity of recombinant rotavirus ΔVP8* subunit parenteral vaccines. Vaccine. Jul. 31, 2014;32(35):4420-4427. doi: 10.1016/j.vaccine.2014.06.060. Epub Jun. 21, 2014.

West et al., Gene expression in adeno-associated virus vectors: the effects of chimeric mRNA structure, helper virus, and adenovirus VA1 RNA. Virology. Sep. 1987;160(1):38-47. doi: 10.1016/0042-6822(87)90041-9.

Wharton et al., A new-specificity mutant of 434 repressor that defines an amino acid-base pair contact. Nature. Apr. 30-May 6, 1987;326(6116):888-91.

Wharton et al., Changing the binding specificity of a repressor by redesigning an alpha-helix. Nature. Aug. 15-21, 1985;316(6029):601-5.

Wheeler et al., The thermostability and specificity of ancient proteins. Curr Opin Struct Biol. Jun. 2016;38:37-43. doi: 10.1016/j.sbi.2016.05.015. Epub Jun. 9, 2016.

Wiedenheft et al., RNA-guided genetic silencing systems in bacteria and archaea. Nature. Feb. 15, 2012;482(7385):331-8. doi: 10.1038/nature10886. Review.

Wijesinghe et al., Efficient deamination of 5-methylcytosines in DNA by human APOBEC3A, but not by AID or APOBEC3G. Nucleic Acids Res. Oct. 2012;40(18):9206-17. doi: 10.1093/nar/gks685. Epub Jul. 13, 2012.

Wijnker et al., Managing meiotic recombination in plant breeding. Trends Plant Sci. Dec. 2008;13(12):640-6. doi: 10.1016/j.tplants.2008.09.004. Epub Oct. 22, 2008.

Williams et al., Assessing the accuracy of ancestral protein reconstruction methods. PLoS Comput Biol. Jun. 23, 2006;2(6):e69. doi: 10.1371/journal.pcbi.0020069. Epub Jun. 23, 2006.

Wills et al., Pseudoknot-dependent read-through of retroviral gag termination codons: importance of sequences in the spacer and loop 2. EMBO J. Sep. 1, 1994;13(17):4137-44. doi: 10.1002/j.1460-2075.1994.tb06731.x.

Wilson et al., Assessing annotation transfer for genomics: quantifying the relations between protein sequence, structure and function through traditional and probabilistic scores. J Mol Biol 2000;297:233-49.

Wilson et al., Formation of infectious hybrid virions with gibbon ape leukemia virus and human T-cell leukemia virus retroviral envelope glycoproteins and the gag and pol proteins of Moloney murine leukemia virus. J Virol. May 1989;63(5):2374-8. doi: 10.1128/JVI.63.5.2374-2378.1989.

Wilson et al., In Vitro Selection of Functional Nucleic Acids. Annu Rev Biochem. 1999;68:611-47. doi: 10.1146/annurev.biochem.68.1.611.

Wilson et al., Kinase dynamics. Using ancient protein kinases to unravel a modern cancer drug's mechanism. Science. Feb. 20, 2015;347(6224):882-6. doi: 10.1126/science.aaa1823.

Winkler et al., An mRNA structure that controls gene expression by binding FMN. Proc Natl Acad Sci U S A. Dec. 10, 2002;99(25):15908-13. Epub Nov. 27, 2002.

Winkler et al., Control of gene expression by a natural metabolite-responsive ribozyme. Nature. Mar. 18, 2004;428(6980):281-6.

Winkler et al., Thiamine derivatives bind messenger RNAs directly to regulate bacterial gene expression. Nature. Oct. 31, 2002;419(6910):952-6. Epub Oct. 16, 2002.

Winoto et al., A novel, inducible and T cell-specific enhancer located at the 3' end of the T cell receptor alpha locus. EMBO J. Mar. 1989;8(3):729-33.

Winter et al., Drug Development. Phthalimide conjugation as a strategy for in vivo target protein degradation. Science. Jun. 19, 2015;348(6241):1376-81. doi:; 10.1126/science.aab1433. Epub May 21, 2015.

Wirth et al., Mildly affected patients with spinal muscular atrophy are partially protected by an increased SMN2 copy number. Hum Genet. May 2006;119(4):422-8. doi: 10.1007/s00439-006-0156-7. Epub Mar. 1, 2006.

Wold, Replication protein A: a heterotrimeric, single-stranded DNA-binding protein required for eukaryotic DNA metabolism. Annu Rev Biochem. 1997;66:61-92. doi: 10.1146/annurev.biochem.66.1.61.

Wolf et al., tadA, an essential tRNA-specific adenosine deaminase from *Escherichia coli*. EMBO J. Jul. 15, 2002;21(14):3841-51.

Wolfe et al., Analysis of zinc fingers optimized via phage display: evaluating the utility of a recognition code. J Mol Biol. Feb. 5, 1999;285(5):1917-34.

Wong et al., A statistical analysis of random mutagenesis methods used for directed protein evolution. J Mol Biol. Jan. 27, 2006;355(4):858-71. Epub Nov. 17, 2005.

Wong et al., The Diversity Challenge in Directed Protein Evolution. Comb Chem High Throughput Screen. May 2006;9(4):271-88.

Wood et al., A genetic system yields self-cleaving inteins for bioseparations. Nat Biotechnol. Sep. 1999;17(9):889-92. doi: 10.1038/12879.

(56) References Cited

OTHER PUBLICATIONS

Wood et al., Targeted genome editing across species using ZFNs and TALENs. Science. Jul. 15, 2011;333(6040):307. doi: 10.1126/science. 1207773. Epub Jun. 23, 2011.

Woods et al., The phenotype of congenital insensitivity to pain due to the NaV1.9 variant p.L811P. Eur J Hum Genet. May 2015;23(5):561-3. doi: 10.1038/ejhg.2014.166. Epub Aug. 13, 2014.

Wright et al., Continuous in vitro evolution of catalytic function. Science. Apr. 25, 1997;276(5312):614-7.

Wright et al., Rational design of a split-Cas9 enzyme complex. Proc Natl Acad Sci U S A. Mar. 10, 2015;112(10):2984-9. doi: 10.1073/pnas.1501698112. Epub Feb. 23, 2015.

Wu et al., A novel SCN9A mutation responsible for primary erythromelalgia and is resistant to the treatment of sodium channel blockers. PLoS One. 2013;8(1):e55212. doi: 10.1371/journal.pone. 0055212. Epub Jan. 31, 2013. 15 pages.

Wu et al., Correction of a genetic disease in mouse via use of CRISPR-Cas9. Cell Stem Cell. Dec. 5, 2013;13(6):659-62. doi: 10.1016/j.stem.2013.10.016.

Wu et al., Genome-wide binding of the CRISPR endonuclease Cas9 in mammalian cells. Nat Biotechnol. Jul. 2014;32(7):670-6. doi: 10.1038/nbt.2889. Epub Apr. 20, 2014.

Wu et al., Human single-stranded DNA binding proteins: guardians of genome stability. Acta Biochim Biophys Sin (Shanghai). Jul. 2016;48(7):671-7. doi: 10.1093/abbs/gmw044. Epub May 23, 2016.

Wu et al., Protein trans-splicing and functional mini-inteins of a cyanobacterial dnaB intein. Biochim Biophys Acta. Sep. 8, 1998;1387(1-2):422-32. doi: 10.1016/s0167-4838(98)00157-5.

Wu et al., Protein trans-splicing by a split intein encoded in a split DnaE gene of *Synechocystis* sp. PCC6803. Proc Natl Acad Sci U S A. Aug. 4, 1998;95(16):9226-31. doi: 10.1073/pnas.95.16.9226.

Xiao et al., Genetic incorporation of multiple unnatural amino acids into proteins in mammalian cells. Angew Chem Int Ed Engl. Dec. 23, 2013;52(52):14080-3. doi: 10.1002/anie.201308137. Epub Nov. 8, 2013.

Xiao et al., Nuclear m(6)A Reader YTHDC1 Regulates mRNA Splicing. Mol Cell. Feb. 18, 2016;61(4):507-519. doi: 10.1016/j. molcel.2016.01.012. Epub Feb. 11, 2016.

Xie et al., Adjusting the attB site in donor plasmid improves the efficiency of ΦC31 integrase system. DNA Cell Biol. Jul. 2012;31(7):1335-40. doi: 10.1089/dna.2011.1590. Epub Apr. 10, 2012.

Xiong et al., Origin and evolution of retroelements based upon their reverse transcriptase sequences. EMBO J. Oct. 1990;9(10):3353-62.

Xu et al., Accuracy and efficiency define Bxb1 integrase as the best of fifteen candidate serine recombinases for the integration of DNA into the human genome. BMC Biotechnol. Oct. 20, 2013;13:87. doi: 10.1186/1472-6750-13-87.

Xu et al., Chemical ligation of folded recombinant proteins: segmental isotopic labeling of domains for NMR studies. Proc Natl Acad Sci U S A. Jan. 19, 1999;96(2):388-93. doi: 10.1073/pnas. 96.2.388.

Xu et al., Protein splicing: an analysis of the branched intermediate and its resolution by succinimide formation. EMBO J. Dec. 1, 1994;13(23):5517-22.

Xu et al., Sequence determinants of improved CRISPR sgRNA design. Genome Res. Aug. 2015;25(8):1147-57. doi: 10.1101/gr. 191452.115. Epub Jun. 10, 2015.

Xu et al., Structures of human ALKBH5 demethylase reveal a unique binding mode for specific single-stranded N6-methyladenosine RNA demethylation. J Biol Chem. Jun. 20, 2014;289(25):17299-311. doi: 10.1074/jbc.M114.550350. Epub Apr. 28, 2014.

Xu et al., The mechanism of protein splicing and its modulation by mutation. EMBO J. Oct. 1, 1996;15(19):5146-53.

Yamamoto et al., The ons and offs of inducible transgenic technology: a review. Neurobiol Dis. Dec. 2001;8(6):923-32.

Yamamoto et al., Virological and immunological bases for HIV-1 vaccine design. Uirusu 2007;57(2):133-139. https://doi.org/10.2222/jsv.57.133.

Yamane et al., Deep-sequencing identification of the genomic targets of the cytidine deaminase AID and its cofactor RPA in B lymphocytes. Nat Immunol. Jan. 2011;12(1):62-9. doi: 10.1038/ni. 1964. Epub Nov. 28, 2010.

Yamano et al., Crystal Structure of Cpf1 in Complex with Guide RNA and Target DNA. Cell. May 5, 2016;165(4):949-62 and Supplemental Info. doi: 10.1016/j.cell.2016.04.003. Epub Apr. 21, 2016.

Yamano et al., Crystal Structure of Cpf1 in Complex with Guide RNA and Target DNA. Cell. May 5, 2016;165(4):949-62. doi: 10.1016/j.cell.2016.04.003. Epub Apr. 21, 2016.

Yamazaki et al., Segmental Isotope Labeling for Protein NMR Using Peptide Splicing. J. Am. Chem. Soc. May 22, 1998; 120(22):5591-2. https://doi.org/10.1021/ja9807760.

Yang et al., BRCA2 function in DNA binding and recombination from a BRCA2-DSS1-ssDNA structure. Science. Sep. 13, 2002;297(5588):1837-48. doi: 10.1126/science.297.5588.1837.

Yang et al., Construction of an integration-proficient vector based on the site-specific recombination mechanism of enterococcal temperate phage phiFC1. J Bacteriol. Apr. 2002;184(7):1859-64. doi: 10.1128/jb.184.7.1859-1864.2002.

Yang et al., Genome editing with targeted deaminases. BioRxiv. Preprint. First posted online Jul. 28, 2016.

Yang et al., Genome-wide inactivation of porcine endogenous retroviruses (PERVs). Science. Nov. 27, 2015;350(6264):1101-4. doi: 10.1126/science.aad1191. Epub Oct. 11, 2015.

Yang et al., Mutations in SCN9A, encoding a sodium channel alpha subunit, in patients with primary erythermalgia. J Med Genet. Mar. 2004;41(3):171-4. doi: 10.1136/jmg.2003.012153.

Yang et al., One-step generation of mice carrying reporter and conditional alleles by CRISPR/Cas-mediated genome engineering. Cell. Sep. 12, 2013;154(6):1370-9. doi: 10.1016/j.cell.2013.08.022. Epub Aug. 29, 2013.

Yang et al., Permanent genetic memory with >1-byte capacity. Nat Methods. Dec. 2014;11(12):1261-6. doi: 10.1038/nmeth.3147. Epub Oct. 26, 2014.

Yang et al., Preparation of RNA-directed DNA polymerase from spleens of Balb-c mice infected with Rauscher leukemia virus. Biochem Biophys Res Commun. Apr. 28, 1972;47(2):505-11. doi: 10.1016/0006-291x(72)90743-7.

Yang et al., Small-molecule control of insulin and PDGF receptor signaling and the role of membrane attachment. Curr Biol. Jan. 1, 1998;8(1):11-8. doi: 10.1016/s0960-9822(98)70015-6.

Yang et al., The BRCA2 homologue Brh2 nucleates RAD51 filament formation at a dsDNA-ssDNA junction. Nature. Feb. 10, 2005;433(7026):653-7. doi: 10.1038/nature03234.

Yang, Development of Human Genome Editing Tools for the Study of Genetic Variations and Gene Therapies. Doctoral Dissertation. Harvard University. 2013. Accessible via nrs.harvard.edu/urn-3:HUL. InstRepos:11181072. 277 pages.

Yang, Nucleases: diversity of structure, function and mechanism. Q Rev Biophys. Feb. 2011;44(1):1-93. doi: 10.1017/S0033583510000181. Epub Sep. 21, 2010.

Yang, PAML 4: phylogenetic analysis by maximum likelihood. Mol Biol Evol. Aug. 2007;24(8): 1586-91. doi: 10.1093/molbev/msm088. Epub May 4, 2007.

Yanover et al., Extensive protein and DNA backbone sampling improves structure-based specificity prediction for C2H2 zinc fingers. Nucleic Acids Res. Jun. 2011;39(11):4564-76. doi: 10.1093/nar/gkr048. Epub Feb. 22, 2011.

Yasui et al., Miscoding Properties of 2'-Deoxyinosine, a Nitric Oxide-Derived DNA Adduct, during Translesion Synthesis Catalyzed by Human DNA Polymerases. J Molec Biol. Apr. 4, 2008;377(4):1015-23.

Yasui, Alternative excision repair pathways. Cold Spring Harb Perspect Biol. Jun. 1, 2013;5(6):a012617. doi: 10.1101/cshperspect. a012617.

Yasukawa et al., Characterization of Moloney murine leukaemia virus/avian myeloblastosis virus chimeric reverse transcriptases. J Biochem. Mar. 2009;145(3):315-24. doi: 10.1093/jb/mvn166. Epub Dec. 6, 2008.

(56) References Cited

OTHER PUBLICATIONS

Yazaki et al., Hereditary systemic amyloidosis associated with a new apolipoprotein AII stop codon mutation Stop78Arg. Kidney Int. Jul. 2003;64(1):11-6.

Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.

Yokoe et al., Spatial dynamics of GFP-tagged proteins investigated by local fluorescence enhancement. Nat Biotechnol. Oct. 1996;14(10):1252-6. doi: 10.1038/nbt1096-1252.

Young et al., Beyond the canonical 20 amino acids: expanding the genetic lexicon. J Biol Chem. Apr. 9, 2010;285(15):11039-44. doi: 10.1074/jbc.R109.091306. Epub Feb. 10, 2010.

Yu et al., Circular permutation: a different way to engineer enzyme structure and function. Trends Biotechnol. Jan. 2011;29(1):18-25. doi: 10.1016/j.tibtech.2010.10.004. Epub Nov. 17, 2010.

Yu et al., Dynamic control of Rad51 recombinase by self-association and interaction with BRCA2. Mol Cell. Oct. 2003;12(4):1029-41. doi: 10.1016/s1097-2765(03)00394-0.

Yu et al., Liposome-mediated in vivo E1A gene transfer suppressed dissemination of ovarian cancer cells that overexpress HER-2/neu. Oncogene. Oct. 5, 1995;11(7):1383-8.

Yu et al., Progress towards gene therapy for HIV infection. Gene Ther. Jan. 1994;1(1):13-26.

Yu et al., Small molecules enhance CRISPR genome editing in pluripotent stem cells. Cell Stem Cell. Feb. 5, 2015;16(2):142-7. doi: 10.1016/j.stem.2015.01.003.

Yu et al., Synthesis-dependent microhomology-mediated end joining accounts for multiple types of repair junctions. Nucleic Acids Res. Sep. 2010;38(17):5706-17. doi: 10.1093/nar/gkq379. Epub May 11, 2010.

Yuan et al., Laboratory-directed protein evolution. Microbiol Mol Biol Rev. 2005; 69(3):373-92. PMID: 16148303.

Yuan et al., Tetrameric structure of a serine integrase catalytic domain. Structure. Aug. 6, 2008;16(8):1275-86. doi: 10.1016/j.str.2008.04.018.

Yuen et al., Control of transcription factor activity and osteoblast differentiation in mammalian cells using an evolved small-molecule-dependent intein. J Am Chem Soc. Jul. 12, 2006;128(27):8939-46.

Zalatan et al., Engineering complex synthetic transcriptional programs with CRISPR RNA scaffolds. Cell. Jan. 15, 2015;160(1-2):339-50. doi: 10.1016/j.cell.2014.11.052. Epub Dec. 18, 2014.

Zetsche et al., A split-Cas9 architecture for inducible genome editing and transcription modulation. Nat Biotechnol. Feb. 2015;33(2):139-42. doi: 10.1038/nbt.3149.

Zetsche et al., Cpf1 is a single RNA-guided endonuclease of a class 2 CRISPR-Cas system. Cell. Oct. 22, 2015;163(3):759-71 and Supplemental Info. doi: 10.1016/j.cell.2015.09.038. Epub Sep. 25, 2015.

Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.

Zettler et al., The naturally split Npu DnaE intein exhibits an extraordinarily high rate in the protein trans-splicing reaction. FEBS Lett. Mar. 4, 2009;583(5):909-14. doi: 10.1016/j.febslet.2009.02.003. Epub Feb. 10, 2009.

Zhang et al., II-Clamp-mediated cysteine conjugation. Nat Chem. Feb. 2016;8(2):120-8. doi: 10.1038/nchem.2413. Epub Dec. 21, 2015.

Zhang et al., A new strategy for the site-specific modification of proteins in vivo. Biochemistry. Jun. 10, 2003;42(22):6735-46.

Zhang et al., Circular intronic long noncoding RNAs. Mol Cell. Sep. 26, 2013;51(6):792-806. doi: 10.1016/j.molcel.2013.08.017. Epub Sep. 12, 2013.

Zhang et al., Comparison of non-canonical PAMs for CRISPR/Cas9-mediated DNA cleavage in human cells. Sci Rep. Jun. 2014;4:5405.

Zhang et al., Conditional gene manipulation: Cre-ating a new biological era. J Zhejiang Univ Sci B. Jul. 2012;13(7):511-24. doi: 10.1631/jzus.B1200042. Review.

Zhang et al., Copy number variation in human health, disease, and evolution. Annu Rev Genomics Hum Genet. 2009;10:451-81. doi: 10.1146/annurev.genom.9.081307.164217.

Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.

Zhang et al., Global analysis of small RNA and mRNA targets of Hfq. Mol Microbiol. Nov. 2003;50(4):1111-24. doi: 10.1046/j.1365-2958.2003.03734.x.

Zhang et al., Large genomic fragment deletions and insertions in mouse using CRISPR/Cas9. PLoS One. Mar. 24, 2015;10(3):e0120396. doi: 10.1371/journal.pone.0120396. 14 pages.

Zhang et al., Ribozymes and Riboswitches: Modulation of RNA Function by Small Molecules. Biochemistry. Nov. 2, 2010;49(43):9123-31. doi: 10.1021/bi1012645.

Zhang et al., Stabilized plasmid-lipid particles for regional gene therapy: formulation and transfection properties. Gene Ther. Aug. 1999;6(8):1438-47.

Zhao et al., Crystal structures of a group II intron maturase reveal a missing link in spliceosome evolution. Nat Struct Mol Biol. Jun. 2016;23(6):558-65. doi: 10.1038/nsmb.3224. Epub May 2, 2016.

Zheng et al., ALKBH5 is a mammalian RNA demethylase that impacts RNA metabolism and mouse fertility. Mol Cell. Jan. 10, 2013;49(1):18-29. doi: 10.1016/j.molcel.2012.10.015. Epub Nov. 21, 2012.

Zhou et al., Dynamic m(6)A mRNA methylation directs translational control of heat shock response. Nature. Oct. 22, 2015;526(7574):591-4. doi: 10.1038/nature15377. Epub Oct. 12, 2015.

Zhou et al., GISSD: Group I Intron Sequence and Structure Database. Nucleic Acids Res. Jan. 2008;36(Database issue):D31-7. doi: 10.1093/nar/gkm766. Epub Oct. 16, 2007.

Zhou et al., Protective V127 prion variant prevents prion disease by interrupting the formation of dimer and fibril from molecular dynamics simulations. Sci Rep. Feb. 24, 2016;6:21804. doi: 10.1038/srep21804.

Zielenski, Genotype and phenotype in cystic fibrosis. Respiration. 2000;67(2):117-33. doi: 10.1159/000029497.

Zimmerly et al., An Unexplored Diversity of Reverse Transcriptases in Bacteria. Microbiol Spectr. Apr. 2015;3(2):MDNA3-0058-2014. doi: 10.1128/microbiolspec.MDNA3-0058-2014.

Zimmerly et al., Group II intron mobility occurs by target DNA-primed reverse transcription. Cell. Aug. 25, 1995;82(4):545-54. doi: 10.1016/0092-8674(95)90027-6.

Zimmermann et al., Molecular interactions and metal binding in the theophylline-binding core of an RNA aptamer. RNA. May 2000;6(5):659-67.

Zolotukhin et al., Production and purification of serotype 1, 2, and 5 recombinant adeno-associated viral vectors. Methods. Oct. 2002;28(2):158-67. doi: 10.1016/s1046-2023(02)00220-7.

Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epub Jun. 18, 2009.

Zufferey et al., Woodchuck hepatitis virus posttranscriptional regulatory element enhances expression of transgenes delivered by retroviral vectors. J Virol. Apr. 1999;73(4):2886-92. doi: 10.1128/JVI.73.4.2886-2892.1999.

Zuker et al., Optimal computer folding of large RNA sequences using thermodynamics and auxiliary information. Nucleic Acids Res. Jan. 10, 1981;9(1):133-48. doi: 10.1093/nar/9.1.133.

Zuris et al., Cationic lipid-mediated delivery of proteins enables efficient protein-based genome editing in vitro and in vivo. Nat Biotechnol. 2015;33:73-80.

Extended European Search Report for EP20205536.4, mailed Jun. 2, 2021.

[No Author Listed] NCBI Reference Sequence: WP_032188360.1. Apr. 6, 2015. 1 page.

[No Author Listed], MutL homolog 1. UniProtKB Acc. No. F1MPG0. May 3, 2011. Accessible at https://rest.uniprot.org/unisave/F1MPG0?format=txt&versions=1. 1 page.

(56) References Cited

OTHER PUBLICATIONS

[No Author Listed], tRNA-specific adenosine deaminase. Uniprot Accession No. U2JUU0. Nov. 13, 2013. Accessible at https://www.uniprot.org/uniprotkb/U2JUU0/entry. 11 pages.

[No Author Listed], tRNA-specific adenosine deaminase [Candidatus Moranella endobia PCVAL]. GenBank Acc. No. AGJ61179.1. Accessible at https://www.ncbi.nlm.nih.gov/protein/AGJ61179. Jan. 30, 2014. 3 pages.

[No Author Listed], tRNA-specific adenosine deaminase [*Escherichia coli*]. GenBank Acc. No. CTS26096.1. Accessible at https://www.ncbi.nlm.nih.gov/protein/CTS26096.1. Aug. 22, 2015. 1 page.

Acharya et al., hMSH2 forms specific mispair-binding complexes with hMSH3 and hMSH6. Proc Natl Acad Sci U S A. Nov. 26, 1996;93(24):13629-34. doi: 10.1073/pnas.93.24.13629.

Alves et al., Immunogenicity of the carcinoembryonic antigen derived peptide 694 in HLA-A2 healthy donors and colorectal carcinoma patients. Cancer Immunol Immunother. Nov. 2007;56(11):1795-805. doi: 10.1007/s00262-007-0323-2. Epub Apr. 20, 2007.

Asemissen et al., Identification of a highly immunogenic HLA-A*01-binding T cell epitope of WT1. Clin Cancer Res. Dec. 15, 2006;12(24):7476-82. doi: 10.1158/1078-0432.CCR-06-1337.

Attia et al., Autoimmunity correlates with tumor regression in patients with metastatic melanoma treated with anti-cytotoxic T-lymphocyte antigen-4. J Clin Oncol. Sep. 1, 2005;23(25):6043-53. doi: 10.1200/JCO.2005.06.205. Epub Aug. 8, 2005.

Aurisicchio et al., A novel minigene scaffold for therapeutic cancer vaccines. Oncoimmunology. Jan. 1, 2014;3(1):e27529. doi: 10.4161/onci.27529. Epub Jan. 16, 2014.

Avidan et al., Expression and characterization of a recombinant novel reverse transcriptase of a porcine endogenous retrovirus. Virology. Mar. 15, 2003;307(2):341-57. doi: 10.1016/s0042-6822(02)00131-9.

Bae et al., Heteroclitic CD33 peptide with enhanced anti-acute myeloid leukemic immunogenicity. Clin Cancer Res. Oct. 15, 2004;10(20):7043-52. doi: 10.1158/1078-0432.CCR-04-0322.

Bae et al., Identification of novel CD33 antigen-specific peptides for the generation of cytotoxic T lymphocytes against acute myeloid leukemia. Cell Immunol. Jan. 2004;227(1):38-50. doi: 10.1016/j.cellimm.2004.01.002.

Bakker et al., Analogues of CTL epitopes with improved MHC class-I binding capacity elicit anti-melanoma CTL recognizing the wild-type epitope. Int J Cancer. Jan. 27, 1997;70(3):302-9. doi: 10.1002/(sici)1097-0215(19970127)70:3<302::aid-ijc10>3.0.co;2-h.

Banerjee et al., Viral glycoproteins: biological role and application in diagnosis. Virusdisease. Mar. 2016;27(1):1-11. doi: 10.1007/s13337-015-0293-5. Epub Jan. 18, 2016.

Barve et al., Induction of immune responses and clinical efficacy in a phase II trial of IDM-2101, a 10-epitope cytotoxic T-lymphocyte vaccine, in metastatic non-small-cell lung cancer. J Clin Oncol. Sep. 20, 2008;26(27):4418-25. doi: 10.1200/JCO.2008.16.6462.

Baños-sanz et al., Crystal structure and functional insights into uracil-DNA glycosylase inhibition by phage Φ29 DNA mimic protein p56. Nucleic Acids Res. Jul. 2013;41(13):6761-73. doi: 10.1093/nar/gkt395. Epub May 13, 2013.

Benlalam et al., Identification of five new HLA-B*3501-restricted epitopes derived from common melanoma-associated antigens, spontaneously recognized by tumor-infiltrating lymphocytes. J Immunol. Dec. 1, 2003;171(11):6283-9. doi: 10.4049/jimmunol.171.11.6283.

Bernatchez et al., Altered decamer and nonamer from an HLA-A0201-restricted epitope of Survivin differentially stimulate T-cell responses in different individuals. Vaccine. Apr. 5, 2011;29(16):3021-30. doi: 10.1016/j.vaccine.2011.01.115. Epub Feb. 12, 2011.

Bertsimas et al., Simulated annealing. Statistical Science. Feb. 1993;8(1):10-15. doi: 10.1214/ss/1177011077.

Bibikova et al., Targeted chromosomal cleavage and mutagenesis in *Drosophila* using zinc-finger nucleases. Genetics. Jul. 2002;161(3):1169-75. doi: 10.1093/genetics/161.3.1169.

Bioley et al., Melan-A/MART-1-specific CD4 T cells in melanoma patients: identification of new epitopes and ex vivo visualization of specific T cells by MHC class II tetramers. J Immunol. Nov. 15, 2006;177(10):6769-79. doi: 10.4049/jimmunol.177.10.6769.

Blanchet et al., A new generation of Melan-A/MART-1 peptides that fulfill both increased immunogenicity and high resistance to biodegradation: implication for molecular anti-melanoma immunotherapy. J Immunol. Nov. 15, 2001;167(10):5852-61. doi: 10.4049/jimmunol.167.10.5852.

Borbulevych et al., Increased immunogenicity of an anchor-modified tumor-associated antigen is due to the enhanced stability of the peptide/MHC complex: implications for vaccine design. J Immunol. Apr. 15, 2005;174(8):4812-20. doi: 10.4049/jimmunol.174.8.4812.

Brichard et al., A tyrosinase nonapeptide presented by HLA-B44 is recognized on a human melanoma by autologous cytolytic T lymphocytes. Eur J Immunol. Jan. 1996;26(1):224-30. doi: 10.1002/eji.1830260135.

Campi et al., CD4(+) T cells from healthy subjects and colon cancer patients recognize a carcinoembryonic antigen-specific immunodominant epitope. Cancer Res. Dec. 1, 2003;63(23):8481-6.

Carlier et al., Genome Sequence of Burkholderia cenocepacia H111, a Cystic Fibrosis Airway Isolate. Genome Announc. Apr. 10, 2014;2(2):e00298-14. doi: 10.1128/genomeA.00298-14.

Casnici et al., Immunologic evaluation of peptides derived from BCR/ABL-out-of-frame fusion protein in HLA A2.1 transgenic mice. J Immunother. May 2012;35(4):321-8. doi: 10.1097/CJI.0b013e3182562d37.

Casnici et al., Out of frame peptides from BCR/ABL alternative splicing are immunogenic in HLA A2.1 transgenic mice. Cancer Lett. Apr. 8, 2009;276(1):61-7. doi: 10.1016/j.canlet.2008.10.032. Epub Dec. 4, 2008.

Castelli et al., Mass spectrometric identification of a naturally processed melanoma peptide recognized by CD8+ cytotoxic T lymphocytes. J Exp Med. Jan. 1, 1995;181(1):363-8. doi: 10.1084/jem.181.1.363.

Castelli et al., Novel HLA-Cw8-restricted T cell epitopes derived from tyrosinase-related protein-2 and gp100 melanoma antigens. J Immunol. Feb. 1, 1999;162(3):1739-48.

Castle et al., Exploiting the mutanome for tumor vaccination. Cancer Res. Mar. 1, 2012;72(5):1081-91. doi: 10.1158/0008-5472.CAN-11-3722. Epub Jan. 11, 2012.

Cervera et al., Generation of HIV-1 Gag VLPs by transient transfection of HEK 293 suspension cell cultures using an optimized animal-derived component free medium. J Biotechnol. Jul. 20, 2013;166(4):152-65. doi: 10.1016/j.jbiotec.2013.05.001. Epub May 17, 2013.

Chen et al., Dynamic imaging of genomic loci in living human cells by an optimized CRISPR/Cas system. Cell. Dec. 19, 2013;155(7):1479-91. doi: 10.1016/j.cell.2013.12.001. Erratum in: Cell. Jan. 16, 2014;156(1-2):373.

Chen et al., Identification of NY-ESO-1 peptide analogues capable of improved stimulation of tumor-reactive CTL. J Immunol. Jul. 15, 2000;165(2):948-55. doi: 10.4049/jimmunol.165.2.948.

Cheriyan et al., Faster protein splicing with the Nostoc punctiforme DnaE intein using non-native extein residues. J Biol Chem. Mar. 1, 2013;288(9):6202-11. doi: 10.1074/jbc.M112.433094. Epub Jan. 10, 2013.

Cho et al., Optimized peptide vaccines eliciting extensive CD8 T-cell responses with therapeutic antitumor effects. Cancer Res. Dec. 1, 2009;69(23):9012-9. doi: 10.1158/0008-5472.CAN-09-2019 Epub Nov. 10, 2009.

Choi et al., Lentivirus pre-packed with Cas9 protein for safer gene editing. Gene Ther. Jul. 2016;23(7):627-33. doi: 10.1038/gt.2016.27. Epub Apr. 7, 2016.

Choi et al., Optimization of AAV expression cassettes to improve packaging capacity and transgene expression in neurons. Mol Brain. Mar. 11, 2014;7:17. doi: 10.1186/1756-6606-7-17.

Christensen et al., Melan-A/MART1 analog peptide triggers anti-myeloma T-cells through crossreactivity with HM1.24. J Immunother. Jul.-Aug. 2009;32(6):613-21. doi: 10.1097/CJI.0b013e3181a95198.

(56) References Cited

OTHER PUBLICATIONS

Correale et al., In vitro generation of human cytotoxic T lymphocytes specific for peptides derived from prostate-specific antigen. J Natl Cancer Inst. Feb. 19, 1997;89(4):293-300. doi: 10.1093/jnci/89.4.293.

Courtney et al., CRISPR/Cas9 DNA cleavage at SNP-derived PAM enables both in vitro and in vivo KRT12 mutation-specific targeting. Gene Ther. Jan. 2016;23(1):108-12. doi: 10.1038/gt.2015.82. Epub Aug. 20, 2015.

Cox et al., Identification of a peptide recognized by five melanoma-specific human cytotoxic T cell lines. Science. Apr. 29, 1994;264(5159):716-9. doi: 10.1126/science.7513441.

Cronin et al., Altering the tropism of lentiviral vectors through pseudotyping. Curr Gene Ther. Aug. 2005;5(4):387-98. doi: 10.2174/1566523054546224. Erratum in: Curr Gene Ther. Oct. 2005;5(5):531. Author Manuscript, 19 pages.

Crosti et al., Identification of novel subdominant epitopes on the carcinoembryonic antigen recognized by CD4+ T cells of lung cancer patients. J Immunol. Apr. 15, 2006;176(8):5093-9. doi: 10.4049/jimmunol.176.8.5093.

Dalet et al., An antigenic peptide produced by reverse splicing and double asparagine deamidation. Proc Natl Acad Sci U S A. Jul. 19, 2011;108(29):E323-31. doi: 10.1073/pnas.1101892108. Epub Jun. 13, 2011.

Damdindorj et al., A comparative analysis of constitutive promoters located in adeno-associated viral vectors. PLoS One. Aug. 29, 2014;9(8):e106472. doi: 10.1371/journal.pone.0106472.

Depontieu et al., Identification of tumor-associated, MHC class II-restricted phosphopeptides as targets for immunotherapy. Proc Natl Acad Sci U S A. Jul. 21, 2009;106(29):12073-8. doi: 10.1073/pnas.0903852106. Epub Jul. 6, 2009.

Di Stasi et al., Review of the Results of WT1 Peptide Vaccination Strategies for Myelodysplastic Syndromes and Acute Myeloid Leukemia from Nine Different Studies. Front Immunol. Feb. 4, 2015;6:36. doi: 10.3389/fimmu.2015.00036.

Dickinson et al., A system for the continuous directed evolution of proteases rapidly reveals drug-resistance mutations. Nat Commun. Oct. 30, 2014;5:5352. doi: 10.1038/ncomms6352.

Ding et al., Gene therapy for cardiovascular disease. Journal of Shanghai University (Natural Science Edition) . 2016;3:270-9 . DOI: 10.3969/j.issn.1007-2861.2016.03.013.

Duan et al., Immune rejection of mouse tumors expressing mutated self. Cancer Res. Apr. 15, 2009;69(8):3545-53. doi: 10.1158/0008-5472.CAN-08-2779. Epub Apr. 7, 2009. Author Manuscript. 18 pages.

Duportet et al., A platform for rapid prototyping of synthetic gene networks in mammalian cells. Nucleic Acids Res. Dec. 1, 2014;42(21):13440-51. doi: 10.1093/nar/gku1082. Epub Nov. 5, 2014.

Ekstrand et al., Frequent alterations of the PI3K/AKT/mTOR pathways in hereditary nonpolyposis colorectal cancer. Fam Cancer. Jun. 2010;9(2):125-9. doi: 10.1007/s10689-009-9293-1.

Entin-Meer et al., The role of phenylalanine-119 of the reverse transcriptase of mouse mammary tumour virus in DNA synthesis, ribose selection and drug resistance. Biochem J. Oct. 15, 2002;367(Pt 2):381-91. doi: 10.1042/BJ20020712.

Fang et al., Human strand-specific mismatch repair occurs by a bidirectional mechanism similar to that of the bacterial reaction. J Biol Chem. Jun. 5, 1993;268(16):11838-44.

Fang et al., The Menu of Features that Define Primary MicroRNAs and Enable De Novo Design of MicroRNA Genes. Mol Cell. Oct. 1, 2015;60(1):131-45. doi: 10.1016/j.molcel.2015.08.015. Epub Sep. 24, 2015.

Feng et al., Efficient genome editing in plants using a CRISPR/Cas system. Cell Res. Oct. 2013;23(10):1229-32. doi: 10.1038/cr.2013.114. Epub Aug. 20, 2013.

Fikes et al., Design of multi-epitope, analogue-based cancer vaccines. Expert Opin Biol Ther. Sep. 2003;3(6):985-93. doi: 10.1517/14712598.3.6.985.

Fishel et al., The human mutator gene homolog MSH2 and its association with hereditary nonpolyposis colon cancer. Cell. Dec. 3, 1993;75(5):1027-38. doi: 10.1016/0092-8674(93)90546-3. Erratum in: Cell. Apr. 8, 1994;77(1):1 p following 166.

Fontana et al., Rabies virus-like particles expressed in HEK293 cells. Vaccine. May 19, 2014;32(24):2799-804. doi: 10.1016/j.vaccine.2014.02.031. Epub Mar. 12, 2014.

Fonteneau et al., The Tumor Antigen NY-ESO-1 Mediates Direct Recognition of Melanoma Cells by CD4+ T Cells after Intercellular Antigen Transfer. J Immunol. Jan. 1, 2016;196(1):64-71. doi: 10.4049/jimmunol.1402664. Epub Nov. 25, 2015.

Fourcade et al., PD-1 and Tim-3 regulate the expansion of tumor antigen-specific CD8? T cells induced by melanoma vaccines. Cancer Res. Feb. 15, 2014;74(4):1045-55. doi: 10.1158/0008-5472.CAN-13-2908. Epub Dec. 16, 2013.

Fridman et al., An efficient T-cell epitope discovery strategy using in silico prediction and the iTopia assay platform. Oncoimmunology. Nov. 1, 2012;1(8):1258-1270. doi: 10.4161/onci.21355.

Fu et al., Targeted genome editing in human cells using CRISPR/Cas nucleases and truncated guide RNAs. Methods Enzymol. 2014;546:21-45. doi: 10.1016/B978-0-12-801185-0.00002-7.

Fujiki et al., Identification and characterization of a WT1 (Wilms Tumor Gene) protein-derived HLA-DRB1*0405-restricted 16-mer helper peptide that promotes the induction and activation of WT1-specific cytotoxic T lymphocytes. J Immunother. Apr. 2007;30(3):282-93. doi: 10.1097/01.cji.0000211337.91513.94.

Geisberg et al., Global analysis of mRNA isoform half-lives reveals stabilizing and destabilizing elements in yeast. Cell. Feb. 13, 2014;156(4):812-24. doi: 10.1016/j.cell.2013.12.026.

GenBank Access No. BAP64357. Aug. 1, 2013. 1 page.

GenBank Submission; NIH/NCBI, Accession No. NC_000001.11. Gregory et al., Jun. 6, 2016. 3 pages.

GenBank Submission; NIH/NCBI, Accession No. NP_060228.2. Bi et al., Dec. 21, 2005. 1 page.

GenBank Submission; NIH/NCBI, Accession No. NP_062826.2. Bokar et al., Sep. 18, 2004. 2 pages.

GenBank Submission; NIH/NCBI, Accession No. NP_066012.1. Ota et al., Apr. 3, 2005. 2 pages.

GenBank Submission; NIH/NCBI, Accession No. WP_042518169. 1. No Author, Feb. 10, 2015. 1 page.

Geng et al., In vitro studies of DNA mismatch repair proteins. Anal Biochem. Jun. 15, 2011;413(2):179-84. doi: 10.1016/j.ab.2011.02.017. Epub Feb. 15, 2011.

Genschel et al., Human exonuclease I is required for 5' and 3' mismatch repair. J Biol Chem. Apr. 12, 2002;277(15):13302-11. doi: 10.1074/jbc.M111854200. Epub Jan. 24, 2002.

Genschel et al., Isolation of MutSbeta from human cells and comparison of the mismatch repair specificities of MutSbeta and MutSalpha. J Biol Chem. Jul. 3, 19981;273(31):19895-901. doi: 10.1074/jbc.273.31.19895. Erratum in: J Biol Chem Oct. 9, 1998;273(41):27034.

Geynisman et al., A randomized pilot phase I study of modified carcinoembryonic antigen (CEA) peptide (CAP1-6D)/montanide/GM-CSF-vaccine in patients with pancreatic adenocarcinoma. J Immunother Cancer. Jun. 27, 2013;1:8. doi: 10.1186/2051-1426-1-8.

Ghosh et al., Synapsis in phage Bxb1 integration: selection mechanism for the correct pair of recombination sites. J Mol Biol. Jun. 3, 2005;349(2):331-48. doi: 10.1016/j.jmb.2005.03.043. Epub Apr. 7, 2005.

Girard-Gagnepain et al., Baboon envelope pseudotyped LVs outperform VSV-G-LVs for gene transfer into early-cytokine-stimulated and resting HSCs. Blood. Aug. 21, 2014;124(8):1221-31. doi: 10.1182/blood-2014-02-558163. Epub Jun. 20, 2014.

Godefroy et al., Identification of two Melan-A CD4+ T cell epitopes presented by frequently expressed MHC class II alleles. Clin Immunol. Oct. 2006;121(1):54-62. doi: 10.1016/j.clim.2006.05.007. Epub Jun. 30, 2006.

Graff-Dubois et al., Generation of CTL recognizing an HLA-A*0201-restricted epitope shared by MAGE-A1, -A2, -A3, -A4, -A6, -A10, and -A12 tumor antigens: implication in a broad-spectrum tumor immunotherapy. J Immunol. Jul. 1, 2002;169(1):575-80. doi: 10.4049/jimmunol.169.1.575.

(56)     References Cited

OTHER PUBLICATIONS

Grati et al., Localization of PDZD7 to the stereocilia ankle-link associates this scaffolding protein with the Usher syndrome protein network. J Neurosci. Oct. 10, 2012;32(41):14288-93. doi: 10.1523/JNEUROSCI.3071-12.2012.

Green et al., Characterization of the mechanical unfolding of RNA pseudoknots. J Mol Biol. Jan. 11, 2008;375(2):511-28. doi: 10.1016/j.jmb.2007.05.058. Epub May 26, 2007.

Gross et al., High vaccination efficiency of low-affinity epitopes in antitumor immunotherapy. J Clin Invest. Feb. 2004;113(3):425-33. doi: 10.1172/JCI19418.

Gueneau et al., Structure of the MutLα C-terminal domain reveals how Mlh1 contributes to Pms1 endonuclease site. Nat Struct Mol Biol. Apr. 2013;20(4):461-8. doi: 10.1038/nsmb.2511. Epub Feb. 24, 2013.

Guerrette et al., The interaction of the human MutL homologues in hereditary nonpolyposis colon cancer. J Biol Chem. Mar. 5, 1999;274(10):6336-41. doi: 10.1074/jbc.274.10.6336.

Guevara-Patiño et al., Optimization of a self antigen for presentation of multiple epitopes in cancer immunity. J Clin Invest. May 2006;116(5):1382-90. doi: 10.1172/JCI25591. Epub Apr. 13, 2006.

Guibinga et al., Cell surface heparan sulfate is a receptor for attachment of envelope protein-free retrovirus-like particles and VSV-G pseudotyped MLV-derived retrovirus vectors to target cells. Mol Ther. May 2002;5(5 Pt 1):538-46. doi: 10.1006/mthe.2002.0578.

Gulley et al., Combining a Recombinant Cancer Vaccine with Standard Definitive Radiotherapy in Patients with Localized Prostate Cancer. Clin Cancer Res. May 2, 2005;11(9):3353-62. doi: 10.1158/1078-0432.CCR-04-2062.

Guo et al., Direct recognition and lysis of leukemia cells by WT1-specific CD4+ T lymphocytes in an HLA class II-restricted manner. Blood. Aug. 15, 2005;106(4):1415-8. doi: 10.1182/blood-2005-01-0413. Epub Apr. 21, 2005.

Gupta et al., Mechanism of mismatch recognition revealed by human MutSβ bound to unpaired DNA loops. Nat Struct Mol Biol. Dec. 18, 2011;19(1):72-8. doi: 10.1038/nsmb.2175.

Haeussler et al., Genome Editing with CRISPR-Cas9: Can It Get Any Better? J Genet Genomics. May 20, 2016;43(5):239-50. doi: 10.1016/j.jgg.2016.04.008. Epub Apr. 24, 2016. Author Manuscript. 22 pages.

Hawley-Nelson et al., Transfection of Cultured Eukaryotic Cells Using Cationic Lipid Reagents. Curr Prot Mol Biol. Jan. 2008;9.4. 1-9.4.17. doi: 10.102/0471142727.mb0904s81. 17 pages.

Herbst-Kralovetz et al., Norwalk virus-like particles as vaccines. Expert Rev Vaccines. Mar. 2010;9(3):299-307. doi: 10.1586/erv.09.163. Author Manuscript, 16 pages.

Heyer et al., Regulation of homologous recombination in eukaryotes. Annu Rev Genet. 2010;44:113-39. doi: 10.1146/annurev-genet-051710-150955. Author Manuscript. 33 pages.

Hirohashi et al., An HLA-A24-restricted cytotoxic T lymphocyte epitope of a tumor-associated protein, survivin. Clin Cancer Res. Jun. 2002;8(6):1731-9.

Hizi et al., Retroviral reverse transcriptases (other than those of HIV-1 and murine leukemia virus): a comparison of their molecular and biochemical properties. Virus Res. Jun. 2008;134(1-2):203-20. doi: 10.1016/j.virusres.2007.12.008. Epub Mar. 3, 2008.

Hong et al., Novel recombinant hepatitis B virus vectors efficiently deliver protein and RNA encoding genes into primary hepatocytes. J Virol. Jun. 2013;87(12):6615-24. doi: 10.1128/JVI.03328-12. Epub Apr. 3, 2013.

Houck-Loomis et al., An equilibrium-dependent retroviral mRNA switch regulates translational recoding. Nature. Nov. 27, 2011;480(7378):561-4. doi: 10.1038/nature 10657.

Houghton et al., Immunological validation of the EpitOptimizer program for streamlined design of heteroclitic epitopes. Vaccine. Jul. 20, 2007;25(29):5330-42. doi: 10.1016/j.vaccine.2007.05.008. Epub Jun. 4, 2007.

Houseley et al., The many pathways of RNA degradation. Cell. Feb. 20, 2009;136(4):763-76. doi: 10.1016/j.cell.2009.01.019.

Hwang et al., Heritable and precise zebrafish genome editing using a CRISPR-Cas system. PLoS One. Jul. 9, 2013;8(7):e68708. doi: 10.1371/journal.pone.0068708.

Iaccarino et al., hMSH2 and hMSH6 play distinct roles in mismatch binding and contribute differently to the ATPase activity of hMutSalpha. EMBO J. May 1, 1998;17(9):2677-86. doi: 10.1093/emboj/17.9.2677.

Ibrahim et al., RNA recognition by 3'-to-5' exonucleases: the substrate perspective. Biochim Biophys Acta. Apr. 2008;1779(4):256-65. doi: 10.1016/j.bbagrm.2007.11.004. Epub Dec. 3, 2007.

Iyer et al., DNA mismatch repair: functions and mechanisms. Chem Rev. Feb. 2006;106(2):302-23. doi: 10.1021/cr0404794.

Jalaguier et al., Efficient production of HIV-1 virus-like particles from a mammalian expression vector requires the N-terminal capsid domain. PLoS One. 2011;6(11):e28314. doi: 10.1371/journal.pone. 0028314. Epub Nov. 30, 2011.

Jaramillo et al., Identification of HLA-A3-restricted CD8+ T cell epitopes derived from mammaglobin-A, a tumor-associated antigen of human breast cancer. Int J Cancer. Dec. 10, 2002;102(5):499-506. doi: 10.1002/ijc.10736.

Kaczmarczyk et al., Protein delivery using engineered virus-like particles. Proc Natl Acad Sci U S A. Oct. 11, 2011;108(41):16998-7003. doi: 10.1073/pnas.1101874108. Epub Sep. 26, 2011.

Kadyrov et al., Endonucleolytic function of MutLalpha in human mismatch repair. Cell. Jul. 28, 2006;126(2):297-308. doi: 10.1016/j.cell.2006.05.039.

Kang et al., Chimeric rabies virus-like particles containing membrane-anchored GM-CSF enhances the immune response against rabies virus. Viruses. Mar. 11, 2015;7(3):1134-52. doi: 10.3390/v7031134.

Kang et al., Identification of a tyrosinase epitope recognized by HLA-A24-restricted, tumor-infiltrating lymphocytes. J Immunol. Aug. 1, 1995;155(3):1343-8.

Karbach et al., Long-term complete remission following radiosurgery and immunotherapy in a melanoma patient with brain metastasis: immunologic correlates. Cancer Immunol Res. May 2014;2(5):404-9. doi: 10.1158/2326-6066.CIR-13-0200. Epub Feb. 5, 2014.

Kato et al., A lentiviral strategy for highly efficient retrograde gene transfer by pseudotyping with fusion envelope glycoprotein. Hum Gene Ther. Feb. 2011;22(2):197-206. doi: 10.1089/hum.2009.179. Epub Jan. 27, 2011.

Kato et al., Selective neural pathway targeting reveals key roles of thalamostriatal projection in the control of visual discrimination. J Neurosci. Nov. 23, 2011;31(47):17169-79. doi: 10.1523/JNEUROSCI. 4005-11.2011.

Kawakami et al., Identification of a human melanoma antigen recognized by tumor-infiltrating lymphocytes associated with in vivo tumor rejection. Proc Natl Acad Sci U S A. Jul. 5, 1994;91(14):6458-62. doi: 10.1073/pnas.91.14.6458.

Kawakami et al., Identification of new melanoma epitopes on melanosomal proteins recognized by tumor infiltrating T lymphocytes restricted by HLA-A1, -A2, and -A3 alleles. J Immunol. Dec. 15, 1998;161(12):6985-92.

Kawakami et al., Identification of the immunodominant peptides of the MART-1 human melanoma antigen recognized by the majority of HLA-A2-restricted tumor infiltrating lymphocytes. J Exp Med. Jul. 1, 1994;180(1):347-52. doi: 10.1084/jem.180.1.347.

Kawakami et al., Recognition of multiple epitopes in the human melanoma antigen gp100 by tumor-infiltrating T lymphocytes associated with in vivo tumor regression. J Immunol. Apr. 15, 1995;154(8):3961-8.

Kawashima et al., Identification of gp100-derived, melanoma-specific cytotoxic T-lymphocyte epitopes restricted by HLA-A3 supertype molecules by primary in vitro immunization with peptide-pulsed dendritic cells. Int J Cancer. Nov. 9, 1998;78(4):518-24. doi: 10.1002/(sici)1097-0215(19981109)78:4<518::aid-ijc20>3.0.co;2-0.

Kawashima et al., Identification of HLA-A3-restricted cytotoxic T lymphocyte epitopes from carcinoembryonic antigen and HER-2/neu by primary in vitro immunization with peptide-pulsed dendritic cells. Cancer Res. Jan. 15, 1999;59(2):431-5.

Kawashima et al., The multi-epitope approach for immunotherapy for cancer: identification of several CTL epitopes from various

(56)     References Cited

OTHER PUBLICATIONS tumor-associated antigens expressed on solid epithelial tumors. Hum Immunol. Jan. 1998;59(1):1-14. doi: 10.1016/s0198-8859(97)00255-3.

Kemmler et al., Elevated tumor-associated antigen expression suppresses variant peptide vaccine responses. J Immunol. Nov. 1, 2011;187(9):4431-9. doi: 10.4049/jimmunol.1101555. Epub Sep. 21, 2011.

Kirshenboim et al., Expression and characterization of a novel reverse transcriptase of the LTR retrotransposon Tf1. Virology. Sep. 30, 2007;366(2):263-76. doi: 10.1016/j.virol.2007.04.002. Epub May 23, 2007.

Kittlesen et al., Human melanoma patients recognize an HLA-A1-restricted CTL epitope from tyrosinase containing two cysteine residues: implications for tumor vaccine development. J Immunol. Mar. 1, 1998;160(5):2099-106. Erratum in: J Immunol Mar. 1, 1999;162(5):3106. Shabanowitz JA [corrected to Shabanowitz J].

Kizer et al., Application of functional genomics to pathway optimization for increased isoprenoid production. Appl Environ Microbiol. May 2008;74(10):3229-41. doi: 10.1128/AEM.02750-07. Epub Mar. 14, 2008.

Kobayashi et al., CD4+ T cells from peripheral blood of a melanoma patient recognize peptides derived from nonmutated tyrosinase. Cancer Res. Jan. 15, 1998;58(2):296-301.

Kobayashi et al., Identification of an antigenic epitope for helper T lymphocytes from carcinoembryonic antigen. Clin Cancer Res. Oct. 2002;8(10):3219-25.

Kobayashi et al., Identification of helper T-cell epitopes that encompass or lie proximal to cytotoxic T-cell epitopes in the gp100 melanoma tumor antigen. Cancer Res. Oct. 15, 2001;61(20):7577-84.

Konishi et al., Amino acid substitutions away from the RNase H catalytic site increase the thermal stability of Moloney murine leukemia virus reverse transcriptase through RNase H inactivation. Biochem Biophys Res Commun. Nov. 14, 2014;454(2):269-74. doi: 10.1016/j.bbrc.2014.10.044. Epub Oct. 17, 2014.

Kotterman et al., Engineering adeno-associated viruses for clinical gene therapy. Nat Rev Genet. Jul. 2014;15(7):445-51. doi: 10.1038/nrg3742. Epub May 20, 2014.

Ku et al., Nucleic Acid Aptamers: An Emerging Tool for Biotechnology and Biomedical Sensing. Sensors (Basel). Jul. 6, 2015;15(7):16281-313. doi: 10.3390/s150716281.

Kueh et al., The new editor-targeted genome engineering in the absence of homology-directed repair. Cell Death Discov. Jun. 13, 2016;2:16042. doi: 10.1038/cddiscovery.2016.42.

Kunkel et al., DNA mismatch repair. Annu Rev Biochem. 2005;74:681-710. doi: 10.1146/annurev.biochem.74.082803.133243.

Kushnir et al., Virus-like particles as a highly efficient vaccine platform: diversity of targets and production systems and advances in clinical development. Vaccine. Dec. 17, 2012;31(1):58-83. doi: 10.1016/j.vaccine.2012.10.083. Epub Nov. 6, 2012.

Lahue et al., DNA mismatch correction in a defined system. Science. Jul. 14, 1989;245(4914):160-4. doi: 10.1126/science. 2665076.

Lally et al., Unmasking cryptic epitopes after loss of immunodominant tumor antigen expression through epitope spreading. Int J Cancer. Sep. 2001;93(6):841-7. doi: 10.1002/ijc.1420.

Langer et al., Chemical and Physical Structure of Polymers as Carriers for Controlled Release of Bioactive Agents: A Review. J Macromol Sci, Part C, 1983;23(1):61-126. doi: 10.1080/07366578308079439.

Lapointe et al., Retrovirally transduced human dendritic cells can generate T cells recognizing multiple MHC class I and class II epitopes from the melanoma antigen glycoprotein 100. J Immunol. Oct. 15, 2001;167(8):4758-64. doi: 10.4049/jimmunol.167.8.4758.

Larrieu et al., A HLA-Cw*0701 restricted Melan-A/MART1 epitope presented by melanoma tumor cells to CD8+ tumor infiltrating lymphocytes. Cancer Immunol Immunother. May 2008;57(5):745-52. doi: 10.1007/s00262-007-0436-7. Epub Dec. 21, 2007.

Latham et al., Formation of wild-type and chimeric influenza virus-like particles following simultaneous expression of only four structural proteins. J Virol. Jul. 2001;75(13):6154-65. doi: 10.1128/JVI.75.13.6154-6165.2001.

Leach et al., Mutations of a mutS homolog in hereditary nonpolyposis colorectal cancer. Cell. Dec. 17, 1993;75(6):1215-25. doi: 10.1016/0092-8674(93)90330-s.

Lennerz et al., The response of autologous T cells to a human melanoma is dominated by mutated neoantigens. Proc Natl Acad Sci U S A. Nov. 1, 2005;102(44):16013-8. doi: 10.1073/pnas. 0500090102. Epub Oct. 24, 2005.

Li et al., Expression and self-assembly of empty virus-like particles of hepatitis E virus. J Virol. Oct. 1997;71(10):7207-13. doi: 10.1128/JVI.71.10.7207-7213.1997.

Lin et al., HLA-DPB1*05: 01-restricted WT1332-specific TCR-transduced CD4+ T lymphocytes display a helper activity for WT1-specific CTL induction and a cytotoxicity against leukemia cells. J Immunother. Apr. 2013;36(3):159-70. doi: 10.1097/CJI. 0b013e3182873581.

Liu et al., Usherin is required for maintenance of retinal photoreceptors and normal development of cochlear hair cells. Proc Natl Acad Sci U S A. Mar. 13, 2007;104(11):4413-8. doi: 10.1073/pnas. 0610950104. Epub Mar. 5, 2007.

Lu, Periodic Chart of Amino Acid PDF. Accessed on the internet at https://figshare.com/articles/figure/periodic_chart_of_amino_acid_pdf/3445001/1. Posted Jun. 21, 2016. www.bachem.com. 1 page.

Ludwig et al., Virus-like particles-universal molecular toolboxes. Curr Opin Biotechnol. Dec. 2007;18(6):537-45. doi: 10.1016/j. copbio.2007.10.013.

Lujan et al., Heterogeneous polymerase fidelity and mismatch repair bias genome variation and composition. Genome Res. Nov. 2014;24(11):1751-64. doi: 10.1101/gr.178335.114. Epub Sep. 12, 2014.

Lupetti et al., Translation of a retained intron in tyrosinase-related protein (TRP) 2 mRNA generates a new cytotoxic T lymphocyte (CTL)-defined and shared human melanoma antigen not expressed in normal cells of the melanocytic lineage. J Exp Med. Sep. 21, 1998;188(6): 1005-16. doi: 10.1084/jem.188.6.1005.

Maerker et al., A novel Usher protein network at the periciliary reloading point between molecular transport machineries in vertebrate photoreceptor cells. Hum Mol Genet. Jan. 1, 2008;17(1):71-86. doi: 10.1093/hmg/ddm285. Epub Sep. 28, 2007.

Maetzig et al., Retroviral protein transfer: falling apart to make an impact. Curr Gene Ther. Oct. 2012;12(5):389-409. doi: 10.2174/156652312802762581.

Mahoney et al., The Next Immune-Checkpoint Inhibitors: PD-1/PD-L1 Blockade in Melanoma. Clin Ther. Apr. 1, 2015;37(4):764-82. doi: 10.1016/j.clinthera.2015.02.018. Epub Mar. 29, 2015.

Mali et al., CAS9 transcriptional activators for target specificity screening and paired nickases for cooperative genome engineering. Nat Biotechnol. Sep. 2013;31(9):833-8, Supplemental Info. doi: 10.1038/nbt.2675. Epub Aug. 1, 2013.

Mandic et al., The alternative open reading frame of LAGE-1 gives rise to multiple promiscuous HLA-DR-restricted epitopes recognized by T-helper 1-type tumor-reactive CD4+ T cells. Cancer Res. Oct. 1, 2003;63(19):6506-15.

Mangeot et al., A universal transgene silencing method based on RNA interference. Nucleic Acids Res. Jul. 12, 2004;32(12):e102. doi: 10.1093/nar/gnh105.

Mangeot et al., Development of minimal lentivirus vectors derived from simian immunodeficiency virus (SIVmac251) and their use for gene transfer into human dendritic cells. J Virol. Sep. 2000;74(18):8307-15. doi: 10.1128/jvi.74.18.8307-8315.2000.

Mangeot et al., Protein transfer into human cells by VSV-G-induced nanovesicles. Mol Ther. Sep. 2011;19(9):1656-66. doi: 10.1038/mt. 2011.138. Epub Jul. 12, 2011.

Marcovitz et al., Frustration in protein-DNA binding influences conformational switching and target search kinetics. Proc Natl Acad Sci U S A. Nov. 1, 2011;108(44):17957-62. doi: 10.1073/pnas. 1109594108. Epub Oct. 14, 2011.

Mariani et al., Species-specific exclusion of APOBEC3G from HIV-1 virions by Vif. Cell. Jul. 11, 2003;114(1):21-31. doi: 10.1016/s0092-8674(03)00515-4.

(56)　　　　　References Cited

OTHER PUBLICATIONS

Meng et al., Identification of an HLA-DPB1*0501 restricted Melan-A/MART-1 epitope recognized by CD4+ T lymphocytes: prevalence for immunotherapy in Asian populations. J Immunother. Sep. 2011;34(7):525-34. doi: 10.1097/CJI.0b013e318226bd45. Author Manuscript. 16 pages.

Michaux et al., A spliced antigenic peptide comprising a single spliced amino acid is produced in the proteasome by reverse splicing of a longer peptide fragment followed by trimming. J Immunol. Feb. 15, 2014;192(4):1962-71. doi: 10.4049/jimmunol.1302032. Epub Jan. 22, 2014.

Micozzi et al., Human cytidine deaminase: a biochemical characterization of its naturally occurring variants. Int J Biol Macromol. Feb. 2014;63:64-74. doi: 10.1016/j.ijbiomac.2013.10.029. Epub Oct. 29, 2013. Erratum in: Int J Biol Macromol. Feb. 2014;63:262.

Millevoi et al., G-quadruplexes in RNA biology. Wiley Interdiscip Rev RNA. Jul.- Aug. 2012;3(4):495-507. doi: 10.1002/wrna. 1113. Epub Apr. 4, 2012.

Misra et al., An enzymatically active chimeric HIV-1 reverse transcriptase (RT) with the RNase-H domain of murine leukemia virus RT exists as a monomer. J Biol Chem. Apr. 17, 1998;273(16):9785-9. doi: 10.1074/jbc.273.16.9785.

Morel et al., A tyrosinase peptide presented by HLA-B35 is recognized on a human melanoma by autologous cytotoxic T lymphocytes. Int J Cancer. Dec. 10, 1999;83(6):755-9. doi: 10.1002/(sici)1097-0215(19991210)83:6<755::aid-ijc10>3.0.co;2-s.

Mselli-Lakhal et al., Gene transfer system derived from the caprine arthritis-encephalitis lentivirus. J Virol Methods. Sep. 2006;136(1-2):177-84. doi: 10.1016/j.jviromet.2006.05.006. Epub Jun. 21, 2006.

Murawski et al., Newcastle disease virus-like particles containing respiratory syncytial virus G protein induced protection in BALB/c mice, with no evidence of immunopathology. J Virol. Jan. 2010;84(2):1110-23. doi: 10.1128/JVI.01709-09. Epub Nov. 4, 2009.

Naskalska et al., Virus Like Particles as Immunogens and Universal Nanocarriers. Pol J Microbiol. 2015;64(1):3-13.

Negre et al., Characterization of novel safe lentiviral vectors derived from simian immunodeficiency virus (SIVmac251) that efficiently transduce mature human dendritic cells. Gene Ther. Oct. 2000;7(19):1613-23. doi: 10.1038/sj.gt.3301292.

Niemeyer, C.M., Semisynthetic DNA-protein conjugates for biosensing and nanofabrication. Angew Chem Int Ed Engl. Feb. 8, 2010;49(7):1200-16. doi: 10.1002/anie.200904930.

Noppen et al., Naturally processed and concealed HLA-A2.1-restricted epitopes from tumor-associated antigen tyrosinase-related protein-2. Int J Cancer. Jul. 15, 2000;87(2):241-6.

Nowak et al., Ty3 reverse transcriptase complexed with an RNA-DNA hybrid shows structural and functional asymmetry. Nat Struct Mol Biol. Apr. 2014;21(4):389-96. doi: 10.1038/nsmb.2785. Epub Mar. 9, 2014. Author Manuscript, 22 pages.

Nukaya et al., Identification of HLA-A24 epitope peptides of carcinoembryonic antigen which induce tumor-reactive cytotoxic T lymphocyte. Int J Cancer. Jan. 5, 1999;80(1):92-7. doi: 10.1002/(sici)1097-0215(19990105)80:1<92::aid-ijc18>3.0.co;2-m.

Ogasawara et al., Recombinant viral-like particles of parvovirus B19 as antigen carriers of anthrax protective antigen. In Vivo. May-Jun. 2006;20(3):319-24.

Ohminami et al., HLA class I-restricted lysis of leukemia cells by a CD8(+) cytotoxic T-lymphocyte clone specific for WT1 peptide. Blood. Jan. 1, 2000;95(1):286-93.

Oka et al., WT1 peptide vaccine for the treatment of cancer. Curr Opin Immunol. Apr. 2008;20(2):211-20. doi: 10.1016/j.coi.2008.04.009. Epub May 24, 2008.

Olsen, J.C., Gene transfer vectors derived from equine infectious anemia virus. Gene Ther. Nov. 1998;5(11):1481-7. doi: 10.1038/sj.gt.3300768.

Olson et al., HLA-A2-restricted T-cell epitopes specific for prostatic acid phosphatase. Cancer Immunol Immunother. Jun. 2010;59(6):943-53. doi: 10.1007/s00262-010-0820-6. Epub Feb. 6, 2010.

Osen et al., Screening of human tumor antigens for CD4 T cell epitopes by combination of HLA-transgenic mice, recombinant adenovirus and antigen peptide libraries. PLoS One. Nov. 30, 2010;5(11):e14137. doi: 10.1371/journal.pone.0014137.

Ousterout et al., Multiplex CRISPR/Cas9-based genome editing for correction of dystrophin mutations that cause Duchenne muscular dystrophy. Nat Commun. Feb. 18, 2015;6:6244. doi: 10.1038/ncomms7244.

Pandey et al., Effect of loops and G-quartets on the stability of RNA G-quadruplexes. J Phys Chem B. Jun. 13, 2013;117(23):6896-905. doi: 10.1021/jp401739m. Epub May 29, 2013. Supplementary Information, 21 pages.

Parkhurst et al., Identification of a shared HLA-A*0201-restricted T-cell epitope from the melanoma antigen tyrosinase-related protein 2 (TRP2). Cancer Res. Nov. 1, 1998;58(21):4895-901.

Parkhurst et al., Induction of CD4+ Th1 lymphocytes that recognize known and novel class II MHC restricted epitopes from the melanoma antigen gp100 by stimulation with recombinant protein. J Immunother. Mar.-Apr. 2004;27(2):79-91. doi: 10.1097/00002371-200403000-00001. Author Manuscript. 22 pages.

Parsons et al., Hypermutability and mismatch repair deficiency in RER+ tumor cells. Cell. Dec. 17, 1993;75(6):1227-36. doi: 10.1016/0092-8674(93)90331-j.

Paschen et al., Detection of spontaneous CD4+ T-cell responses in melanoma patients against a tyrosinase-related protein-2-derived epitope identified in HLA-DRB1*0301 transgenic mice. Clin Cancer Res. Jul. 15, 2005;11(14):5241-7. doi: 10.1158/1078-0432.CCR-05-0170.

Petit et al., Powerful mutators lurking in the genome. Philos Trans R Soc Lond B Biol Sci. Mar. 12, 2009;364(1517):705-15. doi: 10.1098/rstb.2008.0272.

Pinilla et al., Combinatorial peptide libraries as an alternative approach to the identification of ligands for tumor-reactive cytolytic T lymphocytes. Cancer Res. Jul. 1, 2001;61(13):5153-60.

Pinilla-Ibarz et al., Improved human T-cell responses against synthetic HLA-0201 analog peptides derived from the WT1 oncoprotein. Leukemia. Nov. 2006;20(11):2025-33. doi: 10.1038/sj.leu.2404380. Epub Aug. 31, 2006.

Piotukh et al., Directed evolution of sortase A mutants with altered substrate selectivity profiles. J Am Chem Soc. Nov. 9, 2011;133(44):17536-9. doi: 10.1021/ja205630g. Epub Oct. 13, 2011.

Plotz et al., N-terminus of hMLH1 confers interaction of hMutLalpha and hMutLbeta with hMutSalpha. Nucleic Acids Res. Jun. 15, 2003;31(12):3217-26. doi: 10.1093/nar/gkg420.

Prather et al., De novo biosynthetic pathways: rational design of microbial chemical factories. Curr Opin Biotechnol. Oct. 2008;19(5):468-74. doi: 10.1016/j.copbio.2008.07.009. Epub Sep. 5, 2008.

Quan et al., Influenza M1 VLPs containing neuraminidase induce heterosubtypic cross-protection. Virology. Sep. 1, 2012;430(2):127-35. doi: 10.1016/j.virol.2012.05.006. Epub Jun. 2, 2012.

Rasmussen et al., Characterization of virus-like particles produced by a recombinant baculovirus containing the gag gene of the bovine immunodeficiency-like virus. Virology. Oct. 1990;178(2):435-51. doi: 10.1016/0042-6822(90)90341-n.

Reiners et al., Scaffold protein harmonin (USH1C) provides molecular links between Usher syndrome type 1 and type 2. Hum Mol Genet. Dec. 15, 2005;14(24):3933-43. doi: 10.1093/hmg/ddi417. Epub Nov. 21, 2005.

Riddle et al., Frameshift suppression: a nucleotide addition in the anticodon of a glycine transfer RNA. Nat New Biol. Apr. 25, 1973;242(121):230-4. doi: 10.1038/newbio242230a0.

Riddle et al., Frameshift suppressors. II. Genetic mapping and dominance studies. J Mol Biol. May 28, 1972;66(3):483-93. doi: 10.1016/0022-2836(72)90428-7.

Riddle et al., Suppressors of frameshift mutations in Salmonella typhimurium. J Mol Biol. Nov. 28, 1970;54(1):131-44. doi: 10.1016/0022-2836(70)90451-1.

Riley et al., Identification of a new shared HLA-A2.1 restricted epitope from the melanoma antigen tyrosinase. J Immunother. May-Jun. 2001;24(3):212-20.

Rimoldi et al., Efficient simultaneous presentation of NY-ESO-1/LAGE-1 primary and nonprimary open reading frame-derived CTL epitopes in melanoma. J Immunol. Dec. 15, 2000;165(12):7253-61. doi: 10.4049/jimmunol.165.12.7253.

(56)        References Cited

OTHER PUBLICATIONS

Robbins et al., Multiple HLA class II-restricted melanocyte differentiation antigens are recognized by tumor-infiltrating lymphocytes from a patient with melanoma. J Immunol. Nov. 15, 2002;169(10):6036-47. doi: 10.4049/jimmunol.169.10.6036.

Robbins et al., The intronic region of an incompletely spliced gp100 gene transcript encodes an epitope recognized by melanoma-reactive tumor-infiltrating lymphocytes. J Immunol. Jul. 1, 1997;159(1):303-8.

Rosenberg et al., Immunologic and therapeutic evaluation of a synthetic peptide vaccine for the treatment of patients with metastatic melanoma. Nat Med. Mar. 1998;4(3):321-7. doi: 10.1038/nm0398-321.

Rubio-Godoy et al., Toward synthetic combinatorial peptide libraries in positional scanning format (PS-SCL)-based identification of CD8+ Tumor-reactive T-Cell Ligands: a comparative analysis of PS-SCL recognition by a single tumor-reactive CD8+ cytolytic T-lymphocyte clone. Cancer Res. Apr. 1, 2002;62(7):2058-63.

Ruiz et al., Identification and characterization of a T-helper peptide from carcinoembryonic antigen. Clin Cancer Res. Apr. 15, 2004;10(8):2860-7. doi: 10.1158/1078-0432.ccr-03-0476.

Rusk, Cas9 and the importance of asymmetry. Nat Methods. Apr. 2016;13(4):286-7. doi: 10.1038/nmeth.3826.

Räschle et al., Mutations within the hMLH1 and hPMS2 subunits of the human MutLalpha mismatch repair factor affect its ATPase activity, but not its ability to interact with hMutSalpha. J Biol Chem. Jun. 14, 2002;277(24):21810-20. doi: 10.1074/jbc.M108787200. Epub Apr. 10, 2002.

Saayman et al., The therapeutic application of CRISPR/Cas9 technologies for HIV. Expert Opin Biol Ther. Jun. 2015;15(6):819-30. doi: 10.1517/14712598.2015.1036736. Epub Apr. 12, 2015.

Sadowski et al., The sequence-structure relationship and protein function prediction. Curr Opin Struct Biol. Jun. 2009;19(3):357-62. doi: 10.1016/j.sbi.2009.03.008. Epub May 4, 2009.

Saenger et al., Improved tumor immunity using anti-tyrosinase related protein-1 monoclonal antibody combined with DNA vaccines in murine melanoma. Cancer Res. Dec. 1, 2008;68(23):9884-91. doi: 10.1158/0008-5472.CAN-08-2233. Author Manuscript. 19 pages.

Saenz et al., Feline immunodeficiency virus-based lentiviral vectors. Cold Spring Harb Protoc. Jan. 1, 2012;2012(1):71-6. doi: 10.1101/pdb.ip067579.

Saenz et al., Production, harvest, and concentration of feline immunodeficiency virus-based lentiviral vector from cells grown in CF10 or CF2 devices. Cold Spring Harb Protoc. Jan. 1, 2012;2012(1):118-23. doi: 10.1101/pdb.prot067546.

Sakuma et al., Multiplex genome engineering in human cells using all-in-one CRISPR/Cas9 vector system. Sci Rep. Jun. 23, 2014;4:5400. doi: 10.1038/srep05400.

Schneider et al., Overlapping peptides of melanocyte differentiation antigen Melan-A/MART-1 recognized by autologous cytolytic T lymphocytes in association with HLA-B45.1 and HLA-A2.1. Int J Cancer. Jan. 30, 1998;75(3):451-8. doi: 10.1002/(sici)1097-0215(Jan. 30, 1998)75:3<451::aid-ijc20>3.0.co;2-a.

Score Results for US 2014-0186919 A1 to Zhang et al. Aug. 28, 2014. 3 pages.

Seffernick et al., Melamine deaminase and atrazine chlorohydrolase: 98 percent identical but functionally different. J Bacteriol. Apr. 2001;183(8):2405-10. doi: 10.1128/JB.183.8.2405-2410.2001.

Sensi et al., Identification of a novel gp100/pMel17 peptide presented by HLA-A*6801 and recognized on human melanoma by cytolytic T cell clones. Tissue Antigens. Apr. 2002;59(4):273-9. doi: 10.1034/j.1399-0039.2002.590404.x.

Shang et al., The spontaneous CD8+ T-cell response to HLA-A2-restricted NY-ESO-1b peptide in hepatocellular carcinoma patients. Clin Cancer Res. Oct. 15, 2004;10(20):6946-55. doi: 10.1158/1078-0432.CCR-04-0502.

Sharma et al., Noninfectious virus-like particles produced by Moloney murine leukemia virus-based retrovirus packaging cells deficient in viral envelope become infectious in the presence of lipofection reagents. Proc Natl Acad Sci U S A. Sep. 30, 1997;94(20):10803-8. doi: 10.1073/pnas.94.20.10803.

Shcherbakova et al., Mutator phenotypes conferred by MLH1 overexpression and by heterozygosity for mlh1 mutations. Mol Cell Biol. Apr. 1999;19(4):3177-83. doi: 10.1128/MCB.19.4.3177.

Shellenberger et al., A recombinant polypeptide extends the in vivo half-life of peptides and proteins in a tunable manner. Nat Biotechnol. Dec. 2009;27(12):1186-90. doi: 10.1038/nbt.1588.

Shen et al., Identification of a MHC class-II restricted epitope in carcinoembryonic antigen. Cancer Immunol Immunother. May 2004;53(5):391-403. doi: 10.1007/s00262-003-0455-y. Epub Nov. 18, 2003.

Skipper et al., An HLA-A2-restricted tyrosinase antigen on melanoma cells results from posttranslational modification and suggests a novel pathway for processing of membrane proteins. J Exp Med. Feb. 1, 1996;183(2):527-34. doi: 10.1084/jem.183.2.527.

Skipper et al., Shared epitopes for HLA-A3-restricted melanoma-reactive human CTL include a naturally processed epitope from Pmel-17/gp100. J Immunol. Dec. 1, 1996;157(11):5027-33.

Slansky et al., Enhanced antigen-specific antitumor immunity with altered peptide ligands that stabilize the MHC-peptide-TCR complex. Immunity. Oct. 2000;13(4):529-38. doi: 10.1016/s1074-7613(00)00052-2.

Slingluff et al., Clinical and immunologic results of a randomized phase II trial of vaccination using four melanoma peptides either administered in granulocyte-macrophage colony-stimulating factor in adjuvant or pulsed on dendritic cells. J Clin Oncol. Nov. 1, 2003;21(21):4016-26. doi: 10.1200/JCO.2003.10.005.

Slingluff et al., Immunologic and clinical outcomes of vaccination with a multiepitope melanoma peptide vaccine plus low-dose interleukin-2 administered either concurrently or on a delayed schedule. J Clin Oncol. Nov. 15, 2004;22(22):4474-85. doi: 10.1200/JCO.2004.10.212.

Strand et al., Destabilization of tracts of simple repetitive DNA in yeast by mutations affecting DNA mismatch repair. Nature. Sep. 16, 1993;365(6443):274-6. doi: 10.1038/365274a0. Erratum in: Nature Apr. 7, 1994;368(6471);569.

Studebaker et al., Depletion of uracil-DNA glycosylase activity is associated with decreased cell proliferation. Biochem Biophys Res Commun. Aug. 26, 2005;334(2):509-15. doi: 10.1016/j.bbrc.2005.06.118.

Su et al., Mispair specificity of methyl-directed DNA mismatch correction in vitro. J Biol Chem. May 15, 1988;263(14):6829-35. Erratum in: J Biol Chem Aug. 5, 1988;263(22):11015.

Sugawara et al., Heteroduplex rejection during single-strand annealing requires Sgs1 helicase and mismatch repair proteins Msh2 and Msh6 but not Pms1. Proc Natl Acad Sci U S A. Jun. 22, 2004;101(25):9315-20. doi: 10.1073/pnas.0305749101. Epub Jun. 15, 2004.

Supek et al., Differential DNA mismatch repair underlies mutation rate variation across the human genome. Nature. May 7, 2015;521(7550):81-4. doi: 10.1038/nature14173. Epub Feb. 23, 2015.

Svitashev et al., Targeted Mutagenesis, Precise Gene Editing, and Site-Specific Gene Insertion in Maize Using Cas9 and Guide RNA. Plant Physiol. Oct. 2015;169(2):931-45. doi: 10.1104/pp.15.00793. Epub Aug. 12, 2015.

Tang et al., Identification of Dehalobacter reductive dehalogenases that catalyse dechlorination of chloroform, 1,1,1-trichloroethane and 1,1-dichloroethane. Philos Trans R Soc Lond B Biol Sci. Mar. 11, 2013;368(1616):20120318. doi: 10.1098/rstb.2012.0318.

Tangri et al., Structural features of peptide analogs of human histocompatibility leukocyte antigen class I epitopes that are more potent and immunogenic than wild-type peptide. J Exp Med. Sep. 17, 2001;194(6):833-46. doi: 10.1084/jem.194.6.833.

Thomas et al., Heteroduplex repair in extracts of human HeLa cells. J Biol Chem. Feb. 25, 1991;266(6):3744-51.

Tomer et al., Contribution of human mlh1 and pms2 ATPase activities to DNA mismatch repair. J Biol Chem. Jun. 14, 2002;277(24):21801-9. doi: 10.1074/jbc.M111342200. Epub Mar. 15, 2002.

(56) References Cited

OTHER PUBLICATIONS

Tomé-Amat et al., Secreted production of assembled Norovirus virus-like particles from Pichia pastoris. Microb Cell Fact. Sep. 10, 2014;13:134. doi: 10.1186/s12934-014-0134-z.

Topalian et al., Melanoma-specific CD4+ T cells recognize nonmutated HLA-DR-restricted tyrosinase epitopes. J Exp Med. May 1, 1996;183(5):1965-71. doi: 10.1084/jem.183.5.1965.

Toro et al., Comprehensive phylogenetic analysis of bacterial reverse transcriptases. PLoS One. Nov. 25, 2014;9(11):e114083. doi: 10.1371/journal.pone.0114083.

Touloukian et al., Expression of a "self-"antigen by human tumor cells enhances tumor antigen-specific CD4(+) T-cell function. Cancer Res. Sep. 15, 2002;62(18):5144-7. Author Manuscript. 11 pages.

Touloukian et al., Identification of a MHC class II-restricted human gp100 epitope using DR4-IE transgenic mice. J Immunol. Apr. 1, 2000;164(7):3535-42. doi: 10.4049/jimmunol.164.7.3535.

Touloukian et al., Normal tissue depresses while tumor tissue enhances human T cell responses in vivo to a novel self/tumor melanoma antigen, OA1. J Immunol. Feb. 1, 2003;170(3):1579-85. doi: 10.4049/jimmunol.170.3.1579.

Tran et al., Hypermutability of homonucleotide runs in mismatch repair and DNA polymerase proofreading yeast mutants. Mol Cell Biol. May 1997;17(5):2859-65. doi: 10.1128/MCB.17.5.2859.

Trojan et al., Generation of cytotoxic T lymphocytes against native and altered peptides of human leukocyte antigen-A*0201 restricted epitopes from the human epithelial cell adhesion molecule. Cancer Res. Jun. 15, 2001;61(12):4761-5.

Tsai et al., Identification of subdominant CTL epitopes of the GP100 melanoma-associated tumor antigen by primary in vitro immunization with peptide-pulsed dendritic cells. J Immunol. Feb. 15, 1997;158(4):1796-802.

Tsang et al., A human cytotoxic T-lymphocyte epitope and its agonist epitope from the nonvariable number of tandem repeat sequence of MUC-1. Clin Cancer Res. Mar. 15, 2004;10(6):2139-49. doi: 10.1158/1078-0432.ccr-1011-03.

Tsang et al., Generation of human cytotoxic T cells specific for human carcinoembryonic antigen epitopes from patients immunized with recombinant vaccinia-CEA vaccine. J Natl Cancer Inst. Jul. 5, 1995;87(13):982-90. doi: 10.1093/jnci/87.13.982.

Tsuboi et al., Enhanced induction of human WT1-specific cytotoxic T lymphocytes with a 9-mer WT1 peptide modified at HLA-A*2402-binding residues. Cancer Immunol Immunother. Dec. 2002;51(11-12):614-20. doi: 10.1007/s00262-002-0328-9. Epub Oct. 18, 2002.

Tycko et al., Methods for Optimizing CRISPR-Cas9 Genome Editing Specificity. Mol Cell. Aug. 4, 2016;63(3):355-70. doi: 10.1016/j.molcel.2016.07.004.

Umar et al., DNA loop repair by human cell extracts. Science. Nov. 4, 1994;266(5186):814-6. doi: 10.1126/science.7973637.

Valmori et al., Analysis of the cytolytic T lymphocyte response of melanoma patients to the naturally HLA-A*0201-associated tyrosinase peptide 368-376. Cancer Res. Aug. 15, 1999;59(16):4050-5.

Valmori et al., Enhanced generation of specific tumor-reactive CTL in vitro by selected Melan-A/MART-1 immunodominant peptide analogues. J Immunol. Feb. 15, 1998;160(4):1750-8.

Valmori et al., Naturally occurring human lymphocyte antigen-A2 restricted CD8+ T-cell response to the cancer testis antigen NY-ESO-1 in melanoma patients. Cancer Res. Aug. 15, 2000;60(16):4499-506.

Vidal et al., Yeast forward and reverse 'n'-hybrid systems. Nucleic Acids Res. Feb. 15, 1999;27(4):919-29. doi: 10.1093/nar/27.4.919.

Vigneron et al., A peptide derived from melanocytic protein gp100 and presented by HLA-B35 is recognized by autologous cytolytic T lymphocytes on melanoma cells. Tissue Antigens. Feb. 2005;65(2):156-62. doi: 10.1111/j.1399-0039.2005.00365.x.

Vigneron et al., An antigenic peptide produced by peptide splicing in the proteasome. Science. Apr. 23, 2004;304(5670):587-90. doi: 10.1126/science.1095522.

Visseren et al., Affinity, specificity and T-cell-receptor diversity of melanoma-specific CTL generated in vitro against a single tyrosinase epitope. Int J Cancer. Sep. 17, 1997;72(6):1122-8. doi: 10.1002/(sici)1097-0215(19970917)72:6<1122::aid-ijc30>3.0.co;2-3.

Voelkel et al., Protein transduction from retroviral Gag precursors. Proc Natl Acad Sci U S A. Apr. 27, 2010;107(17):7805-10. doi: 10.1073/pnas.0914517107. Epub Apr. 12, 2010.

Volpe et al., Alternative BCR/ABL splice variants in Philadelphia chromosome-positive leukemias result in novel tumor-specific fusion proteins that may represent potential targets for immunotherapy approaches. Cancer Res. Jun. 1, 2007;67(11):5300-7. doi: 10.1158/0008-5472.CAN-06-3737.

Walpita et al., Mammalian Cell-Derived Respiratory Syncytial Virus-Like Particles Protect the Lower as well as the Upper Respiratory Tract. PLoS One. Jul. 14, 2015;10(7):e0130755. doi: 10.1371/journal.pone.0130755.

Walton et al., Spontaneous CD8 T cell responses against the melanocyte differentiation antigen RAB38/NY-MEL-1 in melanoma patients. J Immunol. Dec. 1, 2006;177(11):8212-8. doi: 10.4049/jimmunol.177.11.8212.

Wang et al., CRISPR/Cas9 in Genome Editing and Beyond. Annu Rev Biochem. Jun. 2, 2016;85:227-64. doi: 10.1146/annurev-biochem-060815-014607. Epub Apr. 25, 2016.

Wang et al., Recognition of an antigenic peptide derived from tyrosinase-related protein-2 by CTL in the context of HLA-A31 and -A33. J Immunol. Jan. 15, 1998;160(2):890-7.

Wang et al., Recognition of breast cancer cells by CD8+ cytotoxic T-cell clones specific for NY-BR-1. Cancer Res. Jul. 1, 2006;66(13):6826-33. doi: 10.1158/0008-5472.CAN-05-3529.

Wang et al., Utilization of an alternative open reading frame of a normal gene in generating a novel human cancer antigen. J Exp Med. Mar. 1, 1996;183(3):1131-40. doi: 10.1084/jem.183.3.1131.

Wang et al., Virus-like particles for the prevention of human papillomavirus-associated malignancies. Expert Rev Vaccines. Feb. 2013;12(2):129-41. doi: 10.1586/erv.12.151. Author Manuscript, 22 pages.

Warren et al., Structure of the human MutSalpha DNA lesion recognition complex. Mol Cell. May 25, 2007;26(4):579-92. doi: 10.1016/j.molcel.2007.04.018.

Witkowski et al., Conversion of a beta-ketoacyl synthase to a malonyl decarboxylase by replacement of the active-site cysteine with glutamine. Biochemistry. Sep. 7, 1999;38(36):11643-50. doi: 10.1021/bi990993h.

Wu et al., MLV based viral-like-particles for delivery of toxic proteins and nuclear transcription factors. Biomaterials. Sep. 2014;35(29):8416-26. doi: 10.1016/j.biomaterials.2014.06.006. Epub Jul. 3, 2014.

Wölfel et al., Two tyrosinase nonapeptides recognized on HLA-A2 melanomas by autologous cytolytic T lymphocytes. Eur J Immunol. Mar. 1994;24(3):759-64. doi: 10.1002/eji.1830240340.

Xi et al., C-terminal Loop Mutations Determine Folding and Secretion Properties of PCSK9. Biochem Mol Biol J. 2016;2(3):17. doi: 10.21767/2471-8084.100026. 12 pages.

Yang et al., HIV-1 virus-like particles produced by stably transfected Drosophila S2 cells: a desirable vaccine component. J Virol. Jul. 2012;86(14):7662-76. doi: 10.1128/JVI.07164-11. Epub May 2, 2012.

Yee et al., A general method for the generation of high-titer, pantropic retroviral vectors: highly efficient infection of primary hepatocytes. Proc Natl Acad Sci U S A. Sep. 27, 1994;91(20):9564-8. doi: 10.1073/pnas.91.20.9564.

Yi et al., Engineering of TEV protease variants by yeast ER sequestration screening (YESS) of combinatorial libraries. Proc Natl Acad Sci U S A. Apr. 30, 2013;110(18):7229-34. doi: 10.1073/pnas.1215994110. Epub Apr. 15, 2013.

Yu et al., Poor immunogenicity of a self/tumor antigen derives from peptide-MHC-I instability and is independent of tolerance. J Clin Invest. Aug. 2004;114(4):551-9. doi: 10.1172/JCI21695.

Zarour et al., Melan-A/MART-1(51-73) represents an immunogenic HLA-DR4-restricted epitope recognized by melanoma-reactive CD4(+) T cells. Proc Natl Acad Sci U S A. Jan. 4, 2000;97(1):400-5. doi: 10.1073/pnas.97.1.400.

Zeltins, A., Construction and characterization of virus-like particles: a review. Mol Biotechnol. Jan. 2013;53(1):92-107. doi: 10.1007/s12033-012-9598-4.

(56) References Cited

OTHER PUBLICATIONS

Zhang et al., Cell-specific targeting of lentiviral vectors mediated by fusion proteins derived from Sindbis virus, vesicular stomatitis virus, or avian sarcoma/leukosis virus. Retrovirology. Jan. 25, 2010;7:3. doi: 10.1186/1742-4690-7-3.

Zhang et al., Reconstitution of 5'-directed human mismatch repair in a purified system. Cell. Sep. 9, 2005;122(5):693-705. doi: 10.1016/j.cell.2005.06.027.

[No Author Listed], *Homo sapiens* signal transducer and activator of transcription 3 (acute-phase response factor) (STAT3) gene, complete cds. GenBank Acc. No. AYS572796.1. Accessible at https://www.ncbi.nlm.nih.gov/nucleotide/AYS572796.1?report= genbank&log$=nuclalign&blast_rank=2&RID=BEG3KP4D014. Mar. 22, 2004. 36 pages.

Abifadel et al., Mutations in PCSK9 cause autosomal dominant hypercholesterolemia. Nat Genet. Jun. 2003;34(2):154-6. doi: 10.1038/ng1161.

Addgene Plasmid # 44246. pdCas9-humanized, 2017, Stanley Qi.

Addgene Plasmid # 73021. PCMV-BE3, 2017, David Liu.

Addgene Plasmid # 79620. pcDNA3.1_pCMV-nCas-PmCDA1-ugi pH1-gRNA(HPRT), 2017, Akihiko Kondo.

Addgene Plasmid #42234. pMJ920. 2013. Retrieved Jan. 22, 2025. 3 pages.

Ayala-Ramirez et al., A new autosomal recessive syndrome consisting of posterior microphthalmos, retinitis pigmentosa, foveoschisis, and optic disc drusen is caused by a MFRP gene mutation. Mol Vis. Dec. 4, 2006;12:1483-9.

Bandiera et al., Genetic variations creating microRNA target sites in the FXN 3'-UTR affect frataxin expression in Friedreich ataxia. PLoS One. 2013;8(1):e54791. doi: 10.1371/journal.pone.0054791. Epub Jan. 30, 2013.

Bender et al., Receptor-Targeted Nipah Virus Glycoproteins Improve Cell-Type Selective Gene Delivery and Reveal a Preference for Membrane-Proximal Cell Attachment. PLoS Pathog. Jun. 9, 2016;12(6):e1005641. doi: 10.1371/journal.ppat.1005641.

Bernardi et al., Nucleotide sequence at the binding site for coat protein on RNA of bacteriophage R17. Proc Natl Acad Sci U S A. Oct. 1972;69(10):3033-7. doi: 10.1073/pnas.69.10.3033.

Bidichandani et al., Friedreich Ataxia. Dec. 18, 1998 [updated Apr. 10, 2025]. In: Adam MP, Feldman J, Mirzaa GM, Pagon RA, Wallace SE, Amemiya A, editors. GeneReviews® [Internet]. Seattle (WA): University of Washington, Seattle; 1993-2025. 41 pages.

Bikard et al., Programmable repression and activation of bacterial gene expression using an engineered CRISPR-Cas system. Nucleic Acids Res. Aug. 2013;41(15):7429-37. doi: 10.1093/nar/gkt520. Epub Jun. 12, 2013.

Billon et al., CRISPR-Mediated Base Editing Enables Efficient Disruption of Eukaryotic Genes through Induction of STOP Codons. Mol Cell. Sep. 21, 2017;67(6):1068-1079.e4. doi: 10.1016/j.molcel.2017.08.008. Epub Sep. 7, 2017.

Bolukbasi et al., DNA-binding-domain fusions enhance the targeting range and precision of Cas9. Nat Methods. Dec. 2015;12(12):1150-6. doi: 10.1038/nmeth.3624. Epub Oct. 19, 2015.

Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38. doi: 10.1083/jcb.111.5.2129.

Burstein et al., New CRISPR-Cas systems from uncultivated microbes. Nature Feb. 2017;542(7640):237-240.

Buvoli et al., Suppression of nonsense mutations in cell culture and mice by multimerized suppressor tRNA genes. Mol Cell Biol. May 2000;20(9):3116-24. doi: 10.1128/MCB.20.9.3116-3124.2000.

Cai et al. Targeted genome editing by lentiviral protein transduction of zinc-finger and TAL-effector nucleases. Elife. Apr. 24, 2014;3:e01911. doi: 10.7554/eLife.01911.

Cai et al., Abstract OR021: Targeted Genome Editing by Lentiviral Protein Transduction of ZFN and Cas9 Proteins Abstract, Presented at Proceedings of the ESGCT and NVGCT Collaborative Congress: The Hague. Human Gene Therapy. 2014. 15 pages.

Cai, Protein Transduction Using Lentiviral Vectors for Transposition and Site-directed Gene Editing. Thesis for the degree of Doctor of Philosophy, Aarhus University, Department of Biomedicine. 2014. 74 pages.

Canver et al., BCL11A enhancer dissection by Cas9-mediated in situ saturating mutagenesis. Nature. Nov. 1, 2015;527(7577):192-7. doi: 10.1038/nature15521. Epub Sep. 16, 2015.

Chadwick et al., In Vivo Base Editing of PCSK9 (Proprotein Convertase Subtilisin/Kexin Type 9) as a Therapeutic Alternative to Genome Editing. Arterioscler Thromb Vasc Biol. Sep. 2017;37(9):1741-1747. doi: 10.1161/ATVBAHA.117.309881. Epub Jul. 27, 2017.

Chan et al., GtRNAdb 2.0: an expanded database of transfer RNA genes identified in complete and draft genomes. Nucleic Acids Res. Jan. 4, 2016;44(D1):D184-9. doi: 10.1093/nar/gkv1309. Epub Dec. 15, 2015.

Chang et al., Functional characterization of the placental fusogenic membrane protein syncytin. Biol Reprod. Dec. 2004;71(6):1956-62. doi: 10.1095/biolreprod.104.033340. Epub Jul. 21, 2004.

Chelico et al., APOBEC3G DNA deaminase acts processively 3' → 5' on single-stranded DNA. Nat Struct Mol Biol. May 2006;13(5):392-9. doi: 10.1038/nsmb1086. Epub Apr. 23, 2006.

Chen et al., DNA methylation and demethylation in mammals. J Biol Chem. May 27, 2011;286(21):18347-53. doi: 10.1074/jbc.R110.205286. Epub Mar. 24, 2011.

Chester et al., Optimization of apolipoprotein B mRNA editing by APOBEC1 apoenzyme and the role of its auxiliary factor, ACF. RNA. Sep. 2004;10(9):1399-411. doi: 10.1261/rna.7490704. Epub Jul. 23, 2004.

Cho et al., Heritable gene knockout in Caenorhabditis elegans by direct injection of Cas9-sgRNA ribonucleoproteins. Genetics. Nov. 2013;195(3):1177-80. doi: 10.1534/genetics.113.155853. Epub Aug. 26, 2013.

Chylinski et al., The tracrRNA and Cas9 families of type II CRISPR-Cas immunity systems. RNA Biol. May 2013;10(5):Supplementary Material. doi: 10.4161/rna.24321. Epub Apr. 5, 2013. 12 pages.

Cideciyan, Leber congenital amaurosis due to RPE65 mutations and its treatment with gene therapy. Prog Retin Eye Res. Sep. 2010;29(5):398-427. doi: 10.1016/j.preteyeres.2010.04.002. Epub Apr. 24, 2010.

Clark et al., Expansion of GAA triplet repeats in the human genome: unique origin of the FRDA mutation at the center of an Alu. Genomics. Mar. 2004;83(3):373-83. doi: 10.1016/j.ygeno.2003.09.001.

Cnop et al., Diabetes in Friedreich ataxia. J Neurochem. Aug. 2013;126 Suppl 1:94-102. doi: 10.1111/jnc.12216.

Cohen et al., Low LDL cholesterol in individuals of African descent resulting from frequent nonsense mutations in PCSK9. Nat Genet. Feb. 2005;37(2):161-5. doi: 10.1038/ng1509. Epub Jan. 16, 2005. Erratum in: Nat Genet. Mar. 2005;37(3):328.

Cohen et al., Sequence variations in PCSK9, low LDL, and protection against coronary heart disease. N Engl J Med. Mar. 23, 2006;354(12):1264-72. doi: 10.1056/NEJMoa054013.

Contreras-Galindo et al., Human Endogenous Retrovirus Type K (HERV-K) Particles Package and Transmit HERV-K-Related Sequences. J Virol. Jul. 2015;89(14):7187-201. doi: 10.1128/JVI.00544-15. Epub Apr. 29, 2015.

Covino et al., The CCL2/CCR2 Axis in the Pathogenesis of HIV-1 Infection: A New Cellular Target for Therapy? Current Drug Targets Dec. 2016; 17(1):76-110. DOI: 10.2174/1389450117011512171109017.

De Biase et al., Progressive GAA expansions in dorsal root ganglia of Friedreich's ataxia patients. Ann Neurol. Jan. 2007;61(1):55-60. doi: 10.1002/ana.21052.

Den Hollander et al., Leber congenital amaurosis: genes, proteins and disease mechanisms. Prog Retin Eye Res. Jul. 2008;27(4):391-419. doi: 10.1016/j.preteyeres.2008.05.003. Epub Jun. 1, 2008.

Duvoisin et al., Human U6 promoter drives stronger shRNA activity than its schistosome orthologue in Schistosoma mansoni and human fibrosarcoma cells. Transgenic Res. Jun. 2012;21(3):511-21. doi: 10.1007/s11248-011-9548-0. Epub Sep. 28, 2011.

East-Seletsky et al., Two distinct RNase activities of CRISPR-C2c2 enable guide-RNA processing and RNA detection. Nature Oct. 2016;538(7624):270-3.

(56)        References Cited

OTHER PUBLICATIONS

Esashi et al., Stabilization of RAD51 nucleoprotein filaments by the C-terminal region of BRCA2. Nat Struct Mol Biol. Jun. 2007;14(6):468-74. doi: 10.1038/nsmb1245. Epub May 21, 2007.

Fehér et al., Characterization of the murine leukemia virus protease and its comparison with the human immunodeficiency virus type 1 protease. J Gen Virol. May 2006;87(Pt 5):1321-1330. doi: 10.1099/vir.0.81382-0.

Felletti et al., Twister Ribozymes as Highly Versatile Expression Platforms for Artificial Riboswitches. Nat Commun. Sep. 27, 2016;7:12834. doi: 10.1038/ncomms12834.

Ferry et al., Rational design of inducible CRISPR guide RNAs for de novo assembly of transcriptional programs. Nat Commun. Mar. 3, 2017;8:14633. doi: 10.1038/ncomms14633.

Fisher et al., Transduction with recombinant adeno-associated virus for gene therapy is limited by leading-strand synthesis. J Virol. Jan. 1996;70(1):520-32. doi: 10.1128/JVI.70.1.520-532.1996.

Fishman-Lobell et al., Two alternative pathways of double-strand break repair that are kinetically separable and independently modulated. Mol Cell Biol. Mar. 1992;12(3):1292-303. doi: 10.1128/mcb.12.3.1292-1303.1992.

Fitzgerald et al., Effect of an RNA interference drug on the synthesis of proprotein convertase subtilisin/kexin type 9 (PCSK9) and the concentration of serum LDL cholesterol in healthy volunteers: a randomised, single-blind, placebo-controlled, phase 1 trial. Lancet. Jan. 4, 2014;383(9911):60-68. doi: 10.1016/S0140-6736(13)61914-5. Epub Oct. 3, 2013.

Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013. Supplementary Information. 67 pages.

Garcia et al., Identification of the rate-determining step of tRNA-guanine transglycosylase from Escherichia coli. Biochemistry. Dec. 1, 2009;48(47):11243-51. doi: 10.1021/bi901501a.

Garnier et al., WW domains and retrovirus budding. Nature. Jun. 27, 1996;381(6585):744-5. doi: 10.1038/381744a0.

GenBank Accession No. AAH57574.1 2009. 2 pages.

GenBank Submission; NIH/NCBI, Accession No. YP_009283008.1. Bernardini et al., Sep. 23, 2016. 2 pages.

Giegé et al., Universal rules and idiosyncratic features in tRNA identity. Nucleic Acids Res. Nov. 15, 1998;26(22):5017-35. doi: 10.1093/nar/26.22.5017.

Golczak et al., Importance of membrane structural integrity for RPE65 retinoid isomerization activity. J Biol Chem. Mar. 26, 2010;285(13):9667-9682. doi: 10.1074/jbc.M109.063941. Epub Jan. 25, 2010.

Goldstein et al., The tangled bank of amino acids. Protein Sci. Jul. 2016;25(7):1354-62. doi: 10.1002/pro.2930. Epub May 12, 2016.

Greene et al., Repeat-induced epigenetic changes in intron 1 of the frataxin gene and its consequences in Friedreich ataxia. Nucleic Acids Res. 2007;35(10):3383-90. doi: 10.1093/nar/gkm271. Epub May 3, 2007.

Grimm et al., Helper virus-free, optically controllable, and two-plasmid-based production of adeno-associated virus vectors of serotypes 1 to 6. Mol Ther. Jun. 2003;7(6):839-50. doi: 10.1016/s1525-0016(03)00095-9.

Grimm et al., Novel tools for production and purification of recombinant adenoassociated virus vectors. Hum Gene Ther. Dec. 10, 1998;9(18):2745-60. doi: 10.1089/hum.1998.9.18-2745.

Gusel'nikova et al., NeuN As a Neuronal Nuclear Antigen and Neuron Differentiation Marker. Acta Naturae. Apr.-Jun. 2015;7(2):42-7.

Heintze et al., A CRISPR CASe for high-throughput silencing. Front Genet. Oct. 7, 2013;4:193. doi: 10.3389/fgene.2013.00193.

Hess et al., Directed evolution using dCas9-targeted somatic hypermutation in mammalian cells. Nat Methods. Dec. 2016;13(12):1036-1042. doi: 10.1038/nmeth.4038. Epub Oct. 31, 2016.

Himeno et al., Only one nucleotide insertion to the long variable arm confers an efficient serine acceptor activity upon Sac-charomyces cerevisiae tRNA(Leu) in vitro. J Mol Biol. May 1, 19976;268(4):704-11. doi: 10.1006/jmbi.1997.0991.

Hooper et al., The C679X mutation in PCSK9 is present and lowers blood cholesterol in a Southern African population. Atherosclerosis. Aug. 2007;193(2):445-8. doi: 10.1016/j.atherosclerosis.2006.08.039. Epub Sep. 20, 2006.

Hubbard et al., Continuous directed evolution of DNA-binding proteins to improve TALEN specificity. Nat Methods. Oct. 2015;12(10):939-42. doi: 10.1038/nmeth.3515. Epub Aug. 10, 2015.

Iascone et al., Spinal muscular atrophy: from tissue specificity to therapeutic strategies. F1000Prime Rep. Jan. 5, 2015;7:04. doi: 10.12703/P7-04.

Iben et al., tRNA gene copy number variation in humans. Gene. Feb. 25, 2014;536(2):376-84. doi: 10.1016/j.gene.2013.11.049. Epub Dec. 14, 2013.

Jacobs et al., DNA glycosylases: in DNA repair and beyond. Chromosoma. Feb. 2012;121(1):1-20. doi: 10.1007/s00412-011-0347-4. Epub Nov. 3, 2011. 20 pages.

Jinek et al., A programmable dual-RNA-guided DNA endonuclease in adaptive bacterial immunity. Science. Aug. 17, 2012;337(6096):Supplementary Material. doi: 10.1126/science.1225829. Epub Jun. 28, 2012. 37 pages.

Jiralerspong et al., Frataxin shows developmentally regulated tissue-specific expression in the mouse embryo. Neurobiol Dis. 1997;4(2):103-13. doi: 10.1006/nbdi.1997.0139.

Kameya et al., Mfrp, a gene encoding a frizzled related protein, is mutated in the mouse retinal degeneration 6. Hum Mol Genet. Aug. 1, 2002;11(16):1879-86. doi: 10.1093/hmg/11.16.1879.

Karijolich et al., Therapeutic suppression of premature termination codons: mechanisms and clinical considerations (review). Int J Mol Med. Aug. 2014;34(2):355-62. doi: 10.3892/ijmm.2014.1809. Epub Jun. 17, 2014.

Katoh et al., Exploitation of the interaction of measles virus fusogenic envelope proteins with the surface receptor CD46 on human cells for microcell-mediated chromosome transfer. BMC Biotechnol. May 6, 2010;10:37. doi: 10.1186/1472-6750-10-37.

Kawakami, K., Tol2: a versatile gene transfer vector in vertebrates. Genome Biol. 2007;8 Suppl 1(Suppl 1):S7. doi: 10.1186/gb-2007-8-s1-s7.

Kern et al., Identification of a heparin-binding motif on adeno-associated virus type 2 capsids. J Virol. Oct. 2003;77(20):11072-81. doi: 10.1128/jvi.77.20.11072-11081.2003.

Kim et al., Genome-wide target specificity of CRISPR RNA-guided adenine base editors. Nat Biotechnol. Apr. 2019;37(4):430-435. doi: 10.1038/s41587-019-0050-1. Epub Mar. 4, 2019.

Kim et al., Highly efficient RNA-guided base editing in mouse embryos. Nat Biotechnol. May 2017;35(5):435-437. doi: 10.1038/nbt.3816. Epub Feb. 27, 2017.

Kim et al., Increasing the genome-targeting scope and precision of base editing with engineered Cas9-cytidine deaminase fusions. Nat Biotechnol. Apr. 2017;35(4):371-376. doi: 10.1038/nbt.3803. Epub Feb. 13, 2017.

Kleinstiver et al., Broadening the targeting range of Staphylococcus aureus CRISPR-Cas9 by modifying PAM recognition. Nat Biotechnol. Dec. 2015;33(12):1293-1298. doi: 10.1038/nbt.3404. Epub Nov. 2, 2015. Author Manuscript, 14 pages.

Kneissl et al., Measles virus glycoprotein-based lentiviral targeting vectors that avoid neutralizing antibodies. PLoS One. 2012;7(10):e46667. doi: 10.1371/journal.pone.0046667. Epub Oct. 10, 2012.

Kobori et al., Deep Sequencing Analysis of Aptazyme Variants Based on a Pistol Ribozyme. ACS Synth Biol. Jul. 21, 2017;6(7):1283-1288. doi: 10.1021/acssynbio.7b00057. Epub Apr. 14, 2017.

Komor et al., CRISPR-Based Technologies for the Manipulation of Eukaryotic Genomes. Cell. Jan. 12, 2017;168(1-2):20-36. doi: 10.1016/j.cell.2016.10.044.

Komor et al., Improved base excision repair inhibition and bacteriophage Mu Gam protein yields C:G-to-T:A base editors with higher efficiency and product purity. Sci Adv. Aug. 30, 2017;3(8):eaao4774. doi: 10.1126/sciadv.aao4774. eCollection Aug. 2017.

(56) References Cited

OTHER PUBLICATIONS

Koonin et al., Diversity, classification and evolution of CRISPR-Cas systems. Curr Opin Microbiol. 2017;37:67-78. doi:10.1016/j.mib.2017.05.008.

Kronenberg et al., A conformational change in the adeno-associated virus type 2 capsid leads to the exposure of hidden VP1 N termini. J Virol. May 2005;79(9):5296-303. doi: 10.1128/JVI.79.9.5296-5303.2005.

Kury et al., De Novo Disruption of the Proteasome Regulatory Subunit PSMD12 Causes a Syndromic Neurodevelopmental Disorder. Am J Hum Genet. Feb. 2, 2017;100(2):352-363. doi: 10.1016/j.ajhg.2017.01.003. Epub Jan. 26, 2017.

Kuscu et al., CRISPR-STOP: gene silencing through base-editing-induced nonsense mutations. Nat Methods. Jul. 2017;14(7):710-712. doi: 10.1038/nmeth.4327. Epub Jun. 5, 2017.

Lazaropoulos et al., Frataxin levels in peripheral tissue in Friedreich ataxia. Ann Clin Transl Neurol. Aug. 2015;2(8):831-42. doi: 10.1002/acn3.225. Epub Jul. 1, 2015.

Lee et al., Failure to detect DNA-guided genome editing using Natronobacterium gregoryi Argonaute. Nat Biotechnol. Nov. 28, 2016;35(1):17-18. doi: 10.1038/nbt.3753.

Lee et al., Reconstitution of an infectious human endogenous retrovirus. PLoS Pathog. Jan. 2007;3(1):e10. doi: 10.1371/journal.ppat.0030010.

Lee et al., Ribozyme Mediated gRNA Generation for In Vitro and In Vivo CRISPR/Cas9 Mutagenesis. PLoS One. Nov. 10, 2016;11(11):e0166020. doi: 10.1371/journal.pone.0166020. eCollection 2016.

Leenay et al., Identifying and Visualizing Functional PAM Diversity across CRISPR-Cas Systems. Mol Cell. Apr. 7, 2016;62(1):137-47. doi: 10.1016/j.molcel.2016.02.031. Epub Mar. 31, 2016.

Leibundgut-Landmann et al., Mini-review: Specificity and expression of CIITA, the master regulator of MHC class II genes. Eur J Immunol. Jun. 2004;34(6):1513-25. doi: 10.1002/eji.200424964.

Lewis et al., Building the Class 2 CRISPR-Cas Arsenal. Mol Cell 2017;65(3);377-379.

Li et al., A dominant-negative form of mouse SOX2 induces trophectoderm differentiation and progressive polyploidy in mouse embryonic stem cells. J Biol Chem. Jul. 6, 2007;282(27):19481-92. doi: 10.1074/jbc.M702056200. Epub May 15, 2007.

Li et al., Base editing with a Cpf1-cytidine deaminase fusion. Nat Biotechnol. Apr. 2018;36(4):324-327. doi: 10.1038/nbt.4102. Epub Mar. 19, 2018.

Li et al., Excision of Expanded GAA Repeats Alleviates the Molecular Phenotype of Friedreich's Ataxia. Mol Ther. Jun. 2015;23(6):1055-1065. doi: 10.1038/mt.2015.41. Epub Mar. 11, 2015.

Li et al., Generation of Targeted Point Mutations in Rice by a Modified CRISPR/Cas9 System. Mol Plant. Mar. 6, 2017;10(3):526-529. doi: 10.1016/j.molp.2016.12.001. Epub Dec. 8, 2016.

Li et al., Highly efficient and precise base editing in discarded human tripronuclear embryos. Protein Cell. Aug. 19, 2017. doi: 10.1007/s13238-017-0458-7. [Epub ahead of print].

Lim et al., Specific insertions of zinc finger domains into Gag-Pol yield engineered retroviral vectors with selective integration properties. Proc Natl Acad Sci U S A. Jul. 13, 2010;107(28):12475-80. doi: 10.1073/pnas.1001402107. Epub Jun. 28, 2010.

Lin et al., Structure-function relationships in glucagon: properties of highly purified des-His-1-, monoiodo-, and (des-Asn-28, Thr-29)(homoserine lactone-27)-glucagon. Biochemistry. Apr. 22, 1975;14(8):1559-63. doi: 10.1021/bi00679a002.

Liu et al., C2c1-sgRNA Complex Structure Reveals RNA-Guided DNA Cleavage Mechanism. Molecular Cell Jan. 2017;65(2):310-22.

Liu et al., DNA base excision repair: a mechanism of trinucleotide repeat expansion. Trends Biochem Sci. Apr. 2012;37(4):162-72. doi: 10.1016/j.tibs.2011.12.002. Epub Jan. 27, 2012.

Liu et al., Editing DNA Methylation in the Mammalian Genome. Cell. Sep. 22, 2016;167(1):233-247.e17. doi: 10.1016/j.cell.2016.08.056.

Lu et al., Precise Editing of a Target Base in the Rice Genome Using a Modified CRISPR/Cas9 System. Mol Plant. Mar. 6, 2017;10(3):523-525. doi: 10.1016/j.molp.2016.11.013. Epub Dec. 6, 2016.

Ma et al., A new mutation in BFSP2 (G1091A) causes autosomal dominant congenital lamellar cataracts. Mol Vis. 2008;14:1906-11. Epub Oct. 24, 2008.

Ma et al., Pol III Promoters to Express Small RNAs: Delineation of Transcription Initiation. Mol Ther Nucleic Acids. May 6, 2014;3(5):e161. doi: 10.1038/mtna.2014.12.

Ma et al., Targeted AID-mediated mutagenesis (TAM) enables efficient genomic diversification in mammalian cells. Nature Methods. Oct. 2016;13:1029-35. doi:10.1038/nmeth.4027.

Martín et al., Envelope-targeted retrovirus vectors transduce melanoma xenografts but not spleen or liver. Mol Ther. Mar. 2002;5(3):269-74. doi: 10.1006/mthe.2002.0550.

Mason et al., Coiled coil domains: stability, specificity, and biological implications. Chembiochem. Feb. 6, 2004;5(2):170-6. doi: 10.1002/cbic.200300781.

Meyer et al., Improving single injection CSF delivery of AAV9-mediated gene therapy for SMA: a dose-response study in mice and nonhuman primates. Mol Ther. Mar. 2015;23(3):477-87. doi: 10.1038/mt.2014.210. Epub Oct. 31, 2014.

Miller et al., Cell-surface receptors for retroviruses and implications for gene transfer. Proc Natl Acad Sci U S A. Oct. 15, 1996;93(21):11407-13. doi: 10.1073/pnas.93.21.11407.

Mohr et al., Dominant-negative activity of the STAT3-Y705F mutant depends on the N-terminal domain. Cell Commun Signal. Nov. 5, 2013;11:83. doi: 10.1186/1478-811X-11-83.

Momose et al., Diving into marine genomics with CRISPR/Cas9 systems. Mar Genomics. Dec. 2016;30:55-65. doi: 10.1016/j.margen.2016.10.003. Epub Oct. 12, 2016.

Mort et al., A meta-analysis of nonsense mutations causing human genetic disease. Hum Mutat. Aug. 2008;29(8):1037-47. doi: 10.1002/humu.20763.

Moullier et al., International efforts for recombinant adeno-associated viral vector reference standards. Mol Ther. Jul. 2008;16(7):1185-8. doi: 10.1038/mt.2008.125.

Naryshkin et al., Motor neuron disease. SMN2 splicing modifiers improve motor function and longevity in mice with spinal muscular atrophy. Science. Aug. 8, 2014;345(6197):688-93. doi: 10.1126/science.1250127.

Nesbitt, Targeted Intracellular Therapeutic Delivery Using Liposomes Formulated with Multifunctional FAST proteins. Electronic Thesis and Dissertation Repository. The University of Western Ontario. 2012. 126 pages.

Nonekowski et al., The *Escherichia coli* tRNA-guanine transglycosylase can recognize and modify DNA. J Biol Chem. Mar. 1, 2002;277(9):7178-82. doi: 10.1074/jbc.M111077200. Epub Dec. 21, 2001.

Nowak et al., Guide RNA Engineering for Versatile Cas9 Functionality. Nucleic Acids Res. Nov. 16, 2016;44(20):9555-9564. doi: 10.1093/nar/gkw908. Epub Oct. 12, 2016.

Nunez et al., Chemical and Biophysical Modulation of Cas9 for Tunable Genome Engineering. ACS Chem Biol. Mar. 18, 2016;11(3):681-8. doi: 10.1021/acschembio.5b01019. Epub Feb. 9, 2016.

Ohshima et al., A nonpathogenic GAAGGA repeat in the Friedreich gene: implications for pathogenesis. Neurology. Nov. 10, 1999;53(8):1854-7. doi: 10.1212/wnl.53.8.1854.

Pan et al., Biodistribution and toxicity studies of VSVG-pseudotyped lentiviral vector after intravenous administration in mice with the observation of in vivo transduction of bone marrow. Mol Ther. Jul. 2002;6(1):19-29. doi: 10.1006/mthe.2002.0630.

Pan et al., Identification of a nuclear localization signal in OCT4 and generation of a dominant negative mutant by its ablation. J Biol Chem. Aug. 27, 2004;279(35):37013-20. doi: 10.1074/jbc.M405117200. Epub Jun. 24, 2004.

Pandolfo, M., Friedreich ataxia: new pathways. J Child Neurol. Sep. 2012;27(9):1204-11. doi: 10.1177/0883073812448534. Epub Jun. 29, 2012.

Pang et al., Retinal degeneration 12 (rd12): a new, spontaneously arising mouse model for human Leber congenital amaurosis (LCA). Mol Vis. Feb. 28, 2005;11:152-62.

(56) References Cited

OTHER PUBLICATIONS

Parr-Brownlie et al., Lentiviral vectors as tools to understand central nervous system biology in mammalian model organisms. Front Mol Neurosci. May 18, 2015;8:14. doi: 10.3389/fnmol.2015.00014.

Pavlov et al., Roles of DNA polymerases in replication, repair, and recombination in eukaryotes. Int Rev Cytol. 2006;255:41-132. doi: 10.1016/S0074-7696(06)55002-8.

Pelletier, CRISPR-Cas systems for the study of the immune function. Nov. 15, 2016. https://doi.org/10.1002/9780470015902. a0026896.

Perkel, J.M., Crispr Is Still on Point When It Comes to Genome Editing. Biocompare. Jun. 2, 2016. Accessed from < https://www.biocompare.com/Editorial-Articles/187183-CRISPR-Is-Still-on-Point-When-It-Comes-to-Genome-Editing/>. 8 pages.

Pettersen et al., UCSF Chimera—a visualization system for exploratory research and analysis. J Comput Chem. Oct. 2004;25(13):1605-12. doi: 10.1002/jcc.20084.

Podbilewicz, Virus and cell fusion mechanisms. Annu Rev Cell Dev Biol. 2014;30:111-39. doi: 10.1146/annurev-cellbio-101512-122422. Epub Jun. 27, 2014.

Prasad et al., Rev1 is a base excision repair enzyme with 5'-deoxyribose phosphate lyase activity. Nucleic Acids Res. Dec. 15, 2016;44(22):10824-10833. doi: 10.1093/nar/gkw869. Epub Sep. 28, 2016.

Punga et al., Long intronic GAA repeats causing Friedreich ataxia impede transcription elongation. EMBO Mol Med. Apr. 2010;2(4):120-9. doi: 10.1002/emmm.201000064.

Puppo et al., Retinal transduction profiles by high-capacity viral vectors. Gene Ther. Oct. 2014;21(10):855-65. doi: 10.1038/gt.2014. 57. Epub Jul. 3, 2014.

Puspasari et al., Long range regulation of human FXN gene expression. PLoS One. 2011;6(7):e22001. doi: 10.1371/journal.pone. 0022001. Epub Jul. 8, 2011.

Qi et al., Repurposing CRISPR as an RNA-guided platform for sequence-specific control of gene expression. Cell. Feb. 28, 2013;152(5):Supplementary Material. doi: 10.1016/j.cell.2013.02. 022. 4 pages.

Ramiro et al., Transcription enhances AID-mediated cytidine deamination by exposing single-stranded DNA on the nontemplate strand. Nat Immunol. May 2003;4(5):452-6. doi: 10.1038/ni920.

Rees et al., Improving the DNA specificity and applicability of base editing through protein engineering and protein delivery. Nat Commun. Jun. 6, 2017;8:15790. doi: 10.1038/ncomms15790.

Reetz et al., Biological and clinical characteristics of the European Friedreich's Ataxia Consortium for Translational Studies (EFACTS) cohort: a cross-sectional analysis of baseline data. Lancet Neurol. Feb. 2015;14(2):174-82. doi: 10.1016/S1474-4422(14)70321-7. Epub Jan. 5, 2015.

Remington et al., Complete nucleotide sequence of a neuropathogenic variant of Friend murine leukemia virus PVC-211. Nucleic Acids Res. Jun. 25, 1992;20(12):3249. doi: 10.1093/nar/20.12.3249.

Rolfsmeier et al., Stabilizing effects of interruptions on trinucleotide repeat expansions in *Saccharomyces cerevisiae*. Mol Cell Biol. Jan. 2000;20(1):173-80. doi: 10.1128/MCB.20.1.173-180.2000.

Romero et al., Exploring protein fitness landscapes by directed evolution. Nat Rev Mol Cell Biol. Dec. 2009;10(12):866-76. doi: 10.1038/nrm2805.

Roth, J.R., Frameshift suppression. Cell. Jun. 1981;24(3):601-2. doi: 10.1016/0092-8674(81)90086-6.

Rudin et al., Efficient repair of HO-induced chromosomal breaks in *Saccharomyces cerevisiae* by recombination between flanking homologous sequences. Mol Cell Biol. Sep. 1988;8(9):3918-28. doi: 10.1128/mcb.8.9.3918-3928.1988.

Sakamoto et al., GGA*TCC-interrupted triplets in long GAA*TTC repeats inhibit the formation of triplex and sticky DNA structures, alleviate transcription inhibition, and reduce genetic instabilities. J Biol Chem. Jul. 20, 2001;276(29):27178-87. doi: 10.1074/jbc. M101852200. Epub Apr. 26, 2001.

Sanjana et al., Improved vectors and genome-wide libraries for CRISPR screening. Nat Methods. Aug. 2014;11(8):783-784. doi: 10.1038/nmeth.3047.

Santos et al., Friedreich ataxia: molecular mechanisms, redox considerations, and therapeutic opportunities. Antioxid Redox Signal. Sep. 1, 2010;13(5):651-90. doi: 10.1089/ars.2009.3015.

Sapir et al., Viral and developmental cell fusion mechanisms: conservation and divergence. Dev Cell. Jan. 2008;14(1):11-21. doi: 10.1016/j.devcel.2007.12.008.

Schellekens, Bioequivalence and the immunogenicity of biopharmaceuticals. Nat Rev Drug Discov. Jun. 2002;1(6):457-62. doi: 10.1038/nrd818.

Schneider et al., MuLV IN mutants responsive to HDAC inhibitors enhance transcription from unintegrated retroviral DNA. Virology. May 10, 2012;426(2):188-96. doi: 10.1016/j.virol.2012.01.034. Epub Feb. 23, 2012.

Schwartz et al., A superactive insulin: [B10-aspartic acid]insulin(human). Proc Natl Acad Sci U S A. Sep. 1987;84(18):6408-11. doi: 10.1073/pnas.84.18.6408.

Semple et al., Brain development in rodents and humans: Identifying benchmarks of maturation and vulnerability to injury across species. Prog Neurobiol. Jul.-Aug. 2013;106-107:1-16. doi: 10.1016/j.pneurobio.2013.04.001. Epub Apr. 11, 2013.

Serreze et al., Major histocompatibility complex class I-deficient NOD-B2mnull mice are diabetes and insulitis resistant. Diabetes. Mar. 1994;43(3):505-9. doi: 10.2337/diab.43.3.505.

Shen et al., Activation-induced cytidine deaminase (AID) can target both DNA strands when the DNA is supercoiled. Proc Natl Acad Sci U S A. Aug. 31, 2004;101(35):12997-3002. doi: 10.1073/pnas. 0404974101. Epub Aug. 24, 2004.

Shishkin et al., Large-scale expansions of Friedreich's ataxia GAA repeats in yeast. Mol Cell. Jul. 10, 2009;35(1):82-92. doi: 10.1016/j.molcel.2009.06.017.

Silva et al., Expanded GAA repeats impair FXN gene expression and reposition the FXN locus to the nuclear lamina in single cells. Hum Mol Genet. Jun. 15, 2015;24(12):3457-71. doi: 10.1093/hmg/ddv096. Epub Mar. 26, 2015.

Singh et al., Real-time observation of DNA recognition and rejection by the RNA-guided endonuclease Cas9. Nat Commun. Sep. 14, 2016;7:12778. doi: 10.1038/ncomms12778.

Singh et al., Real-time observation of DNA target interrogation and product release by the RNA-guided endonuclease CRISPR Cpf1 (Cas12a). Proc Natl Acad Sci U S A. May 22, 2018;115(21):5444-5449. doi: 10.1073/pnas.1718686115. Epub May 7, 2018.

Skipper et al., Delivering the Goods for Genome Engineering and Editing. Hum Gene Ther. Aug. 2015;26(8):486-97. doi: 10.1089/hum.2015.063.

Sledz et al., Structural insights into the molecular mechanism of the m(6)A writer complex. Elife. Sep. 14, 2016;5:e18434. doi: 10.7554/eLife.18434.

Soragni et al., Long intronic GAA*TTC repeats induce epigenetic changes and reporter gene silencing in a molecular model of Friedreich ataxia. Nucleic Acids Res. Nov. 2008;36(19):6056-65. doi: 10.1093/nar/gkn604. Epub Sep. 27, 2008.

Stevens et al., Design of a Split Intein with Exceptional Protein Splicing Activity. J Am Chem Soc. Feb. 24, 2016;138(7):2162-5. doi: 10.1021/jacs.5b13528. Epub Feb. 8, 2016. Abstract Only. 1 page.

Swami et al., Somatic expansion of the Huntington's disease CAG repeat in the brain is associated with an earlier age of disease onset. Hum Mol Genet. Aug. 15, 2009;18(16):3039-47. doi: 10.1093/hmg/ddp242. Epub May 23, 2009.

Swiech et al., In vivo interrogation of gene function in the mammalian brain using CRISPR-Cas9. Nat Biotechnol. Jan. 2015;33(1):102-6. doi: 10.1038/nbt.3055. Epub Oct. 19, 2014. Author Manuscript. 22 pages.

Takahashi et al., Induction of pluripotent stem cells from mouse embryonic and adult fibroblast cultures by defined factors. Cell. Aug. 25, 2006;126(4):663-76. doi: 10.1016/j.cell.2006.07.024. Epub Aug. 10, 2006.

Tang et al., Aptazyme-embedded guide RNAs enable ligand-responsive genome editing and transcriptional activation. Nat Commun. Jun. 28, 2017;8:15939. doi: 10.1038/ncomms15939.

(56) References Cited

OTHER PUBLICATIONS

Taylor, Ocular immune privilege. Eye (Lond). Oct. 2009;23(10):1885-9. doi: 10.1038/eye.2008.382. Epub Jan. 9, 2009.

Thakore et al., Highly specific epigenome editing by CRISPR-Cas9 repressors for silencing of distal regulatory elements. Nat Methods. Dec. 2015;12(12):1143-9. doi: 10.1038/nmeth.3630. Epub Oct. 26, 2015.

Thorne et al., In vivo diffusion analysis with quantum dots and dextrans predicts the width of brain extracellular space. Proc Natl Acad Sci U S A. Apr. 4, 2006;103(14):5567-72. doi: 10.1073/pnas.0509425103. Epub Mar. 27, 2006.

Tokuriki et al., Stability effects of mutations and protein evolvability. Curr Opin Struct Biol. Oct. 2009;19(5):596-604. doi: 10.1016/j.sbi.2009.08.003. Epub Sep. 16, 2009.

Tözsér, Comparative studies on retroviral proteases: substrate specificity. Viruses. Jan. 2010;2(1):147-165. doi: 10.3390/v2010147. Epub Jan. 14, 2010.

UniprotKB Submission; Accession No. P0DOC6. No Author Listed., Oct. 5, 2016. 5 pages.

Urano et al., Substitution of the myristoylation signal of human immunodeficiency virus type 1 Pr55Gag with the phospholipase C-deltal pleckstrin homology domain results in infectious pseudovirion production. J Gen Virol. Dec. 2008;89(Pt 12):3144-3149. doi: 10.1099/vir.0.2008/004820-0.

Voisset et al., Phylogeny of a novel family of human endogenous retrovirus sequences, HERV-W, in humans and other primates. AIDS Res Hum Retroviruses. Nov. 20, 1999;15(17):1529-33. doi: 10.1089/088922299309810.

Wang et al., Characterization of an MPS I-H knock-in mouse that carries a nonsense mutation analogous to the human IDUA-W402X mutation. Mol Genet Metab. Jan. 2010;99(1):62-71. doi: 10.1016/j.ymgme.2009.08.002. Erratum in: Mol Genet Metab. Apr. 2010;99(4):439.

Wang et al., Influence of the polyanion on the physico-chemical properties and biological activities of polyanion/DNA/polycation ternary polyplexes. Acta Biomater. Aug. 2012;8(8):3014-26. doi: 10.1016/j.actbio.2012.04.034. Epub Apr. 27, 2012.

Wheeler et al., Proteomics analysis of cellular components in lentiviral vector production using Gel-LC-MS/MS. Proteomics Clin Appl. Feb. 2007;1(2):224-30. doi: 10.1002/prca.200600522. Epub Jan. 22, 2007.

Worgall et al., Treatment of late infantile neuronal ceroid lipofuscinosis by CNS administration of a serotype 2 adeno-associated virus expressing CLN2 cDNA. Hum Gene Ther. May 2008;19(5):463-74. doi: 10.1089/hum.2008.022.

Wu et al., Effect of genome size on AAV vector packaging. Mol Ther. Jan. 2010;18(1):80-6. doi: 10.1038/mt.2009.255. Epub Nov. 10, 2009.

Xu et al., Cas9-based tools for targeted genome editing and transcriptional control. Appl Environ Microbiol. Mar. 2014;80(5):1544-52. doi: 10.1128/AEM.03786-13. Epub Jan. 3, 2014.

Xu et al., Sequence and structural analyses of nuclear export signals in the NESdb database. Mol Biol Cell. Sep. 2012;23(18):3677-93. doi: 10.1091/mbc.E12-01-0046. Epub Jul. 25, 2012.

Yang et al., APOBEC: From mutator to editor. J Genet Genomics. Sep. 20, 2017;44(9):423-437. doi: 10.1016/j.jgg.2017.04.009. Epub Aug. 7, 2017.

Yang et al., Engineering and optimising deaminase fusions for genome editing. Nat Commun. Nov. 2, 2016;7:13330. doi: 10.1038/ncomms13330.

Yang et al., PAM-dependent Target DNA Recognition and Cleavage by C2C1 CRISPR-Cas endonuclease. Cell Dec. 2016;167(7):1814-28.

Yang et al., Time-dependent maturation of cationic liposome-DNA complex for serum resistance. Gene Ther. Mar. 1998;5(3):380-7. doi: 10.1038/sj.gt.3300596.

Zakas et al., Enhancing the pharmaceutical properties of protein drugs by ancestral sequence reconstruction. Nat Biotechnol. Jan. 2017;35(1):35-37. doi: 10.1038/nbt.3677. Epub Sep. 26, 2016.

Zhang et al., Morphology and ultrastructure of retrovirus particles. AIMS Biophys. 2015;2(3):343-369. doi: 10.3934/biophy.2015.3.343. Epub Aug. 18, 2015. Author Manuscript. 33 pages.

Zhang et al., Programmable base editing of zebrafish genome using a modified CRISPR-Cas9 system. Nat Commun. Jul. 25, 2017;8(1):118. doi: 10.1038/s41467-017-00175-6.

Zhao et al., Study on p21 gene knock out in G401 cell line by using CRISPR/Cas9 system. Tianjin Med J. Oct. 2016;44(10):1190-1194.

Zheng et al., DNA editing in DNA/RNA hybrids by adenosine deaminases that act on RNA. Nucleic Acids Res. Apr. 7, 2017;45(6):3369-3377. doi: 10.1093/nar/gkx050.

Zhong et al., Rational Design of Aptazyme Riboswitches for Efficient Control of Gene Expression in Mammalian Cells. Elife. Nov. 2, 2016;5:e18858. doi: 10.7554/eLife.18858.

Zong et al., Precise base editing in rice, wheat and maize with a Cas9-cytidine deaminase fusion. Nat Biotechnol. May 2017;35(5):438-440. doi: 10.1038/nbt.3811. Epub Feb. 27, 2017.

* cited by examiner untreated EmGFP-HEK293 cells

Cas9 and gRNA expression plasmid transfection

EmGFP-HEK293 cells transfected with wild-type Cas9 and gRNAs clonal population of cells expressing EmGFP transfection of Cas9 and gRNA expression plasmids Cas9 cleavage EmGFP error-prone NHEJ of Cas9-cleaved EmGFP gene mixed population of modified and unmodified cells NHEJ-derived indel

| name | NLS-linker-Fok1 | Fok1-linker-dCas9 |
|---|---|---|
| Fok1-(GGS)x3 | GGS | GGSGGSGGS |
| Fok1-(GGS)x6 | GGS | GGSGGSGGSGGSGGSGGS |
| Fok1-L0 | GGS | - |
| Fok1-L1 | GGS | MKIIEQLPSA |
| Fok1-L2 | GGS | VRHKLKRVGS |
| Fok1-L3 | GGS | VPFLLEPDNINGKTC |
| Fok1-L4 | GGS | GHGTGSTGSGSS |
| Fok1-L5 | GGS | MSRPDPA |
| Fok1-L6 | GGS | GSAGSAAGSGEF |
| Fok1-L7 | GGS | SGSETPGTSESA |
| Fok1-L8 | GGS | SGSETPGTSESATPES |
| Fok1-L9 | GGS | SGSETPGTSESATPEGGSGGS |
| NLS-(GGS) | GGS | GGSM |
| NLS-(GGS)x3 | GGSGGSGGS | GGSM |
| NLS-L1 | VPFLLEPDNINGKTC | GGSM |
| NLS-L2 | GSAGSAAGSGEF | GGSM |
| NLS-L3 | SIVAQLSRPDPA | GGSM |
| wild-type Cas9 | N/A | N/A |
| Cas9 nickase | N/A | N/A |

FIG. 12A

Spacer (bp)

orientation A:

CLTA-1
CCCCAAGTCTAGCAAGCAGGCCAAAGATGTCTCCCGCATGGCCTCAGTCCTCATCTCCCTCAAGCAGG
CCCCAAGTCTAGCAAGCAGGCCA (C1)
                    AGTCCTCATCTCCCTCAAGCAGG (C2)    22

CLTA-2
CCCTGTGGAAACACTACACATCTGCAATATCTTAATCCTACTCAGTGAAGCTCTTCACAGTCATTGG
CCCTGTGGAAACACTACACATCTGC (C3)
                     GTGAAGCTCTTCACAGTCATTGG (C4)    19

HBC
CCGTTACTGCCCTGTGGGGCAAGGTGAACGTGGATGAAGTTGGTGGTGTGAGGCCCTGGGCAGGTTGGTATCAAGGTTACAAGACAGGTTTAAGG
CCGTTACTGCCCTGTGGGGCAAG(H1)   5
CGTGGATGAAGTTGGTGGTGGTGGG (H2)   11
TGAAGTTGGTGGTGAGGCCCTGG (H3)   16
TTGGTGGTGAGGCCCTGGGCAGG (H4)   20
TGGTGAGGCCCTGGGCAGGTTGG (H5)   28
CCCTGGGCAGGTTGGTATCAAGG (H6)
AAGGTTACAAGACAGGTTTAAGG (H7)   47

EMX
CCCTTCTTCTTCTGCTCGGACTCAGGCCCTTCCTCCTCCAGCTTCTGCCGTTTGTACTTTGTCCTCCGGTTCTGG
CCCTTCTTCTTCTGCTCGGACTC (E1)
GCCGTTTGTACTTTGTCCTCCGG (E2)   23
TGTACTTTGTCCTCCGGTTCTGG (E3)   29

VEGF
CCAGGAGCAAACTCCCCCACCCCCTTTCCAAAGCCCATTCCCTTTAGCCAGAGCCGGGGTGTGCAGACGG
CCAGGAGCAAACTCCCCCACCCC (V1)
ATTCCCTTTAGCCAGAGCCGGGG (V2)   14
TCCCTCTTTAGCCAGAGCCGGGG (V3)   16
CCAGAGCCGGGGTGTGCAGACGG (V4)   27

FIG. 13 (continued)

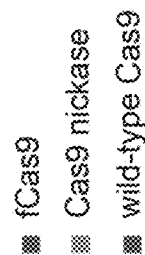
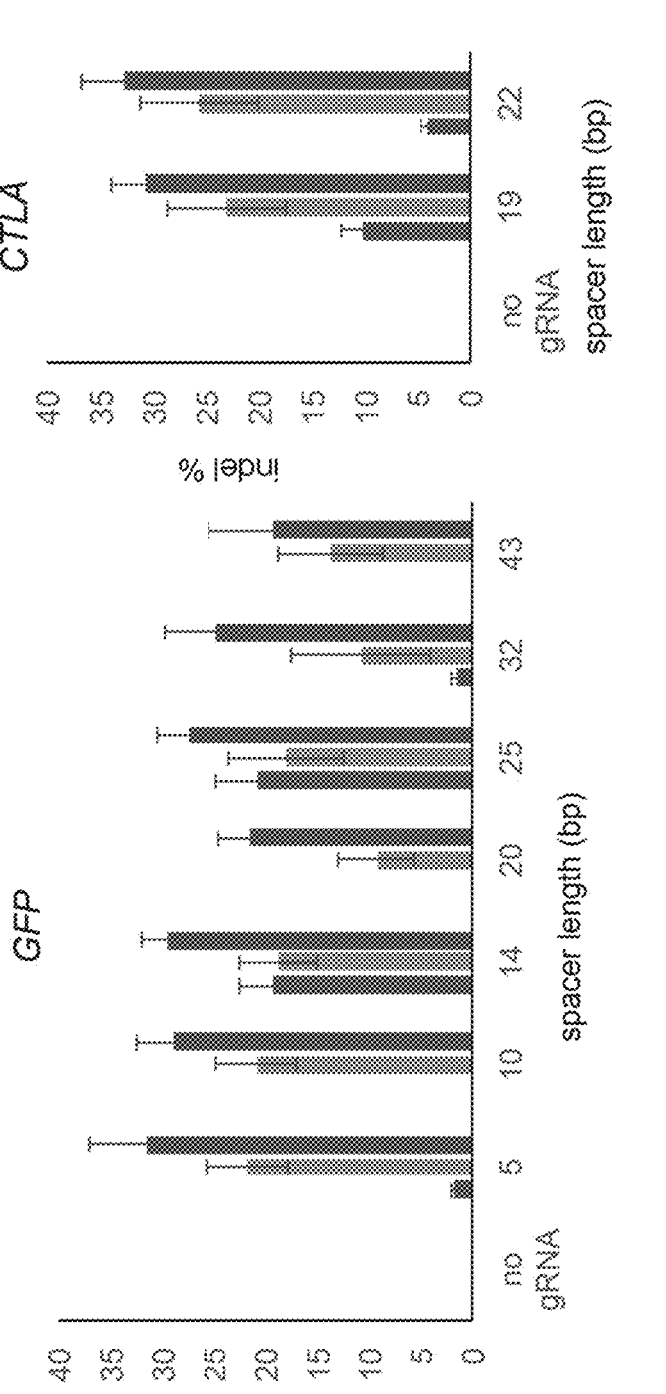
FIG. 14B
FIG. 14A

Wild-type Cas9 nuclease modifications of VEGF on-target site:

Cas9 nickase modifications of VEGF on-target site:

fCas9 nuclease modifications of VEGF on-target site:

FIG. 18A

Wild-type Cas9 nuclease modifications of VEG_OFF1:

Cas9 nickase modifications of VEG_OFF1:

fCas9 nuclease modifications of VEG_OFF1:

FIG. 18B

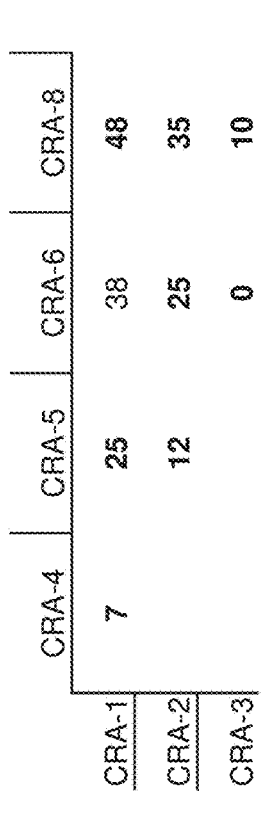

CRA
CCAGCAAGAGAGGCTCCCGAGCGAGCAAGCTCAGTTTACACCCGATCCACTGGGGGAGCAGGAAATATCTGTGGGCTTGTGACACGGACTCAAGTGGGCTGG

CCAGCAAGAGAGGCTCCCGAGCGAG (CRA-1)
CCCGAGCGAGCAAGCTCAGTTTA (CRA-2)
CCCGATCCACTGGGGGAGCAGGAA (CRA-3)
AGTTTACACCCGATCCACTGGGG (CRA-4)
TGGGGGAGCAGGAAATATCTGTGG (CRA-5)
ATATCTGTGGGCTTGTGACACGG (CRA-6)
GCTTGTGACACGGACTCAAGTGG (CRA-8)
TGACACGGACTCAAGTGGGCTGG (CRA-7)

guide RNA spacer length (bp)

|       | CRA-4 | CRA-5 | CRA-6 | CRA-8 |
|-------|-------|-------|-------|-------|
| CRA-1 | 7     | 25    | 38    | 48    |
| CRA-2 |       | 12    | 25    | 35    |
| CRA-3 |       |       | 0     | 10    |

FIG. 19A

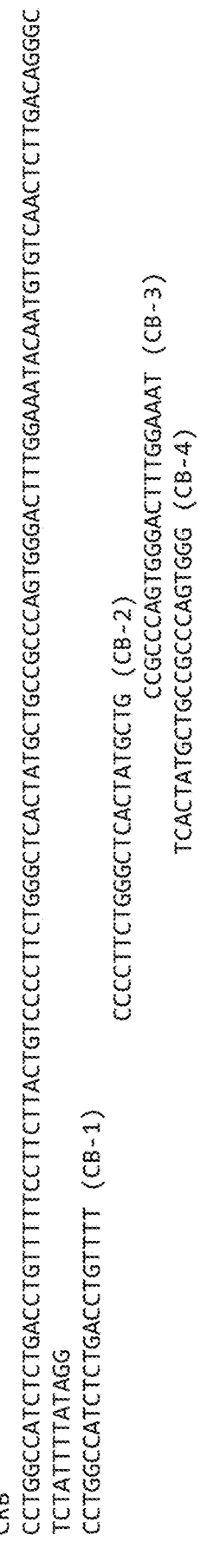

CRB
CCTGGCCATCTCTGACCTGTTTTCCTTCTTTACTGTCCCTTCTGGGCTCACTATGTGCGCGCCCAGTGGGACTTTGGAAATACAATGTGTCAACTCTTGACAGGGC
TCTATTTTATAGG
CCTGGCCATCTCTGACCTGTTTT (CB-1)

CCCCTTCTGGGCTCACTATGCTG (CB-2)
CGGCCCAGTGGGACTTTGGAAAT (CB-3)
TCACTATGCTGCGCCCAGTGGG (CB-4)

CAATGTGTCAACTCTTGACAGGG (CB-5)
TTGACAGGGCTCTATTTTATAGG (CB-6)

guide RNA spacer length (bp)

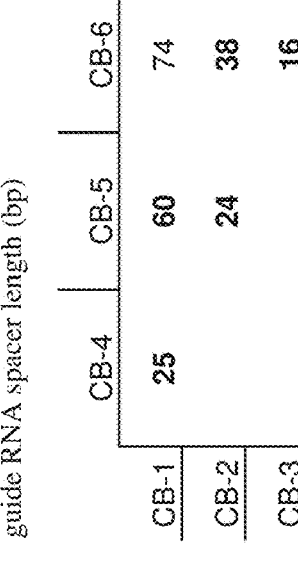

| | CB-4 | CB-5 | CB-6 |
|------|------|------|------|
| CB-1 | 25 | 60 | 74 |
| CB-2 | | 24 | 38 |
| CB-3 | | | 16 |

FIG. 19B

Cas9 VARIANTS AND USES THEREOF

RELATED APPLICATION

This application is a continuation of and claims priority under 35 U.S.C. § 120 to U.S. patent application U.S. Ser. No. 17/103,233, filed Nov. 24, 2020, which is a continuation of and claims priority under 35 U.S.C. § 120 to U.S. patent application U.S. Ser. No. 14/916,681, filed Mar. 4, 2016, which is a national stage filing under 35 U.S.C. 371 of international PCT application, PCT/US2014/054291, filed Sep. 5, 2014, which claims priority under 35 U.S.C. § 365(c) to U.S. application, U.S. Ser. No. 14/320,498, filed Jun. 30, 2014, and to U.S. application, U.S. Ser. No. 14/320,467, filed Jun. 30, 2014, and each of which also claims priority under 35 U.S.C. § 119(e) to U.S. provisional applications, U.S. Ser. No. 61/874,609, filed Sep. 6, 2013; U.S. Ser. No. 61/915,414, filed Dec. 12, 2013; and U.S. Ser. No. 61/980, 315, filed Apr. 16, 2014; each of which is incorporated herein by reference.

GOVERNMENT SUPPORT

This invention was made with government support under HR0011-11-2-0003 awarded by the U.S. Department of Defense. The government has certain rights in the invention.

REFERENCE TO AN ELECTRONIC SEQUENCE LISTING

The contents of the electronic sequence listing (H082470146US07-SEQ-AZW.xml; Size: 501,204 bytes; and Date of Creation: Sep. 30, 2022) is herein incorporated by reference in its entirety.

BACKGROUND OF THE INVENTION

Site-specific endonucleases theoretically allow for the targeted manipulation of a single site within a genome and are useful in the context of gene targeting for therapeutic and research applications. In a variety of organisms, including mammals, site-specific endonucleases have been used for genome engineering by stimulating either non-homologous end joining or homologous recombination. In addition to providing powerful research tools, site-specific nucleases also have potential as gene therapy agents, and two site-specific endonucleases have recently entered clinical trials: (1) CCR5-2246, targeting a human CCR-5 allele as part of an anti-HIV therapeutic approach (NCT00842634, NCT01044654, NCT01252641); and (2) VF24684, targeting the human VEGF-A promoter as part of an anti-cancer therapeutic approach (NCT01082926).

Specific cleavage of the intended nuclease target site without or with only minimal off-target activity is a prerequisite for clinical applications of site-specific endonuclease, and also for high-efficiency genomic manipulations in basic research applications. For example, imperfect specificity of engineered site-specific binding domains has been linked to cellular toxicity and undesired alterations of genomic loci other than the intended target. Most nucleases available today, however, exhibit significant off-target activity, and thus may not be suitable for clinical applications. An emerging nuclease platform for use in clinical and research settings are the RNA-guided nucleases, such as Cas9. While these nucleases are able to bind guide RNAs (gRNAs) that direct cleavage of specific target sites, off-target activity is still observed for certain Cas9:gRNA complexes (Pattanayak et al., "High-throughput profiling of off-target DNA cleavage reveals RNA-programmed Cas9 nuclease specificity." *Nat Biotechnol.* 2013; doi: 10.1038/nbt.2673). Technology for engineering nucleases with improved specificity is therefore needed.

Another class of enzymes useful for targeted genetic manipulations are site-specific recombinases (SSRs). These enzymes perform rearrangements of DNA segments by recognizing and binding to short DNA sequences, at which they cleave the DNA backbone, exchange the two DNA helices involved and rejoin the DNA strands. Such rearrangements allow for the targeted insertion, inversion, excision, or translocation of DNA segments. However, like site-specific endonucleases, naturally-occurring SSRs typically recognize and bind specific consensus sequences, and are thus limited in this respect. Technology for engineering recombinases with altered and/or improved specificity is also needed.

SUMMARY OF THE INVENTION

Some aspects of this disclosure are based on the recognition that the reported toxicity of some engineered site-specific endonucleases is based on off-target DNA cleavage. Thus certain aspects described herein relate to the discovery that increasing the number of sequences (e.g., having a nuclease bind at more than one site at a desired target), and/or splitting the activities (e.g., target binding and target cleaving) of a nuclease between two or more proteins, will increase the specificity of a nuclease and thereby decrease the likelihood of off-target effects. Accordingly, some aspects of this disclosure provide strategies, compositions, systems, and methods to improve the specificity of site-specific nucleases, in particular, RNA-programmable endonucleases, such as Cas9 endonuclease. Certain aspects of this disclosure provide variants of Cas9 endonuclease engineered to have improved specificity.

Other aspects of this disclosure are based on the recognition that site-specific recombinases (SSRs) available today are typically limited to recognizing and binding distinct consensus sequences. Thus certain aspects described herein relate to the discovery that fusions between RNA-programmable (nuclease-inactivated) nucleases (or RNA-binding domains thereof), and a recombinase domain, provide novel recombinases theoretically capable of binding and recombining DNA at any site chosen, e.g., by a practitioner (e.g., sites specified by guide RNAs (gRNAs) that are engineered or selected according the sequence of the area to be recombined). Such novel recombinases are therefore useful, inter alia, for the targeted insertion, deletion, inversion, translocation or other genomic modifications. Thus, also provided are methods of using these inventive recombinase fusion proteins, e.g., for such targeted genomic manipulations.

Accordingly, one embodiment of the disclosure provides fusion proteins and dimers thereof, for example, fusion proteins comprising two domains: (i) a nuclease-inactivated Cas9 domain; and (ii) a nuclease domain (e.g., a monomer of the FokI DNA cleavage domain). See e.g., FIGS. 1A, 6D. The fusion protein may further comprise a nuclear localization signal (NLS) domain, which signals for the fusion proteins to be transported into the nucleus of a cell. In some embodiments, one or more domains of the fusion proteins are separated by a linker. In certain embodiments, the linker is a non-peptidic linker. In certain embodiments, the linker is a peptide linker. In the case of peptide linkers, the peptide linker may comprise an XTEN linker, an amino acid sequence comprising one or more repeats of the tri-peptide GGS, or any sequence as provided in FIG. 12A. In some embodiments, the fusion protein is encoded by a nucleotide sequence set forth as SEQ ID NO:9, SEQ ID NO:10, SEQ ID NO:11, or SEQ ID NO:12, or a variant or fragment of any one of SEQ ID NO:9, SEQ ID NO:10, SEQ ID NO:11, or SEQ ID NO:12. The nuclease-inactivated Cas9 domain is capable of binding a guide RNA (gRNA). In certain embodiments, having dimers of such fusion protein each comprising a gRNA binding two distinct regions of a target nucleic acid provides for improved specificity, for example as compared to monomeric RNA-guided nucleases comprising a single gRNA to direct binding to the target nucleic acid.

According to another aspect of the invention, methods for site-specific DNA cleavage using the inventive Cas9 variants are provided. The methods typically comprise (a) contacting DNA with a fusion protein of the invention (e.g., a fusion protein comprising a nuclease-inactivated Cas9 domain and a FokI DNA cleavage domain), wherein the inactive Cas9 domain binds a gRNA that hybridizes to a region of the DNA; (b) contacting the DNA with a second fusion protein (e.g., a fusion protein comprising a nuclease-inactivated Cas9 and FokI DNA cleavage domain), wherein the inactive Cas9 domain of the second fusion protein binds a second gRNA that hybridizes to a second region of DNA; wherein the binding of the fusion proteins in steps (a) and (b) results in the dimerization of the nuclease domains of the fusion proteins, such that the DNA is cleaved in a region between the bound fusion proteins. In some embodiments, the gRNAs of steps (a) and (b) hybridize to the same strand of the DNA, or the gRNAs of steps (a) and (b) hybridize to opposite strands of the DNA. In some embodiments, the gRNAs of steps (a) and (b) hybridize to regions of the DNA that are no more than 10, no more than 15, no more than 20, no more than 25, no more than 30, no more than 40, no more than 50, no more than 60, no more than 70, no more than 80, no more than 90, or no more than 100 base pairs apart. In some embodiments, the DNA is in a cell, for example, a eukaryotic cell or a prokaryotic cell, which may be in an individual, such as a human.

According to another embodiments, a complex comprising a dimer of fusion proteins of the invention (e.g., a dimer of a fusion protein comprising a nuclease-inactivated Cas9 and a FokI DNA cleavage domain) are provided. In some embodiments, the nuclease-inactivated Cas9 domain of each fusion protein of the dimer binds a single extended gRNA, such that one fusion protein of the dimer binds a portion of the gRNA, and the other fusion protein of the dimer binds another portion of the gRNA. See e.g., FIG. 1B. In some embodiments, the gRNA is at least 50, at least 75, at least 100, at least 150, at least 200, at least 250, or at least 300 nucleotides in length. In some embodiments, the regions of the extended gRNA that hybridize to a target nucleic acid comprise 15-25, 19-21, or 20 nucleotides.

In another embodiment, methods for site-specific DNA cleavage are provided comprising contacting a DNA with a complex of two inventive fusion proteins bound to a single extended gRNA. In some embodiments, the gRNA contains two portions that hybridize to two separate regions of the DNA to be cleaved; the complex binds the DNA as a result of the portions of the gRNA hybridizing to the two regions; and binding of the complex results in dimerization of the nuclease domains of the fusion proteins, such that the domains cleave the DNA in a region between the bound fusion proteins. In some embodiments, the two portions of the gRNA hybridize to the same strand of the DNA. In other embodiments, the two portions of the gRNA hybridize to opposing strands of the DNA. In some embodiments, the two portions of the gRNA hybridize to regions of the DNA that are no more 10, no more than 15, no more than 20, no more than 25, no more than 30, no more than 40, no more than 50, no more than 60, no more than 70, no more than 80, no more than 90, or no more than 100 base pairs apart. In some embodiments, the DNA is in a cell, for example, a eukaryotic cell or a prokaryotic cell, which may be in an individual, such as a human.

According to another embodiment of the invention, split Cas9 proteins (including fusion proteins comprising a split Cas9 protein) comprising fragments of a Cas9 protein are provided. In some embodiments, a protein is provided that includes a gRNA binding domain of Cas9 but does not include a DNA cleavage domain. In other embodiments, proteins comprising a DNA cleavage domain of Cas9, but not a gRNA binding domain, are provided. In some embodiments, a fusion protein comprising two domains: (i) a nuclease-inactivated Cas9 domain, and (ii) a gRNA binding domain of Cas9 are provided, for example, wherein domain (ii) does not include a DNA cleavage domain. See e.g., FIG. 2B. In some embodiments, fusion proteins comprising two domains: (i) a nuclease-inactivated Cas9 domain, and (ii) a DNA cleavage domain are provided, for example, wherein domain (ii) does not include a gRNA binding domain. See e.g., FIG. 2C (fusion protein on right side, comprising a "B" domain). In some embodiments, protein dimers of any of the proteins described herein are provided. For example, in some embodiments, a dimer comprises two halves of a split Cas9 protein, for example, (i) a protein comprising a gRNA binding domain of Cas9, but not a DNA cleavage domain, and (ii) a protein comprising a DNA cleavage domain of Cas9, but not a gRNA binding domain. See e.g., FIG. 2A. In some embodiments, a dimer comprises one half of a split Cas9 protein, and a fusion protein comprising the other half of the split Cas9 protein. See e.g., FIG. 2B. For example, in certain embodiments such a dimer comprises (i) a protein comprising a gRNA binding domain of Cas9, but not a DNA cleavage domain, and (ii) a fusion protein comprising a nuclease-inactivated Cas9 and a DNA cleavage domain. In other embodiments, the dimer comprises (i) a protein comprising a DNA cleavage domain of Cas9, but not a gRNA binding domain, and (ii) a fusion protein comprising a nuclease-inactivated Cas9 and a gRNA binding domain of Cas9. In some embodiments, a dimer is provided that comprises two fusion proteins, each fusion protein comprising a nuclease-inactivated Cas9 and one half of a split Cas9. See e.g., FIG. 2C. For example, in certain embodiments, such a dimer comprises: (i) a fusion protein comprising a nuclease-inactivated Cas9 and a gRNA binding domain of Cas9, and (ii) a fusion protein comprising a nuclease-inactivated Cas9 and a DNA cleavage domain. In some embodiments, any of the provided protein dimers is associated with one or more gRNA(s).

In some embodiments, methods for site-specific DNA cleavage utilizing the inventive protein dimers are provided. For example, in some embodiments, such a method comprises contacting DNA with a protein dimer that comprises (i) a protein comprising a gRNA binding domain of Cas9, but not a DNA cleavage domain, and (ii) a protein comprising a DNA cleavage domain of Cas9, but not a gRNA binding domain, wherein the dimer binds a gRNA that hybridizes to a region of the DNA, and cleavage of the DNA occurs. See e.g., FIG. 2A. In some embodiments, the protein dimer used for site-specific DNA cleavage comprises (i) a protein comprising a gRNA binding domain of Cas9, but not a DNA cleavage domain, and (ii) a fusion protein comprising a nuclease-inactivated Cas9 and a DNA cleavage. See e.g., FIG. 2B. In some embodiments, the dimer used for site-specific DNA cleavage comprises (i) a protein comprising a DNA cleavage domain of Cas9, but not a gRNA binding domain, and (ii) a fusion protein comprising a nuclease-inactivated Cas9 and a gRNA binding domain of Cas9. In some embodiments, the protein dimer binds two gRNAs that hybridize to two regions of the DNA, and cleavage of the DNA occurs. See e.g., FIG. 2B. In some embodiments, the two gRNAs hybridize to regions of the DNA that are no more than 10, no more than 15, no more than 20, no more than 25, no more than 30, no more than 40, no more than 50, no more than 60, no more than 70, no more than 80, no more than 90, or no more than 100 base pairs apart. In some embodiments, the dimer used for site-specific DNA cleavage comprises two fusion proteins: (i) a fusion protein comprising a nuclease-inactivated Cas9 and a gRNA binding domain of Cas9, and (ii) a fusion protein comprising a nuclease-inactivated Cas9 and a DNA cleavage domain. In some embodiments, the protein dimer binds three gRNAs that hybridize to three regions of the DNA, and cleavage of the DNA occurs. Having such an arrangement, e.g., targeting more than one region of a target nucleic acid, for example using dimers associated with more than one gRNA (or a gRNA comprising more than one region that hybridizes to the target) increases the specificity of cleavage as compared to a nuclease binding a single region of a target nucleic acid. In some embodiments, the three gRNAs hybridize to regions of the DNA that are no more than 10, no more than 15, no more than 20, no more than 25, no more than 30, no more than 40, no more than 50, no more than 60, no more than 70, no more than 80, no more than 90, or no more than 100 base pairs apart between the first and second, and the second and third regions. In some embodiments, the DNA is in a cell, for example, a eukaryotic cell or a prokaryotic cell, which may be in an individual, such as a human.

According to another embodiment, minimal Cas9 proteins are provided, for example, wherein the protein comprises N-and/or C-terminal truncations and retains RNA binding and DNA cleavage activity. In some embodiments, the N-terminal truncation removes at least 5, at least 10, at least 15, at least 20, at least 25, at least 40, at least 40, at least 50, at least 75, at least 100, or at least 150 amino acids. In some embodiments, the C-terminal truncation removes at least 5, at least 10, at least 15, at least 20, at least 25, at least 40, at least 40, at least 50, at least 75, at least 100, or at least 150 amino acids. In some embodiments, the minimized Cas9 protein further comprises a bound gRNA.

In some embodiments, methods for site-specific DNA cleavage are provided comprising contacting a DNA with minimized Cas9 protein:gRNA complex.

According to another embodiment, dimers of Cas9 (or fragments thereof) wherein the dimer is coordinated through a single gRNA are provided. In some embodiments, the single gRNA comprises at least two portions that (i) are each able to bind a Cas9 protein and (ii) each hybridize to a target nucleic acid sequence (e.g., DNA sequence). In some embodiments, the portions of the gRNA that hybridize to the target nucleic acid each comprise no more than 5, no more than 10, or no more than 15 nucleotides complementary to the target nucleic acid sequence. In some embodiments, the portions of the gRNA that hybridize to the target nucleic acid are separated by a linker sequence. In some embodiments, the linker sequence hybridizes to the target nucleic acid. See e.g., FIG. 4. In some embodiments, methods for site-specific DNA cleavage are provided comprising contacting DNA with a dimer of Cas9 proteins coordinated through a single gRNA.

According to another embodiment, the disclosure provides fusion proteins and dimers and tetramers thereof, for example, fusion proteins comprising two domains: (i) a nuclease-inactivated Cas9 domain; and (ii) a recombinase catalytic domain. See, e.g., FIG. 5. The recombinase catalytic domain, in some embodiments, is derived from the recombinase catalytic domain of Hin recombinase, Gin recombinase, or Tn3 resolvase. The nuclease-inactivated Cas9 domain is capable of binding a gRNA, e.g., to target the fusion protein to a target nucleic acid sequence. The fusion proteins may further comprise a nuclear localization signal (NLS) domain, which signals for the fusion proteins to be transported into the nucleus of a cell. In some embodiments, one or more domains of the fusion proteins are separated by a linker. In certain embodiments, the linker is a non-peptidic linker. In certain embodiments, the linker is a peptide linker. In the case of peptide linkers, the peptide linker may comprise an XTEN linker, an amino acid sequence comprising one or more repeats of the tri-peptide GGS, or any sequence as provided in FIG. 12A.

In another embodiment, methods for site-specific recombination are provided, which utilize the inventive RNA-guided recombinase fusion proteins described herein. In some embodiments, the method is useful for recombining two separate DNA molecules, and comprises (a) contacting a first DNA with a first RNA-guided recombinase fusion protein, wherein the nuclease-inactivated Cas9 domain binds a first gRNA that hybridizes to a region of the first DNA; (b) contacting the first DNA with a second RNA-guided recombinase fusion protein, wherein the nuclease-inactivated Cas9 domain of the second fusion protein binds a second gRNA that hybridizes to a second region of the first DNA; (c) contacting a second DNA with a third RNA-guided recombinase fusion protein, wherein the nuclease-inactivated Cas9 domain of the third fusion protein binds a third gRNA that hybridizes to a region of the second DNA; and (d) contacting the second DNA with a fourth RNA-guided recombinase fusion protein, wherein the nuclease-inactivated Cas9 domain of the fourth fusion protein binds a fourth gRNA that hybridizes to a second region of the second DNA, wherein the binding of the fusion proteins in steps (a)-(d) results in the tetramerization of the recombinase catalytic domains of the fusion proteins, under conditions such that the DNAs are recombined. In some embodiments, methods for site-specific recombination between two regions of a single DNA molecule are provided. In some embodiments, the method comprises (a) contacting a DNA with a first RNA-guided recombinase fusion protein, wherein the nuclease-inactivated Cas9 domain binds a first gRNA that hybridizes to a region of the DNA; (b) contacting the DNA with a second RNA-guided recombinase fusion protein, wherein the nuclease-inactivated Cas9 domain of the second fusion protein binds a second gRNA that hybridizes to a second region of the DNA; (c) contacting the DNA with a third RNA-guided recombinase fusion protein, wherein the nuclease-inactivated Cas9 domain of the third fusion protein binds a third gRNA that hybridizes to a third region of the DNA; (d) contacting the DNA with a fourth RNA-guided recombinase fusion protein, wherein the nuclease-inactivated Cas9 domain of the fourth fusion protein binds a fourth gRNA that hybridizes to a fourth region of the DNA; wherein the binding of the fusion proteins in steps (a)-(d) results in the tetramerization of the recombinase catalytic domains of the fusion proteins, under conditions such that the DNA is recombined. In some embodiments involving methods for site-specific recombination, gRNAs hybridizing to the same DNA molecule hybridize to opposing strands of the DNA molecule. In some embodiments, e.g., involving site-specific recombination of a single DNA molecule, two gRNAs hybridize to one strand of the DNA, and the other two gRNAs hybridize to the opposing strand. In some embodiments, the gRNAs hybridize to regions of their respective DNAs (e.g., on the same strand) that are no more than 10, no more than 15, no more than 20, no more than 25, no more than 30, no more than 40, no more than 50, no more than 60, no more than 70, no more than 80, no more than 90, or no more than 100 base pairs apart. In some embodiments, the DNA is in a cell, for example, a eukaryotic cell or a prokaryotic cell, which may be in or obtained from an individual, such as a human.

According to another embodiment, polynucleotides are provided, for example, that encode any of the Cas9 proteins described herein (e.g., Cas9 variants, Cas9 dimers, Cas9 fusion proteins, Cas9 fragments, minimized Cas9 proteins, Cas9 variants without a cleavage domain, Cas9 variants without a gRNA domain, Cas9-recombinase fusions, etc.). In some embodiments, polynucleotides encoding any of the gRNAs described herein are provided. In some embodiments, polynucleotides encoding any inventive Cas9 protein described herein and any combination of gRNA(s) as described herein are provided. In some embodiments, vectors that comprise a polynucleotide described herein are provided. In some embodiments, vectors for recombinant protein expression comprising a polynucleotide encoding any of the Cas9 proteins and/or gRNAs described herein are provided. In some embodiments, cells comprising genetic constructs for expressing any of the Cas9 proteins and/or gRNAs described herein are provided.

In some embodiments, kits are provided. For example, kits comprising any of the Cas9 proteins and/or gRNAs described herein are provided. In some embodiments, kits comprising any of the polynucleotides described herein, e.g., those encoding a Cas9 protein and/or gRNA, are provided. In some embodiments, kits comprising a vector for recombinant protein expression, wherein the vectors comprise a polynucleotide encoding any of the Cas9 proteins and/or gRNAs described herein, are provided. In some embodiments, kits comprising a cell comprising genetic constructs for expressing any of the Cas9 proteins and/or gRNAs described herein are provided.

Other advantages, features, and uses of the invention will be apparent from the Detailed Description of Certain Non-Limiting Embodiments of the Invention; the Drawings, which are schematic and not intended to be drawn to scale; and the Claims.

BRIEF DESCRIPTION OF THE DRAWINGS

FIG. 1A. In this embodiment, nuclease-inactivated Cas9 protein is fused to a monomer of the FokI nuclease domain. Double-strand DNA-cleavage is achieved through dimerization of FokI monomers at the target site and is dependent on the simultaneous binding of two distinct Cas9:gRNA complexes. FIG. 1B. In this embodiment, an alternate configuration is provided, wherein two Cas9-FokI fusions are coordinated through the action of a single extended gRNA containing two distinct gRNA motifs. The gRNA motifs comprise regions that hybridize the target in distinct regions, as well as regions that bind each fusion protein. The extended gRNA may enhance cooperative binding and alter the specificity profile of the fusions.

FIG. 2A. In this embodiment, dimeric split Cas9 separates A) gRNA-binding ability from B) dsDNA cleavage. DNA cleavage occurs when both halves of the protein are co-localized to associate and refold into a nuclease-active state. FIG. 2B. In this embodiment, nuclease-inactivated Cas9 mutant is fused to the A-half (or in some embodiments, the B-half) of the split Cas9 nuclease. Upon binding of both the Cas9-A-half (or Cas9-B-half) fusion and the inactive gRNA-binding Cas9 B-half (or A-half, respectively) at the target site, dsDNA is enabled following split protein reassembly. This split Cas9-pairing can use two distinct gRNA-binding Cas9 proteins to ensure the split nuclease-active Cas9 reassembles only on the correct target sequence. FIG. 2C. In this embodiment, nuclease-inactivated Cas9 mutant is fused to the A-half of the split Cas9 nuclease. A separate nuclease-inactivated Cas9 mutant is fused to the B-half of the split Cas9 nuclease. Upon binding of one nuclease-inactivated Cas9 mutant to a gRNA target site and binding of the other nuclease-inactivated Cas9 mutant to a second gRNA target site, the split Cas9 halves can dimerize and bind a third gRNA target to become a fully active Cas9 nuclease that can cleave dsDNA. This split Cas9-pairing uses three distinct gRNA-binding Cas9 proteins to ensure the split nuclease-active Cas9 reassembles only on the correct target sequence. Any other DNA-binding domain in place of the inactive Cas9 (zinc fingers, TALE proteins, etc.) can be used to complete the reassembly of the split Cas9 nuclease.

FIG. 5A Site-specific recombination is achieved through dimerization of the recombinase catalytic domain monomers at the target site, and then tetramerization (FIG. 5B) of two dimers assembled on separate Cas9-recombination sites. The fusion to dCas9:gRNA complexes determines the sequence identity of the flanking target sites while the recombinase catalytic domain determines the identity of the core sequence (the sequence between the two dCas9-binding sites). (FIG. 5B) Recombination proceeds through strand cleavage, exchange, and re-ligation within the dCas9-recombinase tetramer complex.

FIG. 6A Cas9 protein in complex with a guide RNA (gRNA) binds to target DNA. The *S. pyogenes* Cas9 protein recognizes the PAM sequence NGG, initiating unwinding of dsDNA and gRNA:DNA base pairing. FIG. 6B FokI-dCas9 fusion architectures tested. Four distinct configurations of NLS, FokI nuclease, and dCas9 were assembled. Seventeen (17) protein linker variants were also tested. FIG. 6C gRNA target sites tested within GFP. Seven gRNA target sites were chosen to test FokI-dCas9 activity in an orientation in which the PAM is distal from the cleaved spacer sequence (orientation A). Together, these seven gRNAs enabled testing of FokI-dCas9 fusion variants across spacer lengths ranging from 5 to 43 bp. See FIG. 9 for guide RNAs used to test orientation B, in which the PAM is adjacent to the spacer sequence. FIG. 6D Monomers of FokI nuclease fused to dCas9 bind to separate sites within the target locus. Only adjacently bound FokI-dCas9 monomers can assemble a catalytically active FokI nuclease dimer, triggering dsDNA cleavage. The sequences shown in FIG. 6C. are identified as follows: "EmGFP (bp 326-415)" corresponds to SEQ ID NO:204; "G1" corresponds to SEQ ID NO:205; "G2" corresponds to SEQ ID NO:206; "G3" corresponds to SEQ ID NO:207; "G4" corresponds to SEQ ID NO:208; "G5" corresponds to SEQ ID NO:209; "G6" corresponds to SEQ ID NO:210; and "G7" corresponds to SEQ ID NO:211.

FIG. 7A shows a graph depicting GFP disruption activity of fCas9, Cas9 nickase, or wild-type Cas9 with either no gRNA, or gRNA pairs of variable spacer length targeting the GFP gene in orientation A. FIG. 7B is an image of a gel showing Indel modification efficiency from PAGE analysis of a Surveyor cleavage assay of renatured target-site DNA amplified from cells treated with fCas9, Cas9 nickase, or wild-type Cas9 and two gRNAs spaced 14 bp apart targeting the GFP site (gRNAs G3 and G7; FIG. 6C), each gRNA individually, or no gRNAs. The Indel modification percentage is shown below each lane for samples with modification above the detection limit (~2%). FIGS. 7C-G show graphs depicting Indel modification efficiency for (FIG. 7C) two pairs of gRNAs spaced 14 or 25 bp apart targeting the GFP site, (FIG. 7D) one pair of gRNAs spaced 19 bp apart targeting the CLTA site, (FIG. 7E) one pair of gRNAs spaced 23 bp apart targeting the EMX site, (FIG. 7F) one pair of gRNAs spaced 16 bp apart targeting the HBB site, and (FIG. 7G) two pairs of gRNAs spaced 14 or 16 bp apart targeting the VEGF site. Error bars reflect standard error of the mean from three biological replicates performed on different days.

FIG. 8A shows a graph depicting GFP gene disruption by wild-type Cas9, Cas9 nickase, and fCas9 using gRNA pairs in orientation A. High activity of fCas9 requires spacer lengths of ~15 and 25 bp, roughly one DNA helical turn apart. FIG. 8B shows a graph depicting GFP gene disruption using gRNA pairs in orientation B. Cas9 nickase, but not fCas9, accepts either orientation of gRNA pairs. FIG. 8C shows a graph depicting GFP gene disruption by fCas9, but not Cas9 nickase or wild-type Cas9, which depends on the presence of two gRNAs. Four single gRNAs were tested along with three gRNA pairs of varying spacer length. In the presence of gRNA pairs in orientation A with spacer lengths of 14 or 25 bp (gRNAs 1+5, and gRNAs 3+7, respectively), fCas9 is active, but not when a gRNA pair with a 10-bp spacer (gRNAs 1+4) is used. In FIGS. 8A-8C, "no treatment" refers to cells receiving no plasmid DNA. FIGS. 8D-8F show graphs depicting the indel mutation frequency from high-throughput DNA sequencing of amplified genomic on-target sites and off-target sites from human cells treated with fCas9, Cas9 nickase, or wild-type Cas9 and (FIG. 8D) two gRNAs spaced 19 bp apart targeting the CLTA site (gRNAs C1 and C2), (FIG. 8E) two gRNAs spaced 23 bp apart targeting the EMX site (gRNAs E1 and E2), or (FIG. 8F, FIG. 8G) two gRNAs spaced 14 bp apart targeting the VEGF site (gRNAs V1 and V2). (G) shows a graph depicting two in-depth trials to measure genome modification at VEGF off-target site 1. Trial 1 used 150 ng of genomic input DNA and $>8\times10^5$ sequence reads for each sample; trial 2 used 600 ng of genomic input DNA and $>23\times10^5$ sequence reads for each sample. In (D-G), all significant (P value <0.005 Fisher's Exact Test) indel frequencies are shown. P values are listed in Table 3. For (D-F) each on- and off-target sample was sequenced once with >10,000 sequences analyzed per on-target sample and an average of 76,260 sequences analyzed per off-target sample (Table 3). The sequences shown in FIG. 8C are identified as follows, from top to bottom: the sequence found at the top of FIG. 8C corresponds to SEQ ID NO:204; "G1" corresponds to SEQ ID NO:205; "G3" corresponds to SEQ ID NO:207; "G5" corresponds to SEQ ID NO:209; "G7" corresponds to SEQ ID NO:211; "G1+4" corresponds to SEQ ID NO:205 and SEQ ID NO:208; "G1+5" corresponds to SEQ ID NO:205 and SEQ ID NO:209; "G3+7" corresponds to SEQ ID NO:207 and SEQ ID NO:211.

FIG. 10A depicts schematically a HEK293-derived cell line constitutively expressing a genomically integrated EmGFP gene used to test the activity of candidate FokI-dCas9 fusion constructs. Co-transfection of these cells with appropriate nuclease and gRNA expression plasmids leads to dsDNA cleavage within the EmGFP coding sequence, stimulating error-prone NHEJ and generating indels that can disrupt the expression of GFP, leading to loss of cellular fluorescence. The fraction of cells displaying a loss of GFP fluorescence is then quantitated by flow cytometry. FIG. 10B shows typical epifluorescence microscopy images at 200× magnification of EmGFP-HEK293 cells before and after co-transfection with wild-type Cas9 and gRNA expression plasmids.

FIG. 12A-12B shows the optimization of protein linkers in NLS-FokI-dCas9. FIG. 12A shows a table of all linker variants tested. Wild-type Cas9 and Cas9 nickase were included for comparison. The initial active construct NLS-FokI-dCas9 with a $(GGS)_3$ (SEQ ID NO:14) linker between FokI and dCas9 was tested across a range of alternate linkers. The final choice of linkers for fCas9 is highlighted. FIG. 12B shows a graph depicting the activity of FokI-dCas9 fusions with linker variants. Each variant was tested across a range of spacer lengths from 5 to 43 bp using gRNA pair orientation A. A control lacking gRNA ("no gRNA") was included for each separate fusion construct. NLS-FokI-dCas9 variant L8 showed the best activity, approaching the activity of Cas9 nickase. Variants L4 through L9 show peak activity with 14- and 25-bp spacer lengths, suggesting two optimal spacer lengths roughly one helical turn of dsDNA apart. The sequences shown in FIG. 12A are identified as follows: GGSGGSGGS corresponds to SEQ ID NO:14; GGSGGSGGSGGSGGSGGS corresponds to SEQ ID NO:15; MKIIEQLPSA corresponds to SEQ ID NO:22; VRHKLKRVGS corresponds to SEQ ID NO:23; VPFLLEPDNINGKTC corresponds to SEQ ID NO:19; GHGTGSTGSGSS corresponds to SEQ ID NO:24; MSRPDPA corresponds to SEQ ID NO:25; GSAGSAAGSGEF corresponds to SEQ ID NO:20; SGSETPGTSESA corresponds to SEQ ID NO:17; SGSETPGTSESATPES corresponds to SEQ ID NO:16; SGSETPGTSESATPEGGSGGS corresponds to SEQ ID NO:18; GGSM corresponds to SEQ ID NO:301; and SIVAQLSRPDPA corresponds to SEQ ID NO:21.

FIG. 14A-14E shows graphs depicting spacer length preference of genomic DNA modification by fCas9, Cas9 nickase, and wild-type Cas9. Indel modification efficiency for (FIG. 14A) pairs of gRNAs targeting the GFP site, (FIG. 14B) pairs of gRNAs targeting the CLTA site, (FIG. 14C) pairs of gRNAs targeting the EMX site (FIG. 14D) pairs of gRNAs targeting the HBB site, and (FIG. 14E) pairs of gRNAs targeting the VEGF site. Error bars reflect standard error of the mean from three biological replicates performed on different days.

Figures 15A, 15B, 15C:
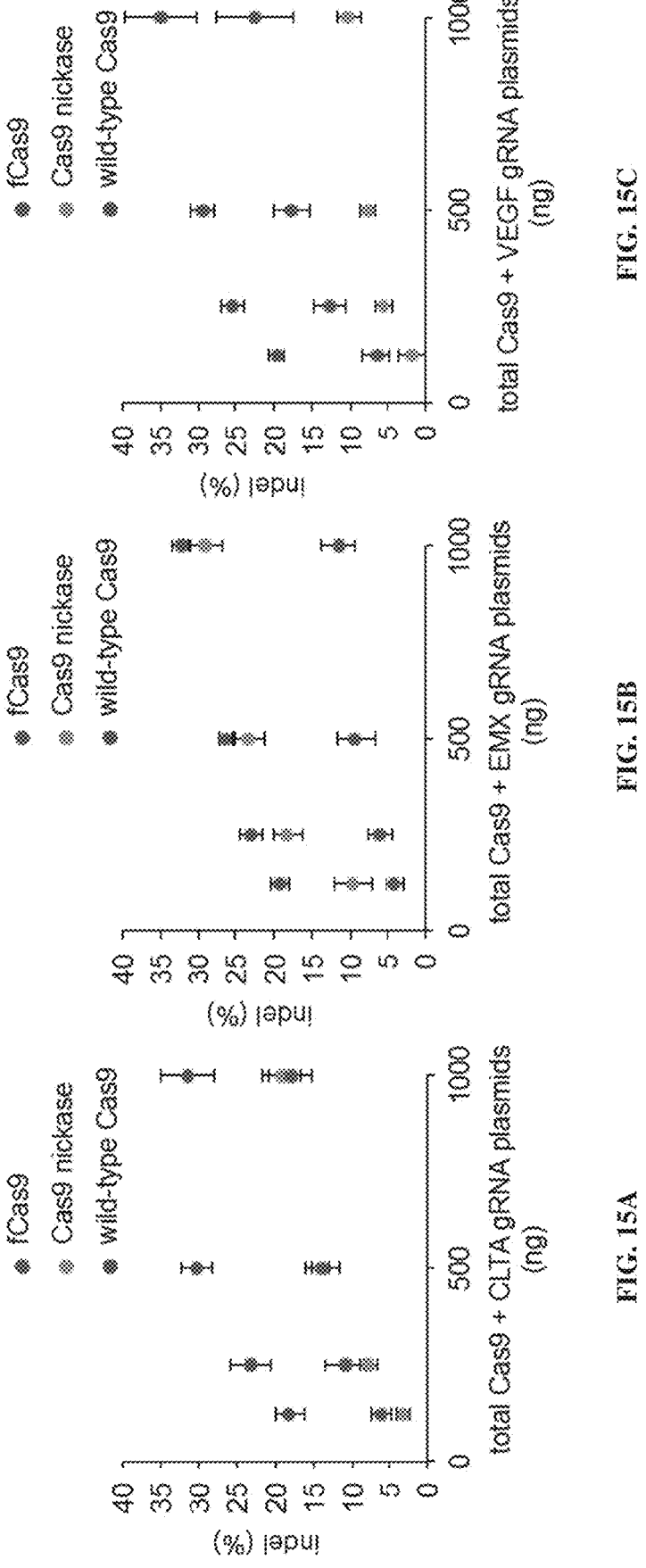

FIG. 15A-15C shows graphs depicting the efficiency of genomic DNA modification by fCas9, Cas9 nickase, and wild-type Cas9 with varying amounts of Cas9 and gRNA expression plasmids. Indel modification efficiency from a Surveyor assay of renatured target-site DNA amplified from a population of cells treated with fCas9, Cas9 nickase, or wild-type Cas9 and two target site gRNAs. Either 700 ng of Cas9 expression plasmid with 250 ng of gRNA expression plasmid (950 ng total), 350 ng of Cas9 expression plasmid with 125 ng of gRNA expression plasmid (475 ng in total), 175 ng of Cas9 expression plasmid with 62.5 ng of gRNA expression plasmid (238 ng in total) or 88 ng of Cas9 expression plasmid with 31 ng of gRNA expression plasmid (119 ng in total) were transfected with an appropriate amount of inert, carrier plasmid to ensure uniform transfection of 950 ng of plasmid across all treatments. Indel modification efficiency for (FIG. 15A) gRNAs spaced 19-bp apart targeting the CLTA site, (FIG. 15B) gRNAs spaced 23 bp apart targeting the EMX site, and (FIG. 15C) gRNAs spaced 14 bp apart targeting the VEGF site. Error bars represent the standard error of the mean from three biological replicates performed on separate days.

Figures 16A, 16B:
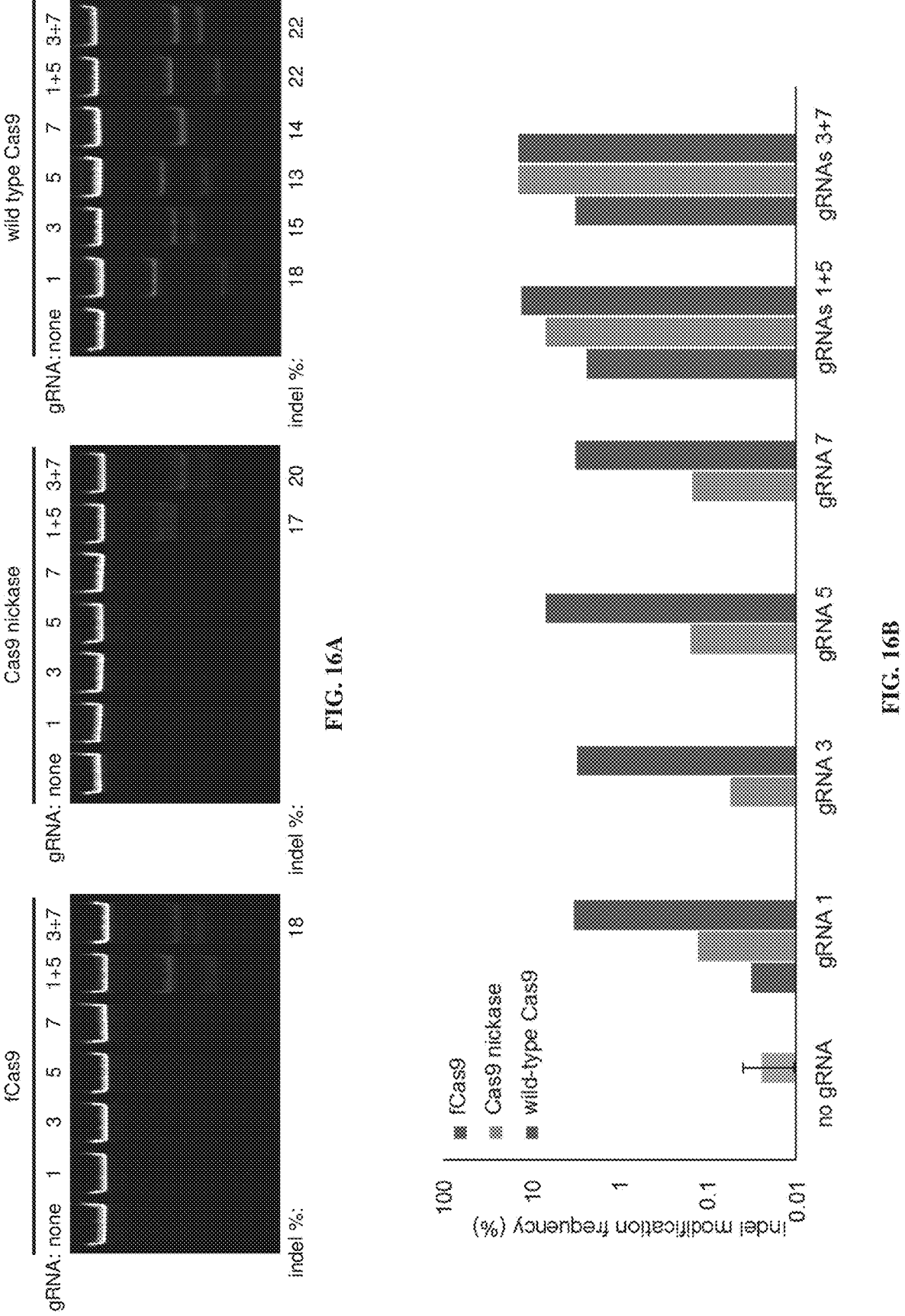

FIG. 16A-16B shows the ability of fCas9, Cas9 nickase, and wild-type Cas9 to modify genomic DNA in the presence of a single gRNA. FIG. 16A shows images of gels depicting Surveyor assay of a genomic GFP target from DNA of cells treated with the indicated combination of Cas9 protein and gRNA(s). Single gRNAs do not induce genome modification at a detectable level (<2% modification) for both fCas9 and Cas9 nickase. Wild-type Cas9 effectively modifies the GFP target for all tested single and paired gRNAs. For both fCas9 and Cas9 nickase, appropriately paired gRNAs induce genome modification at levels comparable to those of wild-type Cas9. FIG. 16B shows a graph depicting the results from sequencing GFP on-target sites amplified from 150 ng genomic DNA isolated from human cells treated with a plasmid expressing either wild-type Cas9, Cas9 nickase, or fCas9 and either a single plasmid expressing a single gRNAs (G1, G3, G5 or G7), or two plasmids each expressing a different gRNA (G1+G5, or G3+G7). As a negative control, transfection and sequencing were performed in triplicate as above without any gRNA expression plasmids. Error bars represent s.d. Sequences with more than one insertion or deletion at the GFP target site (the start of the G1 binding site to the end of the G7 binding site) were considered indels. Indel percentages were calculated by dividing the number of indels by total number of sequences. While wild-type Cas9 produced indels across all gRNA treatments, fCas9 and Cas9 nickase produced indels efficiently (>1%) only when paired gRNAs were present. Indels induced by fCas9 and single gRNAs were not detected above the no-gRNA control, while Cas9 nickase and single gRNAs modified the target GFP sequence at an average rate of 0.12%.

Figure 17:
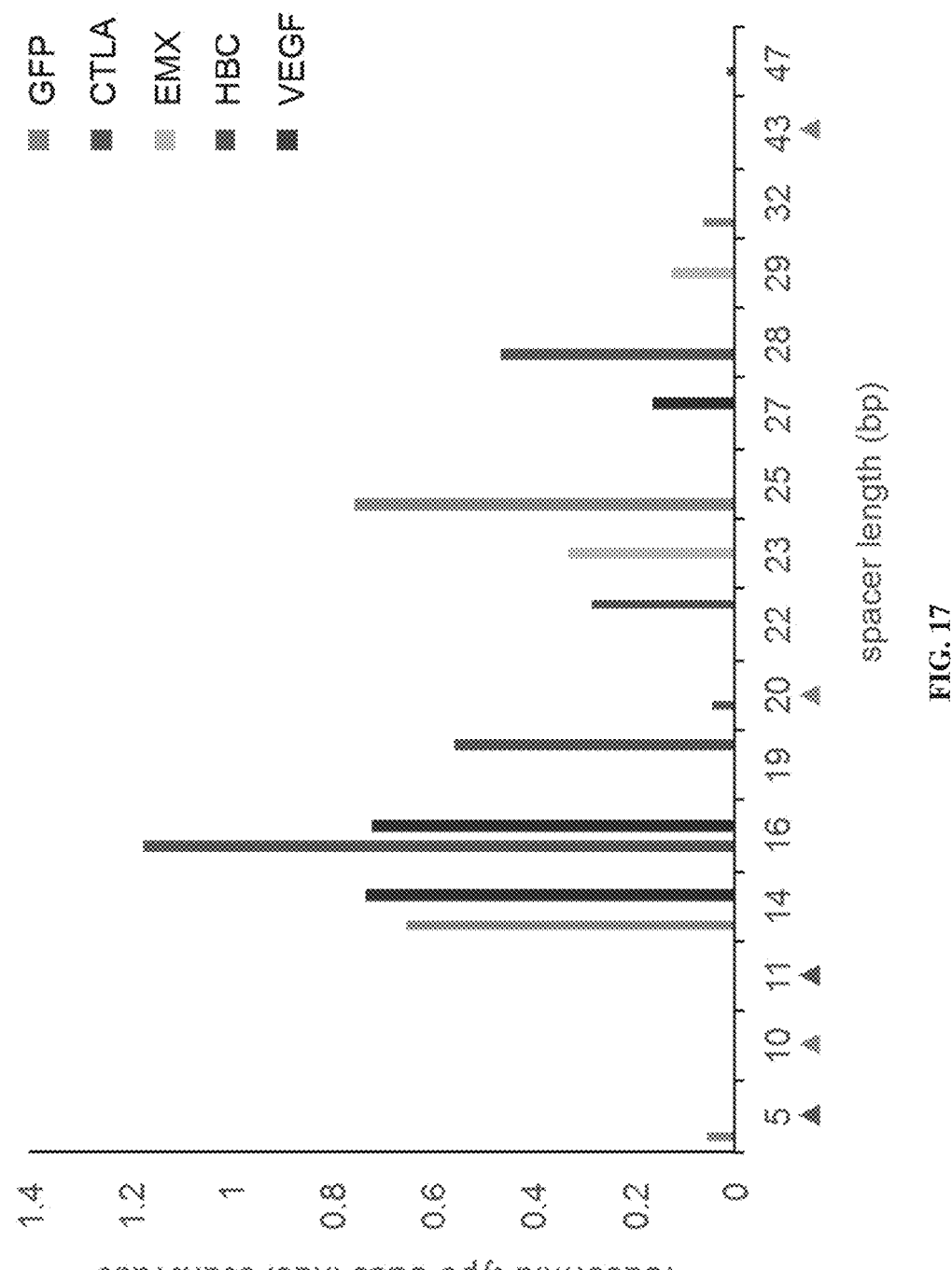

FIG. 17 shows a graph depicting how fCas9 indel frequency of genomic targets reflects gRNA pair spacer length preference. The graph shows the relationship between spacer length (number of bp between two gRNAs) and the indel modification efficiency of fCas9 normalized to the indel modification efficiency of the same gRNAs co-expressed with wild-type Cas9 nuclease. Colored triangles below the X-axis denote spacer lengths that were tested but which yielded no detectable indels for the indicated target gene. These results suggest that fCas9 requires ~15 bp or ~25 bp between half-sites to efficiently cleave DNA.

Figure 18C:
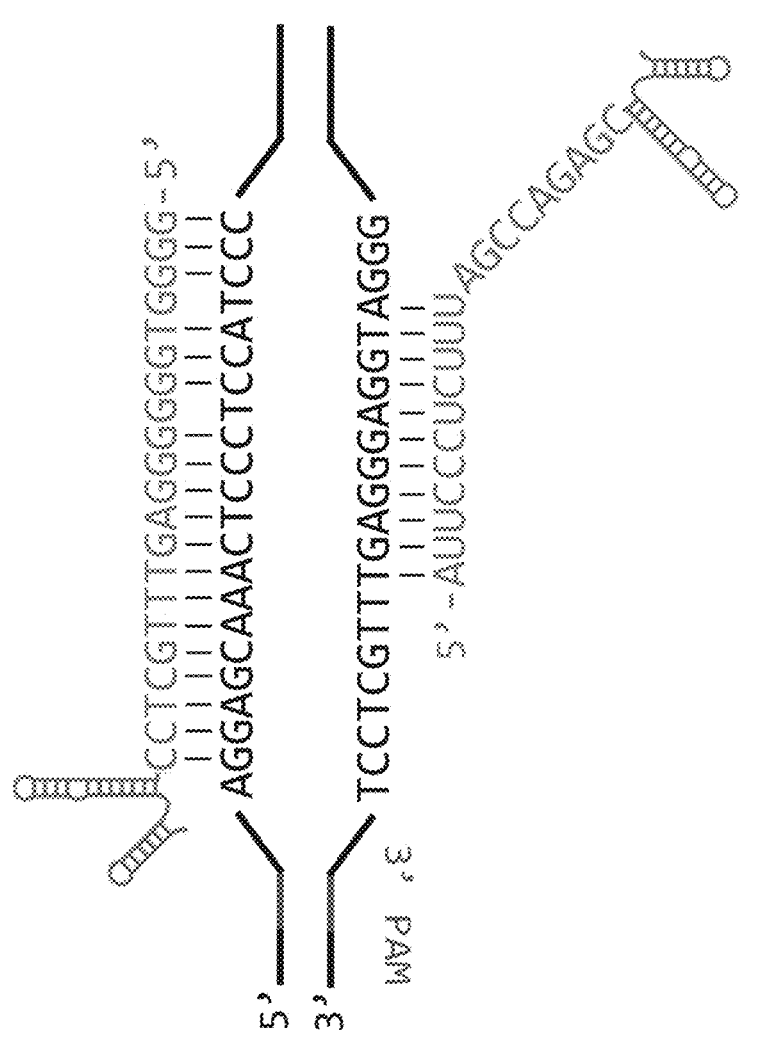

FIG. 18A-18C shows modifications induced by Cas9 nuclease, Cas9 nickases, or fCas9 nucleases at endogenous loci. FIG. 18A shows examples of modified sequences at the VEGF on-target site with wild-type Cas9 nuclease, Cas9 nickases, or fCas9 nucleases and a single plasmid expressing two gRNAs targeting the VEGF on-target site (gRNA V1 and gRNA V2). For each example shown, the unmodified genomic site is the first sequence, followed by the top eight sequences containing deletions. The numbers before each sequence indicate sequencing counts. The gRNA target sites are bold and capitalized. FIG. 18B is an identical analysis as in (A) for VEGF off-target site 1VEG_Off1. FIG. 18C shows the potential binding mode of two gRNAs to VEGF off-target site 1. The top strand is bound in a canonical mode, while the bottom strand binds the second gRNA, gRNA V2, through gRNA:DNA base pairing that includes G:U base pairs. The sequences shown in FIG. 18A are identified, top to bottom, as follows: SEQ ID NO:243; SEQ ID NO:244; SEQ ID NO:245; SEQ ID NO:246; SEQ ID NO:247; SEQ ID NO:248; SEQ ID NO:249; SEQ ID NO:250; SEQ ID NO:251; SEQ ID NO:252; SEQ ID NO:253; SEQ ID NO:254; SEQ ID NO:255; SEQ ID NO:256; SEQ ID NO:257; SEQ ID NO:258; SEQ ID NO:259; SEQ ID NO:260; SEQ ID NO:261; SEQ ID NO:262; SEQ ID NO:263; SEQ ID NO:264; SEQ ID NO:265; SEQ ID NO:266; SEQ ID NO:267; SEQ ID NO:268; and SEQ ID NO:269. The sequences shown in FIG. 18B are identified, top to bottom, as follows: SEQ ID NO:270; SEQ ID NO:271; SEQ ID NO:272; SEQ ID NO:273; SEQ ID NO:274; SEQ ID NO:275; SEQ ID NO:276; SEQ ID NO:277; SEQ ID NO:278; SEQ ID NO:279; SEQ ID NO:280; SEQ ID NO:281; SEQ ID NO:282; SEQ ID NO:283; SEQ ID NO:284; SEQ ID NO:285; SEQ ID NO:286; SEQ ID NO:287; SEQ ID NO:288; SEQ ID NO:289; SEQ ID NO:290; SEQ ID NO:291; SEQ ID NO:292; SEQ ID NO:293; SEQ ID NO:294; SEQ ID NO:295; and SEQ ID NO:296. The sequences shown in FIG. 18C are identified, top to bottom, as follows: SEQ ID NO:297; SEQ ID NO:298; SEQ ID NO:299; and SEQ ID NO:300.

FIG. 19A-19B shows the target DNA sequences in a genomic CCR5 gene. (FIG. 19A) Eight gRNA target sites were identified for testing Cas9 variant (e.g., FokI-dCas9) activity in an orientation in which the PAM is adjacent to the cleaved spacer sequence (orientation A). (FIG. 19B) Six gRNA target sites were identified for testing Cas9 variant (e.g., FokI-dCas9) activity in an orientation in which the PAM is adjacent to the cleaved spacer sequence (orientation B). Together, these fourteen gRNAs enable testing of Cas9 fusion variants across spacer lengths ranging from 0 to 74 bp. The sequences shown in FIG. 19A are identified as follows: "CRA" corresponds to SEQ ID NO:302; "CRA-1" corresponds to SEQ ID NO:303; "CRA-2" corresponds to SEQ ID NO:304; "CRA-3" corresponds to SEQ ID NO:305; "CRA-4" corresponds to SEQ ID NO:306; "CRA-5" corresponds to SEQ ID NO:307; "CRA-6" corresponds to SEQ ID NO:308; "CRA-7" corresponds to SEQ ID NO:309; and "CRA-8" corresponds to SEQ ID NO:310. The sequences shown in FIG. 19B are identified as follows: "CRB" corresponds to SEQ ID NO:311; "CB-1" corresponds to SEQ ID NO:312; "CB-2" corresponds to SEQ ID NO:313; "CB-3" corresponds to SEQ ID NO:314; "CB-4" corresponds to SEQ ID NO:315; "CB-5" corresponds to SEQ ID NO:316; and "CB-6" corresponds to SEQ ID NO:317.

Figure 20:
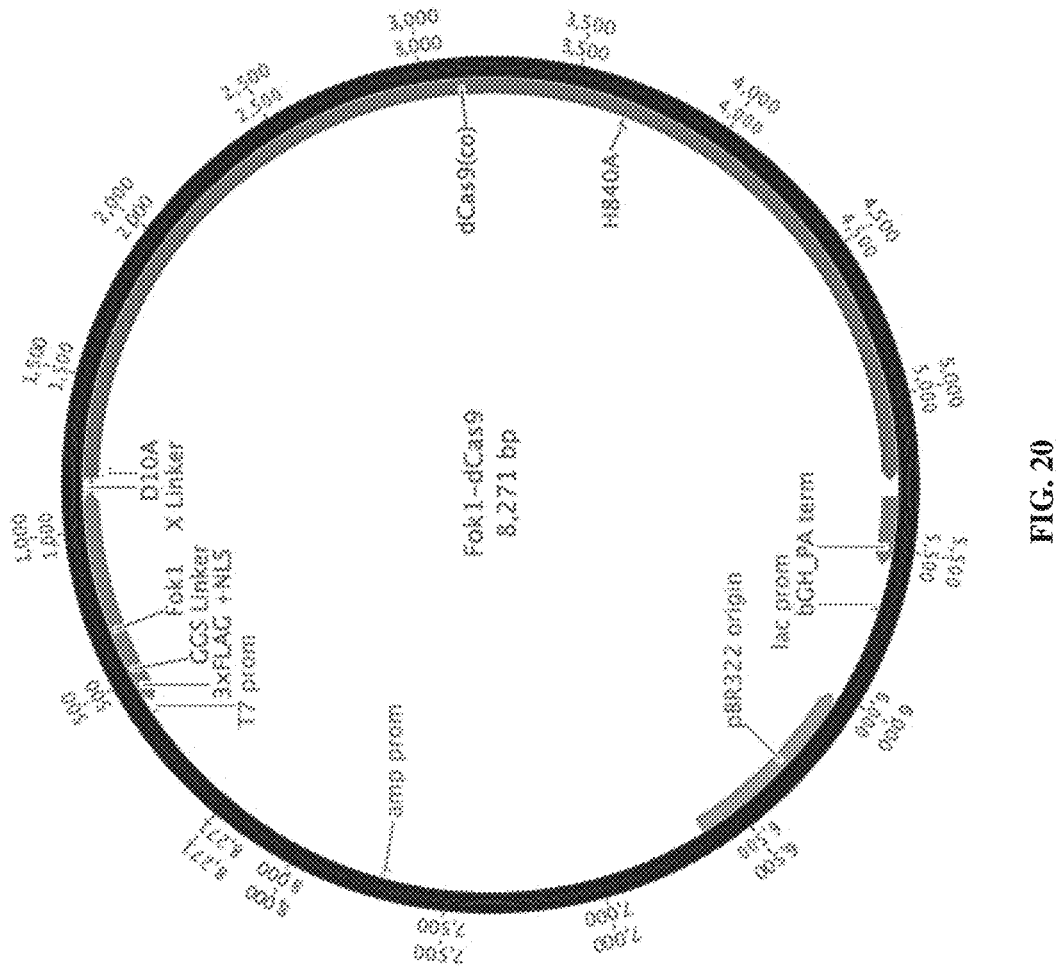

FIG. 20 depicts a vector map detailing an exemplary plasmid containing a Fok1-dCas9 (fCas9) construct.

DEFINITIONS

As used herein and in the claims, the singular forms "a," "an," and "the" include the singular and the plural reference unless the context clearly indicates otherwise. Thus, for example, a reference to "an agent" includes a single agent and a plurality of such agents.

The term "Cas9" or "Cas9 nuclease" refers to an RNA-guided nuclease comprising a Cas9 protein, or a fragment thereof (e.g., a protein comprising an active or inactive DNA cleavage domain of Cas9, and/or the gRNA binding domain of Cas9). A Cas9 nuclease is also referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNA. However, single guide RNAs ("sgRNA", or simply "gNRA") can be engineered so as to incorporate aspects of both the crRNA and tracrRNA into a single RNA species. See e.g., Jinek M., Chylinski K., Fonfara I., Hauer M., Doudna J. A., Charpentier E. *Science* 337:816-821 (2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821(2012), the entire contents of each of which are incorporated herein by reference). Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, a Cas9 nuclease has an inactive (e.g., an inactivated) DNA cleavage domain. A nuclease-inactivated Cas9 protein may interchangeably be referred to as a "dCas9" protein (for nuclease "dead" Cas9). In some embodiments, dCas9 corresponds to, or comprises in part or in whole, the amino acid set forth as SEQ ID NO:5, below. In some embodiments, variants of dCas9 (e.g., variants of SEQ ID NO:5) are provided. For example, in some embodiments, variants having mutations other than D10A and H840A are provided, which e.g., result in nuclease inactivated Cas9 (dCas9). Such mutations, by way of example, include other amino acid substitutions at D10 and H840, or other substitutions within the nuclease domains of Cas9 (e.g., substitutions in the HNH nuclease subdomain and/or the RuvC1 subdomain). In some embodiments, variants or homologues of dCas9 (e.g., variants of SEQ ID NO:5) are provided which are at least about 70% identical, at least about 80% identical, at least about 90% identical, at least about 95% identical, at least about 98% identical, at least about 99% identical, at least about 99.5% identical, or at least about 99.9% to SEQ ID NO:5. In some embodiments, variants of dCas9 (e.g., variants of SEQ ID NO:5) are provided having amino acid sequences which are shorter, or longer than SEQ ID NO:5, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

dCas9 (D10A and H840A):

(SEQ ID NO: 5)

```
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK
```

-continued

```
YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD
```

Methods for generating a Cas9 protein (or a fragment thereof) having an inactive DNA cleavage domain are known (See, e.g., the Examples; and Jinek et al., *Science.* 337:816-821(2012); Qi et al., "Repurposing CRISPR as an RNA-Guided Platform for Sequence-Specific Control of Gene Expression" (2013) *Cell.* 28; 152(5):1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of *S. pyogenes* Cas9 (See e.g., the Examples; and Jinek et al., *Science.* 337:816-821(2012); Qi et al., *Cell.* 28; 152(5):1173-83 (2013)). In some embodiments, proteins comprising fragments of Cas9 are provided. For example, in some embodiments, a protein comprises one of two Cas9 domains: (1) the gRNA binding domain of Cas9; or (2) the DNA cleavage domain of Cas9. In some embodiments, proteins comprising Cas9 or fragments thereof are referred to as "Cas9 variants." A Cas9 variant shares homology to Cas9, or a fragment thereof. For example a Cas9 variant is at least about 70% identical, at least about 80% identical, at least about 90% identical, at least about 95% identical, at least about 98% identical, at least about 99% identical, at least about 99.5% identical, or at least about 99.9% to wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 98% identical, at least about 99% identical, at least about 99.5% identical, or at least about 99.9% to the corresponding fragment of wild type Cas9. In some embodiments, wild type Cas9 corresponds to Cas9 from *Streptococcus pyogenes* (NCBI Reference Sequence: NC_017053.1, SEQ ID NO:1 (nucleotide); SEQ ID NO:2 (amino acid)).

(SEQ ID NO: 1)

ATGGATAAGAAATACTCAATAGGCTTAGATATCGGCACAAATAGCGTCGGATGGGCGGTGATCACTGATG

ATTATAAGGTTCCGTCTAAAAAGTTCAAGGTTCTGGGAAATACAGACCGCCACAGTATCAAAAAAAATCT

TATAGGGGCTCTTTTATTTGGCAGTGGAGAGACAGCGGAAGCGACTCGTCTCAAACGGACAGCTCGTAGA

AGGTATACACGTCGGAAGAATCGTATTTGTTATCTACAGGAGATTTTTTCAAATGAGATGGCGAAAGTAG

ATGATAGTTTCTTTCATCGACTTGAAGAGTCTTTTTTGGTGGAAGAAGACAAGAAGCATGAACGTCATCC

TATTTTTGGAAATATAGTAGATGAAGTTGCTTATCATGAGAAATATCCAACTATCTATCATCTGCGAAAA

AAATTGGCAGATTCTACTGATAAAGCGGATTTGCGCTTAATCTATTTGGCCTTAGCGCATATGATTAAGT

TTCGTGGTCATTTTTTGATTGAGGGAGATTTAAATCCTGATAATAGTGATGTGGACAAACTATTTATCCA

GTTGGTACAAATCTACAATCAATTATTTGAAGAAAACCCTATTAACGCAAGTAGAGTAGATGCTAAAGCG

ATTCTTTCTGCACGATTGAGTAAATCAAGACGATTAGAAAATCTCATTGCTCAGCTCCCCGGTGAGAAGA

GAAATGGCTTGTTTGGGAATCTCATTGCTTTGTCATTGGGATTGACCCCTAATTTTAAATCAAATTTTGA

TTTGGCAGAAGATGCTAAATTACAGCTTTCAAAAGATACTTACGATGATGATTTAGATAATTTATTGGCG

CAAATTGGAGATCAATATGCTGATTTGTTTTTGGCAGCTAAGAATTTATCAGATGCTATTTTACTTTCAG

ATATCCTAAGAGTAAATAGTGAAATAACTAAGGCTCCCCTATCAGCTTCAATGATTAAGCGCTACGATGA

ACATCATCAAGACTTGACTCTTTTAAAAGCTTTAGTTCGACAACAACTTCCAGAAAAGTATAAAGAAATC

TTTTTTGATCAATCAAAAAACGGATATGCAGGTTATATTGATGGGGGAGCTAGCCAAGAAGAATTTTATA

AATTTATCAAACCAATTTTAGAAAAAATGGATGGTACTGAGGAATTATTGGTGAAACTAAATCGTGAAGA

TTTGCTGCGCAAGCAACGGACCTTTGACAACGGCTCTATTCCCCATCAAATTCACTTGGGTGAGCTGCAT

GCTATTTTGAGAAGACAAGAAGACTTTTATCCATTTTTAAAAGACAATCGTGAGAAGATTGAAAAAATCT

TGACTTTTCGAATTCCTTATTATGTTGGTCCATTGGCGCGTGGCAATAGTCGTTTTGCATGGATGACTCG

GAAGTCTGAAGAAACAATTACCCCATGGAATTTTGAAGAAGTTGTCGATAAAGGTGCTTCAGCTCAATCA

TTTATTGAACGCATGACAAACTTTGATAAAAATCTTCCAAATGAAAAAGTACTACCAAAACATAGTTTGC

TTTATGAGTATTTTACGGTTTATAACGAATTGACAAAGGTCAAATATGTTACTGAGGGAATGCGAAAACC

AGCATTTCTTTCAGGTGAACAGAAGAAAGCCATTGTTGATTTACTCTTCAAAACAAATCGAAAAGTAACC

GTTAAGCAATTAAAAGAAGATTATTTCAAAAAAATAGAATGTTTTGATAGTGTTGAAATTTCAGGAGTTG

AAGATAGATTTAATGCTTCATTAGGCGCCTACCATGATTTGCTAAAAATTATTAAAGATAAAGATTTTTT

GGATAATGAAGAAATGAAGATATCTTAGAGGATATTGTTTTAACATTGACCTTATTTGAAGATAGGGGG

ATGATTGAGGAAAGACTTAAAACATATGCTCACCTCTTTGATGATAAGGTGATGAAACAGCTTAAACGTC

GCCGTTATACTGGTTGGGGACGTTTGTCTCGAAAATTGATTAATGGTATTAGGGATAAGCAATCTGGCAA

AACAATATTAGATTTTTTGAAATCAGATGGTTTTGCCAATCGCAATTTTATGCAGCTGATCCATGATGAT

AGTTTGACATTTAAAGAAGATATTCAAAAAGCACAGGTGTCTGGACAAGGCCATAGTTTACATGAACAGA

TTGCTAACTTAGCTGGCAGTCCTGCTATTAAAAAAGGTATTTTACAGACTGTAAAAATTGTTGATGAACT

GGTCAAAGTAATGGGGCATAAGCCAGAAAATATCGTTATTGAAATGGCACGTGAAAATCAGACAACTCAA

AAGGGCCAGAAAAATTCGCGAGAGCGTATGAAACGAATCGAAGAAGGTATCAAAGAATTAGGAAGTCAGA

TTCTTAAAGAGCATCCTGTTGAAAATACTCAATTGCAAAATGAAAAGCTCTATCTCTATTATCTACAAAA

TGGAAGAGACATGTATGTGGACCAAGAATTAGATATTAATCGTTTAAGTGATTATGATGTCGATCACATT

GTTCCACAAAGTTTCATTAAAGACGATTCAATAGACAATAAGGTACTAACGCGTTCTGATAAAAATCGTG

GTAAATCGGATAACGTTCCAAGTGAAGAAGTAGTCAAAAAGATGAAAAACTATTGGAGACAACTTCTAAA

CGCCAAGTTAATCACTCAACGTAAGTTTGATAATTTAACGAAAGCTGAACGTGGAGGTTTGAGTGAACTT

GATAAAGCTGGTTTTATCAAACGCCAATTGGTTGAAACTCGCCAAATCACTAAGCATGTGGCACAAATTT

-continued

TGGATAGTCGCATGAATACTAAATACGATGAAAATGATAAACTTATTCGAGAGGTTAAAGTGATTACCTT

AAAATCTAAATTAGTTTCTGACTTCCGAAAAGATTTCCAATTCTATAAAGTACGTGAGATTAACAATTAG

CATCATGCCCATGATGCGTATCTAAATGCCGTCGTTGGAACTGCTTTGATTAAGAAATATCCAAAACTTG

AATCGGAGTTTGTCTATGGTGATTATAAAGTTTATGATGTTCGTAAAATGATTGCTAAGTCTGAGCAAGA

AATAGGCAAAGCAACCGCAAAATATTTCTTTTACTCTAATATCATGAACTTCTTCAAAACAGAAATTACA

CTTGCAAATGGAGAGATTCGCAAACGCCCTCTAATCGAAACTAATGGGGAAACTGGAGAAATTGTCTGGG

ATAAAGGGCGAGATTTTGCCACAGTGCGCAAAGTATTGTCCATGCCCCAAGTCAATATTGTCAAGAAAAC

AGAAGTACAGACAGGCGGATTCTCCAAGGAGTCAATTTTACCAAAAAGAAATTCGGACAAGCTTATTGCT

CGTAAAAAAGACTGGGATCCAAAAAAATATGGTGGTTTTGATAGTCCAACGGTAGCTTATTCAGTCCTAG

TGGTTGCTAAGGTGGAAAAAGGGAAATCGAAGAAGTTAAAATCCGTTAAAGAGTTACTAGGGATCACAAT

TATGGAAAGAAGTTCCTTTGAAAAAAATCCGATTGACTTTTTAGAAGCTAAAGGATATAAGGAAGTTAAA

AAAGACTTAATCATTAAACTACCTAAATATAGTCTTTTTGAGTTAGAAAACGGTCGTAAACGGATGCTGG

CTAGTGCCGGAGAATTACAAAAAGGAAATGAGCTGGCTCTGCCAAGCAAATATGTGAATTTTTTATATTT

AGCTAGTCATTATGAAAAGTTGAAGGGTAGTCCAGAAGATAACGAACAAAAACAATTGTTTGTGGAGCAG

CATAAGCATTATTTAGATGAGATTATTGAGCAAATCAGTGAATTTTCTAAGCGTGTTATTTTAGCAGATG

CCAATTTAGATAAAGTTCTTAGTGCATATAACAAACATAGAGACAAACCAATACGTGAACAAGCAGAAAA

TATTATTCATTTATTTACGTTGACGAATCTTGGAGCTCCCGCTGCTTTTAAATATTTTGATACAACAATT

GATCGTAAACGATATACGTCTACAAAAGAAGTTTTAGATGCCACTCTTATCCATCAATCCATCACTGGTC

TTTATGAAACACGCATTGATTTGAGTCAGCTAGGAGGTGACTGA (SEQ ID NO: 2)
MDKKYSIGLDIGTNSVGWAVITDDYKVPSKKFKVLGNTDRHSIKKNLIGALLFGSGETAEATRLKRTARR

RYTRRKNRICYLQEIFSNEMAKVDDSFFHRLEESFLVEEDKKHERHPIFGNIVDEVAYHEKYPTIYHLRK

KLADSTDKADLRLIYLALAHMIKFRGHFLIEGDLNPDNSDVDKLFIQLVQIYNQLFEENPINASRVDAKA

ILSARLSKSRRLENLIAQLPGEKRNGLFGNLIALSLGLTPNFKSNFDLAEDAKLQLSKDTYDDDLDNLLA

QIGDQYADLFLAAKNLSDAILLSDILRVNSEITKAPLSASMIKRYDEHHQDLTLLKALVRQQLPEKYKEI

FFDQSKNGYAGYIDGGASQEEFYKFIKPILEKMDGTEELLVKLNREDLLRKQRTFDNGSIPHQIHLGELH

AILRRQEDFYPFLKDNREKIEKILTFRIPYYVGPLARGNSRFAWMTRKSEETITPWNFEEVVDKGASAQS

FIERMTNFDKNLPNEKVLPKHSLLYEYFTVYNELTKVKYVTEGMRKPAFLSGEQKKAIVDLLFKTNRKVT

VKQLKEDYFKKIECFDSVEISGVEDRFNASLGAYHDLLKIIKDKDFLDNEENEDILEDIVLTLTLFEDRG

MIEERLKTYAHLFDDKVMKQLKRRRYTGWGRLSRKLINGIRDKQSGKTILDFLKSDGFANRNFMQLIHDD

SLTFKEDIQKAQVSGQGHSLHEQIANLAGSPAIKKGILQTVKIVDELVKVMGHKPENIVIEMARENQTTQ

KGQKNSRERMKRIEEGIKELGSQILKEHPVENTQLQNEKLYLYYLQNGRDMYVDQELDINRLSDYDVDHI

VPQSFIKDDSIDNKVLTRSDKNRGKSDNVPSEEVVKKMKNYWRQLLNAKLITQRKFDNLTKAERGGLSEL

DKAGFIKRQLVETRQITKHVAQILDSRMNTKYDENDKLIREVKVITLKSKLVSDFRKDFQFYKVREINNY

HHAHDAYLNAVVGTALIKKYPKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQTGGFSKESILPKRNSDKLIA

RKKDWDPKKYGGFDSPTVAYSVLVVAKVEKGKSKKLKSVKELLGITIMERSSFEKNPIDFLEAKGYKEVK

KDLIIKLPKYSLFELENGRKRMLASAGELQKGNELALPSKYVNFLYLASHYEKLKGSPEDNEQKQLFVEQ

HKHYLDEIIEQISEFSKRVILADANLDKVLSAYNKHRDKPIREQAENIIHLFTLTNLGAPAAFKYFDTTI

DRKRYTSTKEVLDATLIHQSITGLYETRIDLSQLGGD

In some embodiments, wild type Cas9 corresponds to, or comprises, SEQ ID NO:3 (nucleotide) and/or SEQ ID NO:4 (amino acid).

```
                                                       (SEQ ID NO: 3)
ATGGATAAAAAGTATTCTATTGGTTTAGACATCGGCACTAATTCCGTTGGATGGGCTGTCATAACCGATGAATAC

AAAGTACCTTCAAAGAAATTTAAGGTGTTGGGGAACACAGACCGTCATTCGATTAAAAAGAATCTTATCGGTGCC

CTCCTATTCGATAGTGGCGAAACGGCAGAGGCGACTCGCCTGAAACGAACCGCTCGGAGAAGGTATACACGTCGC

AAGAACCGAATATGTTACTTACAAGAAATTTTTAGCAATGAGATGGCCAAAGTTGACGATTCTTTCTTTCACCGT

TTGGAAGAGTCCTTCCTTGTCGAAGAGGACAAGAAACATGAACGGCACCCCATCTTTGGAAACATAGTAGATGAG

GTGGCATATCATGAAAAGTACCCAACGATTTATCACCTCAGAAAAAAGCTAGTTGACTCAACTGATAAAGCGGAC

CTGAGGTTAATCTACTTGGCTCTTGCCCATATGATAAAGTTCCGTGGGCACTTTCTCATTGAGGGTGATCTAAAT

CCGGACAACTCGGATGTCGACAAACTGTTCATCCAGTTAGTACAAACCTATAATCAGTTGTTTGAAGAGAACCCT

ATAAATGCAAGTGGCGTGGATGCGAAGGCTATTCTTAGCGCCCGCCTCTCTAAATCCCGACGGCTAGAAAACCTG

ATCGCACAATTACCCGGAGAGAAGAAAAATGGGTTGTTCGGTAACCTTATAGCGCTCTCACTAGGCCTGACACCA

AATTTTAAGTCGAACTTCGACTTAGCTGAAGATGCCAAATTGCAGCTTAGTAAGGACACGTACGATGACGATCTC

GACAATCTACTGGCACAAATTGGAGATCAGTATGCGGACTTATTTTTGGCTGCCAAAAACCTTAGCGATGCAATC

CTCCTATCTGACATACTGAGAGTTAATACTGAGATTACCAAGGCGCCGTTATCCGCTTCAATGATCAAAAGGTAC

GATGAACATCACCAAGACTTGACACTTCTCAAGGCCCTAGTCCGTCAGCAACTGCCTGAGAAATATAAGGAAATA

TTCTTTGATCAGTCGAAAAACGGGTACGCAGGTTATATTGACGGCGGAGCGAGTCAAGAGGAATTCTACAAGTTT

ATCAAACCCATATTAGAGAAGATGGATGGGACGGAAGAGTTGCTTGTAAAACTCAATCGCGAAGATCTACTGCGA

AAGCAGCGGACTTTCGACAACGGTAGCATTCCACATCAAATCCACTTAGGCGAATTGCATGCTATACTTAGAAGG

CAGGAGGATTTTTATCCGTTCCTCAAAGACAATCGTGAAAAGATTGAGAAAATCCTAACCTTTCGCATACCTTAC

TATGTGGGACCCCTGGCCCGAGGGAACTCTCGGTTCGCATGGATGACAAGAAAGTCCGAAGAAACGATTACTCCA

TGGAATTTTGAGGAAGTTGTCGATAAAGGTGCGTCAGCTCAATCGTTCATCGAGAGGATGACCAACTTTGACAAG

AATTTACCGAACGAAAAGTATTGCCTAAGCACAGTTTACTTTACGAGTATTTCACAGTGTACAATGAACTCACG

AAAGTTAAGTATGTCACTGAGGGCATGCGTAAACCCGCCTTTCTAAGCGGAGAACAGAAGAAAGCAATAGTAGAT

CTGTTATTCAAGACCAACCGCAAAGTGACAGTTAAGCAATTGAAAGAGGACTACTTTAAGAAAATTGAATGCTTC

GATTCTGTCGAGATCTCCGGGGTAGAAGATCGATTTAATGCGTCACTTGGTACGTATCATGACCTCCTAAAGATA

ATTAAAGATAAGGACTTCCTGGATAACGAAGAGAATGAAGATATCTTAGAAGATATAGTGTTGACTCTTACCCTC

TTTGAAGATCGGGAAATGATTGAGGAAAGACTAAAAACATACGCTCACCTGTTCGACGATAAGGTTATGAAACAG

TTAAAGAGGCGTCGCTATACGGGCTGGGGACGATTGTCGCGGAAACTTATCAACGGGATAAGAGACAAGCAAAGT

GGTAAAACTATTCTCGATTTTCTAAAGAGCGACGGCTTCGCCAATAGGAACTTTATGCAGCTGATCCATGATGAC

TCTTTAACCTTCAAAGAGGATATACAAAAGGCACAGGTTTCCGGACAAGGGGACTCATTGCACGAACATATTGCG

AATCTTGCTGGTTCGCCAGCCATCAAAAAGGGCATACTCCAGACAGTCAAAGTAGTGGATGAGCTAGTTAAGGTC

ATGGGACGTCACAAACCGGAAAACATTGTAATCGAGATGGCACGCGAAAATCAAACGACTCAGAAGGGGCAAAAA

AACAGTCGAGAGCGGATGAAGAGAATAGAAGAGGGTATTAAAGAACTGGGCAGCCAGATCTTAAAGGAGCATCCT

GTGGAAAATACCCAATTGCAGAACGAGAAACTTTACCTCTATTACCTACAAAATGGAAGGGACATGTATGTTGAT

CAGGAACTGGACATAAACCGTTTATCTGATTACGACGTCGATCACATTGTACCCCAATCCTTTTTGAAGGACGAT

TCAATCGACAATAAAGTGCTTACACGCTCGGATAAGAACCGAGGGAAAGTGACAATGTTCCAAGCGAGGAAGTC

GTAAAGAAAATGAAGAACTATTGGCGGCAGCTCCTAAATGCGAAACTGATAACGCAAAGAAAGTTCGATAACTTA

ACTAAAGCTGAGAGGGGTGGCTTGTCTGAACTTGACAAGGCCGGATTTATTAAACGTCAGCTCGTGGAAACCCGC

CAAATCACAAAGCATGTTGCACAGATACTAGATTCCCGAATGAATACGAAATACGACGAGAACGATAAGCTGATT
```

-continued

CGGGAAGTCAAAGTAATCACTTTAAAGTCAAAATTGGTGTCGGACTTCAGAAAGGATTTTCAATTCTATAAAGTT

AGGGAGATAAATAACTACCACCATGCGCACGACGCTTATCTTAATGCCGTCGTAGGGACCGCACTCATTAAGAAA

TACCCGAAGCTAGAAAGTGAGTTTGTGTATGGTGATTACAAAGTTTATGACGTCCGTAAGATGATCGCGAAAAGC

GAACAGGAGATAGGCAAGGCTACAGCCAAATACTTCTTTTATTCTAACATTATGAATTTCTTTAAGACGGAAATC

ACTCTGGCAAACGGAGAGATACGCAAACGACCTTTAATTGAAACCAATGGGGAGACAGGTGAAATCGTATGGGAT

AAGGGCCGGGACTTCGCGACGGTGAGAAAAGTTTTGTCCATGCCCCAAGTCAACATAGTAAAGAAAACTGAGGTG

CAGACCGGAGGGTTTTCAAAGGAATCGATTCTTCCAAAAAGGAATAGTGATAAGCTCATCGCTCGTAAAAAGGAC

TGGGACCCGAAAAAGTACGGTGGCTTCGATAGCCCTACAGTTGCCTATTCTGTCCTAGTAGTGGCAAAAGTTGAG

AAGGGAAAATCCAAGAAACTGAAGTCAGTCAAAGAATTATTGGGGATAACGATTATGGAGCGCTCGTCTTTTGAA

AAGAACCCCATCGACTTCCTTGAGGCGAAAGGTTACAAGGAAGTAAAAAAGGATCTCATAATTAAACTACCAAAG

TATAGTCTGTTTGAGTTAGAAAATGGCCGAAAACGGATGTTGGCTAGCGCCGGAGAGCTTCAAAAGGGGAACGAA

CTCGCACTACCGTCTAAATACGTGAATTTCCTGTATTTAGCGTCCCATTACGAGAAGTTGAAAGGTTCACCTGAA

GATAACGAACAGAAGCAACTTTTTGTTGAGCAGCACAAACATTATCTCGACGAAATCATAGAGCAAATTTCGGAA

TTCAGTAAGAGAGTCATCCTAGCTGATGCCAATCTGGACAAAGTATTAAGCGCATACAACAAGCACAGGGATAAA

CCCATACGTGAGCAGGCGGAAAATATTATCCATTTGTTTACTCTTACCAACCTCGGCGCTCCAGCCGCATTCAAG

TATTTTGACACAACGATAGATCGCAAACGATACACTTCTACCAAGGAGGTGCTAGACGCGACACTGATTCACCAA

TCCATCACGGGATTATATGAAACTCGGATAGATTTGTCACAGCTTGGGGGTGACGGATCCCCCAAGAAGAAGAGG

AAAGTCTCGAGCGACTACAAAGACCATGACGGTGATTATAAAGATCATGACATCGATTACAAGGATGACGATGAC

AAGGCTGCAGGA (SEQ ID NO: 4)
MDKKYSIGLAIGTNSVGWAVITDEYKVPSKKFKVLGNTDRHSIKKNLIGALLFDSGETAEATRLKRTARRRYTRR

KNRICYLQEIFSNEMAKVDDSFFHRLEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENPINASGVDAKAILSARLSKSRRLENL

IAQLPGEKKNGLFGNLIALSLGLTPNFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEIFFDQSKNGYAGYIDGGASQEEFYKF

IKPILEKMDGTEELLVKLNREDLLRKQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDKNLPNEKVLPKHSLLYEYFTVYNELT

KVKYVTEGMRKPAFLSGEQKKAIVDLLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQLKRRYTGWGRLSRKLINGIRDKQS

GKTILDFLKSDGFANRNFMQLIHDDSLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHPVENTQLQNEKLYLYYLQNGRDMYVD

QELDINRLSDYDVDHIVPQSFLKDDSIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKD

WDPKKYGGFDSPTVAYSVLVVAKVEKGKSKKLKSVKELLGITIMERSSFEKNPIDFLEAKGYKEVKKDLIIKLPK

YSLFELENGRKRMLASAGELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRKRYTSTKEVLDATLIHQ

SITGLYETRIDLSQLGGD

In some embodiments, Cas9 refers to Cas9 from: *Coryne-bacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisl* (NCBI Ref: NC_018721.1); *Streptococcus thermophilus* (NCBI Ref: YP_820832.1), *Listeria innocua* (NCBI Ref: NP_472073.1), *Campylobacter jejuni* (NCBI Ref: YP_002344900.1) or *Neisseria. meningitidis* (NCBI Ref: YP_002342100.1).

The terms "conjugating," "conjugated," and "conjuga-tion" refer to an association of two entities, for example, of two molecules such as two proteins, two domains (e.g., a binding domain and a cleavage domain), or a protein and an agent, e.g., a protein binding domain and a small molecule. In some aspects, the association is between a protein (e.g., RNA-programmable nuclease) and a nucleic acid (e.g., a guide RNA). The association can be, for example, via a direct or indirect (e.g., via a linker) covalent linkage. In some embodiments, the association is covalent. In some embodiments, two molecules are conjugated via a linker connecting both molecules. For example, in some embodi-ments where two proteins are conjugated to each other, e.g., a binding domain and a cleavage domain of an engineered nuclease, to form a protein fusion, the two proteins may be conjugated via a polypeptide linker, e.g., an amino acid sequence connecting the C-terminus of one protein to the N-terminus of the other protein.

The term "consensus sequence," as used herein in the context of nucleic acid sequences, refers to a calculated sequence representing the most frequent nucleotide residues found at each position in a plurality of similar sequences. Typically, a consensus sequence is determined by sequence alignment in which similar sequences are compared to each other and similar sequence motifs are calculated. In the context of nuclease target site sequences, a consensus sequence of a nuclease target site may, in some embodi-ments, be the sequence most frequently bound, or bound with the highest affinity, by a given nuclease. In the context of recombinase target site sequences, a consensus sequence of a recombinase target site may, in some embodiments, be the sequence most frequently bound, or bound with the highest affinity, by a given recombinase.

The term "engineered," as used herein refers to a protein molecule, a nucleic acid, complex, substance, or entity that has been designed, produced, prepared, synthesized, and/or manufactured by a human. Accordingly, an engineered prod-uct is a product that does not occur in nature.

The term "effective amount," as used herein, refers to an amount of a biologically active agent that is sufficient to elicit a desired biological response. For example, in some embodiments, an effective amount of a nuclease may refer to the amount of the nuclease that is sufficient to induce cleavage of a target site specifically bound and cleaved by the nuclease. In some embodiments, an effective amount of a recombinase may refer to the amount of the recombinase that is sufficient to induce recombination at a target site specifically bound and recombined by the recombinase. As will be appreciated by the skilled artisan, the effective amount of an agent, e.g., a nuclease, a recombinase, a hybrid protein, a fusion protein, a protein dimer, a complex of a protein (or protein dimer) and a polynucleotide, or a poly-nucleotide, may vary depending on various factors as, for example, on the desired biological response, the specific allele, genome, target site, cell, or tissue being targeted, and the agent being used.

The term "homologous," as used herein is an art-under-stood term that refers to nucleic acids or polypeptides that are highly related at the level of nucleotide and/or amino acid sequence. Nucleic acids or polypeptides that are homologous to each other are termed "homologues." Homology between two sequences can be determined by sequence alignment methods known to those of skill in the art. In accordance with the invention, two sequences are considered to be homologous if they are at least about 50-60% identical, e.g., share identical residues (e.g., amino acid residues) in at least about 50-60% of all residues comprised in one or the other sequence, at least about 70% identical, at least about 80% identical, at least about 90% identical, at least about 95% identical, at least about 98% identical, at least about 99% identical, at least about 99.5% identical, or at least about 99.9% identical, for at least one stretch of at least 20, at least 30, at least 40, at least 50, at least 60, at least 70, at least 80, at least 90, at least 100, at least 120, at least 150, or at least 200 amino acids.

The term "linker," as used herein, refers to a chemical group or a molecule linking two adjacent molecules or moieties, e.g., a binding domain (e.g., dCas9) and a cleavage domain of a nuclease (e.g., FokI). In some embodiments, a linker joins a nuclear localization signal (NLS) domain to another protein (e.g., a Cas9 protein or a nuclease or recombinase or a fusion thereof). In some embodiments, a linker joins a gRNA binding domain of an RNA-program-mable nuclease and the catalytic domain of a recombinase. In some embodiments, a linker joins a dCas9 and a recom-binase. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is a peptide linker. In some embodiments, the peptide linker is any stretch of amino acids having at least 1, at least 2, at least 3, at least 4, at least 5, at least 6, at least 7, at least 8, at least 9, at least 10, at least 15, at least 20, at least 25, at least 30, at least 40, at least 50, or more amino acids. In some embodiments, the peptide linker comprises repeats of the tri-peptide Gly-Gly-Ser, e.g., comprising the sequence $(GGS)_n$, wherein n represents at least 1, 2, 3, 4, 5, 6, 7, 8, 9, 10, or more repeats. In some embodiments, the linker comprises the sequence $(GGS)_6$ (SEQ ID NO:15). In some embodiments, the peptide linker is the 16 residue "XTEN" linker, or a variant thereof (See, e.g., the Examples; and Schellenberger et al. A recombinant polypeptide extends the in vivo half-life of peptides and proteins in a tunable manner. *Nat. Biotechnol.* 27, 1186-1190 (2009)). In some embodi-ments, the XTEN linker comprises the sequence SGSETPGTSESATPES (SEQ ID NO:16), SGSETPGTS-ESA (SEQ ID NO:17), or SGSETPGTSESATPEGGSGGS (SEQ ID NO:18). In some embodiments, the peptide linker is any linker as provided in FIG. 12A, for example, one or more selected from VPFLLEPDNINGKTC (SEQ ID NO:19), GSAGSAAGSGEF (SEQ ID NO:20), SIVAQLSRPDPA (SEQ ID NO:21), MKIIEQLPSA (SEQ ID NO:22), VRHKLKRVGS (SEQ ID NO:23), GHGTG-STGSGSS (SEQ ID NO:24), MSRPDPA (SEQ ID NO:25); or GGSM (SEQ ID NO:301).

The term "mutation," as used herein, refers to a substi-tution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, *Molecular Cloning: A Laboratory Manual* (4<sup>th</sup> ed., Cold Spring Harbor Laboratory Press, Cold Spring Harbor, N.Y. (2012)).

The term "nuclease," as used herein, refers to an agent, for example, a protein, capable of cleaving a phosphodiester bond connecting two nucleotide residues in a nucleic acid molecule. In some embodiments, "nuclease" refers to a protein having an inactive DNA cleavage domain, such that the nuclease is incapable of cleaving a phosphodiester bond. In some embodiments, a nuclease is a protein, e.g., an enzyme that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain. In some embodiments, a nuclease is a site-specific nuclease, binding and/or cleaving a specific phosphodiester bond within a specific nucleotide sequence, which is also referred to herein as the "recognition sequence," the "nuclease target site," or the "target site." In some embodiments, a nuclease is a RNA-guided (i.e., RNA-programmable) nuclease, which is associated with (e.g., binds to) an RNA (e.g., a guide RNA, "gRNA") having a sequence that complements a target site, thereby providing the sequence specificity of the nuclease. In some embodiments, a nuclease recognizes a single stranded target site, while in other embodiments, a nuclease recognizes a double-stranded target site, for example, a double-stranded DNA target site. The target sites of many naturally occurring nucleases, for example, many naturally occurring DNA restriction nucleases, are well known to those of skill in the art. In many cases, a DNA nuclease, such as EcoRI, HindIII, or BamHI, recognize a palindromic, double-stranded DNA target site of 4 to 10 base pairs in length, and cut each of the two DNA strands at a specific position within the target site. Some endonucleases cut a double-stranded nucleic acid target site symmetrically, i.e., cutting both strands at the same position so that the ends comprise base-paired nucleotides, also referred to herein as blunt ends. Other endonucleases cut a double-stranded nucleic acid target sites asymmetrically, i.e., cutting each strand at a different position so that the ends comprise unpaired nucleotides. Unpaired nucleotides at the end of a double-stranded DNA molecule are also referred to as "overhangs," e.g., as "5'-overhang" or as "3'-overhang," depending on whether the unpaired nucleotide(s) form(s) the 5' or the 5' end of the respective DNA strand. Double-stranded DNA molecule ends ending with unpaired nucleotide(s) are also referred to as sticky ends, as they can "stick to" other double-stranded DNA molecule ends comprising complementary unpaired nucleotide(s). A nuclease protein typically comprises a "binding domain" that mediates the interaction of the protein with the nucleic acid substrate, and also, in some cases, specifically binds to a target site, and a "cleavage domain" that catalyzes the cleavage of the phosphodiester bond within the nucleic acid backbone. In some embodiments a nuclease protein can bind and cleave a nucleic acid molecule in a monomeric form, while, in other embodiments, a nuclease protein has to dimerize or multimerize in order to cleave a target nucleic acid molecule. Binding domains and cleavage domains of naturally occurring nucleases, as well as modular binding domains and cleavage domains that can be fused to create nucleases binding specific target sites, are well known to those of skill in the art. For example, the binding domain of RNA-programmable nucleases (e.g., Cas9), or a Cas9 protein having an inactive DNA cleavage domain, can be used as a binding domain (e.g., that binds a gRNA to direct binding to a target site) to specifically bind a desired target site, and fused or conjugated to a cleavage domain, for example, the cleavage domain of FokI, to create an engineered nuclease cleaving the target site. In some embodiments, Cas9 fusion proteins provided herein comprise the cleavage domain of FokI, and are therefore referred to as "fCas9" proteins. In some embodiments, the cleavage domain of FokI, e.g., in a fCas9 protein corresponds to, or comprises in part or whole, the amino acid sequence (or variants thereof) set forth as SEQ ID NO:6, below. In some embodiments, variants or homologues of the FokI cleavage domain include any variant or homologue capable of dimerizing (e.g., as part of fCas9 fusion protein) with another FokI cleavage domain at a target site in a target nucleic acid, thereby resulting in cleavage of the target nucleic acid. In some embodiments, variants of the FokI cleavage domain (e.g., variants of SEQ ID NO:6) are provided which are at least about 70% identical, at least about 80% identical, at least about 90% identical, at least about 95% identical, at least about 98% identical, at least about 99% identical, at least about 99.5% identical, or at least about 99.9% to SEQ ID NO:6. In some embodiments, variants of the FokI cleavage domain (e.g., variants of SEQ ID NO:6) are provided having an amino acid sequence which is shorter, or longer than SEQ ID NO:6, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

Cleavage Domain of FokI:

```
                                            (SEQ ID NO: 6)
GSQLVKSELEEKKSELRHKLKYVPHEYIELIEIARNSTQDRILEMKVMEF

FMKVYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGNYKAQ

LTRLNHITNCNGAVLSVEELLIGGEMIKAGTLTLEEVRRKFNNGEINE
```

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, gRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "pharmaceutical composition," as used herein, refers to a composition that can be administrated to a subject in the context of treatment and/or prevention of a disease or disorder. In some embodiments, a pharmaceutical composition comprises an active ingredient, e.g., a nuclease or recombinase fused to a Cas9 protein, or fragment thereof (or a nucleic acid encoding a such a fusion), and optionally a pharmaceutically acceptable excipient. In some embodiments, a pharmaceutical composition comprises inventive Cas9 variant/fusion (e.g., fCas9) protein(s) and gRNA(s) suitable for targeting the Cas9 variant/fusion protein(s) to a target nucleic acid. In some embodiments, the target nucleic acid is a gene. In some embodiments, the target nucleic acid is an allele associated with a disease, whereby the allele is cleaved by the action of the Cas9 variant/fusion protein(s). In some embodiments, the allele is an allele of the CLTA gene, the EMX gene, the HBB gene, the VEGF gene, or the CCR5 gene. See e.g., the Examples; FIGS. 7, 8, 13, 14, 15, 17 and 19.

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasia is also referred to as cancer. In some embodiments, the compositions and methods provided herein are useful for treating a proliferative disease. For example, in some embodiments, pharmaceutical compositions comprising Cas9 (e.g., fCas9) protein(s) and gRNA(s) suitable for targeting the Cas9 protein(s) to an VEGF allele, whereby the allele is inactivated by the action of the Cas9 protein(s). See, e.g., the Examples.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* (4th ed., Cold Spring Harbor Laboratory Press, Cold Spring Harbor, N.Y. (2012)), the entire contents of which are incorporated herein by reference.

Figures 1A, 1B:
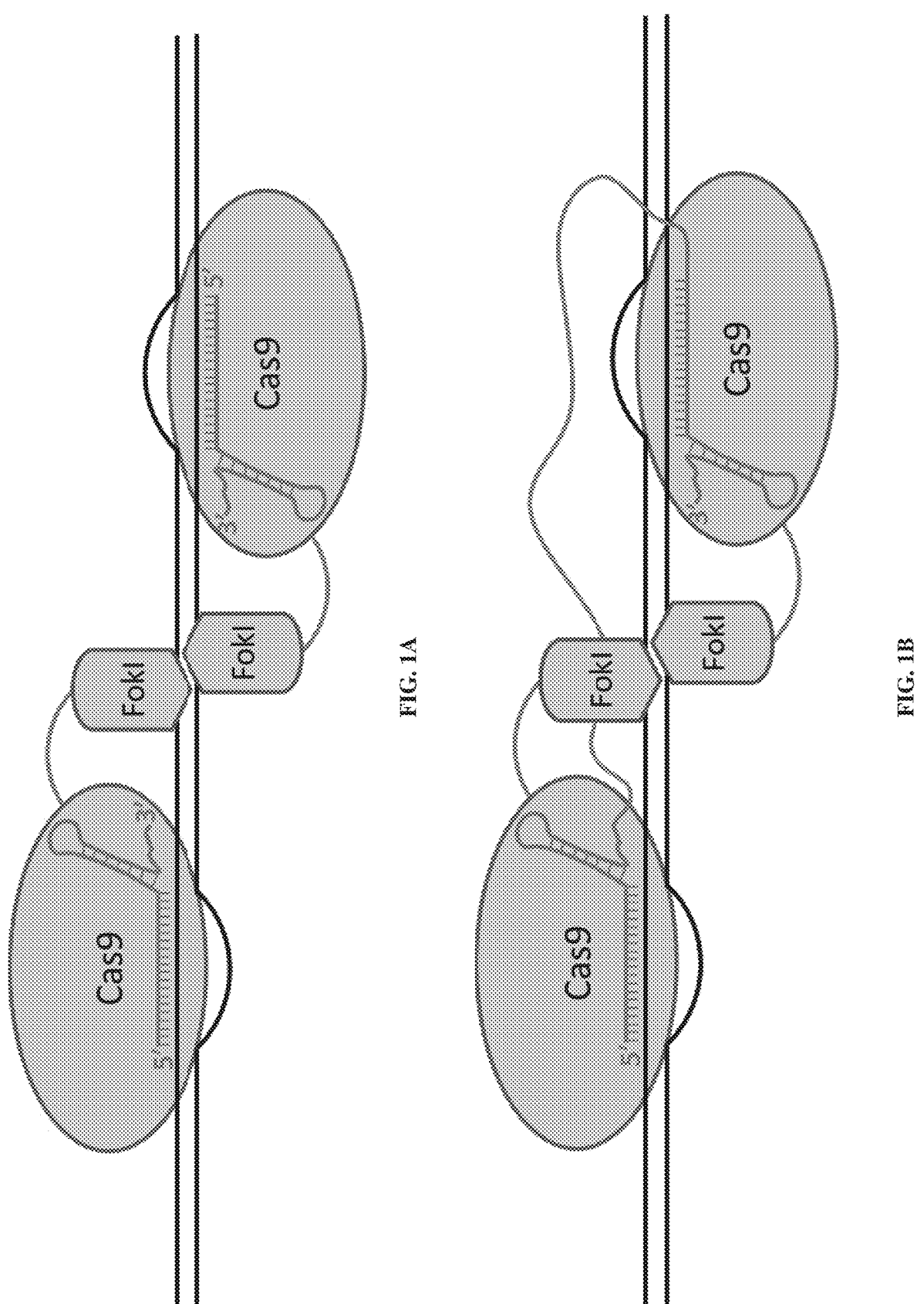
FIG. 1A-1B is a schematic detailing certain embodiments of the invention.

The term "RNA-programmable nuclease," and "RNA-guided nuclease" are used interchangeably herein and refer to a nuclease that forms a complex with (e.g., binds or associates with) one or more RNA that is not a target for cleavage. In some embodiments, an RNA-programmable nuclease, when in a complex with an RNA, may be referred to as a nuclease:RNA complex. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeably to refer to guide RNAs that exist as either single molecules or as a complex of two or more molecules. Typically, gRNAs that exist as single RNA species comprise two domains: (1) a domain that shares homology to a target nucleic acid (e.g., and directs binding of a Cas9 complex to the target); and (2) a domain that binds a Cas9 protein. In some embodiments, domain (2) corresponds to a sequence known as a tracrRNA, and comprises a stem-loop structure. For example, in some embodiments, domain (2) is homologous to a tracrRNA as depicted in FIG. 1E of Jinek et al., *Science* 337:816-821(2012), the entire contents of which is incorporated herein by reference. Other examples of gRNAs (e.g., those including domain 2) can be found in U.S. Provisional Patent Application, U.S. Ser. No. 61/874,682, filed Sep. 6, 2013, entitled "Switchable Cas9 Nucleases And Uses Thereof;" U.S. Provisional Patent Application, U.S. Ser. No. 61/874,746, filed Sep. 6, 2013, entitled "Delivery System For Functional Nucleases;" PCT Application WO 2013/176722, filed Mar. 15, 2013, entitled "Methods and Compositions for RNA-Directed Target DNA Modification and for RNA-Directed Modulation of Transcription;" and PCT Application WO 2013/142578, filed Mar. 20, 2013, entitled "RNA-Directed DNA Cleavage by the Cas9-crRNA Complex;" the entire contents of each are hereby incorporated by reference in their entirety. Still other examples of gRNAs and gRNA structure are provided herein. See e.g., the Examples. In some embodiments, a gRNA comprises two or more of domains (1) and (2), and may be referred to as an "extended gRNA." For example, an extended gRNA will e.g., bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example Cas9 (Csnl) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference.

Because RNA-programmable nucleases (e.g., Cas9) use RNA:DNA hybridization to determine target DNA cleavage sites, these proteins are able to cleave, in principle, any sequence specified by the guide RNA. Methods of using RNA-programmable nucleases, such as Cas9, for site-specific cleavage (e.g., to modify a genome) are known in the art (see e.g., Cong, L. et al. Multiplex genome engineering using CRISPR/Cas systems. *Science* 339, 819-823 (2013); *Mali*, P. et al. RNA-guided human genome engineering via Cas9. *Science* 339, 823-826 (2013); Hwang, W. Y. et al. Efficient genome editing in zebrafish using a CRISPR-Cas system. *Nature biotechnology* 31, 227-229 (2013); Jinek, M. et al. RNA-programmed genome editing in human cells. *eLife* 2, e00471 (2013); Dicarlo, J. E. et al. Genome engineering in *Saccharomyces cerevisiae* using CRISPR-Cas systems. *Nucleic acids research* (2013); Jiang, W. et al. RNA-guided editing of bacterial genomes using CRISPR-Cas systems. *Nature biotechnology* 31, 233-239 (2013); the entire contents of each of which are incorporated herein by reference).

The term "recombinase," as used herein, refers to a site-specific enzyme that mediates the recombination of DNA between recombinase recognition sequences, which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, γδ, Bxb1, φC31, TP901, TG1, φBT1, R4, φRV1, φFC1, MR11, A118, U153, and gp29. Examples of tyrosine recombinases include, without limitation, Cre, FLP, R, Lambda, HK101, HK022, and pSAM2. The serine and tyrosine recombinase names stem from the conserved nucleophilic amino acid residue that the recombinase uses to attack the DNA and which becomes covalently linked to the DNA during strand exchange. Recombinases have numerous applications, including the creation of gene knockouts/knock-ins and gene therapy applications. See, e.g., Brown et al., "Serine recombinases as tools for genome engineering." *Methods.* 2011; 53(4):372-9; Hirano et al., "Site-specific recombinases as tools for heterologous gene integration." *Appl. Microbiol. Biotechnol.* 2011; 92(2):227-39; Chavez and Calos, "Therapeutic applications of the ΦC31 integrase system." *Curr. Gene Ther.* 2011; 11(5):375-81; Turan and Bode, "Site-specific recombinases: from tag-and-target- to tag-and-exchange-based genomic modifications." *FASEB J.* 2011; 25(12):4088-107; Venken and Bellen, "Genome-wide manipulations of *Drosophila melanogaster* with transposons, Flp recombinase, and ΦC31 integrase." *Methods Mol. Biol.* 2012; 859:203-28; Murphy, "Phage recombinases and their applications." *Adv. Virus Res.* 2012; 83:367-414; Zhang et al., "Conditional gene manipulation: Cre-ating a new biological era." *J. Zhejiang Univ. Sci. B.* 2012; 13(7):511-24; Karpenshif and Bernstein, "From yeast to mammals: recent advances in genetic control of homologous recombination." *DNA Repair (Amst).* 2012; 1; 11(10):781-8; the entire contents of each are hereby incorporated by reference in their entirety. The recombinases provided herein are not meant to be exclusive examples of recombinases that can be used in embodiments of the invention. The methods and compositions of the invention can be expanded by mining databases for new orthogonal recombinases or designing synthetic recombinases with defined DNA specificities (See, e.g., Groth et al., "Phage integrases: biology and applications." *J. Mol. Biol.* 2004; 335, 667-678; Gordley et al., "Synthesis of programmable integrases." *Proc. Natl. Acad. Sci. USA.* 2009; 106, 5053-5058; the entire contents of each are hereby incorporated by reference in their entirety). Other examples of recombinases that are useful in the methods and compositions described herein are known to those of skill in the art, and any new recombinase that is discovered or generated is expected to be able to be used in the different embodiments of the invention. In some embodiments, the catalytic domains of a recombinase are fused to a nuclease-inactivated RNA-programmable nuclease (e.g., dCas9, or a fragment thereof), such that the recombinase domain does not comprise a nucleic acid binding domain or is unable to bind to a target nucleic acid (e.g., the recombinase domain is engineered such that it does not have specific DNA binding activity). Recombinases lacking DNA binding activity and methods for engineering such are known, and include those described by Klippel et al., "Isolation and characterisation of unusual gin mutants." *EMBO J.* 1988; 7: 3983-3989: Burke et al., "Activating mutations of Tn3 resolvase marking interfaces important in recombination catalysis and its regulation. *Mol Microbiol.* 2004; 51: 937-948; Olorunniji et al., "Synapsis and catalysis by activated Tn3 resolvase mutants." *Nucleic Acids Res.* 2008; 36: 7181-7191; Rowland et al., "Regulatory mutations in Sin recombinase support a structure-based model of the synaptosome." *Mol Microbiol.* 2009; 74: 282-298; Akopian et al., "Chimeric recombinases with designed DNA sequence recognition." *Proc Natl Acad Sci USA.* 2003; 100: 8688-8691; Gordley et al., "Evolution of programmable zinc finger-recombinases with activity in human cells. *J Mol Biol.* 2007; 367: 802-813; Gordley et al., "Synthesis of programmable integrases." *Proc Natl Acad Sci USA.* 2009; 106: 5053-5058; Arnold et al., "Mutants of Tn3 resolvase which do not require accessory binding sites for recombination activity." *EMBO J.* 1999; 18: 1407-1414; Gaj et al., "Structure-guided reprogramming of serine recombinase DNA sequence specificity." *Proc Nat Acad Sci USA.* 2011; 108(2):498-503; and Proudfoot et al., "Zinc finger recombinases with adaptable DNA sequence specificity." *PLoS One.* 2011; 6(4):e19537; the entire contents of each are hereby incorporated by reference. For example, serine recombinases of the resolvase-invertase group, e.g., Tn3 and γδ resolvases and the Hin and Gin invertases, have modular structures with autonomous catalytic and DNA-binding domains (See, e.g., Grindley et al., "Mechanism of site-specific recombination." *Ann Rev Biochem.* 2006; 75: 567-605, the entire contents of which are incorporated by reference). The catalytic domains of these recombinases are thus amenable to being recombined with nuclease-inactivated RNA-programmable nucleases (e.g., dCas9, or a fragment thereof) as described herein, e.g., following the isolation of 'activated' recombinase mutants which do not require any accessory factors (e.g., DNA binding activities) (See, e.g., Klippel et al., "Isolation and characterisation of unusual gin mutants." *EMBO J.* 1988; 7: 3983-3989; Burke et al., "Activating mutations of Tn3 resolvase marking interfaces important in recombination catalysis and its regulation. *Mol Microbiol.* 2004; 51: 937-948; Olorunniji et al., "Synapsis and catalysis by activated Tn3 resolvase mutants." *Nucleic Acids Res.* 2008; 36: 7181-7191; Rowland et al., "Regulatory mutations in Sin recombinase support a structure-based model of the synaptosome." *Mol Microbiol.* 2009; 74: 282-298; Akopian et al., "Chimeric recombinases with designed DNA sequence recognition." *Proc Natl Acad Sci USA.* 2003; 100: 8688-8691). Additionally, many other natural serine recombinases having an N-terminal catalytic domain and a C-terminal DNA binding domain are known (e.g., phiC31 integrase, TnpX transposase, IS607 transposase), and their catalytic domains can be co-opted to engineer programmable site-specific recombinases as described herein (See, e.g., Smith et al., "Diversity in the serine recombinases." *Mol Microbiol.* 2002; 44: 299-307, the entire contents of which are incorporated by reference). Similarly, the core catalytic domains of tyrosine recombinases (e.g., Cre, λ integrase) are known, and can be similarly co-opted to engineer programmable site-specific recombinases as described herein (See, e.g., Guo et al., "Structure of Cre recombinase complexed with DNA in a site-specific recombination synapse." *Nature.* 1997; 389:40-46; Hartung et al., "Cre mutants with altered DNA binding properties." *J Biol Chem* 1998; 273:22884-22891; Shaikh et al., "Chimeras of the Flp and Cre recombinases: Tests of the mode of cleavage by Flp and Cre. *J Mol Biol.* 2000; 302:27-48; Rongrong et al., "Effect of deletion mutation on the recombination activity of Cre recombinase." *Acta Biochim Pol.* 2005; 52:541-544; Kilbride et al., "Determinants of product topology in a hybrid Cre-Tn3 resolvase site-specific recombination system." *J Mol Biol.* 2006; 355:185-195; Warren et al., "A chimeric cre recombinase with regulated directionality." *Proc Natl Acad Sci USA.* 2008 105:18278-18283; Van Duyne, "Teaching Cre to follow directions." *Proc Natl Acad Sci USA.* 2009 Jan. 6; 106(1):4-5; Numrych et al., "A comparison of the effects of single-base and triple-base changes in the integrase arm-type binding sites on the site-specific recombination of bacteriophage λ." *Nucleic Acids Res.* 1990; 18:3953-3959; Tirumalai et al., "The recognition of core-type DNA sites by λ integrase." *J Mol Biol.* 1998; 279:513-527; Aihara et al., "A conformational switch controls the DNA cleavage activity of λ integrase." *Mol Cell.* 2003; 12:187-198; Biswas et al., "A structural basis for allosteric control of DNA recombination by λ integrase." *Nature.* 2005; 435:1059-1066; and Warren et al., "Mutations in the amino-terminal domain of λ-integrase have differential effects on integrative and excisive recombination." *Mol Microbiol.* 2005; 55:1104-1112; the entire contents of each are incorporated by reference).

The term "recombine," or "recombination," in the context of a nucleic acid modification (e.g., a genomic modification), is used to refer to the process by which two or more nucleic acid molecules, or two or more regions of a single nucleic acid molecule, are modified by the action of a recombinase protein (e.g., an inventive recombinase fusion protein provided herein). Recombination can result in, inter alia, the insertion, inversion, excision or translocation of nucleic acids, e.g., in or between one or more nucleic acid molecules.

The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development.

The terms "target nucleic acid," and "target genome," as used herein in the context of nucleases, refer to a nucleic acid molecule or a genome, respectively, that comprises at least one target site of a given nuclease. In the context of fusions comprising a (nuclease-inactivated) RNA-programmable nuclease and a recombinase domain, a "target nucleic acid" and a "target genome" refers to one or more nucleic acid molecule(s), or a genome, respectively, that comprises at least one target site. In some embodiments, the target nucleic acid(s) comprises at least two, at least three, or at least four target sites. In some embodiments, the target nucleic acid(s) comprise four target sites.

The term "target site" refers to a sequence within a nucleic acid molecule that is either (1) bound and cleaved by a nuclease (e.g., Cas9 fusion proteins provided herein), or (2) bound and recombined (e.g., at or nearby the target site) by a recombinase (e.g., a dCas9-recombinase fusion protein provided herein). A target site may be single-stranded or double-stranded. In the context of RNA-guided (e.g., RNA-programmable) nucleases (e.g., a protein dimer comprising a Cas9 gRNA binding domain and an active Cas9 DNA cleavage domain or other nuclease domain such as FokI), a target site typically comprises a nucleotide sequence that is complementary to the gRNA(s) of the RNA-programmable nuclease, and a protospacer adjacent motif (PAM) at the 3' end adjacent to the gRNA-complementary sequence(s). In some embodiments, such as those involving fCas9, a target site can encompass the particular sequences to which fCas9 monomers bind, and/or the intervening sequence between the bound monomers that are cleaved by the dimerized FokI domains (See e.g., the Examples; and FIGS. 1A, 6D). In the context of fusions between RNA-guided (e.g., RNA-programmable, nuclease-inactivated) nucleases and a recombinase (e.g., a catalytic domain of a recombinase), a target site typically comprises a nucleotide sequence that is complementary to the gRNA of the RNA-programmable nuclease domain, and a protospacer adjacent motif (PAM) at the 3' end adjacent to the gRNA-complementary sequence. For example, in some embodiments, four recombinase monomers are coordinated to recombine a target nucleic acid(s), each monomer being fused to a (nuclease-inactivated) Cas9 protein guided by a gRNA. In such an example, each Cas9 domain is guided by a distinct gRNA to bind a target nucleic acid(s), thus the target nucleic acid comprises four target sites, each site targeted by a separate dCas9-recombinase fusion (thereby coordinating four recombinase monomers which recombine the target nucleic acid(s)). For the RNA-guided nuclease Cas9 (or gRNA-binding domain thereof) and inventive fusions of Cas9, the target site may be, in some embodiments, 17-20 base pairs plus a 3 base pair PAM (e.g., NNN, wherein N independently represents any nucleotide). Typically, the first nucleotide of a PAM can be any nucleotide, while the two downstream nucleotides are specified depending on the specific RNA-guided nuclease. Exemplary target sites (e.g., comprising a PAM) for RNA-guided nucleases, such as Cas9, are known to those of skill in the art and include, without limitation, NNG, NGN, NAG, and NGG, wherein N independently represents any nucleotide. In addition, Cas9 nucleases from different species (e.g., S. thermophilus instead of S. pyogenes) recognizes a PAM that comprises the sequence NGGNG. Additional PAM sequences are known, including, but not limited to, NNA-GAAW and NAAR (see, e.g., Esvelt and Wang, Molecular Systems Biology, 9:641 (2013), the entire contents of which are incorporated herein by reference). In some aspects, the target site of an RNA-guided nuclease, such as, e.g., Cas9, may comprise the structure [Nz]-[PAM], where each N is, independently, any nucleotide, and z is an integer between 1 and 50, inclusive. In some embodiments, z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, z is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, z is 20. In some embodiments, "target site" may also refer to a sequence within a nucleic acid molecule that is bound but not cleaved by a nuclease. For example, certain embodiments described herein provide proteins comprising an inactive (or inactivated) Cas9 DNA cleavage domain. Such proteins (e.g., when also including a Cas9 RNA binding domain) are able to bind the target site specified by the gRNA; however, because the DNA cleavage site is inactivated, the target site is not cleaved by the particular protein. However, such proteins as described herein are typically conjugated, fused, or bound to another protein (e.g., a nuclease) or molecule that mediates cleavage of the nucleic acid molecule. In other embodiments, such proteins are conjugated, fused, or bound to a recombinase (or a catalytic domain of a recombinase), which mediates recombination of the target nucleic acid. In some embodiments, the sequence actually cleaved or recombined will depend on the protein (e.g., nuclease or recombinase) or molecule that mediates cleavage or recombination of the nucleic acid molecule, and in some cases, for example, will relate to the proximity or distance from which the inactivated Cas9 protein(s) is/are bound.

In the context of inventive proteins that dimerize (or multimerize), for example, dimers of a protein comprising a nuclease-inactivated Cas9 (or a Cas9 RNA binding domain) and a DNA cleavage domain (e.g., FokI cleavage domain or an active Cas9 cleavage domain), or fusions between a nuclease-inactivated Cas9 (or a Cas9 gRNA binding domain) and a recombinase (or catalytic domain of a recombinase), a target site typically comprises a left-half site (bound by one protein), a right-half site (bound by the second protein), and a spacer sequence between the half sites in which the cut or recombination is made. In some embodiments, either the left-half site or the right half-site (and not the spacer sequence) is cut or recombined. In other embodiments, the spacer sequence is cut or recombined. This structure ([left-half site]-[spacer sequence]-[right-half site]) is referred to herein as an LSR structure. In some embodiments, the left-half site and/or the right-half site correspond to an RNA-guided target site (e.g., a Cas9 target site). In some embodiments, either or both half-sites are shorter or longer than e.g., a typical region targeted by Cas9, for example shorter or longer than 20 nucleotides. In some embodiments, the left and right half sites comprise different nucleic acid sequences. In some embodiments involving inventive nucleases, the target site is a sequence comprising three (3) RNA-guided nuclease target site sequences, for example, three sequences corresponding to Cas9 target site sequences (See, e.g., FIG. 2C), in which the first and second, and second and third Cas9 target site sequences are separated by a spacer sequence. In some embodiments, the spacer sequence is at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 60, at least 70, at least 80, at least 90, at least 100, at least 125, at least 150, at least 175, at least 200, or at least 250 bp long. In some embodiments, the spacer sequence is between approximately 15 bp and approximately 25 bp long. In some embodiments, the spacer sequence is approximately 15 bp long. In some embodiments, the spacer sequence is approximately 25 bp long.

The term "Transcriptional Activator-Like Effector," (TALE) as used herein, refers to bacterial proteins comprising a DNA binding domain, which contains a highly conserved 33-34 amino acid sequence comprising a highly variable two-amino acid motif (Repeat Variable Diresidue, RVD). The RVD motif determines binding specificity to a nucleic acid sequence and can be engineered according to methods known to those of skill in the art to specifically bind a desired DNA sequence (see, e.g., Miller, Jeffrey; et. al. (February 2011). "A TALE nuclease architecture for efficient genome editing". Nature Biotechnology 29 (2): 143-8; Zhang, Feng; et. al. (February 2011). "Efficient construction of sequence-specific TAL effectors for modulating mammalian transcription" Nature Biotechnology 29 (2): 149-53; Geißler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". PLoS ONE 6 (5): e19509; Boch, Jens (February 2011). "TALEs of genome targeting". Nature Biotechnology 29 (2): 135-6; Boch, Jens; et. al. (December 2009). "Breaking the Code of DNA Binding Specificity of TAL-Type III Effectors". Science 326 (5959): 1509-12; and Moscou, Matthew J.; Adam J. Bogdanove (December 2009). "A Simple Cipher Governs DNA Recognition by TAL Effectors" Science 326 (5959): 1501; the entire contents of each of which are incorporated herein by reference). The simple relationship between amino acid sequence and DNA recognition has allowed for the engineering of specific DNA binding domains by selecting a combination of repeat segments containing the appropriate RVDs.

The term "Transcriptional Activator-Like Element Nuclease," (TALEN) as used herein, refers to an artificial nuclease comprising a transcriptional activator-like effector DNA binding domain to a DNA cleavage domain, for example, a FokI domain. A number of modular assembly schemes for generating engineered TALE constructs have been reported (see e.g., Zhang, Feng; et. al. (February 2011). "Efficient construction of sequence-specific TAL effectors for modulating mammalian transcription". *Nature Biotechnology* 29 (2): 149-53; Geißler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Cermak, T.; Doyle, E. L.; Christian, M.; Wang, L.; Zhang, Y.; Schmidt, C.; Baller, J. A.; Somia, N. V. et al. (2011). "Efficient design and assembly of custom TALEN and other TAL effector-based constructs for DNA targeting". *Nucleic Acids Research*; Morbitzer, R.; Elsaesser, J.; Hausner, J.; Lahaye, T. (2011). "Assembly of custom TALE-type DNA binding domains by modular cloning". *Nucleic Acids Research*; Li, T.; Huang, S.; Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". *Nucleic Acids Research*; Weber, E.; Gruetzner, R.; Werner, S.; Engler, C.; Marillonnet, S. (2011). Bendahmane, Mohammed. ed. "Assembly of Designer TAL Effectors by Golden Gate Cloning". *PLoS ONE* 6 (5): e19722; the entire contents of each of which are incorporated herein by reference).

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

The term "vector" refers to a polynucleotide comprising one or more recombinant polynucleotides of the present invention, e.g., those encoding a Cas9 protein (or fusion thereof) and/or gRNA provided herein. Vectors include, but are not limited to, plasmids, viral vectors, cosmids, artificial chromosomes, and phagemids. The vector is able to replicate in a host cell and is further characterized by one or more endonuclease restriction sites at which the vector may be cut and into which a desired nucleic acid sequence may be inserted. Vectors may contain one or more marker sequences suitable for use in the identification and/or selection of cells which have or have not been transformed or genomically modified with the vector. Markers include, for example, genes encoding proteins which increase or decrease either resistance or sensitivity to antibiotics (e.g., kanamycin, ampicillin) or other compounds, genes which encode enzymes whose activities are detectable by standard assays known in the art (e.g., β-galactosidase, alkaline phosphatase, or luciferase), and genes which visibly affect the phenotype of transformed or transfected cells, hosts, colonies, or plaques. Any vector suitable for the transformation of a host cell (e.g., *E. coli*, mammalian cells such as CHO cell, insect cells, etc.) as embraced by the present invention, for example, vectors belonging to the pUC series, pGEM series, pET series, pBAD series, pTET series, or pGEX series. In some embodiments, the vector is suitable for transforming a host cell for recombinant protein production. Methods for selecting and engineering vectors and host cells for expressing proteins (e.g., those provided herein), transforming cells, and expressing/purifying recombinant proteins are well known in the art, and are provided by, for example, Green and Sambrook, *Molecular Cloning: A Laboratory Manual* (4$^{th}$ ed., Cold Spring Harbor Laboratory Press, Cold Spring Harbor, N.Y. (2012)).

The term "zinc finger," as used herein, refers to a small nucleic acid-binding protein structural motif characterized by a fold and the coordination of one or more zinc ions that stabilize the fold. Zinc fingers encompass a wide variety of differing protein structures (see, e.g., Klug A, Rhodes D (1987). "Zinc fingers: a novel protein fold for nucleic acid recognition". *Cold Spring Harb. Symp. Quant. Biol.* 52: 473-82, the entire contents of which are incorporated herein by reference). Zinc fingers can be designed to bind a specific sequence of nucleotides, and zinc finger arrays comprising fusions of a series of zinc fingers, can be designed to bind virtually any desired target sequence. Such zinc finger arrays can form a binding domain of a protein, for example, of a nuclease, e.g., if conjugated to a nucleic acid cleavage domain. Different types of zinc finger motifs are known to those of skill in the art, including, but not limited to, $Cys_2His_2$, Gag knuckle, Treble clef, Zinc ribbon, $Zn_2/Cys_6$, and TAZ2 domain-like motifs (see, e.g., Krishna S S, Majumdar I, Grishin N V (January 2003). "Structural classification of zinc fingers: survey and summary". *Nucleic Acids Res.* 31 (2): 532-50). Typically, a single zinc finger motif binds 3 or 4 nucleotides of a nucleic acid molecule. Accordingly, a zinc finger domain comprising 2 zinc finger motifs may bind 6-8 nucleotides, a zinc finger domain comprising 3 zinc finger motifs may bind 9-12 nucleotides, a zinc finger domain comprising 4 zinc finger motifs may bind 12-16 nucleotides, and so forth. Any suitable protein engineering technique can be employed to alter the DNA-binding specificity of zinc fingers and/or design novel zinc finger fusions to bind virtually any desired target sequence from 3-30 nucleotides in length (see, e.g., Pabo C O, Peisach E, Grant R A (2001). "Design and selection of novel cys2His2 Zinc finger proteins". *Annual Review of Biochemistry* 70: 313-340; Jamieson A C, Miller J C, Pabo C O (2003). "Drug discovery with engineered zinc-finger proteins". *Nature Reviews Drug Discovery* 2 (5): 361-368; and Liu Q, Segal D J, Ghiara J B, Barbas C F (May 1997). "Design of polydactyl zinc-finger proteins for unique addressing within complex genomes". *Proc. Natl. Acad. Sci. U.S.A.* 94 (11); the entire contents of each of which are incorporated herein by reference). Fusions between engineered zinc finger arrays and protein domains that cleave a nucleic acid can be used to generate a "zinc finger nuclease." A zinc finger nuclease typically comprises a zinc finger domain that binds a specific target site within a nucleic acid molecule, and a nucleic acid cleavage domain that cuts the nucleic acid molecule within or in proximity to the target site bound by the binding domain. Typical engineered zinc finger nucleases comprise a binding domain having between 3 and 6 individual zinc finger motifs and binding target sites ranging from 9 base pairs to 18 base pairs in length. Longer target sites are particularly attractive in situations where it is desired to bind and cleave a target site that is unique in a given genome.

The term "zinc finger nuclease," as used herein, refers to a nuclease comprising a nucleic acid cleavage domain conjugated to a binding domain that comprises a zinc finger array. In some embodiments, the cleavage domain is the cleavage domain of the type II restriction endonuclease FokI. Zinc finger nucleases can be designed to target virtually any desired sequence in a given nucleic acid molecule for cleavage, and the possibility to design zinc finger binding domains to bind unique sites in the context of complex genomes allows for targeted cleavage of a single genomic site in living cells, for example, to achieve a targeted genomic alteration of therapeutic value. Targeting a double-strand break to a desired genomic locus can be used to introduce frame-shift mutations into the coding sequence of a gene due to the error-prone nature of the non-homologous DNA repair pathway. Zinc finger nucleases can be generated to target a site of interest by methods well known to those of skill in the art. For example, zinc finger binding domains with a desired specificity can be designed by combining individual zinc finger motifs of known specificity. The structure of the zinc finger protein Zif268 bound to DNA has informed much of the work in this field and the concept of obtaining zinc fingers for each of the 64 possible base pair triplets and then mixing and matching these modular zinc fingers to design proteins with any desired sequence specificity has been described (Pavletich N P, Pabo C O (May 1991). "Zinc finger-DNA recognition: crystal structure of a Zif268-DNA complex at 2.1 A". *Science* 252 (5007): 809-17, the entire contents of which are incorporated herein). In some embodiments, separate zinc fingers that each recognizes a 3 base pair DNA sequence are combined to generate 3-, 4-, 5-, or 6-finger arrays that recognize target sites ranging from 9 base pairs to 18 base pairs in length. In some embodiments, longer arrays are contemplated. In other embodiments, 2-finger modules recognizing 6-8 nucleotides are combined to generate 4-, 6-, or 8-zinc finger arrays. In some embodiments, bacterial or phage display is employed to develop a zinc finger domain that recognizes a desired nucleic acid sequence, for example, a desired nuclease target site of 3-30 bp in length. Zinc finger nucleases, in some embodiments, comprise a zinc finger binding domain and a cleavage domain fused or otherwise conjugated to each other via a linker, for example, a polypeptide linker. The length of the linker determines the distance of the cut from the nucleic acid sequence bound by the zinc finger domain. If a shorter linker is used, the cleavage domain will cut the nucleic acid closer to the bound nucleic acid sequence, while a longer linker will result in a greater distance between the cut and the bound nucleic acid sequence. In some embodiments, the cleavage domain of a zinc finger nuclease has to dimerize in order to cut a bound nucleic acid. In some such embodiments, the dimer is a heterodimer of two monomers, each of which comprise a different zinc finger binding domain. For example, in some embodiments, the dimer may comprise one monomer comprising zinc finger domain A conjugated to a FokI cleavage domain, and one monomer comprising zinc finger domain B conjugated to a FokI cleavage domain. In this non-limiting example, zinc finger domain A binds a nucleic acid sequence on one side of the target site, zinc finger domain B binds a nucleic acid sequence on the other side of the target site, and the dimerize FokI domain cuts the nucleic acid in between the zinc finger domain binding sites.

DETAILED DESCRIPTION OF CERTAIN EMBODIMENTS OF THE INVENTION

Site-specific nucleases and site-specific recombinases are powerful tools for targeted genome modification in vitro and in vivo. It has been reported that nuclease cleavage in living cells triggers a DNA repair mechanism that frequently results in a modification of the cleaved and repaired genomic sequence, for example, via homologous recombination. Accordingly, the targeted cleavage of a specific unique sequence within a genome opens up new avenues for gene targeting and gene modification in living cells, including cells that are hard to manipulate with conventional gene targeting methods, such as many human somatic or embryonic stem cells. Another approach utilizes site-specific recombinases, which possess all the functionality required to bring about efficient, precise integration, deletion, inversion, or translocation of specified DNA segments.

Nuclease-mediated modification of disease-related sequences, e.g., the CCR-5 allele in HIV/AIDS patients, or of genes necessary for tumor neovascularization, can be used in the clinical context, and two site specific nucleases are currently in clinical trials (Perez, E. E. et al., "Establishment of HIV-1 resistance in CD4+ T cells by genome editing using zinc-finger nucleases." *Nature biotechnology.* 26, 808-816 (2008); ClinicalTrials.gov identifiers: NCT00842634, NCT01044654, NCT01252641, NCT01082926). Accordingly, nearly any genetic disease can be treated using site-specific nucleases and/or recombinases and include, for example, diseases associated with triplet expansion (e.g., Huntington's disease, myotonic dystrophy, spinocerebellar ataxias, etc.), cystic fibrosis (by targeting the CFTR gene), hematological disease (e.g., hemoglobinopathies), cancer, autoimmune diseases, and viral infections. Other diseases that can be treated using the inventive compositions and/or methods provided herein include, but are not limited to, achondroplasia, achromatopsia, acid maltase deficiency, adenosine deaminase deficiency, adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the 6th codon of beta-globin (HbC), hemophilia, Hurler Syndrome, hypophosphatasia, Klinefleter syndrome, Krabbes Disease, Langer-Giedion Syndrome, leukocyte adhesion deficiency (LAD), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, and X-linked lymphoproliferative syndrome (XLP).

One aspect of site-specific genomic modification is the possibility of off-target nuclease or recombinase effects, e.g., the cleavage or recombination of genomic sequences that differ from the intended target sequence by one or more nucleotides. Undesired side effects of off-target cleavage/recombination range from insertion into unwanted loci during a gene targeting event to severe complications in a clinical scenario. Off-target cleavage or recombination of sequences encoding essential gene functions or tumor suppressor genes by an endonuclease or recombinase administered to a subject may result in disease or even death of the subject. Accordingly, it is desirable to employ new strategies in designing nucleases and recombinases having the greatest chance of minimizing off-target effects.

The methods and compositions of the present disclosure represent, in some aspects, an improvement over previous methods and compositions providing nucleases (and methods of their use) and recombinases (and methods of their use) engineered to have improved specificity for their intended targets. For example, nucleases and recombinases known in the art, both naturally occurring and those engineered, typically have a target (e.g., DNA) binding domain that recognizes a particular sequence. Additionally, known nucleases and recombinases may comprise a DNA binding domain and a catalytic domain in a single protein capable of inducing cleavage or recombination, and as such the chance for off-target effects are increased as cleavage or recombination likely occurs upon off-target binding of the nuclease or recombinase, respectively. Aspects of the present invention relate to the recognition that increasing the number of sequences (e.g., having a nuclease bind at more than one site at a desired target), and/or splitting the activities (e.g., target binding and target cleaving) of a nuclease between two or more proteins, will increase the specificity of a nuclease and thereby decrease the likelihood of off-target effects. Other aspects of the present invention relate to the recognition that fusions between the catalytic domain of recombinases (or recombinases having inactive DNA binding domains) and nuclease-inactivated RNA-programmable nucleases allow for the targeted recombination of DNA at any location.

In the context of site-specific nucleases, the strategies, methods, compositions, and systems provided herein can be utilized to improve the specificity of any site-specific nuclease, for example, variants of the Cas9 endonuclease, Zinc Finger Nucleases (ZFNs) and Transcription Activator-Like Effector Nucleases (TALENs). Suitable nucleases for modification as described herein will be apparent to those of skill in the art based on this disclosure.

In certain embodiments, the strategies, methods, compositions, and systems provided herein are utilized to improve the specificity of the RNA-guided (e.g., RNA-programmable) endonuclease Cas9. Whereas typical endonucleases recognize and cleave a single target sequence, Cas9 endonuclease uses RNA:DNA hybridization to determine target DNA cleavage sites, enabling a single monomeric protein to cleave, in principle, any sequence specified by the guide RNA (gRNA). While Cas9:guide RNA complexes have been successfully used to modify both cells (Cong, L. et al. Multiplex genome engineering using CRISPR/Cas systems. *Science*. 339, 819-823 (2013); *Mali*, P. et al. RNA-guided human genome engineering via Cas9. *Science*. 339, 823-826 (2013); Jinek, M. et al. RNA-programmed genome editing in human cells. *eLife* 2, e00471 (2013)) and organisms (Hwang, W. Y. et al. Efficient genome editing in zebrafish using a CRISPR-Cas system. *Nature Biotechnology*. 31, 227-229 (2013)), a study using Cas9:guide RNA complexes to modify zebrafish embryos observed toxicity (e.g., off-target effects) at a rate similar to that of ZFNs and TALENs (Hwang, W. Y. et al. *Nature Biotechnology*. 31, 227-229 (2013)). Further, while recently engineered variants of Cas9 that cleave only one DNA strand ("nickases") enable double-stranded breaks to be specified by two distinct gRNA sequences (Cho, S. W. et al. Analysis of off-target effects of CRISPR/Cas-derived RNA-guided endonucleases and nickases. *Genome Res*. 24, 132-141 (2013); Ran, F. A. et al. Double Nicking by RNA-Guided CRISPR Cas9 for Enhanced Genome Editing Specificity. *Cell* 154, 1380-1389 (2013); *Mali*, P. et al. CAS9 transcriptional activators for target specificity screening and paired nickases for cooperative genome engineering. *Nat. Biotechnol*. 31, 833-838 (2013)), these variants still suffer from off-target cleavage activity (Ran, F. A. et al. Double Nicking by RNA-Guided CRISPR Cas9 for Enhanced Genome Editing Specificity. *Cell* 154, 1380-1389 (2013); Fu, Y., et al., Improving CRISPR-Cas nuclease specificity using truncated guide RNAs. *Nat. Biotechnol*. (2014)) arising from the ability of each monomeric nickase to remain active when individually bound to DNA (Cong, L. et al. Multiplex Genome Engineering Using CRISPR/Cas Systems. *Science* 339, 819-823 (2013); Jinek, M. et al. *Science* 337, 816-821 (2012); Gasiunas, G., et al., Cas9-crRNA ribonucleoprotein complex mediates specific DNA cleavage for adaptive immunity in bacteria. *Proc. Natl. Acad. Sci*. 109, E2579-E2586 (2012). Accordingly, aspects of the present disclosure aim at reducing the chances for Cas9 off-target effects using novel engineered Cas9 variants. In one example, a Cas9 variant (e.g., fCas9) is provided which has improved specificity as compared to the Cas9 nickases or wild type Cas9, exhibiting, e.g., >10-fold, >50-fold, >100-fold, >140-fold, >200-fold, or more, higher specificity than wild type Cas9 (see e.g., the Examples).

Other aspects of the present disclosure provide strategies, methods, compositions, and systems utilizing inventive RNA-guided (e.g., RNA-programmable) Cas9-recombinase fusion proteins. Whereas typical recombinases recognize and recombine distinct target sequences, the Cas9-recombinase fusions provided herein use RNA:DNA hybridization to determine target DNA recombination sites, enabling the fusion proteins to recombine, in principle, any region specified by the gRNA(s).

While of particular relevance to DNA and DNA-cleaving nucleases and/or recombinases, the inventive concepts, methods, strategies and systems provided herein are not limited in this respect, but can be applied to any nucleic acid:nuclease or nucleic acid:recombinase system.

Nucleases

Some aspects of this disclosure provide site-specific nucleases with enhanced specificity that are designed using the methods and strategies described herein. Some embodiments of this disclosure provide nucleic acids encoding such nucleases. Some embodiments of this disclosure provide expression constructs comprising such encoding nucleic acids (See, e.g., FIG. 20). For example, in some embodiments an isolated nuclease is provided that has been engineered to cleave a desired target site within a genome. In some embodiments, the isolated nuclease is a variant of an RNA-programmable nuclease, such as a Cas9 nuclease.

In one embodiment, fusion proteins are provided comprising two domains: (i) an RNA-programmable nuclease (e.g., Cas9 protein, or fragment thereof) domain fused or linked to (ii) a nuclease domain. For example, in some aspects, the Cas9 protein (e.g., the Cas9 domain of the fusion protein) comprises a nuclease-inactivated Cas9 (e.g., a Cas9 lacking DNA cleavage activity; "dCas9") that retains RNA (gRNA) binding activity and is thus able to bind a target site complementary to a gRNA. In some aspects, the nuclease fused to the nuclease-inactivated Cas9 domain is any nuclease requiring dimerization (e.g., the coming together of two monomers of the nuclease) in order to cleave a target nucleic acid (e.g., DNA). In some embodiments, the nuclease fused to the nuclease-inactivated Cas9 is a monomer of the FokI DNA cleavage domain, e.g., thereby producing the Cas9 variant referred to as fCas9. The FokI DNA cleavage domain is known, and in some aspects corresponds to amino acids 388-583 of FokI (NCBI accession number J04623). In some embodiments, the FokI DNA cleavage domain corresponds to amino acids 300-583, 320-583, 340-583, or 360-583 of FokI. See also Wah et al., "Structure of FokI has implications for DNA cleavage" Proc. Natl. Acad. Sci. USA. 1998; 1; 95(18):10564-9; Li et al., "TAL nucleases (TALNs): hybrid proteins composed of TAL effectors and FokI DNA-cleavage domain" Nucleic Acids Res. 2011; 39(1):359-72; Kim et al., "Hybrid restriction enzymes: zinc finger fusions to Fok I cleavage domain" Proc. Natl Acad. Sci. USA. 1996; 93:1156-1160; the entire contents of each are herein incorporated by reference). In some embodiments, the FokI DNA cleavage domain corresponds to, or comprises in part or whole, the amino acid sequence set forth as SEQ ID NO:6. In some embodiments, the FokI DNA cleavage domain is a variant of FokI (e.g., a variant of SEQ ID NO:6), as described herein.

In some embodiments, a dimer of the fusion protein is provided, e.g., dimers of fCas9. For example, in some embodiments, the fusion protein forms a dimer with itself to mediate cleavage of the target nucleic acid. In some embodiments, the fusion proteins, or dimers thereof, are associated with one or more gRNAs. In some aspects, because the dimer contains two fusion proteins, each having a Cas9 domain having gRNA binding activity, a target nucleic acid is targeted using two distinct gRNA sequences that complement two distinct regions of the nucleic acid target. See, e.g., FIGS. 1A, 6D. Thus, in this example, cleavage of the target nucleic acid does not occur until both fusion proteins bind the target nucleic acid (e.g., as specified by the gRNA:target nucleic acid base pairing), and the nuclease domains dimerize (e.g., the FokI DNA cleavage domains; as a result of their proximity based on the binding of the Cas9:gRNA domains of the fusion proteins) and cleave the target nucleic acid, e.g., in the region between the bound Cas9 fusion proteins (the "spacer sequence"). This is exemplified by the schematics shown in FIGS. 1A and 6D. This approach represents a notable improvement over wild type Cas9 and other Cas9 variants, such as the nickases (Ran et al. Double Nicking by RNA-Guided CRISPR Cas9 for Enhanced Genome Editing Specificity. Cell 154, 1380-1389 (2013);

Mali et al. CAS9 transcriptional activators for target specificity screening and paired nickases for cooperative genome engineering. Nat. Biotechnol. 31, 833-838 (2013)), which do not require the dimerization of nuclease domains to cleave a nucleic acid. These nickase variants, as described in the Examples, can induce cleaving, or nicking upon binding of a single nickase to a nucleic acid, which can occur at on- and off-target sites, and nicking is known to induce mutagenesis. An exemplary nucleotide encoding a Cas9 nickase (SEQ ID NO:7) and an exemplary amino acid sequence of Cas9 nickase (SEQ ID NO:8) are provided below. As the variants provided herein require the binding of two Cas9 variants in proximity to one another to induce target nucleic acid cleavage, the chances of inducing off-target cleavage is reduced. See, e.g., the Examples. For example, in some embodiments, a Cas9 variant fused to a nuclease domain (e.g., fCas9) has an on-target:off-target modification ratio that is at least 2-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, at least 110-fold, at least 120-fold, at least 130-fold, at least 140-fold, at least 150-fold, at least 175-fold, at least 200-fold, at least 250-fold, or more higher than the on-target:off-target modification ratio of a wild type Cas9 or other Cas9 variant (e.g., nickase). In some embodiments, a Cas9 variant fused to a nuclease domain (e.g., fCas9) has an on-target:off-target modification ratio that is between about 60- to 180-fold, between about 80- to 160-fold, between about 100- to 150-fold, or between about 120- to 140-fold higher than the on-target:off-target modification ratio of a wild type Cas9 or other Cas9 variant. Methods for determining on-target:off-target modification ratios are known, and include those described in the Examples. In certain embodiments, the on-target:off-target modification ratios are determined by measuring the number or amount of modifications of known Cas9 off-target sites in certain genes. For example, the Cas9 off-target sites of the CLTA, EMX, and VEGF genes are known, and modifications at these sites can be measured and compared between test proteins and controls. The target site and its corresponding known off-target sites (see, e.g., Table 5 for CLTA, EMX, and VEGF off-target sites) are amplified from genomic DNA isolated from cells (e.g., HEK293) treated with a particular Cas9 protein or variant. The modifications are then analyzed by high-throughput sequencing. Sequences containing insertions or deletions of two or more base pairs in potential genomic off-target sites and present in significantly greater numbers (P value <0.005, Fisher's exact test) in the target gRNA-treated samples versus the control gRNA-treated samples are considered Cas9 nuclease-induced genome modifications.

Cas9 Nickase (Nucleotide Sequence):

(SEQ ID NO: 7)

```
ATGGACTATAAGGACCACGACGGAGACTACAAGGATCATGATATTGATTACAAAGACGATGACGATAAGATGGCC

CCAAAGAAGAAGCGGAAGGTCGGTATCCACGGAGTCCCAGCAGCCGATAAAAAGTATTCTATTGGTTTAGCTATC

GGCACTAATTCCGTTGGATGGGCTGTCATAACCGATGAATACAAAGTACCTTCAAAGAAATTTAAGGTGTTGGGG

AACACAGACCGTCATTCGATTAAAAAGAATCTTATCGGTGCCCTCCTATTCGATAGTGGCGAAACGGCAGAGGCG

ACTCGCCTGAAACGAACCGCTCGGAGAAGGTATACACGTCGCAAGAACCGAATATGTTACTTACAAGAAATTTTT

AGCAATGAGATGGCCAAAGTTGACGATTCTTTCTTTCACCGTTTGGAAGAGTCCTTCCTTGTCGAAGAGGACAAG

AAACATGAACGGCACCCCATCTTTGGAAACATAGTAGATGAGGTGGCATATCATGAAAAGTACCCAACGATTTAT

CACCTCAGAAAAAAGCTAGTTGACTCAACTGATAAAGCGGACCTGAGGTTAATCTACTTGGCTCTTGCCCATATG
```

-continued

```
ATAAAGTTCCGTGGGCACTTTCTCATTGAGGGTGATCTAAATCCGGACAACTCGGATGTCGACAAACTGTTCATC

CAGTTAGTACAAACCTATAATCAGTTGTTTGAAGAGAACCCTATAAATGCAAGTGGCGTGGATGCGAAGGCTATT

CTTAGCGCCCGCCTCTCTAAATCCCGACGGCTAGAAAACCTGATCGCACAATTACCCGGAGAGAAGAAAAATGGG

TTGTTCGGTAACCTTATAGCGCTCTCACTAGGCCTGACACCAAATTTTAAGTCGAACTTCGACTTAGCTGAAGAT

GCCAAATTGCAGCTTAGTAAGGACACGTACGATGACGATCTCGACAATCTACTGGCACAAATTGGAGATCAGTAT

GCGGACTTATTTTTGGCTGCCAAAAACCTTAGCGATGCAATCCTCCTATCTGACATACTGAGAGTTAATACTGAG

ATTACCAAGGCGCCGTTATCCGCTTCAATGATCAAAAGGTACGATGAACATCACCAAGACTTGACACTTCTCAAG

GCCCTAGTCCGTCAGCAACTGCCTGAGAAATATAAGGAAATATTCTTTGATCAGTCGAAAAACGGGTACGCAGGT

TATATTGACGGCGGAGCGAGTCAAGAGGAATTCTACAAGTTTATCAAACCCATATTAGAGAAGATGGATGGGACG

GAAGAGTTGCTTGTAAAACTCAATCGCGAAGATCTACTGCGAAAGCAGCGGACTTTCGACAACGGTAGCATTCCA

CATCAAATCCACTTAGGCGAATTGCATGCTATACTTAGAAGGCAGGAGGATTTTTATCCGTTCCTCAAAGACAAT

CGTGAAAAGATTGAGAAAATCCTAACCTTTCGCATACCTTACTATGTGGGACCCCTGGCCCGAGGGAACTCTCGG

TTCGCATGGATGACAAGAAAGTCCGAAGAAACGATTACTCCATGGAATTTTGAGGAAGTTGTCGATAAAGGTGCG

TCAGCTCAATCGTTCATCGAGAGGATGACCAACTTTGACAAGAATTTACCGAACGAAAAAGTATTGCCTAAGCAC

AGTTTACTTTACGAGTATTTCACAGTGTACAATGAACTCACGAAAGTTAAGTATGTCACTGAGGGCATGCGTAAA

CCCGCCTTTCTAAGCGGAGAACAGAAGAAAGCAATAGTAGATCTGTTATTCAAGACCAACCGCAAAGTGACAGTT

AAGCAATTGAAAGAGGACTACTTTAAGAAAATTGAATGCTTCGATTCTGTCGAGATCTCCGGGGTAGAAGATCGA

TTTAATGCGTCACTTGGTACGTATCATGACCTCCTAAAGATAATTAAAGATAAGGACTTCCTGGATAACGAAGAG

AATGAAGATATCTTAGAAGATATAGTGTTGACTCTTACCCTCTTTGAAGATCGGGAAATGATTGAGGAAAGACTA

AAAACATACGCTCACCTGTTCGACGATAAGGTTATGAAACAGTTAAAGAGGCGTCGCTATACGGGCTGGGGACGA

TTGTCGCGGAAACTTATCAACGGGATAAGAGACAAGCAAAGTGGTAAAACTATTCTCGATTTTCTAAAGAGCGAC

GGCTTCGCCAATAGGAACTTTATGCAGCTGATCCATGATGACTCTTTAACCTTCAAAGAGGATATACAAAAGGCA

CAGGTTTCCGGACAAGGGGACTCATTGCACGAACATATTGCGAATCTTGCTGGTTCGCCAGCCATCAAAAAGGGC

ATACTCCAGACAGTCAAAGTAGTGGATGAGCTAGTTAAGGTCATGGGACGTCACAAACCGGAAAACATTGTAATC

GAGATGGCACGCGAAAATCAAACGACTCAGAAGGGGCAAAAAAACAGTCGAGAGCGGATGAAGAGAATAGAAGAG

GGTATTAAAGAACTGGGCAGCCAGATCTTAAAGGAGCATCCTGTGGAAAATACCCAATTGCAGAACGAGAAACTT

TACCTCTATTACCTACAAAATGGAAGGGACATGTATGTTGATCAGGAACTGGACATAAACCGTTTATCTGATTAC

GACGTCGATCACATTGTACCCCAATCCTTTTTGAAGGACGATTCAATCGACAATAAAGTGCTTACACGCTCGGAT

AAGAACCGAGGGAAAAGTGACAATGTTCCAAGCGAGGAAGTCGTAAAGAAAATGAAGAACTATTGGCGGCAGCTC

CTAAATGCGAAACTGATAACGCAAAGAAAGTTCGATAACTTAACTAAAGCTGAGAGGGGTGGCTTGTCTGAACTT

GACAAGGCCGGATTTATTAAACGTCAGCTCGTGGAAACCCGCCAAATCACAAAGCATGTTGCACAGATACTAGAT

TCCCGAATGAATACGAAATACGACGAGAACGATAAGCTGATTCGGGAAGTCAAAGTAATCACTTTAAAGTCAAAA

TTGGTGTCGGACTTCAGAAAGGATTTTCAATTCTATAAAGTTAGGGAGATAAATAACTACCACCATGCGCACGAC

GCTTATCTTAATGCCGTCGTAGGGACCGCACTCATTAAGAAATACCCGAAGCTAGAAAGTGAGTTTGTGTATGGT

GATTACAAAGTTTATGACGTCCGTAAGATGATCGCGAAAAGCGAACAGGAGATAGGCAAGGCTACAGCCAAATAC

TTCTTTTATTCTAACATTATGAATTTCTTTAAGACGGAAATCACTCTGGCAAACGGAGAGATACGCAAACGACCT

TTAATTGAAACCAATGGGGAGACAGGTGAAATCGTATGGGATAAGGGCCGGGACTTCGCGACGGTGAGAAAAGTT

TTGTCCATGCCCCAAGTCAACATAGTAAAGAAAACTGAGGTGCAGACCGGAGGGTTTTCAAAGGAATCGATTCTT

CCAAAAAGGAATAGTGATAAGCTCATCGCTCGTAAAAAGGACTGGGACCCGAAAAAGTACGGTGGCTTCGATAGC

CCTACAGTTGCCTATTCTGTCCTAGTAGTGGCAAAAGTTGAGAAGGGAAAATCCAAGAAACTGAAGTCAGTCAAA
```

```
                                  -continued
GAATTATTGGGGATAACGATTATGGAGCGCTCGTCTTTTGAAAAGAACCCCATCGACTTCCTTGAGGCGAAAGGT

TACAAGGAAGTAAAAAAGGATCTCATAATTAAACTACCAAAGTATAGTCTGTTTGAGTTAGAAAATGGCCGAAAA

CGGATGTTGGCTAGCGCCGGAGAGCTTCAAAAGGGGAACGAACTCGCACTACCGTCTAAATACGTGAATTTCCTG

TATTTAGCGTCCCATTACGAGAAGTTGAAAGGTTCACCTGAAGATAACGAACAGAAGCAACTTTTTGTTGAGCAG

CACAAACATTATCTCGACGAAATCATAGAGCAAATTTCGGAATTCAGTAAGAGAGTCATCCTAGCTGATGCCAAT

CTGGACAAAGTATTAAGCGCATACAACAAGCACAGGGATAAACCCATACGTGAGCAGGCGGAAAATATTATCCAT

TTGTTTACTCTTACCAACCTCGGCGCTCCAGCCGCATTCAAGTATTTTGACACAACGATAGATCGCAAACGATAC

ACTTCTACCAAGGAGGTGCTAGACGCGACACTGATTCACCAATCCATCACGGGATTATATGAAACTCGGATAGAT

TTGTCACAGCTTGGGGGTGAC
```

Cas9 Nickase (D10A)(Amino Acid Sequence):

(SEQ ID NO: 8)
```
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD
```

Figure 9:
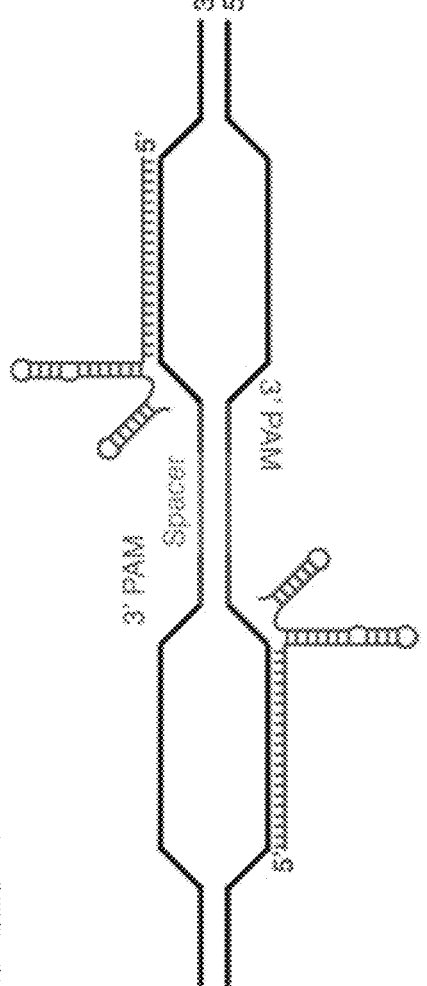
FIG. 9 shows the target DNA sequences in a genomic GFP gene. Seven gRNA target sites were chosen to test FokI-dCas9 candidate activity in an orientation in which the PAM is adjacent to the cleaved spacer sequence (orientation B). Together, these seven gRNAs enabled testing of FokI-dCas9 fusion variants across six spacer lengths ranging from 4 to 42 bp. The sequences shown are identified as follows: "EmGFP (bp 297-388)" corresponds to SEQ ID NO:212; "G8" corresponds to SEQ ID NO:213; "G9" corresponds to SEQ ID NO:214; "G10" corresponds to SEQ ID NO:215; "G11" corresponds to SEQ ID NO:216; "G12" corresponds to SEQ ID NO:217; "G13" corresponds to SEQ ID NO:218; and "G14" corresponds to SEQ ID NO:219.

In some embodiments, the gRNAs which bind the Cas9 variants (e.g., fCas9) can be oriented in one of two ways, with respect to the spacer sequence, deemed the "A" and "B" orientations. In orientation A, the region of the gRNAs that bind the PAM motifs is distal to the spacer sequence with the 5' ends of the gRNAs adjacent to the spacer sequence (FIG. 6C); whereas in orientation B, the region of the gRNAs that bind the PAM motifs is adjacent to the spacer sequence (FIG. 9). In some embodiments, the gRNAs are engineered or selected to bind (e.g., as part of a complex with a Cas9 variant, such as fCas9) to a target nucleic acid in the A or B orientation. In some embodiments, the gRNAs are engineered or selected to bind (e.g., as part of a complex with a Cas9 variant such as fCas9) to a target nucleic acid in the A orientation. In some embodiments, the gRNAs are engineered or selected to bind (e.g., as part of a complex with a Cas9 variant, such as fCas9) to a target nucleic acid in the B orientation.

In some embodiments, the domains of the fusion protein are linked via a linker e.g., as described herein. In certain embodiments, the linker is a peptide linker. In other embodiments, the linker is a non-peptidic linker. In some embodiments, a functional domain is linked via a peptide linker (e.g., fused) or a non-peptidic linker to an inventive fusion protein. In some embodiments, the functional domain is a nuclear localization signal (NLS) domain. An NLS domain comprises an amino acid sequence that "tags" or signals a protein for import into the cell nucleus by nuclear transport. Typically, this signal consists of one or more short sequences of positively charged lysines or arginines exposed on the protein surface. NLS sequences are well known in the art (See e.g., Lange et al., "Classical nuclear localization signals: definition, function, and interaction with importin alpha." *J Biol Chem.* 2007 Feb. 23; 282(8):5101-5; the entire contents of which is hereby incorporated by reference), and include, for example those described in the Examples section. In some embodiments, the NLS sequence comprises, in part or in whole, the amino acid sequence MAPKKKRKVGIHRGVP (SEQ ID NO:318). The domains (e.g., two or more of a gRNA binding domain (dCas9 domain), a catalytic nuclease domain, and a NLS domain) associated via a linker can be linked in any orientation or order. For example, in some embodiments, any domain can be at the N-terminus, the C-terminus, or in between the domains at the N- and C-termini of the fusion protein. In some embodiments, the orientation or order of the domains in an inventive fusion protein are as provided in FIG. 6B. In some embodiments, wherein the fusion protein comprises three domains (e.g., a gRNA binding domain (e.g., dCas9 domain), a nuclease domain (e.g., FokI), and an NLS domain), each domain is connected via a linker, as provided herein. In some embodiments, the domains are not connected via a linker. In some embodiments, one or more of the domains is/are connected via a linker.

In some embodiments, an inventive fusion protein (e.g., fCas9) comprising three domains (e.g., a gRNA binding domain (e.g., dCas9 domain), a nuclease domain (e.g., FokI), and an NLS domain) is encoded by a nucleotide sequence (or fragment or variant thereof) set forth as SEQ ID NO:9, SEQ ID NO:10, SEQ ID NO:11, SEQ ID NO:12, or SEQ ID NO:319, as shown below.

fCas9 (e.g., dCas9-NLS-GGS3Linker-FokI):

(SEQ ID NO: 9)

```
ATGGATAAAAAGTATTCTATTGGTTTAGCTATCGGCACTAATTCCGTTGGATGGGCTGTCATAACCGATGAATAC

AAAGTACCTTCAAAGAAATTTAAGGTGTTGGGGAACACAGACCGTCATTCGATTAAAAAGAATCTTATCGGTGCC

CTCCTATTCGATAGTGGCGAAACGGCAGAGGCGACTCGCCTGAAACGAACCGCTCGGAGAAGGTATACACGTCGC

AAGAACCGAATATGTTACTTACAAGAAATTTTTAGCAATGAGATGGCCAAAGTTGACGATTCTTTCTTTCACCGT

TTGGAAGAGTCCTTCCTTGTCGAAGAGGACAAGAAACATGAACGGCACCCCATCTTTGGAAACATAGTAGATGAG

GTGGCATATCATGAAAAGTACCCAACGATTTATCACCTCAGAAAAAAGCTAGTTGACTCAACTGATAAAGCGGAC

CTGAGGTTAATCTACTTGGCTCTTGCCCATATGATAAAGTTCCGTGGGCACTTTCTCATTGAGGGTGATCTAAAT

CCGGACAACTCGGATGTCGACAAACTGTTCATCCAGTTAGTACAAACCTATAATCAGTTGTTTGAAGAGAACCCT

ATAAATGCAAGTGGCGTGGATGCGAAGGCTATTCTTAGCGCCCGCCTCTCTAAATCCCGACGGCTAGAAAACCTG

ATCGCACAATTACCCGGAGAGAAGAAAAATGGGTTGTTCGGTAACCTTATAGCGCTCTCACTAGGCCTGACACCA

AATTTTAAGTCGAACTTCGACTTAGCTGAAGATGCCAAATTGCAGCTTAGTAAGGACACGTACGATGACGATCTC

GACAATCTACTGGCACAAATTGGAGATCAGTATGCGGACTTATTTTTGGCTGCCAAAAACCTTAGCGATGCAATC

CTCCTATCTGACATACTGAGAGTTAATACTGAGATTACCAAGGCGCCGTTATCCGCTTCAATGATCAAAAGGTAC

GATGAACATCACCAAGACTTGACACTTCTCAAGGCCCTAGTCCGTCAGCAACTGCCTGAGAAATATAAGGAAATA

TTCTTTGATCAGTCGAAAAACGGGTACGCAGGTTATATTGACGGCGGAGCGAGTCAAGAGGAATTCTACAAGTTT

ATCAAACCCATATTAGAGAAGATGGATGGGACGGAAGAGTTGCTTGTAAAACTCAATCGCGAAGATCTACTGCGA

AAGCAGCGGACTTTCGACAACGGTAGCATTCCACATCAAATCCACTTAGGCGAATTGCATGCTATACTTAGAAGG

CAGGAGGATTTTTATCCGTTCCTCAAAGACAATCGTGAAAAGATTGAGAAAATCCTAACCTTTCGCATACCTTAC

TATGTGGGACCCCTGGCCCGAGGGAACTCTCGGTTCGCATGGATGACAAGAAAGTCCGAAGAAACGATTACTCCA

TGGAATTTTGAGGAAGTTGTCGATAAAGGTGCGTCAGCTCAATCGTTCATCGAGAGGATGACCAACTTTGACAAG

AATTTACCGAACGAAAAAGTATTGCCTAAGCACAGTTTACTTTACGAGTATTTCACAGTGTACAATGAACTCACG

AAAGTTAAGTATGTCACTGAGGGCATGCGTAAACCCGCCTTTCTAAGCGGAGAACAGAAGAAAGCAATAGTAGAT

CTGTTATTCAAGACCAACCGCAAAGTGACAGTTAAGCAATTGAAAGAGGACTACTTTAAGAAAATTGAATGCTTC

GATTCTGTCGAGATCTCCGGGGTAGAAGATCGATTTAATGCGTCACTTGGTACGTATCATGACCTCCTAAAGATA

ATTAAAGATAAGGACTTCCTGGATAACGAAGAGAATGAAGATATCTTAGAAGATATAGTGTTGACTCTTACCCTC

TTTGAAGATCGGGAAATGATTGAGGAAAGACTAAAAACATACGCTCACCTGTTCGACGATAAGGTTATGAAACAG

TTAAAGAGGCGTCGCTATACGGGCTGGGGACGATTGTCGCGGAAACTTATCAACGGGATAAGAGACAAGCAAGT

GGTAAAACTATTCTCGATTTTCTAAAGAGCGACGGCTTCGCCAATAGGAACTTTATGCAGCTGATCCATGATGAC

TCTTTAACCTTCAAAGAGGATATACAAAAGGCACAGGTTTCCGGACAAGGGGACTCATTGCACGAACATATTGCG

AATCTTGCTGGTTCGCCAGCCATCAAAAAGGGCATACTCCAGACAGTCAAAGTAGTGGATGAGCTAGTTAAGGTC

ATGGGACGTCACAAACCGGAAAACATTGTAATCGAGATGGCACGCGAAAATCAAACGACTCAGAAGGGGCAAAAA

AACAGTCGAGAGCGGATGAAGAGAATAGAAGAGGGTATTAAAGAACTGGGCAGCCAGATCTTAAAGGAGCATCCT

GTGGAAAATACCCAATTGCAGAACGAGAAACTTTACCTCTATTACCTACAAAATGGAAGGGACATGTATGTTGAT

CAGGAACTGGACATAAACCGTTTATCTGATTACGACGTCGATGCCATTGTACCCCAATCCTTTTTGAAGGACGAT

TCAATCGACAATAAAGTGCTTACACGCTCGGATAAGAACCGAGGGAAAGTGACAATGTTCCAAGCGAGGAAGTC

GTAAAGAAAATGAAGAACTATTGGCGGCAGCTCCTAAATGCGAAACTGATAACGCAAAGAAAGTTCGATAACTTA

ACTAAAGCTGAGAGGGGTGGCTTGTCTGAACTTGACAAGGCCGGATTTATTAAACGTCAGCTCGTGGAAACCCGC
```

-continued

```
CAAATCACAAAGCATGTTGCACAGATACTAGATTCCCGAATGAATACGAAATACGACGAGAACGATAAGCTGATT

CGGGAAGTCAAAGTAATCACTTTAAAGTCAAAATTGGTGTCGGACTTCAGAAAGGATTTTCAATTCTATAAAGTT

AGGGAGATAAATAACTACCACCATGCGCACGACGCTTATCTTAATGCCGTCGTAGGGACCGCACTCATTAAGAAA

TACCCGAAGCTAGAAAGTGAGTTTGTGTATGGTGATTACAAAGTTTATGACGTCCGTAAGATGATCGCGAAAAGC

GAACAGGAGATAGGCAAGGCTACAGCCAAATACTTCTTTTATTCTAACATTATGAATTTCTTTAAGACGGAAATC

ACTCTGGCAAACGGAGAGATACGCAAACGACCTTTAATTGAAACCAATGGGGAGACAGGTGAAATCGTATGGGAT

AAGGGCCGGGACTTCGCGACGGTGAGAAAAGTTTTGTCCATGCCCCAAGTCAACATAGTAAAGAAAACTGAGGTG

CAGACCGGAGGGTTTTCAAAGGAATCGATTCTTCCAAAAAGGAATAGTGATAAGCTCATCGCTCGTAAAAAGGAC

TGGGACCCGAAAAAGTACGGTGGCTTCGATAGCCCTACAGTTGCCTATTCTGTCCTAGTAGTGGCAAAAGTTGAG

AAGGGAAAATCCAAGAAACTGAAGTCAGTCAAAGAATTATTGGGGATAACGATTATGGAGCGCTCGTCTTTTGAA

AAGAACCCCATCGACTTCCTTGAGGCGAAAGGTTACAAGGAAGTAAAAAAGGATCTCATAATTAAACTACCAAAG

TATAGTCTGTTTGAGTTAGAAAATGGCCGAAAACGGATGTTGGCTAGCGCCGGAGAGCTTCAAAAGGGGAACGAA

CTCGCACTACCGTCTAAATACGTGAATTTCCTGTATTTAGCGTCCCATTACGAGAAGTTGAAAGGTTCACCTGAA

GATAACGAACAGAAGCAACTTTTTGTTGAGCAGCACAAACATTATCTCGACGAAATCATAGAGCAAATTTCGGAA

TTCAGTAAGAGAGTCATCCTAGCTGATGCCAATCTGGACAAAGTATTAAGCGCATACAACAAGCACAGGGATAAA

CCCATACGTGAGCAGGCGGAAAATATTATCCATTTGTTTACTCTTACCAACCTCGGCGCTCCAGCCGCATTCAAG

TATTTTGACACAACGATAGATCGCAAACGATACACTTCTACCAAGGAGGTGCTAGACGCGACACTGATTCACCAA

TCCATCACGGGATTATATGAAACTCGGATAGATTTGTCACAGCTTGGGGGTGACGGATCCCCCAAGAAGAAGAGG

AAAGTCTCGAGCGACTACAAAGACCATGACGGTGATTATAAAGATCATGACATCGATTACAAGGATGACGATGAC

AAGGCTGCAGGATCAGGTGGAAGTGGCGGCAGCGGAGGTTCTGGATCCCAACTAGTCAAAAGTGAACTGGAGGAG

AAGAAATCTGAACTTCGTCATAAATTGAAATATGTGCCTCATGAATATATTGAATTAATTGAAATTGCCAGAAAT

TCCACTCAGGATAGAATTCTTGAAATGAAGGTAATGGAATTTTTTATGAAAGTTTATGGATATAGAGGTAAACAT

TTGGGTGGATCAAGGAAACCGGACGGAGCAATTTATACTGTCGGATCTCCTATTGATTACGGTGTGATCGTGGAT

ACTAAAGCTTATAGCGGAGGTTATAATCTGCCAATTGGCCAAGCAGATGAAATGCAACGATATGTCGAAGAAAAT

CAAACACGAAACAAACATATCAACCCTAATGAATGGTGGAAAGTCTATCCATCTTCTGTAACGGAATTTAAGTTT

TTATTTGTGAGTGGTCACTTTAAAGGAAACTACAAAGCTCAGCTTACACGATTAAATCATATCACTAATTGTAAT

GGAGCTGTTCTTAGTGTAGAAGAGCTTTTAATTGGTGGAGAAATGATTAAAGCCGGCACATTAACCTTAGAGGAA

GTCAGACGGAAATTTAATAACGGCGAGATAAACTTT
``` fCas9 (e.g., NLS-dCas9-GGS3Linker-FokI):

```
                                                                    (SEQ ID NO: 10)
ATGGACTACAAAGACCATGACGGTGATTATAAAGATCATGACATCGATTACAAGGATGACGATGACAAGATGGCC

CCCAAGAAGAAGAGGAAGGTGGGCATTCACCGCGGGGTACCTATGGATAAAAAGTATTCTATTGGTTTAGCTATC

GGCACTAATTCCGTTGGATGGGCTGTCATAACCGATGAATACAAAGTACCTTCAAAGAAATTTAAGGTGTTGGGG

AACACAGACCGTCATTCGATTAAAAAGAATCTTATCGGTGCCCTCCTATTCGATAGTGGCGAAACGGCAGAGGCG

ACTCGCCTGAAACGAACCGCTCGGAGAAGGTATACACGTCGCAAGAACCGAATATGTTACTTACAAGAAATTTTT

AGCAATGAGATGGCCAAAGTTGACGATTCTTTCTTTCACCGTTTGGAAGAGTCCTTCCTTGTCGAAGAGGACAAG

AAACATGAACGGCACCCCATCTTTGGAAACATAGTAGATGAGGTGGCATATCATGAAAAGTACCCAACGATTTAT

CACCTCAGAAAAAAGCTAGTTGACTCAACTGATAAAGCGGACCTGAGGTTAATCTACTTGGCTCTTGCCCATATG

ATAAAGTTCCGTGGGCACTTTCTCATTGAGGGTGATCTAAATCCGGACAACTCGGATGTCGACAAACTGTTCATC

CAGTTAGTACAAACCTATAATCAGTTGTTTGAAGAGAACCCTATAAATGCAAGTGGCGTGGATGCGAAGGCTATT
```

-continued

```
CTTAGCGCCCGCCTCTCTAAATCCCGACGGCTAGAAAACCTGATCGCACAATTACCCGGAGAGAAGAAAAATGGG

TTGTTCGGTAACCTTATAGCGCTCTCACTAGGCCTGACACCAAATTTTAAGTCGAACTTCGACTTAGCTGAAGAT

GCCAAATTGCAGCTTAGTAAGGACACGTACGATGACGATCTCGACAATCTACTGGCACAAATTGGAGATCAGTAT

GCGGACTTATTTTTGGCTGCCAAAAACCTTAGCGATGCAATCCTCCTATCTGACATACTGAGAGTTAATACTGAG

ATTACCAAGGCGCCGTTATCCGCTTCAATGATCAAAAGGTACGATGAACATCACCAAGACTTGACACTTCTCAAG

GCCCTAGTCCGTCAGCAACTGCCTGAGAAATATAAGGAAATATTCTTTGATCAGTCGAAAAACGGGTACGCAGGT

TATATTGACGGCGGAGCGAGTCAAGAGGAATTCTACAAGTTTATCAAACCCATATTAGAGAAGATGGATGGGACG

GAAGAGTTGCTTGTAAAACTCAATCGCGAAGATCTACTGCGAAAGCAGCGGACTTTCGACAACGGTAGCATTCCA

CATCAAATCCACTTAGGCGAATTGCATGCTATACTTAGAAGGCAGGAGGATTTTTATCCGTTCCTCAAAGACAAT

CGTGAAAAGATTGAGAAAATCCTAACCTTTCGCATACCTTACTATGTGGGACCCCTGGCCCGAGGGAACTCTCGG

TTCGCATGGATGACAAGAAAGTCCGAAGAACGATTACTCCATGGAATTTTGAGGAAGTTGTCGATAAAGGTGCG

TCAGCTCAATCGTTCATCGAGAGGATGACCAACTTTGACAAGAATTTACCGAACGAAAAAGTATTGCCTAAGCAC

AGTTTACTTTACGAGTATTTCACAGTGTACAATGAACTCACGAAAGTTAAGTATGTCACTGAGGGCATGCGTAAA

CCCGCCTTTCTAAGCGGAGAACAGAAGAAAGCAATAGTAGATCTGTTATTCAAGACCAACCGCAAAGTGACAGTT

AAGCAATTGAAAGAGGACTACTTTAAGAAAATTGAATGCTTCGATTCTGTCGAGATCTCCGGGGTAGAAGATCGA

TTTAATGCGTCACTTGGTACGTATCATGACCTCCTAAAGATAATTAAAGATAAGGACTTCCTGGATAACGAAGAG

AATGAAGATATCTTAGAAGATATAGTGTTGACTCTTACCCTCTTTGAAGATCGGGAAATGATTGAGGAAAGACTA

AAAACATACGCTCACCTGTTCGACGATAAGGTTATGAAACAGTTAAAGAGGCGTCGCTATACGGGCTGGGGACGA

TTGTCGCGGAAACTTATCAACGGGATAAGAGACAAGCAAAGTGGTAAAACTATTCTCGATTTTCTAAAGAGCGAC

GGCTTCGCCAATAGGAACTTTATGCAGCTGATCCATGATGACTCTTTAACCTTCAAAGAGGATATACAAAAGGCA

CAGGTTTCCGGACAAGGGGACTCATTGCACGAACATATTGCGAATCTTGCTGGTTCGCCAGCCATCAAAAAGGGC

ATACTCCAGACAGTCAAAGTAGTGGATGAGCTAGTTAAGGTCATGGGACGTCACAAACCGGAAAACATTGTAATC

GAGATGGCACGCGAAAATCAAACGACTCAGAAGGGGCAAAAAAACAGTCGAGAGCGGATGAAGAGAATAGAAGAG

GGTATTAAAGAACTGGGCAGCCAGATCTTAAAGGAGCATCCTGTGGAAAATACCCAATTGCAGAACGAGAAACTT

TACCTCTATTACCTACAAAATGGAAGGGACATGTATGTTGATCAGGAACTGGACATAAACCGTTTATCTGATTAC

GACGTCGATGCCATTGTACCCCAATCCTTTTTGAAGGACGATTCAATCGACAATAAAGTGCTTACACGCTCGGAT

AAGAACCGAGGGAAAAGTGACAATGTTCCAAGCGAGGAAGTCGTAAAGAAAATGAAGAACTATTGGCGGCAGCTC

CTAAATGCGAAACTGATAACGCAAAGAAAGTTCGATAACTTAACTAAAGCTGAGAGGGGTGGCTTGTCTGAACTT

GACAAGGCCGGATTTATTAAACGTCAGCTCGTGGAAACCCGCCAAATCACAAAGCATGTTGCACAGATACTAGAT

TCCCGAATGAATACGAAATACGACGAGAACGATAAGCTGATTCGGGAAGTCAAAGTAATCACTTTAAAGTCAAAA

TTGGTGTCGGACTTCAGAAAGGATTTTCAATTCTATAAAGTTAGGGAGATAAATAACTACCACCATGCGCACGAC

GCTTATCTTAATGCCGTCGTAGGGACCGCACTCATTAAGAAATACCCGAAGCTAGAAAGTGAGTTTGTGTATGGT

GATTACAAAGTTTATGACGTCCGTAAGATGATCGCGAAAAGCGAACAGGAGATAGGCAAGGCTACAGCCAAATAC

TTCTTTTATTCTAACATTATGAATTTCTTTAAGACGGAAATCACTCTGGCAAACGGAGAGATACGCAAACGACCT

TTAATTGAAACCAATGGGGAGACAGGTGAAATCGTATGGGATAAGGGCCGGGACTTCGCGACGGTGAGAAAAGTT

TTGTCCATGCCCCAAGTCAACATAGTAAAGAAAACTGAGGTGCAGACCGGAGGGTTTTCAAAGGAATCGATTCTT

CCAAAAAGGAATAGTGATAAGCTCATCGCTCGTAAAAAGGACTGGGACCCGAAAAAGTACGGTGGCTTCGATAGC

CCTACAGTTGCCTATTCTGTCCTAGTAGTGGCAAAAGTTGAGAAGGGAAAATCCAAGAAACTGAAGTCAGTCAAA

GAATTATTGGGGATAACGATTATGGAGCGCTCGTCTTTTGAAAAGAACCCCATCGACTTCCTTGAGGCGAAAGGT

TACAAGGAAGTAAAAAAGGATCTCATAATTAAACTACCAAAGTATAGTCTGTTTGAGTTAGAAAATGGCCGAAAA
```

-continued

```
CGGATGTTGGCTAGCGCCGGAGAGCTTCAAAAGGGGAACGAACTCGCACTACCGTCTAAATACGTGAATTTCCTG

TATTTAGCGTCCCATTACGAGAAGTTGAAAGGTTCACCTGAAGATAACGAACAGAAGCAACTTTTTGTTGAGCAG

CACAAACATTATCTCGACGAAATCATAGAGCAAATTTCGGAATTCAGTAAGAGAGTCATCCTAGCTGATGCCAAT

CTGGACAAAGTATTAAGCGCATACAACAAGCACAGGGATAAACCCATACGTGAGCAGGCGGAAAATATTATCCAT

TTGTTTACTCTTACCAACCTCGGCGCTCCAGCCGCATTCAAGTATTTTGACACAACGATAGATCGCAAACGATAC

ACTTCTACCAAGGAGGTGCTAGACGCGACACTGATTCACCAATCCATCACGGGATTATATGAAACTCGGATAGAT

TTGTCACAGCTTGGGGGTGACTCAGGTGGAAGTGGCGGCAGCGGAGGTTCTGGATCCCAACTAGTCAAAAGTGAA

CTGGAGGAGAAGAAATCTGAACTTCGTCATAAATTGAAATATGTGCCTCATGAATATATTGAATTAATTGAAATT

GCCAGAAATTCCACTCAGGATAGAATTCTTGAAATGAAGGTAATGGAATTTTTTATGAAAGTTTATGGATATAGA

GGTAAACATTTGGGTGGATCAAGGAAACCGGACGGAGCAATTTATACTGTCGGATCTCCTATTGATTACGGTGTG

ATCGTGGATACTAAAGCTTATAGCGGAGGTTATAATCTGCCAATTGGCCAAGCAGATGAAATGCAACGATATGTC

GAAGAAAATCAAACACGAAACAAACATATCAACCCTAATGAATGGTGGAAAGTCTATCCATCTTCTGTAACGGAA

TTTAAGTTTTTATTTGTGAGTGGTCACTTTAAAGGAAACTACAAAGCTCAGCTTACACGATTAAATCATATCACT

AATTGTAATGGAGCTGTTCTTAGTGTAGAAGAGCTTTTAATTGGTGGAGAAATGATTAAAGCCGGCACATTAACC

TTAGAGGAAGTCAGACGGAAATTTAATAACGGCGAGATAAACTTT
``` fCas9 (e.g., FokI-GGS3Linker-dCas9-NLS):

(SEQ ID NO: 11)
```
ATGGGATCCCAACTAGTCAAAAGTGAACTGGAGGAGAAGAAATCTGAACTTCGTCATAAATTGAAATATGTGCCT

CATGAATATATTGAATTAATTGAAATTGCCAGAAATTCCACTCAGGATAGAATTCTTGAAATGAAGGTAATGGAA

TTTTTTATGAAAGTTTATGGATATAGAGGTAAACATTTGGGTGGATCAAGGAAACCGGACGGAGCAATTTATACT

GTCGGATCTCCTATTGATTACGGTGTGATCGTGGATACTAAAGCTTATAGCGGAGGTTATAATCTGCCAATTGGC

CAAGCAGATGAAATGCAACGATATGTCGAAGAAAATCAAACACGAAACAAACATATCAACCCTAATGAATGGTGG

AAAGTCTATCCATCTTCTGTAACGGAATTTAAGTTTTTATTTGTGAGTGGTCACTTTAAAGGAAACTACAAAGCT

CAGCTTACACGATTAAATCATATCACTAATTGTAATGGAGCTGTTCTTAGTGTAGAAGAGCTTTTAATTGGTGGA

GAAATGATTAAAGCCGGCACATTAACCTTAGAGGAAGTCAGACGGAAATTTAATAACGGCGAGATAAACTTTGGC

GGTAGTGGGGGATCTGGGGGAAGTATGGATAAAAAGTATTCTATTGGTTTAGCTATCGGCACTAATTCCGTTGGA

TGGGCTGTCATAACCGATGAATACAAAGTACCTTCAAAGAAATTTAAGGTGTTGGGGAACACAGACCGTCATTCG

ATTAAAAAGAATCTTATCGGTGCCCTCCTATTCGATAGTGGCGAAACGGCAGAGGCGACTCGCCTGAAACGAACC

GCTCGGAGAAGGTATACACGTCGCAAGAACCGAATATGTTACTTACAAGAAATTTTTAGCAATGAGATGGCCAAA

GTTGACGATTCTTTCTTTCACCGTTTGGAAGAGTCCTTCCTTGTCGAAGAGGACAAGAAACATGAACGGCACCCC

ATCTTTGGAAACATAGTAGATGAGGTGGCATATCATGAAAAGTACCCAACGATTTATCACCTCAGAAAAAAGCTA

GTTGACTCAACTGATAAAGCGGACCTGAGGTTAATCTACTTGGCTCTTGCCCATATGATAAAGTTCCGTGGGCAC

TTTCTCATTGAGGGTGATCTAAATCCGGACAACTCGGATGTCGACAAACTGTTCATCCAGTTAGTACAAACCTAT

AATCAGTTGTTTGAAGAGAACCCTATAAATGCAAGTGGCGTGGATGCGAAGGCTATTCTTAGCGCCCGCCTCTCT

AAATCCCGACGGCTAGAAAACCTGATCGCACAATTACCCGGAGAGAAGAAAAATGGGTTGTTCGGTAACCTTATA

GCGCTCTCACTAGGCCTGACACCAAATTTTAAGTCGAACTTCGACTTAGCTGAAGATGCCAAATTGCAGCTTAGT

AAGGACACGTACGATGACGATCTCGACAATCTACTGGCACAAATTGGAGATCAGTATGCGGACTTATTTTTGGCT

GCCAAAAACCTTAGCGATGCAATCCTCCTATCTGACATACTGAGAGTTAATACTGAGATTACCAAGGCGCCGTTA

TCCGCTTCAATGATCAAAAGGTACGATGAACATCACCAAGACTTGACACTTCTCAAGGCCCTAGTCCGTCAGCAA

CTGCCTGAGAAATATAAGGAAATATTCTTTGATCAGTCGAAAAACGGGTACGCAGGTTATATTGACGGCGGAGCG
```

-continued

```
AGTCAAGAGGAATTCTACAAGTTTATCAAACCCATATTAGAGAAGATGGATGGGACGGAAGAGTTGCTTGTAAAA

CTCAATCGCGAAGATCTACTGCGAAAGCAGCGGACTTTCGACAACGGTAGCATTCCACATCAAATCCACTTAGGC

GAATTGCATGCTATACTTAGAAGGCAGGAGGATTTTTATCCGTTCCTCAAAGACAATCGTGAAAGATTGAGAAA

ATCCTAACCTTTCGCATACCTTACTATGTGGGACCCCTGGCCCGAGGGAACTCTCGGTTCGCATGGATGACAAGA

AAGTCCGAAGAAACGATTACTCCATGGAATTTTGAGGAAGTTGTCGATAAAGGTGCGTCAGCTCAATCGTTCATC

GAGAGGATGACCAACTTTGACAAGAATTTACCGAACGAAAAAGTATTGCCTAAGCACAGTTTACTTTACGAGTAT

TTCACAGTGTACAATGAACTCACGAAAGTTAAGTATGTCACTGAGGGCATGCGTAAACCCGCCTTTCTAAGCGGA

GAACAGAAGAAAGCAATAGTAGATCTGTTATTCAAGACCAACCGCAAAGTGACAGTTAAGCAATTGAAAGAGGAC

TACTTTAAGAAAATTGAATGCTTCGATTCTGTCGAGATCTCCGGGGTAGAAGATCGATTTAATGCGTCACTTGGT

ACGTATCATGACCTCCTAAAGATAATTAAAGATAAGGACTTCCTGGATAACGAAGAGAATGAAGATATCTTAGAA

GATATAGTGTTGACTCTTACCCTCTTTGAAGATCGGGAAATGATTGAGGAAAGACTAAAAACATACGCTCACCTG

TTCGACGATAAGGTTATGAAACAGTTAAAGAGGCGTCGCTATACGGGCTGGGGACGATTGTCGCGGAAACTTATC

AACGGGATAAGAGACAAGCAAAGTGGTAAAACTATTCTCGATTTTCTAAAGAGCGACGGCTTCGCCAATAGGAAC

TTTATGCAGCTGATCCATGATGACTCTTTAACCTTCAAAGAGGATATACAAAAGGCACAGGTTTCCGGACAAGGG

GACTCATTGCACGAACATATTGCGAATCTTGCTGGTTCGCCAGCCATCAAAAAGGGCATACTCCAGACAGTCAAA

GTAGTGGATGAGCTAGTTAAGGTCATGGGACGTCACAAACCGGAAAACATTGTAATCGAGATGGCACGCGAAAAT

CAAACGACTCAGAAGGGGCAAAAAAACAGTCGAGAGCGGATGAAGAGAATAGAAGAGGGTATTAAAGAACTGGGC

AGCCAGATCTTAAAGGAGCATCCTGTGGAAAATACCCAATTGCAGAACGAGAAACTTTACCTCTATTACCTACAA

AATGGAAGGGACATGTATGTTGATCAGGAACTGGACATAAACCGTTTATCTGATTACGACGTCGATGCCATTGTA

CCCCAATCCTTTTTGAAGGACGATTCAATCGACAATAAAGTGCTTACACGCTCGGATAAGAACCGAGGGAAAAGT

GACAATGTTCCAAGCGAGGAAGTCGTAAAGAAAATGAAGAACTATTGGCGGCAGCTCCTAAATGCGAAACTGATA

ACGCAAAGAAAGTTCGATAACTTAACTAAAGCTGAGAGGGGTGGCTTGTCTGAACTTGACAAGGCCGGATTTATT

AAACGTCAGCTCGTGGAAACCCGCCAAATCACAAAGCATGTTGCACAGATACTAGATTCCCGAATGAATACGAAA

TACGACGAGAACGATAAGCTGATTCGGGAAGTCAAAGTAATCACTTTAAAGTCAAAATTGGTGTCGGACTTCAGA

AAGGATTTTCAATTCTATAAAGTTAGGGAGATAAATAACTACCACCATGCGCACGACGCTTATCTTAATGCCGTC

GTAGGGACCGCACTCATTAAGAAATACCCGAAGCTAGAAAGTGAGTTTGTGTATGGTGATTACAAAGTTTATGAC

GTCCGTAAGATGATCGCGAAAAGCGAACAGGAGATAGGCAAGGCTACAGCCAAATACTTCTTTTATTCTAACATT

ATGAATTTCTTTAAGACGGAAATCACTCTGGCAAACGGAGAGATACGCAAACGACCTTTAATTGAAACCAATGGG

GAGACAGGTGAAATCGTATGGGATAAGGGCCGGGACTTCGCGACGGTGAGAAAAGTTTTGTCCATGCCCCAAGTC

AACATAGTAAAGAAAACTGAGGTGCAGACCGGAGGGTTTTCAAAGGAATCGATTCTTCCAAAAAGGAATAGTGAT

AAGCTCATCGCTCGTAAAAAGGACTGGGACCCGAAAAAGTACGGTGGCTTCGATAGCCCTACAGTTGCCTATTCT

GTCCTAGTAGTGGCAAAAGTTGAGAAGGGAAAATCCAAGAAACTGAAGTCAGTCAAAGAATTATTGGGGATAACG

ATTATGGAGCGCTCGTCTTTTGAAAAGAACCCCATCGACTTCCTTGAGGCGAAAGGTTACAAGGAAGTAAAAAAG

GATCTCATAATTAAACTACCAAAGTATAGTCTGTTTGAGTTAGAAAATGGCCGAAAACGGATGTTGGCTAGCGCC

GGAGAGCTTCAAAAGGGGAACGAACTCGCACTACCGTCTAAATACGTGAATTTCCTGTATTTAGCGTCCCATTAC

GAGAAGTTGAAAGGTTCACCTGAAGATAACGAACAGAAGCAACTTTTTGTTGAGCAGCACAAACATTATCTCGAC

GAAATCATAGAGCAAATTTCGGAATTCAGTAAGAGAGTCATCCTAGCTGATGCCAATCTGGACAAAGTATTAAGC

GCATACAACAAGCACAGGGATAAACCCATACGTGAGCAGGCGGAAAATATTATCCATTTGTTTACTCTTACCAAC

CTCGGCGCTCCAGCCGCATTCAAGTATTTTGACACAACGATAGATCGCAAACGATACACTTCTACCAAGGAGGTG
```

-continued

```
CTAGACGCGACACTGATTCACCAATCCATCACGGGATTATATGAAACTCGGATAGATTTGTCACAGCTTGGGGGT

GACGGATCCCCCAAGAAGAAGAGGAAAGTCTCGAGCGACTACAAAGACCATGACGGTGATTATAAAGATCATGAC

ATCGATTACAAGGATGAGGATGACAAGGCTGCAGGA
``` fCas9 (e.g., NLS-FokI-GGS3Linker-dCas9):

(SEQ ID NO: 12)
```
ATGGACTACAAAGACCATGACGGTGATTATAAAGATCATGACATCGATTACAAGGATGACGATGACAAGATGGCC

CCCAAGAAGAAGAGGAAGGTGGGCATTCACCGCGGGGTACCTGGAGGTTCTATGGGATCCCAACTAGTCAAAAGT

GAACTGGAGGAGAAGAAATCTGAACTTCGTCATAAATTGAAATATGTGCCTCATGAATATATTGAATTAATTGAA

ATTGCCAGAAATTCCACTCAGGATAGAATTCTTGAAATGAAGGTAATGGAATTTTTTATGAAAGTTTATGGATAT

AGAGGTAAACATTTGGGTGGATCAAGGAAACCGGACGGAGCAATTTATACTGTCGGATCTCCTATTGATTACGGT

GTGATCGTGGATACTAAAGCTTATAGCGGAGGTTATAATCTGCCAATTGGCCAAGCAGATGAAATGCAACGATAT

GTCGAAGAAATCAAACACGAAACAAACATATCAACCCTAATGAATGGTGGAAAGTCTATCCATCTTCTGTAACG

GAATTTAAGTTTTTATTTGTGAGTGGTCACTTTAAAGGAAACTACAAAGCTCAGCTTACACGATTAAATCATATC

ACTAATTGTAATGGAGCTGTTCTTAGTGTAGAAGAGCTTTTAATTGGTGGAGAAATGATTAAAGCCGGCACATTA

ACCTTAGAGGAAGTCAGACGGAAATTTAATAACGGCGAGATAAACTTTGGCGGTAGTGGGGGATCTGGGGGAAGT

ATGGATAAAAAGTATTCTATTGGTTTAGCTATCGGCACTAATTCCGTTGGATGGGCTGTCATAACCGATGAATAC

AAAGTACCTTCAAAGAAATTTAAGGTGTTGGGGAACACAGACCGTCATTCGATTAAAAAGAATCTTATCGGTGCC

CTCCTATTCGATAGTGGCGAAACGGCAGAGGCGACTCGCCTGAAACGAACCGCTCGGAGAAGGTATACACGTCGC

AAGAACCGAATATGTTACTTACAAGAAATTTTTAGCAATGAGATGGCCAAAGTTGACGATTCTTTCTTTCACCGT

TTGGAAGAGTCCTTCCTTGTCGAAGAGGACAAGAAACATGAACGGCACCCCATCTTTGGAAACATAGTAGATGAG

GTGGCATATCATGAAAAGTACCCAACGATTTATCACCTCAGAAAAAAGCTAGTTGACTCAACTGATAAAGCGGAC

CTGAGGTTAATCTACTTGGCTCTTGCCCATATGATAAAGTTCCGTGGGCACTTTCTCATTGAGGGTGATCTAAAT

CCGGACAACTCGGATGTCGACAAACTGTTCATCCAGTTAGTACAAACCTATAATCAGTTGTTTGAAGAGAACCCT

ATAAATGCAAGTGGCGTGGATGCGAAGGCTATTCTTAGCGCCCGCCTCTCTAAATCCCGACGGCTAGAAAACCTG

ATCGCACAATTACCCGGAGAGAAGAAAAATGGGTTGTTCGGTAACCTTATAGCGCTCTCACTAGGCCTGACACCA

AATTTTAAGTCGAACTTCGACTTAGCTGAAGATGCCAAATTGCAGCTTAGTAAGGACACGTACGATGACGATCTC

GACAATCTACTGGCACAAATTGGAGATCAGTATGCGGACTTATTTTTGGCTGCCAAAAACCTTAGCGATGCAATC

CTCCTATCTGACATACTGAGAGTTAATACTGAGATTACCAAGGCGCCGTTATCCGCTTCAATGATCAAAAGGTAC

GATGAACATCACCAAGACTTGACACTTCTCAAGGCCCTAGTCCGTCAGCAACTGCCTGAGAAATATAAGGAAATA

TTCTTTGATCAGTCGAAAAACGGGTACGCAGGTTATATTGACGGCGGAGCGAGTCAAGAGGAATTCTACAAGTTT

ATCAAACCCATATTAGAGAAGATGGATGGGACGGAAGAGTTGCTTGTAAAACTCAATCGCGAAGATCTACTGCGA

AAGCAGCGGACTTTCGACAACGGTAGCATTCCACATCAAATCCACTTAGGCGAATTGCATGCTATACTTAGAAGG

CAGGAGGATTTTTATCCGTTCCTCAAAGACAATCGTGAAAAGATTGAGAAAATCCTAACCTTTCGCATACCTTAC

TATGTGGGACCCCTGGCCCGAGGGAACTCTCGGTTCGCATGGATGACAAGAAAGTCCGAAGAAACGATTACTCCA

TGGAATTTTGAGGAAGTTGTCGATAAAGGTGCGTCAGCTCAATCGTTCATCGAGAGGATGACCAACTTTGACAAG

AATTTACCGAACGAAAAGTATTGCCTAAGCACAGTTTACTTTACGAGTATTTCACAGTGTACAATGAACTCACG

AAAGTTAAGTATGTCACTGAGGGCATGCGTAAACCCGCCTTTCTAAGCGGAGAACAGAAGAAAGCAATAGTAGAT

CTGTTATTCAAGACCAACCGCAAAGTGACAGTTAAGCAATTGAAAGAGGACTACTTTAAGAAAATTGAATGCTTC

GATTCTGTCGAGATCTCCGGGGTAGAAGATCGATTTAATGCGTCACTTGGTACGTATCATGACCTCCTAAAGATA

ATTAAAGATAAGGACTTCCTGGATAACGAAGAGAATGAAGATATCTTAGAAGATATAGTGTTGACTCTTACCCTC
```

TTTGAAGATCGGGAAATGATTGAGGAAAGACTAAAAACATACGCTCACCTGTTCGACGATAAGGTTATGAAACAG

TTAAAGAGGCGTCGCTATACGGGCTGGGGACGATTGTCGCGGAAACTTATCAACGGGATAAGAGACAAGCAAAGT

GGTAAAACTATTCTCGATTTTCTAAAGAGCGACGGCTTCGCCAATAGGAACTTTATGCAGCTGATCCATGATGAC

TCTTTAACCTTCAAAGAGGATATACAAAAGGCACAGGTTTCCGGACAAGGGGACTCATTGCACGAACATATTGCG

AATCTTGCTGGTTCGCCAGCCATCAAAAAGGGCATACTCCAGACAGTCAAAGTAGTGGATGAGCTAGTTAAGGTC

ATGGGACGTCACAAACCGGAAAACATTGTAATCGAGATGGCACGCGAAAATCAAACGACTCAGAAGGGGCAAAAA

AACAGTCGAGAGCGGATGAAGAGAATAGAAGAGGGTATTAAAGAACTGGGCAGCCAGATCTTAAAGGAGCATCCT

GTGGAAAATACCCAATTGCAGAACGAGAAACTTTACCTCTATTACCTACAAAATGGAAGGGACATGTATGTTGAT

CAGGAACTGGACATAAACCGTTTATCTGATTACGACGTCGATGCCATTGTACCCCAATCCTTTTTGAAGGACGAT

TCAATCGACAATAAAGTGCTTACACGCTCGGATAAGAACCGAGGGAAAAGTGACAATGTTCCAAGCGAGGAAGTC

GTAAAGAAAATGAAGAACTATTGGCGGCAGCTCCTAAATGCGAAACTGATAACGCAAAGAAAGTTCGATAACTTA

ACTAAAGCTGAGAGGGGTGGCTTGTCTGAACTTGACAAGGCCGGATTTATTAAACGTCAGCTCGTGGAAACCCGC

CAAATCACAAAGCATGTTGCACAGATACTAGATTCCCGAATGAATACGAAATACGACGAGAACGATAAGCTGATT

CGGGAAGTCAAAGTAATCACTTTAAAGTCAAAATTGGTGTCGGACTTCAGAAAGGATTTTCAATTCTATAAAGTT

AGGGAGATAAATAACTACCACCATGCGCACGACGCTTATCTTAATGCCGTCGTAGGGACCGCACTCATTAAGAAA

TACCCGAAGCTAGAAAGTGAGTTTGTGTATGGTGATTACAAAGTTTATGACGTCCGTAAGATGATCGCGAAAAGC

GAACAGGAGATAGGCAAGGCTACAGCCAAATACTTCTTTTATTCTAACATTATGAATTTCTTTAAGACGGAAATC

ACTCTGGCAAACGGAGAGATACGCAAACGACCTTTAATTGAAACCAATGGGGAGACAGGTGAAATCGTATGGGAT

AAGGGCCGGGACTTCGCGACGGTGAGAAAAGTTTTGTCCATGCCCCAAGTCAACATAGTAAAGAAAACTGAGGTG

CAGACCGGAGGGTTTTCAAAGGAATCGATTCTTCCAAAAAGGAATAGTGATAAGCTCATCGCTCGTAAAAAGGAC

TGGGACCCGAAAAAGTACGGTGGCTTCGATAGCCCTACAGTTGCCTATTCTGTCCTAGTAGTGGCAAAAGTTGAG

AAGGGAAAATCCAAGAAACTGAAGTCAGTCAAAGAATTATTGGGGATAACGATTATGGAGCGCTCGTCTTTTGAA

AAGAACCCCATCGACTTCCTTGAGGCGAAAGGTTACAAGGAAGTAAAAAAGGATCTCATAATTAAACTACCAAAG

TATAGTCTGTTTGAGTTAGAAAATGGCCGAAAACGGATGTTGGCTAGCGCCGGAGAGCTTCAAAAGGGGAACGAA

CTCGCACTACCGTCTAAATACGTGAATTTCCTGTATTTAGCGTCCCATTACGAGAAGTTGAAAGGTTCACCTGAA

GATAACGAACAGAAGCAACTTTTTGTTGAGCAGCACAAACATTATCTCGACGAAATCATAGAGCAAATTTCGGAA

TTCAGTAAGAGAGTCATCCTAGCTGATGCCAATCTGGACAAAGTATTAAGCGCATACAACAAGCACAGGGATAAA

CCCATACGTGAGCAGGCGGAAAATATTATCCATTTGTTTACTCTTACCAACCTCGGCGCTCCAGCCGCATTCAAG

TATTTTGACACAACGATAGATCGCAAACGATACACTTCTACCAAGGAGGTGCTAGACGCGACACTGATTCACCAA

TCCATCACGGGATTATATGAAACTCGGATAGATTTGTCACAGCTTGGGGGTGAC fCas9:

(SEQ ID NO: 319)
ATGGACTACAAAGACCATGACGGTGATTATAAAGATCATGACATCGATTACAAGGATGACGATGACAAGATGGCC

CCCAAGAAGAAGAGGAAGGTGGGCATTCACCGCGGGGTACCTGGAGGTTCTGGATCCCAACTAGTCAAAAGTGAA

CTGGAGGAGAAGAAATCTGAACTTCGTCATAAATTGAAATATGTGCCTCATGAATATATTGAATTAATTGAAATT

GCCAGAAATTCCACTCAGGATAGAATTCTTGAAATGAAGGTAATGGAATTTTTTATGAAAGTTTATGGATATAGA

GGTAAACATTTGGGTGGATCAAGGAAACCGGACGGAGCAATTTATACTGTCGGATCTCCTATTGATTACGGTGTG

ATCGTGGATACTAAAGCTTATAGCGGAGGTTATAATCTGCCAATTGGCCAAGCAGATGAAATGCAACGATATGTC

GAAGAAAATCAAACACGAAACAAACATATCAACCCTAATGAATGGTGGAAAGTCTATCCATCTTCTGTAACGGAA

TTTAAGTTTTTATTTGTGAGTGGTCACTTTAAAGGAAACTACAAAGCTCAGCTTACACGATTAAATCATATCACT

-continued

```
AATTGTAATGGAGCTGTTCTTAGTGTAGAAGAGCTTTTAATTGGTGGAGAAATGATTAAAGCCGGCACATTAACC

TTAGAGGAAGTCAGACGGAAATTTAATAACGGCGAGATAAACTTTAGCGGCAGCGAGACTCCCGGGACCTCAGAG

TCCGCCACACCCGAAAGTGATAAAAAGTATTCTATTGGTTTAGCTATCGGCACTAATTCCGTTGGATGGGCTGTC

ATAACCGATGAATACAAAGTACCTTCAAAGAAATTTAAGGTGTTGGGGAACACAGACCGTCATTCGATTAAAAAG

AATCTTATCGGTGCCCTCCTATTCGATAGTGGCGAAACGGCAGAGGCGACTCGCCTGAAACGAACCGCTCGGAGA

AGGTATACACGTCGCAAGAACCGAATATGTTACTTACAAGAAATTTTTAGCAATGAGATGGCCAAAGTTGACGAT

TCTTTCTTTCACCGTTTGGAAGAGTCCTTCCTTGTCGAAGAGGACAAGAAACATGAACGGCACCCCATCTTTGGA

AACATAGTAGATGAGGTGGCATATCATGAAAAGTACCCAACGATTTATCACCTCAGAAAAAAGCTAGTTGACTCA

ACTGATAAAGCGGACCTGAGGTTAATCTACTTGGCTCTTGCCCATATGATAAAGTTCCGTGGGCACTTTCTCATT

GAGGGTGATCTAAATCCGGACAACTCGGATGTCGACAAACTGTTCATCCAGTTAGTACAAACCTATAATCAGTTG

TTTGAAGAGAACCCTATAAATGCAAGTGGCGTGGATGCGAAGGCTATTCTTAGCGCCCGCCTCTCTAAATCCCGA

CGGCTAGAAAACCTGATCGCACAATTACCCGGAGAGAAGAAAAATGGGTTGTTCGGTAACCTTATAGCGCTCTCA

CTAGGCCTGACACCAAATTTTAAGTCGAACTTCGACTTAGCTGAAGATGCCAAATTGCAGCTTAGTAAGGACACG

TACGATGACGATCTCGACAATCTACTGGCACAAATTGGAGATCAGTATGCGGACTTATTTTTGGCTGCCAAAAAC

CTTAGCGATGCAATCCTCCTATCTGACATACTGAGAGTTAATACTGAGATTACCAAGGCGCCGTTATCCGCTTCA

ATGATCAAAAGGTACGATGAACATCACCAAGACTTGACACTTCTCAAGGCCCTAGTCCGTCAGCAACTGCCTGAG

AAATATAAGGAAATATTCTTTGATCAGTCGAAAAACGGGTACGCAGGTTATATTGACGGCGGAGCGAGTCAAGAG

GAATTCTACAAGTTTATCAAACCCATATTAGAGAAGATGGATGGGACGGAAGAGTTGCTTGTAAAACTCAATCGC

GAAGATCTACTGCGAAAGCAGCGGACTTTCGACAACGGTAGCATTCCACATCAAATCCACTTAGGCGAATTGCAT

GCTATACTTAGAAGGCAGGAGGATTTTTATCCGTTCCTCAAAGACAATCGTGAAAAGATTGAGAAAATCCTAACC

TTTCGCATACCTTACTATGTGGGACCCCTGGCCCGAGGGAACTCTCGGTTCGCATGGATGACAAGAAAGTCCGAA

GAAACGATTACTCCATGGAATTTTGAGGAAGTTGTCGATAAAGGTGCGTCAGCTCAATCGTTCATCGAGAGGATG

ACCAACTTTGACAAGAATTTACCGAACGAAAAAGTATTGCCTAAGCACAGTTTACTTTACGAGTATTTCACAGTG

TACAATGAACTCACGAAAGTTAAGTATGTCACTGAGGGCATGCGTAAACCCGCCTTTCTAAGCGGAGAACAGAAG

AAAGCAATAGTAGATCTGTTATTCAAGACCAACCGCAAAGTGACAGTTAAGCAATTGAAAGAGGACTACTTTAAG

AAAATTGAATGCTTCGATTCTGTCGAGATCTCCGGGGTAGAAGATCGATTTAATGCGTCACTTGGTACGTATCAT

GACCTCCTAAAGATAATTAAAGATAAGGACTTCCTGGATAACGAAGAGAATGAAGATATCTTAGAAGATATAGTG

TTGACTCTTACCCTCTTTGAAGATCGGGAAATGATTGAGGAAAGACTAAAAACATACGCTCACCTGTTCGACGAT

AAGGTTATGAAACAGTTAAAGAGGCGTCGCTATACGGGCTGGGGACGATTGTCGCGGAAACTTATCAACGGGATA

AGAGACAAGCAAAGTGGTAAAACTATTCTCGATTTTCTAAAGAGCGACGGCTTCGCCAATAGGAACTTTATGCAG

CTGATCCATGATGACTCTTTAACCTTCAAAGAGGATATACAAAAGGCACAGGTTTCCGGACAAGGGGACTCATTG

CACGAACATATTGCGAATCTTGCTGGTTCGCCAGCCATCAAAAAGGGCATACTCCAGACAGTCAAAGTAGTGGAT

GAGCTAGTTAAGGTCATGGGACGTCACAAACCGGAAAACATTGTAATCGAGATGGCACGCGAAAATCAAACGACT

CAGAAGGGGCAAAAAAACAGTCGAGAGCGGATGAAGAGAATAGAAGAGGGTATTAAAGAACTGGGCAGCCAGATC

TTAAAGGAGCATCCTGTGGAAAATACCCAATTGCAGAACGAGAAACTTTACCTCTATTACCTACAAAATGGAAGG

GACATGTATGTTGATCAGGAACTGGACATAAACCGTTTATCTGATTACGACGTCGATGCCATTGTACCCCAATCC

TTTTTGAAGGACGATTCAATCGACAATAAAGTGCTTACACGCTCGGATAAGAACCGAGGGAAAAGTGACAATGTT

CCAAGCGAGGAAGTCGTAAAGAAAATGAAGAACTATTGGCGGCAGCTCCTAAATGCGAAACTGATAACGCAAAGA

AAGTTCGATAACTTAACTAAAGCTGAGAGGGGTGGCTTGTCTGAACTTGACAAGGCCGGATTTATTAAACGTCAG

CTCGTGGAAACCCGCCAAATCACAAAGCATGTTGCACAGATACTAGATTCCCGAATGAATACGAAATACGACGAG
```

```
                              -continued
AACGATAAGCTGATTCGGGAAGTCAAAGTAATCACTTTAAAGTCAAAATTGGTGTCGGACTTCAGAAAGGATTTT

CAATTCTATAAAGTTAGGGAGATAAATAACTACCACCATGCGCACGACGCTTATCTTAATGCCGTCGTAGGGACC

GCACTCATTAAGAAATACCCGAAGCTAGAAAGTGAGTTTGTGTATGGTGATTACAAAGTTTATGACGTCCGTAAG

ATGATCGCGAAAAGCGAACAGGAGATAGGCAAGGCTACAGCCAAATACTTCTTTTATTCTAACATTATGAATTTC

TTTAAGACGGAAATCACTCTGGCAAACGGAGAGATACGCAAACGACCTTTAATTGAAACCAATGGGGAGACAGGT

GAAATCGTATGGGATAAGGGCCGGGACTTCGCGACGGTGAGAAAAGTTTTGTCCATGCCCCAAGTCAACATAGTA

AAGAAAACTGAGGTGCAGACCGGAGGGTTTTCAAAGGAATCGATTCTTCCAAAAAGGAATAGTGATAAGCTCATC

GCTCGTAAAAAGGACTGGGACCCGAAAAAGTACGGTGGCTTCGATAGCCCTACAGTTGCCTATTCTGTCCTAGTA

GTGGCAAAAGTTGAGAAGGGAAAATCCAAGAAACTGAAGTCAGTCAAAGAATTATTGGGGATAACGATTATGGAG

CGCTCGTCTTTTGAAAAGAACCCCATCGACTTCCTTGAGGCGAAAGGTTACAAGGAAGTAAAAAAGGATCTCATA

ATTAAACTACCAAAGTATAGTCTGTTTGAGTTAGAAAATGGCCGAAAACGGATGTTGGCTAGCGCCGGAGAGCTT

CAAAAGGGGAACGAACTCGCACTACCGTCTAAATACGTGAATTTCCTGTATTTAGCGTCCCATTACGAGAAGTTG

AAAGGTTCACCTGAAGATAACGAACAGAAGCAACTTTTTGTTGAGCAGCACAAACATTATCTCGACGAAATCATA

GAGCAAATTTCGGAATTCAGTAAGAGAGTCATCCTAGCTGATGCCAATCTGGACAAAGTATTAAGCGCATACAAC

AAGCACAGGGATAAACCCATACGTGAGCAGGCGGAAAATATTATCCATTTGTTTACTCTTACCAACCTCGGCGCT

CCAGCCGCATTCAAGTATTTTGACACAACGATAGATCGCAAACGATACACTTCTACCAAGGAGGTGCTAGACGCG

ACACTGATTCACCAATCCATCACGGGATTATATGAAACTCGGATAGATTTGTCACAGCTTGGGGGTGAC
```

In some embodiments, an inventive fusion protein (e.g., fCas9) corresponds to or is encoded by a homologue of any one of SEQ ID NO:9-12 or SEQ ID NO:319.

In some embodiments, an inventive fusion protein (e.g., fCas9) comprises, in part of in whole, one or more of the amino acid sequences set forth as SEQ ID NO:5, SEQ ID NO:320, SEQ ID NO:6, SEQ ID NO:16, SEQ ID NO:318, and SEQ ID NO:321, as provided herein and shown below. The various domains corresponding to SEQ ID NO:5, SEQ ID NO:320, SEQ ID NO:6, SEQ ID NO:16, SEQ ID NO:318, and SEQ ID NO:321 may be arranged in any order with respect to each other. For example, in some embodiments, a dCas9 domain (e.g., SEQ ID NO:5 or SEQ ID NO:320) is at the amino or carboxy terminus, or is somewhere in between the amino and carboxy termini. Similarly, each of the other domains corresponding to SEQ ID NO:6, SEQ ID NO:16, SEQ ID NO:318, and SEQ ID NO:321 may be at the amino or carboxy terminus, or somewhere in between the amino and carboxy termini of an inventive fusion protein (e.g., fCas9). Examples of inventive fusion proteins having various domain arrangements include the inventive fusion proteins corresponding to SEQ ID NOs:9-12 and SEQ ID NO:319. In some embodiments, an inventive fusion protein comprises additional or other domains, such as other linkers, other NLS domains, other nuclease domains, or other Cas9 domains, which may be in addition to or substituted for any of the domains as provided herein. FokI Cleavage Domain:

```
                                      (SEQ ID NO: 6)
GSQLVKSELEEKKSELRHKLKYVPHEYIELIEIARNSTQDRILEMKVMEF

FMKVYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGNYKAQ

LTRLNHITNCNGAVLSVEELLIGGEMIKAGTLTLEEVRRKFNNGEINF
``` dCas9:

```
                                    (SEQ ID NO: 320)
DKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKII

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDAIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT
```

-continued

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKRYTSTKEVLDATLIHQS

ITGLYETRIDLSQLGGD

3×FLAG TAG:

(SEQ ID NO: 321)
                    MDYKDHDGDYKDHDIDYKDDDDK

NLS Domain:

(SEQ ID NO: 318)
                    MAPKKKRKVGIHRGVP

XTEN Linker:

(SEQ ID NO: 16)
                    SGSETPGTSESATPES

In some embodiments, the fusion proteins forming the dimer are coordinated through the action of a single extended gRNA (e.g., as opposed to two separate gRNAs, each binding a monomer of the fusion protein dimer). Thus, in some aspects, the single extended gRNA contains at least two portions, separated by a linker sequence, that complement the target nucleic acid (e.g., bind the target nucleic acid at two distinct sites), and the gRNA is able to bind at least two fusion proteins, as described herein. This is exemplified by the schematic shown in FIG. 1B. In some embodiments, the linker sequence separating the two portions in the extended gRNA has complementarity with the target sequence. In some embodiments, the extended gRNA is at least 50, at least 60, at least 70, at least 80, at least 90, at least 100, at least 125, at least 150, at least 175, at least 200, at least 250, at least 300, at least 350, at least 400, at least 500, at least 600, at least 700, at least 800, at least 900, or at least 1000 or more nucleotides in length. Whether the fusion proteins are coordinated through separate or a single gRNA, to form dimers that can cleave a target nucleic acid, it is expected that the specificity of such cleavage is enhanced (e.g., reduced or no off-target cleavage) as compared to nucleases having a single target nucleic acid binding site. Methods for determining the specificity of a nuclease are known (see e.g., published PCT Application, WO 2013/066438; provisional application U.S. 61/864,289; and Pattanayak, V., Ramirez, C. L., Joung, J. K. & Liu, D. R. Revealing off-target cleavage specificities of zinc-finger nucleases by in vitro selection. *Nature Methods* 8, 765-770 (2011), the entire contents of each of which are incorporated herein by reference).

Figure 4:
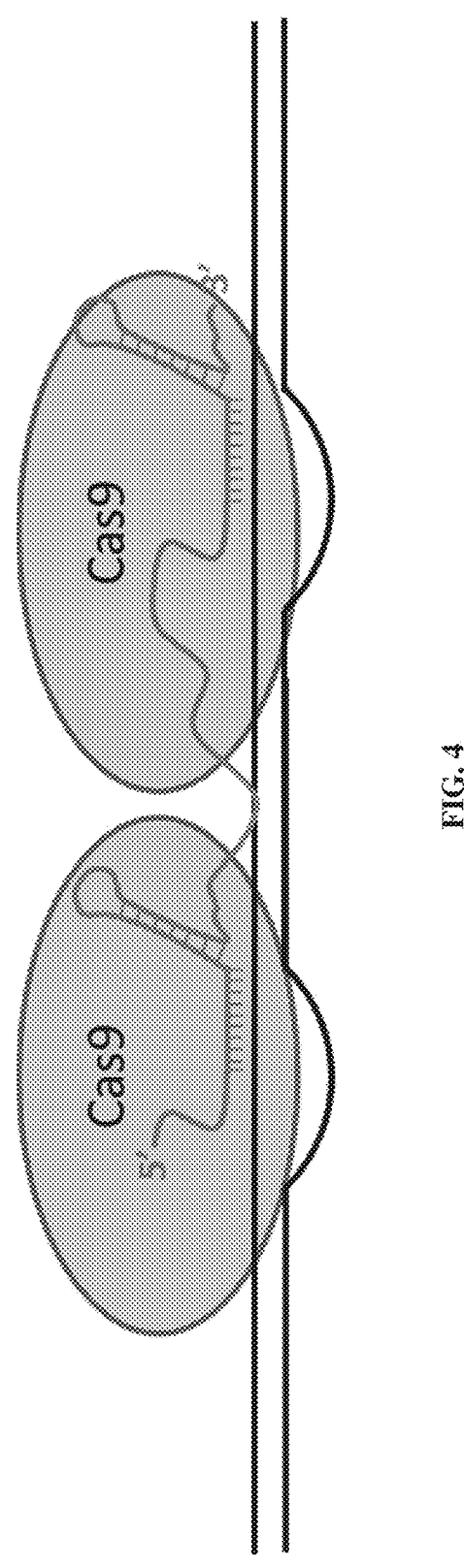
FIG. 4 shows how two Cas9 proteins can be coordinated through the action of a single extended RNA containing two distinct gRNA motifs. Each gRNA targeting region is shortened, such that a single Cas9:gRNA unit cannot bind efficiently by itself. The normal 20 nt targeting sequence has been altered so that some portion (e.g., the 5' initial 10 nt) has been changed to some non-specific linker sequence, such as AAAAAAAAAA (SEQ ID NO:13), with only 10 nt of the gRNA remaining to direct target binding (alternatively this 5' 10 nt is truncated entirely). This "low-affinity" gRNA unit exists as part of a tandem gRNA construct with a second, distinct low-affinity gRNA unit downstream, separated by a linker sequence. In some embodiments, there are more than two low-affinity gRNA units (e.g., at least 3, at least 4, at least 5, etc.). In some embodiments, the linker comprises a target nucleic acid complementary sequence (e.g., as depicted by the linker region contacting the DNA target).

According to another embodiment, dimers of Cas9 protein are provided. In some embodiments, the dimers are coordinated through the action of a single extended gRNA that comprises at least two portions that complement the target nucleic acid. In some embodiments, the portions complementary to the target nucleic acid comprise no more than 25, no more than 24, no more than 23, no more than 22, no more than 21, no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, or no more than 5 nucleotides that complement the target nucleic acid. In some embodiments, the portions complementary to the target nucleic acid comprise 5-30, 5-25, or 5-20 nucleotides. In some embodiments, the portions complementary to the target nucleic acid comprise 15-25, 19-21, or 20 nucleotides. In some embodiments, the portions comprise the same number of nucleotides that complement the target nucleic acid. In some embodiments, the portions comprise different numbers of nucleotides that complement the target nucleic acid. For example, in some embodiments, the extended gRNA comprises two portions that complement (e.g., and hybridize to) the target nucleic acid, each portion comprising 5-19, 10-15, or 10 nucleotides that complement the target nucleic acid. Without wishing to be bound by any particular theory, having the portions comprise fewer than approximately 20 nucleotides typical of gRNAs (e.g., having the portions comprise approximately 5-19, 10-15, or 10 complementary nucleotides), ensures that a single Cas9:gRNA unit cannot bind efficiently by itself. Thus the cooperative binding between Cas9 proteins coordinated by such an extended gRNA improves the specificity and cleavage of intended target nucleic acids. In some embodiments, the linker sequence separating the two portions of the extended gRNA has complementarity with the target sequence. For example, in some embodiments, the linker sequence has at least 5, at least 6, at least 7, at least 8, at least 9, at least 10, at least 11, at least 12, at least 13, at least 14, at least 15, at least 20, at least 25, at least 30, at least 40, or at least 50 nucleotides that complement the target nucleic acid. Without wishing to be bound by any particular theory, it is believed that having an extended gRNA that comprises multiple binding sites (e.g., multiple low-affinity binding sites), including those that are bound by a Cas9 protein as well as those in the linker sequence, provides for increased specificity by promoting cooperative binding. Certain aspects of this embodiment are shown in FIG. 4. In some embodiments, any of the Cas9 proteins described herein may be coordinated through a single extended gRNA.

Figures 2A, 2B, 2C:
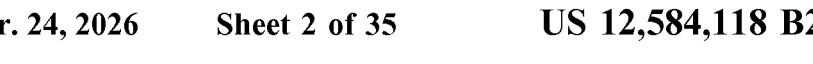
FIG. 2A-2C is a schematic detailing certain embodiments of the invention.
Figure 3:
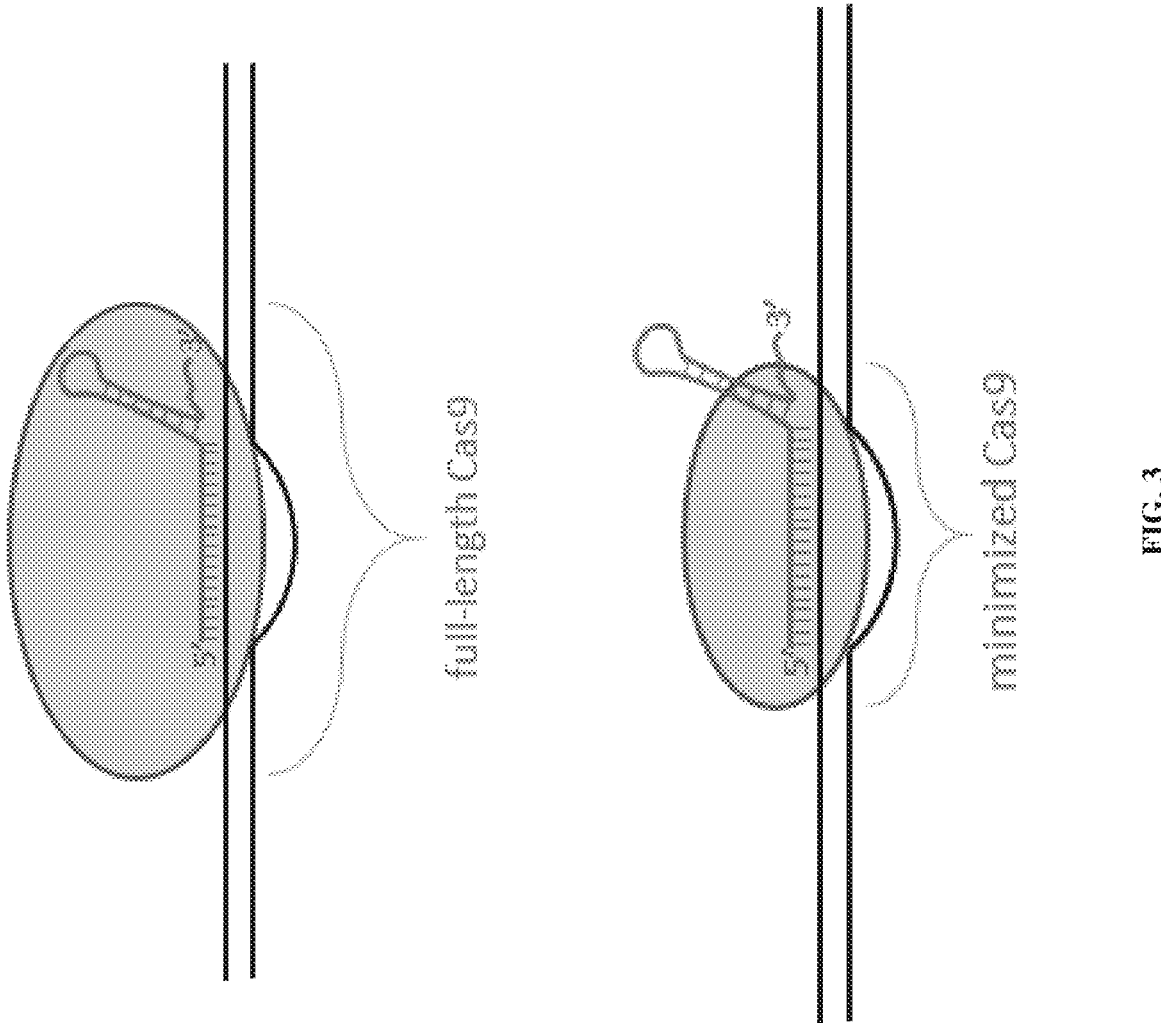
FIG. 3 shows schematically a minimal Cas9 protein that comprises the essential domains for Cas9 activity. Full-length Cas9 is a 4.1 kb gene which results in a protein of >150 kDa. Specific deletions and/or truncations decrease the size of Cas9 without affecting its activity (e.g., gRNA binding and DNA cleavage activity). The minimized Cas9 protein increases the efficacy of, for example, delivery to cells using viral vectors such as AAV (accommodating sequences~<4700 bp) or lentivirus (accommodating sequences~<9 kb), or when pursuing multiplexed gRNA/Cas9 approaches.

In another embodiment, proteins comprising a fragment of an RNA-programmable nuclease (e.g., Cas9) are provided. For example, in some embodiments, a protein comprising the gRNA binding domain of Cas9 is provided. In some embodiments, the protein comprising the gRNA binding domain of Cas9 does not comprise a DNA cleavage domain (referred to herein as the "A-half" of Cas9). In other embodiments, proteins comprising the DNA cleavage domain(s) (e.g., the HNH, RuvC1 subdomains) of Cas9 are provided. In some embodiments, the "DNA cleavage domain" refers collectively to the portions of Cas9 required for double-stranded DNA cleavage (e.g., the HNH, RuvC1 subdomains). In some embodiments, the protein comprising the DNA cleavage domain of Cas9 does not comprise a gRNA binding domain (referred to herein as the "B-half" of Cas9). In some embodiments, dimers are provided that comprise (i) a protein comprising the gRNA binding domain of Cas9 (e.g., the A-half), and (ii) a protein comprising the DNA cleavage domain of Cas9 (e.g., the B-half). In some embodiments, the dimer is bound by a gRNA. For example, such dimers are expected to recapitulate the binding and cleaving activities of a full length Cas9 protein. In some embodiments, such dimers are referred to herein as "dimeric split Cas9." Using a dimeric split Cas9 to cleave a target nucleic acid is expected to provide for increased specificity as compared to a single full length Cas9 protein because both halves of the protein must be co-localized to associate and re-fold into a nuclease-active state. This strategy is shown in the schematic of FIG. 2A.

In some embodiments, fusion proteins comprising two domains are provided: (i) a protein capable of specifically binding a target nucleic acid (e.g., a nuclease-inactivated RNA programmable nuclease, such as a nuclease-inactivated Cas9, as described herein) fused or linked to (ii) a fragment of an RNA-programmable nuclease (e.g., the A- or B-half of Cas9, as described herein). In some embodiments, domain (i) of the aforementioned fusion protein comprises a DNA binding domain, for example, a DNA binding domain of a zinc finger or TALE protein. In some embodiments, the fusion protein comprises (i) a nuclease-inactivated Cas9, and (ii) a gRNA binding domain of Cas9 (e.g., Cas9 A-half). In some embodiments, domain (ii) of the fusion protein does not include a DNA cleavage domain. In other embodiments, the fusion protein comprises (i) a nuclease-inactivated Cas9, and (ii) a DNA cleavage domain (e.g., Cas9 B-half). In some embodiments, domain (ii) of the fusion protein does not include a gRNA binding domain.

In some embodiments, dimers are provided that comprise two proteins: (i) a fusion protein comprising a nuclease-inactivated Cas9 and a gRNA binding domain of Cas9 (e.g., nuclease-inactivated Cas9 fused to Cas9 A-half), and (ii) a protein comprising the DNA cleavage domain of Cas9 (e.g., Cas9 B-half). In other embodiments, the dimer comprises (i) a fusion protein comprising a nuclease-inactivated Cas9 and a DNA cleavage domain of Cas9 (e.g., nuclease-inactivated Cas9 fused to Cas9 B-half), and (ii) a protein comprising the gRNA binding domain of Cas9 (e.g., Cas9 A-half). In some embodiments, the protein dimers include one or more gRNAs. For example, in some embodiments, the dimers include two gRNAs: one bound by the nuclease-inactivated Cas9 domain of the fusion protein; the other bound by the A-half domain (e.g., either the A-half of the fusion protein, or the A-half of the dimer not part of the fusion protein). Such a dimer (e.g., associated with two gRNAs having sequences binding separate regions of a target nucleic acid) is expected to have improved specificity compared to e.g., a Cas9 protein having a single gRNA. This strategy is shown in FIG. 2B.

In some embodiments, a protein dimer is provided that comprises two fusion proteins: (i) a fusion protein comprising a nuclease-inactivated Cas9 and a gRNA binding domain of Cas9 (e.g., a nuclease-inactivated Cas9 fused to a Cas9 A-half), and (ii) a fusion protein comprising a nuclease-inactivated Cas9 and a DNA cleavage domain (e.g., a nuclease-inactivated Cas9 fused to a Cas9 B-half). In some embodiments, the dimer is associated with (e.g., binds) one or more distinct gRNAs. For example, in some embodiments, the dimer is associated with two or three gRNAs. In some embodiments, the dimer is associated with three gRNAs. For example, upon binding of one nuclease-inactivated Cas9:gRNA to a region of a nucleic acid target, and binding of the other nuclease-inactivated Cas9:gRNA to a second region of the nucleic acid target, the split Cas9 halves (e.g., A-half and B-half of the fusion proteins) can dimerize and bind a third gRNA complementary to a third region of the nucleic acid target, to become a fully active Cas9 nuclease, which can cleave dsDNA. This strategy is illustrated in FIG. 2C.

According to another aspect of the invention, minimized Cas9 proteins are provided. By "minimized," it is meant that the Cas9 protein comprises amino acid deletions and/or truncations, as compared to the wild type protein, but retains gRNA binding activity, DNA cleavage activity, or both. Any of the embodiments herein describing Cas9 proteins (e.g., split Cas9 proteins, Cas9 A-half, Cas9 B-half, nuclease-inactivated Cas9 fusion proteins, etc.) can utilize a minimized Cas9 protein. In some embodiments, minimized Cas9 proteins comprising N-terminal deletions and/or truncations are provided. In some embodiments, minimized Cas9 proteins comprising C-terminal deletions and/or truncations are provided. In some embodiments, minimized Cas9 proteins are provided that comprise N- and/or C-terminal deletions and/or truncations. In some embodiments, the minimized Cas9 protein retains both gRNA binding and DNA cleavage activities. In some embodiments, the minimized Cas9 protein comprises an N-terminal truncation that removes at least 5, at least 10, at least 15, at least 20, at least 25, at least 40, at least 40, at least 50, at least 75, at least 100, at least 150, at least 200, at least 250, at least 300, at least 350, at least 400, at least 450, or at least 500 amino acids. In some embodiments, the minimized Cas9 protein comprises a C-terminal truncation that removes at least 5, at least 10, at least 15, at least 20, at least 25, at least 40, at least 40, at least 50, at least 75, at least 100, at least 150, at least 200, at least 250, at least 300, at least 350, at least 400, at least 450, or at least 500 amino acids. In some embodiments, deletions are made within Cas9, for example in regions not affecting gRNA binding and/or DNA cleavage. In some embodiments, the minimized Cas9 protein is associated with one or more gRNAs. In certain embodiments, the minimized Cas9 protein is associated with one gRNA.

Recombinases

Some aspects of this disclosure provide RNA-guided recombinase fusion proteins that are designed using the methods and strategies described herein. Some embodiments of this disclosure provide nucleic acids encoding such recombinases. Some embodiments of this disclosure provide expression constructs comprising such encoding nucleic acids. For example, in some embodiments an isolated recombinase is provided that has been engineered to recombine a desired target site (e.g., a site targeted by one or more gRNAs bound to one or more of the engineered recombinases) within a genome, e.g., with another site in the genome or with an exogenous nucleic acid. In some embodiments, the isolated recombinase comprises a variant of an RNA-programmable nuclease, such as a Cas9 nuclease. In some embodiments, the Cas9 variant is a nuclease-inactivated Cas9 (e.g., dCas9). In some embodiments, dCas9 is encoded by a nucleotide sequence comprising in part or in whole, SEQ ID NO:5 or SEQ ID NO:320. In some embodiments, dCas9 is encoded by a nucleotide sequence comprising a variant of SEQ ID NO:5 or SEQ ID NO:320.

In one embodiment, an RNA-guided recombinase fusion protein is provided. Typically, the fusion protein comprises two or more domains. In some embodiments, the fusion protein comprises two domains. In some embodiments, one of the two or more domains is a nuclease-inactivated Cas9 (or fragment thereof, e.g., Cas9 A-half), for example, those described herein (e.g., dCas9). The Cas9 domain of the recombinase fusion protein is capable of binding one or more gRNAs, and thereby directs or targets the recombinase fusion protein(s) to a target nucleic acid, e.g., as described herein. Another domain of the two or more domains is a recombinase, or a fragment thereof, e.g., a catalytic domain of a recombinase. By "catalytic domain of a recombinase," it is meant that a fusion protein includes a domain comprising an amino acid sequence of (e.g., derived from) a recombinase, such that the domain is sufficient to induce recombination when contacted with a target nucleic acid (either alone or with additional factors including other recombinase catalytic domains which may or may not form part of the fusion protein). In some embodiments, a catalytic domain of a recombinase excludes a DNA binding domain of the recombinase. In some embodiments, the catalytic domain of a recombinase includes part or all of a recombinase, e.g., the catalytic domain may include a recombinase domain and a DNA binding domain, or parts thereof, or the catalytic domain may include a recombinase domain and a DNA binding domain that is mutated or truncated to abolish DNA binding activity. Recombinases and catalytic domains of recombinases are known to those of skill in the art, and include, for example, those described herein. In some embodiments, the catalytic domain is derived from any recombinase. In some embodiments, the recombinase catalytic domain is a catalytic domain of aTn3 resolvase, a Hin recombinase, or a Gin recombinase. In some embodiments, the catalytic domain comprises a Tn3 resolvase (e.g., Stark Tn3 recombinase) that is encoded by a nucleotide sequence comprising, in part or in whole, SEQ ID NO:322, as provided below. In some embodiments, a Tn3 catalytic domain is encoded by a variant of SEQ ID NO:322. In some embodiments, a Tn3 catalytic domain is encoded by a polynucleotide (or a variant thereof) that encodes the polypeptide corresponding to SEQ ID NO:325. In some embodiments, the catalytic domain comprises a Hin recombinase that is encoded by a nucleotide sequence comprising, in part or in whole, SEQ ID NO:323, as provided below. In some embodiments, a Hin catalytic domain is encoded by a variant of SEQ ID NO:323. In some embodiments, a Hin catalytic domain is encoded by a polynucleotide (or a variant thereof) that encodes the polypeptide corresponding to SEQ ID NO:326. In some embodiments, the catalytic domain comprises a Gin recombinase (e.g., Gin beta recombinase) that is encoded by a nucleotide sequence comprising, in part or in whole, SEQ ID NO:324, as provided below. In some embodiments, a Gin catalytic domain is encoded by a variant of SEQ ID NO:324. In some embodiments, a Gin catalytic domain is encoded by a polynucleotide (or a variant thereof) that encodes the polypeptide corresponding to SEQ ID NO:327.

Stark Tn3 Recombinase (Nucleotide: SEQ ID NO:322; Amino Acid: SEQ ID NO:325):

```
                                    (SEQ ID NO: 322)
ATGGCCCTGTTTGGCTACGCACGCGTGTCTACCAGTCAACAGTCACTCGA

TTTGCAAGTGAGGGCTCTTAAAGATGCCGGAGTGAAGGCAAACAGAATTT

TTACTGATAAGGCCAGCGGAAGCAGCACAGACAGAGAGGGGCTGGATCTC

CTGAGAATGAAGGTAAAGGAGGGTGATGTGATCTTGGTCAAAAAATTGGA

TCGACTGGGGAGAGACACAGCTGATATGCTTCAGCTTATTAAAGAGTTTG

ACGCTCAGGGTGTTGCCGTGAGGTTTATCGATGACGGCATCTCAACCGAC

TCCTACATTGGTCTTATGTTTGTGACAATTTTGTCCGCTGTGGCTCAGGC

TGAGCGGAGAAGGATTCTCGAAAGGACGAATGAGGGACGGCAAGCAGCTA

AGTTGAAAGGTATCAAATTTGGCAGACGAAGG
```

```
                                    (SEQ ID NO: 325)
MALFGYARVSTSQQSLDLQVRALKDAGVKANRIFTDKASGSSTDREGLDL

LRMKVKEGDVILVKKLDRLGRDTADMLQLIKEFDAQGVAVRFIDDGISTD

SYIGLMFVTILSAVAQAERRRILERTNEGRQAAKLKGIKFGRRR
```

Hin Recombinase (Nucleotide: SEQ ID NO:323; Amino Acid: SEQ ID NO:326):

```
                                    (SEQ ID NO: 323)
ATGGCAACCATTGGCTACATAAGGGGTGTCTACCATCGACCAAAATATCGA

CCTGCAGCGCAACGCTCTGACATCCGCCAACTGCGATCGGATCTTCGAGG

ATAGGATCAGTGGCAAGATCGCCAACCGGCCCGGTCTGAAGCGGGCTCTG

AAGTACGTGAATAAGGGCGATACTCTGGTTGTGTGGAAGTTGGATCGCTT

GGGTAGATCAGTGAAGAATCTCGTAGCCCTGATAAGCGAGCTGCACGAGA

GGGGTGCACATTTCCATTCTCTGACCGATTCCATCGATACGTCTAGCGCC

ATGGGCCGATTCTTCTTTTACGTCATGTCCGCCCTCGCTGAAATGGAGCG

CGAACTTATTGTTGAACGGACTTTGGCTGGACTGGCAGCGGCTAGAGCAC

AGGGCCGACTTGGA
```

```
                                    (SEQ ID NO: 326)
MATIGYIRVSTIDQNIDLQRNALTSANCDRIFEDRISGKIANRPGLKRAL

KYVNKGDTLVVWKLDRLGRSVKNLVALISELHERGAHFHSLTDSIDTSSA

MGRFFFYVMSALAEMERELIVERTLAGLAAARAQGRLG
```

Gin Beta Recombinase (Nucleotide: SEQ ID NO:324; Amino Acid: SEQ ID NO:327):

```
                                    (SEQ ID NO: 324)
ATGCTCATTGGCTATGTAAGGGTCAGCACCAATGACCAAAACACAGACTT

GCAACGCAATGCTTTGGTTTGCGCCGGATGTGAACAGATATTTGAAGATA

AACTGAGCGGCACTCGGACAGACAGACCTGGGCTTAAGAGAGCACTGAAA

AGACTGCAGAAGGGGGACACCCTGGTCGTCTGGAAACTGGATCGCCTCGG

ACGCAGCATGAAACATCTGATTAGCCTGGTTGGTGAGCTTAGGGAGAGAG

GAATCAACTTCAGAAGCCTGACCGACTCCATCGACACCAGTAGCCCCATG

GGACGATTCTTCTTCTATGTGATGGGAGCACTTGCTGAGATGGAAAGAGA

GCTTATTATCGAAAGAACTATGGCTGGTATCGCTGCTGCCCGGAACAAAG

GCAGACGGTTCGGCAGACCGCCGAAGAGCGGC
```

```
                                    (SEQ ID NO: 327)
MLIGYVRVSTNDQNTDLQRNALVCAGCEQIFEDKLSGTRTDRPGLKRALK

RLQKGDTLVVWKLDRLGRSMKHLISLVGELRERGINFRSLTDSIDTSSPM

GRFFFYVMGALAEMERELIIERTMAGIAAARNKGRRFGRPPKSG
```

In some embodiments, the recombinase catalytic domain is fused to the N-terminus, the C-terminus, or somewhere in between the N- and C-termini of a Cas9 protein (e.g., sCas9). In some embodiments, the fusion protein further comprises a nuclear localization signal (NLS; e.g., any of those provided herein). For example, in some embodiments, the general architecture of exemplary RNA-guided recombinase fusion proteins (e.g., Cas9-recombinase fusions) comprise one of the following structures:

[NH$_2$]-[Cas9]-[recombinase]-[COOH],
  [NH2]-[recombinase]-[Cas9],
[NH$_2$]-[NLS]-[Cas9]-[recombinase]-[COOH],
[NH$_2$]-[NLS]-[recombinase]-[Cas9]-[COOH],
[NH$_2$]-[Cas9]-[NLS]-[recombinase]-[COOH],
[NH$_2$]-[recombinase]-[NLS]-[Cas9]-[COOH],
[NH$_2$]-[Cas9]-[recombinase]-[NLS]-[COOH], or
[NH$_2$]-[recombinase]-[Cas9]-[NLS]-[COOH]

wherein NLS is a nuclear localization signal, NH$_2$ is the N-terminus of the fusion protein, and COOH is the C-terminus of the fusion protein. In some embodiments, a linker is inserted between the Cas9 domain and the recombinase domain, e.g., any linker provided herein. Additional features, such as sequence tags (e.g., any of those provided herein), may also be present.

Pharmaceutical Compositions

In some embodiments, any of the nucleases (e.g., fusion proteins comprising nucleases or nuclease domains) and recombinases (e.g., fusion proteins comprising recombinases or recombinase catalytic domains) described herein are provided as part of a pharmaceutical composition. For example, some embodiments provide pharmaceutical compositions comprising a nuclease and/or recombinase as provided herein, or a nucleic acid encoding such a nuclease and/or recombinase, and a pharmaceutically acceptable excipient. Pharmaceutical compositions may optionally comprise one or more additional therapeutically active substances.

In some embodiments, compositions provided herein are administered to a subject, for example, to a human subject, in order to effect a targeted genomic modification within the subject. In some embodiments, cells are obtained from the subject and are contacted with a nuclease and/or recombinase ex vivo. In some embodiments, cells removed from a subject and contacted ex vivo with an inventive nuclease and/or recombinase are re-introduced into the subject, optionally after the desired genomic modification has been effected or detected in the cells. Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, domesticated animals, pets, and commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient, and then, if necessary and/or desirable, shaping and/or packaging the product into a desired single- or multi-dose unit.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro (Lippincott, Williams & Wilkins, Baltimore, Md., 2006; incorporated in its entirety herein by reference) discloses various excipients used in formulating pharmaceutical compositions and known techniques for the preparation thereof. See also PCT application PCT/US2010/055131, incorporated in its entirety herein by reference, for additional suitable methods, reagents, excipients and solvents for producing pharmaceutical compositions comprising a nuclease. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, compositions in accordance with the present invention may be used for treatment of any of a variety of diseases, disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

Methods for Site-Specific Nucleic Acid Cleavage

In another embodiment of this disclosure, methods for site-specific nucleic acid (e.g., DNA) cleavage are provided. In some embodiments, the methods comprise contacting a DNA with any of the Cas9:gRNA complexes described herein. For example, in some embodiments, the method comprises contacting a DNA with a fusion protein (e.g., fCas9) that comprises two domains: (i) a nuclease-inactivated Cas9 (dCas9); and (ii) a nuclease (e.g., a FokI DNA cleavage domain), wherein the wherein the inactive Cas9 domain binds a gRNA that hybridizes to a region of the DNA. In some embodiments, the method further comprises contacting the DNA with a second fusion protein described herein (e.g., fCas9), wherein the nuclease-inactivated Cas9 (dCas9) domain of the second fusion protein binds a second gRNA that hybridizes to a second region of DNA, wherein the binding of the fusion proteins results in the dimerization of the nuclease domains of the fusion proteins, such that the DNA is cleaved in a region between the bound fusion proteins. See e.g., FIGS. 1A, 6D. In some embodiments, the gRNAs bound to each fusion protein hybridize to the same strand of the DNA, or they hybridize to opposing strands of the DNA. In some embodiments, the gRNAs hybridize to regions of the DNA that are no more than 10, no more than 15, no more than 20, no more than 25, no more than 30, no more than 40, 50, no more than 60, no more than 70, no more than 80, no more than 90, or no more than 100 base pairs apart. The region between the bound Cas9:gRNA complexes may be referred to as the "spacer sequence," which is typically where the target nucleic acid is cleaved. See, e.g., FIGS. 6C-D. In some embodiments, the spacer sequence is at least 5, at least 10, at least 15, at least 20, at least 25, at least 30 at least 35, at least 40, at least 45, at least 50, at least 60, at least 70, at least 80, at least 90, or at least 100 base pairs in length. In some embodiments, the spacer sequence is between about 5 and about 50 base pairs, about 10 and about 40, or about 15 and about 30 base pairs in length. In some embodiments, the spacer sequence is about 15 to about 25 base pairs in length. In some embodiments, the spacer sequence is about 15, about 20, or about 25 base pairs in length. In some embodiments, the Cas9:gRNA complexes are bound in the A orientation, as described herein. In some embodiments, the Cas9:gRNA complexes are bound in the B orientation, as described herein. In some embodiments, the method has an on-target:off-target modification ratio that is at least 2-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, at least 110-fold, at least 120-fold, at least 130-fold, at least 140-fold, at least 150-fold, at least 175-fold, at least 200-fold, or at least 250-fold or more higher than the on-target:off-target modification ratio of methods utilizing a wild type Cas9 or other Cas9 variant. In some embodiments, the method has an on-target:off-target modification ratio that is between about 60- to about 180-fold, between about 80- to about 160-fold, between about 100- to about 150-fold, or between about 120- to about 140-fold higher than the on-target:off-target modification ratio of methods utilizing a wild type Cas9 or other Cas9 variant. Methods for determining on-target:off-target modification ratios are known, and include those described in the Examples. In some embodiments, the fusion proteins are coordinated or associated through a single gRNA, e.g., as described herein.

In some embodiments, the method comprises contacting a nucleic acid with a dimer of Cas9 proteins (or fragments thereof) coordinated with (e.g., bound by) a single gRNA as described herein. In some embodiments, the single gRNA comprises at least two portions that hybridize to the nucleic acid. In some embodiments, the portions comprise at least 5, at least 10, at least 15, or at least 19 complementary nucleotides. In some embodiments, the portions comprise fewer than 20 complementary nucleotides. In some embodiments, a linker sequence separates the portions, wherein the linker sequence also comprises nucleotides complementary to the target nucleic acid (e.g., but are not bound by a Cas9 protein). In some embodiments, the linker sequence does not hybridize to the target nucleic acid.

In some embodiments, the methods comprise contacting a DNA with a protein dimer of fusion proteins described herein, wherein the fusion proteins are bound by one or more gRNAs. For example, in some embodiments, one fusion protein of the dimer comprises a gRNA binding domain of Cas9 (e.g., Cas9 A-half), wherein the protein does not comprise a DNA cleavage domain (e.g., Cas9 B-half); and the other fusion protein of the dimer comprises a DNA cleavage domain of Cas9 (e.g., Cas9 B-half), wherein the protein does not comprise a gRNA binding domain (e.g., Cas9 A-half). Thus, in some embodiments, the binding of a gRNA (e.g., that hybridizes to a target nucleic acid) to one or both of the monomers of the dimer co-localizes the dimer to the target nucleic acid, allowing the dimer to re-fold into a nuclease-active state and cleave the target nucleic acid.

In some embodiments, the method comprises contacting a nucleic acid with protein dimers comprising two proteins: (i) a fusion protein comprising a nuclease-inactivated Cas9 and a gRNA binding domain of Cas9 (e.g., nuclease-inactivated Cas9 fused to Cas9 A-half), and (ii) a protein comprising the DNA cleavage domain of Cas9 (e.g., Cas9 B-half). In other embodiments, the dimer comprises (i) a fusion protein comprising a nuclease-inactivated Cas9 and a DNA cleavage domain of Cas9 (e.g., nuclease-inactivated Cas9 fused to Cas9 B-half), and (ii) a protein comprising the gRNA binding domain of Cas9 (e.g., Cas9 A-half). In some embodiments, the protein dimers are associated with one or more gRNAs. For example, in some embodiments, the dimers are associated with two gRNAs: one bound by the nuclease-inactivated Cas9 domain of the fusion protein; the other bound by the A-half domain (e.g., either the A-half of the fusion protein, or the A-half of the dimer not part of the fusion protein). In some embodiments, the protein dimer comprises (i) a fusion protein comprising a nuclease-inactivated Cas9 and a gRNA binding domain of Cas9 (e.g., a nuclease-inactivated Cas9 fused to a Cas9 A-half), and (ii) a fusion protein comprising a nuclease-inactivated Cas9 and a DNA cleavage domain (e.g., a nuclease-inactivated Cas9 fused to a Cas9 B-half). In some embodiments, the dimer is associated with one or more distinct gRNAs. For example, in some embodiments, the dimer is associated with two or three gRNAs. In some embodiments, the dimer is associated with three gRNAs. For example, upon binding of one nuclease-inactivated Cas9:gRNA to a region of a nucleic acid target, and binding of the other nuclease-inactivated Cas9:gRNA to a second region of the nucleic acid target, the split Cas9 halves (e.g., A-half and B-half of the fusion proteins) dimerize and bind a third gRNA complementary to a third region of the nucleic acid target, to become a fully active Cas9 nuclease leading to cleave of the target DNA.

In some embodiments, a method for site-specific cleavage of a nucleic acid comprises contacting a nucleic acid (e.g., DNA) with a minimized Cas9 protein (e.g., as described herein) associated with a gRNA.

In some embodiments, any of the methods provided herein can be performed on DNA in a cell, for example a bacterium, a yeast cell, or a mammalian cell. In some embodiments, the DNA contacted by any Cas9 protein provided herein is in a eukaryotic cell. In some embodiments, the methods can be performed on a cell or tissue in vitro or ex vivo. In some embodiments, the eukaryotic cell is in an individual, such as a patient or research animal. In some embodiments, the individual is a human.

Methods for Site-Specific Recombination

In another embodiment of this disclosure, methods for site-specific nucleic acid (e.g., DNA) recombination are provided. In some embodiments, the methods are useful for inducing recombination of or between two or more regions of two or more nucleic acid (e.g., DNA) molecules. In other embodiments, the methods are useful for inducing recombination of or between two or more regions in a single nucleic acid molecule (e.g., DNA). In some embodiments, the recombination of one or more target nucleic acid molecules requires the formation of a tetrameric complex at the target site. Typically, the tetramer comprises four (4) inventive RNA-guided recombinase fusion proteins (e.g., a complex of any four inventive recombinase fusion protein provided herein). In some embodiments, each recombinase fusion protein of the tetramer targets a particular DNA sequence via a distinct gRNA bound to each recombinase fusion protein (See, e.g., FIG. 5).

In some embodiments, the method for site-specific recombination between two DNA molecules comprises (a) contacting a first DNA with a first RNA-guided recombinase fusion protein, wherein the nuclease-inactivated Cas9 domain binds a first gRNA that hybridizes to a region of the first DNA; (b) contacting the first DNA with a second RNA-guided recombinase fusion protein, wherein the nuclease-inactivated Cas9 domain of the second fusion protein binds a second gRNA that hybridizes to a second region of the first DNA; (c) contacting a second DNA with a third RNA-guided recombinase fusion protein, wherein the nuclease-inactivated Cas9 domain of the third fusion protein binds a third gRNA that hybridizes to a region of the second DNA; and (d) contacting the second DNA with a fourth RNA-guided recombinase fusion protein, wherein the nuclease-inactivated Cas9 domain of the fourth fusion protein binds a fourth gRNA that hybridizes to a second region of the second DNA. The binding of the fusion proteins in steps (a)-(d) results in the tetramerization of the recombinase catalytic domains of the fusion proteins, such that the DNAs are recombined. In some embodiments, the gRNAs of steps (a) and (b) hybridize to opposing strands of the first DNA, and the gRNAs of steps (c) and (d) hybridize to opposing strands of the second DNA. In some embodiments, the target sites of the gRNAs of steps (a)-(d) are spaced to allow for tetramerization of the recombinase catalytic domains. For example, in some embodiments, the target sites of the gRNAs of steps (a)-(d) are no more than 10, no more 15, no more than 20, no more than 25, no more than 30, no more than 40, no more than 50, no more than 60, no more than 70, no more than 80, no more than 90, or no more than 100 base pairs apart. In some embodiments, the two regions of the two DNA molecules being recombined share homology, such that the regions being recombined are at least 80%, at least 90%, at least 95%, at least 98%, or are 100% homologous.

In another embodiment, methods for site-specific recombination between two regions of a single DNA molecule are provided. In some embodiments, the methods comprise (a) contacting a DNA with a first RNA-guided recombinase fusion protein, wherein the nuclease-inactivated Cas9 domain binds a first gRNA that hybridizes to a region of the DNA; (b) contacting the DNA with a second RNA-guided recombinase fusion protein, wherein the nuclease-inactivated Cas9 domain of the second fusion protein binds a second gRNA that hybridizes to a second region of the DNA; (c) contacting the DNA with a third RNA-guided recombinase fusion protein, wherein the nuclease-inactivated Cas9 domain of the third fusion protein binds a third gRNA that hybridizes to a third region of the DNA; and (d) contacting the DNA with a fourth RNA-guided recombinase fusion protein, wherein the nuclease-inactivated Cas9 domain of the fourth fusion protein binds a fourth gRNA that hybridizes to a fourth region of the DNA. The binding of the fusion proteins in steps (a)-(d) results in the tetramerization of the recombinase catalytic domains of the fusion proteins, such that the DNA is recombined. In some embodiments, two of the gRNAs of steps (a)-(d) hybridize to the same strand of the DNA, and the other two gRNAs of steps (a)-(d) hybridize to the opposing strand of the DNA. In some embodiments, the gRNAs of steps (a) and (b) hybridize to regions of the DNA that are no more 10, no more than 15, no more than 20, no more than 25, no more than 30, no more than 40, no more than 50, no more than 60, no more than 70, no more than 80, no more than 90, or no more than 100 base pairs apart, and the gRNAs of steps (c) and (d) hybridize to regions of the DNA that are no more than 10, no more 15, no more than 20, no more than 25, no more than 30, no more than 40, no more than 50, no more than 60, no more than 70, no more than 80, no more than 90, or no more than 100 base pairs apart. In some embodiments, the two regions of the DNA molecule being recombined share homology, such that the regions being recombined are at least 80%, at least 90%, at least 95%, at least 98%, or are 100% homologous.

In some embodiments, any of the inventive methods for site-specific recombination are amenable for inducing recombination, such that the recombination results in excision (e.g., a segment of DNA is excised from a target DNA molecule), insertion (e.g., a segment of DNA is inserted into a target DNA molecule), inversion (e.g., a segment of DNA is inverted in a target DNA molecule), or translocation (e.g., the exchange of DNA segments between one or more target DNA molecule(s)). In some embodiments, the particular recombination event (e.g., excision, insertion, inversion, translocation, etc.) depends, inter alia, on the orientation (e.g., with respect to the target DNA molecule(s)) of the bound RNA-guided recombinase fusion protein(s). In some embodiments, the orientation, or direction, in which a RNA-guided recombinase fusion protein binds a target nucleic acid can be controlled, e.g., by the particular sequence of the gRNA bound to the RNA-guided recombinase fusion protein(s). Methods for controlling or directing a particular recombination event are known in the art, and include, for example, those described by Turan and Bode, "Site-specific recombinases: from tag-and-target- to tag-and-exchange-based genomic modifications." *FASEB J.* 2011; December; 25(12):4088-107, the entire contents of which are hereby incorporated by reference.

In some embodiments, any of the methods for site-specific recombination can be performed in vivo or in vitro. In some embodiments, any of the methods for site-specific recombination are performed in a cell (e.g., recombine genomic DNA in a cell). The cell can be prokaryotic or eukaryotic. The cell, such as a eukaryotic cell, can be in an individual, such as a subject, as described herein (e.g., a human subject). The methods described herein are useful for the genetic modification of cells in vitro and in vivo, for example, in the context of the generation of transgenic cells, cell lines, or animals, or in the alteration of genomic sequence, e.g., the correction of a genetic defect, in a cell in or obtained from a subject. In some embodiments, a cell obtained from a subject and modified according to the methods provided herein, is re-introduced into a subject (e.g., the same subject), e.g., to treat a disease, or for the production of genetically modified organisms in agriculture or biological research.

In applications in which it is desirable to recombine two or more nucleic acids so as to insert a nucleic acid sequence into a target nucleic acid, a nucleic acid comprising a donor sequence to be inserted is also provided, e.g., to a cell. By a "donor sequence" it is meant a nucleic acid sequence to be inserted at the target site induced by one or more RNA-guided recombinase fusion protein(s). In some embodiments, e.g., in the context of genomic modifications, the donor sequence will share homology to a genomic sequence at the target site, e.g., 1%, 2%, 3%, 4%, 5%, 10%, 20%, 30%, 40%, 50%, 60%, 70%, 80%, 85%, 90%, 95%, or 100% homology with the nucleotide sequences flanking the target site, e.g., within about 100 bases or less of the target site, e.g. within about 90 bases, within about 80 bases, within about 70 bases, within about 60 bases, within about 50 bases, within about 40 bases, within about 30 bases, within about 15 bases, within about 10 bases, within about 5 bases, or immediately flanking the target site. In some embodiments, the donor sequence does not share any homology with the target nucleic acid, e.g., does not share homology to a genomic sequence at the target site. Donor sequences can be of any length, e.g., 10 nucleotides or more, 50 nucleotides or more, 100 nucleotides or more, 250 nucleotides or more, 500 nucleotides or more, 1000 nucleotides or more, 5000 nucleotides or more, 10000 nucleotides or more, 100000 nucleotides or more, etc.

Typically, the donor sequence is not identical to the target sequence that it replaces or is inserted into. In some embodiments, the donor sequence contains at least one or more single base changes, insertions, deletions, inversions or rearrangements with respect to the target sequence (e.g., target genomic sequence). In some embodiments, donor sequences also comprise a vector backbone containing sequences that are not homologous to the DNA region of interest and that are not intended for insertion into the DNA region of interest.

The donor sequence may comprise certain sequence differences as compared to the target (e.g., genomic) sequence, for example restriction sites, nucleotide polymorphisms, selectable markers (e.g., drug resistance genes, fluorescent proteins, enzymes etc.), which can be used to assess for successful insertion of the donor sequence at the target site or in some cases may be used for other purposes (e.g., to signify expression at the targeted genomic locus). In some embodiments, if located in a coding region, such nucleotide sequence differences will not change the amino acid sequence, or will make silent amino acid changes (e.g., changes which do not affect the structure or function of the protein). In some embodiments, these sequences differences may include flanking recombination sequences such as FLPs, loxP sequences, or the like, that can be activated at a later time for removal of e.g., a marker sequence.

The donor sequence may be provided to the cell as single-stranded DNA, single-stranded RNA, double-stranded DNA, or double-stranded RNA. It may be introduced into a cell in linear or circular form. If introduced in linear form, the ends of the donor sequence may be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, e.g., Chang et al., *Proc. Natl. Acad Sci USA.* 1987; 84:4959-4963; Nehls et al., *Science.* 1996; 272:886-889. In some embodiments, a donor sequence can be introduced into a cell as part of a vector molecule having additional sequences such as, for example, replication origins, promoters and genes encoding antibiotic resistance. In some embodiments, donor sequences can be introduced as naked nucleic acid, as nucleic acid complexed with an agent such as a liposome or poloxamer, or can be delivered by viruses (e.g., adenovirus, AAV, etc.).

Polynucleotides, Vectors, Cells, Kits

In another embodiment of this disclosure, polynucleotides encoding one or more of the inventive proteins and/or gRNAs are provided. For example, polynucleotides encoding any of the proteins described herein are provided, e.g., for recombinant expression and purification of isolated nucleases and recombinases, e.g., comprising Cas9 variants. In some embodiments, an isolated polynucleotide comprises one or more sequences encoding a Cas9 half site (e.g., A-half and/or B-half). In some embodiments, an isolated polynucleotide comprises one or more sequences encoding a Cas9 fusion protein, for example, any of the Cas9 fusion proteins described herein (e.g., those comprising a nuclease-inactivated Cas9). In some embodiments, an isolated polynucleotides comprises one or more sequences encoding a gRNA, alone or in combination with a sequence encoding any of the proteins described herein.

In some embodiments, vectors encoding any of the proteins described herein are provided, e.g., for recombinant expression and purification of Cas9 proteins, and/or fusions comprising Cas9 proteins (e.g., variants). In some embodiments, the vector comprises or is engineered to include an isolated polynucleotide, e.g., those described herein. In some embodiments, the vector comprises one or more sequences encoding a Cas9 protein (as described herein), a gRNA, or combinations thereof, as described herein. Typically, the vector comprises a sequence encoding an inventive protein operably linked to a promoter, such that the fusion protein is expressed in a host cell.

In some embodiments, cells are provided, e.g., for recombinant expression and purification of any of the Cas9 proteins provided herein. The cells include any cell suitable for recombinant protein expression, for example, cells comprising a genetic construct expressing or capable of expressing an inventive protein (e.g., cells that have been transformed with one or more vectors described herein, or cells having genomic modifications, for example, those that express a protein provided herein from an allele that has been incorporated in the cell's genome). Methods for transforming cells, genetically modifying cells, and expressing genes and proteins in such cells are well known in the art, and include those provided by, for example, Green and Sambrook, *Molecular Cloning: A Laboratory Manual* (4th ed., Cold Spring Harbor Laboratory Press, Cold Spring Harbor, N.Y. (2012)) and Friedman and Rossi, *Gene Transfer: Delivery and Expression of DNA and RNA, A Laboratory Manual* (1st ed., Cold Spring Harbor Laboratory Press, Cold Spring Harbor, N.Y. (2006)).

Some aspects of this disclosure provide kits comprising a Cas9 variant and/or nuclease and/or recombinase, as provided herein. In some embodiments, the kit comprises a polynucleotide encoding an inventive Cas9 variant, nuclease, and/or recombinase, e.g., as provided herein. In some embodiments, the kit comprises a vector for recombinant protein expression, wherein the vector comprises a polynucleotide encoding any of the proteins provided herein. In some embodiments, the kit comprises a cell (e.g., any cell suitable for expressing Cas9 proteins or fusions comprising Cas9 proteins, such as bacterial, yeast, or mammalian cells) that comprises a genetic construct for expressing any of the proteins provided herein. In some embodiments, any of the kits provided herein further comprise one or more gRNAs and/or vectors for expressing one or more gRNAs. In some embodiments, the kit comprises an excipient and instructions for contacting the nuclease and/or recombinase with the excipient to generate a composition suitable for contacting a nucleic acid with the nuclease and/or recombinase such that hybridization to and cleavage and/or recombination of a target nucleic acid occurs. In some embodiments, the composition is suitable for delivering a Cas9 protein to a cell. In some embodiments, the composition is suitable for delivering a Cas9 protein to a subject. In some embodiments, the excipient is a pharmaceutically acceptable excipient.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Example 1: Fusion of Inactivated Cas9 to FokI Nuclease Improves Genome Modification Specificity Methods:
Oligonucleotides and PCR
All oligonucleotides were purchased from Integrated DNA Technologies (IDT). Oligonucleotide sequences are listed in Table 1. PCR was performed with 0.4 µL of 2 U/µL Phusion Hot Start Flex DNA polymerase (NEB) in 50 µL with 1×HF Buffer, 0.2 mM dNTP mix (0.2 mM dATP, 0.2 mM dCTP, 0.2 mM dGTP, 0.2 mM dTTP) (NEB), 0.5 µM of each primer and a program of: 98° C., 1 min; 35 cycles of [98° C., 15 s; 65° C., 15 s; 72° C., 30 s] unless otherwise noted.

Construction of FokI-dCas9, Cas9 Nickase and gRNA Expression Plasmids

The human codon-optimized *Streptococcus pyogenes* Cas9 nuclease with NLS and 3×FLAG tag (Addgene plasmid 43861)[2] was used as the wild-type Cas9 expression plasmid. PCR (72° C., 3 min) products of wild-type Cas9 expression plasmid as template with Cas9_Exp primers listed in Table 1 below were assembled with Gibson Assembly Cloning Kit (New England Biolabs) to construct Cas9 and FokI-dCas9 variants. Expression plasmids encoding a single gRNA construct (gRNA G1 through G13) were cloned as previously described. Briefly, gRNA oligonucleotides listed in Table 1 containing the 20-bp protospacer target sequence were annealed and the resulting 4-bp overhangs were ligated into BsmBI-digested gRNA expression plasmid. gRNA expression plasmids encoding expression of two separate gRNA constructs from separate promoters on a single plasmid were cloned in a two-step process. First, one gRNA (gRNA E1, V1, C1, C3, H1, G1, G2 or G3) was cloned as above and used as template for PCR (72° C., 3 min) with PCR_Pla-fwd and PCR_Pla-rev primers, 1 µl DpnI (NEB) was added, and the reaction was incubated at 37° C. for 30 min and then subjected to QIAquick PCR Purification Kit (Qiagen) for the "1st gRNA+vector DNA". PCR (72° C., 3 min) of 100 pg of BsmBI-digested gRNA expression plasmid as template with PCR_gRNA-fwd1, PCR_gRNA-rev1, PCR_gRNA-rev2 and appropriate PCR_gRNA primer listed in Table 1 was DpnI treated and purified as above for the "2nd gRNA insert DNA". ~200 ng of "1st gRNA+vector DNA" and ~200 ng of "2nd gRNA insert DNA" were blunt-end ligated in 1×T4 DNA Ligase Buffer, 1 µl of T4 DNA Ligase (400 U/µl, NEB) in a total volume of 20 µl at room temperature (~21° C.) for 15 min. For all cloning, 1 µl of ligation or assembly reaction was transformed into Mach1 chemically competent cells (Life Technologies).

TABLE 1

| Oligonucleotides. '/5Phos/' indicates 5' phosphorylated oligonucleotides. | |
|---|---|
| dCas9-NLS-FokI primers: | |
| Cas9_Exp_CNF_Fok1 + Plas-Fwd | CGGCGAGATAAACTTTTAA TGACCGGTCATCATCACCA (SEQ ID NO: 26) |
| Cas9_Exp_CNF_Cas9coD10-Rev | CCAACGGAATTAGTGCCGATAGCTAAACCAATAGAATACTTTTTATC (SEQ ID NO: 27) |
| Cas9_Exp_CNF_Cas9coD10-Fwd | GATAAAAAGTATTCTATTGGTTTAGCTATCGGCACTAATTCCGTTGG (SEQ ID NO: 28) |
| Cas9_Exp_CNF_Cas9coH850-Rev | TTCAAAAAGGATTGGGGTACAATGGCATCGACGTCGTAATCAGATA AAC (SEQ ID NO: 29) |
| Cas9_Exp_CNF_Cas9coH850-Fwd | GTTTATCTGATTACGACGTCGATGCCATTGTACCCCAATCCTTTTTGA A (SEQ ID NO: 30) |
| Cas9_Exp_CNF_(Cas9)NLS + GGS-Fok-Rev | TTGGGATCCAGAACCTCCTCCTGCAGCCTTGTCATCG (SEQ ID NO: 31) |
| Cas9_Exp_CNF_(Cas9)NLS + GGS 3-Fok-Rev | TTGGGATCCAGAACCTCC GCTGCCGCCACTTCCACCTGA TCCTGCAGCCTTGTCATCG (SEQ ID NO: 32) |
| Cas9_Exp_CNF_(Cas9)NLS + GGS-Fok-Fwd | CGATGACAAGGCTGCAGGAGGAGGTTCTGGATCCCAA (SEQ ID NO: 33) |
| Cas9_Exp_CNF_(Cas9)NLS + GGS3-Fok-Fwd | CGATGACAAGGCTGCAGGA TCAGGTGGAAGTGGCGGCAGC GGAGGTTCTGGATCCCAA (SEQ ID NO: 34) |
| Cas9_Exp_CNF_Fok1 + Plas-Rev | TGGTGATGATGACCGGTCA TTAAAAGTTTATCTCGCCG (SEQ ID NO: 35) |
| NLS-dCas9-FokI primers: | |
| Cas9_Exp_NCF_Fok1 + Plas-Fwd | CGGCGAGATAAACTTTTAA TGACCGGTCATCATCACCA (SEQ ID NO: 36) |
| Cas9_Exp_NCF_PlasS + FLAG (NLS-Fok1-Rev | TAGGGAGAGCCGCCACCATGGACTACAAAGACCATGACGG (SEQ ID NO: 37) |
| Cas9_Exp_NCF_NLS + Cas9coD10-Rev | TAAACCAATAGAATACTTTTTATC CATAGGTACCCGCGGTGAATG (SEQ ID NO: 38) |
| Cas9_Exp_NCF_Cas9coD10-Fwd | GATAAAAAGTATTCTATTGGTTTAGCTATCGGCACTAATTCCGTTGG (SEQ ID NO: 39) |
| Cas9_Exp_NCF_Cas9coH850-Rev | TTCAAAAAGGATTGGGGTACAATGGCATCGACGTCGTAATCAGATA AAC (SEQ ID NO: 40) |

TABLE 1-continued

Oligonucleotides. '/5Phos/' indicates 5' phosphorylated oligonucleotides.

| | |
|---|---|
| Cas9_Exp_NCF_Cas9coH850-Fwd | GTTTATCTGATTACGACGTCGATGCCATTGTACCCCAATCCTTTTTGA A (SEQ ID NO: 41) |
| Cas9_Exp_NCF_Cas9End + GGS-Fok-Rev | TTGGGATCCAGAACCTCCGTCACCCCCAAGCTGTG (SEQ ID NO: 42) |
| Cas9_Exp_NCF_Cas9End + GGS 3-Fok-Rev | TTGGGATCCAGAACCTCC GCTGCCGCCACTTCCACCTGA GTCACCCCCAAGCTGTG (SEQ ID NO: 43) |
| Cas9_Exp_NCF_Cas9End + GGS-Fok-Fwd | CACAGCTTGGGGGTGACGGAGGTTCTGGATCCCAA (SEQ ID NO: 44) |
| Cas9_Exp_NCF_Cas9End + GGS3-Fok-Fwd | CACAGCTTGGGGGTGAC TCAGGTGGAAGTGGCGGCAGC GGAGGTTCTGGATCCCAA (SEQ ID NO: 45) |
| Cas9_Exp_NCF_Fokl + Plas-Rev | TGGTGATGATGACCGGTCA TTAAAAGTTTATCTCGCCG (SEQ ID NO: 46) |

FokI-dCas9-NLS primers:

| | |
|---|---|
| Cas9_Exp_FCN_PlasS + Fok-Fwd | TAGGGAGAGCCGCCACCATGGGATCCCAACTAGTCAAAAG (SEQ ID NO: 47) |
| Cas9_Exp_FCN_Fok1GGS + Cas-Rev | ACCAATAGAATACTTTTTATCCATGCTGCCACCAAAGTTTATCTC (SEQ ID NO: 48) |
| Cas9_Exp_FCN_Fok1GGS3 + Cas-Rev | ACCAATAGAATACTTTTTATCCATGCTGCCGCCACTTCCACCTG (SEQ ID NO: 49) |
| Cas9_Exp_FCN_Cas9coD10-Fwd | GATAAAAAGTATTCTATTGGTTTAGCTATCGGCACTAATTCCGTTGG (SEQ ID NO: 50) |
| Cas9_Exp_FCN_Cas9coH850-Rev | CCAACGGAATTAGTGCCGATAGCTAAACCAATAGAATACTTTTTATC (SEQ ID NO: 51) |
| Cas9_Exp_FCN_Cas9coH850-Fwd | GTTTATCTGATTACGACGTCGATGCCATTGTACCCCAATCCTTTTTGA A (SEQ ID NO: 52) |
| Cas9_Exp_FCN_Cas9End + PlasmidEn-Rev | TGGTGATGATGACCGGTCA GTCACCCCCAAGCTGTG (SEQ ID NO: 53) |
| Cas9_Exp_FCN_Cas9End + PlasmidEn-Fwd | CACAGCTTGGGGGTGAC TGACCGGTCATCATCACCA (SEQ ID NO: 54) |
| Cas9_Exp_FCN_PlasS + Fok-Rev | CTTTTGACTAGTTGGGATCCCATGGTGGCGGCTCTCCCTA (SEQ ID NO: 55) |
| gRNA_G1-top | ACACCCCTCGAACTTCACCTCGGCGG (SEQ ID NO: 56) |
| gRNA_G2-top | ACACCGTCGCCCTCGAACTTCACCTG (SEQ ID NO: 57) |
| gRNA_G3-top | ACACCCAGCTCGATGCGGTTCACCAG (SEQ ID NO: 58) |
| gRNA_G4-top | ACACCGGTGAACCGCATCGAGCTGAG (SEQ ID NO: 59) |
| gRNA_G5-top | ACACCGCTGAAGGGCATCGACTTCAG (SEQ ID NO: 60) |
| gRNA_G6-top | ACACCGGCATCGACTTCAAGGAGGAG (SEQ ID NO: 61) |
| gRNA_G7-top | ACACCCAAGGAGGACGGCAACATCCG (SEQ ID NO: 62) |
| gRNA_G8-top | ACACCACCATCTTCTTCAAGGACGAG (SEQ ID NO: 63) |
| gRNA_G9-top | ACACCCAACTACAAGACCCGCGCCGG (SEQ ID NO: 64) |
| gRNA_G10-top | ACACCCCGCGCCGAGGTGAAGTTCGG (SEQ ID NO: 65) |
| gRNA_G11-top | ACACCGAAGTTCGAGGGCGACACCCG (SEQ ID NO: 66) |
| gRNA_G12-top | ACACCTTCGAACTTCACCTCGGCGCG (SEQ ID NO: 67) |
| gRNA_G13-top | ACACCTCAGCTCGATGCGGTTCACCG (SEQ ID NO: 68) |
| gRNA_G14-top | ACACCCGATGCCCTTCAGCTCGATGG (SEQ ID NO: 69) |
| gRNA_G1-bottom | AAAACCGCCGAGGTGAAGTTCGAGGG (SEQ ID NO: 70) |

TABLE 1-continued

Oligonucleotides. '/5Phos/' indicates 5' phosphorylated oligonucleotides.

| | |
|---|---|
| gRNA_G2-bottom | AAAACAGGTGAAGTTCGAGGGCGACG (SEQ ID NO: 71) |
| gRNA_G3-bottom | AAAACTGGTGAACCGCATCGAGCTGG (SEQ ID NO: 72) |
| gRNA_G4-bottom | AAAACTCAGCTCGATGCGGTTCACCG (SEQ ID NO: 73) |
| gRNA_G5-bottom | AAAACTGAAGTCGATGCCCTTCAGCG (SEQ ID NO: 74) |
| gRNA_G6-bottom | AAAACTCCTCCTTGAAGTCGATGCCG (SEQ ID NO: 75) |
| gRNA_G7-bottom | AAAACGGATGTTGCCGTCCTCCTTGG (SEQ ID NO: 76) |
| gRNA_G8-bottom | AAAACTCGTCCTTGAAGAAGATGGTG (SEQ ID NO: 77) |
| gRNA_G9-bottom | AAAACCGGCGCGGGTCTTGTAGTTGG (SEQ ID NO: 78) |
| gRNA_G10-bottom | AAAACCGAACTTCACCTCGGCGCGGG (SEQ ID NO: 79) |
| gRNA_G11-bottom | AAAACGGGTGTCGCCCTCGAACTTCG (SEQ ID NO: 80) |
| gRNA_G12-bottom | AAAACGCGCCGAGGTGAAGTTCGAAG (SEQ ID NO: 81) |
| gRNA_G13-bottom | AAAACGGTGAACCGCATCGAGCTGAG (SEQ ID NO: 82) |
| gRNA_G14-bottom | AAAACCATCGAGCTGAAGGGCATCGG (SEQ ID NO: 83) |
| gRNA_C1-top | ACACCTGGCCTGCTTGCTAGACTTGG (SEQ ID NO: 84) |
| gRNA_C3-top | ACACCGCAGATGTAGTGTTTCCACAG (SEQ ID NO: 85) |
| gRNA_H1-top | ACACCCTTGCCCCACAGGGCAGTAAG (SEQ ID NO: 86) |
| gRNA_E1-top | ACACCGAGTCCGAGCAGAAGAAGAAG (SEQ ID NO: 87) |
| gRNA_V1-top | ACACCGGGTGGGGGGAGTTTGCTCCG (SEQ ID NO: 88) |
| gRNA_C1-bottom | AAAACCAAGTCTAGCAAGCAGGCCAG (SEQ ID NO: 89) |
| gRNA_C3-bottom | AAAACTGTGGAAACACTACATCTGCG (SEQ ID NO: 90) |
| gRNA_H1-bottom | AAAACTTCTTCTTCTGCTCGGACTCG (SEQ ID NO: 91) |
| gRNA_E1-bottom | AAAACTTACTGCCCTGTGGGGCAAGG (SEQ ID NO: 92) |
| gRNA_V1-bottom | AAAACGGAGCAAACTCCCCCCACCCG (SEQ ID NO: 93) |
| PCR_Pla-fwd | AGG AAA GAA CAT GTG AGC AAA AG (SEQ ID NO: 94) |
| PCR_Pla-rev | CAGCGAGTCAGTGAGCGA (SEQ ID NO: 95) |
| PCR_gRNA-fwd1 | CTGTACAAAAAAGCAGGCTTTA (SEQ ID NO: 96) |
| PCR_gRNA-rev1 | AACGTAGGTCTCTACCGCTGTACAAAAAAGCAGGCTTTA (SEQ ID NO: 97) |
| PCR_gRNA-rev2 | AAAAAAAGCACCGACTCGGTGCCACTTTTTCAAGTTGATAACGGACT AGCCTTATTTTAACTTGCTATTTCTAGCTCTAAAAC (SEQ ID NO: 98) |
| PCR_gRNA_G1 | TTGCTATTTCTAGCTCTAAAACCGCCGAGGTGAAGTTCGAGGGGTGT TTCGTCCTTTCCA (SEQ ID NO: 99) |
| PCR_gRNA_G2 | TTGCTATTTCTAGCTCTAAAACAGGTGAAGTTCGAGGGCGACGGTGT TTCGTCCTTTCCA (SEQ ID NO: 100) |
| PCR_gRNA_G3 | TTGCTATTTCTAGCTCTAAAACTGGTGAACCGCATCGAGCTGGGTGT TTCGTCCTTTCCA (SEQ ID NO: 101) |
| PCR_gRNA_G4 | TTGCTATTTCTAGCTCTAAAACTCAGCTCGATGCGGTTCACCGGTGTT TCGTCCTTTCCA (SEQ ID NO: 102) |
| PCR_gRNA_G5 | TTGCTATTTCTAGCTCTAAAACTGAAGTCGATGCCCTTCAGCGGTGTT TCGTCCTTTCCA (SEQ ID NO: 103) |
| PCR_gRNA_G6 | TTGCTATTTCTAGCTCTAAAACTCCTCCTTGAAGTCGATGCCGGTGTT TCGTCCTTTCCA (SEQ ID NO: 104) |
| PCR_gRNA_G7 | TTGCTATTTCTAGCTCTAAAACGGATGTTGCCGTCCTCCTTGGGTGTT TCGTCCTTTCCA (SEQ ID NO: 105) |

TABLE 1-continued

Oligonucleotides. '/5Phos/' indicates 5' phosphorylated oligonucleotides.

| | |
|---|---|
| PCR_gRNA_C2 | TTGCTATTTCTAGCTCTAAAACGCTTGAGGGAGATGAGGACTGGTGT<br>TTCGTCCTTTCCA (SEQ ID NO: 106) |
| PCR_gRNA_C4 | TTGCTATTTCTAGCTCTAAAACATGACTGTGAAGAGCTTCACGGTGT<br>TTCGTCCTTTCCA (SEQ ID NO: 107) |
| PCR_gRNA_E2 | TTGCTATTTCTAGCTCTAAAACGAGGACAAAGTACAAACGGCGGTGT<br>TTCGTCCTTTCCA (SEQ ID NO: 108) |
| PCR_gRNA_E3 | TTGCTATTTCTAGCTCTAAAACGAACCGGAGGACAAAGTACAGGTGT<br>TTCGTCCTTTCCA (SEQ ID NO: 109) |
| PCR_gRNA_H2 | TTGCTATTTCTAGCTCTAAAACCACCACCAACTTCATCCACGGGTGTT<br>TCGTCCTTTCCA (SEQ ID NO: 110) |
| PCR_gRNA_H3 | TTGCTATTTCTAGCTCTAAAACGGGCCTCACCACCAACTTCAGGTGT<br>TTCGTCCTTTCCA (SEQ ID NO: 111) |
| PCR_gRNA_H4 | TTGCTATTTCTAGCTCTAAAACGCCCAGGGCCTCACCACCAAGGTGT<br>TTCGTCCTTTCCA (SEQ ID NO: 112) |
| PCR_gRNA_H5 | TTGCTATTTCTAGCTCTAAAACACCTGCCCAGGGCCTCACCAGGTGT<br>TTCGTCCTTTCCA (SEQ ID NO: 113) |
| PCR_gRNA_H6 | TTGCTATTTCTAGCTCTAAAACTGATACCAACCTGCCCAGGGGGTGT<br>TTCGTCCTTTCCA (SEQ ID NO: 114) |
| PCR_gRNA_H7 | TTGCTATTTCTAGCTCTAAAACTAAACCTGTCTTGTAACCTTGGTGTT<br>TCGTCCTTTCCA (SEQ ID NO: 115) |
| PCR_gRNA_V2 | TTGCTATTTCTAGCTCTAAAACGCTCTGGCTAAAGAGGGAATGGTGT<br>TTCGTCCTTTCCA (SEQ ID NO: 116) |
| PCR_gRNA_V3 | TTGCTATTTCTAGCTCTAAAACCGGCTCTGGCTAAAGAGGGAGGTGT<br>TTCGTCCTTTCCA (SEQ ID NO: 117) |
| PCRgRNAV | TTGCTATTTCTAGCTCTAAAACTCTGCACACCCCGGCTCTGGGGTGTT<br>TCGTCCTTTCCA (SEQ ID NO: 118) |
| Survey_GFP-fwd | TACGGCAAGCTGACCCTGAA (SEQ ID NO: 119) |
| Survey_GFP-rev | GTCCATGCCGAGAGTGATCC (SEQ ID NO: 120) |
| Survye_CLTA-fwd | GCCAGGGGCTGTTATCTTGG (SEQ ID NO: 121) |
| Survye_CLTA-rev | ATGCACAGAAGCACAGGTTGA (SEQ ID NO: 122) |
| Survey_EMX-fwd | CTGTGTCCTCTTCCTGCCCT (SEQ ID NO: 123) |
| Survey_EMX-rev | CTCTCCGAGGAGAAGGCCAA (SEQ ID NO: 124) |
| Survey_HBB-fwd | GGTAGACCACCAGCAGCCTA (SEQ ID NO: 125) |
| Survey_HBB-rev | CAGTGCCAGAAGAGCCAAGG (SEQ ID NO: 126) |
| Survey_VEGF-fwd | CCACACAGCTTCCCGTTCTC (SEQ ID NO: 127) |
| Survey_VEGF-rev | GAGAGCCGTTCCCTCTTTGC (SEQ ID NO: 128) |
| HTS_EXM_ON-fwd | CCTCCCCATTGGCCTGCTTC (SEQ ID NO: 129) |
| HTS_EXM_Off1-fwd | TCGTCCTGCTCTCACTTAGAC (SEQ ID NO: 130) |
| HTS_EXM_Off2-fwd | TTTTGTGGCTTGGCCCCAGT (SEQ ID NO: 131) |
| HTS_EXM_Off3-fwd | TGCAGTCTCATGACTTGGCCT (SEQ ID NO: 132) |
| HTS_EXM_Off4-fwd | TTCTGAGGGCTGCTACCTGT (SEQ ID NO: 133) |
| HTS_VEFG_ON-fwd | ACATGAAGCAACTCCAGTCCCA (SEQ ID NO: 134) |
| HTS_EXM_Off1-fwd | AGCAGACCCACTGAGTCAACTG (SEQ ID NO: 135) |
| HTS_EXM_Off2-fwd | CCCGCCACAGTCGTGTCAT (SEQ ID NO: 136) |
| HTS_EXM_Off3-fwd | CGCCCCGGTACAAGGTGA (SEQ ID NO: 137) |

TABLE 1-continued

| Oligonucleotides. '/5Phos/' indicates 5' phosphorylated oligonucleotides. | |
| --- | --- |
| HTS_EXM_Off4-fwd | GTACCGTACATTGTAGGATGTTT (SEQ ID NO:138) |
| HTS_CLTA2_ON-fwd | CCTCATCTCCCTCAAGCAGGC (SEQ ID NO: 139) |
| HTS_CLTA2_Off1-fwd | ATTCTGCTCTTGAGGTTATTTGT (SEQ ID NO: 140) |
| HTS_CLTA2_Off2-fwd | CACCTCTGCCTCAAGAGCAGAAAA (SEQ ID NO: 141) |
| HTS_CLTA2_Off3-fwd | TGTGTGTGTGTGTGTGTAGGACT (SEQ ID NO: 142) |
| HTS_EXM_ON-rev | TCATCTGTGCCCCTCCCTCC (SEQ ID NO: 143) |
| HTS_EXM_Off-rev | CGAGAAGGAGGTGCAGGAG (SEQ ID NO: 144) |
| HTS_EXM_Off-rev | CGGGAGCTGTTCAGAGGCTG (SEQ ID NO: 145) |
| HTS_EXM_Off-rev | CTCACCTGGGCGAGAAAGGT (SEQ ID NO: 146) |
| HTS_EXM_Off-rev | AAAACTCAAAGAAATGCCCAATCA (SEQ ID NO: 147) |
| HTS_VEFG_ON-rev | AGACGCTGCTCGCTCCATTC (SEQ ID NO: 148) |
| HTS_EXM_Off1-rev | ACAGGCATGAATCACTGCACCT (SEQ ID NO: 149) |
| HTS_EXM_Off2-rev | GCGGCAACTTCAGACAACCGA (SEQ ID NO: 150) |
| HTS_EXM_Off3-rev | GACCCAGGGGCACCAGTT (SEQ ID NO: 151) |
| HTS_EXM_Off4-rev | CTGCCTTCATTGCTTAAAAGTGGAT (SEQ ID NO: 152) |
| HTS_CLTA2_ON-rev | ACAGTTGAAGGAAGGAAACATGC (SEQ ID NO: 153) |
| HTS_CLTA2_Off1-rev | GCTGCATTTGCCCATTTCCA (SEQ ID NO: 154) |
| HTS_CLTA2_Off2-rev | GTTGGGGGAGGAGGAGCTTAT (SEQ ID NO: 155) |
| HTS_CLTA2_Off3-rev | CTAAGAGCTATAAGGGCAAATGACT (SEQ ID NO: 156) |

Modification of Genomic GFP

HEK293-GFP stable cells (GenTarget) were used as a cell line constitutively expressing an Emerald GFP gene (GFP) integrated on the genome. Cells were maintained in Dulbecco's modified Eagle medium (DMEM, Life Technologies) supplemented with 10% (vol/vol) fetal bovine serum (FBS, Life Technologies) and penicillin/streptomycin (1×, Amresco). 5×10$^4$ HEK293-GFP cells were plated on 48-well collagen coated Biocoat plates (Becton Dickinson). One day following plating, cells at ~75% confluence were transfected with Lipofecatmine 2000 (Life Technologies) according to the manufacturer's protocol. Briefly, 1.5 μL of Lipofecatmine 2000 was used to transfect 950 ng of total plasmid (Cas9 expression plasmid plus gRNA expression plasmids). 700 ng of Cas9 expression plasmid, 125 ng of one gRNA expression plasmid and 125 ng of the paired gRNA expression plasmid with the pairs of targeted gRNAs listed in FIG. 6D and FIG. 9A. Separate wells were transfected with 1 μg of a near-infrared iRFP670 (Addgene plasmid 45457)[32] as a transfection control. 3.5 days following transfection, cells were trypsinized and resuspended in DMEM supplemented with 10% FBS and analyzed on a C6 flow cytometer (Accuri) with a 488 nm laser excitation and 520 nm filter with a 20 nm band pass. For each sample, transfections and flow cytometry measurements were performed once.

T7 Endonuclease I Surveyor Assays of Genomic Modifications

HEK293-GFP stable cells were transfected with Cas9 expression and gRNA expression plasmids as described above. A single plasmid encoding two separate gRNAs was transfected. For experiments titrating the total amount of expression plasmids (Cas9 expression+gRNA expression plasmid), 700/250, 350/125, 175/62.5, 88/31 ng of Cas9 expression plasmid/ng of gRNA expression plasmid were combined with inert carrier plasmid, pUC19 (NEB), as necessary to reach a total of 950 ng transfected plasmid DNA.

Genomic DNA was isolated from cells 2 days after transfection using a genomic DNA isolation kit, DNAdvance Kit (Agencourt). Briefly, cells in a 48-well plate were incubated with 40 μL of tryspin for 5 min at 37° C. 160 uL of DNAdvance lysis solution was added and the solution incubated for 2 hr at 55° C. and the subsequent steps in the Agencourt DNAdvance kit protocol were followed. 40 ng of isolated genomic DNA was used as template to PCR amplify the targeted genomic loci with flanking Survey primer pairs specified in Table 1. PCR products were purified with a QIAquick PCR Purification Kit (Qiagen) and quantified with Quant-iT™ PicoGreen® dsDNA Kit (Life Technologies). 250 ng of purified PCR DNA was combined with 2 μL of NEBuffer 2 (NEB) in a total volume of 19 μL and denatured then re-annealed with thermocycling at 95° C. for 5 min, 95 to 85° C. at 2° C./s; 85 to 20° C. at 0.2° C./s. The re-annealed DNA was incubated with 1 μl of T7 Endonuclease I (10 U/μl, NEB) at 37° C. for 15 min. 10 μL of 50% glycerol was added to the T7 Endonuclease reaction and 12 μL was analyzed on a 5% TBE 18-well Criterion PAGE gel (Bio-Rad) electrophoresed for 30 min at 150 V, then stained with 1×SYBR Gold (Life Technologies) for 30 min. Cas9-induced cleavage bands and the uncleaved band were visualized on an AlphaImager HP (Alpha Innotech) and quantified using ImageJ software.[33] The peak intensities of the cleaved bands were divided by the total intensity of all bands (uncleaved+cleaved bands) to determine the fraction cleaved which was used to estimate gene modification levels as previously described.[28] For each sample, transfections and subsequent modification measurements were performed in triplicate on different days.

High-Throughput Sequencing of Genomic Modifications

HEK293-GFP stable cells were transfected with Cas9 expression and gRNA expression plasmids, 700 ng of Cas9 expression plasmid plus 250 ng of a single plasmid expression a pair of gRNAs were transfected (high levels) and for just Cas9 nuclease, 88 ng of Cas9 expression plasmid plus 31 ng of a single plasmid expression a pair of gRNAs were transfected (low levels). Genomic DNA was isolated as above and pooled from three biological replicates. 150 ng or 600 ng of pooled genomic DNA was used as template to amplify by PCR the on-target and off-target genomic sites with flanking HTS primer pairs specified in Table 1. Relative amounts of crude PCR products were quantified by gel electrophoresis and samples treated with different gRNA pairs or Cas9 nuclease types were separately pooled in equimolar concentrations before purification with the QIA-quick PCR Purification Kit (Qiagen). ~500 ng of pooled DNA was run a 5% TBE 18-well Criterion PAGE gel (BioRad) for 30 min at 200 V and DNAs of length ~125 bp to ~300 bp were isolated and purified by QIAquick PCR Purification Kit (Qiagen). Purified DNA was PCR amplified with primers containing sequencing adaptors, purified and sequenced on a MiSeq high-throughput DNA sequencer (Illumina) as described previously.[1]

Data Analysis

Illumina sequencing reads were filtered and parsed with scripts written in Unix Bash. All scripts were written in bash.

The Patmatch program[38] was used to search the human genome (GRCh37/hg19 build) for pattern sequences corresponding to Cas9 binding sites (CCN N[20] spacer N[20]NGG for Orientation A and N[20]NGG spacer CCN N[20] for Orientation B). The steps for the identification of ingels in sequences of genomic sites can be found below:

1) Sequence reads were initially filtered removing reads of less than 50 bases and removing reads with greater than 10% of the Illumina base scores not being B-J:

Example SeqA-1st Read:

```
                                    (SEQ ID NO: 157)
TTCTGAGGGCTGCTACCTGTACATCTGCACAAGATTGCCTTTACTCC

ATGCCTTTCTTCTTCTGCTCTAACTCTGACAATCTGTCTTGCCATGCCAT

AAGCCCCTATTCTTTCTGTAACCCCAAGATGGTATAAAAGCATCAATGAT

TGGGC
```

Example SeqA-2st Read:

```
                                    (SEQ ID NO: 158)
AAAACTCAAAGAAATGCCCAATCATTGATGCTTTTATACCATCTTG

GGGTTACAGAAAGAATAGGGGCTTATGGCATGGCAAGACAGATTGTCAGA

GTTAGAGCAGAAGAAGAAAGGCATGGAGTAAAGGCAATCTTGTGCAGATG

TACAGGTAA
```

2) Find the first 20 bases four bases from the start of the reverse complement of SeqA-2nd read in SeqA-1st read allowing for 1 mismatch:

Reverse Complement of SeqA-2nd Read:

```
                                    (SEQ ID NO: 159)
TTACCTGTACATCTGCACAAGATTGCCTTTACTCCATGCCTTTCTT

CTTCTGCTCTAACTCTGACAATCTGTCTTGCCATGCCATAAGCCCCTATT

CTTTCTGTAACCCCAAGATGGTATAAAAGCATCAATGATTGGGCATTTCT

TTGAGTTTT
```

Position in SeqA-1st Read

```
                                    (SEQ ID NO: 160)
TTCTGAGGGCTGCTACCTGTACATCTGCACAAGATTGCCTTTACTCCAT

GCCTTTCTTCTTCTGCTCTAACTCTGACAATCTGTCTTGCCATGCCATA

AGCCCCTATTCTTTCTGTAACCCCAAGATGGTATAAAAGCATCAATGAT

TGGGC
```

3) Align and then combine sequences, removing any sequence with greater than 5% mismatches in the simple base pair alignment:

Combination of SeqA-1st Read and SeqA-2nd Read:

```
                                    (SEQ ID NO: 161)
TTCTGAGGGCTGCTACCTGTACATCTGCACAAGATTGCCTTTACTCCATG

CCTTTCTTCTTCTGCTCTAACTCTGACAATCTGTCTTGCCATGCCATAAG

CCCCTATTCTTTCTGTAACCCCAAGATGGTATAAAAGCATCAATGATTGG

GCATTTCTTTGAGTTTT
```

4) To identify the target site the flanking genomic sequences were searched for with the Patmatch program[38] allowing for varying amounts of bases from 1 to 300 between the flanking genomic sequences (Table 2):

TABLE 2

| Target Site | Patmatch Sequences | |
| --- | --- | --- |
| | Downstream genomic sequence | Upstream genomic sequence |
| EMX_On | GGCCTGCTTCGTGGCAATGC (SEQ ID NO: 162) | ACCTGGGCCAGGGAGGGAGG (SEQ ID NO: 163) |
| EMX_Off1 | CTCACTTAGACTTTCTCTCC (SEQ ID NO: 164) | CTCGGAGTCTAGCTCCTGCA (SEQ ID NO: 165) |
| EMX_Off2 | TGGCCCCAGTCTCTCTTCTA (SEQ ID NO: 166) | CAGCCTCTGAACAGCTCCCG (SEQ ID NO: 167) |
| EMX_Off3 | TGACTTGGCCTTTGTAGGAA (SEQ ID NO: 168) | GAGGCTACTGAAACATAAGT (SEQ ID NO: 169) |
| EMX_Off4 | TGCTACCTGTACATCTGCAC (SEQ ID NO: 170) | CATCAATGATTGGGCATTTC (SEQ ID NO: 171) |
| VEG_On | ACTCCAGTCCCAAATATGTA (SEQ ID NO: 172) | ACTAGGGGGCGCTCGGCCAC (SEQ ID NO: 173) |
| VEG_Off1 | CTGAGTCAACTGTAAGCATT (SEQ ID NO: 174) | GGCCAGGTGCAGTGATTCAT (SEQ ID NO: 175) |
| VEG_Off2 | TCGTGTCATCTTGTTTGTGC (SEQ ID NO: 176) | GGCAGAGCCCAGCGGACACT (SEQ ID NO: 177) |

TABLE 2-continued

Patmatch Sequences

| Target Site | Downstream genomic sequence | Upstream genomic sequence |
|---|---|---|
| VEG_Off3 | CAAGGTGAGCCTGGGTCTGT (SEQ ID NO: 178) | ATCACTGCCCAAGAAGTGCA (SEQ ID NO: 179) |
| VEG_Off4 | TTGTAGGATGTTTAGCAGCA (SEQ ID NO: 180) | ACTTGCTCTCTTTAGAGAAC (SEQ ID NO:181) |
| CLT2_On | CTCAAGCAGGCCCCGCTGGT (SEQ ID NO: 182) | TTTTGGACCAAACCTTTTTG (SEQ ID NO: 183) |
| CLT2_Off1 | TGAGGTTATTTGTCCATTGT (SEQ ID NO: 184) | TAAGGGGAGTATTTACACCA (SEQ ID NO: 185) |
| CLT2_Off2 | TCAAGAGCAGAAAATGTGAC (SEQ ID NO: 186) | CTTGCAGGGACCTTCTGATT (SEQ ID NO: 187) |
| CLT2_Off3 | TGTGTGTAGGACTAAACTCT (SEQ ID NO: 188) | GATAGCAGTATGACCTTGGG (SEQ ID NO: 189) |

Any target site sequences corresponding to the same size as the reference genomic site in the human genome (GRCh37/hg19 build) were considered unmodified and any sequences not the reference size were considered potential insertions or deletions. Sequences not the reference size were aligned with ClustalW[39] to the reference genomic site. Aligned sequences with more than one insertion or one deletion in the DNA spacer sequence in or between the two half-site sequences were considered indels. Since high-throughput sequencing can result in insertions or deletions of one base pairs (mis-phasing) at a low but relevant rates—indels of two bp are more likely to arise from Cas9 induced modifications.

Sample sizes for sequencing experiments were maximized (within practical experimental considerations) to ensure greatest power to detect effects. Statistical analyses for Cas9-modified genomic sites in Table 3 were performed as previously described[34] with multiple comparison correction using the Bonferroni method.

Table 3, referred to in the Results below, shows (A) results from sequencing CLTA on-target and previously reported genomic off-target sites amplified from 150 ng genomic DNA isolated from human cells treated with a plasmid expressing either wild-type Cas9, Cas9 nickase, or fCas9 and a single plasmid expressing two gRNAs targeting the CLTA on-target site (gRNA C3 and gRNA C4). As a negative control, transfection and sequencing were performed as above, but using two gRNAs targeting the GFP gene on-target site (gRNA G1, G2 or G3 and gRNA G4, G5, G6 or G7. Indels: the number of observed sequences containing insertions or deletions consistent with any of the three Cas9 nuclease-induced cleavage. Total: total number of sequence counts while only the first 10,000 sequences were analyzed for the on-target site sequences. Modified: number of indels divided by total number of sequences as percentages. Upper limits of potential modification were calculated for sites with no observed indels by assuming there is less than one indel then dividing by the total sequence count to arrive at an upper limit modification percentage, or taking the theoretical limit of detection (1/49, 500), whichever value was larger. P-values: For wild-type Cas9 nuclease, Cas9 nickase or fCas9 nuclease, P-values were calculated as previously reported[18] using a two-sided Fisher's exact test between each sample treated with two gRNAs targeting the CLTA on-target site and the control sample treated with two gRNAs targeting the GFP on-target site. P-values of <0.0045 were considered significant and shown based on conservative multiple comparison correction using the Bonferroni method. On:off specificity is the ratio of on-target to off-target genomic modification frequency for each site. (B) Shows experimental and analytic methods as in (A) applied to EMX target sites using a single plasmid expressing two gRNAs targeting the EMX on-target site (gRNA E1 and gRNA E2). (C) shows experimental and analytic methods as in (A) applied to VEGF target sites using a single plasmid expressing two gRNAs targeting the VEGF on-target site (gRNA V1 and gRNA v2). (D) shows experimental and analytic methods as in (A) applied to VEGF on-target and VEGF off-target site 1 amplified from 600 ng genomic DNA to increase detection sensitivity to 1/198,000.

TABLE 3

Cellular modification induced by wild-type Cas9, Cas9 nickase, and fCas9 at on-target and off-target genomic sites.

(A)

| | | | Nuclease type: | | | | |
|---|---|---|---|---|---|---|---|
| | wt Cas9 | wt Cas9 | Cas9 nickase | fCas9 | wt Cas9 | Cas9 nickase | fCas9 |
| | | | gRNA pair target: | | | | |
| | CLTA | CLTA | CLTA | CLTA | GFP | GFP | GFP |
| | | | Total expression plasmids (ng): | | | | |
| | 1000 | 125 | 1000 | 1000 | 1000 | 1000 | 1000 |
| CLTA Sites CLT2_On | | | | | | | |
| Indels | 3528 | 1423 | 3400 | 575 | 3 | 13 | 5 |
| Total | 10000 | 10000 | 10000 | 10000 | 10000 | 10000 | 10000 |
| Modified (%) | 35.280 | 14.230 | 34.000 | 5.750 | 0.030 | 0.130 | 0.050 |
| P-value | <1.0E−300 | <1.0E−300 | <1.0E−300 | 1.4E−163 | | | |
| On:off specificity | 1 | 1 | | 1 | | | |
| CLT2_Off1 | | | | | | | |
| Indels | 316 | 44 | 2 | 2 | 1 | 3 | 3 |
| Total | 60620 | 64755 | 71537 | 63079 | 93883 | 91306 | 82055 |

TABLE 3-continued

Cellular modification induced by wild-type Cas9, Cas9 nickase, and fCas9 at on-target and off-target genomic sites.

| | | | | | | | |
|---|---|---|---|---|---|---|---|
| Modified (%) | 0.521 | 0.068 | 0.003 | 0.003 | <0.002 | 0.003 | 0.004 |
| P-value | 1.3E−126 | 2.1E−16 | | | | | |
| On:off specificity | 68 | 209 | | >2850 | | | |
| CLT2_Off2 | | | | | | | |
| Indels | 11 | 5 | 3 | 1 | 1 | 1 | 2 |
| Total | 72596 | 51093 | 59632 | 35541 | 69114 | 64412 | 39978 |
| Modified (%) | 0.015 | 0.010 | 0.005 | 0.003 | <0.002 | <0.002 | 0.005 |
| P-value | 6.5E−03 | | | | | | |
| On:off specificity | 2328 | 1454 | | >2850 | | | |
| CLT2_Off3 | | | | | | | |
| Indels | 11 | 10 | 0 | 0 | 1 | 1 | 1 |
| Total | 52382 | 44212 | 54072 | 48668 | 55670 | 58707 | 54341 |
| Modified (%) | 0.021 | 0.023 | <0.002 | <0.002 | <0.002 | <0.002 | <0.002 |
| P-value | 2.7E−03 | 3.5E−03 | | | | | |
| On:off specificity | 1680 | 629 | | >2850 | | | |

(B)

| | | | | | | | |
|---|---|---|---|---|---|---|---|
| | Nuclease type: | | | | | | |
| | wt Cas9 | wt Cas9 | Cas9 nickase | fCas9 | wt Cas9 | Cas9 nickase | fCas9 |
| | gRNA pair: | | | | | | |
| | EMX | EMX | EMX | EMX | GFP | GFP | GFP |
| | Total expression plasmids (ng): | | | | | | |
| | 1000 | 125 | 1000 | 1000 | 1000 | 1000 | 1000 |
| EMX Site | | | | | | | |
| EMX_On | | | | | | | |
| Indels | 5111 | 2683 | 2267 | 522 | 0 | 0 | 2 |
| Total | 10000 | 10000 | 10000 | 10000 | 10000 | 10000 | 10000 |
| Modified (%) | 51.110 | 26.830 | 22.670 | 5.220 | <0.002 | <0.002 | 0.020 |
| P-value | <1.0E−300 | <1.0E−300 | <1.0E−300 | 1.0E−154 | | | |
| On:off specificity | 1 | 1 | 1 | 1 | | | |
| EMX_Off1 | | | | | | | |
| Indels | 386 | 122 | 7 | 1 | 4 | 9 | 7 |
| Total | 109787 | 83420 | 124564 | 88424 | 102817 | 90020 | 96526 |
| Modified (%) | 0.352 | 0.146 | 0.006 | <0.002 | 0.004 | 0.010 | 0.007 |
| P-value | 1.3E−103 | 2.8E−37 | | | | | |
| On:off specificity | 145 | 183 | >11222 | >2584 | | | |
| EMX_Off2 | | | | | | | |
| Indels | 74 | 58 | 3 | 6 | 3 | 0 | 4 |
| Total | 98568 | 94108 | 105747 | 78871 | 81717 | 79469 | 79193 |
| Modified (%) | 0.075 | 0.062 | 0.003 | 0.008 | 0.004 | <0.002 | 0.005 |
| P-value | 3.2E−16 | 1.4E−12 | | | | | |
| On:off specificity | 681 | 435 | >11222 | >2584 | | | |
| EMX_Off3 | | | | | | | |
| Indels | | | | | | | |
| Total | 72888 | 65139 | 82348 | 59593 | 74341 | 73408 | 75080 |
| Modified (%) | 1.010 | 0.273 | 0.024 | 0.023 | 0.016 | 0.015 | 0.023 |
| P-value | 2.5E−202 | 3.1E−44 | | | | | |
| On:off specificity | 51 | 98 | >11222 | >2584 | | | |
| EMX_Off4 | | | | | | | |
| Indels | 4149 | 620 | 3 | 3 | 6 | 7 | 5 |
| Total | 107537 | 91695 | 91368 | 91605 | 111736 | 119643 | 128088 |
| Modified (%) | 3.858 | 0.676 | 0.003 | 0.003 | 0.005 | 0.006 | 0.004 |
| P-value | <1.0E−300 | 1.9E−202 | | | | | |
| On:off specificity | 13 | 40 | >11222 | >2584 | | | |

TABLE 3-continued

Cellular modification induced by wild-type Cas9, Cas9 nickase, and fCas9 at on-target and off-target genomic sites.

(C)

| | Nuclease type: | | | | | |
|---|---|---|---|---|---|---|
| wt Cas9 | wt Cas9 | Cas9 nickase | fCas9 | wt Cas9 | Cas9 nickase | fCas9 |
| | | | gRNA pair: | | | |
| VEGF | VEGF | VEGF | VEGF | GFP | GFP | GFP |
| | | | Total expression plasmids (ng): | | | |
| 1000 | 125 | 1000 | 1000 | 1000 | 1000 | 1000 |

VEGF Sites
VEG_On

| | wt Cas9 VEGF 1000 | wt Cas9 VEGF 125 | Cas9 nickase VEGF 1000 | fCas9 VEGF 1000 | wt Cas9 GFP 1000 | Cas9 nickase GFP 1000 | fCas9 GFP 1000 |
|---|---|---|---|---|---|---|---|
| Indels | 5253 | 2454 | 1230 | 1041 | 8 | 0 | 1 |
| Total | 10000 | 10000 | 10000 | 10000 | 10000 | 10000 | 10000 |
| Modified (%) | 52.530 | 24.540 | 12.300 | 10.410 | 0.080 | <0.002 | 0.010 |
| P-value | <1.0E−300 | <1.0E−300 | <1.0E−300 | 6.6E−286 | | | |
| On:off specificity | 1 | 1 | 1 | 1 | | | |

VEG_Off1

| | | | | | | | |
|---|---|---|---|---|---|---|---|
| Indels | 2950 | 603 | 22 | 0 | 0 | 4 | 1 |
| Total | 82198 | 71163 | 90434 | 77557 | 74765 | 79738 | 74109 |
| Modified (%) | 3.589 | 0.847 | 0.024 | <0.002 | <0.002 | 0.005 | <0.002 |
| P-value | <1.0E−300 | 3.2E−188 | 2.5E−06 | | | | |
| On:off specificity | 15 | 29 | 506 | >5150 | | | |

VEG_Off2

| | | | | | | | |
|---|---|---|---|---|---|---|---|
| Indels | 863 | 72 | 3 | 3 | 0 | 2 | 1 |
| Total | 102501 | 49836 | 119702 | 65107 | 54247 | 65753 | 61556 |
| Modified (%) | 0.842 | 0.144 | 0.003 | 0.005 | <0.002 | 0.003 | <0.002 |
| P-value | 3.5E−159 | 9.6E−24 | | | | | |
| On:off specificity | 62 | 170 | >6090 | >5150 | | | |

VEG_Off3

| | | | | | | | |
|---|---|---|---|---|---|---|---|
| Indels | 260 | 33 | 3 | 2 | 3 | 1 | 0 |
| Total | 91277 | 83124 | 90063 | 84385 | 62126 | 68165 | 69811 |
| Modified (%) | 0.285 | 0.040 | 0.003 | 0.002 | 0.005 | <0.002 | <0.002 |
| P-value | 6.8E−54 | 1.0E−05 | | | | | |
| On:off specificity | 184 | 618 | >6090 | >5150 | | | |

VEG_Off4

| | | | | | | | |
|---|---|---|---|---|---|---|---|
| Indels | 1305 | 149 | 3 | 2 | 3 | 2 | 4 |
| Total | 59827 | 41203 | 65964 | 57828 | 60906 | 61219 | 62162 |
| Modified (%) | 2.181 | 0.362 | 0.005 | 0.003 | 0.005 | 0.003 | 0.006 |
| P-value | <1.0E−300 | 2.7E−54 | | | | | |
| On:off specificity | 24 | 68 | >6090 | >5150 | | | |

(D)

| | Nuclease type: | | |
|---|---|---|---|
| Cas9 nickase | fCas9 | Cas9 nickase | fCas9 |
| | | gRNA pair: | |
| VEGF | VEGF | GFP | GFP |
| | Total expression plasmids (ng): | | |
| 1000 | 1000 | 1000 | 1000 |

VEGF Sites
VEG_On

| | Cas9 nickase VEGF 1000 | fCas9 VEGF 1000 | Cas9 nickase GFP 1000 | fCas9 GFP 1000 |
|---|---|---|---|---|
| Indels | 2717 | 2122 | 10 | 13 |
| Total | 10000 | 10000 | 10000 | 10000 |
| Modified (%) | 27.170 | 21.220 | 0.100 | 0.130 |
| P-value | <1.0E−300 | <1.0E−300 | | |
| On:off specificity | 1 | 1 | | |

VEG_Off1

| | | | | |
|---|---|---|---|---|
| Indels | 67 | 30 | 3 | 2 |
| Total | 302573 | 233567 | 204454 | 190240 |

TABLE 3-continued

Cellular modification induced by wild-type Cas9, Cas9 nickase, and fCas9 at on-target and off-target genomic sites.

| Modified (%) | 0.022 | 0.013 |
| P-value | 5.9E−12 | 2.5E−06 |
| On:off specificity | 1227 | 1652 |

Results

Recently engineered variants of Cas9 that cleave only one DNA strand ("nickases") enable double-stranded breaks to be specified by two distinct gRNA sequences,[57] but still suffer from off-target cleavage activity[6,8] arising from the ability of each monomeric nickase to remain active when individually bound to DNA.[9-11] In contrast, the development of a FokI nuclease fusion to a catalytically dead Cas9 that requires simultaneous DNA binding and association of two FokI-dCas9 monomers to cleave DNA is described here. Off-target DNA cleavage of the engineered FokI-dCas9 (fCas9) is further reduced by the requirement that only sites flanked by two gRNAs ~15 or 25 base pairs apart are cleaved, a much more stringent spacing requirement than nickases. In human cells, fCas9 modified target DNA sites with efficiency comparable to that of nickases, and with >140-fold higher specificity than wild-type Cas9. Target sites that conform to the substrate requirements of fCas9 are abundant in the human genome, occurring on average once every 34 bp.

In cells, Cas9:gRNA-induced double strand breaks can result in functional gene knockout through non-homologous end joining (NHEJ) or alteration of a target locus to virtually any sequence through homology-directed repair (HDR) with an exogenous DNA template.[9,15,16] Cas9 is an especially convenient genome editing platform,[17] as a genome editing agent for each new target site of interest can be accessed by simply generating the corresponding gRNA. This approach has been widely used to create targeted knockouts and gene insertions in cells and model organisms, and has also been recognized for its potential therapeutic relevance.

While Cas9:gRNA systems provide an unprecedented level of programmability and ease of use, studies[1-5] have reported the ability of Cas9 to cleave off-target genomic sites, resulting in modification of unintended loci that can limit the usefulness and safety of Cas9 as a research tool and as a potential therapeutic. It was hypothesized that engineering Cas9 variants to cleave DNA only when two simultaneous, adjacent Cas9:DNA binding events take place could substantially improve genome editing specificity since the likelihood of two adjacent off-target binding events is much smaller than the likelihood of a single off-target binding event (approximately $1/n^2$ vs. $1/n$). Such an approach is distinct from the recent development of mutant Cas9 proteins that cleave only a single strand of dsDNA, such as nickases. Nickases can be used to nick opposite strands of two nearby target sites, generating what is effectively a double strand break, and paired Cas9 nickases can effect substantial on-target DNA modification with reduced off-target modification.[5,6,8] Because each of the component Cas9 nickases remains catalytically active[9-11] and single-stranded DNA cleavage events are weakly mutagenic,[18,19] nickases can induce genomic modification even when acting as monomers.[5,7,16] Indeed, Cas9 nickases have been previously reported to induce off-target modifications in cells.[6,8] Moreover, since paired Cas9 nickases can efficiently induce dsDNA cleavage-derived modification events when bound up to ~100 bp apart,[6] the statistical number of potential off-target sites for paired nickases is larger than that of a more spatially constrained dimeric Cas9 cleavage system.

Figures 6A, 6B:
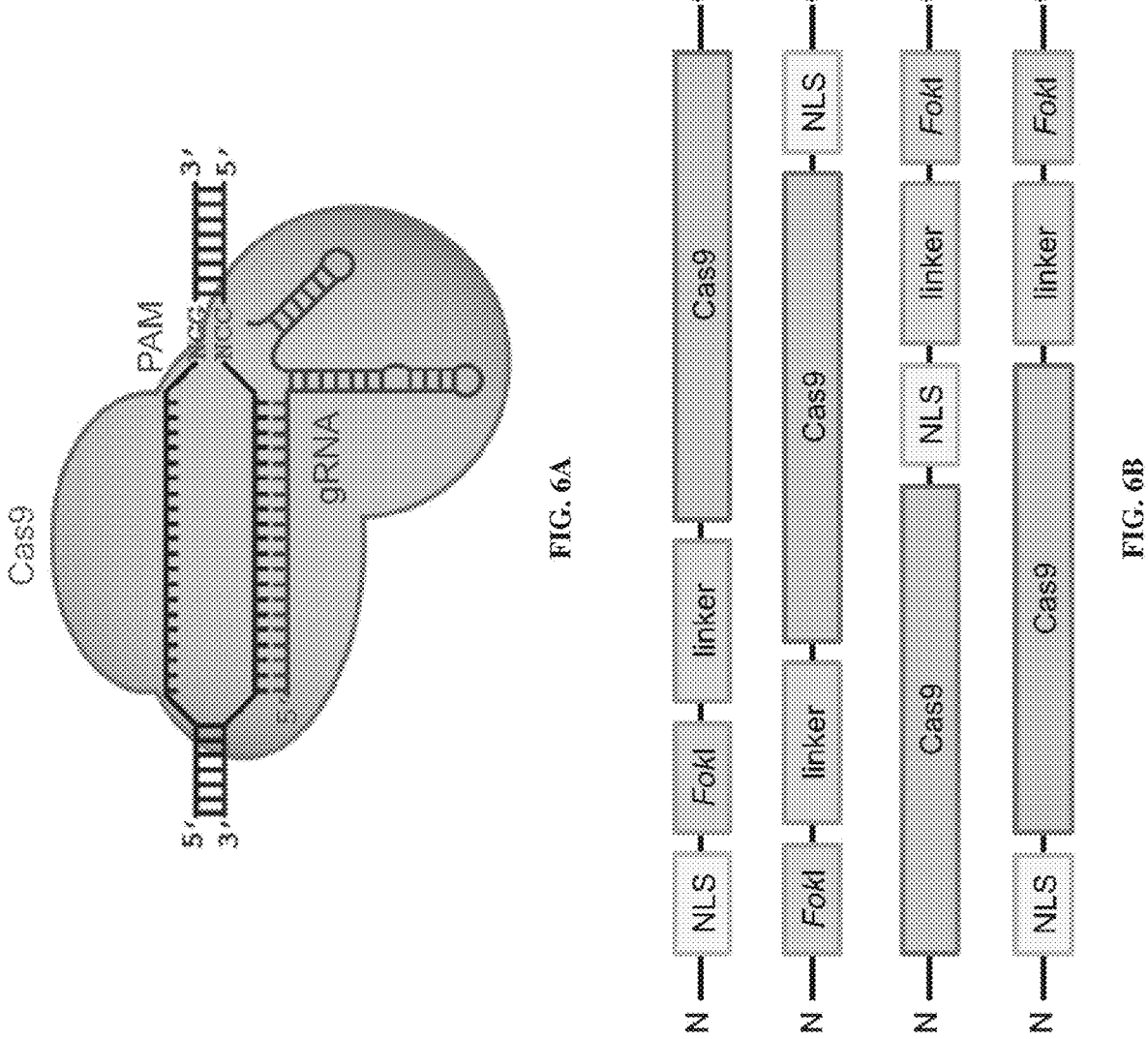
FIG. 6A-6D shows architectures of Cas9 and FokI-dCas9 fusion variants.
Figure 6C:
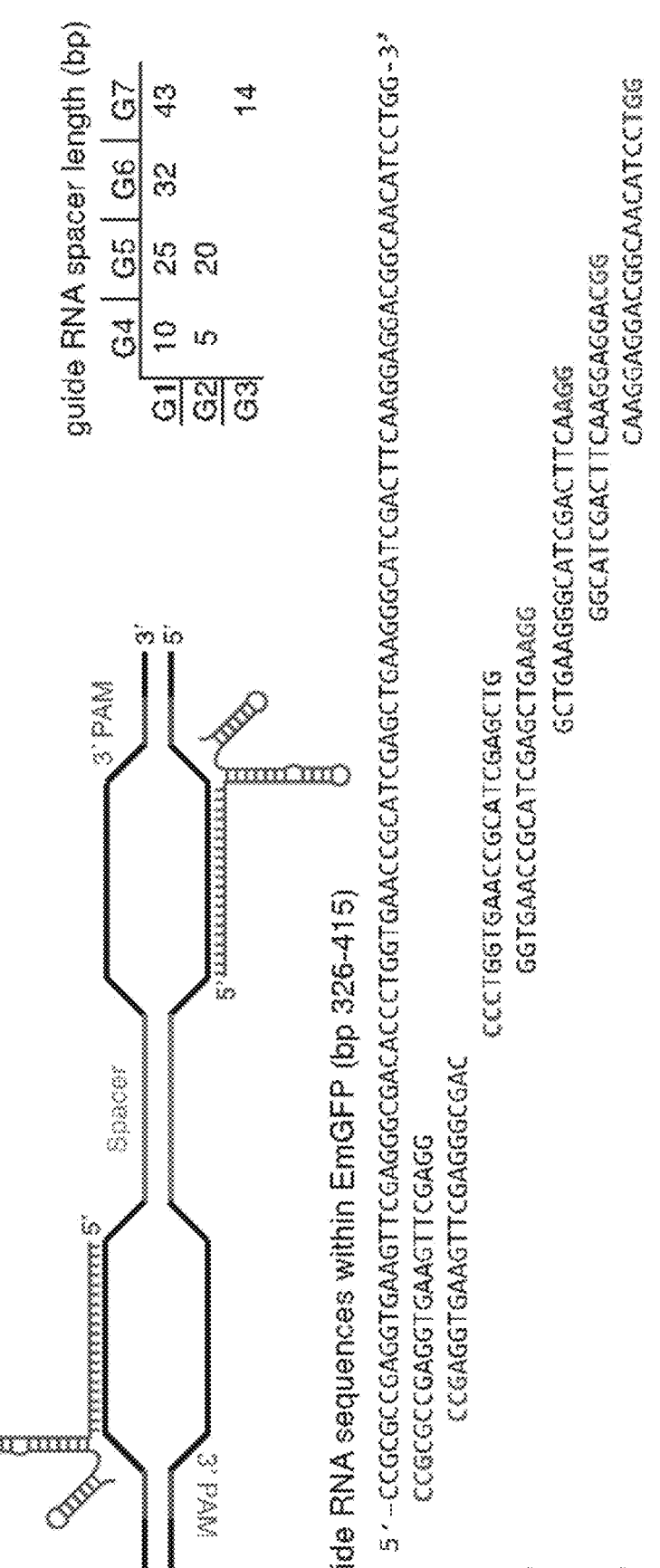
Figure 6D:
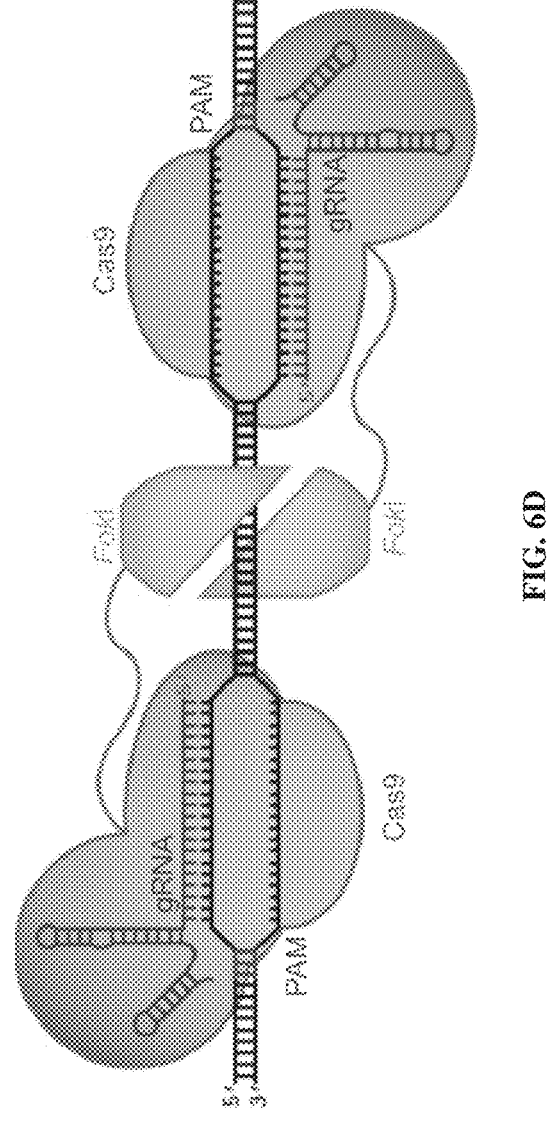

To further improve the specificity of the Cas9:gRNA system, an obligate dimeric Cas9 system is provided herein. In this example, fusing the FokI restriction endonuclease cleavage domain to a catalytically dead Cas9 (dCas9) created an obligate dimeric Cas9 that would cleave DNA only when two distinct FokI-dCas9:gRNA complexes bind to adjacent sites ("half-sites") with particular spacing constraints (FIG. 6D). In contrast with Cas9 nickases, in which single-stranded DNA cleavage by monomers takes place independently, the DNA cleavage of FokI-dCas9 requires simultaneous binding of two distinct FokI-dCas9 monomers because monomeric FokI nuclease domains are not catalytically competent.[21] This approach increased the specificity of DNA cleavage relative to wild-type Cas9 by doubling the number of specified target bases contributed by both monomers of the FokI-dCas9 dimer, and offered improved specificity compared to nickases due to inactivity of monomeric FokI-dCas9:gRNA complexes, and the more stringent spatial requirements for assembly of a FokI-dCas9 dimer.

While fusions of Cas9 to short functional peptide tags have been described to enable gRNA-programmed transcriptional regulation,[22] it is believed that no fusions of Cas9 with active enzyme domains have been previously reported. Therefore a wide variety of FokI-dCas9 fusion proteins were constructed and characterized with distinct configurations of a FokI nuclease domain, dCas9 containing inactivating mutations D10A and H840A, and a nuclear localization sequence (NLS). FokI was fused to either the N- or C-terminus of dCas9, and varied the location of the NLS to be at either terminus or between the two domains (FIG. 6B). The length of the linker sequence was varied as either one or three repeats of Gly-Gly-Ser (GGS) between the FokI and dCas9 domains. Since previously developed dimeric nuclease systems are sensitive to the length of the spacer sequence between half-sites,[23,24] a wide range of spacer sequence lengths was tested between two gRNA binding sites within a test target gene, Emerald GFP (referred to hereafter as GFP) (FIG. 6C and FIG. 9). Two sets of gRNA binding-site pairs with different orientations were chosen within GFP. One set placed the pair of NGG PAM sequences distal from the spacer sequence, with the 5' end of the gRNA adjacent to the spacer (orientation A) (FIG. 6C), while the other placed the PAM sequences immediately adjacent to the spacer (orientation B) (FIG. 9). In total, seven pairs of gRNAs were suitable for orientation A, and nine were suitable for orientation B. By pairwise combination of the gRNA targets, eight spacer lengths were tested in both dimer orientations, ranging from 5 to 43 bp in orientation A, and 4 to 42 bp in orientation B. In total, DNA constructs corresponding to 104 pairs of FokI-dCas9:gRNA complexes were generated and tested, exploring four fusion architectures, 17 protein linker variants (described below), both gRNA orientations and 13 spacer lengths between half-sites.

Figures 10A, 10B:
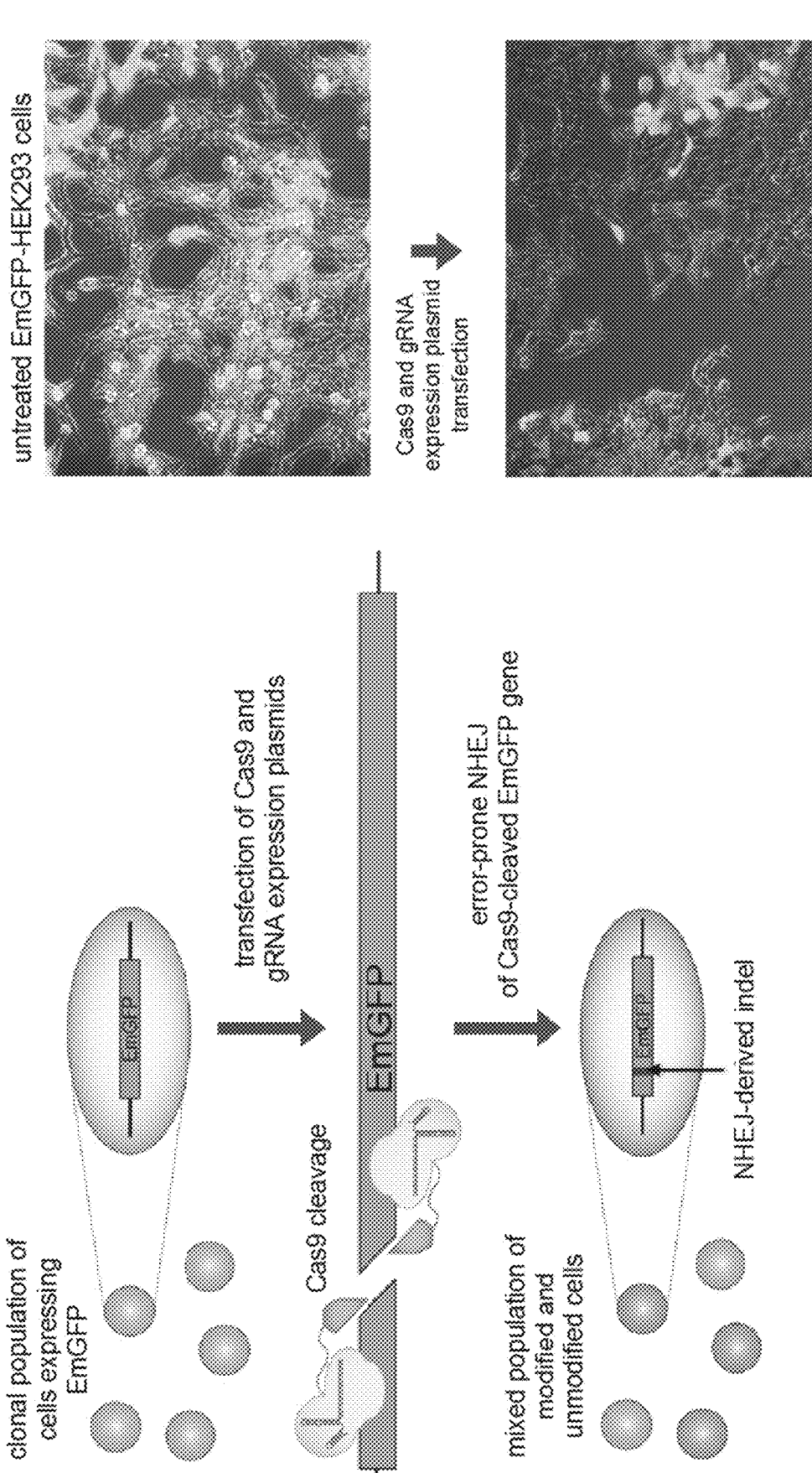
FIG. 10A-B shows a GFP disruption assay for measuring genomic DNA-modification activity.

To assay the activities of these candidate FokI-dCas9:gRNA pairs, a previously described flow cytometry-based fluorescence assay[2,8] in which DNA cleavage and NHEJ of a stably integrated constitutively expressed GFP gene in HEK293 cells leads to loss of cellular fluorescence was used (FIG. 10). For comparison, the initial set of FokI-dCas9 variants were assayed side-by-side with the corresponding Cas9 nickases and wild-type Cas9 in the same expression plasmid across both gRNA spacer orientation sets A and B. Cas9 protein variants and gRNA were generated in cells by transient co-transfection of the corresponding Cas9 protein expression plasmids together with the appropriate pair of gRNA expression plasmids. The FokI-dCas9 variants, nickases, and wild-type Cas9 all targeted identical DNA sites using identical gRNAs.

Figure 11A:
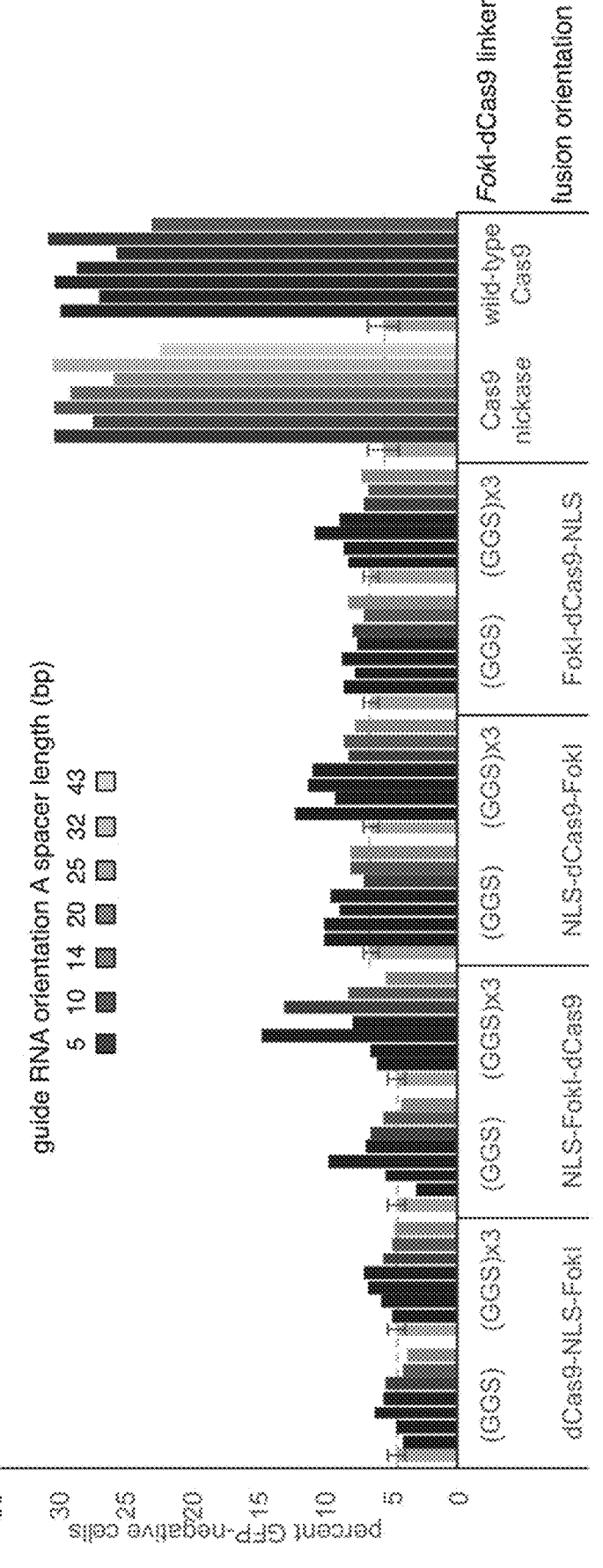
FIG. 11A-11B shows a graph depicting the activities of FokI-dCas9 fusion candidates combined with gRNA pairs of different orientations and varying spacer lengths. The fusion architectures described in FIG. 6B were tested for functionality by flow cytometry using the GFP loss-of-function reporter across all (FIG. 11A) orientation A gRNA spacers and (FIG. 811B) orientation B gRNA spacers (FIG. 6C and FIG. 9). All FokI-dCas9 fusion data shown are the results of single trials. Wild-type Cas9 and Cas9 nickase data are the average of two replicates, while the 'no treatment' negative control data is the average of 6 replicates, with error bars representing one standard deviation. The grey dotted line across the Y-axis corresponds to the average of the 'no treatment' controls performed on the same day. The sequence shown as "(GGS)×3" corresponds to SEQ ID NO:14.
Figure 11B:
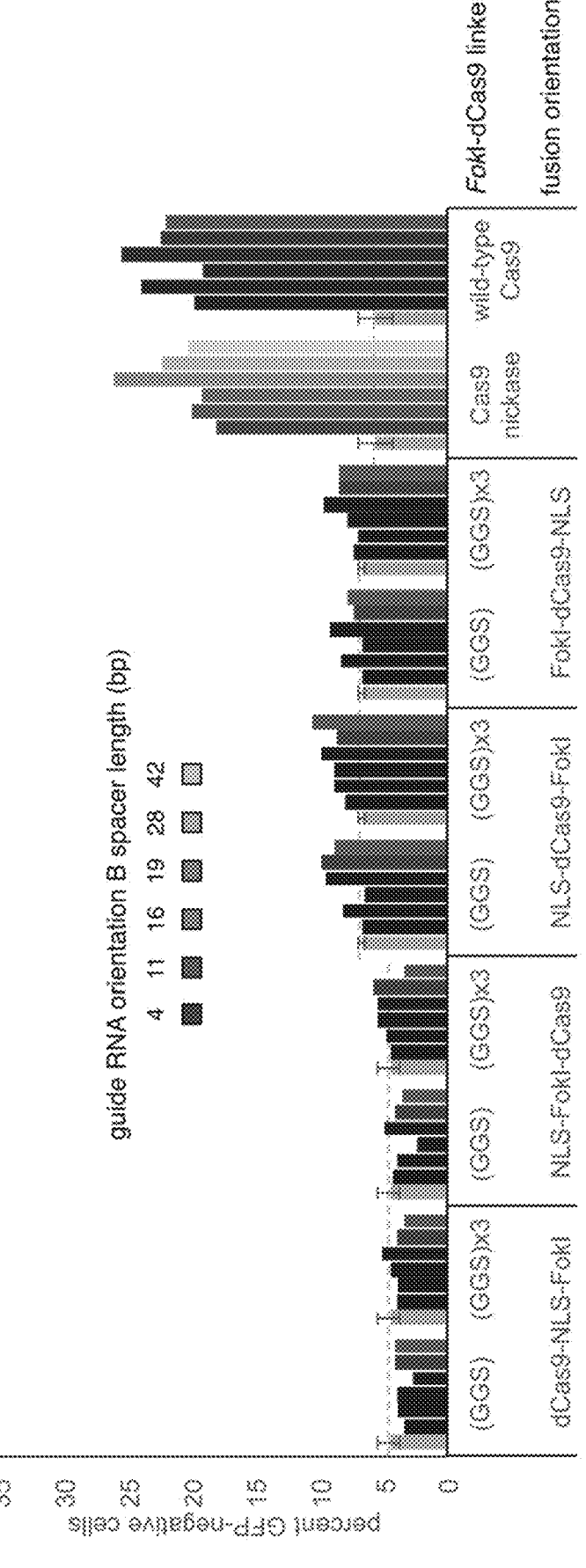

Most of the initial FokI-dCas9 fusion variants were inactive or very weakly active (FIG. 11). The NLS-FokI-dCas9 architecture (listed from N to C terminus), however, resulted in a 10% increase of GFP-negative cells above corresponding the no-gRNA control when used in orientation A, with PAMs distal from the spacer (FIG. 11A). In contrast, NLS-FokI-dCas9 activity was undetectable when used on gRNA pairs with PAMs adjacent to the spacer (FIG. 11B). Examination of the recently reported Cas9 structures[25,26] reveals that the Cas9 N-terminus protrudes from the RuvCI domain, which contacts the 5' end of the gRNA:DNA duplex. Without wishing to be bound by any particular theory, it is speculated that this arrangement places an N-terminally fused FokI distal from the PAM, resulting in a preference for gRNA pairs with PAMs distal from the cleaved spacer (FIG. 6D). While other FokI-dCas9 fusion pairings and the other gRNA orientation in some cases showed modest activity (FIG. 11), NLS-FokI-dCas9 with gRNAs in orientation A were chosen for further development.

Figure 12B:
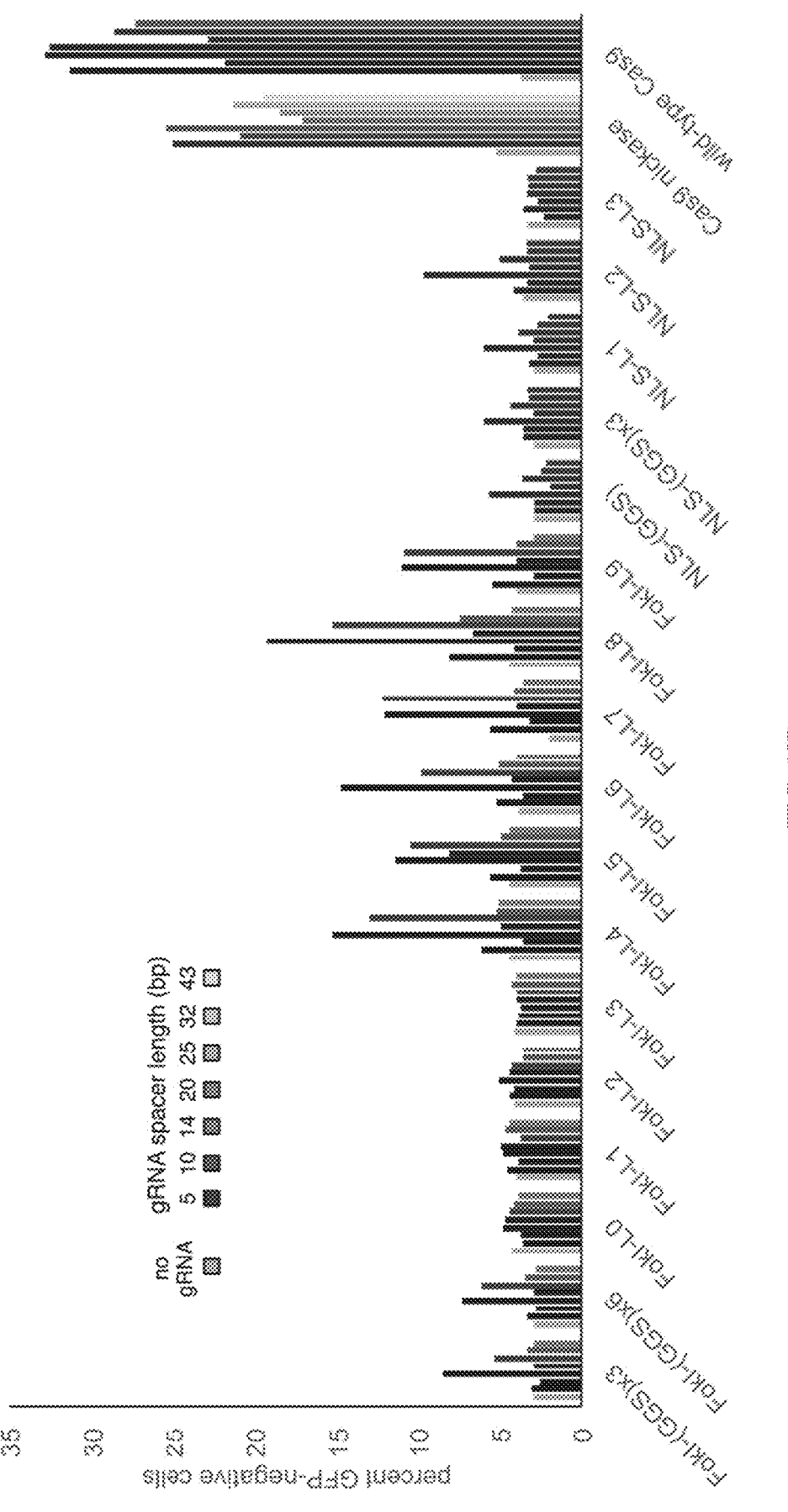

Next the protein linkers between the NLS and FokI domain, and between the FokI domain and dCas9 in the NLS-FokI-dCas9 architecture were optimized. 17 linkers with a wide range of amino acid compositions, predicted flexibilities, and lengths varying from 9 to 21 residues were tested (FIG. 12A). Between the FokI domain and dCas9 a flexible 18-residue linker, $(GGS)_6$ (SEQ ID NO:15), and a 16-residue "XTEN" linker (FokI-L8 in FIG. 12A) were identified based on a previously reported engineered protein with an open, extended conformation,[27] as supporting the highest levels of genomic GFP modification FIG. 12B).

The XTEN protein was originally designed to extend the serum half-life of translationally fused biologic drugs by increasing their hydrodynamic radius, acting as protein-based functional analog to chemical PEGylation.[35] Possessing a chemically stable, non-cationic, and non-hydrophobic primary sequence, and an extended conformation, it is hypothesized that a portion of XTEN could function as a stable, inert linker sequence for fusion proteins. The sequence of the XTEN protein tag from E-XTEN was analyzed, and repeating motifs within the amino acid sequence were aligned. The sequence used in the FokI-dCas9 fusion construct FokI-L8 (FIG. 12A) was derived from the consensus sequence of a common E-XTEN motif, and a 16 amino acid sequence was chosen from within this motif to test as a FokI-dCas9 linker.

Many of the FokI-dCas9 linkers tested including the optimal XTEN linker resulted in nucleases with a marked preference for spacer lengths of ~15 and ~25 bp between half-sites, with all other spacer lengths, including 20 bp, showing substantially lower activity (FIG. 12B). This pattern of linker preference is consistent with a model in which the FokI-dCas9 fusions must bind to opposite faces of the DNA double helix to cleave DNA, with optimal binding taking place ~1.5 or 2.5 helical turns apart. The variation of NLS-FokI linkers did not strongly affect nuclease performance, especially when combined with the XTEN FokI-dCas9 linker (FIG. 12B).

In addition to assaying linkers between the FokI domain and dCas9 in the NLS-FokI-dCas9 architecture, four linker variants between the N-terminal NLS and the FokI domain were also tested (FIG. 12A). Although a NLS-GSAGSAAGSGEF (SEQ ID NO:20)-FokI-dCas9 linker exhibited nearly 2-fold better GFP gene modification than the other NLS-FokI linkers tested when a simple GGS linker was used between the FokI and dCas9 domains (FIG. 12B), the GSAGSAAGSGEF (SEQ ID NO:20) linker did not perform substantially better when combined with the XTEN linker between the FokI and dCas9 domains.

Figure 7A:
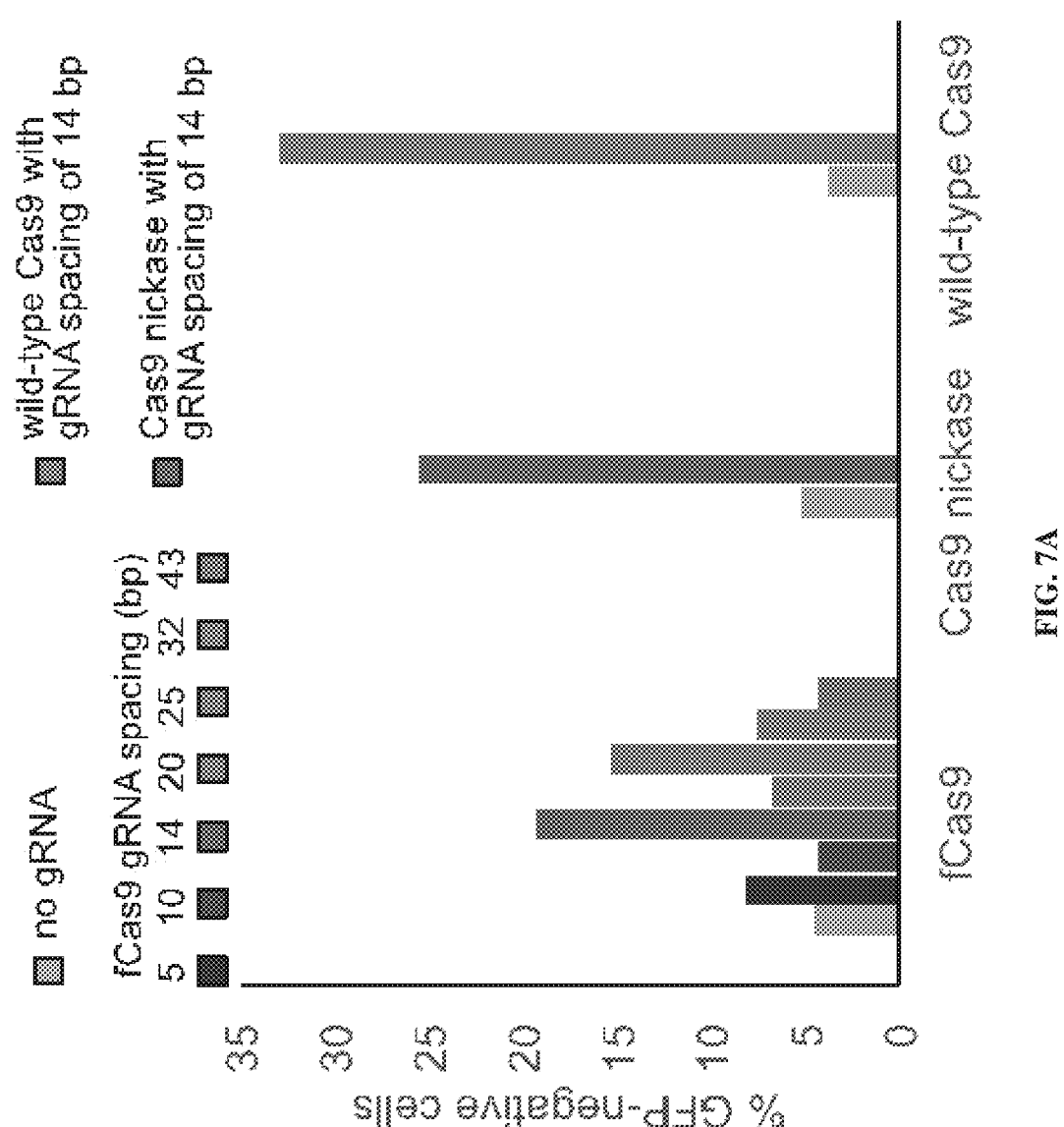
FIG. 7A-7G shows genomic DNA modification by fCas9, Cas9 nickase, and wild-type Cas9.

The NLS-GGS-FokI-XTEN-dCas9 construct consistently exhibited the highest activity among the tested candidates, inducing loss of GFP in ~15% of cells, compared to ~20% and ~30% for Cas9 nickases and wild-type Cas9 nuclease, respectively (FIG. 7A). All subsequent experiments were performed using this construct, hereafter referred to as fCas9. To confirm the ability of fCas9 to efficiently modify genomic target sites, the T7 endonuclease I Surveyor assay[28] was used to measure the amount of mutation at each of seven target sites within the integrated GFP gene in HEK293 cells treated with fCas9, Cas9 nickase, or wild-type Cas9 and either two distinct gRNAs in orientation A or no gRNAs as a negative control. Consistent with the flow cytometry-based studies, fCas9 was able to modify the GFP target sites with optimal spacer lengths of ~15 or ~25 bp at a rate of ~20%, comparable to the efficiency of nickase-induced modification and approximately two-thirds that of wild-type Cas9 (FIG. 7A-C).

Figure 13:
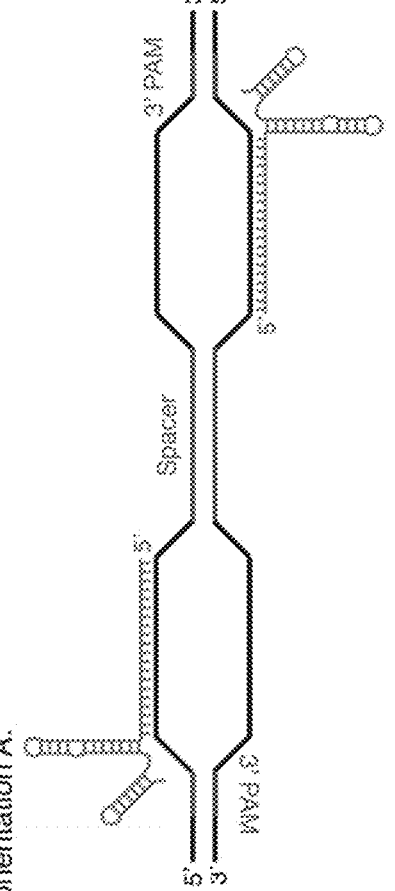
FIG. 13 shows target DNA sequences in endogenous human EMX, VEGF, CLTA, and HBB genes. The gRNA target sites tested within endogenous human EMX, VEGF, CLTA, and HBB genes are shown. Thirteen gRNA target sites were chosen to test the activity of the optimized fCas9 fusion in an orientation in which the PAM is distal from the cleaved spacer sequence (orientation A). Together, these 13 gRNAs enabled testing of fCas9 fusion variants across eight spacer lengths ranging from 5 to 47 bp. The sequences shown are identified as follows: "CLTA-1" corresponds to SEQ ID NO:220; "C1" corresponds to SEQ ID NO:221; "C2" corresponds to SEQ ID NO:222; "C3" corresponds to SEQ ID NO:224; "C4" corresponds to SEQ ID NO:225; "HBC" corresponds to SEQ ID NO:226; "H1" corresponds to SEQ ID NO:227; "H2" corresponds to SEQ ID NO:228; "H3" corresponds to SEQ ID NO:229; "H4" corresponds to SEQ ID NO:230; "H5" corresponds to SEQ ID NO:231; "H6" corresponds to SEQ ID NO:232; "H7" corresponds to SEQ ID NO:233; "EMX" corresponds to SEQ ID NO:234; "E1" corresponds to SEQ ID NO:235; "E2" corresponds to SEQ ID NO:236; "E3" corresponds to SEQ ID NO:237; "VEGF" corresponds to SEQ ID NO:238; "V1" corresponds to SEQ ID NO:239; "V2" corresponds to SEQ ID NO:240; "V3" corresponds to SEQ ID NO:241; and "V4" corresponds to SEQ ID NO:242.
Figures 14C, 14D, 14E:
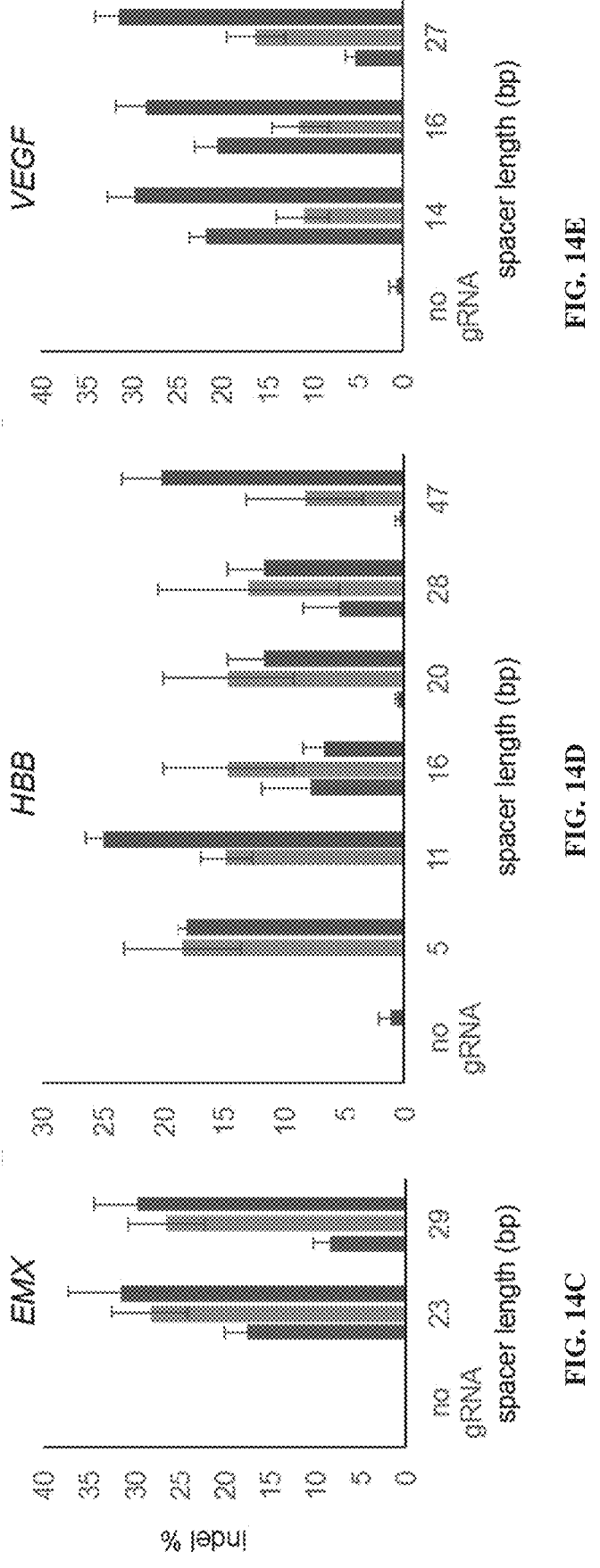

Next the ability of the optimized fCas9 to modify four distinct endogenous genomic loci by Surveyor assay was evaluated. CLTA (two sites), EMX (two sites), HBB (six sites) VEGF (three sites), and were targeted with two gRNAs per site in orientation A spaced at various lengths (FIG. 13). Consistent with the results of the experiments targeting GFP, at appropriately spaced target half-sites fCas9 induced efficient modification of all four genes, ranging from 8% to 22% target chromosomal site modification (FIG. 7D-G and FIG. 14). Among the gRNA spacer lengths resulting in the highest modification at each of the five genes targeted (including GFP), fCas9 induced on average 15.6% (±6.3% s.d.) modification, while Cas9 nickase and wild-type Cas9 induced on average 22.1% (±4.9% s.d.) and 30.4% (±3.1% s.d.) modification, respectively, from their optimal gRNA pairs for each gene. Because decreasing the amount of Cas9 expression plasmid and gRNA expression plasmid during transfection generally did not proportionally decrease genomic modification activity for Cas9 nickase and fCas9 (FIG. 15A-C), expression was likely not limiting under the conditions tested.

Figures 8A, 8B:
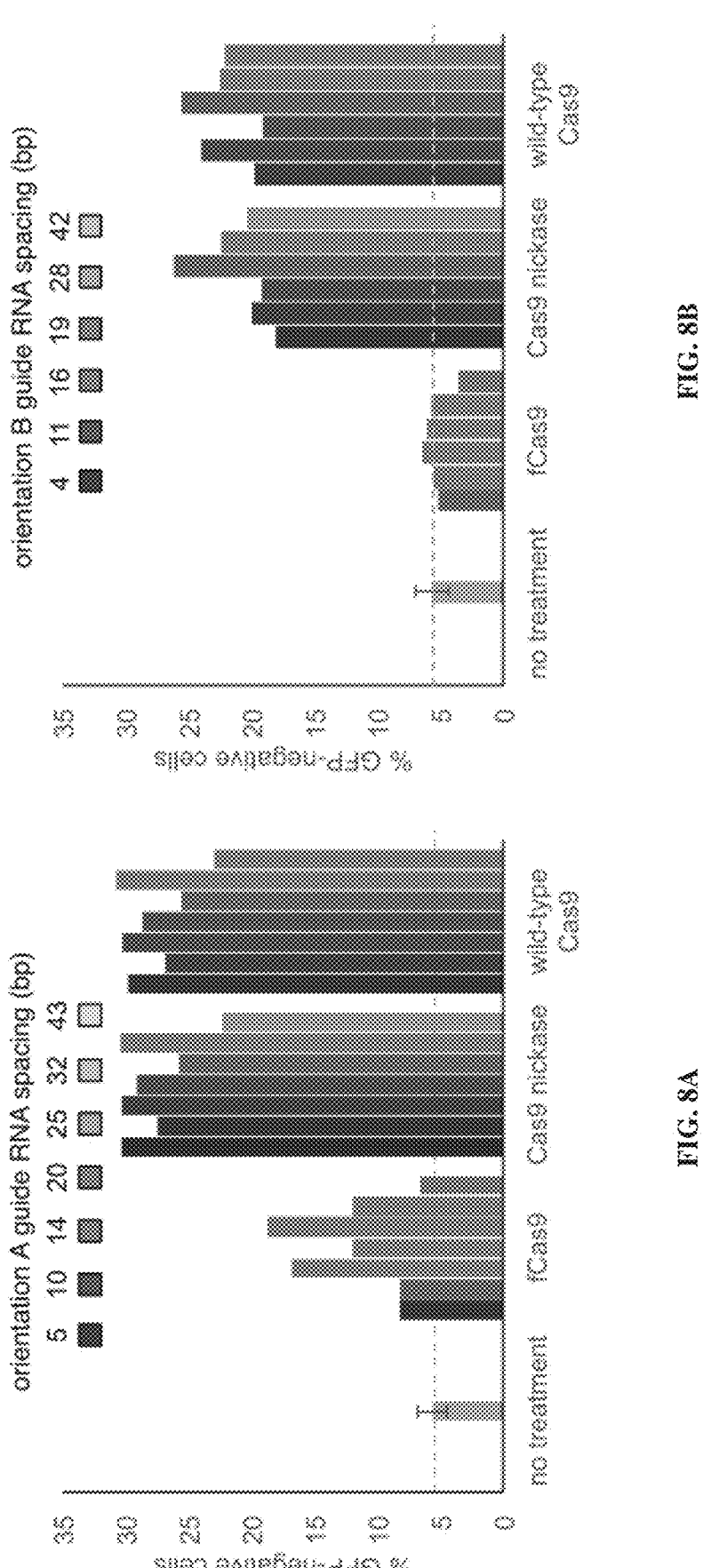
FIG. 8A-8G shows the DNA modification specificity of fCas9, Cas9 nickase, and wild-type Cas9.

As the gRNA requirements of fCas9 potentially restricts the number of potential off-target substrates of fCas9, the effect of guide RNA orientation on the ability of fCas9, Cas9 nickase, and wild-type Cas9 to cleave target GFP sequences were compared. Consistent with previous reports,[5,6,17] Cas9 nickase efficiently cleaved targets when guide RNAs were bound either in orientation A or orientation B, similar to wild-type Cas9 (FIG. 8A, B). In contrast, fCas9 only cleaved the GFP target when guide RNAs were aligned in orientation A (FIG. 8A). This orientation requirement further limits opportunities for undesired off-target DNA cleavage.

Figure 7B:
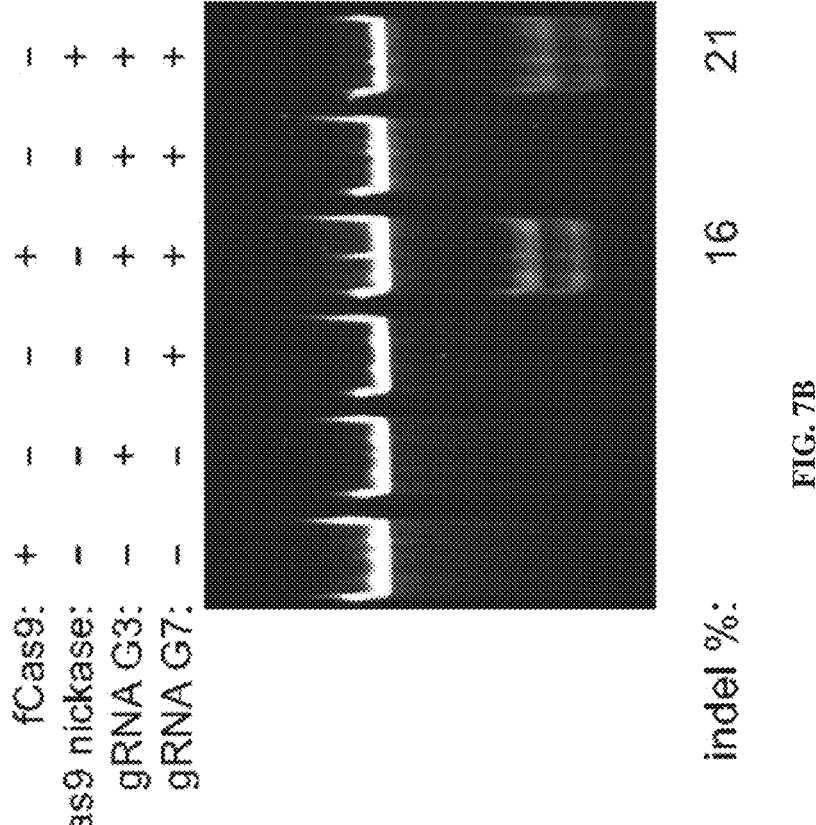
Figures 7C, 7D, 7E:
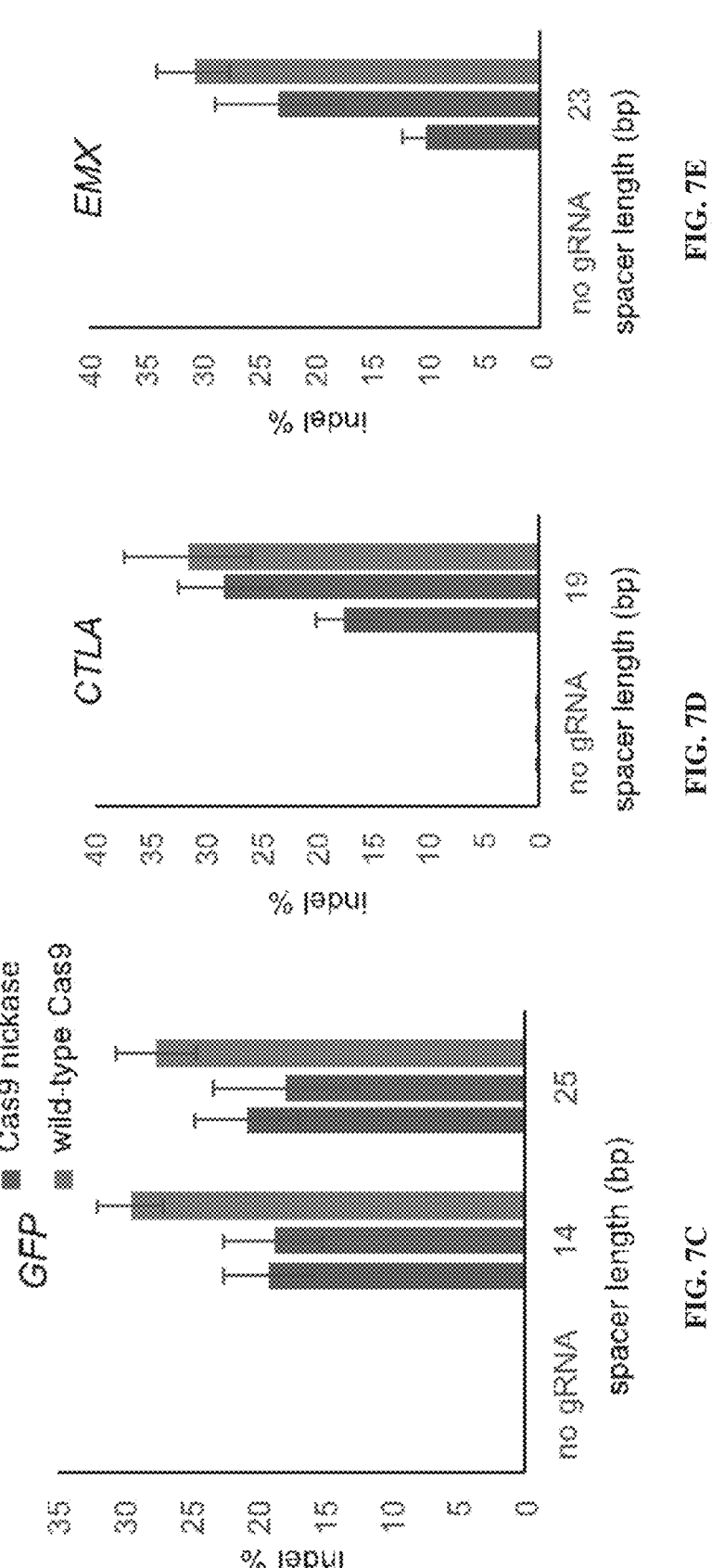
Figure 7G:
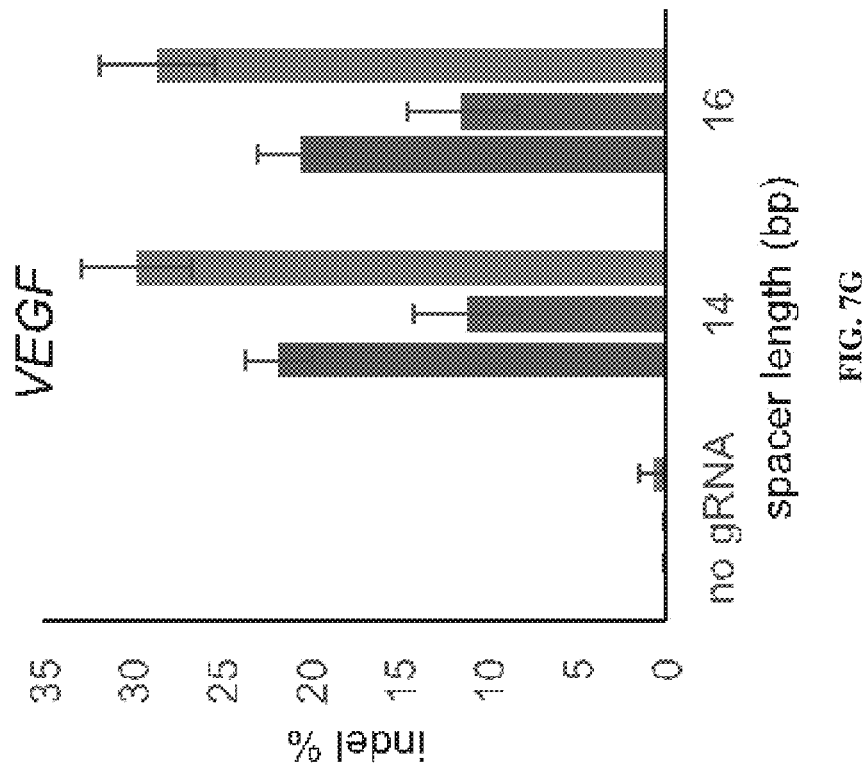
Figure 7F:
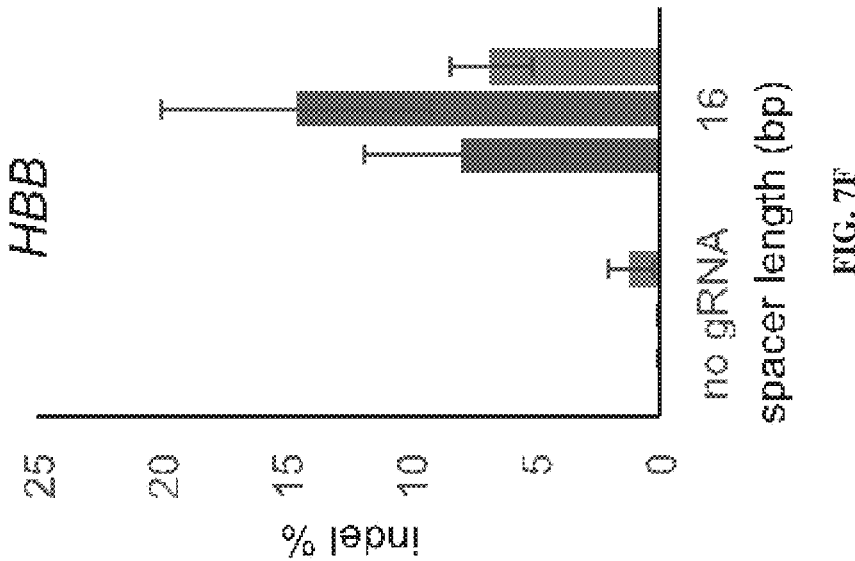
Figure 8C:
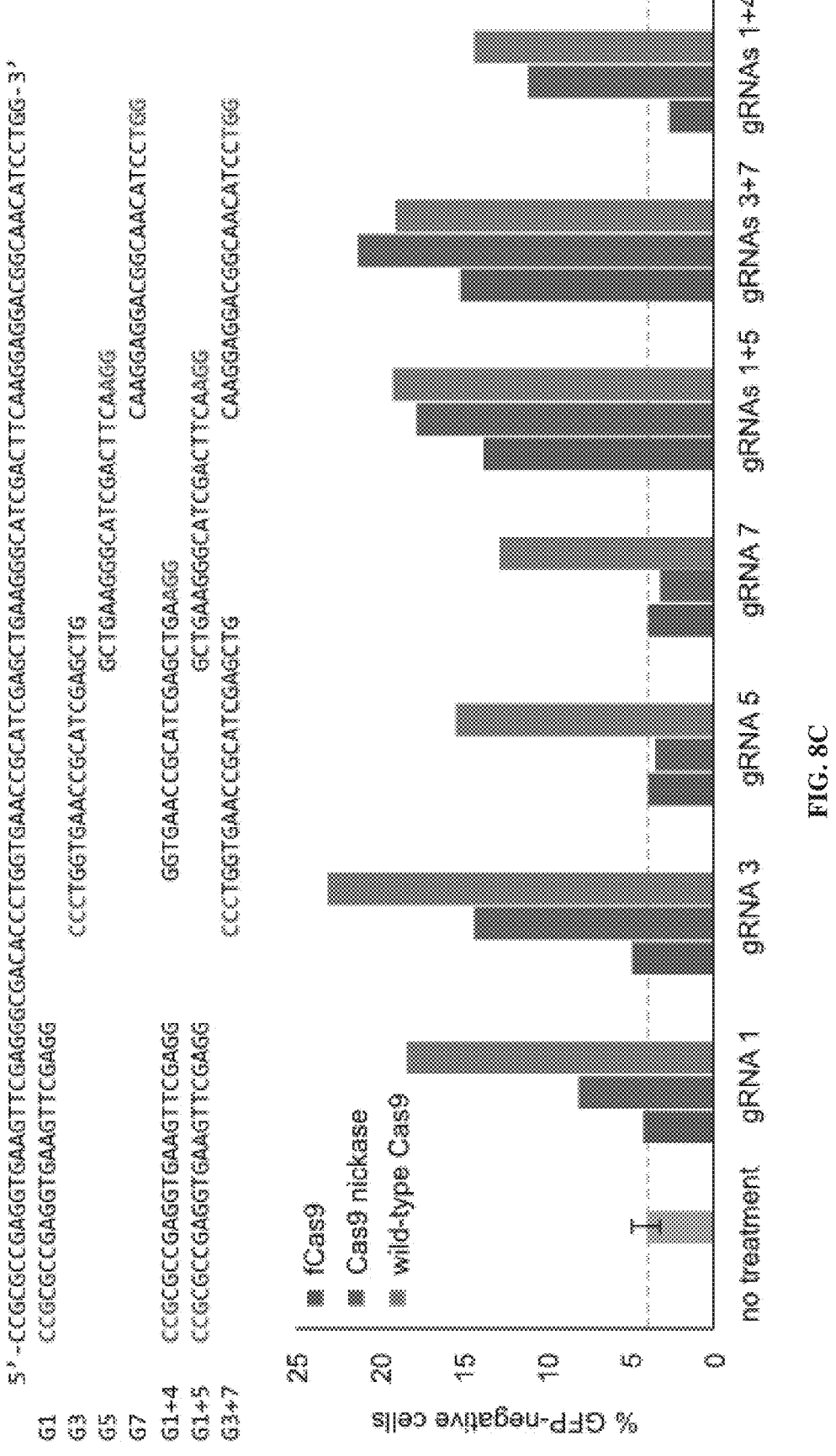

Importantly, no modification was observed by GFP disruption or Surveyor assay when any of four single gRNAs were expressed individually with fCas9, as expected since two simultaneous binding events are required for FokI activity (FIG. 7B and FIG. 8C). In contrast, GFP disruption resulted from expression of any single gRNA with wild-type Cas9 (as expected) and, for two single gRNAs, with Cas9 nickase (FIG. 8C). Surprisingly, Surveyor assay revealed that although GFP was heavily modified by wild-type Cas9 with single gRNAs, neither fCas9 nor Cas9 nickase showed detectable modification (<~2%) in cells treated with single gRNAs (FIG. 16A). High-throughput sequencing to detect indels at the GFP target site in cells treated with a single gRNA and fCas9, Cas9 nickase, or wild-type Cas9 revealed the expected substantial level of modification by wild-type Cas9 (3-7% of sequence reads). Modification by fCas9 in the presence of any of the four single gRNAs was not detected above background (<~0.03% modification), consistent with the requirement of fCas9 to engage two gRNAs in order to cleave DNA. In contrast, Cas9 nickases in the presence of single gRNAs resulted in modification levels ranging from 0.05% to 0.16% at the target site (FIG. 16B). The detection of bona fide indels at target sites following Cas9 nickase treatment with single gRNAs confirms the mutagenic potential of genomic DNA nicking, consistent with previous reports.[5,7,18,19]

The observed rate of nickase-induced DNA modification, however, did not account for the much higher GFP disruption signal in the flow cytometry assay (FIG. 8C). Since the gRNAs that induced GFP signal loss with Cas9 nickase (gRNAs G1 and G3) both target the non-template strand of the GFP gene, and since targeting the non-template strand with dCas9 in the coding region of a gene is known to mediate efficient transcriptional repression,[29] it is speculated that Cas9 nickase combined with the G1 or G3 single guide RNAs induced substantial transcriptional repression, in addition to a low level of genome modification. The same effect was not seen for fCas9, suggesting that fCas9 may be more easily displaced from DNA by transcriptional machinery. Taken together, these results indicate that fCas9 can modify genomic DNA efficiently and in a manner that requires simultaneous engagement of two guide RNAs targeting adjacent sites, unlike the ability of wild-type Cas9 and Cas9 nickase to cleave DNA when bound to a single guide RNA.

The above results collectively reveal much more stringent spacer, gRNA orientation, and guide RNA pairing requirements for fCas9 compared with Cas9 nickase. In contrast with fCas9 (FIG. 17), Cas9 nickase cleaved sites across all spacers assayed (5- to 47-bp in orientation A and 4 to 42 bp in orientation B in this work) (FIG. 8A, B). These observations are consistent with previous reports of Cas9 nickases modifying sites targeted by gRNAs with spacer lengths up to 100 bp apart.[6] The more stringent spacer and gRNA orientation requirements of fCas9 compared with Cas9 nickase reduces the number of potential genomic off-target sites of the former by approximately 10-fold (Table 4). Although the more stringent spacer requirements of fCas9 also reduce the number of potential targetable sites, sequences that conform to the fCas9 spacer and dual PAM requirements exist in the human genome on average once every 34 bp ($9.2 \times 10^7$ sites in $3.1 \times 10^9$ bp) (Table 4). It is also anticipated that the growing number of Cas9 homologs with different PAM specificities[30] are amenable for use as described herein, and will further increase the number of targetable sites using the fCas9 approach.

In Table 4 (A) column 2 shows the number of sites in the human genome with paired gRNA binding sites in orientation A allowing for a spacer length from −8 bp to 25 bp (column 1) between the two gRNA binding sites. gRNA binding sites in orientation A have the NGG PAM sequences distal from the spacer sequence ($CCNN_{20}$-spacer-$N_{20}NGG$). Column 3 shows the number of sites in the human genome with paired gRNA binding sites in orientation B allowing for a spacer length from 4 to 25 bp (column 1) between the two gRNA binding sites. gRNA binding sites in orientation B have the NGG PAM sequences adjacent to the spacer sequence ($N_{20}NGG$ spacer $CCNN_{20}$). NC indicates the number of sites in the human genome was not calculated. Negative spacer lengths refer to target gRNA binding sites that overlap by the indicated number of base pairs. Table 4 (B) shows the sum of the number of paired gRNA binding sites in orientation A with spacer lengths of 13 to 19 bp, or 22 to 29 bp, the spacer preference of fCas9 (FIG. 16). Sum of the number of paired gRNA binding sites with spacer lengths of −8 bp to 100 bp in orientation A, or 4 to 42 bp in orientation B, the spacer preference of Cas9 nickases (4 to 42 bp in orientation B is based on FIG. 8B, C, and −8 bp to 100 bp in orientation A is based on previous reports[36, 37]).

TABLE 4

Paired gRNA target site abundances for fCas9 and Cas9 nickase in the human genome.

| Spacer length (b) | Number of paired gRNA sites in orientation A | Number of paired gRNA sites in orientation B |
|---|---|---|
| (A) | | |
| −8 | 6874293 | NC |
| −7 | 6785996 | NC |
| −6 | 6984064 | NC |
| −5 | 7023260 | NC |
| −4 | 6487302 | NC |
| −3 | 6401348 | NC |
| −2 | 6981383 | NC |
| −1 | 7230098 | NC |
| 0 | 7055143 | NC |
| 1 | 6598582 | NC |
| 2 | 6877046 | NC |
| 3 | 6971447 | NC |
| 4 | 6505614 | 5542549 |
| 5 | 6098107 | 5663458 |
| 6 | 6254974 | 6819289 |
| 7 | 6680118 | 6061225 |

TABLE 4-continued

Paired gRNA target site abundances for fCas9 and Cas9 nickase in the human genome.

| | | |
|---|---|---|
| 8 | 7687598 | 5702252 |
| 9 | 6755736 | 7306646 |
| 10 | 6544849 | 6387485 |
| 11 | 6918186 | 6172852 |
| 12 | 6241723 | 5799496 |
| 13 | 6233385 | 7092283 |
| 14 | 6298717 | 7882433 |
| 15 | 6181422 | 7472725 |
| 16 | 6266909 | 6294684 |
| 17 | 6647352 | 6825904 |
| 18 | 6103603 | 6973590 |
| 19 | 5896092 | 6349456 |
| 20 | 6000683 | 5835825 |
| 21 | 5858015 | 6056352 |
| 22 | 6116108 | 6531913 |
| 23 | 5991254 | 6941816 |
| 24 | 6114969 | 6572849 |
| 25 | 6135119 | 5671641 |

(B)

| Cas9 variant | Preferred spacer lengths (bp) | Total sites |
|---|---|---|
| fCas9 | 13 to 19, or 22 to 29, in orientation A | 92354891 |
| Cas9 nickase | −8 to 100 in orientation A<br>4 to 42 in orientation B | 953048977 |

To evaluate the DNA cleavage specificity of fCas9, the modification of known Cas9 off-target sites of CLTA, EMX, and VEGF genomic target sites were measured.[1,2,6,8] The target site and its corresponding known off-target sites (Table 5) were amplified from genomic DNA isolated from HEK293 cells treated with fCas9, Cas9 nickase, or wild-type Cas9 and two gRNAs spaced 19 bp apart targeting the CLTA site, two gRNAs spaced 23 bp apart targeting the EMX site, two gRNAs spaced 14 bp apart targeting the VEGF site, or two gRNAs targeting an unrelated site (GFP) as a negative control. In total 11 off-target sites were analyzed by high-throughput sequencing.

The sensitivity of the high-throughput sequencing method for detecting genomic off-target cleavage is limited by the amount genomic DNA (gDNA) input into the PCR amplification of each genomic target site. A 1 ng sample of human gDNA represents only ~330 unique genomes, and thus only ~330 unique copies of each genomic site are present. PCR amplification for each genomic target was performed on a total of 150 ng of input gDNA, which provides amplicons derived from at most 50,000 unique gDNA copies. Therefore, the high-throughput sequencing assay cannot detect rare genome modification events that occur at a frequency of less than 1 in 50,000, or 0.002%.

TABLE 5

Known off-target substrates of Cas9 target sites in EMX, VEGF, and CLTA. List of genomic on-target and off-targets sites of the EMX, VEGF, and CLTA are shown with mutations from on-target in lower case and bold. PAMs are shown in upper case bold.

| | Genomic target site |
|---|---|
| EMX_On | GAGTCCGAGCAGAAGAAGAAGGG<br>(SEQ ID NO: 190) |
| EMX_Off1 | GAGgCCGAGCAGAAGAAagACGG<br>(SEQ ID NO: 191) |

TABLE 5-continued

Known off-target substrates of Cas9 target sites in EMX, VEGF, and CLTA. List of genomic on-target and off-targets sites of the EMX, VEGF, and CLTA are shown with mutations from on-target in lower case and bold. PAMs are shown in upper case bold.

| | Genomic target site |
|---|---|
| EMX_Off2 | GAGTCCtAGCAGgAGAAGAAGaG<br>(SEQ ID NO: 192) |
| EMX_Off3 | GAGTCtaAGCAGAAGAAGAAGaG<br>(SEQ ID NO: 193) |
| EMX_Off4 | GAGTtaGAGCAGAAGAAGAAAGG<br>(SEQ ID NO: 194) |
| VEG_On | GGGTGGGGGGAGTTTGCTCCTGG<br>(SEQ ID NO: 195) |
| VEG_Off1 | GGaTGGaGGGAGTTTGCTCCTGG<br>(SEQ ID NO: 196) |
| VEG_Off2 | GGGaGGGtGGAGTTTGCTCCTGG<br>(SEQ ID NO: 197) |
| VEG_Off3 | cGGgGGaGGGAGTTTGCTCCTGG<br>(SEQ ID NO: 198) |
| VEG_Off4 | GGGgaGGGGaAGTTTGCTCCTGG<br>(SEQ ID NO: 199) |
| CLT2_On | GCAGATGTAGTGTTTCCACAGGG<br>(SEQ ID NO:200) |
| CLT2_Off1 | aCAaATGTAGTaTTTCCACAGGG<br>(SEQ ID NO:201) |
| CLT2_Off2 | cCAGATGTAGTaTTcCCACAGGG<br>(SEQ ID NO:202) |
| CLT2_Off3 | ctAGATGaAGTGcTTCCACATGG<br>(SEQ ID NO:203) |

Figures 8D, 8E:
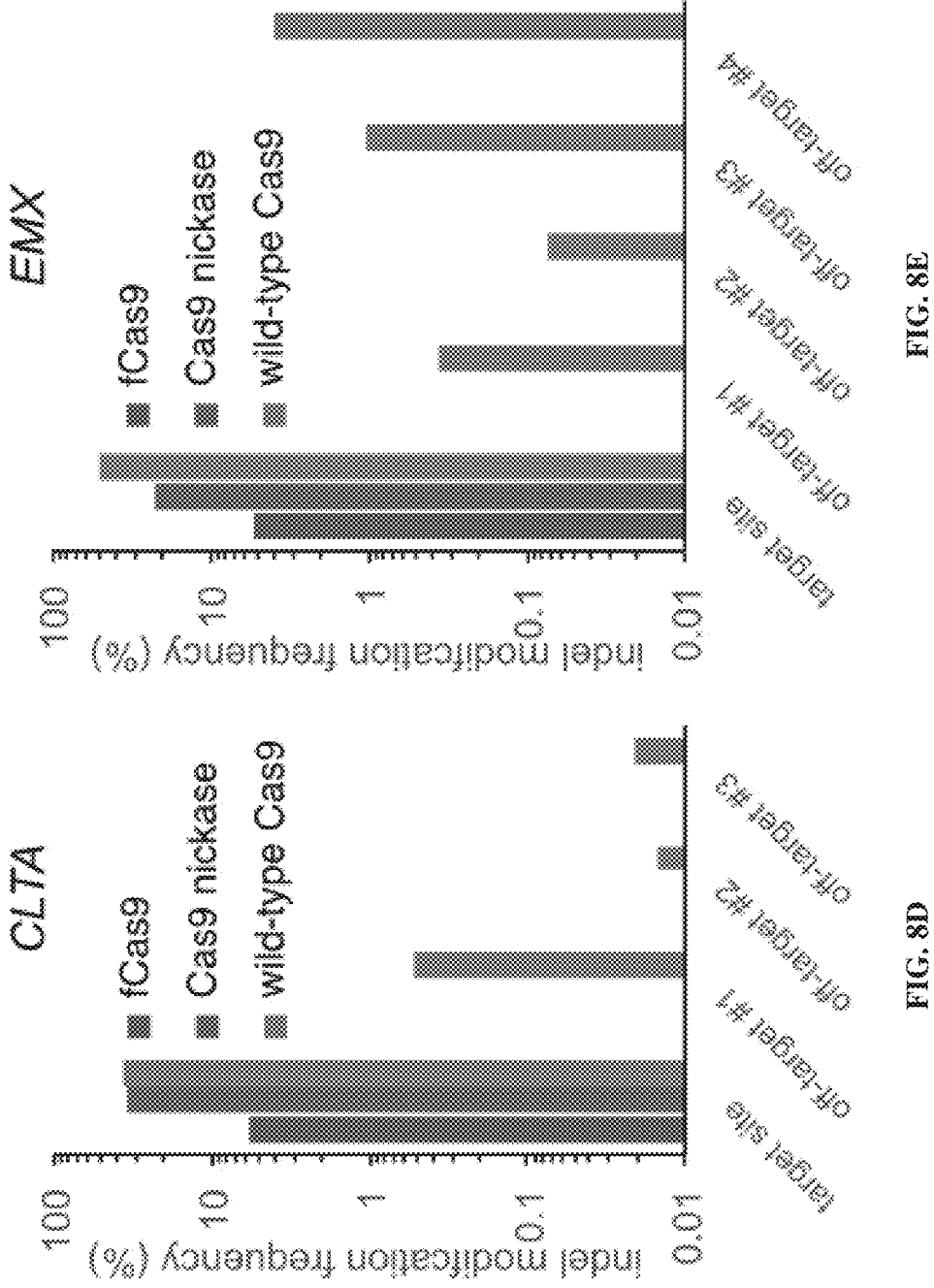
Figures 8F, 8G:
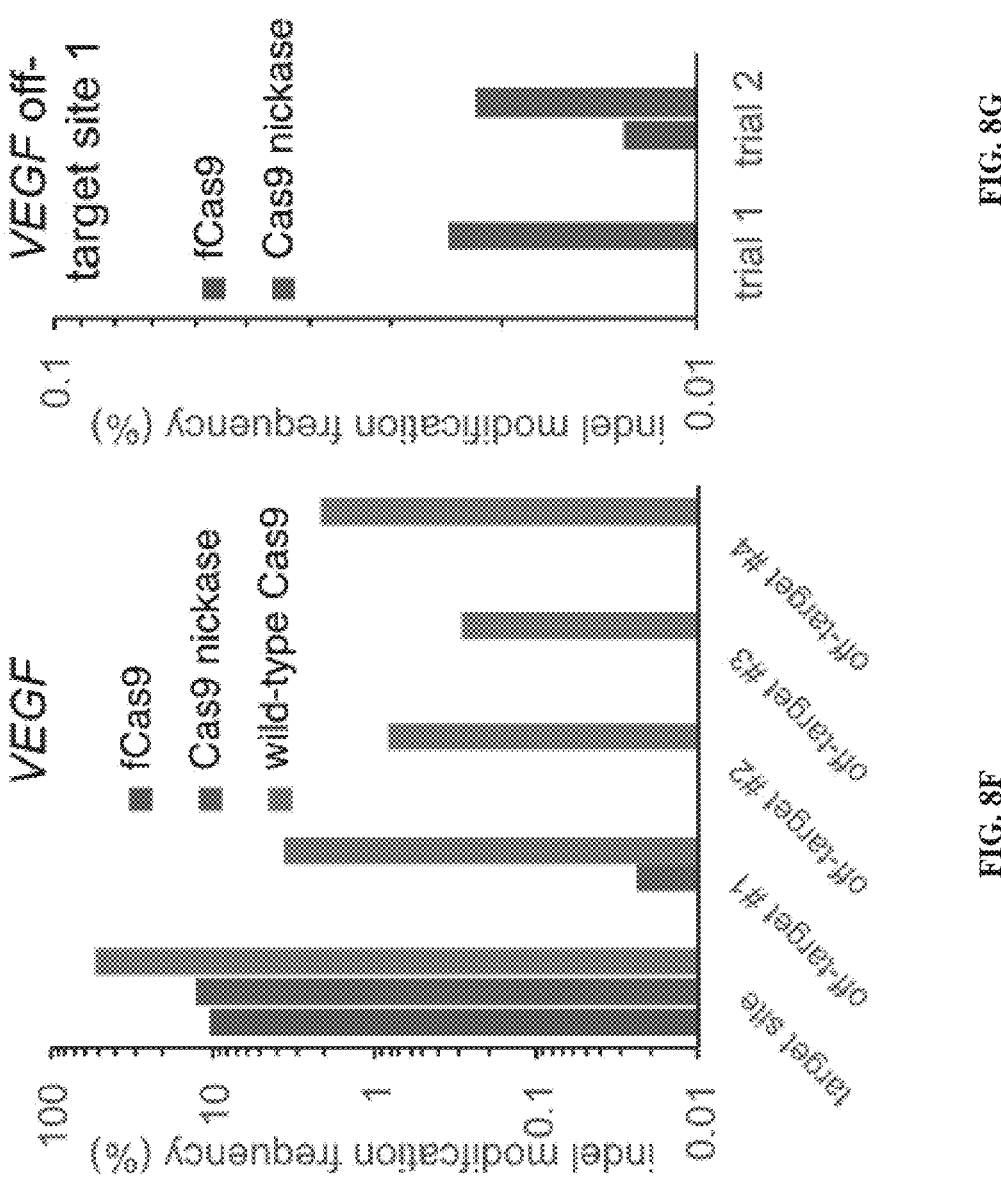

Sequences containing insertions or deletions of two or more base pairs in potential genomic off-target sites and present in significantly greater numbers (P value <0.005, Fisher's exact test) in the target gRNA-treated samples versus the control gRNA-treated samples were considered Cas9 nuclease-induced genome modifications. For 10 of the 11 off-target sites assayed, fCas9 did not result in any detectable genomic off-target modification within the sensitivity limit of the assay (<0.002%,), while demonstrating substantial on-target modification efficiencies of 5% to 10% (FIG. 8D-F and Table 3). The detailed inspection of fCas9-modified VEGF on-target sequences (FIG. 18A) revealed a prevalence of deletions ranging from two to dozens of base pairs consistent with cleavage occurring in the DNA spacer between the two target binding sites, similar to the effects of FokI nuclease domains fused to zinc finger or TALE DNA-binding domains.[31]

In contrast, genomic off-target DNA cleavage was observed for wild-type Cas9 at all 11 sites assayed. Using the detection limit of the assay as an upper bound for off-target fCas9 activity, it was calculated that fCas9 has a much lower off-target modification rate than wild-type Cas9 nuclease. At the 11 off-target sites modified by wild-type Cas9 nuclease, fCas9 resulted in on-target:off-target modification ratios at least 140-fold higher than that of wild-type Cas9 (FIG. 8D-F).

Consistent with previous reports,[5,6,8] Cas9 nickase also induced substantially fewer off-target modification events (1/11 off-target sites modified at a detectable rate) compared to wild-type Cas9. An initial high-throughput sequencing assay revealed significant (P value <10$^{-3}$, Fisher's Exact Test) modification induced by Cas9 nickases in 0.024% of sequences at VEGF off-target site 1. This genomic off-target site was not modified by fCas9 despite similar VEGF on-target modification efficiencies of 12.3% for Cas9 nickase and 10.4% for fCas9 (FIG. 8F and Table 3C). Because Cas9 nickase-induced modification levels were within an order of magnitude of the limit of detection and fCas9 modification levels were undetected, the experiment was repeated with a larger input DNA samples and a greater number of sequence reads (150 versus 600 ng genomic DNA and >8×10$^5$ versus >23×10$^5$ reads for the initial and repeated experiments, respectively) to detect off-target cleavage at this site by Cas9 nickase or fCas9. From this deeper interrogation, it was observed that Cas9 nickase and fCas9 both significantly modify (P value <10$^{-5}$, Fisher's Exact Test) VEGF off-target site 1 (FIG. 8G, Table 3D, FIG. 18B). For both experiments interrogating the modification rates at VEGF off-target site 1, fCas9 exhibited a greater on-target:off-target DNA modification ratio than that of Cas9 nickase (>5,150 and 1,650 for fCas9, versus 510 and 1,230 for Cas9 nickase, FIG. 8G).

On either side of VEGF off-target site 1 there exist no other sites with six or fewer mutations from either of the two half-sites of the VEGF on-target sequence. The first 11 bases of one gRNA (V2) might hybridize to the single-stranded DNA freed by canonical Cas9:gRNA binding within VEGF off-target site 1 (FIG. 18C). Through this gRNA:DNA hybridization it is possible that a second Cas9 nickase or fCas9 could be recruited to modify this off-target site at a very low, but detectable level. Judicious gRNA pair design could eliminate this potential mode of off-target DNA cleavage, as VEGF off-target site 1 is highly unusual in its ability to form 11 consecutive potential base pairs with the second gRNA of a pair. In general, fCas9 was unable to modify the genomic off-target sites tested because of the absence of any adjacent second binding site required to dimerize and activate the FokI nuclease domain.

The optimized FokI-dCas9 fusion architecture developed in this work modified all five genomic loci targeted, demonstrating the generality of using fCas9 to induce genomic modification in human cells, although modification with fCas9 was somewhat less efficient than with wild-type Cas9. The use of fCas9 is straightforward, requiring only that PAM sequences be present with an appropriate spacing and orientation, and using the same gRNAs as wild-type Cas9 or Cas9 nickases. The observed low off-target:on-target modification ratios of fCas9, >140-fold lower than that of wild-type Cas9, likely arises from the distinct mode of action of dimeric FokI, in which DNA cleavage proceeds only if two DNA sites are occupied simultaneously by two FokI domains at a specified distance (here, ~15 bp or ~25 bp apart) and in a specific half-site orientation. The resulting unusually low off-target activity of fCas9 enable applications of Cas9:gRNA-based technologies that require a very high degree of target specificity, such as ex vivo or in vivo therapeutic modification of human cells.

REFERENCES

1. Pattanayak, V. et al. High-throughput profiling of off-target DNA cleavage reveals RNA-programmed Cas9 nuclease specificity. *Nat. Biotechnol.* 31, 839-843 (2013).
2. Fu, Y. et al. High-frequency off-target mutagenesis induced by CRISPR-Cas nucleases in human cells. *Nat. Biotechnol.* 31, 822-826 (2013).
3. Hsu, P. D. et al. DNA targeting specificity of RNA-guided Cas9 nucleases. *Nat. Biotechnol.* 31, 827-832 (2013).
4. Cradick, T. J., Fine, E. J., Antico, C. J. & Bao, G. CRISPR/Cas9 systems targeting—globin and CCR5 genes have substantial off-target activity. *Nucleic Acids Res.* 41, 9584-9592 (2013).
5. Cho, S. W. et al. Analysis of off-target effects of CRISPR/Cas-derived RNA-guided endonucleases and nickases. *Genome Res.* 24, 132-141 (2013).
6. Ran, F. A. et al. Double Nicking by RNA-Guided CRISPR Cas9 for Enhanced Genome Editing Specificity. *Cell* 154, 1380-1389 (2013).
7. Mali, P. et al. CAS9 transcriptional activators for target specificity screening and paired nickases for cooperative genome engineering. *Nat. Biotechnol.* 31, 833-838 (2013).
8. Fu, Y., Sander, J. D., Reyon, D., Cascio, V. M. & Joung, J. K. Improving CRISPR-Cas nuclease specificity using truncated guide RNAs. *Nat. Biotechnol.* (2014). doi: 10.1038/nbt.2808
9. Cong, L. et al. Multiplex Genome Engineering Using CRISPR/Cas Systems. *Science* 339, 819-823 (2013).
10. Jinek, M. et al. A Programmable Dual-RNA-Guided DNA Endonuclease in Adaptive Bacterial Immunity. *Science* 337, 816-821 (2012).
11. Gasiunas, G., Barrangou, R., Horvath, P. & Siksnys, V. Cas9-crRNA ribonucleoprotein complex mediates specific DNA cleavage for adaptive immunity in bacteria. *Proc. Natl. Acad. Sci.* 109, E2579-E2586 (2012).
12. Wang, T., Wei, J. J., Sabatini, D. M. & Lander, E. S. Genetic screens in human cells using the CRISPR-Cas9 system. *Science* 343, 80-84 (2014).
13. Shalem, O. et al. Genome-Scale CRISPR-Cas9 Knockout Screening in Human Cells. *Science* 343, 84-87 (2013).
14. Perez, E. E. et al. Establishment of HIV-1 resistance in CD4+ T cells by genome editing using zinc-finger nucleases. *Nat. Biotechnol.* 26, 808-816 (2008).
15. Jinek, M. et al. RNA-programmed genome editing in human cells. *eLife* 2, e00471-e00471 (2013).

16. Mali, P. et al. RNA-Guided Human Genome Engineering via Cas9. *Science* 339, 823-826 (2013).

17. Mali, P., Esvelt, K. M. & Church, G. M. Cas9 as a versatile tool for engineering biology. *Nat. Methods* 10, 957-963 (2013).

18. Ramirez, C. L. et al. Engineered zinc finger nickases induce homology-directed repair with reduced mutagenic effects. *Nucleic Acids Res.* 40, 5560-5568 (2012).

19. Wang, J. et al. Targeted gene addition to a predetermined site in the human genome using a ZFN-based nicking enzyme. *Genome Res.* 22, 1316-1326 (2012).

20. Gaj, T., Gersbach, C. A. & Barbas, C. F. ZFN, TALEN, and CRISPR/Cas-based methods for genome engineering. *Trends Biotechnol.* 31, 397-405 (2013).

21. Vanamee, É. S., Santagata, S. & Aggarwal, A. K. FokI requires two specific DNA sites for cleavage. *J. Mol. Biol.* 309, 69-78 (2001).

22. Maeder, M. L. et al. CRISPR RNA-guided activation of endogenous human genes. *Nat. Methods* 10, 977-979 (2013).

23. Pattanayak, V., Ramirez, C. L., Joung, J. K. & Liu, D. R. Revealing off-target cleavage specificities of zinc-finger nucleases by in vitro selection. *Nat. Methods* 8, 765-770 (2011).

24. Guilinger, J. P. et al. Broad specificity profiling of TALENs results in engineered nucleases with improved DNA-cleavage specificity. *Nat. Methods* (2014). doi: 10.1038/nmeth.2845

25. Nishimasu, H. et al. Crystal Structure of Cas9 in Complex with Guide RNA and Target DNA. *Cell* (2014). doi:10.1016/j.cell.2014.02.001

26. Jinek, M. et al. Structures of Cas9 Endonucleases Reveal RNA-Mediated Conformational Activation. *Science* (2014). doi:10.1126/science.1247997

27. Schellenberger, V. et al. A recombinant polypeptide extends the in vivo half-life of peptides and proteins in a tunable manner. *Nat. Biotechnol.* 27, 1186-1190 (2009).

28. Guschin, D. Y. et al. in *Eng. Zinc Finger Proteins* (Mackay, J. P. & Segal, D. J.) 649, 247-256 (Humana Press, 2010).

29. Qi, L. S. et al. Repurposing CRISPR as an RNA-guided platform for sequence-specific control of gene expression. *Cell* 152, 1173-1183 (2013).

30. Esvelt, K. M. et al. Orthogonal Cas9 proteins for RNA-guided gene regulation and editing. *Nat. Methods* 10, 1116-1121 (2013).

31. Kim, Y., Kweon, J. & Kim, J.-S. TALENs and ZFNs are associated with different mutation signatures. *Nat. Methods* 10, 185-185 (2013).

32. Shcherbakova, D. M. & Verkhusha, V. V. Near-infrared fluorescent proteins for multicolor in vivo imaging. *Nat. Methods* 10, 751-754 (2013).

33. Schneider, C. A., Rasband, W. S. & Eliceiri, K. W. NIH Image to ImageJ: 25 years of image analysis. *Nat. Methods* 9, 671-675 (2012).

34. Sander, J. D. et al. In silico abstraction of zinc finger nuclease cleavage profiles reveals an expanded landscape of off-target sites. *Nucleic Acids Res.* 41, e181-e181 (2013).

35. Schellenberger, V. et al. A recombinant polypeptide extends the in vivo half-life of peptides and proteins in a tunable manner. *Nat. Biotechnol.* 27, 1186-1190 (2009).

36. Mali, P. et al. CAS9 transcriptional activators for target specificity screening and paired nickases for cooperative genome engineering. *Nat. Biotechnol.* 31, 833-838 (2013).

37. Ran, F. A. et al. Double Nicking by RNA-Guided CRISPR Cas9 for Enhanced Genome Editing Specificity. *Cell* 154, 1380-1389 (2013).

38. Yan, T. et al. PatMatch: a program for finding patterns in peptide and nucleotide sequences. *Nucleic Acids Res.* 33, W262-W266 (2005).

39. Larkin, M. A. et al. Clustal W and Clustal X version 2.0. *Bioinformatics* 23, 2947-2948 (2007).

Example 2: Targeting CCR5 for Cas9 Variant-Mediated Inactivation

In addition to providing powerful research tools, site-specific nucleases also have potential as gene therapy agents, and site-specific zinc finger endonucleases have recently entered clinical trials: CCR5-2246, targeting a human CCR-5 allele as part of an anti-HIV therapeutic approach.

In a similar approach, the inventive Cas9 variants of the present disclosure may be used to inactivate CCR5, for example in autologous T cells obtained from a subject which, once modified by a Cas9 variant, are re-introduced into the subject for the treatment or prevention of HIV infection.

In this example, the CCR5 gene is targeted in T cells obtained from a subject. CCR5 protein is required for certain common types of HIV to bind to and enter T cells, thereby infecting them. T cells are one of the white blood cells used by the body to fight HIV.

Some people are born lacking CCR5 expression on their T cells and remain healthy and are resistant to infection with HIV. Others have low expression of CCR5 on their T cells, and their HIV disease is less severe and is slower to cause disease (AIDS).

In order to delete the CCR5 protein on the T cells, large numbers of T-cells are isolated from a subject. Cas9 variants (e.g., fCas9) and gRNA capable of inactivating CCR5 are then delivered to the isolated T cells using a viral vector, e.g., an adenoviral vector. Examples of suitable Cas9 variants include those inventive fusion proteins provided herein. Examples of suitable target sequences for gRNAs targeting the CCR5 allele include those described in FIG. 19, e.g., SEQ ID NOs:303-310 and 312-317. The viral vector(s) capable of expressing the Cas9 variant and gRNA is/are added to the isolated T cells to knock out the CCR5 protein. When the T cells are returned to subject, there is minimal adenovirus or Cas9 variant protein present. The removal of the CCR5 protein on the T cells subjects receive, however, is permanent. The cells are then reintroduced to the subject for the treatment or prevention of HIV/AIDS.

Example 3: Cas9-Recombinase Fusion Proteins

Exemplary Cas9-recombinase fusion proteins are provided below:

dCas9-NLS-GGS3linker-Tn3

```
                                    (SEQ ID NO: 328)
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP
```

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD<u>MAPKKKRKVGIHRGVP</u>GGSGGSGGSMALFGYA

RVSTSQQSLDLQVRALKDAGVKANRIFTDKASGSSTDREGLDLLRMKVKE

GDVILVKKLDRLGRDTADMLQLIKEFDAQGVAVRFIDDGISTDSYIGLMF

VTILSAVAQAERRRILERTNEGRQAAKLKGIKFGRRR
(underline: nuclear localization signal; bold:
linker sequence)

NLS-dCas9-GGS3linker-Tn3

(SEQ ID NO: 329)
<u>MAPKKKRKVGIHRGVP</u>MDKKYSIGLAIGTNSVGWAVITDEYKVPSKKFKV

LGNTDRHSIKKNLIGALLFDSGETAEATRLKRTARRRYTRRKNRICYLQE

IFSNEMAKVDDSFFHRLEESFLVEEDKKHERHPIFGNIVDEVAYHEKYPT

IYHLRKKLVDSTDKADLRLIYLALAHMIKFRGHFLIEGDLNPDNSDVDKL

FIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGD

QYADLFLAAKNLSDAILLSDILRVNTEITKAPLSASMIKRYDEHHQDLTL

LKALVRQQLPEKYKEIFFDQSKNGYAGYIDGGASQEEFYKFIKPILEKMD

GTEELLVKLNREDLLRKQRTFDNGSIPHQIHLGELHAILRRQEDFYPFLK

DNREKIEKILTFRIPYYVGPLARGNSRFAWMTRKSEETITPWNFEEVVDK

GASAQSFIERMTNFDKNLPNEKVLPKHSLLYEYFTVYNELTKVKYVTEGM

RKPAFLSGEQKKAIVDLLFKTNRKVTVKQLKEDYFKKIECFDSVEISGVE

DRFNASLGTYHDLLKIIKDKDFLDNEENEDILEDIVLTLTLFEDREMIEE

RLKTYAHLFDDKVMKQLKRRRYTGWGRLSRKLINGIRDKQSGKTILDFLK

SDGFANRNFMQLIHDDSLTFKEDIQKAQVSGQGDSLHEHIANLAGSPAIK

KGILQTVKVVDELVKVMGRHKPENIVIEMARENQTTQKGQKNSRERMKRI

EEGIKELGSQILKEHPVENTQLQNEKLYLYYLQNGRDMYVDQELDINRLS

DYDVDAIVPQSFLKDDSIDNKVLTRSDKNRGKSDNVPSEEVVKKMKNYWR

QLLNAKLITQRKFDNLTKAERGGLSELDKAGFIKRQLVETRQITKHVAQI

LDSRMNTKYDENDKLIREVKVITLKSKLVSDFRKDFQFYKVREINNYHHA

HDAYLNAVVGTALIKKYPKLESEFVYGDYKVYDVRKMIAKSEQEIGKATA

KYFFYSNIMNFFKTEITLANGEIRKRPLIETNGETGEIVWDKGRDFATVR

KVLSMPQVNIVKKTEVQTGGFSKESILPKRNSDKLIARKKDWDPKKYGGF

DSPTVAYSVLVVAKVEKGKSKKLKSVKELLGITIMERSSFEKNPIDFLEA

KGYKEVKKDLIIKLPKYSLFELENGRKRMLASAGELQKGNELALPSKYVN

FLYLASHYEKLKGSPEDNEQKQLFVEQHKHYLDEIIEQISEFSKRVILAD

ANLDKVLSAYNKHRDKPIREQAENIIHLFTLTNLGAPAAFKYFDTTIDRK

RYTSTKEVLDATLIHQSITGLYETRIDLSQLGGDGGSGGSGGSMALFGYA

RVSTSQQSLDLQVRALKDAGVKANRIFTDKASGSSTDREGLDLLRMKVKE

GDVILVKKLDRLGRDTADMLQLIKEFDAQGVAVRFIDDGISTDSYIGLMF

VTILSAVAQAERRRILERTNEGRQAAKLKGIKFGRRR
(underline: nuclear localization signal; bold:
linker sequence)

Tn3-GGS3linker-dCas9-NLS (SEQ ID NO: 330)
MALFGYARVSTSQQSLDLQVRALKDAGVKANRIFTDKASGSSTDREGLDL

LRMKVKEGDVILVKKLDRLGRDTADMLQLIKEFDAQGVAVRFIDDGISTD

SYIGLMFVTILSAVAQAERRRILERTNEGRQAAKLKGIKFGRRRGGSGGS

GGSMDKKYSIGLAIGTNSVGWAVITDEYKVPSKKFKVLGNTDRHSIKKNL

IGALLFDSGETAEATRLKRTARRRYTRRKNRICYLQEIFSNEMAKVDDSF

FHRLEESFLVEEDKKHERHPIFGNIVDEVAYHEKYPTIYHLRKKLVDSTD

KADLRLIYLALAHMIKFRGHFLIEGDLNPDNSDVDKLFIQLVQTYNQLFE

ENPINASGVDAKAILSARLSKSRRLENLIAQLPGEKKNGLFGNLIALSLG

LTPNFKSNFDLAEDAKLQLSKDTYDDDLDNLLAQIGDQYADLFLAAKNLS

DAILLSDILRVNTEITKAPLSASMIKRYDEHHQDLTLLKALVRQQLPEKY

KEIFFDQSKNGYAGYIDGGASQEEFYKFIKPILEKMDGTEELLVKLNRED

LLRKQRTFDNGSIPHQIHLGELHAILRRQEDFYPFLKDNREKIEKILTFR

IPYYVGPLARGNSRFAWMTRKSEETITPWNFEEVVDKGASAQSFIERMTN

FDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDL

LKIIKDKDFLDNEENEDILEDIVLTLTLFEDREMIEERLKTYAHLFDDKV

MKQLKRRRYTGWGRLSRKLINGIRDKQSGKTILDFLKSDGFANRNFMQLI

-continued

HDDSLTFKEDIQKAQVSGQGDSLHEHIANLAGSPAIKKGILQTVKVVDEL

VKVMGRHKPENIVIEMARENQTTQKGQKNSRERMKRIEEGIKELGSQILK

EHPVENTQLQNEKLYLYYLQNGRDMYVDQELDINRLSDYDVDAIVPQSFL

KDDSIDNKVLTRSDKNRGKSDNVPSEEVVKKMKNYWRQLLNAKLITQRKF

DNLTKAERGGLSELDKAGFIKRQLVETRQITKHVAQILDSRMNTKYDEND

KLIREVKVITLKSKLVSDFRKDFQFYKVREINNYHHAHDAYLNAVVGTAL

IKKYPKLESEFVYGDYKVYDVRKMIAKSEQEIGKATAKYFFYSNIMNFFK

TEITLANGEIRKRPLIETNGETGEIVWDKGRDFATVRKVLSMPQVNIVKK

TEVQTGGFSKESILPKRNSDKLIARKKDWDPKKYGGFDSPTVAYSVLVVA

KVEKGKSKKLKSVKELLGITIMERSSFEKNPIDFLEAKGYKEVKKDLIIK

LPKYSLFELENGRKRMLASAGELQKGNELALPSKYVNFLYLASHYEKLKG

SPEDNEQKQLFVEQHKHYLDEIIEQISEFSKRVILADANLDKVLSAYNKH

RDKPIREQAENIIHLFTLTNLGAPAAFKYFDTTIDRKRYTSTKEVLDATL

IHQSITGLYETRIDLSQLGGD<u>MAPKKKRKVGIHRGVP</u>
(underline: nuclear localization signal; bold:
linker sequence)

NLS-Tn3-GGS3linker-dCas9

(SEQ ID NO: 331)
<u>MAPKKKRKVGIHRGVP</u>MALFGYARVSTSQQSLDLQVRALKDAGVKANRIF

TDKASGSSTDREGLDLLRMKVKEGDVILVKKLDRLGRDTADMLQLIKEFD

AQGVAVRFIDDGISTDSYIGLMFVTILSAVAQAERRRILERTNEGRQAAK

LKGIKFGRRRGGSGGSGGSMDKKYSIGLAIGTNSVGWAVITDEYKVPSKK

FKVLGNTDRHSIKKNLIGALLFDSGETAEATRLKRTARRRYTRRKNRICY

LQEIFSNEMAKVDDSFFHRLEESFLVEEDKKHERHPIFGNIVDEVAYHEK

YPTIYHLRKKLVDSTDKADLRLIYLALAHMIKFRGHFLIEGDLNPDNSDV

DKLFIQLVQTYNQLFEENPINASGVDAKAILSARLSKSRRLENLIAQLPG

EKKNGLFGNLIALSLGLTPNFKSNFDLAEDAKLQLSKDTYDDDLDNLLAQ

IGDQYADLFLAAKNLSDAILLSDILRVNTEITKAPLSASMIKRYDEHHQD

LTLLKALVRQQLPEKYKEIFFDQSKNGYAGYIDGGASQEEFYKFIKPILE

KMDGTEELLVKLNREDLLRKQRTFDNGSIPHQIHLGELHAILRRQEDFYP

FLKDNREKIEKILTFRIPYYVGPLARGNSRFAWMTRKSEETITPWNFEEV

VDKGASAQSFIERMTNFDKNLPNEKVLPKHSLLYEYFTVYNELTKVKYVT

EGMRKPAFLSGEQKKAIVDLLFKTNRKVTVKQLKEDYFKKIECFDSVEIS

GVEDRFNASLGTYHDLLKIIKDKDFLDNEENEDILEDIVLTLTLFEDREM

IEERLKTYAHLFDDKVMKQLKRRRYTGWGRLSRKLINGIRDKQSGKTILD

FLKSDGFANRNFMQLIHDDSLTFKEDIQKAQVSGQGDSLHEHIANLAGSP

AIKKGILQTVKVVDELVKVMGRHKPENIVIEMARENQTTQKGQKNSRERM

KRIEEGIKELGSQILKEHPVENTQLQNEKLYLYYLQNGRDMYVDQELDIN

RLSDYDVDAIVPQSFLKDDSIDNKVLTRSDKNRGKSDNVPSEEVVKKMKN

YWRQLLNAKLITQRKFDNLTKAERGGLSELDKAGFIKRQLVETRQITKHV

AQILDSRMNTKYDENDKLIREVKVITLKSKLVSDFRKDFQFYKVREINNY

-continued

HHAHDAYLNAVVGTALIKKYPKLESEFVYGDYKVYDVRKMIAKSEQEIGK

ATAKYFFYSNIMNFFKTEITLANGEIRKRPLIETNGETGEIVWDKGRDFA

TVRKVLSMPQVNIVKKTEVQTGGFSKESILPKRNSDKLIARKKDWDPKKY

GGFDSPTVAYSVLVVAKVEKGKSKKLKSVKELLGITIMERSSFEKNPIDF

LEAKGYKEVKKDLIIKLPKYSLFELENGRKRMLASAGELQKGNELALPSK

YVNFLYLASHYEKLKGSPEDNEQKQLFVEQHKHYLDEIIEQISEFSKRVI

LADANLDKVLSAYNKHRDKPIREQAENIIHLFTLTNLGAPAAFKYFDTTI

DRKRYTSTKEVLDATLIHQSITGLYETRIDLSQLGGD
(underline: nuclear localization signal; bold:
linker sequence)

dCas9-NLS-GGS3linker-Hin (SEQ ID NO: 332)
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGDMAPKKKRKVGIHRGVPGGSGGSGGSMATIGYI

RVSTIDQNIDLQRNALTSANCDRIFEDRISGKIANRPGLKRALKYVNKGD

TLVVWKLDRLGRSVKNLVALISELHERGAHFHSLTDSIDTSSAMGRFFFY

VMSALAEMERELIVERTLAGLAAARAQGRLG
(underline: nuclear localization signal; bold:
linker sequence)

NLS-dCas9-GGS3linker-Hin (SEQ ID NO: 333)
MAPKKKRKVGIHRGVPMDKKYSIGLAIGTNSVGWAVITDEYKVPSKKFKV

LGNTDRHSIKKNLIGALLFDSGETAEATRLKRTARRRYTRRKNRICYLQE

IFSNEMAKVDDSFFHRLEESFLVEEDKKHERHPIFGNIVDEVAYHEKYPT

IYHLRKKLVDSTDKADLRLIYLALAHMIKFRGHFLIEGDLNPDNSDVDKL

FIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGD

QYADLFLAAKNLSDAILLSDILRVNTEITKAPLSASMIKRYDEHHQDLTL

LKALVRQQLPEKYKEIFFDQSKNGYAGYIDGGASQEEFYKFIKPILEKMD

GTEELLVKLNREDLLRKQRTFDNGSIPHQIHLGELHAILRRQEDFYPFLK

DNREKIEKILTFRIPYYVGPLARGNSRFAWMTRKSEETITPWNFEEVVDK

GASAQSFIERMTNFDKNLPNEKVLPKHSLLYEYFTVYNELTKVKYVTEGM

RKPAFLSGEQKKAIVDLLFKTNRKVTVKQLKEDYFKKIECFDSVEISGVE

DRFNASLGTYHDLLKIIKDKDFLDNEENEDILEDIVLTLTLFEDREMIEE

RLKTYAHLFDDKVMKQLKRRRYTGWGRLSRKLINGIRDKQSGKTILDFLK

SDGFANRNFMQLIHDDSLTFKEDIQKAQVSGQGDSLHEHIANLAGSPAIK

KGILQTVKVVDELVKVMGRHKPENIVIEMARENQTTQKGQKNSRERMKRI

EEGIKELGSQILKEHPVENTQLQNEKLYLYYLQNGRDMYVDQELDINRLS

DYDVDAIVPQSFLKDDSIDNKVLTRSDKNRGKSDNVPSEEVVKKMKNYWR

QLLNAKLITQRKFDNLTKAERGGLSELDKAGFIKRQLVETRQITKHVAQI

LDSRMNTKYDENDKLIREVKVITLKSKLVSDFRKDFQFYKVREINNYHHA

HDAYLNAVVGTALIKKYPKLESEFVYGDYKVYDVRKMIAKSEQEIGKATA

KYFFYSNIMNFFKTEITLANGEIRKRPLIETNGETEIVWDKGRDFATVR

KVLSMPQVNIVKKTEVQTGGFSKESILPKRNSDKLIARKKDWDPKKYGGF

DSPTVAYSVLVVAKVEKGKSKKLKSVKELLGITIMERSSFEKNPIDFLEA

KGYKEVKKDLIIKLPKYSLFELENGRKRMLASAGELQKGNELALPSKYVN

FLYLASHYEKLKGSPEDNEQKQLFVEQHKHYLDEIIEQISEFSKRVILAD

ANLDKVLSAYNKHRDKPIREQAENIIHLFTLTNLGAPAAFKYFDTTIDRK

RYTSTKEVLDATLIHQSITGLYETRIDLSQLGGDGGSGGSGGSMATIGYI

RVSTIDQNIDLQRNALTSANCDRIFEDRISGKIANRPGLKRALKYVNKGD

TLVVWKLDRLGRSVKNLVALISELHERGAHFHSLTDSIDTSSAMGRFFFY

VMSALAEMERELIVERTLAGLAAARAQGRLG
(underline: nuclear localization signal; bold:
linker sequence)

Hin-GGS3linker-dCas9-NLS (SEQ ID NO:334)
MATIGYIRVSTIDQNIDLQRNALTSANCDRIFEDRISGKIANRPGLKRAL

KYVNKGDTLVVWKLDRLGRSVKNLVALISELHERGAHFHSLTDSIDTSSA

MGRFFFYVMSALAEMERELIVERTLAGLAAARAQGRLGGGSGGSGGSMDK

KYSIGLAIGTNSVGWAVITDEYKVPSKKFKVLGNTDRHSIKKNLIGALLF

DSGETAEATRLKRTARRRYTRRKNRICYLQEIFSNEMAKVDDSFFHRLEE

SFLVEEDKKHERHPIFGNIVDEVAYHEKYPTIYHLRKKLVDSTDKADLRL

IYLALAHMIKFRGHFLIEGDLNPDNSDVDKLFIQLVQTYNQLFEENPINA

SGVDAKAILSARLSKSRRLENLIAQLPGEKKNGLFGNLIALSLGLTPNFK

SNFDLAEDAKLQLSKDTYDDDLDNLLAQIGDQYADLFLAAKNLSDAILLS

DILRVNTEITKAPLSASMIKRYDEHHQDLTLLKALVRQQLPEKYKEIFFD

QSKNGYAGYIDGGASQEEFYKFIKPILEKMDGTEELLVKLNREDLLRKQR

TFDNGSIPHQIHLGELHAILRRQEDFYPFLKDNREKIEKILTFRIPYYVG

PLARGNSRFAWMTRKSEETITPWNFEEVVDKGASAQSFIERMTNFDKNLP

NEKVLPKHSLLYEYFTVYNELTKVKYVTEGMRKPAFLSGEQKKAIVDLLF

KTNRKVTVKQLKEDYFKKIECFDSVEISGVEDRFNASLGTYHDLLKIIKD

KDFLDNEENEDILEDIVLTLTLFEDREMIEERLKTYAHLFDDKVMKQLKR

RRYTGWGRLSRKLINGIRDKQSGKTILDFLKSDGFANRNFMQLIHDDSLT

FKEDIQKAQVSGQGDSLHEHIANLAGSPAIKKGILQTVKVVDELVKVMGR

HKPENIVIEMARENQTTQKGQKNSRERMKRIEEGIKELGSQILKEHPVEN

TQLQNEKLYLYYLQNGRDMYVDQELDINRLSDYDVDAIVPQSFLKDDSID

NKVLTRSDKNRGKSDNVPSEEVVKKMKNYWRQLLNAKLITQRKFDNLTKA

ERGGLSELDKAGFIKRQLVETRQITKHVAQILDSRMNTKYDENDKLIREV

KVITLKSKLVSDFRKDFQFYKVREINNYHHAHDAYLNAVVGTALIKKYPK

LESEFVYGDYKVYDVRKMIAKSEQEIGKATAKYFFYSNIMNFFKTEITLA

NGEIRKRPLIETNGETEIVWDKGRDFATVRKVLSMPQVNIVKKTEVQTG

GFSKESILPKRNSDKLIARKKDWDPKKYGGFDSPTVAYSVLVVAKVEKGK

SKKLKSVKELLGITIMERSSFEKNPIDFLEAKGYKEVKKDLIIKLPKYSL

FELENGRKRMLASAGELQKGNELALPSKYVNFLYLASHYEKLKGSPEDNE

QKQLFVEQHKHYLDEIIEQISEFSKRVILADANLDKVLSAYNKHRDKPIR

EQAENIIHLFTLTNLGAPAAFKYFDTTIDRKRYTSTKEVLDATLIHQSIT

GLYETRIDLSQLGGDMAPKKKRKVGIHRGVP
(underline: nuclear localization signal; bold:
linker sequence)

NLS-Hin-GGS3linker-dCas9

(SEQ ID NO: 335)
MAPKKKRKVGIHRGVPMATIGYIRVSTIDQNIDLQRNALTSANCDRIFED

RISGKIANRPGLKRALKYVNKGDTLVVWKLDRLGRSVKNLVALISELHER

GAHFHSLTDSIDTSSAMGRFFFYVMSALAEMERELIVERTLAGLAAARAQ

GRLGGGSGGGSGGSMDKKYSIGLAIGTNSVGWAVITDEYKVPSKKFKVLGN

TDRHSIKKNLIGALLFDSGETAEATRLKRTARRRYTRRKNRICYLQEIFS

NEMAKVDDSFFHRLEESFLVEEDKKHERHPIFGNIVDEVAYHEKYPTIYH

LRKKLVDSTDKADLRLIYLALAHMIKFRGHFLIEGDLNPDNSDVDKLFIQ

LVQTYNQLFEENPINASGVDAKAILSARLSKSRRLENLIAQLPGEKKNGL

FGNLIALSLGLTPNFKSNFDLAEDAKLQLSKDTYDDDLDNLLAQIGDQYA

DLFLAAKNLSDAILLSDILRVNTEITKAPLSASMIKRYDEHHQDLTLLKA

LVRQQLPEKYKEIFFDQSKNGYAGYIDGGASQEEFYKFIKPILEKMDGTE

ELLVKLNREDLLRKQRTFDNGSIPHQIHLGELHAILRRQEDFYPFLKDNR

EKIEKILTFRIPYYVGPLARGNSRFAWMTRKSEETITPWNFEEVVDKGAS

AQSFIERMTNFDKNLPNEKVLPKHSLLYEYFTVYNELTKVKYVTEGMRKP

AFLSGEQKKAIVDLLFKTNRKVTVKQLKEDYFKKIECFDSVEISGVEDRF

NASLGTYHDLLKIIKDKDFLDNEENEDILEDIVLTLTLFEDREMIEERLK

TYAHLFDDKVMKQLKRRYTGWGRLSRKLINGIRDKQSGKTILDFLKSDG

FANRNFMQLIHDDSLTFKEDIQKAQVSGQGDSLHEHIANLAGSPAIKKGI

LQTVKVVDELVKVMGRHKPENIVIEMARENQTTQKGQKNSRERMKRIEEG

IKELGSQILKEHPVENTQLQNEKLYLYYLQNGRDMYVDQELDINRLSDYD

VDAIVPQSFLKDDSIDNKVLTRSDKNRGKSDNVPSEEVVKKMKNYWRQLL

NAKLITQRKFDNLTKAERGGLSELDKAGFIKRQLVETRQITKHVAQILDS

RMNTKYDENDKLIREVKVITLKSKLVSDFRKDFQFYKVREINNYHHAHDA

YLNAVVGTALIKKYPKLESEFVYGDYKVYDVRKMIAKSEQEIGKATAKYF

FYSNIMNFFKTEITLANGEIRKRPLIETNGETGEIVWDKGRDFATVRKVL

SMPQVNIVKKTEVQTGGFSKESILPKRNSDKLIARKKDWDPKKYGGFDSP

TVAYSVLVVAKVEKGKSKKLKSVKELLGITIMERSSFEKNPIDFLEAKGY

KEVKKDLIIKLPKYSLFELENGRKRMLASAGELQKGNELALPSKYVNFLY

LASHYEKLKGSPEDNEQKQLFVEQHKHYLDEIIEQISEFSKRVILADANL

DKVLSAYNKHRDKPIREQAENIIHLFTLTNLGAPAAFKYFDTTIDRKRYT

STKEVLDATLIHQSITGLYETRIDLSQLGGD
(underline: nuclear localization signal; bold:
linker sequence)

dCas9-NLS-GGS3linker-Gin (SEQ ID NO: 336)
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

-continued

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGDMAPKKKRKVGIHRGVPGGSGGGSGGSMLIGYVR

VSTNDQNTDLQRNALVCAGCEQIFEDKLSGTRTDRPGLKRALKRLQKGDT

LVVWKLDRLGRSMKHLISLVGELRERGINFRSLTDSIDTSSPMGRFFFYV

MGALAEMERELIIERTMAGIAAARNKGRRFGRPPKSG
(underline: nuclear localization signal; bold:
linker sequence)

NLS-dCas9-GGS3linker-Gin (SEQ ID NO: 337)
MAPKKKRKVGIHRGVPMDKKYSIGLAIGTNSVGWAVITDEYKVPSKKFKV

LGNTDRHSIKKNLIGALLFDSGETAEATRLKRTARRRYTRRKNRICYLQE

IFSNEMAKVDDSFFHRLEESFLVEEDKKHERHPIFGNIVDEVAYHEKYPT

IYHLRKKLVDSTDKADLRLIYLALAHMIKFRGHFLIEGDLNPDNSDVDKL

FIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGD

QYADLFLAAKNLSDAILLSDILRVNTEITKAPLSASMIKRYDEHHQDLTL

LKALVRQQLPEKYKEIFFDQSKNGYAGYIDGGASQEEFYKFIKPILEKMD

GTEELLVKLNREDLLRKQRTFDNGSIPHQIHLGELHAILRRQEDFYPFLK

DNREKIEKILTFRIPYYVGPLARGNSRFAWMTRKSEETITPWNFEEVVDK

GASAQSFIERMTNFDKNLPNEKVLPKHSLLYEYFTVYNELTKVKYVTEGM

-continued

RKPAFLSGEQKKAIVDLLFKTNRKVTVKQLKEDYFKKIECFDSVEISGVE

DRFNASLGTYHDLLKIIKDKDFLDNEENEDILEDIVLTLTLFEDREMIEE

RLKTYAHLFDDKVMKQLKRRRYTGWGRLSRKLINGIRDKQSGKTILDFLK

SDGFANRNFMQLIHDDSLTFKEDIQKAQVSGQGDSLHEHIANLAGSPAIK

KGILQTVKVVDELVKVMGRHKPENIVIEMARENQTTQKGQKNSRERMKRI

EEGIKELGSQILKEHPVENTQLQNEKLYLYYLQNGRDMYVDQELDINRLS

DYDVDAIVPQSFLKDDSIDNKVLTRSDKNRGKSDNVPSEEVVKKMKNYWR

QLLNAKLITQRKFDNLTKAERGGLSELDKAGFIKRQLVETRQITKHVAQI

LDSRMNTKYDENDKLIREVKVITLKSKLVSDFRKDFQFYKVREINNYHHA

HDAYLNAVVGTALIKKYPKLESEFVYGDYKVYDVRKMIAKSEQEIGKATA

KYFFYSNIMNFFKTEITLANGEIRKRPLIETNGETEIVWDKGRDFATVR

KVLSMPQVNIVKKTEVQTGGFSKESILPKRNSDKLIARKKDWDPKKYGGF

DSPTVAYSVLVVAKVEKGKSKKLKSVKELLGITIMERSSFEKNPIDFLEA

KGYKEVKKDLIIKLPKYSLFELENGRKRMLASAGELQKGNELALPSKYVN

FLYLASHYEKLKGSPEDNEQKQLFVEQHKYLDEIIEQISEFSKRVILAD

ANLDKVLSAYNKHRDKPIREQAENIIHLFTLTNLGAPAAFKYFDTTIDRK

RYTSTKEVLDATLIHQSITGLYETRIDLSQLGGDGGSGGSGGSMLIGYVR

VSTNDQNTDLQRNALVCAGCEQIFEDKLSGTRTDRPGLKRALKRLQKGDT

LVVWKLDRLGRSMKHLISLVGELRERGINFRSLTDSIDTSSPMGRFFFYV

MGALAEMERELIIERTMAGIAAARNKGRRFGRPPKSG
(underline: nuclear localization signal; bold:
linker sequence)

Gin-GGS3linker-dCas9-NLS (SEQ ID NO: 338)
MLIGYVRVSTNDQNTDLQRNALVCAGCEQIFEDKLSGTRTDRPGLKRALK

RLQKGDTLVVWKLDRLGRSMKHLISLVGELRERGINFRSLTDSIDTSSPM

GRFFFYVMGALAEMERELIIERTMAGIAAARNKGRRFGRPPKSGGGSGGS

GGSMDKKYSIGLAIGTNSVGWAVITDEYKVPSKKFKVLGNTDRHSIKKNL

IGALLFDSGETAEATRLKRTARRRYTRRKNRICYLQEIFSNEMAKVDDSF

FHRLEESFLVEEDKKHERHPIFGNIVDEVAYHEKYPTIYHLRKKLVDSTD

KADLRLIYLALAHMIKFRGHFLIEGDLNPDNSDVDKLFIQLVQTYNQLFE

ENPINASGVDAKAILSARLSKSRRLENLIAQLPGEKKNGLFGNLIALSLG

LTPNFKSNFDLAEDAKLQLSKDTYDDDLDNLLAQIGDQYADLFLAAKNLS

DAILLSDILRVNTEITKAPLSASMIKRYDEHHQDLTLLKALVRQQLPEKY

KEIFFDQSKNGYAGYIDGGASQEEFYKFIKPILEKMDGTEELLVKLNRED

LLRKQRTFDNGSIPHQIHLGELHAILRRQEDFYPFLKDNREKIEKILTFR

IPYYVGPLARGNSRFAWMTRKSEETITPWNFEEVVDKGASAQSFIERMTN

FDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDL

LKIIKDKDFLDNEENEDILEDIVLTLTLFEDREMIEERLKTYAHLFDDKV

MKQLKRRRYTGWGRLSRKLINGIRDKQSGKTILDFLKSDGFANRNFMQLI

-continued

HDDSLTFKEDIQKAQVSGQGDSLHEHIANLAGSPAIKKGILQTVKVVDEL

VKVMGRHKPENIVIEMARENQTTQKGQKNSRERMKRIEEGIKELGSQILK

EHPVENTQLQNEKLYLYYLQNGRDMYVDQELDINRLSDYDVDAIVPQSFL

KDDSIDNKVLTRSDKNRGKSDNVPSEEVVKKMKNYWRQLLNAKLITQRKF

DNLTKAERGGLSELDKAGFIKRQLVETRQITKHVAQILDSRMNTKYDEND

KLIREVKVITLKSKLVSDFRKDFQFYKVREINNYHHAHDAYLNAVVGTAL

IKKYPKLESEFVYGDYKVYDVRKMIAKSEQEIGKATAKYFFYSNIMNFFK

TEITLANGEIRKRPLIETNGETEIVWDKGRDFATVRKVLSMPQVNIVKK

TEVQTGGFSKESILPKRNSDKLIARKKDWDPKKYGGFDSPTVAYSVLVVA

KVEKGKSKKLKSVKELLGITIMERSSFEKNPIDFLEAKGYKEVKKDLIIK

LPKYSLFELENGRKRMLASAGELQKGNELALPSKYVNFLYLASHYEKLKG

SPEDNEQKQLFVEQHKYLDEIIEQISEFSKRVILADANLDKVLSAYNKH

RDKPIREQAENIIHLFTLTNLGAPAAFKYFDTTIDRKRYTSTKEVLDATL

IHQSITGLYETRIDLSQLGGDM<u>APKKKRKVGIHRGVP</u>
(underline: nuclear localization signal; bold:
linker sequence)

NLS-Gin-GGS3linker-dCas9

(SEQ ID NO: 339)
<u>MAPKKKRKVGIHRGVP</u>MLIGYVRVSTNDQNTDLQRNALVCAGCEQIFEDK

LSGTRTDRPGLKRALKRLQKGDTLVVWKLDRLGRSMKHLISLVGELRERG

INFRSLTDSIDTSSPMGRFFFYVMGALAEMERELIIERTMAGIAAARNKG

RRFGRPPKSGGGSGGSGGSMDKKYSIGLAIGTNSVGWAVITDEYKVPSKK

FKVLGNTDRHSIKKNLIGALLFDSGETAEATRLKRTARRRYTRRKNRICY

LQEIFSNEMAKVDDSFFHRLEESFLVEEDKKHERHPIFGNIVDEVAYHEK

YPTIYHLRKKLVDSTDKADLRLIYLALAHMIKFRGHFLIEGDLNPDNSDV

DKLFIQLVQTYNQLFEENPINASGVDAKAILSARLSKSRRLENLIAQLPG

EKKNGLFGNLIALSLGLTPNFKSNFDLAEDAKLQLSKDTYDDDLDNLLAQ

IGDQYADLFLAAKNLSDAILLSDILRVNTEITKAPLSASMIKRYDEHHQD

LTLLKALVRQQLPEKYKEIFFDQSKNGYAGYIDGGASQEEFYKFIKPILE

KMDGTEELLVKLNREDLLRKQRTFDNGSIPHQIHLGELHAILRRQEDFYP

FLKDNREKIEKILTFRIPYYVGPLARGNSRFAWMTRKSEETITPWNFEEV

VDKGASAQSFIERMTNFDKNLPNEKVLPKHSLLYEYFTVYNELTKVKYVT

EGMRKPAFLSGEQKKAIVDLLFKTNRKVTVKQLKEDYFKKIECFDSVEIS

GVEDRFNASLGTYHDLLKIIKDKDFLDNEENEDILEDIVLTLTLFEDREM

IEERLKTYAHLFDDKVMKQLKRRRYTGWGRLSRKLINGIRDKQSGKTILD

FLKSDGFANRNFMQLIHDDSLTFKEDIQKAQVSGQGDSLHEHIANLAGSP

AIKKGILQTVKVVDELVKVMGRHKPENIVIEMARENQTTQKGQKNSRERM

KRIEEGIKELGSQILKEHPVENTQLQNEKLYLYYLQNGRDMYVDQELDIN

RLSDYDVDAIVPQSFLKDDSIDNKVLTRSDKNRGKSDNVPSEEVVKKMKN

YWRQLLNAKLITQRKFDNLTKAERGGLSELDKAGFIKRQLVETRQITKHV

AQILDSRMNTKYDENDKLIREVKVITLKSKLVSDFRKDFQFYKVREINNY

-continued

```
HHAHDAYLNAVVGTALIKKYPKLESEFVYGDYKVYDVRKMIAKSEQEIGK

ATAKYFFYSNIMNFFKTEITLANGEIRKRPLIETNGETGEIVWDKGRDFA

TVRKVLSMPQVNIVKKTEVQTGGFSKESILPKRNSDKLIARKKDWDPKKY

GGFDSPTVAYSVLVVAKVEKGKSKKLKSVKELLGITIMERSSFEKNPIDF

LEAKGYKEVKKDLIIKLPKYSLFELENGRKRMLASAGELQKGNELALPSK

YVNFLYLASHYEKLKGSPEDNEQKQLFVEQHKHYLDEIIEQISEFSKRVI

LADANLDKVLSAYNKHRDKPIREQAENIIHLFTLTNLGAPAAFKYFDTTI

DRKRYTSTKEVLDATLIHQSITGLYETRIDLSQLGGD
(underline: nuclear localization signal; bold:
linker sequence)
```

Figures 5A, 5B:
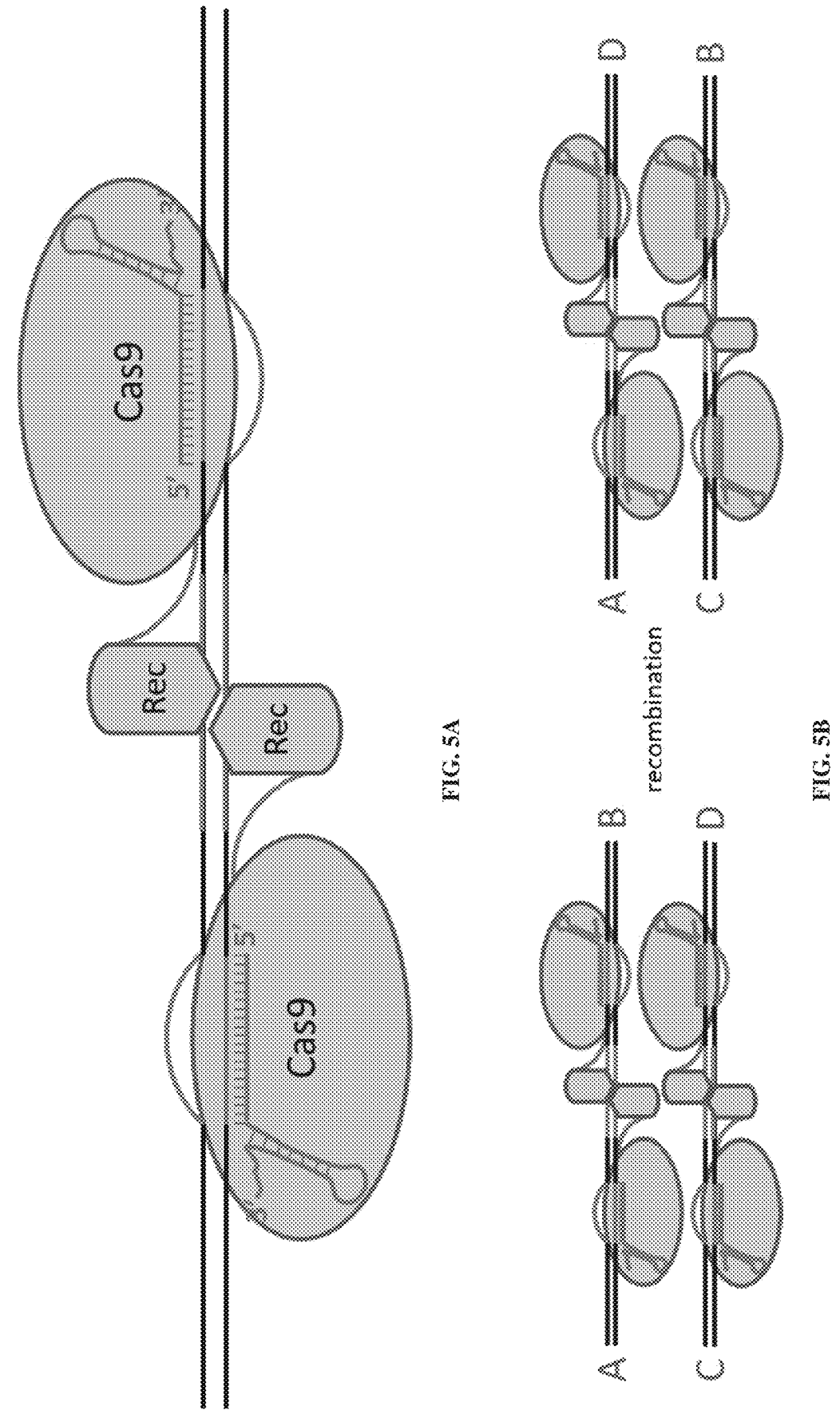
FIG. 5A-5B shows schematically, how Cas9-recombinase fusions can be coordinated through gRNAs to bind and recombine target DNAs at desired sequences (sites). Nuclease-inactivated Cas9 (dCas9) protein is fused to a monomer of a recombinase domain (Rec).

Example 4: Introduction of a Marker Gene by Homologous Recombination Using Cas9-Recombinase Fusion Proteins A vector carrying a green fluorescent protein (GFP) marker gene flanked by genomic sequence of a host cell gene is introduced into a cell, along with an expression construct encoding a dCas9-recombinase fusion protein (any one of SEQ ID NO:328-339) and four appropriately designed gRNAs targeting the GFP marker gene and the genomic locus into which the GFP marker is recombined. Four dCas9-recombinase fusion proteins are coordinated at the genomic locus along with the GFP marker gene through the binding of the gRNAs (FIG. 5B). The four recombinase domains of the fusion proteins tetramerize, and the recombinase activity of the recombinase domains of the fusion protein results in the recombination between the gemomic locus and the marker gene, thereby introducing the marker gene into the genomic locus. Introduction of the marker gene is confirmed by GFP expression and/or by PCR.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

What is claimed is:

1. A fusion protein comprising a clustered regularly interspaced short palindromic repeat (CRISPR) associated protein 9 (Cas9) domain and an additional protein domain having enzymatic activity, wherein the Cas9 domain and the additional protein domain having enzymatic activity are joined by a linker sequence selected from the group consisting of SGSETPGTSESATPES (SEQ ID NO:16), SGSETPGTSESA (SEQ ID NO:17), and SGSETPGTS-ESATPEGGSGGS (SEQ ID NO:18).

2. The fusion protein of claim 1, wherein the linker sequence is SGSETPGTSESATPES (SEQ ID NO:16).

3. The fusion protein of claim 1, wherein the linker sequence is SGSETPGTSESA (SEQ ID NO:17).

4. The fusion protein of claim 1, wherein the linker sequence is SGSETPGTSESATPEGGSGGS (SEQ ID NO:18).

5. The fusion protein of claim 1, wherein the Cas9 domain is a nuclease-inactivated Cas9 (dCas9) domain or a Cas9 nickase domain.

6. The fusion protein of claim 5, wherein the fusion protein further comprises a nuclear localization signal (NLS) domain.

7. The fusion protein of claim 1, wherein the fusion protein further comprises a nuclear localization signal (NLS) domain.

8. The fusion protein of claim 1, wherein the Cas9 domain comprises the amino acid sequence that is at least about 80% identical to SEQ ID NO: 2, 4, or 5.

9. The fusion protein of claim 1, wherein the Cas9 domain comprises the amino acid sequence that is at least about 90% identical to SEQ ID NO: 2, 4, or 5.

10. The fusion protein of claim 1, wherein the Cas9 domain comprises the amino acid sequence that is at least about 95% identical to SEQ ID NO: 2, 4, or 5.

11. The fusion protein of claim 1, wherein the Cas9 domain comprises the amino acid sequence that is at least about 99% identical to SEQ ID NO: 2, 4, or 5.

12. The fusion protein of claim 1, wherein the Cas9 domain comprises the amino acid sequence of SEQ ID NO: 2, 4, or 5.

13. The fusion protein of claim 1, wherein the Cas9 domain binds a guide ribonucleic acid (gRNA).

14. The fusion protein of claim 1, wherein the fusion protein comprises the structure $NH_2$-[the Cas9 domain]-[the additional protein domain]-COOH, and wherein the "]-[" represents the linker sequence.

15. The fusion protein of claim 1, wherein the fusion protein comprises the structure $NH_2$-[the additional protein domain]-[the Cas9 domain]-COOH, and wherein the "]-[" represents the linker sequence.

16. The fusion protein of claim 1, wherein the additional protein domain having enzymatic activity is a nuclease or a recombinase.

17. A pharmaceutical composition comprising the fusion protein of claim 1 and a pharmaceutically acceptable excipient.

18. A kit comprising the fusion protein of claim 1.

19. The kit of claim 18, wherein the kit further comprises one or more gRNAs and/or vectors for expressing one or more gRNAs.

20. A complex comprising the fusion protein of claim 1 and a gRNA.

* * * * *

SEQUENCE LISTING

Sequence total quantity: 340
SEQ ID NO: 1              moltype = DNA   length = 4104
FEATURE                   Location/Qualifiers
source                    1..4104
                          mol_type = genomic DNA
                          organism = Streptococcus pyogenes
SEQUENCE: 1
atggataaga aatactcaat aggcttagat atcggcacaa atagcgtcgg atgggcggtg   60
atcactgatg attataaggt tccgtctaaa aagttcaagg ttctgggaaa tacagaccgc   120
cacagtatca aaaaaaatct tatagggggct ctttttatttg gcagtggaga gacagcggaa   180
gcgactcgtc tcaaacggac agctcgtaga aggtatacac gtcgtgaagaa tcgtatttgt   240
tatctacagg agatttttttc aaatgagatg gcgaaagtag atgatagttt ctttcatcga   300
cttgaagagt cttttttggt ggaagaagac aagaagcatg aacgtcatcc tattttttgga   360
aatatagtag atgaagttgc ttatcatgag aaatatccaa ctatctatca tctgcgaaaa   420
aaattggcag attctactga taaagcggat ttgcgcttaa tctatttggc cttagcgcat   480
atgattaagt ttcgtggtca ttttttgatt gagggagatt taaatcctga taatagtgat   540
gtggacaaac tatttatcca gttggtacaa atctacaatc aattatttga agaaaaccct   600
attaacgcaa gtagagtaga tgctaaagcg attctttctg cacgattgag taaatcaaga   660
cgattagaaa atctcattgc tcagctcccc ggtgagaaga gaaatggctt gtttgggaat   720
ctcattgctt tgtcattggg attgacccct aattttaaat caaattttga tttggcagaa   780
gatgctaaat tacagctttc aaaagatact tacgatgatg atttagataa tttattggcg   840
caaattggag atcaatatgc tgatttgttt ttggcagcta agaatttatc agatgctatt   900
ttactttcag atatcctaag agtaaatagt gaaataacta aggctcccct atcagcttca   960
atgattaagc gctacgatga acatcatcaa gacttgactc ttttaaaagc tttagttcga   1020
caacaacttc cagaaaagta taaagaaatc ttttttgatc aatcaaaaaa cggatatgca   1080
ggttatattg atgggggagc tagccaagaa gaatttttata aatttatcaa accaatttta   1140
gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctattttga agacaagaga agactttttat ccattttttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa tttttgaagaa   1440
gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgagggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gtttttgacag tgttgaaatt   1740
tcaggagttg aagatagatt taatgcttca ttaggcgcct accatgattt gctaaaaatt   1800
attaaagata aagatttttt ggataatgaa gaaatgaag atatcttaga ggatattgtt   1860
ttaacattga ccttatttga agatagggg atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttttga aatcagatgg ttttgccaat cgcaatttta tgcagctgat ccatgatgat   2100
agtttgacat ttaaagaaga tattcaaaaa gcacaggtgt ctggacaagg ccatagttta   2160
catgaacaga ttgctaactt agctggcagt cctgctatta aaaaggtat tttacagact   2220
gtaaaaattg ttgatgaact ggtcaaagta atggggcata gccagaaaa tatcgttatt   2280
gaaatggcac gtgaaaatca gacaactcaa aagggccaga aaaattcgcg agagcgtatg   2340
aaacgaatcg aagaaggtat caaagaatta ggaagtcaga ttcttaaaga gcatcctgtt   2400
gaaaatactc aattgcaaaa tgaaaagctc tatctctatt atctacaaaa tggaagagac   2460
atgtatgtgg accaagaatt agatattaat cgtttaagtg attatgatgt cgatcacatt   2520
gttccacaaa gtttcattaa agacgattca atagacaata aggtactaac gcgttctgat   2580
aaaaatcgtg gtaaatcgga taacgttcca agtgaagaag tagtcaaaaa gatgaaaaac   2640
tattggagac aacttctaaa cgccaagtta atcactcaac gtaagtttga taatttaacg   2700
aaagctgaac gtggaggttt gagtgaactt gataaagctg gttttatcaa acgccaattg   2760
gttgaaactc gccaaatcac taagcatgtg gcacaaattt tggatagtcg catgaatact   2820
aaatacgatg aaaatgataa acttattcga gaggttaaag tgattacctt aaaatctaaa   2880
ttagtttctg acttccgaaa agatttccaa ttctataaag tacgtgagat taacaattac   2940
catcatgccc atgatgcgta tctaaatgcc gtcgttggaa ctgctttgat taagaaatat   3000
ccaaaacttg aatcggagtt tgtctatggt gattataaag tttatgatgt tcgtaaaatg   3060
attgctaagt ctgagcaaga aataggcaaa gcaaccgcaa aatatttctt ttactctaat   3120
atcatgaact tcttccaaaac agaaattaca cttgcaaatg gagagattcg caaacgccct   3180
ctaatcgaaa ctaatgggga aactggagaa attgtctggg ataaagggag agatttttgcg   3240
acagtgcgca aagtattgtc catgccccaa gtcaatattg tcaagaaaac agaagtacag   3300
acaggcggat tctccaagga gtcaatttta ccaaaaagaa attcggacaa gcttattgct   3360
cgtaaaaaag actgggatcc aaaaaaatat ggtggttttg atagtccaac ggtagcttat   3420
tcagtcctag tggttgctaa ggtggaaaaa gggaaatcga agaagttaaa atccgttaaa   3480
gagttactag gatcacaat atggaaaga agttcctttg aaaaaaatcc gattgacttt   3540
ttagaagcta aaggatataa ggaagttaaa aagacttaa tcattaaact acctaaatat   3600
agtctttttg agttagaaaa cggtcgtaaa cggatgctgg ctagtgccgg agaattacaa   3660
aaaggaaatg agctggctct gccaagcaaa tatgtgaatt ttttatattt agctagtcat   3720
tatgaaaagt tgaagggtag tccagaagat aacgaacaaa aacaattgtt tgtggagcag   3780
cataagcatt atttagatga gattattgag caaatcagtg aatttttctaa gcgtgttatt   3840
ttagcagatg ccaatttaga taaagttctt agtgcatata acaaacatag agacaaacca   3900
atacgtgaac aagcagaaaa tattattcat ttatttacgt tgacgaatct tggagctccc   3960
gctgctttta aatattttga tacaacaatt gatcgtaaac gatatacgtc tacaaaagaa   4020
gtttttagatg ccactcttat ccatcaatcc atcactggtc tttatgaaac acgcattgat   4080
ttgagtcagc taggaggtga ctga                                          4104

SEQ ID NO: 2              moltype = AA   length = 1367

```
FEATURE           Location/Qualifiers
source            1..1367
                  mol_type = protein
                  organism = Streptococcus pyogenes
SEQUENCE: 2
MDKKYSIGLD IGTNSVGWAV ITDDYKVPSK KFKVLGNTDR HSIKKNLIGA LLFGSGETAE   60
ATRLKRTARR RYTRRKNRIC YLQEIFSNEM AKVDDSFFHR LEESFLVEED KKHERHPIFG  120
NIVDEVAYHE KYPTIYHLRK KLADSTDKAD LRLIYLALAH MIKFRGHFLI EGDLNPDNSD  180
VDKLFIQLVQ IYNQLFEENP INASRVDAKA ILSARLSKSR RLENLIAQLP GEKRNGLFGN  240
LIALSLGLTP NFKSNFDLAE DAKLQLSKDT YDDDLDNLLA QIGDQYADLF LAAKNLSDAI  300
LLSDILRVNS EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGAYHDLLKI  600
IKDKDFLDNE ENEDILEDIV LTLTLFEDRG MIEERLKTYA HLFDDKVMKQ LKRRRYTGWG  660
RLSRKLINGI RDKQSGKTIL DFLKSDGFAN RNFMQLIHDD SLTFKEDIQK AQVSGQGHSL  720
HEQIANLAGS PAIKKGILQT VKIVDELVKV MGHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFIKDDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM 1020
IAKSEQEIGK ATAKYFFYSN IMNFFKTEIT LANGEIRKRP LIETNGETGE IVWDKGRDFA 1080
TVRKVLSMPQ VNIVKKTEVQ TGGFSKESIL PKRNSDKLIA RKKDWDPKKY GGFDSPTVAY 1140
SVLVVAKVEK GKSKKLKSVK ELLGITIMER SSFEKNPIDF LEAKGYKEVK KDLIIKLPKY 1200
SLFELENGRK RMLASAGELQ KGNELALPSK YVNFLYLASH YEKLKGSPED NEQKQLFVEQ 1260
HKHYLDEIIE QISEFSKRVI LADANLDKVL SAYNKHRDKP IREQAENIIH LFTLTNLGAP 1320
AAFKYFDTTI DRKRYTSTKE VLDATLIHQS ITGLYETRID LSQLGGD            1367

SEQ ID NO: 3       moltype = DNA   length = 4212
FEATURE            Location/Qualifiers
misc_feature       1..4212
                   note = Synthetic Polynucleotide
source             1..4212
                   mol_type = other DNA
                   organism = synthetic construct
SEQUENCE: 3
atggataaaa agtattctat tggtttagac atcggcacta attccgttgg atgggctgtc   60
ataaccgatg aatacaaagt accttcaaag aaatttaagg tgttggggaa cacagaccgt  120
cattcgatta aaaagaatct tatcggtgcc ctcctattcg atagtggcga aacggcagag  180
gcgactcgcc tgaaacgaac cgctcggaga aggtatacac gtcgcaagaa ccgaatatgt  240
tacttacaag aaatttttag caatgagatg gccaaagttg acgattcttt ctttcaccgt  300
ttggaagagt ccttccttgt cgaagaggac aagaaacatg aacggcaccc catctttggg  360
aacatagtag atgaggtggc atatcatgaa aagtacccaa cgatttatca cctcagaaaa  420
aagctagttg actcaactga taaagcggac ctgaggttaa tctacttggc tcttgcccat  480
atgataaagt tccgtgggca ctttctcatt gagggtgatc taaatccgga caactcggat  540
gtcgacaaac tgttcatcca gttagtacaa acctataatc agttgtttga agagaaccct  600
ataaatgcaa gtggcgtgga tgcgaaggct attcttagcg cccgcctctc taaatcccga  660
cggctagaaa acctgatcgc acaattaccc ggagagaaga aaatgggtt gttcggtaac  720
cttatagcgc tctcactagg cctgacacca aattttaagt cgaacttcga cttagctgaa  780
gatgccaaat tgcagcttag taaggacacg tacgatgacg atctcgacaa tctactggca  840
caaattggag atcagtatgc ggacttattt ttggctgcca aaaaccttag cgatgcaatc  900
ctcctatctg acatactgag agttaatact gagattacca aggcgccgtt atccgcttca  960
atgatcaaaa ggtacgatga acatcaccaa gacttgacac ttctcaaggc cctagtccgt 1020
cagcaactgc ctgagaaata taaggaaata ttctttgatc agtcgaaaaa cgggtacgca 1080
ggttatattg acggcggagc gagtcaagag gaattctaca gtttatcaa acccatatta 1140
gagaagatgg atgggacgga agagttgctt gtaaaactca atcgcgaaga tctactgcga 1200
aagcagcgga ctttcgacaa cggtagcatt ccacatcaaa tccacttagg cgaattgcat 1260
gctatactta gaaggcagga ggattttat ccgttcctca aagacaatcg tgaaaagatt 1320
gagaaaatcc taacctttcg catacccttac tatgtgggac ccctggcccg agggaactgt 1380
cggttcgcat ggatgacaag aaagtccgaa gaaacgatta ctccatggaa ttttgaggaa 1440
gttgtcgata aaggtgcgtc agctcaatcg ttcatcgaga ggatgaccaa ctttgacaag 1500
aatttaccga acgaaaaagt attgcctaag cacagtttac tttacgagta tttcacagtg 1560
tacaatgaac tcacgaaagt taagtatgtc actgagggga tgcgtaaacc cgcctttca 1620
agcggagaac agaagaaagc aatagtagat ctgttattca agaccaaccg caaagtgaca 1680
gttaagcaat tgaaagagga ctactttaag aaaattgaat gcttcgattc tgtcgagatc 1740
tccgggtag aagatcgatt taatgcgtca cttggtacgt atcatgacct cctaaagata 1800
attaaagata aggacttcct ggataacgaa gagaatgaag atatcttaga agatatagtg 1860
ttgactctta ccctctttga agatcgggaa atgattgagg aaagactaaa aacatacgct 1920
cacctgttcg acgataaggt tatgaaacag ttaaagaggc gtcgctatac gggctgggga 1980
cgattgtcgc ggaaacttat caacgggata agagacaagc aaagtggtaa aactattctc 2040
gattttctaa agagcgacgg cttcgccaat aggaacttta tgcagctgat ccatgatgac 2100
tctttaacct tcaaagagga tatacaaaag gcacaggttt ccggacaagg ggactcattg 2160
cacgaacata ttgcgaatct tgctggttcg ccagccatca aaaagggcat actccgacaa 2220
gtcaaagtag tggatgagct agttaaggtc atgggacgtc acaaccggaa aacattgta 2280
atcgagatgg cacgcgaaaa tcaaacgact cagaaggggc aaaaaaacag tcgagagcgg 2340
atgaagagaa tagaagaggg tattaaagaa ctgggcagcc agatcttaaa ggagcatcct 2400
gtggaaaata cccaattgca gaacgagaaa ctttacctct attacctaca aaatggaagg 2460
gacatgtatg ttgatcagga actggacata aaccgtttat ctgattacga cgtcgatcac 2520
```

```
attgtacccc aatccttttt gaaggacgat tcaatcgaca ataaagtgct tacacgctcg  2580
gataagaacc gagggaaaag tgacaatgtt ccaagcgagg aagtcgtaaa gaaaatgaag  2640
aactattggc ggcagctcct aaatgcgaaa ctgataacgc aaagaaagtt cgataactta  2700
actaaagctg agaggggtgg cttgtctgaa cttgacaagg ccggatttat taaacgtcag  2760
ctcgtggaaa cccgccaaat cacaaagcat gttgcacaga tactagattc ccgaatgaat  2820
acgaaatacg acgagaacga taagctgatt cgggaagtca aagtaatcac tttaaagtca  2880
aaattggtgt cggacttcag aaaggatttt caattctata aagttaggga gataaataac  2940
taccaccatg cgcacgacgc ttatcttaat gccgtcgtag ggaccgcact cattaagaaa  3000
tacccgaagc tagaaagtga gtttgtgtat ggtgattaca aagtttatga cgtccgtaag  3060
atgatcgcga aaagcgaaca ggagataggc aaggctacag ccaaatactt cttttattct  3120
aacattatga atttctttaa gacggaaatc actctggcaa acggagagat acgcaaacga  3180
cctttaattg aaaccaatgg ggagacaggt gaaatcgtat gggataaggg ccgggacttc  3240
gcgacggtga gaaaagtttt gtccatgccc caagtcaaca tagtaaagaa aactgaggtg  3300
cagaccggag ggttttcaaa ggaatcgatt cttccaaaga gaatagtga taagctcatc  3360
gctcgtaaaa aggactggga cccgaaaaag tacggtggct tcgatagccc tacagttgcc  3420
tattctgtcc tagtagtggc aaaagttgag aagggaaaat ccaagaaact gaagtcagtc  3480
aaagaattat tggggataac gattatggag cgctcgtctt ttgaaaagaa ccccatcgac  3540
ttccttgagg cgaaaggtta caaggaagta aaaaaggatc tcataattaa actaccaaag  3600
tatagtctgt ttgagttaga aaatggccga aaacgggatgt tggctagcgc cggagagctt  3660
caaaagggga acgaactcgc actaccgtct aaatacgtga atttcctgta tttagcgtcc  3720
cattacgaga agttgaaagg ttcacctgaa gataacgaac agaagcaact ttttgttgag  3780
cagcacaaac attatctcga cgaaatcata gagcaaattt cggaattcag taagagagtc  3840
atcctagctg atgccaatct ggacaaagta ttaagcgcat acaacaagca cagggataaa  3900
cccatacgtg agcaggcgga aaatattatc catttgttta ctcttaccaa cctcggcgct  3960
ccagccgcat tcaagtattt tgacacaacg atagatcgca aacgatacac ttctaccaag  4020
gaggtgctag acgcgacact gattcaccaa tccatcacgg gattatatga aactcggata  4080
gatttgtcac agcttggggg tgacggatcc cccaagaaga gaggaaagt ctcgagcgac  4140
tacaaagacc atgacggtga ttataaagat catgacatcg attacaagga tgacgatgac  4200
aaggctgcag ga                                                       4212
```

SEQ ID NO: 4              moltype = AA  length = 1368
FEATURE                   Location/Qualifiers
REGION                    1..1368
                          note = Synthetic Polypeptide
source                    1..1368
                          mol_type = protein
                          organism = synthetic construct
SEQUENCE: 4
```
MDKKYSIGLA IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGD             1368
```

SEQ ID NO: 5              moltype = AA  length = 1368
FEATURE                   Location/Qualifiers
REGION                    1..1368
                          note = Synthetic Polypeptide
source                    1..1368
                          mol_type = protein
                          organism = synthetic construct
SEQUENCE: 5
```
MDKKYSIGLA IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
```

```
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDA   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD           1368

SEQ ID NO: 6              moltype = AA  length = 198
FEATURE                  Location/Qualifiers
REGION                   1..198
                         note = Synthetic Polypeptide
source                   1..198
                         mol_type = protein
                         organism = synthetic construct
SEQUENCE: 6
GSQLVKSELE EKKSELRHKL KYVPHEYIEL IEIARNSTQD RILEMKVMEF FMKVYGYRGK   60
HLGGSRKPDG AIYTVGSPID YGVIVDTKAY SGGYNLPIGQ ADEMQRYVEE NQTRNKHINP  120
NEWWKVYPSS VTEFKPLFVS GHFKGNYKAQ LTRLNHITNC NGAVLSVEEL LIGGEMIKAG  180
TLTLEEVRRK FNNGEINF                                             198

SEQ ID NO: 7              moltype = DNA  length = 4221
FEATURE                  Location/Qualifiers
misc_feature             1..4221
                         note = Synthetic Polynucleotide
source                   1..4221
                         mol_type = other DNA
                         organism = synthetic construct
SEQUENCE: 7
atggactata aggaccacga cggagactac aaggatcatg atattgatta caaagacgat   60
gacgataaga tggccccaaa gaagaagcgg aaggtcggta tccacggagt cccagcagcc  120
gataaaaagt attctaattg tttagctatc ggcactaatt ccgttggatg ggctgtcata  180
accgatgaat acaaagtacc ttcaaagaaa tttaaggtgt ggggaacac agaccgtcat  240
tcgattaaaa agaatcttat cggtgccctc ctattcgata gtggcgaaac ggcagaggcg  300
actcgcctga aacgaaccgc tcggagaagg tatacacgtc gcaagaaccg aatatgttac  360
ttacaagaaa tttttagcaa tgagatggcc aaagttgacg attctttctt tcaccgtttg  420
gaagagtcct tccttgtcga gaggacaag aaacatgaac ggcaccccat ctttggaaac  480
atagtagatg aggtggcata tcatgaaaag tacccaacga tttatcacct cagaaaaaag  540
ctagttgact caactgataa agcggacctg aggttaatct acttggctct tgcccatatg  600
ataaagttcc gtgggcactt tctcattgag ggtgatctaa atccggacaa ctcggatgtc  660
gacaaactgt tcatccagtt agtacaaacc tataatcagt tgtttgaaga gaaccctata  720
aatgcaagtg gcgtggatgc gaaggctatt cttagcgccc gcctctctaa atcccgacgg  780
ctagaaaacc tgatcgcaca attacccgga gagaagaaaa atgggttgtt cggtaacctt  840
atagcgctct cactaggcct gacaccaaat tttaagtcga acttcgactt agctgaagat  900
gccaaattgc agcttagtaa ggacacgtac gatgacgatc tcgacaatct actggcacaa  960
attggagatc agtatgcgga cttattttg gctgccaaaa accttagcga tgcaatcctc 1020
ctatctgaca tactgagagt taatactgag attaccaagg cgccgttatc cgcttcaatg 1080
atcaaaaggt acgatgaaca tcaccaagac ttgcacttc tcaaggcct agtccgtcag 1140
caactgcctg agaaatataa ggaaatattc tttgatcagt cgaaaaacgg gtacgcaggt 1200
tatattgacg gcggagcgag tcaagaggaa ttctacaagt ttatcaaacc catattagag 1260
aagatggatg ggacggaaga gttgcttgta aaactcaatc gcgaagatct actgcgaaag 1320
cagcggactt cgacaacgg tagcattcca catcaaatcc acttaggcga attgcatgct 1380
atacttagaa ggcaggagga ttttttatccg ttcctcaaag acaatcgtga aagagattgag 1440
aaaatcctaa cctttcgcat accttactat gtgggacccc tggcccgagg gaactctcgg 1500
ttcgcatgga tgacaagaaa gtccgaagaa acgattactc catggaattt tgaggaagtt 1560
gtcgataaag gtgcgtcagc tcaatcgttc atcgagagga tgaccaactt tgacaagaat 1620
ttaccgaacg aaaaagtatt gcctaagcac agtttactt acgagtattt cacagtgtac 1680
aatgaactca cgaaagttaa gtatgtcact gagggcatgc gtaaacccgc ctttctaagc 1740
ggagaacaga agaaagcaat agtagatctg ttattcaaga ccaaccgcaa agtgacagtt 1800
aagcaattga agaggacta ctttaagaaa attgaatgct cgattctgt cgagatctcc 1860
ggggtagaag atcgatttaa tgcgtcactt ggtacgtatc atgacctcct aaagataatt 1920
aaagataagg acttcctgga taacgaagag aatgaagata tcttagaaga tatagtgttg 1980
actcttaccc tctttgaaga tcgggaaatg attgaggaaa gactaaaaac atacgctcac 2040
ctgttcgacg ataaggttat gaaacagtta aagaggcgtc gctatacggg ctggggacga 2100
ttgtcgcgga aacttatcaa cgggataaga gacaagcaaa gtggtaaaac tattctcgat 2160
tttctaaaga gcgacggctt cgccaatagg aactttatgc agctgatcca tgatgactct 2220
ttaaccttca aagaggatat acaaaaggca caggtttccg gacaagggga ctcattgcac 2280
gaacatattg cgaatcttgc tggttcgcca gccatcaaaa agggcatact ccagacagtc 2340
aaagtagtgg atgagctagt taggtcatg ggacgtcaca aaccggaaaa cattgtaatc 2400
gagatggcac gcgaaaatca aacgactcag aaggggcaaa aaacagtcg agagcggatg 2460
aagagaatag aagagggtat taaagaactg ggcagccaga tcttaaagga gcatcctgtg 2520
gaaaataccc aattgcagaa cgagaaactt tacctctatt acctacaaaa tggaagggac 2580
```

```
atgtatgttg atcaggaact ggacataaac cgtttatctg attacgacgt cgatcacatt   2640
gtaccccaat cctttttgaa ggacgattca atcgacaata aagtgcttac acgtcggat    2700
aagaaccgag ggaaaagtga caatgttcca agcgaggaag tcgtaaagaa aatgaagaac    2760
tattggcggc agctcctaaa tgcgaaactg ataacgcaaa gaaagttcga taacttaact    2820
aaagctgaga ggggtggctt gtctgaactt gacaaggccg gatttattaa acgtcagctc    2880
gtggaaaccc gccaaatcac aaagcatgtt gcacagatac tagattcccg aatgaatacg    2940
aaatacgacg agaacgataa gctgattcgg gaagtcaaag taatcacttt aaagtcaaaa    3000
ttggtgtcgg acttcagaaa ggattttcaa ttctataaag ttagggagat aaataactac    3060
caccatgcgc acgacgctta tcttaatgcc gtcgtaggga ccgcactcat taagaaatac    3120
ccgaagctag aaagtgagtt tgtgtatggt gattacaaag tttatgacgt ccgtaagatg    3180
atcgcgaaaa gcgaacagga gataggcaag gctacagcca aatacttctt ttattctaac    3240
attatgaatt tctttaagac ggaaatcact ctggcaaacg gagagatacg caaacgacct    3300
ttaattgaaa ccaatgggga gacaggtgaa atcgtatgg ataagggccg ggacttcgcg     3360
acggtggaga aagtttttgtc catgccccaa gtcaacatag taaagaaaac tgaggtgcag    3420
accggagggt tttcaaagga atcgattctt ccaaaaagga atagtgataa gctcatcgct    3480
cgtaaaaagg actgggaccc gaaaaagtac ggtggcttcg atagccctac agttgcctat    3540
tctgtcctag tagtggcaaa agttgagaag ggaaatcca agaaactgaa gtcagtcaaa     3600
gaattattgg ggataacgat tatggagcgc tcgtcttttg aaagaaaccc catcgacttc    3660
cttgaggcga aaggttacaa ggaagtaaaa aaggatctca taattaaact accaaagtat    3720
agtctgtttg agttagaaaa tggccgaaaa cggatgttgg ctagcgccgg agagcttcaa    3780
aaggggaacg aactcgcact accgtctaaa tacgtgaatt tcctgtattt agcgtcccat    3840
tacgagaagt tgaaaggttc acctgaagat aacgaacaga agcaactttt tgttgagcag    3900
cacaaacatt atctcgacga aatcatagag caaatttcgg aattcagtaa gagagtcatc    3960
ctagctgatg ccaatctgga caaagtatta agcgcataca acaagcacag ggataaaccc     4020
atacgtgagc aggcggaaaa tattatccat ttgtttactc ttaccaacct cggcgctcca    4080
gccgcattca agtattttga cacaacgata gatcgcaaac gatacacttc taccaaggag    4140
gtgctagacg cgacactgat tcaccaatcc atcacgggat tatatgaaac tcggatagat    4200
ttgtcacagc ttggggggtga c                                              4221
```

```
SEQ ID NO: 8            moltype = AA   length = 1368
FEATURE                 Location/Qualifiers
REGION                  1..1368
                        note = Synthetic Polypeptide
source                  1..1368
                        mol_type = protein
                        organism = synthetic construct
SEQUENCE: 8
MDKKYSIGLA IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG    120
NIVDEVAYHE KYPTIYHLRK KLVDSTDKAD LRLIYLALAH MIKFRGHFLI EGDLNPDNSD    180
VDKLFIQLVQ TYNQLFEENP INASGVDAKA ILSARLSKSR RLENLIAQLP GEKKNGLFGN    240
LIALSLGLTP NFKSNFDLAE DAKLQLSKDT YDDDLDNLLA QIGDQYADLF LAAKNLSDAI    300
LLSDILRVNT EITKAPLSAS MIKRYDEHHQ DLTLLKALVR QQLPEKYKEI FFDQSKNGYA    360
GYIDGGASQE EFYKFIKPIL EKMDGTEELL VKLNREDLLR KQRTFDNGSI PHQIHLGELH    420
AILRRQEDFY PFLKDNREKI EKILTFRIPY YVGPLARGNS RFAWMTRKSE ETITPWNFEE    480
VVDKGASAQS FIERMTNFDK NLPNEKVLPK HSLLYEYFTV YNELTKVKYV TEGMRKPAFL    540
SGEQKKAIVD LLFKTNRKVT VKQLKEDYFK KIECFDSVEI SGVEDRFNAS LGTYHDLLKI    600
IKDKDFLDNE ENEDILEDIV LTLTLFEDRE MIEERLKTYA HLFDDKVMKQ LKRRRYTGWG    660
RLSRKLINGI RDKQSGKTIL DFLKSDGFAN RNFMQLIHDD SLTFKEDIQK AQVSGQGDSL    720
HEHIANLAGS PAIKKGILQT VKVVDELVKV MGRHKPENIV IEMARENQTT QKGQKNSRER    780
MKRIEEGIKE LGSQILKEHP VENTQLQNEK LYLYYLQNGR DMYVDQELDI NRLSDYDVDH    840
IVPQSFLKDD SIDNKVLTRS DKNRGKSDNV PSEEVVKKMK NYWRQLLNAK LITQRKFDNL    900
TKAERGGLSE LDKAGFIKRQ LVETRQITKH VAQILDSRMN TKYDENDKLI REVKVITLKS    960
KLVSDFRKDF QFYKVREINN YHHAHDAYLN AVVGTALIKK YPKLESEFVY GDYKVYDVRK    1020
MIAKSEQEIG KATAKYFFYS NIMNFFKTEI TLANGEIRKR PLIETNGETG EIVWDKGRDF    1080
ATVRKVLSMP QVNIVKKTEV QTGGFSKESI LPKRNSDKLI ARKKDWDPKK YGGFDSPTVA    1140
YSVLVVAKVE KGKSKKLKSV KELLGITIME RSSFEKNPID FLEAKGYKEV KKDLIIKLPK    1200
YSLFELENGR KRMLASAGEL QKGNELALPS KYVNFLYLAS HYEKLKGSPE DNEQKQLFVE    1260
QHKHYLDEII EQISEFSKRV ILADANLDKV LSAYNKHRDK PIREQAENII HLFTLTNLGA    1320
PAAFKYFDTT IDRKRYTSTK EVLDATLIHQ SITGLYETRI DLSQLGGD               1368
```

```
SEQ ID NO: 9            moltype = DNA   length = 4836
FEATURE                 Location/Qualifiers
misc_feature           1..4836
                        note = Synthetic Polynucleotide
source                  1..4836
                        mol_type = other DNA
                        organism = synthetic construct
SEQUENCE: 9
atggataaaa agtattctat tggtttagct atcggcacta attccgttgg atgggctgtc    60
ataaccgatg aatacaaagt accttcaaag aaatttaagg tgttggggaa cacagaccgt    120
cattcgatta aaaagaatct tatcggtgcc ctcctattcg atagtggcga acggcgcagag   180
gcgactcgc tgaaacgaac cgctcggaga aggtatacac gtcgcaagaa ccgaatatgt      240
tacttacaag aaatttttag caatgagatg gccaaagttg acgattcttt ctttcaccgt    300
ttggaagagt ccttccttgt cgaagaggac aagaaacatg aacggcaccc catctttgga    360
aacatagtag atgaggtggc atatcatgaa aagtacccaa cgatttatca cctcagaaaa    420
aagctagtta actcaactga taaagcggac ctgaggttaa tctacttggc tcttgcccat    480
atgataaagt tccgtgggca ctttctcatt gagggtgatc taaatccgga caactcggat    540
gtcgacaaac tgttcatcca gttagtacaa acctataatc agttgtttga agagaaccct    600
```

```
ataaaatgcaa gtggcgtgga tgcgaaggct attcttagcg cccgcctctc taaatcccga  660
cggctagaaa acctgatcgc acaattaccc ggagagaaga aaaatgggtt gttcggtaac  720
cttatagcgc tctcactagg cctgacacca aattttaagt cgaacttcga cttagctgaa  780
gatgccaaat tgcagcttag taaggacacg tacgatgacg atctcgacaa tctactggca  840
caaattggag atcagtatgc ggacttattt ttggctgcca aaaaccttag cgatgcaatc  900
ctcctatctg acatactgag agttaatact gagattacca aggcgccgtt atccgcttca  960
atgatcaaaa ggtacgatga acatcaccaa gacttgacac ttctcaaggc cctagtccgt  1020
cagcaactgc ctgagaaata taaggaaata ttctttgatc agtcgaaaaa cgggtacgca  1080
ggttatattg acggcggagc gagtcaagag gaattctaca agtttatcaa acccatatta  1140
gagaagatgg atgggacgga agagttgctt gtaaaactca atcgcgaaga tctactgcga  1200
aagcagcgga ctttcgacaa cggtagcatt ccacatcaaa tccacttagg cgaattgcat  1260
gctatactta gaaggcagga ggattttat ccgttcctca aagacaatcg tgaaaagatt  1320
gagaaaatcc taacctttcg cataccttac tatgtgggac ccctggcccg agggaactct  1380
cggttcgcat ggatgacaag aaagtccgaa gaaacgatta ctccatggaa ttttgaggaa  1440
gttgtcgata aaggtgcgtc agctcaatcg ttcatcgaga ggatgaccaa cttttgacaag 1500
aatttaccga acgaaaaagt attgcctaag cacagtttac tttacgagta tttcacagtg  1560
tacaatgaac tcacgaaagt taagtatgtc actgagggca tgcgtaaacc cgcctttcta  1620
agcggagaac agaagaaagc aatagtagat ctgttattca agaccaaccg caaagtgaca  1680
gttaagcaat tgaaagagga ctactttaag aaaattgaat gcttcgattc tgtcgagatc  1740
tccggggtag aagatcgatt taatgcgtca cttggtacgt atcatgacct cctaaagata  1800
attaaagata aggacttcct ggataacgaa gagaatgaag atatcttaga agatatagtg  1860
ttgactctta ccctctttga agatcgggaa atgattgagg aaagactaaa aacatacgct  1920
cacctgttcg acgataaggt tatgaaacag ttaaagaggc gtcgctatac gggctgggga  1980
cgattgtcgc ggaaacttat caacgggata agagacaagc aaagtggtaa aactattctc  2040
gattttctaa agagcgacgg cttcgccaat aggaacttta tgcagctgat ccatgatgac  2100
tctttaacct tcaaagagga tatacaaaag gcacaggttt ccggacaagg ggactcattg  2160
cacgaacata ttgcgaatct tgctggttcg ccagccatca aaaagggcat actccagaca  2220
gtcaaagtag tggatgagct agttaaggtc atgggacgtc acaaaccgga aaacattgta  2280
atcgagatgc cacgcgaaaa tcaaacgact cagaaggggc aaaaaaacag tcgagagcgg  2340
atgaagagaa tagaagaggg tattaaagaa ctgggcagcc agatcttaaa ggagcatcct  2400
gtggaaaata cccaattgca gaacgagaaa ctttacctct attacctaca aaatggaagg  2460
gacatgtatg ttgatcagga actggacata aaccgtttat ctgattacga cgtcgatgcc  2520
attgtacccc aatccttttt gaaggacgat tcaatcgaca ataaagtgct tacacgctcg  2580
gataagaacc gagggaaaag tgacaatgtt ccaagcgagg aagtcgtaaa gaaaatgaag  2640
aactattggc ggcagctcct aaatgcgaaa ctgataacgc aaagaaagtt cgataactta  2700
actaaagctg agaggggtgg cttgtctgaa cttgacaagg ccggatttat taaacgtcag  2760
ctcgtggaaa cccgccaaat cacaaagcat gttgcacaga tactagattc ccgaatgaat  2820
acgaaatacg acgagaacga taagctgatt cgggaagtca aagtaatcac tttaaagtca  2880
aaattggtgt cggacttcag aaaggatttt caattctata aagttaggga gataaataac  2940
taccaccatg cgcacgacgc ttatcttaat gccgtcgtag ggaccgcact cattaagaaa  3000
tacccgaagc tagaaagtga gtttgtgtat ggtgattaca aagtttatga cgtccgtaag  3060
atgatcgcga aaagcgaaca ggagataggc aaggctacag ccaaatactt cttttattct  3120
aacattatga atttctttaa gacggaaatc actctggcaa acggagagat acgcaaacga  3180
cctttaattg aaaccaatgg ggagacaggt gaaatcgtat gggataaggg ccgggacttc  3240
gcgacggtga gaaaagtttt gtccatgccc caagtcaaca tagtaaagaa aactgaggtg  3300
cagaccggag ggtttcaaa ggaatcgatt cttccaaaaa ggaatagtga taagctcatc  3360
gctcgtaaaa aggactggga cccgaaaaag tacggtggct tcgatagccc tacagttgcc  3420
tattctgtcc tagtagtggc aaaagttgag aagggaaaat ccaagaaact gaagtcagtc  3480
aaagaattat tggggataac gattatggag cgctcgtctt ttgaaaagaa ccccatcgac  3540
ttccttgagg cgaaaggtta caaggaagta aaaaaggatc tcataattaa actaccaaag  3600
tatgtctgt ttgagttaga aaatggccga aacgtatgt tggctagcgc cggagagcgtt  3660
caaaagggga acgaactcgc actaccgtct aaatacgtga atttcctgta tttagcgtcc  3720
cattacgaga agttgaaagg ttcacctgaa gataacgaac agaagcaact ttttgttgag  3780
cagcacaaac attatctcga cgaaatcata gagcaaattt cggaattcag taagagagtc  3840
atcctagctg atgccaatct ggacaaagta ttaagcgcat acaacaagca cagggataaa  3900
cccatacgtg agcaggcgga aaatattatc catttgttta ctcttaccaa cctcggcgct  3960
ccagccgcat tcaagtattt tgacacaacg atagatcgca aacgatacac ttctaccaag  4020
gaggtgctag acgcgacact gattcaccaa tccatcacgg gattatatga aactcggata  4080
gatttgtcac agcttggggg tgacggatcc cccaagaaga agggaaagt ctcgagcgac  4140
tacaaagacc atgacggtga ttataaagat catgacatcg attacaagga tgacgatgac  4200
aaggctgcag gatcaggtgg aagtggcggc agcggaggtt ctggatccca actagtcaaa  4260
agtgaactgg aggagaagaa atctgaactt cgtcataaat tgaaatatgt gcctcatgaa  4320
tatattgaat taattgaaat tgccagaaat tccactcagg atagaattct tgaaatgaag  4380
gtaatggaat tttttatgaa agtttatgga tatagaggta aacattttgg tggctagcgc  4440
aaaccggacg gagcaattta tactgtcgga tctcctattg attacggtgg gatcgtggat  4500
actaaagctt atagcggagg ttataatctg ccaattggcc aagcagatga aatgcaacga  4560
tatgtcgaag aaaatcaaac acgaaacaaa catatcaacc ctaatgaatg gtggaaagtc  4620
tatcctctt ctgtaacgga atttaagttt ttatttgtga gtggtcactt taaaggaaac  4680
tacaaagctc agcttacacg attaaatcat atcactaatt gtaatggagc tgttcttagt  4740
gtagaagagc ttttaattgg tggagaaatg attaaagccg gcacattaac cttagaggaa  4800
gtcagacgga aatttaataa cggcgagata aacttt                            4836
```

SEQ ID NO: 10        moltype = DNA   length = 4845
FEATURE             Location/Qualifiers
misc_feature        1..4845
                    note = Synthetic Polynucleotide
source              1..4845
                    mol_type = other DNA
                    organism = synthetic construct

```
SEQUENCE: 10
atggactaca aagaccatga cggtgattat aaagatcatg acatcgatta caaggatgac   60
gatgacaaga tggcccccaa gaagaagagg aaggtgggca ttcaccgcgg ggtacctatg   120
gataaaaagt attctattgg tttagctatc ggcactaatt ccgttggatg ggctgtcata   180
accgatgaat acaaagtacc ttcaaagaaa tttaaggtgt tggggaacac agaccgtcat   240
tcgattaaaa agaatcttat cggtgccctc ctattcgata gtggcgaaac ggcagaggcg   300
actcgcctga aacgaaccgc tcggagaagg tatacacgtc gcaagaaccg aatatgttac   360
ttacaagaaa tttttagcaa tgagatggcc aaagttgacg attctttctt tcaccgtttg   420
gaagagtcct tccttgtcga agaggacaag aaacatgaac ggcaccccat ctttggaaac   480
atagtagatg aggtggcata tcatgaaaag tacccaacga tttatcacct cagaaaaaag   540
ctagttgact caactgataa agcggacctg aggttaatct acttggctct tgcccatatg   600
ataaagttcc gtgggcactt tctcattgag ggtgatctaa atccggacaa ctcggatgtc   660
gacaaactgt tcatccagtt agtacaaacc tataatcagt tgtttgaaga aaccctata    720
aatgcaagtg gcgtggatgc gaaggctatt cttagcgccc gcctctctaa atcccgacgg   780
ctagaaaacc tgatcgcaca attacccgga gagaagaaaa atgggttgtt cggtaacctt   840
atagcgctct cactaggcct gacaccaaat tttaagtcga acttcgactt agctgaagat   900
gccaaattgc agcttagtaa ggacacgtac gatgacgatc tcgacaatct actggcacaa   960
attggagatc agtatgcgga cttatttttg gctgccaaaa accttagcga tgcaatcctc   1020
ctatctgaca tactgagagt taatactgag attaccaagg cgccgttatc cgcttcaatg   1080
atcaaaaggt acgatgaaca tcaccaagac ttgacacttc tcaaggccct agtccgtcag   1140
caactgcctg agaaatataa ggaaatattc tttgatcagt cgaaaaacgg gtacgcaggt   1200
tatattgacg gcggagcgag tcaagaggaa ttctacaagt ttatcaaacc catattagag   1260
aagatggatg ggacggaaga gttgcttgta aaactcaatc gcgaagatct actgcgaaag   1320
cagcggactt cgacaacgg tagcattcca catcaaatcc acttaggcga attgcatgct   1380
atacttagaa ggcaggagga tttttatccg ttcctcaaag acaatcgtga aaagattgag   1440
aaaatcctaa cctttcgcat accttactat gtgggaccct tggcccgagg gaactctcgg   1500
ttcgcatgga tgacaagaaa gtccgaagaa acgattactc catggaattt tgaggaagtt   1560
gtcgataaag gtgcgtcagc tcaatcgttc atcgagagga tgaccaactt tgacaagaat   1620
ttaccgaacc aaaaagtatt gcctaagcac agtttacttt acgagtattt cacagtgtac   1680
aatgaactca cgaaagttaa gtatgtcact gagggcatgc gtaaacccgc ctttctaagc   1740
ggagaacaga agaaagcaat agtagatctg ttattcaaga ccaaccgcaa agtgacagtt   1800
aagcaattga agaggacta ctttaagaaa attgaatgct tcgattctgt cgagatctcc   1860
ggggtagaag atcgatttaa tgcgtcactt ggtacgtatc atgacctcct aaaagataatt  1920
aaagataagg acttcctgga taacgaagag aatgaagata tcttagaaga tatagtgttg  1980
actcttaccc tctttgaaga tcgggaaatg attgaggaaa gactaaaaac atacgctcac  2040
ctgttcgacg ataaggttat gaaacagtta aagaggcgtc gctatacggg ctggggacga  2100
ttgtcgcgga aacttatcaa cgggataaga gacaagcaaa gtggtaaaac tattctcgat  2160
tttctaaaga gcgacggctt cgccaatagg aactttatgc agctgatcca tgatgactct  2220
ttaaccttca aagaggatat acaaaaggca caggtttccg gacaagggga ctcattgcac  2280
gaacatattg cgaatcttgc tggttcgcca gccatcaaaa agggcatact ccagacagtc  2340
aaagtagtgg atgagctagt taaggtcatg ggacgtcaca aaccggaaaa cattgtaatc  2400
gagatggcac gcgaaaatca aacgactcag aaggggcaaa aaaacagtcg agagcggatg  2460
aagagaatag aagagggtat taaagaactg ggcagccaga tcttaaagga gcatcctgtg  2520
gaaaataccc aattgcagaa cgagaaactt tacctctatt acctacaaaa tggaagggac  2580
atgtatgttg atcaggaact ggacataaac cgtttatctg attacgacgt cgatgccatt  2640
gtaccccaat cctttttgaa ggacgattca atcgacaata aagtgcttac acgctcggat  2700
aagaaccgag ggaaaagtga caatgttcca agcgaggaag tcgtaaagaa aatgaagaac  2760
tattggcggc agctcctaaa tgcgaaactg ataacgcaaa gaaagttcga taacttaact  2820
aaagctgaga ggggtggctt gtctgaactt gacaaggccg gatttattaa acgtcagctc  2880
gtggaaaccc gccaaatcac aaagcatgtt gcacagatac tagattcccg aatgaatacg  2940
aaatacgacg agaacgataa gctgattcgg gaagtcaaag taatcactt aaagtcaaaa   3000
ttggtgtcgg acttcagaaa ggattttcaa ttctataaag ttagggagat aaataactac  3060
caccatgcgc acgacgctta tcttaatgcc gtcgtaggga ccgcactcat taagaaatac  3120
ccgaagctag aaagtgagtt tgtgtatggt gattacaaag tttatgacgt ccgtaagatg  3180
atcgcgaaaa gcgaacagga gataggcaag gctacagcca aatacttctt ttattctaac  3240
attatgaatt tctttaagac ggaaatcact ctggcaaacg gagagatacg caaacgacct  3300
ttaattgaaa ccaatgggga gacaggtgaa atcgtatggg ataagggccg ggacttcgcg  3360
acggtgagaa aagttttgtc catgccccaa gtcaacatag taaagaaaac tgaggtgcag  3420
accggagggt tttcaaagga atcgattctt ccaaaaaga atagtgataa gctcatcgct  3480
cgtaaaaagg actgggaccc gaaaaagtac ggtggcttcg atagccctac agttgcctat  3540
tctgtcctag tagtggcaaa agttgagaag ggaaatcca agaaactgaa gtcagtcaaa  3600
gaattattgg ggataacgat tatggagcgc tcgtcttttg aaaagaaccc catcgacttc  3660
cttgaggcga aaggttacaa ggaagtaaaa aaggatctca taattaaact accaaagtat  3720
agtctgtttg agttagaaaa tggccgaaaa cggatgttgg ctagccgg agagcttcaa  3780
aaggggaacg aactcgcact accgtctaaa tacgtgaatt tcctgtattt agcgtcccat  3840
tacgagaagt tgaaaggttc acctgaagat aacgaacaga gcaactttt tgttgagcag  3900
cacaaacatt atctcgacga aatcatagag caaatttcgg aattcagtaa gagagtcatc  3960
ctagctgatg ccaatctgga caaagtatta agcgcataca acaagcacag ggataaaccc  4020
atacgtgagc aggcggaaaa tattatccat ttgtttactc ttaccaacct cggcgctcca  4080
gccgcattca gtattttga cacaacgata gatcgcaaac gatacacttc taccaaggag  4140
gtgctagacg cgacactgat tcaccaatcc atcacgggat tatatgaaac tcggatagat  4200
ttgtcacagc ttggggggtga ctcaggtgga agtggcggca cgcgaggttc tggatcccaa  4260
ctagtcaaaa gtgaactgga ggagaagaaa tctgaacttc gtcataaatt gaaatatgtg  4320
cctcatgaat atattgaatt aattgaaaat gccagaaatt ccactcagga tagaattctt  4380
gaaatgaagg taatgaatt ttttatgaaa gtttatggat atagaggtaa acatttgggt  4440
ggatcaagga aaccggacgg agcaatttat actgtcggat ctcctattga ttacggtgtg  4500
atcgtggata ctaaagctta tagcggaggt tataatctgc caattggcca agcagatgaa  4560
atgcaacgat atgtcgaaga aaatcaaaca cgaaacaaac atatcaaccc taatgaatgg  4620
tggaaagtct atccatcttc tgtaacggaa tttaagtttt tatttgtgag tggtcacttt  4680
```

-continued

```
aaaggaaact acaaagctca gcttacacga ttaaatcata tcactaattg taatggagct    4740
gttcttagtg tagaagagct tttaattggt ggagaaatga ttaaagccgg cacattaacc    4800
ttagaggaag tcagacggaa atttaataac ggcgagataa acttt                    4845

SEQ ID NO: 11          moltype = DNA   length = 4836
FEATURE                Location/Qualifiers
misc_feature           1..4836
                       note = Synthetic Polynucleotide
source                 1..4836
                       mol_type = other DNA
                       organism = synthetic construct
SEQUENCE: 11
atgggatccc aactagtcaa aagtgaactg gaggagaaga aatctgaact tcgtcataaa    60
ttgaaatatg tgcctcatga atatattgaa ttaattgaaa ttgccagaaa ttccactcag    120
gatagaattc ttgaaatgaa ggtaatggaa ttttttatga aagtttatgg atatagaggt    180
aaacatttgg gtggatcaag gaaaccggac ggagcaattt atactgtcgg atctcctatt    240
gattacggtg tgatcgtgga tactaaagct tatagcggag gttataatct gccaattggc    300
caagcagatg aaatgcaacg atatgtcgaa gaaaatcaaa cacgaaacaa acatatcaac    360
cctaatgaat ggtggaaagt ctatccatct tctgtaacgg aatttaagtt tttatttgtg    420
agtggtcact ttaaaggaaa ctacaaagct cagcttacac gattaaatca tatcactaat    480
tgtaatggag ctgttcttag tgtagaagag cttttaattg gtggagaaat gattaaagcc    540
ggcacattaa cctagagga agtcgacgg aaatttaata acggcgagat aaactttggc    600
ggtagtgggg gatctggggg aagtatggat aaaaagtatt ctattggttt agctatcggc    660
actaattccg ttggatgggc tgtcataacc gatgaataca aagtaccttc aaagaaattt    720
aaggtgttgg ggaacacaga ccgtcattcg attaaaaaga atcttatcgg tgccctccta    780
ttcgatagtg gcgaaacggc agaggcgact cgcctgaaac gaaccgctcg gagaaggtat    840
acacgtcgca agaaccgaat atgttactta caagaaattt ttagcaatga gatggccaaa    900
gttgacgatt ctttctttca ccgtttggaa gagtccttcc ttgtcgaaga ggacaagaaa    960
catgaacggc accccatctt tggaaacata gtagatgagg tggcatatca tgaaaagtac    1020
ccaacgattt atcacctcag aaaaaagcta gttgactcaa ctgataaagc ggacctgagg    1080
ttaatctact tggctcttgc ccatatgata aagttccgtg ggcactttct cattgagggt    1140
gatctaaatc cggacaactc ggatgtcgac aaactgttca tccagttagt acaaacctat    1200
aatcagttgt ttgaagagaa ccctataaat gcaagtggcg tggatgcgaa ggctattctt    1260
agcgcccgcc tctctaaatc ccgacggcta gaaaacctga tcgcacaatt acccgggagg    1320
aagaaaaatg ggttgttcgg taaccttata gcgctctcac taggcctgac accaaatttt    1380
aagtcgaact tcgacttagc tgaagatgcc aaattgcagc ttagtaagga cacgtacgat    1440
gacgatctcg acaatctact ggcacaaatt ggagatcagt atgcggactt attttttggct    1500
gccaaaaacc ttagcgatgc aatcctccta tctgacatac tgagagttaa tactgagatt    1560
accaaggcgc cgttatccgc ttcaatgatc aaaaggtacg atgaacatca ccaagacttg    1620
acacttctca aggccctagt ccgtcagcaa ctgcctgaga aatataagga aatattcttt    1680
gatcagtcga aaacgggta cgcaggttat attgacggcg gagcgagtca agaggaattc    1740
tacaagttta tcaaacccat attagagaag atggatggga cggaagagtt gcttgtaaaa    1800
ctcaatcgcg aagatctact gcgaaagcag cggactttcg acaacggtag cattccacat    1860
caaatccact taggcgaatt gcatgctata cttagaaggc aggaggattt ttatccgttc    1920
ctcaaagaca atcgtgaaaa gattgagaaa atcctaacct ttcgcatacc ttactatgtg    1980
ggacccctgg cccgagggaa ctctcggttc gcatggatga caagaaagtc cgaagaaacg    2040
attactccat ggaattttga ggaagttgtc gataaagtg cgtcagctca atcgttcatc    2100
gagaggatga ccaactttga caagaattta ccgaacgaaa aagtattgcc taagcacagt    2160
ttactttacg agtatttcac agtgtacaat gaactcacga aagttaagta tgtcactgag    2220
ggcatgcgta aacccgcctt tctaagcgga gaacagaaga agcaatagt agatctgtta    2280
ttcaagacca accgcaaagt gacagttaag caattgaaag aggactactt taagaaaatt    2340
gaatgcttcg attctgtcga gatctccggg gtagaagatc gatttaatgc gtcacttggt    2400
acgtatcatg acctcctaaa gataattaaa gataaggact tcctggataa cgaagagaat    2460
gaagatatct tagaagatat agtgttgact cttaccctct ttgaagatcg ggaaatgatt    2520
gaggaaagac taaaaacata cgctcacctg ttcgacgata aggttatgaa acagttaaag    2580
aggcgtcgct atacgggctg gggacgattg tcgcggaaac ttatcaacgg gataagagac    2640
aagcaaagtg gtaaaactat tctcgatttt ctaaagagcg acggcttcgc caataggaac    2700
tttatgcagc tgatccatga tgactcttta accttcaaag aggatataca aaaggcacag    2760
gtttccggac aaggggactc attgcacgaa catattgcga tcttgctgg ttcgccaggc    2820
atcaaaaagg gcatactcca gacagtcaaa gtagtggatg agctagttaa ggtcatggga    2880
cgtcacaaac cggaaaacat tgtaatcgag atggcacgcg aaaatcaaac gactcagaag    2940
gggcaaaaaa acagtcgaga gcggatgaag agaatagaag agggtattaa agaactgggc    3000
agccagatct taaaggagca tcctgtggaa aatacccaat tgcagaacga gaaactttac    3060
ctctattacc tacaaaatgg aagggacatg tatgttgatc aagaactgga cataaaccgt    3120
ttatctgatt acgacgtcga tgccattgta ccccaatcct ttttgaagga cgattcaatc    3180
gacaataaag tgcttacacg ctcggataag aaccgaggga aaagtgacaa tgttccaagc    3240
gaggaagtcg taaagaaaat gaagaactat tggcggcagc tcctaaatgc gaaactgata    3300
acgcaaagaa agttcgataa cttaactaaa gctgagaggg gtggcttgtc tgaacttgac    3360
aaggccggat ttattaaacg tcagctcgtg gaaacccgac aaatcacaaa gcatgttgac    3420
cagatactag attcccgaat gaatacgaaa tacgacgaga acgataagct gattcgggaa    3480
gtcaaagtaa tcactttaaa gtcaaaattg gtgtcggact tcagaaagga ttttcaattc    3540
tataaagtta gggagataaa taactaccac catgcgcacg acgcttatct taatgccgtc    3600
gtagggaccg cactcattaa gaaatacccg aagctagaaa gtgagtttgt gtatggtgat    3660
tacaaagttt atgacgtccg taagatgatc gcgaaaagcg aacaggagat aggcaaggct    3720
acagccaaat acttctttta ttctaacatt atgaatttct ttaagacgga aatcactctg    3780
gcaaacggag agatacgcaa acgacctta attgaaacca atggggagac aggtgaaatc    3840
gtatgggata gggccgggga cttcgcgacg gtgagaaaag ttttgtccat gccccaagtc    3900
aacatagtaa agaaaactga ggtgcagacc ggagggtttt caaaggaatc gattcttcca    3960
aaaaggaata gtgataagct catcgctcgt aaaaaggact gggacccgaa aaagtacggt    4020
```

-continued

```
ggcttcgata gccctacagt tgcctattct gtcctagtag tggcaaaagt tgagaaggga   4080
aaatccaaga aactgaagtc agtcaaagaa ttattgggga taacgattat ggagcgctcg   4140
tcttttgaaa agaaccccat cgacttcctt gaggcgaaag gttacaagga agtaaaaaag   4200
gatctcataa ttaaactacc aaagtatagt ctgtttgagt tagaaaatgg ccgaaaacgg   4260
atgttggcta gcgccggaga gcttcaaaag gggaacgaac tcgcactacc gtctaaatac   4320
gtgaatttcc tgtatttagc gtcccattac gagaagttga aaggttcacc tgaagataac   4380
gaacagaagc aactttttgt tgagcagcac aaacattatc tcgacgaaat catagagcaa   4440
atttcggaat tcagtaagag agtcatccta gctgatgcca atctggacaa agtattaagc   4500
gcatacaaca agcacaggga taaacccata cgtgagcagg cggaaaatat tatccatttg   4560
tttactctta ccaacctcgg cgctccagcc gcattcaagt attttgacac aacgatagat   4620
cgcaaacgat acacttctac caaggaggtg ctagacgcga cactgattca ccaatccatc   4680
acgggattat atgaaactcg gatagatttg tcacagcttg ggggtgacgg atcccccaag   4740
aagaagagga aagtctcgag cgactacaaa gaccatgacg gtgattataa agatcatgac   4800
atcgattaca aggatgacga tgacaaggct gcagga                              4836
```

SEQ ID NO: 12          moltype = DNA   length = 4854
FEATURE                Location/Qualifiers
misc_feature           1..4854
                       note = Synthetic Polynucleotide
source                 1..4854
                       mol_type = other DNA
                       organism = synthetic construct
SEQUENCE: 12

```
atggactaca aagaccatga cggtgattat aaagatcatg acatcgatta caaggatgac   60
gatgacaaga tggcccccaa gaagaagagg aaggtgggca ttcaccgcgg ggtacctgga   120
ggttctatgg gatcccaact agtcaaaagt gaactgaagg agaagaaatc tgaacttcgt   180
cataaattga aatatgtgcc tcatgaatat attgaattaa ttgaaattgc cagaaattcc   240
actcaggata gaattcttga aatgaaggta atggaatttt ttatgaaagt ttatggatat   300
agaggtaaac atttgggtgg atcaaggaaa ccggacggag caatttatac tgtcggatct   360
cctattgatt acggtgtgat cgtgatact aaagcttata gcggaggtta taatctgcca   420
attggccaag cagatgaaat gcaacgatat gtcgaagaaa atcaaacacg aaacaaacat   480
atcaacccta atgaatggtg gaaagtctat ccatcttctg taacggaatt taagtttta   540
tttgtgagtg gtcactttaa aggaaactac aaagctcagc ttcacgatt aaatcatatc   600
actaattgta atggagctgt tcttagtgta gaagagcttt taattggtgg agaaatgatt   660
aaagccggca cattaacctt agaggaagtc agacggaaat ttaataacgg cgagataaac   720
tttggcggta gtggggatc tggggggaagt atggataaaa agtattctat tggtttagct   780
atcggcacta ttccgttgg atgggctgtc ataaccgatg aatacaaagt accttcaaag   840
aaatttaagg tgttggggaa cacagaccgt cattcgatta aaaagaatct tatcggtgcc   900
ctcctattcg atagtggcga aacggcagag gcgactcgc tgaaacgaac cgctcggaga   960
aggtatacac gtcgcaagaa ccgaatatgt tacttacaag aaattttag caatgagatg   1020
gccaaagttg acgattcttt ctttcaccgt ttggaagagt ccttccttgt cgaagaggac   1080
aagaaacatg aacggcaccc catctttgga aacatagtag atgaggtggc atatcatgaa   1140
aagtacccaa cgatttatca cctcagaaaa aagctagttg actcaactga taagcggac   1200
ctgaggttaa tctacttggc tcttgcccat atgataaagt tccgtgggca ctttctcatt   1260
gagggtgatc taaatccgga caactcggat gtcgacaaac tgttcatcca gttagtacaa   1320
acctataatc agttgtttga agagaaccct ataaatgcaa gtggcgtgga tgcgaaggct   1380
attcttagcg cccgcctctc taaatcccga cggctagaaa acctgatcgc acaattaccc   1440
ggagagaaga aaaatggggtt gttcggtaac cttatagcgc tctcactagg cctgacacca   1500
aatttttaagt cgaacttcga cttagctgaa gatgccaaat tgcagcttag taaggacacg   1560
tacgatgacg atctcgacaa tctactggca caaattggag atcagtatgc ggacttattt   1620
ttggctgcca aaaaccttag cgatgcaatc ctcctatctg acatactgag agttaatact   1680
gagattacca aggcgccgtt atccgcttca atgatcaaaa ggtacgatga acatcaccaa   1740
gacttgcac ttctcaaggc cctagtccgt cagcaactgc ctgagaaata taggaaaata   1800
ttctttgatc agtcgaaaaa cgggtacgca ggttatattg acggcggagc gagtcaagag   1860
gaattctaca agtttatcaa acccatatta gagaagatgg atgggacaag agagttgctt   1920
gtaaaactca atcgcgaaga tctactgcga aagcagcgga ctttcgacaa cggtagcatt   1980
ccacatcaaa tccacttagg cgaattgcat gctatactta gaaggcagga ggattttat   2040
ccgttcctca aagacaatcg tgaaaagatt gagaaaatcc taacctttcg cataccttac   2100
tatgtgggac ccctggcccg agggaactct cggttcgcat ggatgacaag aaagtccgaa   2160
gaaacgatta ctccatggaa ttttgaggaa gttgtcgata aaggtgcgtc agctcaatcg   2220
ttcatcgaga ggatgaccaa ctttgacaag aatttaccga acgaaaaagt attgcctaag   2280
cacagtttac tttacgagta tttcacagta tacaatgaac tcacgaaagt taagtatgtc   2340
actgagggca tgcgtaaacc cgcctttcta agcggagaac agaagaaagc aatagtagat   2400
ctgttattca agaccaaccg caaagtgaca gttaagcaat tgaaagagga ctactttaag   2460
aaaattgaat gcttcgattc tgtcgagatc tccggggtag aagatcgatt taatgcgtca   2520
cttggtacgt atcatgacct cctaaagata attaaagata aggacttcct ggataacgaa   2580
gagaatgaag atatcttaga agatatagt ttgactctta ccctctttga gatcgggaa   2640
atgattgagg aaagactaaa aacatacgct cacctgttcg acgataaagt tatgaaacag   2700
ttaaagaggc gtcgctatac gggctgggga cgattgtcgc ggaaacttat caacgggata   2760
agagacaagc aaagtggtaa aactattctc gattttctaa agagcgacgg cttcgccaat   2820
aggaacttta tgcagctgat ccatgatgac tctttaacct tcaaagagga tatacaaaag   2880
gcacaggttt ccgacaaggg gactcattg cacgaacata ttgcgaatct tgctggttcg   2940
ccagccatca aaaagggcat actccagaca gtcaaagtag tggatgagct agttaaggtc   3000
atgggacgtc acaaaccgga aaacattgta atcgagatgg cacgcgaaaa tcaaacgact   3060
cagaaggggc aaaaaaacag tcgagagcgg atgaagagaa tagaagaggg tattaaagaa   3120
ctgggcagcc agatcttaaa ggagcatcct gtggaaaata cccaattgca gaacgagaaa   3180
ctttacctct attacctaca aaatggaagg gacatgtatg ttgatcagga actggacata   3240
aaccgtttat ctgattacga cgtcgatgcc attgtacccc aatcctttt gaaggacgat   3300
tcaatcgaca ataaagtgct tacacgctcg gataagaacc gagggaaaag tgacaatgtt   3360
```

```
ccaagcgagg aagtcgtaaa gaaaatgaag aactattggc ggcagctcct aaatgcgaaa  3420
ctgataacgc aaagaaagtt cgataactta actaaagctg agaggggtgg cttgtctgaa  3480
cttgacaagg ccggatttat taaacgtcag ctcgtggaaa cccgccaaat cacaaagcat  3540
gttgcacaga tactagattc ccgaatgaat acgaaatacg acgagaacga taagctgatt  3600
cgggaagtca aagtaatcac tttaaagtca aaattggtgt cggacttcag aaaggatttt  3660
caattctata aagttaggga gataaataac taccaccatg cgcacgacgc ttatcttaat  3720
gccgtcgtag ggaccgcact cattaagaaa tacccgaagc tagaaagtga gtttgtgtat  3780
ggtgattaca aagtttatga cgtccgtaag atgatcgcga aaagcgaaca ggagataggc  3840
aaggctacag ccaaatactt cttttattct aacattatga atttctttaa gacggaaatc  3900
actctggcaa acggagagat acgcaaacga cctttaattg aaaccaatgg ggagacaggt  3960
gaaatcgtat gggataaggg ccgggacttc gcgacggtga gaaaagtttt gtccatgccc  4020
caagtcaaca tagtaaagaa aactgaggtg cagaccggag ggttttcaaa ggaatcgatt  4080
cttccaaaaa ggaatagtga taagctcatc gctcgtaaaa aggactggga cccgaaaaag  4140
tacggtggct tcgatagccc tacagttgcc tattctgtcc tagtagtggc aaaagttgag  4200
aagggaaaat ccaagaaact gaagtcagtc aaagaattat tggggataac gattatggag  4260
cgctcgtctt ttgaaaagaa ccccatcgac ttccttgagg cgaaaggtta caaggaagta  4320
aaaaaggatc tcataattaa actaccaaag tatagtctgt ttgagttaga aaatggccga  4380
aaacggatgt tggctagcgc cggagagctt caaaagggga acgaactcgc actaccgtct  4440
aaatacgtga atttcctgta tttagcgtcc cattacgaga agttgaaagg ttcacctgaa  4500
gataacgaac agaagcaact ttttgttgag cagcacaaac attatctcga cgaaatcata  4560
gagcaaattc cggaattcag taagagagtc atcctagctg atgccaatct ggacaaagta  4620
ttaagcgcat acaacaagca cagggataaa cccatacgtg acgaggcgga aaatattatc  4680
catttgttta ctcttaccaa cctcggcgct ccagccgcat tcaagtattt tgacacaacg  4740
atagatcgca aacgatacac ttctaccaag gaggtgctag acgcgacact gattcaccaa  4800
tccatcacgg gattatatga aactcggata gatttgtcac agcttggggg tgac         4854
```

```
SEQ ID NO: 13           moltype = DNA  length = 10
FEATURE                 Location/Qualifiers
misc_feature            1..10
                        note = Synthetic Polynucleotide
source                  1..10
                        mol_type = other DNA
                        organism = synthetic construct
SEQUENCE: 13
aaaaaaaaaa                                                          10

SEQ ID NO: 14           moltype = AA  length = 9
FEATURE                 Location/Qualifiers
REGION                  1..9
                        note = Synthetic Polypeptide
source                  1..9
                        mol_type = protein
                        organism = synthetic construct
SEQUENCE: 14
GGSGGSGGS                                                           9

SEQ ID NO: 15           moltype = AA  length = 18
FEATURE                 Location/Qualifiers
REGION                  1..18
                        note = Synthetic Polypeptide
source                  1..18
                        mol_type = protein
                        organism = synthetic construct
SEQUENCE: 15
GGSGGSGGSG GSGGSGGS                                                 18

SEQ ID NO: 16           moltype = AA  length = 16
FEATURE                 Location/Qualifiers
REGION                  1..16
                        note = Synthetic Polypeptide
source                  1..16
                        mol_type = protein
                        organism = synthetic construct
SEQUENCE: 16
SGSETPGTSE SATPES                                                   16

SEQ ID NO: 17           moltype = AA  length = 12
FEATURE                 Location/Qualifiers
REGION                  1..12
                        note = Synthetic Polypeptide
source                  1..12
                        mol_type = protein
                        organism = synthetic construct
SEQUENCE: 17
SGSETPGTSE SA                                                       12

SEQ ID NO: 18           moltype = AA  length = 21
FEATURE                 Location/Qualifiers
REGION                  1..21
```

-continued

```
                            note = Synthetic Polypeptide
source                      1..21
                            mol_type = protein
                            organism = synthetic construct
SEQUENCE: 18
SGSETPGTSE SATPEGGSGG S                                       21

SEQ ID NO: 19               moltype = AA  length = 15
FEATURE                     Location/Qualifiers
REGION                      1..15
                            note = Synthetic Polypeptide
source                      1..15
                            mol_type = protein
                            organism = synthetic construct
SEQUENCE: 19
VPFLLEPDNI NGKTC                                              15

SEQ ID NO: 20               moltype = AA  length = 12
FEATURE                     Location/Qualifiers
REGION                      1..12
                            note = Synthetic Polypeptide
source                      1..12
                            mol_type = protein
                            organism = synthetic construct
SEQUENCE: 20
GSAGSAAGSG EF                                                 12

SEQ ID NO: 21               moltype = AA  length = 12
FEATURE                     Location/Qualifiers
REGION                      1..12
                            note = Synthetic Polypeptide
source                      1..12
                            mol_type = protein
                            organism = synthetic construct
SEQUENCE: 21
SIVAQLSRPD PA                                                 12

SEQ ID NO: 22               moltype = AA  length = 10
FEATURE                     Location/Qualifiers
REGION                      1..10
                            note = Synthetic Polypeptide
source                      1..10
                            mol_type = protein
                            organism = synthetic construct
SEQUENCE: 22
MKIIEQLPSA                                                    10

SEQ ID NO: 23               moltype = AA  length = 10
FEATURE                     Location/Qualifiers
REGION                      1..10
                            note = Synthetic Polypeptide
source                      1..10
                            mol_type = protein
                            organism = synthetic construct
SEQUENCE: 23
VRHKLKRVGS                                                    10

SEQ ID NO: 24               moltype = AA  length = 12
FEATURE                     Location/Qualifiers
REGION                      1..12
                            note = Synthetic Polypeptide
source                      1..12
                            mol_type = protein
                            organism = synthetic construct
SEQUENCE: 24
GHGTGSTGSG SS                                                 12

SEQ ID NO: 25               moltype = AA  length = 7
FEATURE                     Location/Qualifiers
REGION                      1..7
                            note = Synthetic Polypeptide
source                      1..7
                            mol_type = protein
                            organism = synthetic construct
SEQUENCE: 25
MSRPDPA                                                       7

SEQ ID NO: 26               moltype = DNA  length = 38
FEATURE                     Location/Qualifiers
```

-continued

```
misc_feature              1..38
                          note = Synthetic Polynucleotide
source                    1..38
                          mol_type = other DNA
                          organism = synthetic construct
SEQUENCE: 26
cggcgagata aacttttaat gaccggtcat catcacca                              38

SEQ ID NO: 27             moltype = DNA  length = 47
FEATURE                   Location/Qualifiers
misc_feature              1..47
                          note = Synthetic Polynucleotide
source                    1..47
                          mol_type = other DNA
                          organism = synthetic construct
SEQUENCE: 27
ccaacggaat tagtgccgat agctaaacca atagaatact ttttatc                    47

SEQ ID NO: 28             moltype = DNA  length = 47
FEATURE                   Location/Qualifiers
misc_feature              1..47
                          note = Synthetic Polynucleotide
source                    1..47
                          mol_type = other DNA
                          organism = synthetic construct
SEQUENCE: 28
gataaaaagt attctattgg tttagctatc ggcactaatt ccgttgg                    47

SEQ ID NO: 29             moltype = DNA  length = 49
FEATURE                   Location/Qualifiers
misc_feature              1..49
                          note = Synthetic Polynucleotide
source                    1..49
                          mol_type = other DNA
                          organism = synthetic construct
SEQUENCE: 29
ttcaaaaagg attggggtac aatggcatcg acgtcgtaat cagataaac                  49

SEQ ID NO: 30             moltype = DNA  length = 49
FEATURE                   Location/Qualifiers
misc_feature              1..49
                          note = Synthetic Polynucleotide
source                    1..49
                          mol_type = other DNA
                          organism = synthetic construct
SEQUENCE: 30
gtttatctga ttacgacgtc gatgccattg taccccaatc cttttttgaa                 49

SEQ ID NO: 31             moltype = DNA  length = 37
FEATURE                   Location/Qualifiers
misc_feature              1..37
                          note = Synthetic Polynucleotide
source                    1..37
                          mol_type = other DNA
                          organism = synthetic construct
SEQUENCE: 31
ttgggatcca gaacctcctc ctgcagcctt gtcatcg                               37

SEQ ID NO: 32             moltype = DNA  length = 58
FEATURE                   Location/Qualifiers
misc_feature              1..58
                          note = Synthetic Polynucleotide
source                    1..58
                          mol_type = other DNA
                          organism = synthetic construct
SEQUENCE: 32
ttgggatcca gaacctccgc tgccgccact tccacctgat cctgcagcct tgtcatcg        58

SEQ ID NO: 33             moltype = DNA  length = 37
FEATURE                   Location/Qualifiers
misc_feature              1..37
                          note = Synthetic Polynucleotide
source                    1..37
                          mol_type = other DNA
                          organism = synthetic construct
SEQUENCE: 33
cgatgacaag gctgcaggag gaggttctgg atcccaa                               37

SEQ ID NO: 34             moltype = DNA  length = 58
```

-continued

```
FEATURE              Location/Qualifiers
misc_feature         1..58
                     note = Synthetic Polynucleotide
source               1..58
                     mol_type = other DNA
                     organism = synthetic construct
SEQUENCE: 34
cgatgacaag gctgcaggat caggtggaag tggcggcagc ggaggttctg gatcccaa     58

SEQ ID NO: 35        moltype = DNA   length = 38
FEATURE              Location/Qualifiers
misc_feature         1..38
                     note = Synthetic Polynucleotide
source               1..38
                     mol_type = other DNA
                     organism = synthetic construct
SEQUENCE: 35
tggtgatgat gaccggtcat taaaagttta tctcgccg                           38

SEQ ID NO: 36        moltype = DNA   length = 38
FEATURE              Location/Qualifiers
misc_feature         1..38
                     note = Synthetic Polynucleotide
source               1..38
                     mol_type = other DNA
                     organism = synthetic construct
SEQUENCE: 36
cggcgagata aacttttaat gaccggtcat catcacca                           38

SEQ ID NO: 37        moltype = DNA   length = 40
FEATURE              Location/Qualifiers
misc_feature         1..40
                     note = Synthetic Polynucleotide
source               1..40
                     mol_type = other DNA
                     organism = synthetic construct
SEQUENCE: 37
taggagagc cgccaccatg gactacaaag accatgacgg                          40

SEQ ID NO: 38        moltype = DNA   length = 46
FEATURE              Location/Qualifiers
misc_feature         1..46
                     note = Synthetic Polynucleotide
source               1..46
                     mol_type = other DNA
                     organism = synthetic construct
SEQUENCE: 38
taaaccaata gaatactttt tatccatagg taccccgcgg tgaatg                  46

SEQ ID NO: 39        moltype = DNA   length = 47
FEATURE              Location/Qualifiers
misc_feature         1..47
                     note = Synthetic Polynucleotide
source               1..47
                     mol_type = other DNA
                     organism = synthetic construct
SEQUENCE: 39
gataaaagt attctattgg tttagctatc ggcactaatt ccgttgg                  47

SEQ ID NO: 40        moltype = DNA   length = 49
FEATURE              Location/Qualifiers
misc_feature         1..49
                     note = Synthetic Polynucleotide
source               1..49
                     mol_type = other DNA
                     organism = synthetic construct
SEQUENCE: 40
ttcaaaaagg attggggtac aatggcatcg acgtcgtaat cagataaac              49

SEQ ID NO: 41        moltype = DNA   length = 49
FEATURE              Location/Qualifiers
misc_feature         1..49
                     note = Synthetic Polynucleotide
source               1..49
                     mol_type = other DNA
                     organism = synthetic construct
SEQUENCE: 41
gtttatctga ttacgacgtc gatgccattg taccccaatc cttttttgaa            49
```

-continued

```
SEQ ID NO: 42          moltype = DNA   length = 35
FEATURE                Location/Qualifiers
misc_feature           1..35
                       note = Synthetic Polynucleotide
source                 1..35
                       mol_type = other DNA
                       organism = synthetic construct
SEQUENCE: 42
ttgggatcca gaacctccgt cacccccaag ctgtg                           35

SEQ ID NO: 43          moltype = DNA   length = 56
FEATURE                Location/Qualifiers
misc_feature           1..56
                       note = Synthetic Polynucleotide
source                 1..56
                       mol_type = other DNA
                       organism = synthetic construct
SEQUENCE: 43
ttgggatcca gaacctccgc tgccgccact ccacctgag tcaccccaa gctgtg       56

SEQ ID NO: 44          moltype = DNA   length = 35
FEATURE                Location/Qualifiers
misc_feature           1..35
                       note = Synthetic Polynucleotide
source                 1..35
                       mol_type = other DNA
                       organism = synthetic construct
SEQUENCE: 44
cacagcttgg gggtgacgga ggttctggat cccaa                           35

SEQ ID NO: 45          moltype = DNA   length = 56
FEATURE                Location/Qualifiers
misc_feature           1..56
                       note = Synthetic Polynucleotide
source                 1..56
                       mol_type = other DNA
                       organism = synthetic construct
SEQUENCE: 45
cacagcttgg gggtgactca ggtggaagtg gcggcagcgg aggttctgga tcccaa     56

SEQ ID NO: 46          moltype = DNA   length = 38
FEATURE                Location/Qualifiers
misc_feature           1..38
                       note = Synthetic Polynucleotide
source                 1..38
                       mol_type = other DNA
                       organism = synthetic construct
SEQUENCE: 46
tggtgatgat gaccggtcat taaaagttta tctcgccg                        38

SEQ ID NO: 47          moltype = DNA   length = 40
FEATURE                Location/Qualifiers
misc_feature           1..40
                       note = Synthetic Polynucleotide
source                 1..40
                       mol_type = other DNA
                       organism = synthetic construct
SEQUENCE: 47
tagggagagc cgccaccatg ggatcccaac tagtcaaaag                      40

SEQ ID NO: 48          moltype = DNA   length = 45
FEATURE                Location/Qualifiers
misc_feature           1..45
                       note = Synthetic Polynucleotide
source                 1..45
                       mol_type = other DNA
                       organism = synthetic construct
SEQUENCE: 48
accaatagaa tactttttat ccatgctgcc accaaagttt atctc                45

SEQ ID NO: 49          moltype = DNA   length = 44
FEATURE                Location/Qualifiers
misc_feature           1..44
                       note = Synthetic Polynucleotide
source                 1..44
                       mol_type = other DNA
                       organism = synthetic construct
SEQUENCE: 49
accaatagaa tactttttat ccatgctgcc gccacttcca cctg                 44
```

-continued

```
SEQ ID NO: 50            moltype = DNA   length = 47
FEATURE                  Location/Qualifiers
misc_feature             1..47
                         note = Synthetic Polynucleotide
source                   1..47
                         mol_type = other DNA
                         organism = synthetic construct
SEQUENCE: 50
gataaaaagt attctattgg tttagctatc ggcactaatt ccgttgg                   47

SEQ ID NO: 51            moltype = DNA   length = 47
FEATURE                  Location/Qualifiers
misc_feature             1..47
                         note = Synthetic Polynucleotide
source                   1..47
                         mol_type = other DNA
                         organism = synthetic construct
SEQUENCE: 51
ccaacggaat tagtgccgat agctaaacca atagaatact ttttatc                   47

SEQ ID NO: 52            moltype = DNA   length = 49
FEATURE                  Location/Qualifiers
misc_feature             1..49
                         note = Synthetic Polynucleotide
source                   1..49
                         mol_type = other DNA
                         organism = synthetic construct
SEQUENCE: 52
gtttatctga ttacgacgtc gatgccattg taccccaatc ctttttgaa                 49

SEQ ID NO: 53            moltype = DNA   length = 36
FEATURE                  Location/Qualifiers
misc_feature             1..36
                         note = Synthetic Polynucleotide
source                   1..36
                         mol_type = other DNA
                         organism = synthetic construct
SEQUENCE: 53
tggtgatgat gaccggtcag tcacccccaa gctgtg                               36

SEQ ID NO: 54            moltype = DNA   length = 36
FEATURE                  Location/Qualifiers
misc_feature             1..36
                         note = Synthetic Polynucleotide
source                   1..36
                         mol_type = other DNA
                         organism = synthetic construct
SEQUENCE: 54
cacagcttgg gggtgactga ccggtcatca tcacca                               36

SEQ ID NO: 55            moltype = DNA   length = 40
FEATURE                  Location/Qualifiers
misc_feature             1..40
                         note = Synthetic Polynucleotide
source                   1..40
                         mol_type = other DNA
                         organism = synthetic construct
SEQUENCE: 55
cttttgacta gttgggatcc catggtggcg gctctcccta                           40

SEQ ID NO: 56            moltype = DNA   length = 26
FEATURE                  Location/Qualifiers
misc_feature             1..26
                         note = Synthetic Polynucleotide
source                   1..26
                         mol_type = other DNA
                         organism = synthetic construct
SEQUENCE: 56
acacccctcg aacttcacct cggcgg                                          26

SEQ ID NO: 57            moltype = DNA   length = 26
FEATURE                  Location/Qualifiers
misc_feature             1..26
                         note = Synthetic Polynucleotide
source                   1..26
                         mol_type = other DNA
                         organism = synthetic construct
SEQUENCE: 57
```

-continued

```
acaccgtcgc cctcgaactt cacctg                                              26

SEQ ID NO: 58          moltype = DNA  length = 26
FEATURE                Location/Qualifiers
misc_feature           1..26
                       note = Synthetic Polynucleotide
source                 1..26
                       mol_type = other DNA
                       organism = synthetic construct
SEQUENCE: 58
acacccagct cgatgcggtt caccag                                              26

SEQ ID NO: 59          moltype = DNA  length = 26
FEATURE                Location/Qualifiers
misc_feature           1..26
                       note = Synthetic Polynucleotide
source                 1..26
                       mol_type = other DNA
                       organism = synthetic construct
SEQUENCE: 59
acaccggtga accgcatcga gctgag                                              26

SEQ ID NO: 60          moltype = DNA  length = 26
FEATURE                Location/Qualifiers
misc_feature           1..26
                       note = Synthetic Polynucleotide
source                 1..26
                       mol_type = other DNA
                       organism = synthetic construct
SEQUENCE: 60
acaccgctga agggcatcga cttcag                                              26

SEQ ID NO: 61          moltype = DNA  length = 26
FEATURE                Location/Qualifiers
misc_feature           1..26
                       note = Synthetic Polynucleotide
source                 1..26
                       mol_type = other DNA
                       organism = synthetic construct
SEQUENCE: 61
acaccggcat cgacttcaag gaggag                                              26

SEQ ID NO: 62          moltype = DNA  length = 26
FEATURE                Location/Qualifiers
misc_feature           1..26
                       note = Synthetic Polynucleotide
source                 1..26
                       mol_type = other DNA
                       organism = synthetic construct
SEQUENCE: 62
acacccaagg aggacggcaa catccg                                              26

SEQ ID NO: 63          moltype = DNA  length = 26
FEATURE                Location/Qualifiers
misc_feature           1..26
                       note = Synthetic Polynucleotide
source                 1..26
                       mol_type = other DNA
                       organism = synthetic construct
SEQUENCE: 63
acaccaccat cttcttcaag gacgag                                              26

SEQ ID NO: 64          moltype = DNA  length = 26
FEATURE                Location/Qualifiers
misc_feature           1..26
                       note = Synthetic Polynucleotide
source                 1..26
                       mol_type = other DNA
                       organism = synthetic construct
SEQUENCE: 64
acacccaact acaagacccg cgccgg                                              26

SEQ ID NO: 65          moltype = DNA  length = 26
FEATURE                Location/Qualifiers
misc_feature           1..26
                       note = Synthetic Polynucleotide
source                 1..26
                       mol_type = other DNA
                       organism = synthetic construct
```

-continued

```
SEQUENCE: 65
acaccccgcg ccgaggtgaa gttcgg                                                      26

SEQ ID NO: 66             moltype = DNA  length = 26
FEATURE                   Location/Qualifiers
misc_feature              1..26
                          note = Synthetic Polynucleotide
source                    1..26
                          mol_type = other DNA
                          organism = synthetic construct
SEQUENCE: 66
acaccgaagt tcgagggcga cacccg                                                      26

SEQ ID NO: 67             moltype = DNA  length = 26
FEATURE                   Location/Qualifiers
misc_feature              1..26
                          note = Synthetic Polynucleotide
source                    1..26
                          mol_type = other DNA
                          organism = synthetic construct
SEQUENCE: 67
acaccttcga acttcacctc ggcgcg                                                      26

SEQ ID NO: 68             moltype = DNA  length = 26
FEATURE                   Location/Qualifiers
misc_feature              1..26
                          note = Synthetic Polynucleotide
source                    1..26
                          mol_type = other DNA
                          organism = synthetic construct
SEQUENCE: 68
acacctcagc tcgatgcggt tcaccg                                                      26

SEQ ID NO: 69             moltype = DNA  length = 26
FEATURE                   Location/Qualifiers
misc_feature              1..26
                          note = Synthetic Polynucleotide
source                    1..26
                          mol_type = other DNA
                          organism = synthetic construct
SEQUENCE: 69
acacccgatg cccttcagct cgatgg                                                      26

SEQ ID NO: 70             moltype = DNA  length = 26
FEATURE                   Location/Qualifiers
misc_feature              1..26
                          note = Synthetic Polynucleotide
source                    1..26
                          mol_type = other DNA
                          organism = synthetic construct
SEQUENCE: 70
aaaaccgccg aggtgaagtt cgaggg                                                      26

SEQ ID NO: 71             moltype = DNA  length = 26
FEATURE                   Location/Qualifiers
misc_feature              1..26
                          note = Synthetic Polynucleotide
source                    1..26
                          mol_type = other DNA
                          organism = synthetic construct
SEQUENCE: 71
aaaacaggtg aagttcgagg gcgacg                                                      26

SEQ ID NO: 72             moltype = DNA  length = 26
FEATURE                   Location/Qualifiers
misc_feature              1..26
                          note = Synthetic Polynucleotide
source                    1..26
                          mol_type = other DNA
                          organism = synthetic construct
SEQUENCE: 72
aaaactggtg aaccgcatcg agctgg                                                      26

SEQ ID NO: 73             moltype = DNA  length = 26
FEATURE                   Location/Qualifiers
misc_feature              1..26
                          note = Synthetic Polynucleotide
source                    1..26
                          mol_type = other DNA
```

```
                         organism = synthetic construct
SEQUENCE: 73
aaaaactcagc tcgatgcggt tcaccg                                        26

SEQ ID NO: 74           moltype = DNA   length = 26
FEATURE                 Location/Qualifiers
misc_feature            1..26
                        note = Synthetic Polynucleotide
source                  1..26
                        mol_type = other DNA
                        organism = synthetic construct
SEQUENCE: 74
aaaactgaag tcgatgccct tcagcg                                         26

SEQ ID NO: 75           moltype = DNA   length = 26
FEATURE                 Location/Qualifiers
misc_feature            1..26
                        note = Synthetic Polynucleotide
source                  1..26
                        mol_type = other DNA
                        organism = synthetic construct
SEQUENCE: 75
aaaactcctc cttgaagtcg atgccg                                         26

SEQ ID NO: 76           moltype = DNA   length = 26
FEATURE                 Location/Qualifiers
misc_feature            1..26
                        note = Synthetic Polynucleotide
source                  1..26
                        mol_type = other DNA
                        organism = synthetic construct
SEQUENCE: 76
aaaacggatg ttgccgtcct ccttgg                                         26

SEQ ID NO: 77           moltype = DNA   length = 26
FEATURE                 Location/Qualifiers
misc_feature            1..26
                        note = Synthetic Polynucleotide
source                  1..26
                        mol_type = other DNA
                        organism = synthetic construct
SEQUENCE: 77
aaaactcgtc cttgaagaag atggtg                                         26

SEQ ID NO: 78           moltype = DNA   length = 26
FEATURE                 Location/Qualifiers
misc_feature            1..26
                        note = Synthetic Polynucleotide
source                  1..26
                        mol_type = other DNA
                        organism = synthetic construct
SEQUENCE: 78
aaaaccggcg cgggtcttgt agttgg                                         26

SEQ ID NO: 79           moltype = DNA   length = 26
FEATURE                 Location/Qualifiers
misc_feature            1..26
                        note = Synthetic Polynucleotide
source                  1..26
                        mol_type = other DNA
                        organism = synthetic construct
SEQUENCE: 79
aaaaccgaac ttcacctcgg cgcggg                                         26

SEQ ID NO: 80           moltype = DNA   length = 26
FEATURE                 Location/Qualifiers
misc_feature            1..26
                        note = Synthetic Polynucleotide
source                  1..26
                        mol_type = other DNA
                        organism = synthetic construct
SEQUENCE: 80
aaaacgggtg tcgccctcga acttcg                                         26

SEQ ID NO: 81           moltype = DNA   length = 26
FEATURE                 Location/Qualifiers
misc_feature            1..26
                        note = Synthetic Polynucleotide
source                  1..26
```

-continued

```
                              mol_type = other DNA
                              organism = synthetic construct
SEQUENCE: 81
aaaacgcgcc gaggtgaagt tcgaag                                          26

SEQ ID NO: 82          moltype = DNA   length = 26
FEATURE                Location/Qualifiers
misc_feature           1..26
                              note = Synthetic Polynucleotide
source                 1..26
                              mol_type = other DNA
                              organism = synthetic construct
SEQUENCE: 82
aaaacggtga accgcatcga gctgag                                          26

SEQ ID NO: 83          moltype = DNA   length = 26
FEATURE                Location/Qualifiers
misc_feature           1..26
                              note = Synthetic Polynucleotide
source                 1..26
                              mol_type = other DNA
                              organism = synthetic construct
SEQUENCE: 83
aaaaccatcg agctgaaggg catcgg                                          26

SEQ ID NO: 84          moltype = DNA   length = 26
FEATURE                Location/Qualifiers
misc_feature           1..26
                              note = Synthetic Polynucleotide
source                 1..26
                              mol_type = other DNA
                              organism = synthetic construct
SEQUENCE: 84
acacctggcc tgcttgctag acttgg                                          26

SEQ ID NO: 85          moltype = DNA   length = 26
FEATURE                Location/Qualifiers
misc_feature           1..26
                              note = Synthetic Polynucleotide
source                 1..26
                              mol_type = other DNA
                              organism = synthetic construct
SEQUENCE: 85
acaccgcaga tgtagtgttt ccacag                                          26

SEQ ID NO: 86          moltype = DNA   length = 26
FEATURE                Location/Qualifiers
misc_feature           1..26
                              note = Synthetic Polynucleotide
source                 1..26
                              mol_type = other DNA
                              organism = synthetic construct
SEQUENCE: 86
acacccttgc cccacagggc agtaag                                          26

SEQ ID NO: 87          moltype = DNA   length = 26
FEATURE                Location/Qualifiers
misc_feature           1..26
                              note = Synthetic Polynucleotide
source                 1..26
                              mol_type = other DNA
                              organism = synthetic construct
SEQUENCE: 87
acaccgagtc cgagcagaag aagaag                                          26

SEQ ID NO: 88          moltype = DNA   length = 26
FEATURE                Location/Qualifiers
misc_feature           1..26
                              note = Synthetic Polynucleotide
source                 1..26
                              mol_type = other DNA
                              organism = synthetic construct
SEQUENCE: 88
acaccgggtg gggggagttt gctccg                                          26

SEQ ID NO: 89          moltype = DNA   length = 26
FEATURE                Location/Qualifiers
misc_feature           1..26
                              note = Synthetic Polynucleotide
```

-continued

```
source                    1..26
                          mol_type = other DNA
                          organism = synthetic construct
SEQUENCE: 89
aaaaccaagt ctagcaagca ggccag                                     26

SEQ ID NO: 90             moltype = DNA   length = 26
FEATURE                   Location/Qualifiers
misc_feature              1..26
                          note = Synthetic Polynucleotide
source                    1..26
                          mol_type = other DNA
                          organism = synthetic construct
SEQUENCE: 90
aaaactgtgg aaacactaca tctgcg                                     26

SEQ ID NO: 91             moltype = DNA   length = 26
FEATURE                   Location/Qualifiers
misc_feature              1..26
                          note = Synthetic Polynucleotide
source                    1..26
                          mol_type = other DNA
                          organism = synthetic construct
SEQUENCE: 91
aaaacttctt cttctgctcg gactcg                                     26

SEQ ID NO: 92             moltype = DNA   length = 26
FEATURE                   Location/Qualifiers
misc_feature              1..26
                          note = Synthetic Polynucleotide
source                    1..26
                          mol_type = other DNA
                          organism = synthetic construct
SEQUENCE: 92
aaaacttact gccctgtggg gcaagg                                     26

SEQ ID NO: 93             moltype = DNA   length = 26
FEATURE                   Location/Qualifiers
misc_feature              1..26
                          note = Synthetic Polynucleotide
source                    1..26
                          mol_type = other DNA
                          organism = synthetic construct
SEQUENCE: 93
aaaacggagc aaactccccc cacccg                                     26

SEQ ID NO: 94             moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 94
aggaaagaac atgtgagcaa aag                                        23

SEQ ID NO: 95             moltype = DNA   length = 18
FEATURE                   Location/Qualifiers
misc_feature              1..18
                          note = Synthetic Polynucleotide
source                    1..18
                          mol_type = other DNA
                          organism = synthetic construct
SEQUENCE: 95
cagcgagtca gtgagcga                                              18

SEQ ID NO: 96             moltype = DNA   length = 22
FEATURE                   Location/Qualifiers
misc_feature              1..22
                          note = Synthetic Polynucleotide
source                    1..22
                          mol_type = other DNA
                          organism = synthetic construct
SEQUENCE: 96
ctgtacaaaa aagcaggctt ta                                         22

SEQ ID NO: 97             moltype = DNA   length = 39
FEATURE                   Location/Qualifiers
misc_feature              1..39
```

```
                              note = Synthetic Polynucleotide
source                        1..39
                              mol_type = other DNA
                              organism = synthetic construct
SEQUENCE: 97
aacgtaggtc tctaccgctg tacaaaaaag caggcttta                                    39

SEQ ID NO: 98                 moltype = DNA  length = 83
FEATURE                       Location/Qualifiers
misc_feature                  1..83
                              note = Synthetic Polynucleotide
source                        1..83
                              mol_type = other DNA
                              organism = synthetic construct
SEQUENCE: 98
aaaaaaagca ccgactcggt gccacttttt caagttgata acggactagc cttattttaa   60
cttgctattt ctagctctaa aac                                           83

SEQ ID NO: 99                 moltype = DNA  length = 60
FEATURE                       Location/Qualifiers
misc_feature                  1..60
                              note = Synthetic Polynucleotide
source                        1..60
                              mol_type = other DNA
                              organism = synthetic construct
SEQUENCE: 99
ttgctatttc tagctctaaa accgccgagg tgaagttcga ggggtgtttc gtcctttcca   60

SEQ ID NO: 100                moltype = DNA  length = 60
FEATURE                       Location/Qualifiers
misc_feature                  1..60
                              note = Synthetic Polynucleotide
source                        1..60
                              mol_type = other DNA
                              organism = synthetic construct
SEQUENCE: 100
ttgctatttc tagctctaaa acaggtgaag ttcgagggcg acggtgtttc gtcctttcca   60

SEQ ID NO: 101                moltype = DNA  length = 60
FEATURE                       Location/Qualifiers
misc_feature                  1..60
                              note = Synthetic Polynucleotide
source                        1..60
                              mol_type = other DNA
                              organism = synthetic construct
SEQUENCE: 101
ttgctatttc tagctctaaa actggtgaac cgcatcgagc tgggtgtttc gtcctttcca   60

SEQ ID NO: 102                moltype = DNA  length = 60
FEATURE                       Location/Qualifiers
misc_feature                  1..60
                              note = Synthetic Polynucleotide
source                        1..60
                              mol_type = other DNA
                              organism = synthetic construct
SEQUENCE: 102
ttgctatttc tagctctaaa actcagctcg atgcggttca ccggtgtttc gtcctttcca   60

SEQ ID NO: 103                moltype = DNA  length = 60
FEATURE                       Location/Qualifiers
misc_feature                  1..60
                              note = Synthetic Polynucleotide
source                        1..60
                              mol_type = other DNA
                              organism = synthetic construct
SEQUENCE: 103
ttgctatttc tagctctaaa actgaagtcg atgcccttca gcggtgtttc gtcctttcca   60

SEQ ID NO: 104                moltype = DNA  length = 60
FEATURE                       Location/Qualifiers
misc_feature                  1..60
                              note = Synthetic Polynucleotide
source                        1..60
                              mol_type = other DNA
                              organism = synthetic construct
SEQUENCE: 104
ttgctatttc tagctctaaa actcctcctt gaagtcgatg ccggtgtttc gtcctttcca   60

SEQ ID NO: 105                moltype = DNA  length = 60
```

```
FEATURE               Location/Qualifiers
misc_feature          1..60
                      note = Synthetic Polynucleotide
source                1..60
                      mol_type = other DNA
                      organism = synthetic construct
SEQUENCE: 105
ttgctatttc tagctctaaa acggatgttg ccgtcctcct tgggtgtttc gtcctttcca   60

SEQ ID NO: 106        moltype = DNA   length = 60
FEATURE               Location/Qualifiers
misc_feature          1..60
                      note = Synthetic Polynucleotide
source                1..60
                      mol_type = other DNA
                      organism = synthetic construct
SEQUENCE: 106
ttgctatttc tagctctaaa acgcttgagg gagatgagga ctggtgtttc gtcctttcca   60

SEQ ID NO: 107        moltype = DNA   length = 60
FEATURE               Location/Qualifiers
misc_feature          1..60
                      note = Synthetic Polynucleotide
source                1..60
                      mol_type = other DNA
                      organism = synthetic construct
SEQUENCE: 107
ttgctatttc tagctctaaa acatgactgt gaagagcttc acggtgtttc gtcctttcca   60

SEQ ID NO: 108        moltype = DNA   length = 60
FEATURE               Location/Qualifiers
misc_feature          1..60
                      note = Synthetic Polynucleotide
source                1..60
                      mol_type = other DNA
                      organism = synthetic construct
SEQUENCE: 108
ttgctatttc tagctctaaa acgaggacaa agtacaaacg gcggtgtttc gtcctttcca   60

SEQ ID NO: 109        moltype = DNA   length = 60
FEATURE               Location/Qualifiers
misc_feature          1..60
                      note = Synthetic Polynucleotide
source                1..60
                      mol_type = other DNA
                      organism = synthetic construct
SEQUENCE: 109
ttgctatttc tagctctaaa acgaaccgga ggacaaagta caggtgtttc gtcctttcca   60

SEQ ID NO: 110        moltype = DNA   length = 60
FEATURE               Location/Qualifiers
misc_feature          1..60
                      note = Synthetic Polynucleotide
source                1..60
                      mol_type = other DNA
                      organism = synthetic construct
SEQUENCE: 110
ttgctatttc tagctctaaa accaccacca acttcatcca cgggtgtttc gtcctttcca   60

SEQ ID NO: 111        moltype = DNA   length = 60
FEATURE               Location/Qualifiers
misc_feature          1..60
                      note = Synthetic Polynucleotide
source                1..60
                      mol_type = other DNA
                      organism = synthetic construct
SEQUENCE: 111
ttgctatttc tagctctaaa acgggcctca ccaccaactt caggtgtttc gtcctttcca   60

SEQ ID NO: 112        moltype = DNA   length = 60
FEATURE               Location/Qualifiers
misc_feature          1..60
                      note = Synthetic Polynucleotide
source                1..60
                      mol_type = other DNA
                      organism = synthetic construct
SEQUENCE: 112
ttgctatttc tagctctaaa acgcccaggg cctcaccacc aaggtgtttc gtcctttcca   60
```

-continued

```
SEQ ID NO: 113          moltype = DNA   length = 60
FEATURE                 Location/Qualifiers
misc_feature            1..60
                        note = Synthetic Polynucleotide
source                  1..60
                        mol_type = other DNA
                        organism = synthetic construct
SEQUENCE: 113
ttgctatttc tagctctaaa acacctgccc agggcctcac caggtgtttc gtcctttcca   60

SEQ ID NO: 114          moltype = DNA   length = 60
FEATURE                 Location/Qualifiers
misc_feature            1..60
                        note = Synthetic Polynucleotide
source                  1..60
                        mol_type = other DNA
                        organism = synthetic construct
SEQUENCE: 114
ttgctatttc tagctctaaa actgatacca acctgcccag ggggtgtttc gtcctttcca   60

SEQ ID NO: 115          moltype = DNA   length = 60
FEATURE                 Location/Qualifiers
misc_feature            1..60
                        note = Synthetic Polynucleotide
source                  1..60
                        mol_type = other DNA
                        organism = synthetic construct
SEQUENCE: 115
ttgctatttc tagctctaaa actaaacctg tcttgtaacc ttggtgtttc gtcctttcca   60

SEQ ID NO: 116          moltype = DNA   length = 60
FEATURE                 Location/Qualifiers
misc_feature            1..60
                        note = Synthetic Polynucleotide
source                  1..60
                        mol_type = other DNA
                        organism = synthetic construct
SEQUENCE: 116
ttgctatttc tagctctaaa acgctctggc taaagaggga atggtgtttc gtcctttcca   60

SEQ ID NO: 117          moltype = DNA   length = 60
FEATURE                 Location/Qualifiers
misc_feature            1..60
                        note = Synthetic Polynucleotide
source                  1..60
                        mol_type = other DNA
                        organism = synthetic construct
SEQUENCE: 117
ttgctatttc tagctctaaa accggctctg gctaaagagg gaggtgtttc gtcctttcca   60

SEQ ID NO: 118          moltype = DNA   length = 60
FEATURE                 Location/Qualifiers
misc_feature            1..60
                        note = Synthetic Polynucleotide
source                  1..60
                        mol_type = other DNA
                        organism = synthetic construct
SEQUENCE: 118
ttgctatttc tagctctaaa actctgcaca ccccggctct ggggtgtttc gtcctttcca   60

SEQ ID NO: 119          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 119
tacggcaagc tgaccctgaa                                               20

SEQ ID NO: 120          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 120
gtccatgccg agagtgatcc                                               20
```

-continued

```
SEQ ID NO: 121          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 121
gccaggggct gttatcttgg                                                    20

SEQ ID NO: 122          moltype = DNA  length = 21
FEATURE                 Location/Qualifiers
misc_feature            1..21
                        note = Synthetic Polynucleotide
source                  1..21
                        mol_type = other DNA
                        organism = synthetic construct
SEQUENCE: 122
atgcacagaa gcacaggttg a                                                  21

SEQ ID NO: 123          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 123
ctgtgtcctc ttcctgccct                                                    20

SEQ ID NO: 124          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 124
ctctccgagg agaaggccaa                                                    20

SEQ ID NO: 125          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 125
ggtagaccac cagcagccta                                                    20

SEQ ID NO: 126          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 126
cagtgccaga agagccaagg                                                    20

SEQ ID NO: 127          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 127
ccacacagct tcccgttctc                                                    20

SEQ ID NO: 128          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 128
```

```
gagagccgtt ccctctttgc                                               20

SEQ ID NO: 129          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 129
cctccccatt ggcctgcttc                                               20

SEQ ID NO: 130          moltype = DNA   length = 21
FEATURE                 Location/Qualifiers
misc_feature            1..21
                        note = Synthetic Polynucleotide
source                  1..21
                        mol_type = other DNA
                        organism = synthetic construct
SEQUENCE: 130
tcgtcctgct ctcacttaga c                                             21

SEQ ID NO: 131          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 131
ttttgtggct tggccccagt                                               20

SEQ ID NO: 132          moltype = DNA   length = 21
FEATURE                 Location/Qualifiers
misc_feature            1..21
                        note = Synthetic Polynucleotide
source                  1..21
                        mol_type = other DNA
                        organism = synthetic construct
SEQUENCE: 132
tgcagtctca tgacttggcc t                                             21

SEQ ID NO: 133          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 133
ttctgagggc tgctacctgt                                               20

SEQ ID NO: 134          moltype = DNA   length = 22
FEATURE                 Location/Qualifiers
misc_feature            1..22
                        note = Synthetic Polynucleotide
source                  1..22
                        mol_type = other DNA
                        organism = synthetic construct
SEQUENCE: 134
acatgaagca actccagtcc ca                                            22

SEQ ID NO: 135          moltype = DNA   length = 22
FEATURE                 Location/Qualifiers
misc_feature            1..22
                        note = Synthetic Polynucleotide
source                  1..22
                        mol_type = other DNA
                        organism = synthetic construct
SEQUENCE: 135
agcagaccca ctgagtcaac tg                                            22

SEQ ID NO: 136          moltype = DNA   length = 19
FEATURE                 Location/Qualifiers
misc_feature            1..19
                        note = Synthetic Polynucleotide
source                  1..19
                        mol_type = other DNA
                        organism = synthetic construct
```

```
SEQUENCE: 136
cccgccacag tcgtgtcat                                                      19

SEQ ID NO: 137          moltype = DNA  length = 18
FEATURE                 Location/Qualifiers
misc_feature            1..18
                        note = Synthetic Polynucleotide
source                  1..18
                        mol_type = other DNA
                        organism = synthetic construct
SEQUENCE: 137
cgccccggta caaggtga                                                       18

SEQ ID NO: 138          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 138
gtaccgtaca ttgtaggatg ttt                                                 23

SEQ ID NO: 139          moltype = DNA  length = 21
FEATURE                 Location/Qualifiers
misc_feature            1..21
                        note = Synthetic Polynucleotide
source                  1..21
                        mol_type = other DNA
                        organism = synthetic construct
SEQUENCE: 139
cctcatctcc ctcaagcagg c                                                   21

SEQ ID NO: 140          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 140
attctgctct tgaggttatt tgt                                                 23

SEQ ID NO: 141          moltype = DNA  length = 24
FEATURE                 Location/Qualifiers
misc_feature            1..24
                        note = Synthetic Polynucleotide
source                  1..24
                        mol_type = other DNA
                        organism = synthetic construct
SEQUENCE: 141
cacctctgcc tcaagagcag aaaa                                                24

SEQ ID NO: 142          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 142
tgtgtgtgtg tgtgtgtagg act                                                 23

SEQ ID NO: 143          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 143
tcatctgtgc ccctccctcc                                                     20

SEQ ID NO: 144          moltype = DNA  length = 19
FEATURE                 Location/Qualifiers
misc_feature            1..19
                        note = Synthetic Polynucleotide
source                  1..19
                        mol_type = other DNA
```

```
                            organism = synthetic construct
SEQUENCE: 144
cgagaaggag gtgcaggag                                              19

SEQ ID NO: 145       moltype = DNA  length = 20
FEATURE              Location/Qualifiers
misc_feature         1..20
                     note = Synthetic Polynucleotide
source               1..20
                     mol_type = other DNA
                     organism = synthetic construct
SEQUENCE: 145
cgggagctgt tcagaggctg                                             20

SEQ ID NO: 146       moltype = DNA  length = 20
FEATURE              Location/Qualifiers
misc_feature         1..20
                     note = Synthetic Polynucleotide
source               1..20
                     mol_type = other DNA
                     organism = synthetic construct
SEQUENCE: 146
ctcacctggg cgagaaaggt                                             20

SEQ ID NO: 147       moltype = DNA  length = 24
FEATURE              Location/Qualifiers
misc_feature         1..24
                     note = Synthetic Polynucleotide
source               1..24
                     mol_type = other DNA
                     organism = synthetic construct
SEQUENCE: 147
aaaactcaaa gaaatgccca atca                                        24

SEQ ID NO: 148       moltype = DNA  length = 20
FEATURE              Location/Qualifiers
misc_feature         1..20
                     note = Synthetic Polynucleotide
source               1..20
                     mol_type = other DNA
                     organism = synthetic construct
SEQUENCE: 148
agacgctgct cgctccattc                                             20

SEQ ID NO: 149       moltype = DNA  length = 22
FEATURE              Location/Qualifiers
misc_feature         1..22
                     note = Synthetic Polynucleotide
source               1..22
                     mol_type = other DNA
                     organism = synthetic construct
SEQUENCE: 149
acaggcatga atcactgcac ct                                          22

SEQ ID NO: 150       moltype = DNA  length = 21
FEATURE              Location/Qualifiers
misc_feature         1..21
                     note = Synthetic Polynucleotide
source               1..21
                     mol_type = other DNA
                     organism = synthetic construct
SEQUENCE: 150
gcggcaactt cagacaaccg a                                           21

SEQ ID NO: 151       moltype = DNA  length = 18
FEATURE              Location/Qualifiers
misc_feature         1..18
                     note = Synthetic Polynucleotide
source               1..18
                     mol_type = other DNA
                     organism = synthetic construct
SEQUENCE: 151
gacccagggg caccagtt                                               18

SEQ ID NO: 152       moltype = DNA  length = 25
FEATURE              Location/Qualifiers
misc_feature         1..25
                     note = Synthetic Polynucleotide
source               1..25
```

-continued

```
                              mol_type = other DNA
                              organism = synthetic construct
SEQUENCE: 152
ctgccttcat tgcttaaaag tggat                                        25

SEQ ID NO: 153          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 153
acagttgaag gaaggaaaca tgc                                          23

SEQ ID NO: 154          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 154
gctgcatttg cccatttcca                                              20

SEQ ID NO: 155          moltype = DNA   length = 21
FEATURE                 Location/Qualifiers
misc_feature            1..21
                        note = Synthetic Polynucleotide
source                  1..21
                        mol_type = other DNA
                        organism = synthetic construct
SEQUENCE: 155
gttgggggag gaggagctta t                                            21

SEQ ID NO: 156          moltype = DNA   length = 25
FEATURE                 Location/Qualifiers
misc_feature            1..25
                        note = Synthetic Polynucleotide
source                  1..25
                        mol_type = other DNA
                        organism = synthetic construct
SEQUENCE: 156
ctaagagcta taagggcaaa tgact                                        25

SEQ ID NO: 157          moltype = DNA   length = 152
FEATURE                 Location/Qualifiers
misc_feature            1..152
                        note = Synthetic Polynucleotide
source                  1..152
                        mol_type = other DNA
                        organism = synthetic construct
SEQUENCE: 157
ttctgagggc tgctacctgt acatctgcac aagattgcct ttactccatg cctttcttct   60
tctgctctaa ctctgacaat ctgtcttgcc atgccataag cccctattct ttctgtaacc  120
ccaagatggt ataaaagcat caatgattgg gc                                152

SEQ ID NO: 158          moltype = DNA   length = 155
FEATURE                 Location/Qualifiers
misc_feature            1..155
                        note = Synthetic Polynucleotide
source                  1..155
                        mol_type = other DNA
                        organism = synthetic construct
SEQUENCE: 158
aaaactcaaa gaaatgccca atcattgatg cttttatacc atcttggggt tacagaaaga   60
ataggggctt atggcatggc aagacagatt gtcagagtta gagcagaaga agaaaggcat  120
ggagtaaagg caatcttgtg cagatgtaca ggtaa                             155

SEQ ID NO: 159          moltype = DNA   length = 155
FEATURE                 Location/Qualifiers
misc_feature            1..155
                        note = Synthetic Polynucleotide
source                  1..155
                        mol_type = other DNA
                        organism = synthetic construct
SEQUENCE: 159
ttacctgtac atctgcacaa gattgccttt actccatgcc tttcttcttc tgctctaact   60
ctgacaatct gtcttgccat gccataagcc cctattcttt ctgtaacccc aagatggtat  120
```

-continued

```
aaaagcatca atgattgggc atttctttga gtttt                                  155

SEQ ID NO: 160          moltype = DNA   length = 152
FEATURE                 Location/Qualifiers
misc_feature            1..152
                        note = Synthetic Polynucleotide
source                  1..152
                        mol_type = other DNA
                        organism = synthetic construct
SEQUENCE: 160
ttctgagggc tgctacctgt acatctgcac aagattgcct ttactccatg cctttcttct       60
tctgctctaa ctctgacaat ctgtcttgcc atgccataag cccctattct ttctgtaacc      120
ccaagatggt ataaaagcat caatgattgg gc                                    152

SEQ ID NO: 161          moltype = DNA   length = 167
FEATURE                 Location/Qualifiers
misc_feature            1..167
                        note = Synthetic Polynucleotide
source                  1..167
                        mol_type = other DNA
                        organism = synthetic construct
SEQUENCE: 161
ttctgagggc tgctacctgt acatctgcac aagattgcct ttactccatg cctttcttct       60
tctgctctaa ctctgacaat ctgtcttgcc atgccataag cccctattct ttctgtaacc      120
ccaagatggt ataaaagcat caatgattgg gcatttcttt gagtttt                    167

SEQ ID NO: 162          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 162
ggcctgcttc gtggcaatgc                                                    20

SEQ ID NO: 163          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 163
acctgggcca gggagggagg                                                    20

SEQ ID NO: 164          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 164
ctcacttaga ctttctctcc                                                    20

SEQ ID NO: 165          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 165
ctcggagtct agctcctgca                                                    20

SEQ ID NO: 166          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 166
tggccccagt ctctcttcta                                                    20

SEQ ID NO: 167          moltype = DNA   length = 20
FEATURE                 Location/Qualifiers
misc_feature            1..20
```

-continued

```
                          note = Synthetic Polynucleotide
source                    1..20
                          mol_type = other DNA
                          organism = synthetic construct
SEQUENCE: 167
cagcctctga acagctcccg                                                 20

SEQ ID NO: 168           moltype = DNA  length = 20
FEATURE                  Location/Qualifiers
misc_feature             1..20
                          note = Synthetic Polynucleotide
source                    1..20
                          mol_type = other DNA
                          organism = synthetic construct
SEQUENCE: 168
tgacttggcc tttgtaggaa                                                 20

SEQ ID NO: 169           moltype = DNA  length = 20
FEATURE                  Location/Qualifiers
misc_feature             1..20
                          note = Synthetic Polynucleotide
source                    1..20
                          mol_type = other DNA
                          organism = synthetic construct
SEQUENCE: 169
gaggctactg aaacataagt                                                 20

SEQ ID NO: 170           moltype = DNA  length = 20
FEATURE                  Location/Qualifiers
misc_feature             1..20
                          note = Synthetic Polynucleotide
source                    1..20
                          mol_type = other DNA
                          organism = synthetic construct
SEQUENCE: 170
tgctacctgt acatctgcac                                                 20

SEQ ID NO: 171           moltype = DNA  length = 20
FEATURE                  Location/Qualifiers
misc_feature             1..20
                          note = Synthetic Polynucleotide
source                    1..20
                          mol_type = other DNA
                          organism = synthetic construct
SEQUENCE: 171
catcaatgat tgggcatttc                                                 20

SEQ ID NO: 172           moltype = DNA  length = 20
FEATURE                  Location/Qualifiers
misc_feature             1..20
                          note = Synthetic Polynucleotide
source                    1..20
                          mol_type = other DNA
                          organism = synthetic construct
SEQUENCE: 172
actccagtcc caaatatgta                                                 20

SEQ ID NO: 173           moltype = DNA  length = 20
FEATURE                  Location/Qualifiers
misc_feature             1..20
                          note = Synthetic Polynucleotide
source                    1..20
                          mol_type = other DNA
                          organism = synthetic construct
SEQUENCE: 173
actaggggc gctcggccac                                                  20

SEQ ID NO: 174           moltype = DNA  length = 20
FEATURE                  Location/Qualifiers
misc_feature             1..20
                          note = Synthetic Polynucleotide
source                    1..20
                          mol_type = other DNA
                          organism = synthetic construct
SEQUENCE: 174
ctgagtcaac tgtaagcatt                                                 20

SEQ ID NO: 175           moltype = DNA  length = 20
FEATURE                  Location/Qualifiers
```

-continued

```
misc_feature            1..20
                        note = Synthetic Polynucleotide
source                  1..20
                        mol_type = other DNA
                        organism = synthetic construct
SEQUENCE: 175
ggccaggtgc agtgattcat                                              20

SEQ ID NO: 176          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 176
tcgtgtcatc ttgtttgtgc                                              20

SEQ ID NO: 177          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 177
ggcagagccc agcggacact                                              20

SEQ ID NO: 178          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 178
caaggtgagc ctgggtctgt                                              20

SEQ ID NO: 179          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 179
atcactgccc aagaagtgca                                              20

SEQ ID NO: 180          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 180
ttgtaggatg tttagcagca                                              20

SEQ ID NO: 181          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 181
acttgctctc tttagagaac                                              20

SEQ ID NO: 182          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 182
ctcaagcagg ccccgctggt                                              20

SEQ ID NO: 183          moltype = DNA  length = 20
```

-continued

```
FEATURE             Location/Qualifiers
misc_feature        1..20
                    note = Synthetic Polynucleotide
source              1..20
                    mol_type = other DNA
                    organism = synthetic construct
SEQUENCE: 183
ttttggacca aacctttttg                                             20

SEQ ID NO: 184      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 184
tgaggttatt tgtccattgt                                             20

SEQ ID NO: 185      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 185
taaggggagt atttacacca                                             20

SEQ ID NO: 186      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 186
tcaagagcag aaaatgtgac                                             20

SEQ ID NO: 187      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 187
cttgcaggga ccttctgatt                                             20

SEQ ID NO: 188      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 188
tgtgtgtagg actaaactct                                             20

SEQ ID NO: 189      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 189
gatagcagta tgaccttggg                                             20

SEQ ID NO: 190      moltype = DNA   length = 23
FEATURE             Location/Qualifiers
misc_feature        1..23
                    note = Synthetic Polynucleotide
source              1..23
                    mol_type = other DNA
                    organism = synthetic construct
SEQUENCE: 190
gagtccgagc agaagaagaa ggg                                         23
```

```
SEQ ID NO: 191          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 191
gaggccgagc agaagaaaga cgg                                         23

SEQ ID NO: 192          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 192
gagtcctagc aggagaagaa gag                                         23

SEQ ID NO: 193          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 193
gagtctaagc agaagaagaa gag                                         23

SEQ ID NO: 194          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 194
gagttagagc agaagaagaa agg                                         23

SEQ ID NO: 195          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 195
gggtgggggg agtttgctcc tgg                                         23

SEQ ID NO: 196          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 196
ggatggaggg agtttgctcc tgg                                         23

SEQ ID NO: 197          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 197
gggagggtgg agtttgctcc tgg                                         23

SEQ ID NO: 198          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 198
cggggagggg agtttgctcc tgg                                         23
```

```
SEQ ID NO: 199            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 199
ggggagggga agtttgctcc tgg                                        23

SEQ ID NO: 200            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 200
gcagatgtag tgtttccaca ggg                                        23

SEQ ID NO: 201            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 201
acaaatgtag tatttccaca ggg                                        23

SEQ ID NO: 202            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 202
ccagatgtag tattcccaca ggg                                        23

SEQ ID NO: 203            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 203
ctagatgaag tgcttccaca tgg                                        23

SEQ ID NO: 204            moltype = DNA   length = 89
FEATURE                   Location/Qualifiers
source                    1..89
                          mol_type = genomic DNA
                          organism = Homo sapiens
SEQUENCE: 204
ccgcgccgag gtgaagttcg agggcgacac cctggtgaac cgcatcgagc tgaagggcat 60
cgacttcaag gaggacggca acatcctgg                                  89

SEQ ID NO: 205            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 205
ccgcgccgag gtgaagttcg agg                                        23

SEQ ID NO: 206            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 206
ccgaggtgaa gttcgagggc gac                                        23
```

-continued

```
SEQ ID NO: 207            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 207
ccctggtgaa ccgcatcgag ctg                                              23

SEQ ID NO: 208            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 208
ggtgaaccgc atcgagctga agg                                              23

SEQ ID NO: 209            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 209
gctgaagggc atcgacttca agg                                              23

SEQ ID NO: 210            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 210
ggcatcgact tcaaggagga cgg                                              23

SEQ ID NO: 211            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 211
caaggaggac ggcaacatcc tgg                                              23

SEQ ID NO: 212            moltype = DNA   length = 104
FEATURE                   Location/Qualifiers
source                    1..104
                          mol_type = genomic DNA
                          organism = Homo sapiens
SEQUENCE: 212
ggagcgcacc atcttcttca aggacgacgg caactacaag acccgcgccg aggtgaagtt     60
cgagggcgac accctggtga accgcatcga gctgaagggc atcg                      104

SEQ ID NO: 213            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 213
accatcttct tcaaggacga cgg                                              23

SEQ ID NO: 214            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 214
caactacaag acccgcgccg agg                                              23
```

```
SEQ ID NO: 215          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 215
ccgcgccgag gtgaagttcg agg                                             23

SEQ ID NO: 216          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 216
gaagttcgag ggcgacaccc tgg                                             23

SEQ ID NO: 217          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 217
cccgcgccga ggtgaagttc gag                                             23

SEQ ID NO: 218          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 218
cctggtgaac cgcatcgagc tga                                             23

SEQ ID NO: 219          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 219
ccgcatcgag ctgaagggca tcg                                             23

SEQ ID NO: 220          moltype = DNA   length = 68
FEATURE                 Location/Qualifiers
source                  1..68
                        mol_type = genomic DNA
                        organism = Homo sapiens
SEQUENCE: 220
ccccaagtct agcaagcagg ccaaagatgt ctcccgcatg cgctcagtcc tcatctccct  60
caagcagg                                                              68

SEQ ID NO: 221          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 221
ccccaagtct agcaagcagg cca                                             23

SEQ ID NO: 222          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 222
agtcctcatc tccctcaagc agg                                             23
```

-continued

```
SEQ ID NO: 223          moltype = DNA  length = 65
FEATURE                 Location/Qualifiers
source                  1..65
                        mol_type = genomic DNA
                        organism = Homo sapiens
SEQUENCE: 223
ccctgtggaa acactacatc tgcaatatct taatcctact cagtgaagct cttcacagtc   60
attgg                                                               65

SEQ ID NO: 224          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 224
ccctgtggaa acactacatc tgc                                           23

SEQ ID NO: 225          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 225
gtgaagctct tcacagtcat tgg                                           23

SEQ ID NO: 226          moltype = DNA  length = 93
FEATURE                 Location/Qualifiers
misc_feature            1..93
                        note = Synthetic Polynucleotide
source                  1..93
                        mol_type = other DNA
                        organism = synthetic construct
SEQUENCE: 226
ccgttactgc cctgtggggc aaggtgaacg tggatgaagt tggtggtgag gccctgggca   60
ggttggtatc aaggttacaa gacaggttta agg                                93

SEQ ID NO: 227          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 227
ccgttactgc cctgtggggc aag                                           23

SEQ ID NO: 228          moltype = DNA  length = 22
FEATURE                 Location/Qualifiers
misc_feature            1..22
                        note = Synthetic Polynucleotide
source                  1..22
                        mol_type = other DNA
                        organism = synthetic construct
SEQUENCE: 228
cgtggatgaa gttggtggtg gg                                            22

SEQ ID NO: 229          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 229
tgaagttggt ggtgaggccc tgg                                           23

SEQ ID NO: 230          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 230
```

-continued

```
ttggtggtga ggccctgggc agg                                       23

SEQ ID NO: 231         moltype = DNA   length = 23
FEATURE                Location/Qualifiers
misc_feature           1..23
                       note = Synthetic Polynucleotide
source                 1..23
                       mol_type = other DNA
                       organism = synthetic construct
SEQUENCE: 231
tggtgaggcc ctgggcaggt tgg                                        23

SEQ ID NO: 232         moltype = DNA   length = 23
FEATURE                Location/Qualifiers
misc_feature           1..23
                       note = Synthetic Polynucleotide
source                 1..23
                       mol_type = other DNA
                       organism = synthetic construct
SEQUENCE: 232
ccctgggcag gttggtatca agg                                       23

SEQ ID NO: 233         moltype = DNA   length = 23
FEATURE                Location/Qualifiers
misc_feature           1..23
                       note = Synthetic Polynucleotide
source                 1..23
                       mol_type = other DNA
                       organism = synthetic construct
SEQUENCE: 233
aaggttacaa gacaggttta agg                                       23

SEQ ID NO: 234         moltype = DNA   length = 75
FEATURE                Location/Qualifiers
misc_feature           1..75
                       note = Synthetic Polynucleotide
source                 1..75
                       mol_type = other DNA
                       organism = synthetic construct
SEQUENCE: 234
ccctcttct tctgctcgga ctcaggccct tcctcctcca gcttctgccg tttgtacttt   60
gtcctccggt tctgg                                                 75

SEQ ID NO: 235         moltype = DNA   length = 23
FEATURE                Location/Qualifiers
misc_feature           1..23
                       note = Synthetic Polynucleotide
source                 1..23
                       mol_type = other DNA
                       organism = synthetic construct
SEQUENCE: 235
cccttcttct tctgctcgga ctc                                        23

SEQ ID NO: 236         moltype = DNA   length = 23
FEATURE                Location/Qualifiers
misc_feature           1..23
                       note = Synthetic Polynucleotide
source                 1..23
                       mol_type = other DNA
                       organism = synthetic construct
SEQUENCE: 236
gccgtttgta ctttgtcctc cgg                                        23

SEQ ID NO: 237         moltype = DNA   length = 23
FEATURE                Location/Qualifiers
misc_feature           1..23
                       note = Synthetic Polynucleotide
source                 1..23
                       mol_type = other DNA
                       organism = synthetic construct
SEQUENCE: 237
tgtactttgt cctccggttc tgg                                        23

SEQ ID NO: 238         moltype = DNA   length = 73
FEATURE                Location/Qualifiers
misc_feature           1..73
                       note = Synthetic Polynucleotide
source                 1..73
                       mol_type = other DNA
```

-continued

```
                         organism = synthetic construct
SEQUENCE: 238
ccaggagcaa actcccccca ccccctttcc aaagcccatt ccctctttag ccagagccgg    60
ggtgtgcaga cgg                                                       73

SEQ ID NO: 239           moltype = DNA   length = 23
FEATURE                  Location/Qualifiers
misc_feature             1..23
                         note = Synthetic Polynucleotide
source                   1..23
                         mol_type = other DNA
                         organism = synthetic construct
SEQUENCE: 239
ccaggagcaa actcccccca ccc                                            23

SEQ ID NO: 240           moltype = DNA   length = 23
FEATURE                  Location/Qualifiers
misc_feature             1..23
                         note = Synthetic Polynucleotide
source                   1..23
                         mol_type = other DNA
                         organism = synthetic construct
SEQUENCE: 240
attccctctt tagccagagc cgg                                            23

SEQ ID NO: 241           moltype = DNA   length = 23
FEATURE                  Location/Qualifiers
misc_feature             1..23
                         note = Synthetic Polynucleotide
source                   1..23
                         mol_type = other DNA
                         organism = synthetic construct
SEQUENCE: 241
tccctcttta gccagagccg ggg                                            23

SEQ ID NO: 242           moltype = DNA   length = 23
FEATURE                  Location/Qualifiers
misc_feature             1..23
                         note = Synthetic Polynucleotide
source                   1..23
                         mol_type = other DNA
                         organism = synthetic construct
SEQUENCE: 242
ccagagccgg ggtgtgcaga cgg                                            23

SEQ ID NO: 243           moltype = DNA   length = 106
FEATURE                  Location/Qualifiers
misc_feature             1..106
                         note = Synthetic Polynucleotide
source                   1..106
                         mol_type = other DNA
                         organism = synthetic construct
SEQUENCE: 243
gctgtttggg aggtcagaaa taggggggtcc aggagcaaac tcccccacc ccctttccaa    60
agcccattcc ctctttagcc agagccgggg tgtgcagacg gcagtc                   106

SEQ ID NO: 244           moltype = DNA   length = 58
FEATURE                  Location/Qualifiers
misc_feature             1..58
                         note = Synthetic Polynucleotide
source                   1..58
                         mol_type = other DNA
                         organism = synthetic construct
SEQUENCE: 244
gctgtttggg aggtcagaaa taggggggtcc aggaagccgg ggtgtgcaga cggcagtc     58

SEQ ID NO: 245           moltype = DNA   length = 100
FEATURE                  Location/Qualifiers
misc_feature             1..100
                         note = Synthetic Polynucleotide
source                   1..100
                         mol_type = other DNA
                         organism = synthetic construct
SEQUENCE: 245
gctgtttggg aggtcagaaa taggggggtcc aggagcaaac tcccccacc ccctttccaa    60
agcccattcc ctctttagcc ggggtgtgca gacggcagtc                          100

SEQ ID NO: 246           moltype = DNA   length = 59
FEATURE                  Location/Qualifiers
```

```
misc_feature               1..59
                           note = Synthetic Polynucleotide
source                     1..59
                           mol_type = other DNA
                           organism = synthetic construct
SEQUENCE: 246
gctgtttggg aggtcagaaa taggggtcc aggagagccg gggtgtgcag acggcagtc    59

SEQ ID NO: 247             moltype = DNA   length = 45
FEATURE                    Location/Qualifiers
misc_feature               1..45
                           note = Synthetic Polynucleotide
source                     1..45
                           mol_type = other DNA
                           organism = synthetic construct
SEQUENCE: 247
gctgtttggg aggtcagaaa tagccggggt gtgcagacgg cagtc                  45

SEQ ID NO: 248             moltype = DNA   length = 57
FEATURE                    Location/Qualifiers
misc_feature               1..57
                           note = Synthetic Polynucleotide
source                     1..57
                           mol_type = other DNA
                           organism = synthetic construct
SEQUENCE: 248
gctgtttggg aggtcagaaa taggggtcc aggagccggg gtgtgcagac ggcagtc      57

SEQ ID NO: 249             moltype = DNA   length = 54
FEATURE                    Location/Qualifiers
misc_feature               1..54
                           note = Synthetic Polynucleotide
source                     1..54
                           mol_type = other DNA
                           organism = synthetic construct
SEQUENCE: 249
gctgtttggg aggtcagaaa taggggtcc agccggggtg tgcagacggc agtc         54

SEQ ID NO: 250             moltype = DNA   length = 100
FEATURE                    Location/Qualifiers
misc_feature               1..100
                           note = Synthetic Polynucleotide
source                     1..100
                           mol_type = other DNA
                           organism = synthetic construct
SEQUENCE: 250
gctgtttggg aggtcagaaa taggggtcc aggagcaaac ccccccacc cccttttccaa   60
agcccattcc ctctttagcc agggtgtgca gacggcagtc                        100

SEQ ID NO: 251             moltype = DNA   length = 59
FEATURE                    Location/Qualifiers
misc_feature               1..59
                           note = Synthetic Polynucleotide
source                     1..59
                           mol_type = other DNA
                           organism = synthetic construct
SEQUENCE: 251
gctgtttggg aggtcagaaa taggggtcc aggatagccg gggtgtgcag acggcagtc    59

SEQ ID NO: 252             moltype = DNA   length = 106
FEATURE                    Location/Qualifiers
misc_feature               1..106
                           note = Synthetic Polynucleotide
source                     1..106
                           mol_type = other DNA
                           organism = synthetic construct
SEQUENCE: 252
gctgtttggg aggtcagaaa taggggtcc aggagcaaac ccccccacc cccttttccaa   60
agcccattcc ctctttagcc agagccgggg tgtgcagacg gcagtc                 106

SEQ ID NO: 253             moltype = DNA   length = 41
FEATURE                    Location/Qualifiers
misc_feature               1..41
                           note = Synthetic Polynucleotide
source                     1..41
                           mol_type = other DNA
                           organism = synthetic construct
SEQUENCE: 253
gctgtttggg aggtcagaaa taggggtcc agacggcagt c                       41
```

-continued

```
SEQ ID NO: 254          moltype = DNA   length = 84
FEATURE                 Location/Qualifiers
misc_feature            1..84
                        note = Synthetic Polynucleotide
source                  1..84
                        mol_type = other DNA
                        organism = synthetic construct
SEQUENCE: 254
gctgtttggg aggtcagaaa taggggtcc aggagcaaac tcccccacc cctttccaa     60
agccggggtg tgcagacggc agtc                                          84

SEQ ID NO: 255          moltype = DNA   length = 77
FEATURE                 Location/Qualifiers
misc_feature            1..77
                        note = Synthetic Polynucleotide
source                  1..77
                        mol_type = other DNA
                        organism = synthetic construct
SEQUENCE: 255
gctgtttggg aggtcagaaa taggggtcc aaagcccatt ccctctttag ccagagccgg     60
ggtggcagac ggcagtc                                                  77

SEQ ID NO: 256          moltype = DNA   length = 43
FEATURE                 Location/Qualifiers
misc_feature            1..43
                        note = Synthetic Polynucleotide
source                  1..43
                        mol_type = other DNA
                        organism = synthetic construct
SEQUENCE: 256
gctgtttggg aggtcagaaa taggggtgt gcagacggca gtc                      43

SEQ ID NO: 257          moltype = DNA   length = 54
FEATURE                 Location/Qualifiers
misc_feature            1..54
                        note = Synthetic Polynucleotide
source                  1..54
                        mol_type = other DNA
                        organism = synthetic construct
SEQUENCE: 257
gctgtttggg aggtcagaaa taggggtcc agccggggtg tgcagacggc agtc          54

SEQ ID NO: 258          moltype = DNA   length = 50
FEATURE                 Location/Qualifiers
misc_feature            1..50
                        note = Synthetic Polynucleotide
source                  1..50
                        mol_type = other DNA
                        organism = synthetic construct
SEQUENCE: 258
gctgtttggg aggtcagaaa taggggtcc agggtgtgca gacggcagtc               50

SEQ ID NO: 259          moltype = DNA   length = 57
FEATURE                 Location/Qualifiers
misc_feature            1..57
                        note = Synthetic Polynucleotide
source                  1..57
                        mol_type = other DNA
                        organism = synthetic construct
SEQUENCE: 259
gctgtttggg aggtcagaaa gaggggtcc aggagccggg gtgtgcagac ggcagtc       57

SEQ ID NO: 260          moltype = DNA   length = 45
FEATURE                 Location/Qualifiers
misc_feature            1..45
                        note = Synthetic Polynucleotide
source                  1..45
                        mol_type = other DNA
                        organism = synthetic construct
SEQUENCE: 260
gctgtttggg aggtcagaaa tagccggggt gtgcagacgg cagtc                   45

SEQ ID NO: 261          moltype = DNA   length = 106
FEATURE                 Location/Qualifiers
misc_feature            1..106
                        note = Synthetic Polynucleotide
source                  1..106
                        mol_type = other DNA
```

```
                             organism = synthetic construct
SEQUENCE: 261
gctgtttggg aggtcagaaa taggggggtcc aggagcaaac ccctttccaa    60
agcccattcc ctctttagcc agagccgggg tgtgcagacg gcagtc          106

SEQ ID NO: 262              moltype = DNA   length = 94
FEATURE                    Location/Qualifiers
misc_feature               1..94
                           note = Synthetic Polynucleotide
source                     1..94
                           mol_type = other DNA
                           organism = synthetic construct
SEQUENCE: 262
gctgtttggg aggtcagaaa taggggggtcc aggagcaaac tccccccaag cccattccct    60
ctttagccag agccggggtg tgcagacggc agtc                       94

SEQ ID NO: 263              moltype = DNA   length = 95
FEATURE                    Location/Qualifiers
misc_feature               1..95
                           note = Synthetic Polynucleotide
source                     1..95
                           mol_type = other DNA
                           organism = synthetic construct
SEQUENCE: 263
gctgtttggg aggtcagaaa taggggggtcc aggagcaaac tccccccacc cccttttccc    60
tctttagcca gagccggggt gtgcagacgg cagtc                      95

SEQ ID NO: 264              moltype = DNA   length = 94
FEATURE                    Location/Qualifiers
misc_feature               1..94
                           note = Synthetic Polynucleotide
source                     1..94
                           mol_type = other DNA
                           organism = synthetic construct
SEQUENCE: 264
gctgtttggg aggtcagaaa taggggggtcc aggagcaaac tccccccacc cccttttccct    60
ctttagccag agccggggtg tgcagacggc agtc                       94

SEQ ID NO: 265              moltype = DNA   length = 93
FEATURE                    Location/Qualifiers
misc_feature               1..93
                           note = Synthetic Polynucleotide
source                     1..93
                           mol_type = other DNA
                           organism = synthetic construct
SEQUENCE: 265
gctgtttggg aggtcagaaa taggggggtcc aggagcaaac tccccccagc ccattccctc    60
tttagccaga gccggggtgt gcagacggca gtc                        93

SEQ ID NO: 266              moltype = DNA   length = 94
FEATURE                    Location/Qualifiers
misc_feature               1..94
                           note = Synthetic Polynucleotide
source                     1..94
                           mol_type = other DNA
                           organism = synthetic construct
SEQUENCE: 266
gctgtttggg aggtcagaaa taggggggtcc aggagcaaac tccccccacc cccattccct    60
ctttagccag agccggggtg tgcagacggc agtc                       94

SEQ ID NO: 267              moltype = DNA   length = 86
FEATURE                    Location/Qualifiers
misc_feature               1..86
                           note = Synthetic Polynucleotide
source                     1..86
                           mol_type = other DNA
                           organism = synthetic construct
SEQUENCE: 267
gctgtttggg aggtcagaaa taggggggtcc aggagcaaac tccccccacc ccctttagcc    60
agagccgggg tgtgcagacg gcagtc                                86

SEQ ID NO: 268              moltype = DNA   length = 103
FEATURE                    Location/Qualifiers
misc_feature               1..103
                           note = Synthetic Polynucleotide
source                     1..103
                           mol_type = other DNA
                           organism = synthetic construct
SEQUENCE: 268
```

-continued

```
gctgtttggg aggtcagaaa tagggggtcc aggagcaaac tcccccaccc cccttaaagc    60
ccattccctc tttagccaga gccggggtgt gcagacggca gtc                      103

SEQ ID NO: 269          moltype = DNA   length = 93
FEATURE                 Location/Qualifiers
misc_feature            1..93
                        note = Synthetic Polynucleotide
source                  1..93
                        mol_type = other DNA
                        organism = synthetic construct
SEQUENCE: 269
gctgtttggg aggtcagaaa tagggggtcc aggagcaaac tcccccaagc ccattccctc    60
tttagccaga gccggggtgt gcagacggca gtc                                 93

SEQ ID NO: 270          moltype = DNA   length = 132
FEATURE                 Location/Qualifiers
misc_feature            1..132
                        note = Synthetic Polynucleotide
source                  1..132
                        mol_type = other DNA
                        organism = synthetic construct
SEQUENCE: 270
cattcaacag atacttactg aatgctaatg tctcagacag gacattctga caccccagga    60
gcaaactccc tccatcccac aaatccgtcc ttagatgtgc acacccaacc tcctaagaaa   120
tagaaggatg at                                                       132

SEQ ID NO: 271          moltype = DNA   length = 130
FEATURE                 Location/Qualifiers
misc_feature            1..130
                        note = Synthetic Polynucleotide
source                  1..130
                        mol_type = other DNA
                        organism = synthetic construct
SEQUENCE: 271
cattcaacag atacttactg aatgctaatg tctcagacag gacattctga caccccaggc    60
aaactccctc catcccacaa atccgtcctt agatgtgcac acccaacctc ctaagaaata   120
gaaggatgat                                                          130

SEQ ID NO: 272          moltype = DNA   length = 123
FEATURE                 Location/Qualifiers
misc_feature            1..123
                        note = Synthetic Polynucleotide
source                  1..123
                        mol_type = other DNA
                        organism = synthetic construct
SEQUENCE: 272
cattcaacag atacttactg aatgctaatg tctcagacag gacattctga caccccatcc    60
ctccatccca caaatccgtc cttagatgtg cacacccaac ctcctaagaa atagaaggat   120
gat                                                                 123

SEQ ID NO: 273          moltype = DNA   length = 129
FEATURE                 Location/Qualifiers
misc_feature            1..129
                        note = Synthetic Polynucleotide
source                  1..129
                        mol_type = other DNA
                        organism = synthetic construct
SEQUENCE: 273
cattcaacag atacttactg aatgctaatg tctcagacag gacattctga caccccagca    60
aactccctcc atcccacaaa tccgtcctta gatgtgcaca cccaacctcc taagaaatag   120
aaggatgat                                                           129

SEQ ID NO: 274          moltype = DNA   length = 110
FEATURE                 Location/Qualifiers
misc_feature            1..110
                        note = Synthetic Polynucleotide
source                  1..110
                        mol_type = other DNA
                        organism = synthetic construct
SEQUENCE: 274
cattcaacag atacttactg aatgctaatg tctcagacag gacattctga caccccacaa    60
atccgtcctt agatgtgcac acccaacctc ctaagaaata gaaggatgat             110

SEQ ID NO: 275          moltype = DNA   length = 119
FEATURE                 Location/Qualifiers
misc_feature            1..119
                        note = Synthetic Polynucleotide
source                  1..119
                        mol_type = other DNA
```

```
                            organism = synthetic construct
SEQUENCE: 275
cattcaacag atacttactg aatgctaatg tctcagacag gacattctga cactccctcc    60
atcccacaaa tccgtcctta gatgtgcaca cccaacctcc taagaaatag aaggatgat    119

SEQ ID NO: 276          moltype = DNA   length = 118
FEATURE                 Location/Qualifiers
misc_feature            1..118
                        note = Synthetic Polynucleotide
source                  1..118
                        mol_type = other DNA
                        organism = synthetic construct
SEQUENCE: 276
cattcaacag atacttactg aatgctaatg tctcagacag gacattctga cacccctcca    60
tcccacaaat ccgtccttag atgtgcacac ccaacctcct aagaaataga aggatgat     118

SEQ ID NO: 277          moltype = DNA   length = 64
FEATURE                 Location/Qualifiers
misc_feature            1..64
                        note = Synthetic Polynucleotide
source                  1..64
                        mol_type = other DNA
                        organism = synthetic construct
SEQUENCE: 277
cattcaacag atacttactg aatgctaatg tctcagacag gacattctga caccccagga    60
tgat                                                                64

SEQ ID NO: 278          moltype = DNA   length = 117
FEATURE                 Location/Qualifiers
misc_feature            1..117
                        note = Synthetic Polynucleotide
source                  1..117
                        mol_type = other DNA
                        organism = synthetic construct
SEQUENCE: 278
cattcaacag atacttactg aatgctaatg tctcagacag gacattctga ctccctccat    60
cccacaaatc cgtccttaga tgtgcacacc caacctccta agaaatagaa ggatgat      117

SEQ ID NO: 279          moltype = DNA   length = 132
FEATURE                 Location/Qualifiers
source                  1..132
                        mol_type = genomic DNA
                        organism = Homo sapiens
SEQUENCE: 279
cattcaacag atacttactg aatgctaatg tctcagacag gacattctga caccccagga    60
gcaaactccc tccatcccac aaatccgtcc ttagatgtgc acacccaacc tcctaagaaa   120
tagaaggatg at                                                      132

SEQ ID NO: 280          moltype = DNA   length = 111
FEATURE                 Location/Qualifiers
misc_feature            1..111
                        note = Synthetic Polynucleotide
source                  1..111
                        mol_type = other DNA
                        organism = synthetic construct
SEQUENCE: 280
cattcaacag atacttactg aatgctaatg tctcagacag gacattctga caccccagga    60
catccgtcct tagatgtgca cacccaacct cctaagaaat agaaggatga t            111

SEQ ID NO: 281          moltype = DNA   length = 117
FEATURE                 Location/Qualifiers
misc_feature            1..117
                        note = Synthetic Polynucleotide
source                  1..117
                        mol_type = other DNA
                        organism = synthetic construct
SEQUENCE: 281
cattcaacag atacttactg aatgctaatg tctcagacag gacattctga ctccctccat    60
cccacaaatc cgtccttaga tgtgcacacc caacctccta agaaatagaa ggatgat      117

SEQ ID NO: 282          moltype = DNA   length = 99
FEATURE                 Location/Qualifiers
misc_feature            1..99
                        note = Synthetic Polynucleotide
source                  1..99
                        mol_type = other DNA
                        organism = synthetic construct
SEQUENCE: 282
cattcaacag atacttactg aatgctaatg tctcagacag gacattctga tccgtcctta    60
```

```
gatgtgcaca cccaacctcc taagaaatag aaggatgat                             99

SEQ ID NO: 283          moltype = DNA   length = 121
FEATURE                 Location/Qualifiers
misc_feature            1..121
                        note = Synthetic Polynucleotide
source                  1..121
                        mol_type = other DNA
                        organism = synthetic construct
SEQUENCE: 283
cattcaacag atacttactg aatgctaatg tctcagacag gacattctga caccccagca    60
tctgatgaca aatccgtcct tagatgtgca cacccaacct cctaagaaat agaaggatga   120
t                                                                   121

SEQ ID NO: 284          moltype = DNA   length = 130
FEATURE                 Location/Qualifiers
misc_feature            1..130
                        note = Synthetic Polynucleotide
source                  1..130
                        mol_type = other DNA
                        organism = synthetic construct
SEQUENCE: 284
cattcaacag atacttactg aatgctaatg tctcagacag gacattctga caccccagga    60
gcaaactccc tccatcccac aaatccgtcc ttagatgtgc acccaacctc ctaagaaata   120
gaaggatgat                                                          130

SEQ ID NO: 285          moltype = DNA   length = 130
FEATURE                 Location/Qualifiers
misc_feature            1..130
                        note = Synthetic Polynucleotide
source                  1..130
                        mol_type = other DNA
                        organism = synthetic construct
SEQUENCE: 285
cattcaacag atacttactg aatgctaatg tctcagacag gacattctga caccccagga    60
gcaaactccc tccatcccac aaatccgtcc ttatgtgcac acccaacctc ctaagaaata   120
gaaggatgat                                                          130

SEQ ID NO: 286          moltype = DNA   length = 132
FEATURE                 Location/Qualifiers
misc_feature            1..132
                        note = Synthetic Polynucleotide
source                  1..132
                        mol_type = other DNA
                        organism = synthetic construct
SEQUENCE: 286
cattcaacag atacttactg aatgctaatg tctcagacag gacattctga caccccagga    60
gcaaactccc tccatcccac aaatccgtcc ttagatgtgc acacccaacc tcctaagaaa   120
tagaaggatg at                                                       132

SEQ ID NO: 287          moltype = DNA   length = 101
FEATURE                 Location/Qualifiers
misc_feature            1..101
                        note = Synthetic Polynucleotide
source                  1..101
                        mol_type = other DNA
                        organism = synthetic construct
SEQUENCE: 287
cattcaacag atacttactg aatgctaatg tctcagacag gacattctga aatccgtcct    60
tagatgtgca cacccaacct cctaagaaat agaaggatga t                       101

SEQ ID NO: 288          moltype = DNA   length = 132
FEATURE                 Location/Qualifiers
misc_feature            1..132
                        note = Synthetic Polynucleotide
source                  1..132
                        mol_type = other DNA
                        organism = synthetic construct
SEQUENCE: 288
cattcaacag atacttactg aatgctaatg tctcagacag gacattctga caccccagga    60
gcaaactccc tccatcccac aaatccgtcc ttagatgtgc acacccaacc tcctaagaaa   120
tagaaggatg at                                                       132

SEQ ID NO: 289          moltype = DNA   length = 119
FEATURE                 Location/Qualifiers
misc_feature            1..119
                        note = Synthetic Polynucleotide
source                  1..119
                        mol_type = other DNA
```

-continued

```
                              organism = synthetic construct
SEQUENCE: 289
cattcaacag atacttactg aatgctaatg tctcagacag gacattctga cacccccagga   60
gcaaactccc tccgtcctta gatgtgcaca cccaacctcc taagaaatag aaggatgat    119

SEQ ID NO: 290           moltype = DNA   length = 121
FEATURE                  Location/Qualifiers
misc_feature             1..121
                         note = Synthetic Polynucleotide
source                   1..121
                         mol_type = other DNA
                         organism = synthetic construct
SEQUENCE: 290
cattcaacag atacttactg aatgctaatg tctcagacag gacattctga cacccccagga   60
gcaaactccc tctccgtcct tagatgtgca cacccaacct cctaagaaat agaaggatga   120
t                                                                   121

SEQ ID NO: 291           moltype = DNA   length = 124
FEATURE                  Location/Qualifiers
misc_feature             1..124
                         note = Synthetic Polynucleotide
source                   1..124
                         mol_type = other DNA
                         organism = synthetic construct
SEQUENCE: 291
cattcaacag atacttactg aatgctaatg tctcagacag gacattctga cacccccagga   60
gcaaactccc tccattccgt ccttagatgt gcacacccaa cctcctaaga aatagaagga   120
tgat                                                                124

SEQ ID NO: 292           moltype = DNA   length = 130
FEATURE                  Location/Qualifiers
misc_feature             1..130
                         note = Synthetic Polynucleotide
source                   1..130
                         mol_type = other DNA
                         organism = synthetic construct
SEQUENCE: 292
cattcaacag atacttactg aatgctaatg tctcagacag gacattctga cacccccagga   60
gcaaactccc tccatcccac aaatccgtcc ttagatgtgc acccaacctc ctaagaaata   120
gaaggatgat                                                          130

SEQ ID NO: 293           moltype = DNA   length = 122
FEATURE                  Location/Qualifiers
misc_feature             1..122
                         note = Synthetic Polynucleotide
source                   1..122
                         mol_type = other DNA
                         organism = synthetic construct
SEQUENCE: 293
cattcaacag atacttactg aatgctaatg tctcagacag gacattctga cacccccagga   60
gcaaactccc tcctccgtcc ttagatgtgc acacccaacc tcctaagaaa tagaaggatg   120
at                                                                  122

SEQ ID NO: 294           moltype = DNA   length = 123
FEATURE                  Location/Qualifiers
misc_feature             1..123
                         note = Synthetic Polynucleotide
source                   1..123
                         mol_type = other DNA
                         organism = synthetic construct
SEQUENCE: 294
cattcaacag atacttactg aatgctaatg tctcagacag gacattctga cacccccagga   60
gcaaactccc tccatccgtc cttagatgtg cacacccaac ctcctaagaa atagaaggat   120
gat                                                                 123

SEQ ID NO: 295           moltype = DNA   length = 128
FEATURE                  Location/Qualifiers
misc_feature             1..128
                         note = Synthetic Polynucleotide
source                   1..128
                         mol_type = other DNA
                         organism = synthetic construct
SEQUENCE: 295
cattcaacag atacttactg aatgctaatg tctcagacag gacattctga cacccccagga   60
gcaaactccc tccatcccac aaatccgtcc ttagatgtgc acaccctcct aagaaataga   120
aggatgat                                                            128

SEQ ID NO: 296           moltype = DNA   length = 130
FEATURE                  Location/Qualifiers
```

```
misc_feature             1..130
                         note = Synthetic Polynucleotide
source                   1..130
                         mol_type = other DNA
                         organism = synthetic construct
SEQUENCE: 296
cattcaacag atacttactg aatgctaatg tctcagacag gacattctga cacccccagga   60
gcaaactccc tccatcccac aaatccgtcc agatgtgcac acccaacctc ctaagaaata   120
gaaggatgat                                                          130

SEQ ID NO: 297           moltype = DNA   length = 21
FEATURE                  Location/Qualifiers
misc_feature             1..21
                         note = Synthetic Polynucleotide
source                   1..21
                         mol_type = other DNA
                         organism = synthetic construct
SEQUENCE: 297
ggggtggggg gagtttgctc c                                              21

SEQ ID NO: 298           moltype = DNA   length = 22
FEATURE                  Location/Qualifiers
misc_feature             1..22
                         note = Synthetic Polynucleotide
source                   1..22
                         mol_type = other DNA
                         organism = synthetic construct
SEQUENCE: 298
aggagcaaac tccctccatc cc                                             22

SEQ ID NO: 299           moltype = DNA   length = 22
FEATURE                  Location/Qualifiers
misc_feature             1..22
                         note = Synthetic Polynucleotide
source                   1..22
                         mol_type = other DNA
                         organism = synthetic construct
SEQUENCE: 299
gggatggagg gagtttgctc ct                                             22

SEQ ID NO: 300           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 300
attccctctt tagccagagc                                                20

SEQ ID NO: 301           moltype = AA   length = 4
FEATURE                  Location/Qualifiers
REGION                   1..4
                         note = Synthetic Polypeptide
source                   1..4
                         mol_type = protein
                         organism = synthetic construct
SEQUENCE: 301
GGSM                                                                  4

SEQ ID NO: 302           moltype = DNA   length = 99
FEATURE                  Location/Qualifiers
misc_feature             1..99
                         note = Synthetic Polynucleotide
source                   1..99
                         mol_type = other DNA
                         organism = synthetic construct
SEQUENCE: 302
ccagcaagag gctcccgagc gagcaagctc agtttacacc cgatccactg gggagcagga   60
aatatctgtg ggcttgtgac acggactcaa gtgggctgg                          99

SEQ ID NO: 303           moltype = DNA   length = 23
FEATURE                  Location/Qualifiers
misc_feature             1..23
                         note = Synthetic Polynucleotide
source                   1..23
                         mol_type = other DNA
                         organism = synthetic construct
SEQUENCE: 303
```

```
ccagcaagag gctcccgagc gag                                                  23

SEQ ID NO: 304          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 304
cccgagcgag caagctcagt tta                                                  23

SEQ ID NO: 305          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 305
cccgatccac tggggagcag gaa                                                  23

SEQ ID NO: 306          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 306
agtttacacc cgatccactg ggg                                                  23

SEQ ID NO: 307          moltype = DNA   length = 24
FEATURE                 Location/Qualifiers
misc_feature            1..24
                        note = Synthetic Polynucleotide
source                  1..24
                        mol_type = other DNA
                        organism = synthetic construct
SEQUENCE: 307
tggggagcag gaaatatctg tggg                                                 24

SEQ ID NO: 308          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 308
atatctgtgg gcttgtgaca cgg                                                  23

SEQ ID NO: 309          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 309
gcttgtgaca cggactcaag tgg                                                  23

SEQ ID NO: 310          moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 310
tgacacggac tcaagtgggc tgg                                                  23

SEQ ID NO: 311          moltype = DNA   length = 120
FEATURE                 Location/Qualifiers
misc_feature            1..120
                        note = Synthetic Polynucleotide
source                  1..120
                        mol_type = other DNA
                        organism = synthetic construct
```

-continued

```
SEQUENCE: 311
cctggccatc tctgacctgt ttttccttct tactgtcccc ttctgggctc actatgctgc  60
cgcccagtgg gactttggaa atacaatgtg tcaactcttg acagggctct attttatagg  120

SEQ ID NO: 312            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 312
cctggccatc tctgacctgt ttt                                          23

SEQ ID NO: 313            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 313
ccccttctgg gctcactatg ctg                                          23

SEQ ID NO: 314            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 314
ccgcccagtg ggactttgga aat                                          23

SEQ ID NO: 315            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 315
tcactatgct gccgcccagt ggg                                          23

SEQ ID NO: 316            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 316
caatgtgtca actcttgaca ggg                                          23

SEQ ID NO: 317            moltype = DNA   length = 23
FEATURE                   Location/Qualifiers
misc_feature              1..23
                          note = Synthetic Polynucleotide
source                    1..23
                          mol_type = other DNA
                          organism = synthetic construct
SEQUENCE: 317
ttgacagggc tctattttat agg                                          23

SEQ ID NO: 318            moltype = AA   length = 16
FEATURE                   Location/Qualifiers
REGION                    1..16
                          note = Synthetic Polypeptide
source                    1..16
                          mol_type = protein
                          organism = synthetic construct
SEQUENCE: 318
MAPKKKRKVG IHRGVP                                                   16

SEQ ID NO: 319            moltype = DNA   length = 4869
FEATURE                   Location/Qualifiers
misc_feature              1..4869
                          note = Synthetic Polynucleotide
source                    1..4869
```

```
                      mol_type = other DNA
                      organism = synthetic construct
SEQUENCE: 319
atggactaca aagaccatga cggtgattat aaagatcatg acatcgatta caaggatgac   60
gatgacaaga tggcccccaa gaagaagagg aaggtgggac ttcaccgcgg ggtacctgga  120
ggttctggat cccaactagt caaaagtgaa ctggaggaga agaaatctga acttcgtcat  180
aaattgaaat atgtgcctca tgaatatatt gaattaattg aaattgccag aaattccact  240
caggatagaa ttcttgaaat gaaggtaatg gaatttttta tgaaagtta tggatataga  300
ggtaaacatt tgggtggatc aaggaaaccg gacggagcaa tttatactgt cggatctcct  360
attgattacg gtgtgatcgt ggatactaaa gcttatagcg gaggttataa tctgccaatt  420
ggccaagcag atgaaatgca acgatatgtc gaagaaaatc aaaacgaaa caaacatatc  480
aaccctaatg aatggtggaa agtctatcca tcttctgtaa cggaatttaa gttttttattt  540
gtgagtggtc actttaaagg aaactacaaa gctcagctta cacgattaaa tcatatcact  600
aattgtaatg gagctgttct tagtgtagaa gagctttaa ttggtggaga aatgattaaa  660
gccggcacat taaccttaga ggaagtcaga cggaaattta ataacggcga gataaacttt  720
agcggcagcg agactcccgg gacctcagag tccgccacac ccgaaagtga taaaaagtat  780
tctattggtt tagctatcgg cactaattcc gttggatggg ctgtcataac cgatgaatac  840
aaagtacctt caaagaaatt taaggtgttg gggaacacag acctcattc gattaaaaag  900
aatcttatcg gtgccctcct attcgatagt ggcgaaacgg cagaggcgac tcgcctgaaa  960
cgaaccgctc ggagaaggta tacacgtcgc aagaaccgaa tatgttactt acaagaaatt 1020
tttagcaatg agatggccaa agttgacgat tctttcttc accgtttgga agagtccttc 1080
cttgtcgaag aggacaagaa acatgaacgg cacccccatc ttggaaacat agtagatgag 1140
gtggcatatc atgaaaagta cccaacgatt tatcacctca gaaaaaagct agttgactca 1200
actgataaag cggacctgag gttaatctac ttggctcttg cccatatgat aaagttccgt 1260
gggcactttc tcattgaggg tgatctaaat ccggacaact cggatgtcga caaactgttc 1320
atccagttag tacaaaccta taatcagttg tttgaagaga accctataaa tgcaagtggc 1380
gtggatgcga aggctattct tagcgcccgc ctctctaaat cccgacggct agaaaacctg 1440
atcgcacaat tacccggaga gaagaaaaat gggttgttcg gtaaccttat agcgctctca 1500
ctaggcctga caccaaattt taagtcgaac ttcgacttag ctgaagatgc caaattgcag 1560
cttagtaagg acacgtacga tgacgatctc gacaatctac tggcacaaat tggagatcag 1620
tatgcggact tattttttggc tgccaaaaac cttagcgatg caatcctcct atctgacata 1680
ctgagagtta atactgagat taccaaggcg ccgttatccg cttcaatgat caaaaggtac 1740
gatgaacatc accaagactt gacacttctc aaggccctag tccgtcagca actgcctgag 1800
aaatataagg aaatattctt tgatcagtcg aaaaacgggc acgcaggtta tattgacggc 1860
ggagcgagtc aagaggaatt ctacaagttt atcaaaccca tattagagaa gatggatgggg 1920
acggaagagt tgcttgtaaa actcaatcgc gaagatctac tgcgaaagca gcggacttc 1980
gacaacggta gcattccaca tcaaatccac ttaggcgaat tgcatgctat acttagaagg 2040
caggaggatt tttatccgtt cctcaaagac aatcgtgaaa agattgagaa aatcctaacc 2100
tttcgcatac cttactatgt gggaccctg gcccgaggga actctcggtt cgcatggatg 2160
acaagaaagt ccgaagaaac gattactcca tggaattttg aggaagttgt cgataaaggt 2220
gcgtcagctc aatcgttcat cgagaggatg accaactttg acaagaattt accgaacgaa 2280
aaagtattgc ctaagcacag tttactttac gagtatttca cagtgtacaa tgaactcacg 2340
aaagttaagt atgtcactga gggcatgcgt aaaccgcct ttctaagcgg agaacagaag 2400
aaagcaatag tagatctgtt attcaagacc aaccgcaaag tgacagttaa gcaattgaaa 2460
gaggactact ttaagaaaat tgaatgcttc gattctgtcg agatctccgg ggtagaagat 2520
cgatttaatg cgtcacttgg tacgtatcat gacctcctaa agataattaa agataaggac 2580
ttcctggata acgaagagaa tgaagatatc ttagaagata tagtgttgac tcttaccctc 2640
tttgaagatc gggaaatgat tgaggaaaga ctaaaaacat acgctcacct gttcgacgat 2700
aaggttatga aacagttaaa gaggcgtcgc tatacgggct ggggacgatt gtcgcggaaa 2760
cttatcaacg gataagaga caagcaaagt ggtaaaacta ttctcgattt tctaaagagc 2820
gacggcttcg ccaataggaa ctttatgcag ctgatccatg atgactcttt aaccttcaaa 2880
gaggatatac aaaaggcaca ggtttccgga caagggact cattgcacga acatattgcg 2940
aatcttgctg gttcgccagc catcaaaaag ggcatactcc agacagtcaa agtagtggat 3000
gagctagtta aggtcatggg acgtcacaaa ccggaaaaca ttgtaatcga gatggcacgc 3060
gaaaatcaaa cgactcagaa ggggcaaaaa aacagtcgag agcggatgaa gagaataga 3120
gagggtatta agaactgggg cagccagatc ttaaaggagc atcctgtgga aaatacccaa 3180
ttgcagaacg agaaacttta cctctattac ctacaaaatg gaagggacat gtatgttgat 3240
caggaactgg acataaaccg tttatctgat tacgacgtcg atgccattgt acccaatcc 3300
tttttgaagg acgattcaat cgacaataaa gtgcttacac gctcggataa gaaccgaggg 3360
aaaagtgaca atgttccaag cgaggaagtc gtaaagaaa tgaagaacta ttggcggcag 3420
ctcctaaatg cgaaactgat aacgcaaaga aagttcgata acttaactaa agctgagagg 3480
ggtggcttgt ctgaacttga caaggccgga tttattaaac gtcagctcgt ggaaacccgc 3540
caaatcacaa agcatgttgc acagatacta gattcccgaa tgaatacgaa atacgacgag 3600
aacgataagc tgattcggga agtcaaagta atcacttaa agtcaaaatt ggtgtcggac 3660
ttcagaaagg attttcaatt ctataaagtt agggagataa ataactacca ccatgcgcac 3720
gacgcttatc ttaatgccgt cgtagggacc gcactcatta agaaataccc gaagctagaa 3780
agtgagtttg tgtatggtga ttacaaagtt tatgacgtcc gtaagatgat cgcgaaaagc 3840
gaacaggaga taggcaaggc tacagccaaa tacttctttt attctaacat tatgaatttc 3900
tttaagacgg aaatcactct ggcaaacgga gagatacgca aacgaccttt aattgaaacc 3960
aatgggagaa caggtgaaat cgtatggat aagggccggg acttcgcgac ggtgagaaa 4020
gttttgtcca tgcccaagt caacatagta aagaaactg aggtgcagac cggagggttt 4080
tcaaaggaat cgattcttcc aaaaaggaat agtgataagc tcatcgctcg taaaaaggac 4140
tgggacccga aaaagtacgg tggcttcgat agccctacag ttgcctattc tgtcctagta 4200
gtggcaaaag ttgagaaggg aaaatccaag aaactgaagt cagttaagga attattgggg 4260
ataacgatta tggagcgctc gtctttgaa aagaacccca tcgacttcct tgaggcgaaa 4320
ggttacaagg aagtaaaaaa ggatctcata attaaactac aaagtatag tctgtttgag 4380
ttagaaaatg gccgaaaacg gatgttggct agcgccggag agcttcaaaa ggggaacgaa 4440
ctcgcactac cgtctaaata cgtgaatttc ctgtatttag cgtcccatta cgagaagttg 4500
aaaggttcac ctgaagataa cgaacagaag caacttttg ttgagcagca caaacattat 4560
```

```
ctcgacgaaa tcatagagca aaatttcggaa ttcagtaaga gagtcatcct agctgatgcc      4620
aatctggaca aagtattaag cgcatacaac aagcacaggg ataaacccat acgtgagcag      4680
gcggaaaata ttatccattt gtttactctt accaacctcg gcgctccagc cgcattcaag      4740
tattttgaca caacgataga tcgcaaacga tacacttcta ccaaggaggt gctagacgcg      4800
acactgattc accaatccat cacgggatta tatgaaactc ggatagattt gtcacagctt      4860
gggggtgac                                                               4869
```

```
SEQ ID NO: 320            moltype = AA  length = 1367
FEATURE                   Location/Qualifiers
REGION                    1..1367
                          note = Synthetic Polypeptide
source                    1..1367
                          mol_type = protein
                          organism = synthetic construct
SEQUENCE: 320
DKKYSIGLAI GTNSVGWAVI TDEYKVPSKK FKVLGNTDRH SIKKNLIGAL LFDSGETAEA      60
TRLKRTARRR YTRRKNRICY LQEIFSNEMA KVDDSFFHRL EESFLVEEDK KHERHPIFGN      120
IVDEVAYHEK YPTIYHLRKK LVDSTDKADL RLIYLALAHM IKFRGHFLIE GDLNPDNSDV      180
DKLFIQLVQT YNQLFEENPI NASGVDAKAI LSARLSKSRR LENLIAQLPG EKKNGLFGNL      240
IALSLGLTPN FKSNFDLAED AKLQLSKDTY DDDLDNLLAQ IGDQYADLFL AAKNLSDAIL      300
LSDILRVNTE ITKAPLSASM IKRYDEHHQD LTLLKALVRQ QLPEKYKEIF FDQSKNGYAG      360
YIDGGASQEE FYKFIKPILE KMDGTEELLV KLNREDLLRK QRTFDNGSIP HQIHLGELHA      420
ILRRQEDFYP FLKDNREKIE KILTFRIPYY VGPLARGNSR FAWMTRKSEE TITPWNFEEV      480
VDKGASAQSF IERMTNFDKN LPNEKVLPKH SLLYEYFTVY NELTKVKYVT EGMRKPAFLS      540
GEQKKAIVDL LFKTNRKVTV KQLKEDYFKK IECFDSVEIS GVEDRFNASL GTYHDLLKII      600
KDKDFLDNEE NEDILEDIVL TLTLFEDREM IEERLKTYAH LFDDKVMKQL KRRRYTGWGR      660
LSRKLINGIR DKQSGKTILD FLKSDGFANR NFMQLIHDDS LTFKEDIQKA QVSGQGDSLH      720
EHIANLAGSP AIKKGILQTV KVVDELVKVM GRHKPENIVI EMARENQTTQ KGQKNSRERM      780
KRIEEGIKEL GSQILKEHPV ENTQLQNEKL YLYYLQNGRD MYVDQELDIN RLSDYDVDAI      840
VPQSFLKDDS IDNKVLTRSD KNRGKSDNVP SEEVVKKMKN YWRQLLNAKL ITQRKFDNLT      900
KAERGGLSEL DKAGFIKRQL VETRQITKHV AQILDSRMNT KYDENDKLIR EVKVITLKSK      960
LVSDFRKDFQ FYKVREINNY HHAHDAYLNA VVGTALIKKY PKLESEFVYG DYKVYDVRKM      1020
IAKSEQEIGK ATAKYFFYSN IMNFFKTEIT LANGEIRKRP LIETNGETGE IVWDKGRDFA      1080
TVRKVLSMPQ VNIVKKTEVQ TGGFSKESIL PKRNSDKLIA RKKDWDPKKY GGFDSPTVAY      1140
SVLVVAKVEK GKSKKLKSVK ELLGITIMER SSFEKNPIDF LEAKGYKEVK KDLIIKLPKY      1200
SLFELENGRK RMLASAGELQ KGNELALPSK YVNFLYLASH YEKLKGSPED NEQKQLFVEQ      1260
HKHYLDEIIE QISEFSKRVI LADANLDKVL SAYNKHRDKP IREQAENIIH LFTLTNLGAP      1320
AAFKYFDTTI DRKRYTSTKE VLDATLIHQS ITGLYETRID LSQLGGD                    1367
```

```
SEQ ID NO: 321            moltype = AA  length = 23
FEATURE                   Location/Qualifiers
REGION                    1..23
                          note = Synthetic Polypeptide
source                    1..23
                          mol_type = protein
                          organism = synthetic construct
SEQUENCE: 321
MDYKDHDGDY KDHDIDYKDD DDK                                                23
```

```
SEQ ID NO: 322            moltype = DNA  length = 432
FEATURE                   Location/Qualifiers
misc_feature              1..432
                          note = Synthetic Polynucleotide
source                    1..432
                          mol_type = other DNA
                          organism = synthetic construct
SEQUENCE: 322
atggccctgt ttggctacgc acgcgtgtct accagtcaac agtcactcga tttgcaagtg      60
agggctctta aagatgccgg agtgaaggca aacagaattt ttactgataa ggccagcgga      120
agcagcacag acagagaggg gctggatctc ctgagaatga aggtaaagga gggtgatgtg      180
atcttggtca aaaaattgga tcgactgggg agagacacag ctgatatgct tcagcttatt      240
aaaagagttt acgctcaggg tgttgccgtg aggtttatcg atgacggcat ctcaaccgac      300
tcctacattg gtcttatgtt tgtgacaatt ttgtccgctg tggctcaggc tgagcgggaga     360
aggattctcg aaaggacgaa tgaggggacgg caagcagcta agttgaaagg tatcaaattt      420
ggcagacgaa gg                                                           432
```

```
SEQ ID NO: 323            moltype = DNA  length = 414
FEATURE                   Location/Qualifiers
misc_feature              1..414
                          note = Synthetic Polynucleotide
source                    1..414
                          mol_type = other DNA
                          organism = synthetic construct
SEQUENCE: 323
atggcaacca ttggctacat aaagggtgtct accatcgacc aaaatatcga cctgcagcgc      60
aacgctctga catccgccaa ctgcgatcgg atcttcgagg ataggatcag tggcaagatc      120
gccaaccggc ccggtctgaa gcgggctctg aagtacgtga ataagggcga tactctggtt      180
gtgtggaagt tggatcgctt gggtagatca gtgaagaatc tcgtagccct gataagcgag      240
ctgcacgaga ggggtgcaca tttccattct ctgaccgatt ccatcgatac gtctagcgcc      300
```

-continued

```
atgggccgat tcttcttta cgtcatgtcc gccctcgctg aaatggagcg cgaacttatt   360
gttgaacgga ctttggctgg actggcagcg gctagagcac agggccgact tgga          414

SEQ ID NO: 324          moltype = DNA   length = 432
FEATURE                 Location/Qualifiers
misc_feature            1..432
                        note = Synthetic Polynucleotide
source                  1..432
                        mol_type = other DNA
                        organism = synthetic construct
SEQUENCE: 324
atgctcattg ctatgtaag ggtcagcacc aatgaccaaa acacagactt gcaacgcaat    60
gctttggttt gcgccggatg tgaacagata tttgaagata aactgagcgg cactcggaca   120
gacagacctg ggcttaagag agcactgaaa agactgcaga cctggtcgtc               180
tggaaactgg atcgcctcgg acgcagcatg aaacatctga ttagcctggt tggtgagctt   240
agggagagag gaatcaactt cagaagcctg accgactcca tcgacaccag tagccccatg   300
ggacgattct tcttctatgt gatgggagca cttgctgaga tggaaagaga gcttattatc   360
gaaagaacta tggctggtat cgctgctgcc cggaacaaag gcagacggtt cggcagaccg   420
ccgaagagcg gc                                                        432

SEQ ID NO: 325          moltype = AA   length = 144
FEATURE                 Location/Qualifiers
REGION                  1..144
                        note = Synthetic Polypeptide
source                  1..144
                        mol_type = protein
                        organism = synthetic construct
SEQUENCE: 325
MALFGYARVS TSQQSLDLQV RALKDAGVKA NRIFTDKASG SSTDREGLDL LRMKVKEGDV     60
ILVKKLDRLG RDTADMLQLI KEFDAQGVAV RFIDDGISTD SYIGLMFVTI LSAVAQAERR    120
RILERTNEGR QAAKLKGIKF GRRR                                           144

SEQ ID NO: 326          moltype = AA   length = 138
FEATURE                 Location/Qualifiers
REGION                  1..138
                        note = Synthetic Polypeptide
source                  1..138
                        mol_type = protein
                        organism = synthetic construct
SEQUENCE: 326
MATIGYIRVS TIDQNIDLQR NALTSANCDR IFEDRISGKI ANRPGLKRAL KYVNKGDTLV     60
VWKLDRLGRS VKNLVALISE LHERGAHFHS LTDSIDTSSA MGRFFFYVMS ALAEMERELI    120
VERTLAGLAA ARAQGRLG                                                  138

SEQ ID NO: 327          moltype = AA   length = 144
FEATURE                 Location/Qualifiers
REGION                  1..144
                        note = Synthetic Polypeptide
source                  1..144
                        mol_type = protein
                        organism = synthetic construct
SEQUENCE: 327
MLIGYVRVST NDQNTDLQRN ALVCAGCEQI FEDKLSGTRT DRPGLKRALK RLQKGDTLVV     60
WKLDRLGRSM KHLISLVGEL RERGINFRSL TDSIDTSSPM GRFFFYVMGA LAEMERELII    120
ERTMAGIAAA RNKGRRFGRP PKSG                                           144

SEQ ID NO: 328          moltype = AA   length = 1537
FEATURE                 Location/Qualifiers
REGION                  1..1537
                        note = Synthetic Polypeptide
source                  1..1537
                        mol_type = protein
                        organism = synthetic construct
SEQUENCE: 328
MDKKYSIGLA IGTNSVGWAV ITDEYKVPSK KFKVLGNTDR HSIKKNLIGA LLFDSGETAE     60
ATRLKRTARR RYTRRKNRIC YLQEIFSNEM AKVDDSFFHR LEESFLVEED KKHERHPIFG    120
NIVDEVAYHE KYPTIYHLRK KLVDSTDKAD LRLIYLALAH MIKFRGHFLI EGDLNPDNSD    180
VDKLFIQLVQ TYNQLFEENP INASGVDAKA ILSARLSKSR RLENLIAQLP GEKKNGLFGN    240
LIALSLGLTP NFKSNFDLAE DAKLQLSKDT YDDDLDNLLA QIGDQYADLF LAAKNLSDAI    300
LLSDILRVNT EITKAPLSAS MIKRYDEHHQ DLTLLKALVR QQLPEKYKEI FFDQSKNGYA    360
GYIDGGASQE EFYKFIKPIL EKMDGTEELL VKLNREDLLR KQRTFDNGSI PHQIHLGELH    420
AILRRQEDFY PFLKDNREKI EKILTFRIPY YVGPLARGNS RFAWMTRKSE ETITPWNFEE    480
VVDKGASAQS FIERMTNFDK NLPNEKVLPK HSLLYEYFTV YNELTKVKYV TEGMRKPAFL    540
SGEQKKAIVD LLFKTNRKVT VKQLKEDYFK KIECFDSVEI SGVEDRFNAS LGTYHDLLKI    600
IKDKDFLDNE ENEDILEDIV LTLTLFEDRE MIEERLKTYA HLFDDKVMKQ LKRRRYTGWG    660
RLSRKLINGI RDKQSGKTIL DFLKSDGFAN RNFMQLIHDD SLTFKEDIQK AQVSGQGDSL    720
HEHIANLAGS PAIKKGILQT VKVVDELVKV MGRHKPENIV IEMARENQTT QKGQKNSRER    780
MKRIEEGIKE LGSQILKEHP VENTQLQNEK LYLYYLQNGR DMYVDQELDI NRLSDYDVDA    840
IVPQSFLKDD SIDNKVLTRS DKNRGKSDNV PSEEVVKKMK NYWRQLLNAK LITQRKFDNL    900
```

```
TKAERGGLSE LDKAGFIKRQ LVETRQITKH VAQILDSRMN TKYDENDKLI REVKVITLKS    960
KLVSDFRKDF QFYKVREINN YHHAHDAYLN AVVGTALIKK YPKLESEFVY GDYKVYDVRK   1020
MIAKSEQEIG KATAKYFFYS NIMNFFKTEI TLANGEIRKR PLIETNGETG EIVWDKGRDF   1080
ATVRKVLSMP QVNIVKKTEV QTGGFSKESI LPKRNSDKLI ARKKDWDPKK YGGFDSPTVA   1140
YSVLVVAKVE KGKSKKLKSV KELLGITIME RSSFEKNPID FLEAKGYKEV KKDLIIKLPK   1200
YSLFELENGR KRMLASAGEL QKGNELALPS KYVNFLYLAS HYEKLKGSPE DNEQKQLFVE   1260
QHKHYLDEII EQISEFSKRV ILADANLDKV LSAYNKHRDK PIREQAENII HLFTLTNLGA   1320
PAAFKYFDTT IDRKRYTSTK EVLDATLIHQ SITGLYETRI DLSQLGGDMA PKKKRKVGIH   1380
RGVPGGSGGS GGSMALFGYA RVSTSQQSLD LQVRALKDAG VKANRIFTDK ASGSSTDREG   1440
LDLLRMKVKE GDVILVKKLD RLGRDTADML QLIKEFDAQG VAVRFIDDGI STDSYIGLMF   1500
VTILSAVAQA ERRRILERTN EGRQAAKLKG IKFGRRR                           1537

SEQ ID NO: 329        moltype = AA  length = 1537
FEATURE               Location/Qualifiers
REGION                1..1537
                      note = Synthetic Polypeptide
source                1..1537
                      mol_type = protein
                      organism = synthetic construct
SEQUENCE: 329
MAPKKKRKVG IHRGVPMDKK YSIGLAIGTN SVGWAVITDE YKVPSKKFKV LGNTDRHSIK     60
KNLIGALLFD SGETAEATRL KRTARRRYTR RKNRICYLQE IFSNEMAKVD DSFFHRLEES    120
FLVEEDKKHE RHPIFGNIVD EVAYHEKYPT IYHLRKKLVD STDKADLRLI YLALAHMIKF    180
RGHFLIEGDL NPDNSDVDKL FIQLVQTYNQ LFEENPINAS GVDAKAILSA RLSKSRRLEN    240
LIAQLPGEKK NGLFGNLIAL SLGLTPNFKS NFDLAEDAKL QLSKDTYDDD LDNLLAQIGD    300
QYADLFLAAK NLSDAILLSD ILRVNTEITK APLSASMIKR YDEHHQDLTL LKALVRQQLP    360
EKYKEIFFDQ SKNGYAGYID GGASQEEFYK FIKPILEKMD GTEELLVKLN REDLLRKQRT    420
FDNGSIPHQI HLGELHAILR RQEDFYPFLK DNREKIEKIL TFRIPYYVGP LARGNSRFAW    480
MTRKSEETIT PWNFEEVVDK GASAQSFIER MTNFDKNLPN EKVLPKHSLL YEYFTVYNEL    540
TKVKYVTEGM RKPAFLSGEQ KKAIVDLLFK TNRKVTVKQL KEDYFKKIEC FDSVEISGVE    600
DRFNASLGTY HDLLKIIKDK DFLDNEENED ILEDIVLTLT LFEDREMIEE RLKTYAHLFD    660
DKVMKQLKRR RYTGWGRLSR KLINGIRDKQ SGKTILDFLK SDGFANRNFM QLIHDDSLTF    720
KEDIQKAQVS GQGDSLHEHI ANLAGSPAIK KGILQTVKVV DELVKVMGRH KPENIVIEMA    780
RENQTTQKGQ KNSRERMKRI EEGIKELGSQ ILKEHPVENT QLQNEKLYLY LQNGRDMYV    840
DQELDINRLS DYDVDAIVPQ SFLKDDSIDN KVLTRSDKNR GKSDNVPSEE VVKKMKNYWR    900
QLLNAKLITQ RKFDNLTKAE RGGLSELDKA GFIKRQLVET RQITKHVAQI LDSRMNTKYD    960
ENDKLIREVK VITLKSKLVS DFRKDFQFYK VREINNYHHA HDAYLNAVVG TALIKKYPKL   1020
ESEFVYGDYK VYDVRKMIAK SEQEIGKATA KYFFYSNIMN FFKTEITLAN GEIRKRPLIE   1080
TNGETGEIVW DKGRDFATVR KVLSMPQVNI VKKTEVQTGG FSKESILPKR NSDKLIARKK   1140
DWDPKKYGGF DSPTVAYSVL VVAKVEKGKS KKLKSVKELL GITIMERSSF EKNPIDFLEA   1200
KGYKEVKKDL IIKLPKYSLF ELENGRKRML ASAGELQKGN ELALPSKYVN FLYLASHYEK   1260
LKGSPEDNEQ KQLFVEQHKH YLDEIIEQIS EFSKRVILAD ANLDKVLSAY NKHRDKPIRE   1320
QAENIIHLFT LTNLGAPAAF KYFDTTIDRK RYTSTKEVLD ATLIHQSITG LYETRIDLSQ   1380
LGGDGGSGGS GGSMALFGYA RVSTSQQSLD LQVRALKDAG VKANRIFTDK ASGSSTDREG   1440
LDLLRMKVKE GDVILVKKLD RLGRDTADML QLIKEFDAQG VAVRFIDDGI STDSYIGLMF   1500
VTILSAVAQA ERRRILERTN EGRQAAKLKG IKFGRRR                           1537

SEQ ID NO: 330        moltype = AA  length = 1537
FEATURE               Location/Qualifiers
REGION                1..1537
                      note = Synthetic Polypeptide
source                1..1537
                      mol_type = protein
                      organism = synthetic construct
SEQUENCE: 330
MALFGYARVS TSQQSLDLQV RALKDAGVKA NRIFTDKASG SSTDREGLDL LRMKVKEGDV     60
ILVKKLDRLG RDTADMLQLI KEFDAQGVAV RFIDDGISTD SYIGLMFVTI LSAVAQAERR    120
RILERTNEGR QAAKLKGIKF GRRGGSGGS GGSMDKKYSI GLAIGTNSVG WAVITDEYKV    180
PSKKFKVLGN TDRHSIKKNL IGALLFDSGE TAEATRLKRA RRRYTRRKN RICYLQEIFS    240
NEMAKVDDSF FHRLEESFLV EEDKKHERHP IFGNIVDEVA YHEKYPTIYH LRKKLVDSTD    300
KADLRLIYLA LAHMIKFRGH FLIEGDLNPD NSDVDKLFIQ LVQTYNQLFE ENPINASGVD    360
AKAILSARLS KSRRLENLIA QLPGEKKNGL FGNLIALSLG LTPNFKSNFD LAEDAKLQLS    420
KDTYDDDLDN LLAQIGDQYA DLFLAAKNLS DAILLSDILR VNTEITKAPL SASMIKRYDE    480
HHQDLTLLKA LVRQQLPEKY KEIFFDQSKN GYAGYIDGGA SQEEFYKFIK PILEKMDGTE    540
ELLVKLNRED LLRKQRTFDN GSIPHQIHLG ELHAILRRQE DFYPFLKDNR EKIEKILTFR    600
IPYYVGPLAR GNSRFAWMTR KSEETITPWN FEEVVDKGAS AQSFIERMTN FDKNLPNEKV    660
LPKHSLLYEY FTVYNELTKV KYVTEGMRKP AFLSGEQKKA IVDLLFKTNR KVTVKQLKED    720
YFKKIECFDS VEISGVEDRF NASLGTYHDL LKIIKDKDFL DNEENEDILE DIVLTLTLFE    780
DREMIEERLK TYAHLFDDKV MKQLKRRRYT GWGRLSRKLI NGIRDKQSGK TILDFLKSDG    840
FANRNFMQLI HDDSLTFKED IQKAQVSGQG DSLHEHIANL AGSPAIKKGI LQTVKVVDEL    900
VKVMGRHKPE NIVIEMAREN QTTQKGQKNS RERMKRIEEG IKELGSQILK EHPVENTQLQ    960
NEKLYLYLQN GRDMYVDQEL DINRLSDYD VDAIVPQSFL KDDSIDNKVL TRSDKNRGKS   1020
DNVPSEEVVK KMKNYWRQLL NAKLITQRKF DNLTKAERGG LSELDKAGFI KRQLVETRQI   1080
TKHVAQILDS RMNTKYDEND KLIREVKVIT LKSKLVSDFR KDFQFYKVRE INNYHHAHDA   1140
YLNAVVGTAL IKKYPKLESE FVYGDYKVYD VRKMIAKSEQ EIGKATAKYF FYSNIMNFFK   1200
TEITLANGEI RKRPLIETNG ETGEIVWDKG RDFATVRKVL SMPQVNIVKK TEVQTGGFSK   1260
ESILPKRNSD KLIARKKDWD PKKYGGFDSP TVAYSVLVVA KVEKGKSKKL KSVKELLGIT   1320
IMERSSFEKN PIDFLEAKGY KEVKKDLIIK LPKYSLFELE NGRKRMLASA GELQKGNELA   1380
LPSKYVNFLY LASHYEKLKG SPEDNEQKQL FVEQHKHYLD EIIEQISEFS KRVILADANL   1440
```

```
DKVLSAYNKH RDKPIREQAE NIIHLFTLTN LGAPAAFKYF DTTIDRKRYT STKEVLDATL  1500
IHQSITGLYE TRIDLSQLGG DMAPKKKRKV GIHRGVP                             1537

SEQ ID NO: 331          moltype = AA  length = 1537
FEATURE                 Location/Qualifiers
REGION                  1..1537
                        note = Synthetic Polypeptide
source                  1..1537
                        mol_type = protein
                        organism = synthetic construct
SEQUENCE: 331
MAPKKKRKVG IHRGVPMALF GYARVSTSQQ SLDLQVRALK DAGVKANRIF TDKASGSSTD  60
REGLDLLRMK VKEGDVILVK KLDRLGRDTA DMLQLIKEFD AQGVAVRFID DGISTDSYIG  120
LMFVTILSAV AQAERRRILE RTNEGRQAAK LKGIKFGRRR GGSGGSGGSM DKKYSIGLAI  180
GTNSVGWAVI TDEYKVPSKK FKVLGNTDRH SIKKNLIGAL LFDSGETAEA TRLKRTARRR  240
YTRRKNRICY LQEIFSNEMA KVDDSFFHRL EESFLVEEDK KHERHPIFGN IVDEVAYHEK  300
YPTIYHLRKK LVDSTDKADL RLIYLALAHM IKFRGHFLIE GDLNPDNSDV DKLFIQLVQT  360
YNQLFEENPI NASGVDAKAI LSARLSKSRR LENLIAQLPG EKKNGLFGNL IALSLGLTPN  420
FKSNFDLAED AKLQLSKDTY DDDLDNLLAQ IGDQYADLFL AAKNLSDAIL LSDILRVNTE  480
ITKAPLSASM IKRYDEHHQD LTLLKALVRQ QLPEKYKEIF FDQSKNGYAG YIDGGASQEE  540
FYKFIKPILE KMDGTEELLV KLNREDLLRK QRTFDNGSIP HQIHLGELHA ILRRQEDFYP  600
FLKDNREKIE KILTFRIPYY VGPLARGNSR FAWMTRKSEE TITPWNFEEV VDKGASAQSF  660
IERMTNFDKN LPNEKVLPKH SLLYEYFTVY NELTKVKYVT EGMRKPAFLS GEQKKAIVDL  720
LFKTNRKVTV KQLKEDYFKK IECFDSVEIS GVEDRFNASL GTYHDLLKII KDKDFLDNEE  780
NEDILEDIVL TLTLFEDREM IEERLKTYAH LFDDKVMKQL KRRRYTGWGR LSRKLINGIR  840
DKQSGKTILD FLKSDGFANR NFMQLIHDDS LTFKEDIQKA QVSGQGDSLH EHIANLAGSP  900
AIKKGILQTV KVVDELVKVM GRHKPENIVI EMARENQTTQ KGQKNSRERM KRIEEGIKEL  960
GSQILKEHPV ENTQLQNEKL YLYYLQNGRD MYVDQELDIN RLSDYDVDAI VPQSFLKDDS  1020
IDNKVLTRSD KNRGKSDNVP SEEVVKKMKN YWRQLLNAKL ITQRKFDNLT KAERGGLSEL  1080
DKAGFIKRQL VETRQITKHV AQILDSRMNT KYDENDKLIR EVKVITLKSK LVSDFRKDFQ  1140
FYKVREINNY HHAHDAYLNA VVGTALIKKY PKLESEFVYG DYKVYDVRKM IAKSEQEIGK  1200
ATAKYFFYSN IMNFFKTEIT LANGEIRKRP LIETNGETGE IVWDKGRDFA TVRKVLSMPQ  1260
VNIVKKTEVQ TGGFSKESIL PKRNSDKLIA RKKDWDPKKY GGFDSPTVAY SVLVVAKVEK  1320
GKSKKLKSVK ELLGITIMER SSFEKNPIDF LEAKGYKEVK KDLIIKLPKY SLFELENGRK  1380
RMLASAGELQ KGNELALPSK YVNFLYLASH YEKLKGSPED NEQKQLFVEQ HKHYLDEIIE  1440
QISEFSKRVI LADANLDKVL SAYNKHRDKP IREQAENIIH LFTLTNLGAP AAFKYFDTTI  1500
DRKRYTSTKE VLDATLIHQS ITGLYETRID LSQLGGD                            1537

SEQ ID NO: 332          moltype = AA  length = 1531
FEATURE                 Location/Qualifiers
REGION                  1..1531
                        note = Synthetic Polypeptide
source                  1..1531
                        mol_type = protein
                        organism = synthetic construct
SEQUENCE: 332
MDKKYSIGLA IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDA  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDMA PKKKRKVGIH  1380
RGVPGGSGGS GGSMATIGYI RVSTIDQNID LQRNALTSAN CDRIFEDRIS GKIANRPGLK  1440
RALKYVNKGD TLVVWKLDRL GRSVKNLVAL ISELHERGAH FHSLTDSIDT SSAMGRFFFY  1500
VMSALAEMER ELIVERTLAG LAAARAQGRL G                                  1531

SEQ ID NO: 333          moltype = AA  length = 1531
FEATURE                 Location/Qualifiers
REGION                  1..1531
                        note = Synthetic Polypeptide
source                  1..1531
                        mol_type = protein
```

-continued

```
                          organism = synthetic construct
SEQUENCE: 333
MAPKKKRKVG IHRGVPMDKK YSIGLAIGTN SVGWAVITDE YKVPSKKFKV LGNTDRHSIK   60
KNLIGALLFD SGETAEATRL KRTARRRYTR RKNRICYLQE IFSNEMAKVD DSFFHRLEES  120
FLVEEDKKHE RHPIFGNIVD EVAYHEKYPT IYHLRKKLVD STDKADLRLI YLALAHMIKF  180
RGHFLIEGDL NPDNSDVDKL FIQLVQTYNQ LFEENPINAS GVDAKAILSA RLSKSRRLEN  240
LIAQLPGEKK NGLFGNLIAL SLGLTPNFKS NFDLAEDAKL QLSKDTYDDD LDNLLAQIGD  300
QYADLFLAAK NLSDAILLSD ILRVNTEITK APLSASMIKR YDEHHQDLTL LKALVRQQLP  360
EKYKEIFFDQ SKNGYAGYID GGASQEEFYK FIKPILEKMD GTEELLVKLN REDLLRKQRT  420
FDNGSIPHQI HLGELHAILR RQEDFYPFLK DNREKIEKIL TFRIPYYVGP LARGNSRFAW  480
MTRKSEETIT PWNFEEVVDK GASAQSFIER MTNFDKNLPN EKVLPKHSLL YEYFTVYNEL  540
TKVKYVTEGM RKPAFLSGEQ KKAIVDLLFK TNRKVTVKQL KEDYFKKIEC FDSVEISGVE  600
DRFNASLGTY HDLLKIIKDK DFLDNEENED ILEDIVLTLT LFEDREMIEE RLKTYAHLFD  660
DKVMKQLKRR RYTGWGRLSR KLINGIRDKQ SGKTILDFLK SDGFANRNFM QLIHDDSLTF  720
KEDIQKAQVS GQGDSLHEHI ANLAGSPAIK KGILQTVKVV DELVKVMGRH KPENIVIEMA  780
RENQTTQKGQ KNSRERMKRI EEGIKELGSQ ILKEHPVENT QLQNEKLYLY YLQNGRDMYV  840
DQELDINRLS DYDVDAIVPQ SFLKDDSIDN KVLTRSDKNR GKSDNVPSEE VVKKMKNYWR  900
QLLNAKLITQ RKFDNLTKAE RGGLSELDKA GFIKRQLVET RQITKHVAQI LDSRMNTKYD  960
ENDKLIREVK VITLKSKLVS DFRKDFQFYK VREINNYHHA HDAYLNAVVG TALIKKYPKL 1020
ESEFVYGDYK VYDVRKMIAK SEQEIGKATA KYFFYSNIMN FFKTEITLAN GEIRKRPLIE 1080
TNGETGEIVW DKGRDFATVR KVLSMPQVNI VKKTEVQTGG FSKESILPKR NSDKLIARKK 1140
DWDPKKYGGF DSPTVAYSVL VVAKVEKGKS KKLKSVKELL GITIMERSSF EKNPIDFLEA 1200
KGYKEVKKDL IIKLPKYSLF ELENGRKRML ASAGELQKGN ELALPSKYVN FLYLASHYEK 1260
LKGSPEDNEQ KQLFVEQHKH YLDEIIEQIS EFSKRVILAD ANLDKVLSAY NKHRDKPIRE 1320
QAENIIHLFT LTNLGAPAAF KYFDTTIDRK RYTSTKEVLD ATLIHQSITG LYETRIDLSQ 1380
LGGDGGSGGS GGSMATIGYI RVSTIDQNID LQRNALTSAN CDRIFEDRIS GKIANRPGLK 1440
RALKYVNKGD TLVVWKLDRL GRSVKNLVAL ISELHERGAH FHSLTDSIDT SSAMGRFFFY 1500
VMSALAEMER ELIVERTLAG LAAARAQGRL G                                1531

SEQ ID NO: 334        moltype = AA  length = 1531
FEATURE               Location/Qualifiers
REGION                1..1531
                      note = Synthetic Polypeptide
source                1..1531
                      mol_type = protein
                      organism = synthetic construct
SEQUENCE: 334
MATIGYIRVS TIDQNIDLQR NALTSANCDR IFEDRISGKI ANRPGLKRAL KYVNKGDTLV   60
VWKLDRLGRS VKNLVALISE LHERGAHFHS LTDSIDTSSA MGRFFFYVMS ALAEMERELI  120
VERTLAGLAA ARAQGRLGGG SGGSGGSMDK KYSIGLAIGT NSVGWAVITD EYKVPSKKFK  180
VLGNTDRHSI KKNLIGALLF DSGETAEATR LKRTARRRYT RRKNRICYLQ EIFSNEMAKV  240
DDSFFHRLEE SFLVEEDKKH ERHPIFGNIV DEVAYHEKYP TIYHLRKKLV DSTDKADLRL  300
IYLALAHMIK FRGHFLIEGD LNPDNSDVDK LFIQLVQTYN QLFEENPINA SGVDAKAILS  360
ARLSKSRRLE NLIAQLPGEK KNGLFGNLIA LSLGLTPNFK SNFDLAEDAK LQLSKDTYDD  420
DLDNLLAQIG DQYADLFLAA KNLSDAILLS DILRVNTEIT KAPLSASMIK RYDEHHQDLT  480
LLKALVRQQL PEKYKEIFFD QSKNGYAGYI DGGASQEEFY KFIKPILEKM DGTEELLVKL  540
NREDLLRKQR TFDNGSIPHQ IHLGELHAIL RRQEDFYPFL KDNREKIEKI LTFRIPYYVG  600
PLARGNSRFA WMTRKSEETI TPWNFEEVVD KGASAQSFIE RMTNFDKNLP NEKVLPKHSL  660
LYEYFTVYNE LTKVKYVTEG MRKPAFLSGE QKKAIVDLLF KTNRKVTVKQ LKEDYFKKIE  720
CFDSVEISGV EDRFNASLGT YHDLLKIIKD KDFLDNEENE DILEDIVLTL TLFEDREMIE  780
ERLKTYAHLF DDKVMKQLKR RRYTGWGRLS RKLINGIRDK QSGKTILDFL KSDGFANRNF  840
MQLIHDDSLT FKEDIQKAQV SGQGDSLHEH IANLAGSPAI KKGILQTVKV VDELVKVMGR  900
HKPENIVIEM ARENQTTQKG QKNSRERMKR IEEGIKELGS QILKEHPVEN TQLQNEKLYL  960
YYLQNGRDMY VDQELDINRL SDYDVDAIVP QSFLKDDSID NKVLTRSDKN RGKSDNVPSE 1020
EVVKKMKNYW RQLLNAKLIT QRKFDNLTKA ERGGLSELDK AGFIKRQLVE TRQITKHVAQ 1080
ILDSRMNTKY DENDKLIREV KVITLKSKLV SDFRKDFQFY KVREINNYHH AHDAYLNAVV 1140
GTALIKKYPK LESEFVYGDY KVYDVRKMIA KSEQEIGKAT AKYFFYSNIM NFFKTEITLA 1200
NGEIRKRPLI ETNGETGEIV WDKGRDFATV RKVLSMPQVN IVKKTEVQTG GFSKESILPK 1260
RNSDKLIARK KDWDPKKYGG FDSPTVAYSV LVVAKVEKGK SKKLKSVKEL LGITIMERSS 1320
FEKNPIDFLE AKGYKEVKKD LIIKLPKYSL FELENGRKRM LASAGELQKG NELALPSKYV 1380
NFLYLASHYE KLKGSPEDNE QKQLFVEQHK HYLDEIIEQI SEFSKRVILA DANLDKVLSA 1440
YNKHRDKPIR EQAENIIHLF TLTNLGAPAA FKYFDTTIDR KRYTSTKEVL DATLIHQSIT 1500
GLYETRIDLS QLGGDMAPKK KRKVGIHRGV P                                1531

SEQ ID NO: 335        moltype = AA  length = 1531
FEATURE               Location/Qualifiers
REGION                1..1531
                      note = Synthetic Polypeptide
source                1..1531
                      mol_type = protein
                      organism = synthetic construct
SEQUENCE: 335
MAPKKKRKVG IHRGVPMATI GYIRVSTIDQ NIDLQRNALT SANCDRIFED RISGKIANRP   60
GLKRALKYVN KGDTLVVWKL DRLGRSVKNL VALISELHER GAHFHSLTDS IDTSSAMGRF  120
FFYVMSALAE MERELIVERT LAGLAAARAQ GRLGGGSGGS GGSMDKKYSI GLAIGTNSVG  180
WAVITDEYKV PSKKFKVLGN TDRHSIKKNL IGALLFDSGE TAEATRLKRT ARRRYTRRKN  240
RICYLQEIFS NEMAKVDDSF FHRLEESFLV EEDKKHERHP IFGNIVDEVA YHEKYPTIYH  300
LRKKLVDSTD KADLRLIYLA LAHMIKFRGH FLIEGDLNPD NSDVDKLFIQ LVQTYNQLFE  360
ENPINASGVD AKAILSARLS KSRRLENLIA QLPGEKKNGL FGNLIALSLG LTPNFKSNFD  420
```

```
LAEDAKLQLS KDTYDDDLDN LLAQIGDQYA DLFLAAKNLS DAILLSDILR VNTEITKAPL  480
SASMIKRYDE HHQDLTLLKA LVRQQLPEKY KEIFFDQSKN GYAGYIDGGA SQEEFYKFIK  540
PILEKMDGTE ELLVKLNRED LLRKQRTFDN GSIPHQIHLG ELHAILRRQE DFYPFLKDNR  600
EKIEKILTFR IPYYVGPLAR GNSRFAWMTR KSEETITPWN FEEVVDKGAS AQSFIERMTN  660
FDKNLPNEKV LPKHSLLYEY FTVYNELTKV KYVTEGMRKP AFLSGEQKKA IVDLLFKTNR  720
KVTVKQLKED YFKKIECFDS VEISGVEDRF NASLGTYHDL LKIIKDKDFL DNEENEDILE  780
DIVLTLTLFE DREMIEERLK TYAHLFDDKV MKQLKRRRYT GWGRLSRKLI NGIRDKQSGK  840
TILDFLKSDG FANRNFMQLI HDDSLTFKED IQKAQVSGQG DSLHEHIANL AGSPAIKKGI  900
LQTVKVVDEL VKVMGRHKPE NIVIEMAREN QTTQKGQKNS RERMKRIEEG IKELGSQILK  960
EHPVENTQLQ NEKLYLYYLQ NGRDMYVDQE LDINRLSDYD VDAIVPQSFL KDDSIDNKVL 1020
TRSDKNRGKS DNVPSEEVVK KMKNYWRQLL NAKLITQRKF DNLTKAERGG LSELDKAGFI 1080
KRQLVETRQI TKHVAQILDS RMNTKYDEND KLIREVKVIT LKSKLVSDFR KDFQFYKVRE 1140
INNYHHAHDA YLNAVVGTAL IKKYPKLESE FVYGDYKVYD VRKMIAKSEQ EIGKATAKYF 1200
FYSNIMNFFK TEITLANGEI RKRPLIETNG ETGEIVWDKG RDFATVRKVL SMPQVNIVKK 1260
TEVQTGGFSK ESILPKRNSD KLIARKKDWD PKKYGGFDSP TVAYSVLVVA KVEKGKSKKL 1320
KSVKELLGIT IMERSSFEKN PIDFLEAKGY KEVKKDLIIK LPKYSLFELE NGRKRMLASA 1380
GELQKGNELA LPSKYVNFLY LASHYEKLKG SPEDNEQKQL FVEQHKHYLD EIIEQISEFS 1440
KRVILADANL DKVLSAYNKH RDKPIREQAE NIIHLFTLTN LGAPAAFKYF DTTIDRKRYT 1500
STKEVLDATL IHQSITGLYE TRIDLSQLGG D                                1531

SEQ ID NO: 336            moltype = AA   length = 1537
FEATURE                   Location/Qualifiers
REGION                    1..1537
                          note = Synthetic Polypeptide
source                    1..1537
                          mol_type = protein
                          organism = synthetic construct
SEQUENCE: 336
MDKKYSIGLA IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDA  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGDMA PKKKRKVGIH 1380
RGVPGGSGGS GGSMLIGYVR VSTNDQNTDL QRNALVCAGC EQIFEDKLSG TRTDRPGLKR 1440
ALKRLQKGDT LVVWKLDRLG RSMKHLISLV GELRERGINF RSLTDSIDTS SPMGRFFFYV 1500
MGALAEMERE LIIERTMAGI AAARNKGRRF GRPPKSG                          1537

SEQ ID NO: 337            moltype = AA   length = 1537
FEATURE                   Location/Qualifiers
REGION                    1..1537
                          note = Synthetic Polypeptide
source                    1..1537
                          mol_type = protein
                          organism = synthetic construct
SEQUENCE: 337
MAPKKKRKVG IHRGVPMDKK YSIGLAIGTN SVGWAVITDE YKVPSKKFKV LGNTDRHSIK   60
KNLIGALLFD SGETEAATRL KRTARRRYTR RKNRICYLQE IFSNEMAKVD DSFFHRLEES  120
FLVEEDKKHE RHPIFGNIVD EVAYHEKYPT IYHLRKKLVD STDKADLRLI YLALAHMIKF  180
RGHFLIEGDL NPDNSDVDKL FIQLVQTYNQ LFEENPINAS GVDAKAILSA RLSKSRRLEN  240
LIAQLPGEKK NGLFGNLIAL SLGLTPNFKS NFDLAEDAKL QLSKDTYDDD LDNLLAQIGD  300
QYADLFLAAK NLSDAILLSD ILRVNTEITK APLSASMIKR YDEHHQDLTL LKALVRQQLP  360
EKYKEIFFDQ SKNGYAGYID GGASQEEFYK FIKPILEKMD GTEELLVKLN REDLLRKQRT  420
FDNGSIPHQI HLGELHAILR RQEDFYPFLK DNREKIEKIL TFRIPYYVGP LARGNSRFAW  480
MTRKSEETIT PWNFEEVVDK GASAQSFIER MTNFDKNLPN EKVLPKHSLL YEYFTVYNEL  540
TKVKYVTEGM RKPAFLSGEQ KKAIVDLLFK TNRKVTVKQL KEDYFKKIEC FDSVEISGVE  600
DRFNASLGTY HDLLKIIKDK DFLDNEENED ILEDIVLTLT LFEDREMIEE RLKTYAHLFD  660
DKVMKQLKRR RYTGWGRLSR KLINGIRDKQ SGKTILDFLK SDGFANRNFM QLIHDDSLTF  720
KEDIQKAQVS GQGDSLHEHI ANLAGSPAIK KGILQTVKVV DELVKVMGRH KPENIVIEMA  780
RENQTTQKGQ KNSRERMKRI EEGIKELGSQ ILKEHPVENT QLQNEKLYLY LQNGRDMYV  840
DQELDINRLS DYDVDAIVPQ SFLKDDSIDN KVLTRSDKNR GKSDNVPSEE VVKKMKNYWR  900
QLLNAKLITQ RKFDNLTKAE RGGLSELDKA GFIKRQLVET RQITKHVAQI LDSRMNTKYD  960
```

```
ENDKLIREVK VITLKSKLVS DFRKDFQFYK VREINNYHHA HDAYLNAVVG TALIKKYPKL     1020
ESEFVYGDYK VYDVRKMIAK SEQEIGKATA KYFFYSNIMN FFKTEITLAN GEIRKRPLIE     1080
TNGETGEIVW DKGRDFATVR KVLSMPQVNI VKKTEVQTGG FSKESILPKR NSDKLIARKK     1140
DWDPKKYGGF DSPTVAYSVL VVAKVEKGKS KKLKSVKELL GITIMERSSF EKNPIDFLEA     1200
KGYKEVKKDL IIKLPKYSLF ELENGRKRML ASAGELQKGN ELALPSKYVN FLYLASHYEK     1260
LKGSPEDNEQ KQLFVEQHKK YLDEIIEQIS EFSKRVILAD ANLDKVLSAY NKHRDKPIRE     1320
QAENIIHLFT LTNLGAPAAF KYFDTTIDRK RYTSTKEVLD ATLIHQSITG LYETRIDLSQ     1380
LGGDGGSGGS GGSMLIGYVR VSTNDQNTDL QRNALVCAGC EQIFEDKLSG TRTDRPGLKR     1440
ALKRLQKGDT LVVWKLDRLG RSMKHLISLV GELRERGINF RSLTDSIDTS SPMGRFFFYV     1500
MGALAEMERE LIIERTMAGI AAARNKGRRF GRPPKSG                             1537

SEQ ID NO: 338         moltype = AA  length = 1537
FEATURE                Location/Qualifiers
REGION                 1..1537
                       note = Synthetic Polynucleotide
source                 1..1537
                       mol_type = protein
                       organism = synthetic construct
SEQUENCE: 338
MLIGYVRVST NDQNTDLQRN ALVCAGCEQI FEDKLSGTRT DRPGLKRALK RLQKGDTLVV     60
WKLDRLGRSM KHLISLVGEL RERGINFRSL TDSIDTSSPM GRFFFYVMGA LAEMERELII     120
ERTMAGIAAA RNKGRRFGRP PKSGGGSGGS GGSMDKKYSI GLAIGTNSVG WAVITDEYKV     180
PSKKFKVLGN TDRHSIKKNL IGALLFDSGE TAEATRLKRT ARRRYTRRKN RICYLQEIFS     240
NEMAKVDDSF FHRLEESFLV EEDKKHERHP IFGNIVDEVA YHEKYPTIYH LRKKLVDSTD     300
KADLRLIYLA LAHMIKFRGH FLIEGDLNPD NSDVDKLFIQ LVQTYNQLFE ENPINASGVD     360
AKAILSARLS KSRRLENLIA QLPGEKKNGL FGNLIALSLG LTPNFKSNFD LAEDAKLQLS     420
KDTYDDDLDN LLAQIGDQYA DLFLAAKNLS DAILLSDILR VNTEITKAPL SASMIKRYDE     480
HHQDLTLLKA LVRQQLPEKY KEIFFDQSKN GYAGYIDGGA SQEEFYKFIK PILEKMDGTE     540
ELLVKLNRED LLRKQRTFDN GSIPHQIHLG ELHAILRRQE DFYPFLKDNR EKIEKILTFR     600
IPYYVGPLAR GNSRFAWMTR KSEETITPWN FEEVVDKGAS AQSFIERMTN FDKNLPNEKV     660
LPKHSLLYEY FTVYNELTKV KYVTEGMRKP AFLSGEQKKA IVDLLFKTNR KVTVKQLKED     720
YPKKIECFDS VEISGVEDRF NASLGTYHDL LKIIKDKDFL DNEENEDILE DIVLTLTLFE     780
DREMIEERLK TYAHLFDDKV MKQLKRRRYT GWGRLSRKLI NGIRDKQSGK TILDFLKSDG     840
FANRNFMQLI HDDSLTFKED IQKAQVSGQG DSLHEHIANL AGSPAIKKGI LQTVKVVDEL     900
VKVMGRHKPE NIVIEMAREN QTTQKGQKNS RERMKRIEEG IKELGSQILK EHPVENTQLQ     960
NEKLYLYYLQ NGRDMYVDQE LDINRLSDYD VDAIVPQSFL KDDSIDNKVL TRSDKNRGKS     1020
DNVPSEEVVK KMKNYWRQLL NAKLITQRKF DNLTKAERGG LSELDKAGFI KRQLVETRQI     1080
TKHVAQILDS RMNTKYDEND KLIREVKVIT LKSKLVSDFR KDFQFYKVRE INNYHHAHDA     1140
YLNAVVGTAL IKKYPKLESE FVYGDYKVYD VRKMIAKSEQ EIGKATAKYF FYSNIMNFFK     1200
TEITLANGEI RKRPLIETNG ETGEIVWDKG RDFATVRKVL SMPQVNIVKK TEVQTGGFSK     1260
ESILPKRNSD KLIARKKDWD PKKYGGFDSP TVAYSVLVVA KVEKGKSKKL KSVKELLGIT     1320
IMERSSFEKN PIDFLEAKGY KEVKKDLIIK LPKYSLFELE NGRKRMLASA GELQKGNELA     1380
LPSKYVNFLY LASHYEKLKG SPEDNEQKQL FVEQHKYLD EIIEQISEFS KRVILADANL     1440
DKVLSAYNKH RDKPIREQAE NIIHLFTLTN LGAPAAFKYF DTTIDRKRYT STKEVLDATL     1500
IHQSITGLYE TRIDLSQLGG DMAPKKKRKV GIHRGVP                             1537

SEQ ID NO: 339         moltype = AA  length = 1537
FEATURE                Location/Qualifiers
REGION                 1..1537
                       note = Synthetic Polypeptide
source                 1..1537
                       mol_type = protein
                       organism = synthetic construct
SEQUENCE: 339
MAPKKKRKVG IHRGVPMLIG YVRVSTNDQN TDLQRNALVC AGCEQIFEDK LSGTRTDRPG     60
LKRALKRLQK GDTLVVWKLD RLGRSMKHLI SLVGELRERG INFRSLTDSI DTSSPMGRFF     120
FYVMGALAEM ERELIIERTM AGIAAARNKG RRFGRPPKSG GGSGGSGGSM DKKYSIGLAI     180
GTNSVGWAVI TDEYKVPSKK FKVLGNTDRH SIKKNLIGAL LFDSGETAEA TRLKRTARRR     240
YTRRKNRICY LQEIFSNEMA KVDDSFFHRL EESFLVEEDK KHERHPIFGN IVDEVAYHEK     300
YPTIYHLRKK LVDSTDKADL RLIYLALAHM IKFRGHFLIE GDLNPDNSDV DKLFIQLVQT     360
YNQLFEENPI NASGVDAKAI LSARLSKSRR LENLIAQLPG EKKNGLFGNL IALSLGLTPN     420
FKSNFDLAED AKLQLSKDTY DDDLDNLLAQ IGDQYADLFL AAKNLSDAIL LSDILRVNTE     480
ITKAPLSASM IKRYDEHHQD LTLLKALVRQ QLPEKYKEIF FDQSKNGYAG YIDGGASQEE     540
FYKFIKPILE KMDGTEELLV KLNREDLLRK QRTFDNGSIP HQIHLGELHA ILRRQEDFYP     600
FLKDNREKIE KILTFRIPYY VGPLARGNSR FAWMTRKSEE TITPWNFEEV VDKGASAQSF     660
IERMTNFDKN LPNEKVLPKH SLLYEYFTVY NELTKVKYVT EGMRKPAFLS GEQKKAIVDL     720
LFKTNRKVTV KQLKEDYFKK IECFDSVEIS GVEDRFNASL GTYHDLLKII KDKDFLDNEE     780
NEDILEDIVL TLTLFEDREM IEERLKTYAH LFDDKVMKQL KRRRYTGWGR LSRKLINGIR     840
DKQSGKTILD FLKSDGFANR NFMQLIHDDS LTFKEDIQKA QVSGQGDSLH EHIANLAGSP     900
AIKKGILQTV KVVDELVKVM GRHKPENIVI EMARENQTTQ KGQKNSRERM KRIEEGIKEL     960
GSQILKEHPV ENTQLQNEKL YLYYLQNGRD MYVDQELDIN RLSDYDVDAI VPQSFLKDDS     1020
IDNKVLTRSD KNRGKSDNVP SEEVVKKMKN YWRQLLNAKL ITQRKFDNLT KAERGGLSEL     1080
DKAGFIKRQL VETRQITKHV AQILDSRMNT KYDENDKLIR EVKVITLKSK LVSDFRKDFQ     1140
FYKVREINNY HHAHDAYLNA VVGTALIKKY PKLESEFVYG DYKVYDVRKM IAKSEQEIGK     1200
ATAKYFFYSN IMNFFKTEIT LANGEIRKRP LIETNGETGE IVWDKGRDFA TVRKVLSMPQ     1260
VNIVKKTEVQ TGGFSKESIL PKRNSDKLIA RKKDWDPKKY GGFDSPTVAY SVLVVAKVEK     1320
GKSKKLKSVK ELLGITIMER SSFEKNPIDF LEAKGYKEVK KDLIIKLPKY SLFELENGRK     1380
RMLASAGELQ KGNELALPSK YVNFLYLASH YEKLKGSPED NEQKQLFVEQ HKHYLDEIIE     1440
QISEFSKRVI LADANLDKVL SAYNKHRDKP IREQAENIIH LFTLTNLGAP AAFKYFDTTI     1500
```

-continued

```
DRKRYTSTKE VLDATLIHQS ITGLYETRID LSQLGGD                              1537

SEQ ID NO: 340        moltype = AA   length = 583
FEATURE               Location/Qualifiers
source                1..583
                      mol_type = protein
                      note = Flavobacterium okeanokoites
                      organism = unidentified
SEQUENCE: 340
MFLSMVSKIR TFGWVQNPGK FENLKRVVQV FDRNSKVHNE VKNIKIPTLV KESKIQKELV      60
AIMNQHDLIY TYKELVGTGT SIRSEAPCDA IIQATIADQG NKKGYIDNWS SDGFLRWAHA     120
LGFIEYINKS DSFVITDVGL AYSKSADGSA IEKEILIEAI SSYPPAIRIL TLLEDGQHLT     180
KFDLGKNLGF SGESGFTSLP EGILLDTLAN AMPKDKGEIR NNWEGSSDKY ARMIGGWLDK     240
LGLVKQGKKE FIIPTLGKPD NKEFISHAFK ITGEGLKVLR RAKGSTKFTR VPKRVYWEML     300
ATNLTDKEYV RTRRALILEI LIKAGSLKIE QIQDNLKKLG FDEVIETIEN DIKGLINTGI     360
FIEIKGRFYQ LKDHILQFVI PNRGVTKQLV KSELEEKKSE LRHKLKYVPH EYIELIEIAR     420
NSTQDRILEM KVMEFFMKVY GYRGKHLGGS RKPDGAIYTV GSPIDYGVIV DTKAYSGGYN     480
LPIGQADEMQ RYVEENQTRN KHINPNEWWK VYPSSVTEFK FLFVSGHFKG NYKAQLTRLN     540
HITNCNGAVL SVEELLIGGE MIKAGTLTLE EVRRKFNNGE INF                       583
```